US00RE41888E

(19) United States
(12) Reissued Patent
Goddard et al.

(10) Patent Number: US RE41,888 E
(45) Date of Reissued Patent: Oct. 26, 2010

(54) POLYNUCLEOTIDE OVEREXPRESSED IN TUMORS

(75) Inventors: Audrey Goddard, San Francisco, CA (US); Paul J. Godowski, Hillsborough, CA (US); Austin L. Gurney, Belmont, CA (US); Victoria Smith, Burlingame, CA (US); William I. Wood, Hillsborough, CA (US)

(73) Assignee: Genentech, Inc., South San Francisco, CA (US)

(21) Appl. No.: 12/012,201

(22) Filed: Jan. 31, 2008

Related U.S. Patent Documents

Reissue of:
(64) Patent No.: 7,208,316
Issued: Apr. 24, 2007
Appl. No.: 10/227,884
Filed: Aug. 26, 2002

(63) Continuation of application No. 10/119,480, filed on Apr. 9, 2002, now abandoned, which is a continuation-in-part of application No. PCT/US01/21066, filed on Jun. 29, 2001, and a continuation-in-part of application No. PCT/US01/17800, filed on Jun. 1, 2001.

(51) Int. Cl.

| | |
|---|---|
| ***C12N 1/21*** | (2006.01) |
| ***C12N 1/19*** | (2006.01) |
| ***C12N 5/10*** | (2006.01) |
| ***C12N 15/12*** | (2006.01) |
| ***C12N 15/63*** | (2006.01) |

(52) U.S. Cl. ..... 435/325; 435/358; 435/252.3; 435/252.33; 435/254.11; 435/320.1; 435/254.2; 536/23.1; 536/23.5

(58) Field of Classification Search ..... None
See application file for complete search history.

(56) References Cited

U.S. PATENT DOCUMENTS

| | | | |
|---|---|---|---|
| 6,613,515 | B1 | 9/2003 | Xu et al. |
| 6,617,109 | B1 | 9/2003 | Xu et al. |
| 6,710,170 | B2 | 3/2004 | Xu et al. |
| 6,720,146 | B2 | 4/2004 | Stolk et al. |
| 2003/0129192 | A1 | 7/2003 | Chenault et al. |
| 2003/0148408 | A1 | 8/2003 | Frantz et al. |
| 2003/0206918 | A1 | 11/2003 | Fanger et al. |
| 2003/0232056 | A1 | 12/2003 | Fanger et al. |
| 2004/0229277 | A1 | 11/2004 | Frantz et al. |
| 2004/0242860 | A1 | 12/2004 | Frantz et al. |
| 2006/0057141 | A1 | 3/2006 | Fanger |

FOREIGN PATENT DOCUMENTS

| | | | |
|---|---|---|---|
| EP | 1 067 182 | A2 | 1/2001 |
| WO | WO 00/61629 | | 10/2000 |
| WO | 00/77026 | | 12/2000 |
| WO | 01/18046 | | 3/2001 |
| WO | 01/81634 | | 11/2001 |
| WO | 01/92581 | | 12/2001 |
| WO | WO 02/39885 | A2 | 5/2002 |

OTHER PUBLICATIONS

Bork, et al., "Go hunting in sequence databases but watch out for the traps" *Trends in Genetics* 12 (10) :425–427 (Oct. 1996).
Bork, P., "Powers and Pitfalls in Sequence Analysis: The 70% Hurdle" *Genome Research* 10(4) :398–400 (Apr. 2000).
Brenner, S.E., "Errors in genome annotation" *Trends in Genetics* 15(4) :132–133 (Apr. 1999).
Database Search, DNA sequence alignments, (BLASTN 2.2.6 Apr. 9, 2003 NCBI) pp. 1–118.
Database Search, protein sequence alignments, (BLASTP 2.2.6 Apr. 9, 2003 NCBI) pp. 1–18.
Doerks, et al., "Protein annotation: detective work for function prediction" *Trends in Genetics* 14 (6) :248–250 (Jun. 1998).
EMBL Sequence Database Accession No. AA613995 (Oct. 13, 1997).
Explanation of blast hits—DNA sequence alignments: GenBank (Rel 153 Apr. 2006) pp. 119–166.
Explanation of blast hits—protein sequence alignments: Dayhoff Protein Database (Rel 48 Oct. 2005) pp. 19–53.
Fleischhacker et al., "DNA aneuploidy in morphologically normal colons from patients with colon cancer" *Mod Pathol* 8(4) :360–365 (1995).
Hegde et al., "A Concise Guide to cDNA Microarray Analysis" *BioTechniques* 29(3) :548–562 (Sep. 2000).
NCBI Database, Accession No. AB041649 (Jun. 30, 2000).
NCBI Database, Accession No. AX136281 (May 30, 2001).
NCBI Database, Accession No. Q9JJ96 (Oct. 1, 2000).
Ngo et al., "Computational Complexity, Protein Structure Prediction, and the Levinthal Paradox" *The Protein Folding Problem and Tertiary Structure Prediction,* Merz & Le Grand, Boston:Birkhauser pp. 491–495 (1994).
Orntoft, Torben F., et al., "Genome–wide Study of Gene Copy Numbers, Transcripts, and Protein Levels in Pairs of Non–Invasive and Invasive Human Transitional Cell Carcinomas" *Molecular & Cellular Proteomics* 1:37–45 (2002).
Qi et al., "Identification of genes responsible for osteoblast differentiation from human mesodermal progenitor cells" *Proc. Natl. Acad. Sci USA* 100:3305–3310 (2003).
Saito–Hisaminato et al., "Genome–wide profiling of gene expression in 29 normal human tissues with a cDNA microarray"*DNA Res* 9:35–45 (2002).
Sen et al., "Aneuploidy and cancer" *Curr. Opin. Oncol.* 12:82–88 (2000).

(Continued)

*Primary Examiner*—Gary B Nickol
*Assistant Examiner*—Jon M Lockard
(74) *Attorney, Agent, or Firm*—Danielle M. Pasqualone

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

10 Claims, 246 Drawing Sheets

OTHER PUBLICATIONS

Smith, et al., "The challenges of genome sequence annotation or "The devil is in the details"" *Nature Biotechnology* 15 (12):1222–1223 (Nov. 1997).

Strategene Product Catalog, "Prime–IT™ Random Primer Labeling Kit, Catalog #300387" (1991).

Wells, "Additivity of Mutational Effects in Proteins" *Biochemistry* 29:8509–8517 (1990).

NCBI Database, Accession No. AB041649 (Jun. 30, 2000), Osada et al.*

NCBI Database, Accession No. AX136281 (May 30, 2001), Ota et al.*

NCBI Database, Accession No. Q9JJ96 (Oct. 1, 2000), Osada et al.*

Bork, P., "Powers and Pitfalls in Sequence Analysis: The 70% Hurdle" *Genome Research* 10(4) :398–400 (Apr. 2000).*

* cited by examiner

FIGURE 1A

GCAGCCCTAGCAGGGATGGACATGATGCTGTTGGTGCAGGGTGCTTGTTGCTCGAACCAGTG
GCTGGCGGCGGTGCTCCTCAGCCTGTGCTGCCTGCTACCCTCCTGCCTCCCGGCTGGACAGA
GTGTGGACTTCCCCTGGGCGGCCGTGGACAACATGATGGTCAGAAAAGGGGACACGGCGGTG
CTTAGGTGTTATTTGGAAGATGGAGCTTCAAAGGGTGCCTGGCTGAACCGGTCAAGTATTAT
TTTTGCGGGAGGTGATAAGTGGTCAGTGGATCCTCGAGTTTCAATTTCAACATTGAATAAAA
GGGACTACAGCCTCCAGATACAGAATGTAGATGTGACAGATGATGGCCCATACACGTGTTCT
GTTCAGACTCAACATACACCCAGAACAATGCAGGTGCATCTAACTGTGCAAGTTCCTCCTAA
GATATATGACATCTCAAATGATATGACCGTCAATGAAGGAACCAACGTCACTCTTACTTGTT
TGGCCACTGGGAAACCAGAGCCTTCCATTTCTTGGCGACACATCTCCCCATCAGCAAAACCA
TTTGAAAATGGACAATATTTGGACATTTATGGAATTACAAGGGACCAGGCTGGGGAATATGA
ATGCAGTGCGGAAAATGATGTGTCATTCCCAGATGTGAGGAAAGTAAAAGTTGTTGTCAACT
TTGCTCCTACTATTCAGGAAATTAAATCTGGCACCGTGACCCCCGGACGCAGTGGCCTGATA
AGATGTGAAGGTGCAGGTGTGCCGCCTCCAGCCTTTGAATGGTACAAAGGAGAGAAGAAGCT
CTTCAATGGCCAACAAGGAATTATTATTCAAAATTTTAGCACAAGATCCATTCTCACTGTTA
CCAACGTGACACAGGAGCACTTCGGCAATTATACTTGTGTGGCTGCCAACAAGCTAGGCACA
ACCAATGCGAGCCTGCCTCTTAACCCTCCAAGTACAGCCCAGTATGGAATTACCGGGAGCGC
TGATGTTCTTTTCTCCTGCTGGTACCTTGTGTTGACACTGTCCTCTTTCACCAGCATATTCT
ACCTGAAGAATGCCATTCTACAATAAATTCAAAGACCCATAAAAGGCTTTTAAGGATTCTCT
GAAAGTGCTGATGGCTGGATCCAATCTGGTACAGTTTGTTAAAAGCAGCGTGGGATATAATC
AGCAGTGCTTACATGGGGATGATCGCCTTCTGTAGAATTGCTCATTATGTAAATACTTTAAT
TCTACTCTTTTTTGATTAGCTACATTACCTTGTGAAGCAGTACACATTGTCCTTTTTTTAAG
ACGTGAAAGCTCTGAAATTACTTTTAGAGGATATTAATTGTGATTTCATGTTTGTAATCTAC
AACTTTTCAAAAGCATTCAGTCATGGTCTGCTAGGTTGCAGGCTGTAGTTTACAAAAACGAA
TATTGCAGTGAATATGTGATTCTTTAAGGCTGCAATACAAGCATTCAGTTCCCTGTTTCAAT
AAGAGTCAATCCACATTTACAAAGATGCATTTTTTTCTTTTTTGATAAAAAAGCAAATAATA
TTGCCTTCAGATTATTTCTTCAAAATATAACACATATCTAGATTTTTCTGCTCGCATGATAT
TCAGGTTTCAGGAATGAGCCTTGTAATATAACTGGCTGTGCAGCTCTGCTTCTCTTTCCTGT
AAGTTCAGCATGGGTGTGCCTTCATACAATAATATTTTTCTCTTTGTCTCCAACTAATATAA
AATGTTTTGCTAAATCTTACAATTTGAAAGTAAAAATAAACCAGAGTGATCAAGTTAAACCA
TACACTATCTCTAAGTAACGAAGGAGCTATTGGACTGTAAAAATCTCTTCCTGCACTGACAA
TGGGGTTTGAGAATTTTGCCCCACACTAACTCAGTTCTTGTGATGAGAGACAATTTAATAAC
AGTATAGTAAATATACCATATGATTTCTTTAGTTGTAGCTAAATGTTAGATCCACCGTGGGA
AATCATTCCCTTTAAAATGACAGCACAGTCCACTCAAAGGATTGCCTAGCAATACAGCATCT
TTTCCTTTCACTAGTCCAAGCCAAAAATTTTAAGATGATTTGTCAGAAAGGGCACAAAGTCC
TATCACCTAATATTACAAGAGTTGGTAAGCGCTCATCATTAATTTTATTTTGTGGCAGCTAA
GTTAGTATGACAGAGGCAGTGCTCCTGTGGACAGGAGCATTTTGCATATTTTCCATCTGAAA
GTATCACTCAGTTGATAGTCTGGAATGCATGTTATATATTTTAAAACTTCCAAAATATATTA
TAACAAACATTCTATATCGGTATGTAGCAGACCAATCTCTAAAATAGCTAATTCTTCAATAA
AATCTTTCTATATAGCCATTTCAGTGCAAACAAGTAAAATCAAAAAAGACCATCCTTTATTT
TTCCTTACATGATATATGTAAGATGCGATCAAATAAAGACAAAACACCAGTGATGAGAATAT
CTTAAGATAAGTAATTATCAAATTATTGTGAATGTTAAATTATTTCTACTATAAAGAAGCAA
AACTACATTTTTGAAGGAAAATGCTGTTACTCTAACATTAATTTACAGGAATAGTTTGATGG
TTTCACTCTTTACTAAAGAAAGGCCATCACCTTGAAAGCCATTTTACAGGTTTGATGAAGTT
ACCAATTTCAGTACACCTAAATTTCTACAAATAGTCCCCTTTTACAAGTTGTAACAACAAAG
ACCCTATAATAAAATTAGATACAAGAAATTTTGCAGTGGTTATACATATTTGAGATATCTAG
TATGTTGCCCTAGCAGGGATGGCTTAAAAACTGTGATTTTTTTTCTTCAAGTAAAACTTAGT
CCCAAAGTACATCATAAATCAATTTTAATTAGAAAAATGAATCTTAAATGAGGGGACATAAG
TATACTCTTTCCACAAAATGGCAATAATAAGGCATAAAGCTAGTAAATCTACTAACTGTAAT
AAATGTATGACATTATTTTGATTGATACATTAAAAAAGAGTTTTTAGAACAAATATGGCATT
TAACTTTATTATTTATTTGCTTTTAAGAAATATTCTTTGTGGAATTGTTGAATAAACTATAA
AATATTATTTTGTATTGCAGCTTTAAAGTGGCACACTCCATAATAATCTACTTACTAGAAAT

FIGURE 1B

AGTGGTGCTACCACAAAAAATGTTAACCATCAGTACCATTGTTTGGGAGAAAGAAACAGATC
AAGAATGCATATTATTCAGTGACCGCTTTCCTAGAGTTAAAATACCTCCTCTTTGTAAGGTT
TGTAGGTAAATTGAGGTATAAACTATGGATGAACCAAATAATTAGTTCAAAGTGTTGTCATG
ATTCCAAATTTGTGGAGTCTGGTGTTTTTACCATAGAATGTGACAGAAGTACAGTCATAGCT
CAGTAGCTATATGTATTTGCCTTTATGTTAGAAGAGACTTTCTTGAGTGACATTTTTAAATA
GAGGAGGTATTCACTATGTTTTTCTGTATCACAGCAGCATTCCTAGTCCTTAGGCCCTCGGA
CAGAGTGAAATCATGAGTATTTATGAGTTCAATATTGTCAAATAAGGCTACAGTATTTGCTT
TTTTGTGTGAATGTATTGCATATAATGTTCAAGTAGATGATTTTACATTTATGGACATATAA
AATGTCTGATTACCCCATTTTATCAGTCCTGACTGTACAAGATTGTTGCAATTTCAGAATAG
CAGTTTTATAAATTGATTTATCTTTTAATCTATAACAATTTGTGTTAGCTGTTCATTTCAGG
ANTATATTTTCTACAAGTTCCACTTGTGGGACTCCTTTTGTTGCCCCTATTTTTTTTTAAAG
AAGGAAGAAAGAAAAATAAGTAGCAGTTTAAAAATGAGAATGGAGAGAAAAGAAAAAGAATG
AAAAGGAAAGGCAGTAAAGAGGGAAAAAAAAGGAAGGATGGAAGGAATGAAGGAAGGAAGGG
AGGAAGGGGAGAAGGTAGGAAGAAAGAAAGGATGAGAGGGAAGGAAGAATCAGAGTATTAGG
GTAGTTAACTTACACATTTGCATTCTTAGTTTAACTGCAAGTGGTGTAACTATGTTTTTCAA
TGATCGCATTTGAAACATAAGTCCTATTATACCATTAAGTTCCTATTATGCAGCAATTATAT
AATAAAAAGTACTGCCCAAGTTATAGTAATGTGGGTGTTTTTGAGACACTAAAAGATTTGAG
AGGGAGAATTTCAAACTTAAAGCCACTTTTGGGGGGTTTATAACTTAACTGAAAAATTAATG
CTTCATCATAACATTTAAGCTATATCTAGAAAGTAGACTGGAGAACTGAGAAAATTACCCAG
GTAATTCAGGGAAAAAAAAAAATATATATATATATAAATACCCCTACATTTGAAGTCAGAAA
ACTCTGAAAAACTGAATTATCAAAGTCAATCATCTATAATGATCAAATTTACTGAACAATTG
TTAATTTATCCATTGTGCTTAGCTTTGTGACACAGCCAAAAGTTACCTATTTAATCTTTTCA
ATAAAAATTGTTTTTTGAAATCCAGAAATGATTTAAAAAGAGGTCAGGTTTTTAACTATTTA
TTGAAGTATGTGGATGTACAGTATTTCAATAGATATGAATATGAATAAATGGTATGCCTTAA
GATTCTTTGAATATGTATTTACTTTAAAGACTGGAAAAAGCTCTTCCTGTCTTTTAGTAAAA
CATCCATATTTCATAACCTGATGTAAAATATGTTGTACTGTTTCCAATAGGTGAATATAAAC
TCAGTTTATCAATTAAAAAAAAAAAAAAAAAAAAAAAAAAAAAAAAAAAAAAAAAAAAAAAA

FIGURE 2

></usr/seqdb2/sst/DNA/Dnaseqs.full/ss.DNA92259
><subunit 1 of 1, 354 aa, 1 stop
><MW: 38719, pI: 6.12, NX(S/T): 6
MDMMLLVQGACCSNQWLAAVLLSLCCLLPSCLPAGQSVDFPWAAVDNMMVRKGDTAVLRCYL
EDGASKGAWLNRSSIIFAGGDKWSVDPRVSISTLNKRDYSLQIQNVDVTDDGPYTCSVQTQH
TPRTMQVHLTVQVPPKIYDISNDMTVNEGTNVTLTCLATGKPEPSISWRHISPSAKPFENGQ
YLDIYGITRDQAGEYECSAENDVSFPDVRKVKVVVNFAPTIQEIKSGTVTPGRSGLIRCEGA
GVPPPAFEWYKGEKKLFNGQQGIIIQNFSTRSILTVTNVTQEHFGNYTCVAANKLGTTNASL
PLNPPSTAQYGITGSADVLFSCWYLVLTLSSFTSIFYLKNAILQ

Important features of the protein:
Signal peptide:
amino acids 1-33

Transmembrane domain:
amino acids 322-343

N-glycosylation sites.
amino acids 73-77, 155-159, 275-279, 286-290, 294-298, 307-311

Tyrosine kinase phosphorylation site.
amino acids 180-188

N-myristoylation sites.
amino acids 9-15, 65-71, 69-75, 153-159, 241-247, 293-299, 304-310, 321-327

Myelin P0 protein.
amino acids 94-123

FIGURE 3

CACTGCCCGTCCGCTCTTCAGCAGCCGGTCGCGGGCGGTGGAAAAGCGAGTGAAGAGAGCGC
GACGGCGGCGGCGGCGGCGGCGCAGCTATTGCTGGACGGCCAGTGGGAGAGCGAGGCCTGAG
CCTCTGCGTCTAGGATCAAAATGGTTTCAATCCCAGAATACTATGAAGGCAAGAACGTCCTC
CTCACAGGAGCTACCGGTTTTCTAGGGAAGGTGCTTCTGGAAAAGTTGCTGAGGTCTTGTCC
TAAGGTGAATTCAGTATATGTTTTGGTGAGGCAGAAAGCTGGACAGACACCACAAGAGCGAG
TGGAAGAAGTCCTTAGTGGCAAGCTTTTTGACAGATTGAGAGATGAAAATCCAGATTTTAGA
GAGAAAATTATAGCAATCAACAGCGAACTCACCCAACCTAAACTGGCTCTCAGTGAAGAAGA
TAAAGAGGTGATCATAGATTCTACCAATATTATATTCCACTGTGCAGCTACAGTAAGGTTTA
ATGAAAATTTAAGAGATGCTGTTCAGTTAAATGTGATTGCAACGCGACAGCTTATTCTCCTT
GCACAACAAATGAAGAATCTGGAAGTGTTCATGCATGTATCAACAGCATATGCCTACTGTAA
TCGCAAGCATATTGATGAAGTAGTCTATCCACCACCTGTGGATCCCAAGAAGCTGATTGATTCT
TTAGAGTGGATGGATGATGGCCTAGTAAATGATATCACGCCAAAATTGATAGGAGACAGACC
TAATACATACATATACACAAAAGCATTGGCAGAATATGTTGTACAACAAGAAGGAGCAAAAC
TAAATGTGGCAATTGTAAGGCCATCGATTGTTGGTGCCAGTTGGAAAGAACCTTTTCCAGGA
TGGATTGATAACTTTAATGGACCAAGTGGTCTCTTTATTGCGGCAGGGAAAGGAATTCTTCG
AACAATACGTGCCTCCAACAATGCCCTTGCAGATCTTGTTCCTGTAGATGTAGTTGTCAACA
TGAGTCTTGCGGCAGCCTGGTATTCCGGAGTTAATAGACCAAGAAACATCATGGTGTATAAT
TGTACAACAGGCAGCACTAATCCTTTCCACTGGGGTGAAGTTGAGTACCATGTAATTTCCAC
TTTCAAGAGGAATCCTCTCGAACAGGCCTTCAGACGGCCCAATGTAAATCTAACCTCCAATC
ATCTTTTATATCATTACTGGATTGCTGTAAGCCATAAGGCCCCAGCATTCCTGTATGATATC
TACCTCAGGATGACTGGAAGAAGCCCAAGGATGATGAAAACAATAACTCGTCTTCACAAAGC
TATGGTGTTTCTTGAATATTTCACAAGTAATTCTTGGGTTTGGAATACTGAGAATGTCAATA
TGTTAATGAATCAACTAAACCCTGAAGATAAAAAGACCTTCAATATTGATGTACGGCAGTTA
CATTGGGCAGAATATATAGAGAACTACTGCTTGGGAACTAAGAAGTACGTATTGAATGAAGA
AATGTCTGGCCTCCCTGCAGCCAGAAAACATCTGAACAAGTTGCGGAATATACGTTATGGTT
TTAATACTATCCTTGTGATCCTCATCTGGCGCATTTTTATTGCAAGATCACAAATGGCAAGA
AATATCTGGTACTTTGTGGTTAGTCTGTGTTACAAGTTTTTGTCATACTTCCGAGCATCCAG
CACTATGAGATACTGAAGACCAAGGATTCAGCATTAGAACATCTATACATATGGTGATCTAA
ATGTACAAAATGTAAAATGTATAAGTCATCTCACTTTTTGTCAAGACATTAAACCATCTTAG
ATCGGAGTGTGAAGTAAATTATGGTATATTTTATGTAACATTTTAATGTTTATGCTCATAAA
ACTTAGTGAACACACTGTGTTATGCCAGCTCAAATCTACAGTAGCCACCAAAACCATGACTT
AATATTTTGAGCCCTAGAAGAAAGGGGTGTGCTGAGGACAAGAGTGGGGAAATAGGAACACT
GACCAGTATAACTGTGCAATTCTGGAACATATTAATTAAAATAATATGCCTTAACATATAGT
GAATTTCTAATTCTAATGTTCAGTGCAATGGAAGACATTTATTTGGACAGTATACTAGCAAA
GTTGGTAGATATTTGATTCTTCATTTTTTGTTTTTTTCATTAGTTGAAGTGGGTTTTAGTTT
TGTTTAAAATTATAACCAGCGTATTTTCACATCATTCTGTAAGTTAAATGATATCAAACATG
AAAGAGATGTTCTCATTTTTCTTTTTCTGATTAAACGTCTGATGCATATCATTTTTCTATAA
GTAATCAGTTGCTTTTAAAATCAGAAGGCTATATTATTCTAATGACCCTATTCGATCTAAAT
GGGTTTGAGAATCCATATCAGCAACATACGTGTTTTTTGACAGAAAGTGAAAACAAATTCCG
TAAAACTGTTAGTATCAAAAAGAATAGGAATACAGTTTTCTTTTCCACATTATGATCAAATAAA
AATCTTGTGAGATTGTTAAAAA

FIGURE 4

```
></usr/seqdb2/sst/DNA/Dnaseqs.min/ss.DNA94849
><subunit 1 of 1, 515 aa, 1 stop
><MW: 59357, pI: 9.40, NX(S/T): 3
MVSIPEYYEGKNVLLTGATGFLGKVLLEKLLRSCPKVNSVYVLVRQKAGQTPQERVEEVL
SGKLFDRLRDENPDFREKIIAINSELTQPKLALSEEDKEVIIDSTNIIFHCAATVRFNEN
LRDAVQLNVIATRQLILLAQQMKNLEVFMHVSTAYAYCNRKHIDEVVYPPPVDPKKLIDS
LEWMDDGLVNDITPKLIGDRPNTYIYTKALAEYVVQQEGAKLNVAIVRPSIVGASWKEPF
PGWIDNFNGPSGLFIAAGKGILRTIRASNNALADLVPVDVVVNMSLAAAWYSGVNRPRNI
MVYNCTTGSTNPFHWGEVEYHVISTFKRNPLEQAFRRPNVNLTSNHLLYHYWIAVSHKAP
AFLYDIYLRMTGRSPRMMKTITRLHKAMVFLEYFTSNSWVWNTENVNMLMNQLNPEDKKT
FNIDVRQLHWAEYIENYCLGTKKYVLNEEMSGLPAARKHLNKLRNIRYGFNTILVILIWR
IFIARSQMARNIWYFVVSLCYKFLSYFRASSTMRY
```

Important features of the protein:

Transmembrane domain:
Amino acids 469-488

N-glycosylation sites:
Amino acids 283-287;304-308;341-345

Tyrosine kinase phosphorylation site:
Amino acids 160-169

N-myristoylation sites:
Amino acids 219-225;252-258;260-266;452-458

Leucine zipper pattern:
Amino acids 439-461

FIGURE 5

CGATGCCGGCGGTCAGTGGTCCAGGTCCCTTATTCTGCCTTCTCCTCCTGCTCCTGGACCCC
CACAGCCCTGAGACGGGGTGTCCTCCTCTACGCAGGTTTGAGTACAAGCTCAGCTTCAAAGG
CCCAAGGCTGGCATTGCCTGGGGCTGGAATACCCTTCTGGAGCCATCATGGAGACGCCATCC
TGGGCCTGGAGGAAGTGCGGCTGACGCCATCCATGAGGAACCGGAGTGGCGCCGTGTGGAGC
AGGGCCTCTGTCCCCTTCTCTGCCTGGGAAGTAGAGGTGCAGATGAGGGTGACGGGACTGGG
GCGCCGGGGAGCCCAGGGCATGGCCGTGTGGTACACCCGGGGCAGGGGCCATGTAGGCTCTG
TCCTTGGGGGGCTGGCTTCGTGGGACGGCATCGGGATCTTCTTTGACTCTCCGGCAGAGGAT
ACTCAGGACAGTCCTGCCATCCGTGTGCTGGCCAGCGACGGGCACATCCCCTCTGAGCAGCC
TGGGGATGGAGCTAGCCAAGGGCTGGGCTCCTGTCATTGGGACTTCCGGAACCGGCCACACT
CCTTCAGAGCACGGATCACCTACTGGGGGCAGAGGCTGCGCATGTCCTTGAACAGTGGCCTC
ACTCCCAGTGATCCAGGTGAGTTCTGTGTGGATGTGGGGCCCCTGCTTTTGGTCCCTGGAGG
TTTCTTTGGGGTCTCAGCAGCCACCGGCACCCTGGCAGGTGAGGATCCCACTGGACAGGTTC
CCCCTCAGCCCTTCCTGGAGATGCAGCAGCTCCGCCTGGCGAGGCAGCTGGAAGGGCTGTGG
GCAAGGCTGGGCTTGGGCACCAGGGAGGATGTAACTCCAAAATCAGACTCTGAAGCTCAAGG
AGAAGGGGAAAGGCTCTTTGACCTGGAGGAGACGCTGGGCAGACACCGCCGGATCCTGCAGG
CTCTGCGGGGTCTCTCCAAGCAGCTGGCCCAGGCTGAGAGACAATGGAAGAAGCAGCTGGGG
CCCCCAGGCCAAGCCAGGCCTGACGGAGGCTGGGCCCTGGATGCTTCCTGCCAGATTCCATC
CACCCCAGGGAGGGGTGGCCACCTCTCCATGTCACTCAATAAGGACTCTGCCAAGGTCGGTG
CCCTGCTCCATGGACAGTGGACTCTGCTCCAGGCCCTGCAAGAGATGAGGGATGCAGCTGTC
CGCATGGCTGCAGAAGCCCAGGTCTCCTACCTGCCTGTGGGCATTGAGCATCATTTCTTAGA
GCTGGACCACATCCTGGGCCTCCTGCAGGAGGAGCTTCGGGGCCCGGCGAAGGCAGCAGCCA
AGGCCCCCCGCCCACCTGGCCAGCCCCCAAGGGCCTCCTCGTGCCTGCAGCCTGGCATCTTC
CTGTTCTACCTCCTCATTCAGACTGTAGGCTTCTTCGGCTACGTGCACTTCAGGCAGGAGCT
GAACAAGAGCCTTCAGGAGTGTCTGTCCACAGGCAGCCTTCCTCTGGGTCCTGCACCACACA
CCCCCAGGGCCCTGGGGATTCTGAGGAGGCAGCCTCTCCCTGCCAGCATGCCTGCCTGACCC
ACCTCAGAGCCTGCTTTGCATCACTGGGAAGCAGGCAGTGTCTTGGGTGGGGGCTTGGTCAG
TATCCTCTCCGTCTGGGTGCCCAGCTCCCACGCACACCTGAGCTTTCGGCATGCTCCCACCT
CGTTAAAGGTGATTTCCCTCTCCCCAAAAAAAAAAAAAAAAAAAAAAAAAAAAAAAAAAAAA
AAAAAAAAAAAAAAAAAAAAAAA

FIGURE 6

></usr/seqdb2/sst/DNA/Dnaseqs.min/ss.DNA96883
><subunit 1 of 1, 514 aa, 1 stop
><MW: 55687, pI: 8.78, NX(S/T): 2
MPAVSGPGPLFCLLLLLDPHSPETGCPPLRRFEYKLSFKGPRLALPGAGIPFWSHHGDA
ILGLEEVRLTPSMRNRSGAVWSRASVPFSAWEVEVQMRVTGLGRRGAQGMAVWYTRGRGH
VGSVLGGLASWDGIGIFFDSPAEDTQDSPAIRVLASDGHIPSEQPGDGASQGLGSCHWDF
RNRPHSFRARITYWGQRLRMSLNSGLTPSDPGEFCVDVGPLLLVPGGFFGVSAATGTLAG
EDPTGQVPPQPFLEMQQLRLARQLEGLWARLGLGTREDVTPKSDSEAQGEGERLFDLEET
LGRHRRILQALRGLSKQLAQAERQWKKQLGPPGQARPDGGWALDASCQIPSTPGRGGHLS
MSLNKDSAKVGALLHGQWTLLQALQEMRDAAVRMAAEAQVSYLPVGIEHHFLELDHILGL
LQEELRGPAKAAAKAPRPPGQPPRASSCLQPGIFLFYLLIQTVGFFGYVHFRQELNKSLQ
ECLSTGSLPLGPAPHTPRALGILRRQPLPASMPA

Important features of the protein:

Signal peptide:
Amino acids 1-23

Transmembrane domain:
Amino acids 215-232;450-465

N-glycosylation sites:
Amino acids 75-79;476-480

Glycosaminoglycan attachment site:
Amino acids 5-9

N-myristoylation sites:
Amino acids 78-84;122-128;126-132;168-174;172-178;
205-211;226-232;230-236;236-242;356-362

Amidation site:
Amino acids 102-106

FIGURE 7

GCCCCCAGCATGGCTTGGCAGGGCTGGCCCGCGGCGTGGCAGTGGGTCGCCGGCTGCTGGCT
CCTCCTCGTCCTTGTCCTCGTCCTACTTGTGAGCCCCCGCGGCTGCCGAGCGCGGCGGGGCC
TCCGCGGTCTGCTCATGGCGCACAGCCAGCGGCTGCTCTTCCGAATCGGGTACAGCCTGTAC
ACCCGCACCTGGCTCGGGTACCTCTTCTACCGACAGCAGCTGCGCAGGGCTCGGAATCGCTAC
CCTAAAGGCCACTCGAAAACCCAGCCCCGCCTCTTCAATGGAGTGAAGGTGCTTCCCATCCC
TGTCCTCTCGGACAACTACAGCTACCTCATCATCGACACCCAGGCCCAGCTGGCTGTGGCTG
TGGACCCTTCAGACCCTCGGGCTGTGCAGGCTTCCATTGAAAAGGAAGGGGTCACCTTGGTC
GCCATTCTGTGTACTCACAAGCACTGGGACCACAGTGGAGGGAACCGTGACCTCAGCCGGCG
GCACCGGGACTGTCGGGTGTACGGGAGCCCTCAGGACGGCATCCCCTACCTCACCCATCCCC
TGTGTCATCAAGATGTGGTCAGCGTGGGACGGCTTCAGATCCGGGCCCTGGCTACACCTGGC
CACACACAAGGCCATCTGGTCTACCTACTGGATGGGGAGCCCTACAAGGGTCCCTCCTGCCT
CTTCTCAGGGGACCTGCTCTTCCTCTCTGGCTGTGGGCGGACCTTTGAGGGCAATGCAGAGA
CCATGCTGAGCTCACTGGACACTGTGCTGGGGCTAGGGGATGACACCCTTCTGTGGCCTGGT
CATGAGTATGCAGAGGAGAACCTGGGCTTTGCAGGTGTGGTGGAGCCCGAGAACCTGGCCCG
GGAGAGGAAGATGCAGTGGGTGCAGCGGCAGCGGCTGGAGCGCAAGGGCACGTGCCCATCTA
CCCTGGGAGAGGAGCGCTCCTACAACCCGTTCCTGAGAACCCACTGCCTGGCGCTACAGGAG
GCTCTGGGGCCGGGGCCGGGCCCCACTGGGGATGATGACTACTCCCGGGCCCAGCTCCTGGA
AGAGCTCCGCCGGCTGAAGGATATGCACAAGAGCAAGTGATGCCCCCAGCGCCCCCAGCCCA
GCCCACTCCCCGCATGGGGAGGCCGCCACCACCAACACCTCATCATCCTTCTCATCGCTAAC
ACCACCACCTCCATCGGCACCCAAGCGGGCATCATCCCCCCACACTGCTCAGGGGAGGGGAG
GGATCAGGCGATGAGACTGTGAGGCCAAAAGAAGGGGGCCTGTTGGAGGCTGGGAACCCCGC
AGCGCGAGGCTGCCTCATCAACGGCAAGAGGAAAGGAGGGGTCTCGGGACATCTCCAGACCC
TACCAACTGGGAGGGTCCCCTCCTCCTTCCCTACTCCTGGGACGGCAGCAAGGACATGGGGG
CTGCTGTTAGCTTCTCCGTCAGGAGGCCTCATCTCACTGTAGCCCTGGAACCCAGGGTCCAT
CTTGCCCTTCCCCCATCCATGGTTGGGAAAGAAGCTCAGCCCCTCACAGTGGCCTCAAGTGT
GATGCCTTACAAAAGCACCACTCAGATGGGCAGCTGGACTCTGGTGTCCTGAGACTCTGCCC
TCTTCCCACAGCCTCCCTGCCCCACCCATCCCTGCAAAGCCATTTTTCAGACAGAGCCATTC
CTAAGAACACTGAAGGGCTGGAATGCTGGCTGGCCACTCTCTGCCTCAGTGGCCTCCCTACA
GCCTGGAAGAAGGAGGGTCCTGATTGCCAAGGAAACCTCCTCATTGGGCTAAGGAGACACTG
GAGTCTGGAGTGTGGAGCCCCACAGTCTTGCAGGTCACATGCTCTCCTTGCACATCTGGCCT
GGTTGTACCCACTGGCCTCTGCCTCTGCCCTGGGCCAAAAGGGCCCCTCCTTGCCAGGGGAG
AGACAGCCACGGTCCTCTTTGGCCGATGCTGTATTCTCATTTTGGCCCTTGTTCTTAGGCCC
GTCTGCCCGCCCTCCTCCATCTAACCTTTCCTGTTTTATCCGCAGCCCTTTTCTTCTTTGAG
TTAGTAAAGATTTATTCTGTAACCTGACACTCATCTGGCCCTTTGCAGTTTGCCAGCCATATTC
CCATGTGATTTCCCACTGGATCCAGGCCCCCATCCGGCTGGCAGGAGGGGGCTCTGACGTAC
AGGTTGGAAATCAGAAGTCTGTGAGAGCGCGGGAGTGCATGGCAGCTCTGGGTCCCAGACCT
GGCCCGACCCCTCTGCTTCACCTCCAGCTCTGCTGCTCCTCTACTCTTGGGTCGAGATCCCT
TTGGAGCCACAGCGAGGAACCCTGTGGTCCTCAGGCAGGTGTACCTTGAGTCAGCCAGGAGC
CCTCTTTTCCTGTGTCAAAGCCTGCCCTCGGGCTCTGCTCACCTCTGGTGACCCTCCAAGAT
GCCCCTGCCCTCAGTTTCCCCTCATGATCTGGCCTCTGCCCCCTTCTCTAGCCACAGCCTCT
AGTACACTTTAGCAATACCACCAGACTAGTTAGAGTTCCCCACTCACCAAGCAAGACATGCA
GTTTCATGCCTCTGTGCCTTCGCTCATGCTGTTTCTTCCGACTGGAATGCCTTCCCCTGCTC
CTCCTGCCTTGTCTGCCTGGCAAGTTCATCTCTCACGATCCCCTCAAAGGCCCCCTCCTCCA
GGAAGGCAACCCCTGTGCCCCTCCCCTCCAGGCTACCTCTGCACTTTGTCAATGCTTCTCTT
GTGGCACTTATCACACTGTATTTTACTTGTTTACATGTTTGTCTCCCCTTCTAGACTGTGAA
TCCTTAAGGGCATGGACTGTATCTTATGCATCTCTGTATTTCTGCGCCTAGCACGGTGCCTA
GCACACAGTAGGCGCTCAATAAATGTTGAATGAATGAAAAAAAAAAAAAAAAAAAAAAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAA

FIGURE 8

```
></usr/seqdb2/sst/DNA/Dnaseqs.min/ss.DNA96894
><subunit 1 of 1, 361 aa, 1 stop
><MW: 40747, pI: 9.20, NX(S/T): 1
MAWQGWPAAWQWVAGCWLLLVLVLVLLVSPRGCRARRGLRGLLMAHSQRLLFRIGYSLYT
RTWLGYLFYRQQLRRARNRYPKGHSKTQPRLFNGVKVLPIPVLSDNYSYLIIDTQAQLAV
AVDPSDPRAVQASIEKEGVTLVAILCTHKHWDHSGGNRDLSRRHRDCRVYGSPQDGIPYL
THPLCHQDVVSVGRLQIRALATPGHTQGHLVYLLDGEPYKGPSCLFSGDLLFLSGCGRTF
EGNAETMLSSLDTVLGLGDDTLLWPGHEYAEENLGFAGVVEPENLARERKMQWVQRQRLE
RKGTCPSTLGEERSYNPFLRTHCLALQEALGPGPGPTGDDDYSRAQLLEELRRLKDMHKS
K
```

Important features of the protein:

Signal peptide:
Amino acids 1-35

N-glycosylation site:
Amino acids 106-110

Glycosaminoglycan attachment site:
Amino acids 234-238 cAMP- and cGMP-dependent protein kinase phosphorylation site:
Amino acids 301-305

Tyrosine kinase phosphorylation site:
Amino acids 162-171

N-myristoylation sites:
Amino acids 41-47;235-241;242-248;303-309

Prokaryotic membrane lipoprotein lipid attachment site:
Amino acids 6-17 cAMP phosphodiesterases class-II proteins:
Amino acids 144-161

FIGURE 9

GCTGACAATCCCCTTGACGTTCTATCCCGGAAGCTCCACCTGGGGCCCAATGTTGGGCGTGA
TGTTCCTCGCCTGTCTCTGCCTGGAAAACTGGTCTTCCCAAGCTCCACTGGCAGCCACTTCT
CCATGTTGGGCATCGGAGACATCGTTATGCCTGGTCTCCTACTATGCTTTGTCCTTCGCTAT
GACAACTACAAAAAGCAAGCCAGTGGGGACTCCTGTGGGGCCCCTGGACCTGCCAACATCTC
CGGGCGCATGCAGAAGGTCTCCTACTCTCACTGCACCCTCATCGGATACTTTGTAGGCCTGC
TCACTGCTACTGTGGCGTCTCGCATTCACCGGGCCGCCCAGCCCGCCCTTCTCTATTTGGTG
CCATTTACTTTATTGCCACTCCTCACGATGGCCTATTTAAAGGGCGACCTCCGGCGGATGTG
GTCTGAGCCTTTCCACTCCAAGTCCAGCAGCTCCCGATTCCTGGAAGTATGATGGATCACGT
GGAAAGTGACCAGATGGCCGTCATAGTCCTTTTCTCTCAACTCATGGTTTGTTTCCTCTTAG
AGCTGGCCTGGTACTCAGAAATGTACCTGTGTTTAAGGAACTGCCGTGTGACTGGATTTGGC
ATTGAAAGGGAGCTCGTTTGCAGGAGAGAGGTGCTGGAGCCCTGTTTGGTTCCTTCTCTTCC
TGCGGATGTAGAGGTGGGGCCCCTTCCAAGAGGGACAGGCCTCTCCCCAGCGCGCCTTCCTC
CCACGTTTTTATGGATCTGCACCAGACTGTTACCTTCTGGGGGAGATGGAGATTTGACTGTT
TAAAAACTGAAAACAGCGAGGAGTCTTTCTAGAACTTTTGAACACTAAAAGGATGAAAAAAT
TAGC

FIGURE 10

></usr/seqdb2/sst/DNA/Dnaseqs.min/ss.DNA100272
><subunit 1 of 1, 108 aa, 1 stop
><MW: 12055, pI: 4.69, NX(S/T): 0
MMDHVESDQMAVIVLFSQLMVCFLLELAWYSEMYLCLRNCRVTGFGIERELVCRREVLEP
CLVPSLPADVEVGPLPRGTGLSPARLPPTFLWICTRLLPSGGDGDLTV

Important features of the protein:
Signal peptide:
Amino acids 1-30

N-myristoylation site:
Amino acids 80-86

FIGURE 11

TCGCACACTGGTGGCTTCAGAAGAAATTCTCAACACCTAGCTCGCCAGAGAGTCTATGTATG
GGATTGAACAATCTGTAAACTAAAGGATCCTAATCATGAAAATAAGTATGATAAATTATAAG
TCACTATTGGCACTGTTGTTTATATTAGCCTCCTGGATCATTTTTACAGTTTTCCAGAACTC
CACAAAGGTTTGGTCTGCTCTAAACTTATCCATCTCCCTCCATTACTGGAACAACTCCACAA
AGTCCTTATTCCCTAAAACACCACTGATATCATTAAAGCCACTAACAGAGACTGAACTCAGA
ATAAAGGAAATCATAGAGAAACTAGATCAGCAGATCCCACCCAGACCTTTCACCCACGTGAA
CACCACCACCAGCGCCACACATAGCACAGCCACCATCCTCAACCCTCGAGATACGTACTGCA
GGGGAGACCAGCTGCACATCCTGCTGGAGGTGAGGGACCACTTGGGACGCAGGAAGCAATAT
GGCGGGGATTTCCTGAGGGCCAGGATGTCTTCCCCAGCGCTGATGGCAGGTGCTTCAGGAAA
GGTGACTGACTTCAACAACGGCACCTACCTGGTCAGCTTCACTCTGTTCTGGGAGGGCCAGG
TCTCTCTGTCTCTGCTGCTCATCCACCCCAGTGAAGGGGTGTCAGCTCTCTGGAGTGCAAGG
AACCAAGGCTATGACAGGGTGATCTTCACTGGCCAGTTTGTCAATGGCACTTCCCAAGTCCA
CTCTGAATGTGGCCTGATCCTAAACACAAATGCTGAATTGTGCCAGTACCTGGACAACAGAG
ACCAAGAAGGCTTCTACTGTGTGAGGCCTCAACACATGCCCTGTGCTGCACTCACTCACATG
TATTCTAAGAACAAGAAAGTTTCTTATCTTAGCAAACAAGAAAAGAGCCTCTTTGAAAGGTC
AAATGTGGGTGTAGAGATTATGGAAAAATTCAATACAATTAGTGTCTCCAAATGCAACAAAG
AAACAGTTGCAATGAAAGAGAAATGCAAGTTTGGAATGACATCCACAATCCCCAGTGGGCAT
GTCTGGAGAAACACATGGAATCCTGTCTCCTGTAGTTTGGCTACAGTCAAAATGAAGGAATGC
CTGAGAGGAAAACTCATATACCTAATGGGAGATTCCACGATCCGCCAGTGGATGGAATACTT
CAAAGCCAGTATCAACACACTGAAGTCAGTGGATCTGCATGAATCTGGAAAATTGCAACACC
AGCTTGCTGTGGATTTGGATAGGAACATCAACATCCAGTGGCAAAAATATTGTTATCCCTTG
ATAGGATCAATGACCTATTCAGTCAAAGAGATGGAGTACCTCACCCGGGCCATTGACAGAAC
TGGAGGAGAAAAAAATACTGTCATTGTTATTTCCCTGGGCCAGCATTTCAGACCCTTTCCCA
TTGATGTTTTTATCCGAAGGGCCCTCAATGTCCACAAAGCCATTCAGCATCTTCTTCTGAGA
AGCCCAGACACTATGGTTATCATCAAAACAGAAAACATCAGGGAGATGTACAATGATGCAGA
AAGATTTAGTGACTTTCATGGTTACATTCAATATCTCATCATAAAGGACATTTTCCAGGATC
TCAGTGTGAGTATCATTGATGCCTGGGATATAACAATTGCATATGGCACAAATAATGTACAC
CCACCTCAACATGTAGTCGGAAATCAGATTAATATATTATTAAACTATATTTGTTAAATAACAA

FIGURE 12

></usr/seqdb2/sst/DNA/Dnaseqs.min/ss.DNA108696
><subunit 1 of 1, 544 aa, 1 stop
><MW: 62263, pI: 9.17, NX(S/T): 7
MKISMINYKSLLALLFILASWIIFTVFQNSTKVWSALNLSISLHYWNNSTKSLFPKTPLI
SLKPLTETELRIKEIIEKLDQQIPPRPFTHVNTTTSATHSTATILNPRDTYCRGDQLHIL
LEVRDHLGRRKQYGGDFLRARMSSPALMAGASGKVTDFNNGTYLVSFTLFWEGQVSLSLL
LIHPSEGVSALWSARNQGYDRVIFTGQFVNGTSQVHSECGLILNTNAELCQYLDNRDQEG
FYCVRPQHMPCAALTHMYSKNKKVSYLSKQEKSLFERSNVGVEIMEKFNTISVSKCNKET
VAMKEKCKFGMTSTIPSGHVWRNTWNPVSCSLATVKMKECLRGKLIYLMGDSTIRQWMEY
FKASINTLKSVDLHESGKLQHQLAVDLDRNINIQWQKYCYPLIGSMTYSVKEMEYLTRAI
DRTGGEKNTVIVISLGQHFRPFPIDVFIRRALNVHKAIQHLLLRSPDTMVIIKTENIREM
YNDAERFSDFHGYIQYLIIKDIFQDLSVSIIDAWDITIAYGTNNVHPPQHVVGNQINILL
NYIC

Important features of the protein:
Signal peptide:
Amino acids 1-22

N-glycosylation sites:
Amino acids 29-33;38-42;47-51;48-52;92-96;160-164;210-214 cAMP- and cGMP-dependent protein kinase phosphorylation site:
Amino acids 262-266

Tyrosine kinase phosphorylation site:
Amino acids 236-243;486-494

N-myristoylation sites:
Amino acids 206-212;220-226;310-316;424-430;533-539

Amidation site:
Amino acids 127-131

Cell attachment sequence:
Amino acids 113-116

FIGURE 13

GCAAAGAGAAGACTGAAAGACAAACCTGGGTGCAGCCAGAGAGGTCCAGATAGATGAGCTTG
TGGCATCCATTCCCCAAGTTCAGCCTAGGGACTCCACGTACCCCAGCTGGGTCTCATTGTTC
CAGAACTGCATTACTTAAGATTACCCAGACTTGGATTTCAAAGGAATACTTTCATTGTTCCG
TCTGTAACACGAAGTAATTGGGGCCAGCTGGATGTCAGGATGCGTGTGGTTACCATTGTAAT
CTTGCTCTGCTTTTGCAAAGCGGCTGAGCTGCGCAAAGCAAGCCCAGGCAGTGTGAGAAGCC
GAGTGAATCATGGCCGGGCGGGTGGAGGCCGGAGAGGCTCCAACCCGGTCAAACGCTACGCA
CCAGGCCTCCCGTGTGACGTGTACACATATCTCCATGAGAAATACTTAGATTGTCAAGAAAG
AAAATTAGTTTATGTGCTGCCTGGTTGGCCTCAGGATTTGCTGCACATGCTGCTAGCAAGAA
ACAAGATCCGCACATTGAAGAACAACATGTTTTCCAAGTTTAAAAAGCTGAAAAGCCTGGAT
CTGCAGCAGAATGAGATCTCTAAAATTGAGAGTGAGGCGTTCTTTGGTTTAAACAAACTCAC
CACCCTCTTACTGCAGCACAACCAGATCAAAGTCTTGACGGAGGAAGTGTTCATTTACACAC
CTCTCTTGAGCTACCTGCGTCTTTATGACAACCCCTGGCACTGTACTTGTGAGATAGAAACG
CTTATTTCAATGTTGCAGATTCCCAGGAACCGGAATTTGGGGAACTACGCCAAGTGTGAAAG
TCCACAAGAACAAAAAAATAAAAAACTGCGGCAGATAAAATCTGAACAGTTGTGTAATGAAG
AAAAGGAACAATTGGACCCGAAACCCCAAGTGTCAGGGAGACCCCCAGTCATCAAGCCTGAG
GTGGACTCAACTTTTTGCCACAATTATGTGTTTCCCATACAAACACTGGACTGCAAAAGGAA
AGAGTTGAAAAAAGTGCCAAACAACATCCCTCCAGATATTGTTAAACTTGACTTGTCATACA
ATAAAATCAACCAACTTCGACCCAAGGAATTTGAAGATGTTCATGAGCTGAAGAAATTAAAC
CTCAGCAGCAATGGCATTGAATTCATCGATCCTGCCGCTTTTTTAGGGCTCACACATTTAGA
AGAATTAGATTTATCAAACAACAGTCTGCAAAACTTTGACTATGGCGTATTAGAAGACTTGT
ATTTTTTGAAACTCTTGTGGCTCAGAGATAACCCTTGGAGATGTGACTACAACATTCACTAC
CTCTACTACTGGTTAAAGCACCACTACAATGTCCATTTTAATGGCCTGGAATGCAAAACGCCT
GAAGAATACAAAGGATGGTCTGTGGGAAAATATATTAGAAGTTACTATGAAGAATGCCCCAA
AGACAAGTTACCAGCATATCCTGAGTCATTTGACCAAGACACAGAAGATGATGAATGGGAAA
AAAAACATAGAGATCACACCGCAAAGAAGCAAAGCGTAATAATTACTATAGTAGGATAAGGT
AGAAATTGTTCTGATTGTAATTAGTTTTGTATTTTCTATACTGGTGTTAGAAAACATATGTT
TACATTTGATTAACTGTGTTGCCTATTTATGCAGGGTAATCCAGCTAAAGGAAGCTTTCTTT
AATTATAAGTATTATTGTGACTATTATAGTAATCAAGAGAATGCTATCATCCTGCTTGCCTG
TCCATTTGTGGAACAGCATCTGGTGATATGCAATTCCACACTGGTAACCTGCAGCAGTTGGG
TCCTAATGATGGCATTAGACTTTCATAATGTCCTGTATAAATGTTTTTACTGCTTTTAGAAA
ATAAAGAAAAAAAACTTGGTTCATGTTTAAAA

FIGURE 14

></usr/seqdb2/sst/DNA/Dnaseqs.min/ss.DNA117935
><subunit 1 of 1, 440 aa, 1 stop
><MW: 51670, pI: 8.70, NX(S/T): 2
MRVVTIVILLCFCKAAELRKASPGSVRSRVNHGRAGGGRRGSNPVKRYAPGLPCDVYTYL
HEKYLDCQERKLVYVLPGWPQDLLHMLLARNKIRTLKNNMFSKFKKLKSLDLQQNEISKI
ESEAFFGLNKLTTLLLQHNQIKVLTEEVFIYTPLLSYLRLYDNPWHCTCEIETLISMLQI
PRNRNLGNYAKCESPQEQKNKKLRQIKSEQLCNEEKEQLDPKPQVSGRPPVIKPEVDSTF
CHNYVFPIQTLDCKRKELKKVPNNIPPDIVKLDLSYNKINQLRPKEFEDVHELKKLNLSS
NGIEFIDPAAFLGLTHLEELDLSNNSLQNFDYGVLEDLYFLKLLWLRDNPWRCDYNIHYL
YYWLKHHYNVHFNGLECKTPEEYKGWSVGKYIRSYYEECPKDKLPAYPESFDQDTEDDEW
EKKHRDHTAKKQSVIITIVG

Important features of the protein:
Signal peptide:
Amino acids 1-15

N-glycosylation sites:
Amino acids 297-301;324-328 cAMP- and cGMP-dependent protein kinase phosphorylation sites:
Amino acids 19-23;39-43;430-434

N-myristoylation sites:
Amino acids 24-30;37-43

Amidation site:
Amino acids 37-41

FIGURE 15

GCGGCAGCAGCGCGGGCCCCAGCAGCCTCGGCAGCCACAGCCGCTGCAGCCGGGGCAGCCTC
CGCTGCTGTCGCCTCCTCTGATGCGCTTGCCCTCTCCCGGCCCCGGGACTCCGGGAGAATGT
GGGTCCTAGGCATCGCGGCAACTTTTTGCGGATTGTTCTTGCTTCCAGGCTTTGCGCTGCAA
ATCCAGTGCTACCAGTGTGAAGAATTCCAGCTGAACAACGACTGCTCCTCCCCCGAGTTCAT
TGTGAATTGCACGGTGAACGTTCAAGACATGTGTCAGAAAGAAGTGATGGAGCAAAGTGCCG
GGATCATGTACCGCAAGTCCTGTGCATCATCAGCGGCCTGTCTCATCGCCTCTGCCGGGTAC
CAGTCCTTCTGCTCCCCAGGGAAACTGAACTCAGTTTGCATCAGCTGCTGCAACACCCCTCT
TTGTAACGGGCCAAGGCCCAAGAAAAGGGGAAGTTCTGCCTCGGCCCTCAGGCCAGGGCTCC
GCACCACCATCCTGTTCCTCAAATTAGCCCTCTTCTCGGCACACTGCTGAAGCTGAAGGAGA
TGCCACCCCCTCCTGCATTGTTCTTCCAGCCCTCGCCCCCAACCCCCCACCTCCCTGAGTGA
GTTTCTTCTGGGTGTCCTTTTATTCTGGGTAGGGAGCGGGAGTCCGTGTTCTCTTTTGTTCC
TGTGCAAATAATGAAAGAGCTCGGTAAAGCATTCTGAATAAATTCAGCCTGACTGAATTTTC
AGTATGTACTTGAAGGAAGGAGGTGGAGTGAAAGTTCACCCCCATGTCTGTGTAACCGGAGT
CAAGGCCAGGCTGGCAGAGTCAGTCCTTAGAAGTCACTGAGGTGGGCATCTGCCTTTTGTAA
AGCCTCCAGTGTCCATTCCATCCCTGATGGGGGCATAGTTTGAGACTGCAGAGTGAGAGTGA
CGTTTTCTTAGGGCTGGAGGGCCAGTTCCCACTCAAGGCTCCCTCGCTTGACATTCAAACTT
CATGCTCCTGAAAACCATTCTCTGCAGCAGAATTGGCTGGTTTCGCGCCTGAGTTGGGCTCT
AGTGACTCGAGACTCAATGACTGGGACTTAGACTGGGGCTCGGCCTCGCTCTGAAAAGTGCT
TAAGAAAATCTTCTCAGTTCTCCTTGCAGAGGACTGGCGCCGGGACGCGAAGAGCAACGGGC
GCTGCACAAAGCGGGCGCTGTCGGTGGTGGAGTGCGCATGTACGCGCAGGCGCTTCTCGTGG
TTGGCGTGCTGCAGCGACAGGCGGCAGCACAGCACCTGCACGAACACCCGCCGAAACTGCTG
CGAGGACACCGTGTACAGGAGCGGGTTGATGACCGAGCTGAGGTAGAAAAACGTCTCCGAGA
AGGGGAGGAGGATCATGTACGCCCGGAAGTAGGACCTCGTCCAGTCGTGCTTGGGTTTGGCC
GCAGCCATGATCCTCCGAATCTGGTTGGGCATCCAGCATACGGCCAATGTCACAACAATCAG
CCCTGGGCAGACACGAGCAGGAGGGAGAGACAGAGA

FIGURE 16

></usr/seqdb2/sst/DNA/Dnaseqs.min/ss.DNA119474
><subunit 1 of 2, 141 aa, 1 stop
><MW: 15240, pI: 8.47, NX(S/T): 1
MWVLGIAATFCGLFLLPGFALQIQCYQCEEFQLNNDCSSPEFIVNCTVNVQDMCQKEVME
QSAGIMYRKSCASSAACLIASAGYQSFCSPGKLNSVCISCCNTPLCNGPRPKKRGSSASA
LRPGLRTTILFLKLALFSAHC

Important features of the protein:
Signal peptide:
Amino acids 1-22

N-glycosylation site:
Amino acids 45-49 cAMP- and cGMP-dependent protein kinase phosphorylation site:
Amino acids 113-117

N-myristoylation sites:
Amino acids 5-11;115-121;124-130

Ly-6 / u-PAR domain proteins:
Amino acids 94-107

FIGURE 17

CGCAAAGCCGCCCTCGGGGCGCTCATGGCGGGACGCCTCCTGGGAAAGGCTTTAGCCGCGGT
GTCTCTCTCTCTGGCCTTGGCCTCTGTGACTATCAGGTCCTCGCGCTGCCGCGGCATCCAGG
CGTTCAGAAACTCGTTTTCATCTTCTTGGTTTCATCTTAATACCAACGTCATGTCTGGTTCT
AATGGTTCCAAAGAAAATTCTCACAATAAGGCTCGGACGTCTCCTTACCCAGGTTCAAAAGT
TGAACGAAGCCAGGTTCCTAATGAGAAAGTGGGCTGGCTTGTTGAGTGGCAAGACTATAAGC
CTGTGGAATACACTGCAGTCTCTGTCTTGGCTGGACCCAGGTGGGCAGATCCTCAGATCAGT
GAAAGTAATTTTTCTCCCAAGTTTAACGAAAAGGATGGGCATGTTGAGAGAAAGAGCAAGAA
TGGCCTGTATGAGATTGAAAATGGAAGACCGAGAAATCCTGCAGGACGGACTGGACTGGTGG
GCCGGGGGCTTTTGGGGCGATGGGGCCCAAATCACGCTGCAGATCCCATTATAACCAGATGG
AAAAGGGATAGCAGTGGAAATAAAATCATGCATCCTGTTTCTGGGAAGCATATCTTACAATT
TGTTGCAATAAAAAGGAAAGACTGTGGAGAATGGGCAATCCCAGGGGGGATGGTGGATCCAGGA
GAGAAGATTAGTGCCACACTGAAAAGAGAATTTGGTGAGGAAGCTCTCAACTCCTTACAGAA
AACCAGTGCTGAGAAGAGAGAAATAGAGGAAAAGTTGCACAAACTCTTCAGCCAAGACCACC
TAGTGATATATAAGGGATATGTTGATGATCCTCGAAACACTGATAATGCATGGATGGAGACA
GAAGCTGTGAACTACCATGACGAAACAGGTGAGATAATGGATAATCTTATGCTAGAAGCTGG
AGATGATGCTGGAAAAGTGAAATGGGTGGACATCAATGATAAACTGAAGCTTTATGCCAGTC
ACTCTCAATTCATCAAACTTGTGGCTGAGAAACGAGATGCACACTGGAGCGAGGACTCTGAA
GCTGACTGCCATGCGTTGTAGCTGATGGTCTCCGTGTAAGCCAAAGGCCCACAGAGGAGCAT
ATACTGAAAAGAAGGCAGTATCACAGAATTTATACTATAAAAAGGGCAGGGTAGGCCACTTG
GCCTATTTACTTTCAAAACAATTTGCATTTAGAGTGTTTCGCATCAGAATAACATGAGTAAG
ATGAACTGGAACACAAAATTTTCAGCTCTTTGGTCAAAAGGAATATAAGTAATCATATTTTG
TATGTATTCGATTTAAGCATGGCTTAAATTAAATTTAAACAACTAATGCTCTTTGAAGAATC
ATAATCAGAATAAAGATAAATTCTTGATCAGCTATA

FIGURE 18

></usr/seqdb2/sst/DNA/Dnaseqs.min/ss.DNA119498
><subunit 1 of 1, 350 aa, 1 stop
><MW: 39125, pI: 8.53, NX(S/T): 2
MAGRLLGKALAAVSLSLALASVTIRSSRCRGIQAFRNSFSSSWFHLNTNVMSGSNGSKEN
SHNKARTSPYPGSKVERSQVPNEKVGWLVEWQDYKPVEYTAVSVLAGPRWADPQISESNF
SPKFNEKDGHVERKSKNGLYEIENGRPRNPAGRTGLVGRGLLGRWGPNHAADPIITRWKR
DSSGNKIMHPVSGKHILQFVAIKRKDCGEWAIPGGMVDPGEKISATLKREFGEEALNSLQ
KTSAEKREIEEKLHKLFSQDHLVIYKGYVDDPRNTDNAWMETEAVNYHDETGEIMDNLML
EAGDDAGKVKWVDINDKLKLYASHSQFIKLVAEKRDAHWSEDSEADCHAL

Important features of the protein:
Signal peptide:
Amino acids 1-20

N-glycosylation site:
Amino acids 55-59 cAMP- and cGMP-dependent protein kinase phosphorylation site:
Amino acids 179-183

N-myristoylation sites:
Amino acids 53-59;56-62 mutT domain signature:
Amino acids 215-235

FIGURE 19

CGAGGGCTCCTGCTGGTACTGTGTTCGCTGCTGCACAGCAAGGCCCTGCCACCCACCTTCAG
GCCATGCAGCCATGTTCCGGGAGCCCTAATTGCACAGAAGCCCATGGGGAGCTCCAGACTGG
CAGCCCTGCTCCTGCCTCTCCTCCTCATAGTCATCGACCTCTCTGACTCTGCTGGGATTGGC
TTTCGCCACCTGCCCCACTGGAACACCCGCTGTCCTCTGGCCTCCCACACGGATGACAGTTT
CACTGGAAGTTCTGCCTATATCCCTTGCCGCACCTGGTGGGCCCTCTTCTCCACAAAGCCTT
GGTGTGTGCGAGTCTGGCACTGTTCCCGCTGTTTGTGCCAGCATCTGCTGTCAGGTGGCTCA
GGTCTTCAACGGGGCCTCTTCCACCTCCTGGTGCAGAAATCCAAAAAGTCTTCCACATTCAA
GTTCTATAGGAGACACAAGATGCCAGCACCTGCTCAGAGGAAGCTGCTGCCTCGTCGTCACC
TGTCTGAGAAGAGCCATCACATTTCCATCCCCTCCCCAGACATCTCCCACAAGGGACTTCGC
TCTAAAAGGACCCAACCTTCGGATCCAGAGACATGGGAAAGTCTTCCCAGATTGGACTCACA
AAGGCATGGAGGACCCGAGTTCTCCTTTGATTTGCTGCCTGAGGCCCGGGCTATTCGGGTGA
CCATATCTTCAGGCCCTGAGGTCAGCGTGCGTCTTTGTCACCAGTGGGCACTGGAGTGTGAA
GAGCTGAGCAGTCCCTATGATGTCCAGAAAATTGTGTCTGGGGGCCACACTGTAGAGCTGCC
TTATGAATTCCTTCTGCCCTGTCTGTGCATAGAGGCATCCTACCTGCAAGAGGACACTGTGA
GGCGCAAAAAATGTCCCTTCCAGAGCTGGCCAGAAGCCTATGGCTCGGACTTCTGGAAGTCA
GTGCACTTCACTGACTACAGCCAGCACACTCAGATGGTCATGGCCCTGACACTCCGCTGCCC
ACTGAAGCTGGAAGCTGCCCTCTGCCAGAGGCACGACTGGCATACCCTTTGCAAAGACCTCC
CGAATGCCACGGCTCGAGAGTCAGATGGGTGGTATGTTTTGGAGAAGGTGGACCTGCACCCC
CAGCTCTGCTTCAAGTTCTCTTTTGGAAACAGCAGCCATGTTGAATGCCCCCACCAGACTGG
GTCTCTCACATCCTGGAATGTAAGCATGGATACCCAAGCCCAGCAGCTGATTCTTCACTTCT
CCTCAAGAATGCATGCCACCTTCAGTGCTGCCTGGAGCCTCCCAGGCTTGGGGCAGGACACT
TTGGTGCCCCCCGTGTACACTGTCAGCCAGGCCCGGGGCTCAAGCCCAGTGTCACTAGACCT
CATCATTCCCTTCCTGAGGCCAGGGTGCTGTGTCCTGGTGTGGCGGTCAGATGTCCAGTTTG
CCTGGAAGCACCTCTTGTGTCCAGATGTCTCTTACAGACACCTGGGGCTCTTGATCCTGGCA
CTGCTGGCCCTCCTCACCCTACTGGGTGTTGTTCTGGCCCTCACCTGCCGGCGCCCACAGTC
AGGCCCGGGCCCAGCGCGGCCAGTGCTCCTCCTGCACGCGGCGGACTCGGAGGCGCAGCGGC
GCCTGGTGGGAGCGCTGGCTGAACTGCTACGGGCAGCGCTGGGCGGCGGGCGCGACGTGATC
GTGGACCTGTGGGAGGGGAGGCACGTGGCGCGCGTGGGCCCGCTGCCGTGGCTCTGGGCGGC
GCGGACGCGCGTAGCGCGGGAGCAGGGCACTGTGCTGCTGCTGTGGAGCGGCGCCGACCTTC
GCCCGGTCAGCGGCCCCGACCCCCGCGCCGCGCCCCTGCTCGCCCTGCTCCACGCTGCCCCG
CGCCCGCTGCTGCTGCTCGCTTACTTCAGTCGCCTCTGCGCCAAGGGCGACATCCCCCCGCC
GCTGCGCGCCCTGCCGCGCTACCGCCTGCTGCGCGACCTGCCGCGTCTGCTGCGGGCGCTGG
ACGCGCGGCCTTTCGCAGAGGCCACCAGCTGGGGCCGCCTTGGGGCGCGGCAGCGCAGGCAG
AGCCGCCTAGAGCTGTGCAGCCGGCTTGAACGAGAGGCCGCCCGACTTGCAGACCTAGGTTG
AGCAGAGCTCCACCGCAGTCCCGGGTGTCT

FIGURE 20

></usr/seqdb2/sst/DNA/Dnaseqs.min/ss.DNA119502
><subunit 1 of 1, 667 aa, 1 stop
><MW: 74810, pI: 9.55, NX(S/T): 3
MGSSRLAALLLPLLLIVIDLSDSAGIGFRHLPHWNTRCPLASHTDDSFTGSSAYIPCRTW
WALFSTKPWCVRVWHCSRCLCQHLLSGGSGLQRGLFHLLVQKSKKSSTFKFYRRHKMPAP
AQRKLLPRRHLSEKSHHISIPSPDISHKGLRSKRTQPSDPETWESLPRLDSQRHGGPEFS
FDLLPEARAIRVTISSGPEVSVRLCHQWALECEELSSPYDVQKIVSGGHTVELPYEFLLP
CLCIEASYLQEDTVRRKKCPFQSWPEAYGSDFWKSVHFTDYSQHTQMVMALTLRCPLKLE
AALCQRHDWHTLCKDLPNATARESDGWYVLEKVDLHPQLCFKFSFGNSSHVECPHQTGSL
TSWNVSMDTQAQQLILHFSSRMHATFSAAWSLPGLGQDTLVPPVYTVSQARGSSPVSLDL
IIPFLRPGCCVLVWRSDVQFAWKHLLCPDVSYRHLGLLILALLALLTLLGVVLALTCRRP
QSGPGPARPVLLLHAADSEAQRRLVGALAELLRAALGGGRDVIVDLWEGRHVARVGPLPW
LWAARTRVAREQGTVLLLWSGADLRPVSGPDPRAAPLLALLHAAPRPLLLLAYFSRLCAK
GDIPPPLRALPRYRLLRDLPRLLRALDARPFAEATSWGRLGARQRRQSRLELCSRLEREA
ARLADLG

Important features of the protein:
Signal peptide:
Amino acids 1-23

Transmembrane domain:
Amino acids 455-472

N-glycosylation sites:
Amino acids 318-322;347-351;364-368

Glycosaminoglycan attachment site:
Amino acids 482-486 cAMP- and cGMP-dependent protein kinase phosphorylation sites:
Amino acids 104-108;645-649

Tyrosine kinase phosphorylation site:
Amino acids 322-329

N-myristoylation sites:
Amino acids 90-96;358-364;470-476

Eukaryotic cobalamin-binding proteins:
Amino acids 453-462

FIGURE 21

CGGCTCGAGGCCCTTTGTGAGGGCTGTGAGCTGCGCCTGACGGTGGCACCATGAGCAGCTCA
GGTGGGGCGCCCGGGGCGTCCGCCAGCTCTGCGCCGCCCGCGCAGGAAGAGGGCATGACGTG
GTGGTACCGCTGGCTGTGTCGCCTGTCTGGGGTGCTGGGGGCAGTCTCTTGCGCGATCTCTG
GCCTCTTCAACTGCATCACCATCCACCCTCTGAACATCGCGGCCGGCGTGTGGATGATCATG
AATGCCTTCATCTTGTTGCTGTGTGAGGCGCCCTTCTGCTGCCAGTTCATCGAGTTTGCAAA
CACAGTGGCGGAGAAGGTGGACCGGCTGCGCTCCTGGCAGAAGGCTGTCTTCTACTGCGGGA
TGGCGGTCGTTCCCATCGTCATCAGCCTGACCCTGACCACGCTGCTGGGCAACGCCATCGCC
TTTGCTACGGGGGTGCTGTACGGACTCTCTGCTCTGGGCAAAAAGGGCGATGCGATCTCCTA
TGCCAGGATCCAGCAGCAGAGGCAGCAGGCGGATGAGGAGAAGCTCGCGGAGACCCTGGAGG
GGGAGCTGTGAAGGGCTGGGCGCCCCTCCCTCCCTGTCCCCTCTTCTGGCTCTGTGTGGGTC
CAAGTGAGGCCTGGACTGTCCACGCTGAGGCACAGCCTGGAGAGGGGCCTTTGCACGTGTCC
CTACACCTGGAGTCCTCTGCTCCTTTCTCCAGACTGGCTTAAGCCAGGAGCCACTGGCTGCT
GGTGTGAGGGTCTGGGCTGCTGGACTTGAGGCAGAGCCTGCAGCAGCTGTGTGGACACTACC
CAGCCCTACTCCTCTGCTGGGTGGGTCTGCAGATCTCACACCACAGACAGGGCTGCCTGTGA
CCTGCTGTGACCTGGGAGCAGCTTCCCCTGGAGATGCTGGTCCTGGCTTGAGGGGAGGGGCA
AGTGGGACCCTGCCACCTGGGCACTGAGCAGAGGGACCTCCCCCAGCTCTCTTAGCAGGTGG
AGCCCCAGGGCCTGGGACAGCCTGCCGCTGCCAGCAACCTCCCACTGCTGCCTAGGGTGCAG
CGCCCACTGTCACCCTGCCTTCTGAAGAAGCCCACAGGGCTCCTAAGGTGCACCCCGGTACC
TGGAACTGCAGCCTTGGCAGTGACTGGACAGCTGGGTGGGGGATGCTCCCTGCTGGCCCTGG
GAACCTTGGACAGGCCACCTCAAGGCCCCTCGGCTGCCCCTCCTCCCTGGGCCTGCTGGGGC
CCCTAGGTTCTACCCATCACCCCCCGCCCCTGCTGGCCTTGGTGCTAAGGAAGTGGGGAGAG
CAGGCTCTCCCTGGCACCGAGGGTGCCCACCCTCTCCCTGGTGTGGCCCCGTCAACATCAGC
CACAGCCCAGCCCCATTAGTGGGTTAGTGGGTCTGACCTCAGCCCCACTCAGGTGCTCCTGC
TGGCCTGCCCAAGCCCTGCCCTCAGGGAGCTTCTGCCTTTTAAGAACTGGGCAGAGGCCACAGT
CACCTCCCCACACAGAGCTGTCCCCACTGCCCTGGGTGCCAGGCTGTCCGGAGCCAGGCCTA
CCCAGGGAGGATGCAGAGAGCTGGTGCCCAGGATGTGCACCCCCATATTCCCTCTGCCCTGT
GGCCTCAGCCCGCTGGCCTCTCTGACCGTGAGGCTGGCTCTCAGCCATCGGGCAGGTGCCTG
GTCAGGCCTGGCTTAGCCCAGGTGGGGCTTGGCAGAAGCGGGCGGGTGTGGAAGATATTCCA
TCTGGGGCCAACCCCAGGCTGGGCCTGCGCTGAGCTTCTGGAGCGCAGGTACTGGGTCTTGC
TAAGTGAACTGTTTCCCAGGAACACCTCTCGGGCCCATCTGCGTCTGAGGCTGGGAGTGGCA
TCTGAGGCCGGGAGTGGCATCTGAGGCCAGGAGTGGCAGGCTGGTGGGCTGGGCGTGGGGTT
TTCTGGGCCCTGCCCAGTACTGCCCTGGGGACTTGGTGGGCTCCTGGGTCAGCAGCATCCCA
CCCCTGGGAGTCTGGCCAGCTGAGCCCCAGGGTGGCAGGGGCATTATAGCCTGGTGGACATG
TGCCTTCAGGGTTCCTCCGGGGCCACCTTCCTCAGGCCAGTGCTGGGTTCAAAGGGCTGTGT
GTGTGTGTGTTTGTGTGTGTATGTATATGTGTGTGGGTGCACACATCTGTCCCATGTATGCA
GTGAGACCTGTCTACCTCCCACAAGGAGCAAGGGCTCTGCCCGCCCTCTGCTCATTCCTACC
CAGGTAGTGGGACCCCGGGCCCCCTTCTGCCTGGCTTGCCTGCTTCTGCCCTTTCCAGAGGG
GTCTCACTGACAGCCAGAGACAGCAGGAGAAGGGTTGGCTGTGGATCAAGGAAGGCTGCCCC
TGTACCCTGTGGGGAAATGGTGGGTGCATGGCTGGATGCAGAGGTGGAAGGCCCTGGGCCAC
AGGCGAGAGTGGGCGTGTCACCTGTCCCAGGTTCCCAGCAAGTCTGCAGCTGTGCAGTCCTG
GGGTCCCTGACCCTGTCGCCCAGGGGGCGTGCTGTCCAGCAGGGGCCCTGCCTTGCAAGGAA
CGTCTCTCCGGCGGCTGGGCCGCTCCTGCCTGGTCTGGGCTGTGTGTGGCGCCCTTTCCTCC
TTGTTTGTTCCTCTGTGTTCTGTGTGCGTCTTAAGCAATAAAGCGTGGCCGTGGGAAAAAAA
AAAAAAAAAAAAAAAAAAAAAAAAAAAAAAAAAAAAAAAAAAAAAAA

FIGURE 22

></usr/seqdb2/sst/DNA/Dnaseqs.min/ss.DNA119516
><subunit 1 of 1, 172 aa, 1 stop
><MW: 18470, pI: 5.45, NX(S/T): 0
MSSSGGAPGASASSAPPAQEEGMTWWYRWLCRLSGVLGAVSCAISGLFNCITIHPLNIAA
GVWMIMNAFILLLCEAPFCCQFIEFANTVAEKVDRLRSWQKAVFYCGMAVVPIVISLTLT
TLLGNAIAFATGVLYGLSALGKKGDAISYARIQQQRQQADEEKLAETLEGEL

Important features of the protein:
Signal peptide:
Amino acids 1-42

Transmembrane domains:
Amino acids 64-77;109-128

Tyrosine kinase phosphorylation site:
Amino acids 142-150

N-myristoylation sites:
Amino acids 5-11;6-12;9-15;35-41;38-44;46-52;124-130;132-138

Amidation site:
Amino acids 140-144

FIGURE 23

GTGAAACACCCATGGTTTTATGCTCTATTTCTCTTTTCCTCATCTTCTTCCACATCCTCTTT
CTGAATGTATCAAACTACTTCCTTGAAGTGGGGCACCAGGAGGGCCACTCCAGTCTCCAATG
CAGGGACTCAGGGGCAGGGATCTCTGAGAAAGTGGCCATCTCGTTATTAAAGCTCTGTCCTC
TGCTTCCCTCTCACCTCAGAAGCAGCCCGTTTATTCAACAGAGCTCCAGGTTGCCAGCTAGG
GGTTTTCGGGACCATAGACCAAGCAACCCCGAGAGACTGAGTACTGACCTGCAGTTGTTCCAG
AAACTCTGCTGGGAATTAGGTTGTGACCTAGAAGTGAACTGACACTAACAGTGAGAAGGCAG
GGTAAGAATGCAGTCTAGAGCGCAACCTTTCTCCACTAGACTTGTAAGTAATTTAAGTGAAT
CCTGTCCCCCTGGGGTTCTATCCTGGCTGGCTCTGCTGGTGAACTTGACTGGCCAGCATAGG
GCACTTGATGAGACCCTGGAATGCTGAGGCCAGTTGGGCAGCAAGCTTTCACCTCATCCTTC
TGCCCATCTATCCAGCCATTCAAACATTCATTCGCCTGAAGACATTTATCAAGCTCCTGCAA
TGGGTCAGGCATCTGCTAGGCACTGGGGACACAGAGCTCACAGTCTCCTGGAGGGGGTGAGA
GATGACTGACAGGTGGTCTGTGGTGCAGTGTGACCTGGGAATGCACACAGTACTGTGGAAAC
ACGGGAGAGGCATCTAGCACAACCTGAGAGGGCCAGGGGAGGCTTCCTGGCAGGTTTCCCTT
TAACCATCTTAAGGGAAAGAGGCACTAGGTAGGAAAATAAAGGGACAGTGGTGTCCCAGACA
GAGGGCACTCTACATGGAA

FIGURE 24

></usr/seqdb2/sst/DNA/Dnaseqs.min/ss.DNA119530
><subunit 1 of 1, 113 aa, 1 stop
><MW: 12799, pI: 7.53, NX(S/T): 1
MVLCSISLFLIFFHILFLNVSNYFLEVGHQEGHSSLQCRDSGAGISEKVAISLLKLCPLL
PSHLRSSPFIQQSSRLPARGFRDHRPSNPERLSTDLQLFQKLCWELGCDLEVN

Important features of the protein:
Signal peptide:
Amino acids 1-18

N-glycosylation site:
Amino acids 19-23

Glycosaminoglycan attachment site:
Amino acids 41-45

N-myristoylation site:
Amino acids 42-48

FIGURE 25

CGGGCTCCGCGCGGTCCCACTTCCCGGCTCCCTTCGCCTCCAGGATGCGCTGAGCCCTACAA
CACCCCCAGCGGCCGCCGGCTCCCCCACGAGGTGTGAATGACAGAGGTGGTGCCATCCAGCG
CGCTCAGCGAGGTCAGCCTGCGCCTCCTCTGCCACGATGACATAGACACTGTGAAGCACCTG
TGTGGCGACTGGTTCCCCATCGAGTACCCAGACTCATGGTATCGTGATATCACATCCAACAA
GAAGTTCTTTTCCCTTGCTGCAACCTACAGAGGTGCCATTGTGGGAATGATAGTAGCTGAAA
TTAAGAACAGGACCAAAATACATAAAGAGGATGGAGATATTCTAGCAACCAACTTCTCTGTT
GACACACAAGTCGCGTACATCCTAAGTCTGGGCGTCGTGAAAGAGTTCAGGAAGCACGGCAT
AGGTTCCCTCTTACTTGAAAGTTTAAAGGATCACATATCAACCACCGCCCAGGACCACTGCA
AAGCCATTTACCTGCATGTCCTCACCACCAACAACACAGCAATAAACTTCTATGAAAACAGA
GACTTCAAGCAGCACCACTATCTCCCCTATTACTACTCCATTCGAGGGGTCCTCAAAGATGG
CTTCACCTATGTCCTCTACATCAACGGCGGGCACCCTCCCTGGACGATTTTGGACTACATCC
AGCACCTGGGCTCTGCACTAGCCAGCCTGAGCCCCTGCTCCATTCCGCACAGAGTCTACCGC
CAGGCCCACAGCCTGCTCTGCAGCTTCCTGCCATGGTCGGGCATCTCTTCCAAGAGTGGCAT
CGAGTACAGCCGGACCATGTGATGTCGGCTGGGCAGCCGCCACCAGGCCCCACCCTTCAGCC
GCCCGCAGAGCCCGCCTTCCTGTCCATCTGACCCCTTCTGTTTTCTGCAAGGAGCTGCCAGC
CATCTAACTGGGCTCGTCGGCCTGCCCCAGCTGCAGGCCCGGTGCTACACGGGCTCGGGAAC
AGAACATCGTGGGCATGCGCAGAGCATGCCCATCCGTGGCAGGCTCTTCAGCTCCCCTCCCT
GCTTCTGGAAACCTCTGCCTGCTGCCCTGGCCCTGCCCCCCTGCGCATGCACCATCCCCAGC
GCTGACCCAGTGTGGCTGCATTCACTGGGAGGGGCCTGCCCTCACTGGGCCTCTCCCACTCCC
CTGCCTGTTCTTGCAGCTCCTTCCTGGAAAGCTGGAGGGGACTTTCTCCTGCAAGGGAGGAA
CGCAAGTATTATGGACACACTTGACCGTAAAGGCACAGGAGCCTCGGAACAAGGGGGCGCAA
TAAAGGGAATGGCCCGTCCCCTTCCAGAACCAGCCCAAAGAAGCCTGGGGGGTGAGGAGTGG
CCCCCACTCCTCCATGAGGGGCTGATGAGGGGTGGGCAGCCTGGGGGAGGCTTTCCTCGCAA
GCACAGAGCTCTGAGGCTCAGCCCCCTGGCACAGGCGGTCACGCATCAGGACGGTTCCTACT
CCTCAGCACCTTCCGTGCAGTTACCAGTGCCCTGGGAGGTCACACTGCCCGTCGGACCTTGG
CATGCTCCATTCAGCTGACCTGCTGAGGACAGGCATCGCCGAGACTCCTTGGGTCCTCCCCG
CCCTCCCTCATGCTGCCACAAGCTGCTGCTCCAAGGCCTGGCCACATGCAGACAGGAGGAAG
CTGAGCTCGACATTAGGCCTCAAGGCTGCCATCTGTCTTGTAGGGCCTGGCCTTGTGGGCAG
GGGGCAGTCCTGTGCCTTGTGGGCCCTCAGCCTCTGAGGGCAGAGATGCTGTCAGTGCCGCA
GGTGCATCACATACTTCTAGCATCCTCTCCACCCTGCATTCCAAATGCTGCTTGCTGCCTGC
CCTGCCCTCCGATGCAGGGGTGGGGTGGGGGGCGGAGTCCCGCCCAGCATAGCTGCAGTGTC
ACAAAGCCATGGCAGAGGGTCCTAGCGGCGCCACCCTGCCCCAGCCTGAGGAGGAGGGAGAG
GGAGGAACAACCCTGGGCAGACGGGGTCTCAGGGACCTGTGTCCTTCCGCCTCCAGAGCTGC
CCAGCCACGGGCTCTCAGGGTGCTGGGGCAGCCCCAGGTCCCCTCTTGAACTCAGCTGGGGC
CAGGGGCCCTCAGAATGAAGGCAGGCACCAGGCAGGAGCAGCATCCCCCTCCTTGACGGTGC
TGGCAGGAGGGCCGCGCCATGCTGACTGCTTGAACCTCTGCTGACCTGACAGTGCTGGCGGG
AGGGCCGCACCATGCTGACTGCCTGAATCTCTGCTGAGGCTGCCTGCCTGCCGGGCCCAGCT
CAGCGCCCTCTCCACTGCGAATCAGTGGCGATCATGTGATTTCTATTTCTGCCCCACAGGGT
AAGGGACGAGTCTTCTGGAAGGCTCTGCCATGGACATTTGTCCTCGGGCTCAGAGGCCCCAC
CCTGCCCCACACCTGCCCCTAATCACTGCAGTGTCCAGCCCAGTGTTGAACAGATTGTAGCG
TTCTGTCTCATTACGAGCAAATAAATAGACTTTCATTGGGAAAAAAAAAAAAA

FIGURE 26

```
></usr/seqdb2/sst/DNA/Dnaseqs.min/ss.DNA121772
><subunit 1 of 1, 242 aa, 1 stop
><MW: 27465, pI: 7.72, NX(S/T): 3
MTEVVPSSALSEVSLRLLCHDDIDTVKHLCGDWFPIEYPDSWYRDITSNKKFFSLAATYR
GAIVGMIVAEIKNRTKIHKEDGDILATNFSVDTQVAYILSLGVVKEFRKHGIGSLLLESL
KDHISTTAQDHCKAIYLHVLTTNNTAINFYENRDFKQHHYLPYYYSIRGVLKDGFTYVLY
INGGHPPWTILDYIQHLGSALASLSPCSIPHRVYRQAHSLLCSFLPWSGISSKSGIEYSR
TM
```

N-glycosylation sites:
Amino acids 73-77;88-92;143-147

N-myristoylation sites:
Amino acids 61-67;65-71;198-204;235-241

Matrixins cysteine switch motif:
Amino acids 18-31

FIGURE 27

GTTGGGCAGCAGCCACCCGCTCACCTCCATCCCCAGGACTTAGAGGGACGCAGGGCGTTGGG
AACAGAGGACACTCCAGGCGCTGACCCTGGGAGGCCAGGACCAGGGCCAAAGTCCCGTGGGC
AAGAGGAGTCCTCAGAGGTCCTTCATTCAGCGGTTCCGGGAGGTCTGGGAAGCCCACGGCCT
GGCTGGGGCAGGGTCAACGCCGCCAGGCCGCCATGGTCCTGTGCTGGCTGCTGCTTCTGGTG
ATGGCTCTGCCCCCAGGCACGACGGGCGTCAAGGACTGCGTCTTCTGTGAGCTCACCGACTC
CATGCAGTGTCCTGGTACCTACATGCACTGTGGCGATGACGAGGACTGCTTCACAGGCCACG
GGGTCGCCCCGGGCACTGGTCCGGTCATCAACAAAGGCTGCCTGCGAGCCACCAGCTGCGGC
CTTGAGGAACCCGTCAGCTACAGGGGCGTCACCTACAGCCTCACCACCAACTGCTGCACCGG
CCGCCTGTGTAACAGAGCCCCGAGCAGCCAGACAGTGGGGGCCACCACCAGCCTGGCACTGG
GGCTGGGTATGCTGCTTCCTCCACGTTTGCTGTGACCAACAGGGAGGACAGGGCCTGGGACT
GTTCTCCCAGATCCGCCACTCCCCATGTCCCCATGTCCTTCCCCCACTAAATGGCCAGAGAG
GCCCTGGACAACCTCTTGCGGCCCTGGCTTCATCCCTTCTAAGGCTGTCCACCAGGAGCCCG
GTGCTAGGGGAAGCATCCCCAGGCCTGACTGAGCGGCAGGGGAGCACGGCCCGTGGGTTTGA
TTGTATTACTCTGTTCCACTGGTTCTAAGACGCAGAGCTTCTCACATCTCAATCAGGATGCT
TCTCTCCATTGGTAGCACTTTAGAGTCCATGAAATATGGTAAAAAATATATATATATCATAA
TAAATGACAGCTGATGTTCATGGGGGAAAAAAAAAAAAAAAAAAAAAAAAAAAAAAAAAAAA

FIGURE 28

```
></usr/seqdb2/sst/DNA/Dnaseqs.min/ss.DNA125148
><subunit 1 of 1, 124 aa, 1 stop
><MW: 13004, pI: 5.70, NX(S/T): 0
MVLCWLLLLVMALPPGTTGVKDCVFCELTDSMQCPGTYMHCGDDEDCFTGHGVAPGTGPV
INKGCLRATSCGLEEPVSYRGVTYSLTTNCCTGRLCNRAPSSQTVGATTSLALGLGMLLP
PRLL
```

Important features of the protein:
Signal peptide:
Amino acids 1-13

N-myristoylation sites:
Amino acids 19-25;52-58;64-70;81-87;106-112

Ly-6 / u-PAR domain proteins:
Amino acids 84-97

FIGURE 29

GGCATTTTGAAAGCCCAGTGTTGCCCAGGGGGCATCTCCTTTGTGTTTATGAGAGACCTGCA
TTCTCCCTGGCTCAGTTCTCTCAGGCTCTCCAGAGCTCAGGACCTCTGAGAAGAATGGAGCC
CTCCTGGCTTCAGGAACTCATGGCTCACCCCTTCTTGCTGCTGATCCTCCTCTGCATGTCTC
TGCTGCTGTTTCAGGTAATCAGGTTGTACCAGAGGAGGAGATGGATGATCAGAGCCCTGCAC
CTGTTTCCTGCACCCCCTGCCCACTGGTTCTATGGCCACAAGGAGTTTTACCCAGTAAAGGA
GTTTGAGGTGTATCATAAGCTGATGGAAAAATACCCATGTGCTGTTCCCTTGTGGGTTGGAC
CCTTTACGATGTTCTTCAGTGTCCATGACCCAGACTATGCCAAGATTCTCCTGAAAAGACAA
GATCCCAAAAGTGCTGTTAGCCACAAAATCCTTGAATCCTGGGTTGGTCGAGGACTTGTGAC
CCTGGATGGTTCTAAATGGAAAAAGCACCGCCAGATTGTGAAACCTGGCTTCAACATCAGCA
TTCTGAAAATATTCATCACCATGATGTCTGAGAGTGTTCGGATGATGCTGAACAAATGGGAG
GAACACATTGCCCAAAACTCACGTCTGGAGCTCTTTCAACATGTCTCCCTGATGACCCTGGA
CAGCATCATGAAGTGTGCCTTCAGCCACCAGGGCAGCATCCAGTTGGACAGTACCCTGGACT
CATACCTGAAAGCAGTGTTCAACCTTAGCAAAATCTCCAACCAGCGCATGAACAATTTTCTA
CATCACAACGACCTGGTTTTCAAATTCAGCTCTCAAGGCCAAATCTTTTCTAAATTTAACCA
AGAACTTCATCAGTTCACAGAGAAAGTAATCCAGGACCGGAAGGAGTCTCTTAAGGATAAGC
TAAAACAAGATACTACTCAGAAAAGGCGCTGGGATTTTCTGGACATACTTTTGAGTGCCAAA
AGCGAAAACACCAAAGATTTCTCTGAAGCAGATCTCCAGGCTGAAGTGAAAACGTTCATGTT
TGCAGGACATGACACCACATCCAGTGCTATCTCCTGGATCCTTTACTGCTTGGCAAAGTACC
CTGAGCATCAGCAGAGATGCCGAGATGAAATCAGGGAACTCCTAGGGGATGGGTCTTCTATT
ACCTGGGAACACCTGAGCCAGATGCCTTACACCACGATGTGCATCAAGGAATGCCTCCGCCT
CTACGCACCGGTAGTAAACATATCCCGGTTACTCGACAAACCCATCACCTTTCCAGATGGAC
GCTCCTTACCTGCAGGAATAACTGTGTTTATCAATATTTGGGCTCTTCACCACAACCCCTAT
TTCTGGGAAGACCCTCAGGTCTTTAACCCCTTGAGATTCTCCAGGGAAAATTCTGAAAAAAT
ACATCCCTATGCCTTCATACCATTCTCAGCTGGATTAAGGAACTGCATTGGGCAGCATTTTG
CCATAATTGAGTGTAAAGTGGCAGTGGCATTAACTCTGCTCCGCTTCAAGCTGGCTCCAGAC
CACTCAAGGCCTCCCCAGCCTGTTCGTCAAGTTGTCCTCAAGTCCAAGAATGGAATCCATGT
GTTTGCAAAAAAAGTTTGCTAATTTTAAGTCCTTTCGTATAAGAATTAATGAGACAATTTTCCT
ACCAAAGGAAGAACAAAAGGATAAATATAATACAAAATATATGTATATGGTTGTTTGACAAA
TTATATAACTTAGGATACTTCTGACTGGTTTTGACATCCATTAACAGTAATTTTAATTTCTT
TGCTGTATCTGGTGAAACCCACAAAAACACCTGAAAAAACTCAAGCTGACTTCCACTGCGAA
GGGAAATTATTGGTTTGTGTAACTAGTGGTAGAGTGGCTTTCAAGCATAGTTTGATCAAAAC
TCCACTCAGTATCTGCATTACTTTTATCTCTGCAAATATCTGCATGATAGCTTTATTCTCAG
TTATCTTTCCCCATAATAAAAAATATCTGCCAAA

FIGURE 30

></usr/seqdb2/sst/DNA/Dnaseqs.min/ss.DNA125150
><subunit 1 of 1, 505 aa, 1 stop
><MW: 59086, pI: 9.50, NX(S/T): 3
MEPSWLQELMAHPFLLLILLCMSLLLFQVIRLYQRRRWMIRALHLFPAPPAHWFYGHKEF
YPVKEFEVYHKLMEKYPCAVPLWVGPFTMFFSVHDPDYAKILLKRQDPKSAVSHKILESW
VGRGLVTLDGSKWKKHRQIVKPGFNISILKIFITMMSESVRMMLNKWEEHIAQNSRLELF
QHVSLMTLDSIMKCAFSHQGSIQLDSTLDSYLKAVFNLSKISNQRMNNFLHHNDLVFKFS
SQGQIFSKFNQELHQFTEKVIQDRKESLKDKLKQDTTQKRRWDFLDILLSAKSENTKDFS
EADLQAEVKTFMFAGHDTTSSAISWILYCLAKYPEHQQRCRDEIRELLGDGSSITWEHLS
QMPYTTMCIKECLRLYAPVVNISRLLDKPITFPDGRSLPAGITVFINIWALHHNPYFWED
PQVFNPLRFSRENSEKIHPYAFIPFSAGLRNCIGQHFAIIECKVAVALTLLRFKLAPDHS
RPPQPVRQVVLKSKNGIHVFAKKVC

Important features of the protein:
Signal peptide:
Amino acids 1-28

Transmembrane domain:
Amino acids 451-470

N-glycosylation sites:
Amino acids 145-149;217-221;381-385 cAMP- and cGMP-dependent protein kinase phosphorylation site:
Amino acids 264-268

N-myristoylation sites:
Amino acids 243-249;351-357;448-454;454-460

Cytochrome P450 cysteine heme-iron ligand signature:
Amino acids 445-455

Cytochrome P450 cysteine heme-iron ligand proteins:
Amino acids 442-473

FAD-dependent glycerol-3-phosphate dehydrogenase proteins:
Amino acids 124-141

FIGURE 31

TCCGCTGTCGCCCAGTCCCGGCCGCTGGCGGGAACTGACCTGGAGCAAGCAGGACCTTCCCT
CCCACCTCTCCCGCCTGGCCTCCGCGGGAGTCCCCTACGATCCCGCTCAGCAGTGGGGCACT
CGCTGAGGACAGCGAGTCCTGGGAGTGAGCCCAAGGCCACCCCTGGCCAGCCCAGGAGAGAT
AGCCAGGGCAGGCCCAGCAGCCCGAGGCCAGGCTCTGGCCACGGCGGTCTCCGACATGGAGA
GACATTGTCTGCTTTTTATCCTGTTAACCTGTCTTCGGTGGTTGTGCCACGACATTCCCCAG
GGTTCAGGTGCCCGGTGGCCGAGGGTCAGTCCAGTGGTAGAGCCTTGCTCTCCTAGGCTCAT
CCTGCTGGCGGTCCTCCTGCTTCTGCTGTGTGGTGTCACAGCTGGTTGTGTCCGGTTCTGCT
GCCTCCGGAAGCAGGCACAGGCCCAGCCACATCTGCCACCAGCACGGCAGCCCTGCGACGTG
GCAGTCATCCCTATGGACAGTGACAGCCCTGTACACAGCACTGTGACCTCCTACAGCTCCGT
GCAGTACCCACTGGGCATGCGGTTGCCCCTGCCCTTTGGGGAGCTGGACCTGGACTCCACGG
CTCCTCCTGCCTACAGCCTGTACACCCCGGAGCCTCCACCCTCCTACGATGAAGCTGTCAAG
ATGGCCAAGCCCAGAGAGGAAGGACCAGCACTCTCCCAGAAACCCAGCCCTCTCCTTGGGGC
CTCGGGCCTAGAGACCACTCCAGTGCCCCAGGAGTCGGGCCCCAATACTCAACTACCACCTT
GTAGCCCTGGTGCCCCTTGAAGGAGGTAGGAGAACGGACCAGAGCTTGGAGAACTAATGCTT
GGAGCCAAGGGCCCCAGCCCACCCCACCGTCCCACACATTGCTGTGGCCCCAACCTCGGTGC
CATGTTACACCGGCCCCTGGCGTCACCCACTAGGCAGGCTGCTGCTTTCAGCCTCAGCCCCT
GGCCCAGCCCCAGCAGGCCCTCAGCCTGGAAGAGGCCCCTTGGGCCTAAGCCTCGGGTGGGA
GCTCAGGGCCACCTGTGACGTCTGCATCTTCTTGGAGAGAGAATAAAGTTTGTATTTAAGTGGT

FIGURE 32

></usr/seqdb2/sst/DNA/Dnaseqs.min/ss.DNA125151
><subunit 1 of 1, 194 aa, 1 stop
><MW: 20882, pI: 6.44, NX(S/T): 0
MERHCLLFILLTCLRWLCHDIPQGSGARWPRVSPVVEPCSPRLILLAVLLLLLCGVTAGC
VRFCCLRKQAQAQPHLPPARQPCDVAVIPMDSDSPVHSTVTSYSSVQYPLGMRLPLPFGE
LDLDSTAPPAYSLYTPEPPPSYDEAVKMAKPREEGPALSQKPSPLLGASGLETTPVPQES
GPNTQLPPCSPGAP

Important features of the protein:
Signal peptide:
Amino acids 1-20

Transmembrane domain:
Amino acids 39-58

N-myristoylation site:
Amino acids 55-61

Prokaryotic membrane lipoprotein lipid attachment site:
Amino acids 50-61

FIGURE 33

CCTTGCTTGGTGCTTGGCACACACAAATCCAGTGGGCTACACAGGTTTTCCAGAAGCCCCAC
GAGGTGGTAATGGTGCTGCTGATTCAGACCCTGGGGGCCCTCATGCCCTCGCTGCCCTCCTG
CCTCAGCAACGGCGTGGAGAGGGCAGGGCCCGAGCAGGAGCTCACCAGGCTGCTGGAGTTCT
ACGACGCCACCGCCCACTTCGCCAAGGGCTTGGAGATGGCACTGCTCCCCCACCTACATGAA
CACAATCTGGTAAAAGTCACGGAGCTGGTGGATGCTGTGTATGATCCATACAAACCCTACCAG
CTGAAGTATGGCGACATGGAAGAGAGCAACCTCCTCATCCAGATGAGTGCTGTGCCTCTGGA
GCATGGGGAAGTGATTGACTGTGTGCAGGAGCTGAGCCACTCCGTGAACAAGCTGTTTGGTC
TGGCGTCTGCAGCCGTTGACAGATGCGTCAGATTCACCAATGGCCTGGGGACCTGCGGCCTG
TTGTCAGCCCTGAAATCCCTCTTTGCCAAGTATGTGTCTGATTTCACCAGCACTCTCCAGTC
CATACGAAAGAAGTGCAAACTGGACCACATTCCTCCCAACTCCCTCTTCCAGGAAGATTGGA
CGGCTTTTCAGAACTCCATTAGGATAATAGCCACCTGTGGAGAGCTTTTGCGGCATTGTGGG
GACTTCGAGCAGCAGCTAGCCAACAGGATTTTGTCCACAGCTGGGAAGTATCTATCTGATTC
CTGCAGCCCCCGGAGCCTGGCTGGTTTTCAGGAGAGCATCTTGACAGACAAGAAGAACTCTG
CCAAGAACCCATGGCAAGAATATAATTACCTCCAGAAAGATAACCCTGCTGAATATGCCAGT
TTAATGGAAATACTTTATACCCTTAAGGAAAAAGGGTCAAGCAACCACAACCTGCTGGCTGC
ACCTCGAGCAGCGCTGACTCGGCTTAACCAGCAGGCCCACCAGCTGGCTTTCGATTCCGTGT
TCCTGCGCATCAAACAACAGCTGTTGCTTATTTCGAAGATGGACAGCTGGAATACGGCTGGC
ATCGGAGAAACCCTCACAGATGAACTGCCCGCCTTTAGTCTCACCCCTCTCGAGTACATCAG
CAACATCGGGCAGTACATCATGTCCCTCCCCCTGAATCTTGAGCCATTTGTGACTCAGGAGG
ACTCTGCCTTAGAGTTGGCATTGCACGCTGGAAAGCTGCCATTTCCTCCTGAGCAGGGGGAT
GAATTGCCCGAGCTGGACAACATGGCTGACAACTGGCTGGGCTCGATCGCCAGAGCCACAAT
GCAGACCTACTGTGATGCGATCCTACAGATCCCTGAGCTGAGCCCACACTCTGCCAAGCAGC
TGGCCACTGACATCGACTATCTGATCAACGTGATGGATGCCCTGGGCCTGCAGCCGTCCCGC
ACCCTCCAGCACATCGTGACGCTACTGAAGACCAGGCCTGAGGACTATAGACAGGTCAGCAA
AGGCCTGCCCCGTCGCCTGGCCACCACCGTGGCCACCATGCGGAGTGTGAATTACTGACCCC
ACCACACACCGGACCACCAAGAGAGCCAGGGCTGCTGTTTCGTGACTCACCAGCACAGATTT
GCTCAGAAACTCTGCCCAAGATTGGGCAGAAGTTACTTTAAAAAGACTTGGTTCAGCTGGTC
ACGGTGGCTCACGCCTGTAATCCCAGCACTTTGGGAGGCCAAGCCAGATGGATCATGAGGCC
AGGAGTTCGAGACCAGCCTGACCAACATGGTGAAACCCCATCTCTACTAAAAATACAAAAAT
TAACAGCAGAGCGAGACTCTGTCTCAAAAAAAAAAAAAAAAAGACTTGGTTCATTTGTATAA
TCAAAAAGAGTTGTAAATTAAAGATGTATTATTTATCAGAGAAGACTTTTTAGATAATTTTT
TTAAAGGATCAGATCTTGAAAATGGAATAAATAACTACTGTGAAATGCAAAAA

FIGURE 34

```
></usr/seqdb2/sst/DNA/Dnaseqs.min/ss.DNA125181
><subunit 1 of 1, 491 aa, 1 stop
><MW: 54759, pI: 5.61, NX(S/T): 0
MVLLIQTLGALMPSLPSCLSNGVERAGPEQELTRLLEFYDATAHFAKGLEMALLPHLHEH
NLVKVTELVDAVYDPYKPYQLKYGDMEESNLLIQMSAVPLEHGEVIDCVQELSHSVNKLF
GLASAAVDRCVRFTNGLGTCGLLSALKSLFAKYVSDFTSTLQSIRKKCKLDHIPPNSLFQ
EDWTAFQNSIRIIATCGELLRHCGDFEQQLANRILSTAGKYLSDSCSPRSLAGFQESILT
DKKNSAKNPWQEYNYLQKDNPAEYASLMEILYTLKEKGSSNHNLLAAPRAALTRLNQQAH
QLAFDSVFLRIKQQLLLISKMDSWNTAGIGETLTDELPAFSLTPLEYISNIGQYIMSLPL
NLEPFVTQEDSALELALHAGKLPFPPEQGDELPELDNMADNWLGSIARATMQTYCDAILQ
IPELSPHSAKQLATDIDYLINVMDALGLQPSRTLQHIVTLLKTRPEDYRQVSKGLPRRLA
TTVATMRSVNY
```

Important features of the protein:

Signal peptide:

Amino acids 1-20 cAMP- and cGMP-dependent protein kinase phosphorylation site:

Amino acids 242-246

N-myristoylation sites:

Amino acids 22-28;48-54;121-127;136-142;141-147;328-334;
447-453

Leucine zipper pattern:

Amino acids 295-317

FIGURE 35

GCAAGTGCCACCATGCTAGTGTGATTTGGACTTCAGTAAAAGTTAGTTTGCTTCCTTCCCGT
TGTCCCATCTCACTCCTGGGCCACCCATGGGGCTGCTGGTAGCTGGTGTGTGGCTGCTGCTG
GACTGTGTGGCAGTCCATCCATCTGTCAGCAGCCACTGCGGGCCTACTTGCTGGGTGCCCAG
CACCGCACTCACCACTGCAGGCGTGGCCAGGAGCGTGAGATCCCCAGAGCCCATGGCCAGTG
AGAGGCGGCCAGGGATAGGTACCCAGGGAATGCCACAGGAGTTTGCTGGGCTCACGGAGCTC
TTTCACTGGTCAGAGAGGAGTGTGTGTAGGAGAGGACTTCTACTTGGTGTTGAAGGACAGAT
GGGGTTTGGCTGGGAGAGAGGAGGAATGTGGGCGGGCCTTATAGGCAGGCGAGAAGGTGAGA
GCCAAGGCCCTCTGTGGGCAGGGCGAGGTGGCGTGTTGAGGAGACTCGTCCAGCTGGGCAGA
GGCTCATGTTGAGGGATGAGGCAGAGCTGGGGGAGGAGGGAGCCCAGAAATGGCAGGTCCTT
GAATGCAGGTTTGGAAGCAGGGACGCCCTGTGAGGGTACAGAGTCTGGGCTGTTACCTTCTG
TGGCTTTTGCTAGAAGGTGAGATGTCAGGGAGGAAGACAGGACTCCAGGATGTCTCCTGTCTCT
CTCTGGAAAAAGGAGGTGGGCCCCTTTCTCAGCAGTCAGCTGCTGTTTTTGAGGTCTTCTCC
ATGGATAATCCACGGTGTTGGAAGTGGTTAAGGTAATGGATCCTCATGGGCTTACCATAAAA
ATATCTGGAGGCTGGACCATTTTCCTTAAAACGTTATAAAAGCTGGAATTGAATGCCATCGG
TGTCACCCCTGGGAAGTGTGCTTTCTCTTGAGCTCTTTTGGCCCCGAGATAGCAGTCACTCC
ATAGTTTCGTGAAGACCAGCCTGGTGTTGCCTGGTTTTCTGCCATTAGGGAGCAGCTAGAGG
TCTTCCAGTAGCTCCTGTGTAAAGTGATGAAAGAAAAGGGCTGGGTGCTGACTGCTCCTGGA
GAAAAGCAACACACTCCCAAAGTCTTAATTGCCTGCTTCCAGGGAGCTGTGGTGGTTTCCCT
TGGGCAGGGCACACGCCCCAGTGGTTGACTTAATAAGGATACATTTTAATCAGAGGACAAAA
ATGTGCCCTGACTTGATTTCCGCATGGGCTTCCAGCATGGTCAAAGG

FIGURE 36

></usr/seqdb2/sst/DNA/Dnaseqs.min/ss.DNA125192
><subunit 1 of 1, 139 aa, 1 stop
><MW: 14841, pI: 9.20, NX(S/T): 0
MGLLVAGVWLLLDCVAVHPSVSSHCGPTCWVPSTALTTAGVARSVRSPEPMASERRPGIG
TQGMPQEFAGLTELFHWSERSVCRRGLLLGVEGQMGFGWERGGMWAGLIGRREGESQGPL
WAGRGGVLRRLVQLGRGSC

Important features of the protein:
Signal peptide:
Amino acids 1-22

N-myristoylation sites:
Amino acids 2-8;40-46;86-92;102-108;103-109

Amidation site:
Amino acids 109-113

FIGURE 37

GGCCAGGAATGGGGTCCCCGGGCATGGTGCTGGGCCTCCTGGTGCAGATCTGGGCCCTGCAA
GAAGCCTCAAGCCTGAGCGTGCAGCAGGGGCCCAACTTGCTGCAGGTGAGGCAGGGCAGTCA
GGCGACCCTGGTCTGCCAGGTGGACCAGGCCACAGCCTGGGAACGGCTCCGTGTTAAGTGGACA
AAGGATGGGGCCATCCTGTGTCAACCGTACATCACCAACGGCAGCCTCAGCCTGGGGGTCTG
CGGGCCCCAGGGACGGCTCTCCTGGCAGGCACCCAGCCATCTCACCCTGCAGCTGGACCCTG
TGAGCCTCAACCACAGCGGGGCGTACGTGTGCTGGGCGGCCGTAGAGATTCCTGAGTTGGAG
GAGGCTGAGGGCAACATAACAAGGCTCTTTGTGGACCCAGATGACCCCACACAGAACAGAAA
CCGGATCGCAAGCTTCCCAGGATTCCTCTTCGTGCTGCTGGGGGTGGGAAGCATGGGTGTGG
CTGCGATCGTGTGGGGTGCCTGGTTCTGGGGCCGCCGCAGCTGCCAGCAAAGGGACTCAGGA
AATGCATTCTACAGCAACGTCCTATACCGGCCCCGGGGGGCCCCAAAGAAGAGTGAGGACTG
CTCTGGAGAGGGGAAGGACCAGAGGGGCCAGAGCATTTATTCAACCTCCTTCCCGCAACCGG
CCCCCCGCCAGCCGCACCTGGCGTCAAGACCCTGCCCCAGCCCGAGACCCTGCCCCAGCCCC
AGGCCCGGCCACCCCGTCTCTATGGTCAGGGTCTCTCCTAGACCAAGCCCCACCCAGCAGCC
GAGGCCAAAAGGGTTCCCCAAAGTGGGAGAGGAGTGAGAGATCCCAGGAGACCTCAACAGGA
CCCCACCCATAGGTACACACAAAAAAGGGGGGATCGAGGCCAGACACGGTGGCTCACGCCTG
TAATCCCAGCAGTTTGGGAAGCCGAGGCGGGTGGAACACTTGAGGTCAGGGGTTTGAGACCA
GCCTGGCTTGAACCTGGGAGGCGGAGGTTGCAGTGAGCCGAGATTGCGCCACTGCACTCCAG
CCTGGGCGACAGAGTGAGACTCCGTCTCAAAAAAAAAACAAAAAGCAGGAGGATTGGGAGCC
TGTCAGCCCCATCCTGAGACCCCGTCCTCATTTCTGTAATGATGGATCTCGCTCCCACTTTC
CCCCAAGAACCTAATAAAGGCTTGTGAAGAAAAAAAAAAAAAAAA

FIGURE 38

></usr/seqdb2/sst/DNA/Dnaseqs.min/ss.DNA125196
><subunit 1 of 1, 278 aa, 1 stop
><MW: 30319, pI: 9.21, NX(S/T): 3
MGSPGMVLGLLVQIWALQEASSLSVQQGPNLLQVRQGSQATLVCQVDQATAWERLRVKWT
KDGAILCQPYITNGSLSLGVCGPQGRLSWQAPSHLTLQLDPVSLNHSGAYVCWAAVETPE
LEEAEGNITRLFVDPDDPTQNRNRIASFPGFLFVLLGVGSMGVAAIVWGAWFWGRRSCQQ
RDSGNAFYSNVLYRPRGAPKKSEDCSGEGKDQRGQSIYSTSFPQPAPRQPHLASRPCPSP
RPCPSPRPGHPVSMVRVSPRPSPTQQPRPKGFPKVGEE

Important features of the protein:
Signal peptide:
Amino acids 1-22

Transmembrane domain:
Amino acids 149-166

N-glycosylation sites:
Amino acids 73-77;105-109;127-131

Glycosaminoglycan attachment site:
Amino acids 206-210

N-myristoylation sites:
Amino acids 5-11;37-43;63-69;108-114

Amidation site:
Amino acids 173-179

FIGURE 39

ACCAGCAGAAGGCTGGGAGTCTGTAGTTTGTTCCTGCTGCCAGGCTCCACTGAGGGGAACGG
GGACCTGTCTGAAGAGAAGATGCCCCTGCTGACACTCTACCTGCTCCTCTTCTGGCTCTCAG
GCTACTCCATTGCCACTCAAATCACCGGTCCAACAACAGTGAATGGCTTGGAGCGGGGCTCC
TTGACCGTGCAGTGTGTTTACAGATCAGGCTGGGAGACCTACTTGAAGTGGTGGTGTCGAGG
AGCTATTTGGCGTGACTGCAAGATCCTTGTTAAAACCAGTGGGTCAGAGCAGGAGGTGAAGA
GGGACCGGGTGTCCATCAAGGACAATCAGAAAAACCGCACGTTCACTGTGACCATGGAGGAT
CTCATGAAAACTGATGCTGACACTTACTGGTGTGGAATTGAGAAAACTGGAAATGACCTTGG
GGTCACAGTTCAAGTGACCATTGACCCAGCACCAGTCACCCAAGAAGAAACTAGCAGCTCCC
CAACTCTGACCGGCCACCACTTGGACAACAGGCACAAGCTCCTGAAGCTCAGTGTCCTCCTG
CCCCTCATCTTCACCATATTGCTGCTGCTTTTGGTGGCCGCCTCACTCTTGGCTTGGAGGATG
ATGAAGTACCAGCAGAAAGCAGCCGGGATGTCCCCAGAGCAGGTACTGCAGCCCCTGGAGGG
CGACCTCTGCTATGCAGACCTGACCCTGCAGCTGGCCGGAACCTCCCCGCGAAAGGCTACCA
CGAAGCTTTCCTCTGCCCAGGTTGACCAGGTGGAAGTGGAATATGTCACCATGGCTTCCTTG
CCGAAGGAGGACATTTCCTATGCATCTCTGACCTTGGGTGCTGAGGATCAGGAACCGACCTA
CTGCAACATGGGCCACCTCAGTAGCCACCTCCCCGGCAGGGGCCCTGAGGAGCCCACGGAAT
ACAGCACCATCAGCAGGCCTTAGCCTGCACTCCAGGCTCCTTCTTGGACCCCAGGCTGTGAG
CACACTCCTGCCTCATCGACCGTCTGCCCCCTGCTCCCCTCATCAGGACCAACCCGGGGACT
GGTGCCTCTGCCTGATCAGCCAGCATTGCCCCTAGCTCTGGGTTGGGCTTGGGGCCAAGTCT
CAGGGGGCTTCTAGGAGTTGGGGTTTTCTAAACGTCCCCTCCTCTCCTACATAGTTGAGGAG
GGGGCTAGGGATATGCTCTGGGGCTTTCATGGGAATGATGAAGATGATAATGAGAAAAATGT
TATCATTATTATCATGAAGTACCATTATCATAATACAATGAACCTTTATTTATTGCCTACCA
CATGTTATGGGCTGAATAATGGCCCCCAAAGATATCTGTGTCCTAATCCTCAGAACTTGTGA
CTGTTACCTTCTGTGGCAGAAAGGGACAGTGCAGATGTATGTAAGTTAAGGACTTTGAGATA
GAGAGGTTATTCTTGCTGATTCAGGTGGGCCCAAAATATCACCACAAGGGTCCTCATAAGAA
AGAGGCCAGAAGGTCAAAGAGGTAGAGACAAAGTGATGATGGAAGTGGACGTGGGTGTGACG
TGAGCAGGGGCCATGAATGCCGCAGCCTTCAGATGCCAGAAAGGGAAAGGAATGGATTCCCC
TGCCTGGAGCCTCCAAAAGAAACCAGCCCTGCCCACGCCTTGACTTGAGCCCATTGAAACTG
ATCTTGAGCTCCTGGCCTCCAGAATTGCAGGAGAATAAATTTGTGTTGTTTTTAATGAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAG

FIGURE 40

></usr/seqdb2/sst/DNA/Dnaseqs.min/ss.DNA125200
><subunit 1 of 1, 290 aa, 1 stop
><MW: 32335, pI: 5.82, NX(S/T): 1
MPLLTLYLLLFWLSGYSIATQITGPTTVNGLERGSLTVQCVYRSGWETYLKWWCRGAIWR
DCKILVKTSGSEQEVKRDRVSIKDNQKNRTFTVTMEDLMKTDADTYWCGIEKTGNDLGVT
VQVTIDPAPVTQEETSSSPTLTGHHLDNRHKLLKLSVLLPLIFTILLLLLVAASLLAWRM
MKYQQKAAGMSPEQVLQPLEGDLCYADLTLQLAGTSPRKATTKLSSAQVDQVEVEYVTMA
SLPKEDISYASLTLGAEDQEPTYCNMGHLSSHLPGRGPEEPTEYSTISRP

Important features of the protein:
Signal peptide:
Amino acids 1-15

Transmembrane domain:
Amino acids 155-174

N-glycosylation site:
Amino acids 88-92 cAMP- and cGMP-dependent protein kinase phosphorylation site:
Amino acids 218-222

Tyrosine kinase phosphorylation site:
Amino acids 276-285

N-myristoylation sites:
Amino acids 30-36;109-115;114-120

FIGURE 41

AAGAACACTGTTGCTCTTGGTGGACGGGCCCAGAGGAATTCAGAGTTAAACCTTGAGTGCCT
GCGTCCGTGAGAATTCAGCATGGAATGTCTCTACTATTTCCTGGGATTTCTGCTCCTGGCTG
CAAGATTGCCACTTGATGCCGCCAAACGATTTCATGATGTGCTGGGCAATGAAAGACCTTCT
GCTTACATGAGGGAGCACAATCAATTAAATGGCTGGTCTTCTGATGAAAATGACTGGAATGA
AAAACTCTACCCAGTGTGGAAGCGGGGAGACATGAGGTGGAAAAACTCCTGGAAGGGAGGCC
GTGTGCAGGCGGTCCTGACCAGTGACTCACCAGCCCTCGTGGGCTCAAATATAACATTTGCG
GTGAACCTGATATTCCCTAGATGCCAAAAGGAAGATGCCAATGGCAACATAGTCTATGAGAA
GAACTGCAGAAATGAGGCTGGTTTATCTGCTGATCCGTATGTTTACAACTGGACAGCATGGT
CAGAGGACAGTGACGGGGAAAATGGCACCGGCCAAAGCCATCATAACGTCTTCCCTGATGGG
AAACCTTTTCCTCACCACCCCGGATGGAGAAGATGGAATTTCATCTACGTCTTCCACACACTT
GGTCAGTATTTCCAGAAATTGGGACGATGTTCAGTGAGAGTTTCTGTGAACACAGCCAATGT
GACACTTGGGCCTCAACTCATGGAAGTGACTGTCTACAGAAGACATGGACGGGCATATGTTC
CCATCGCACAAGTGAAAGATGTGTACGTGGTAACAGATCAGATTCCTGTGTTTGTGACTATG
TTCCAGAAGAACGATCGAAATTCATCCGACGAAACCTTCCTCAAAGATCTCCCCATTATGTT
TGATGTCCTGATTCATGATCCTAGCCACTTCCTCAATTATTCTACCATTAACTACAAGTGGA
GCTTCGGGGATAATACTGGCCTGTTTGTTTCCACCAATCATACTGTGAATCACACGTATGTG
CTCAATGGAACCTTCAGCCTTAACCTCACTGTGAAAGCTGCAGCACCAGGACCTTGTCCGCC
ACCGCCACCACCACCCAGACCTTCAAAACCCACCCCTTCTTTAGCAACTACTCTAAAATCTT
ATGATTCAAACACCCCAGGACCTACTGGTGACAACCCCCTGGAGCTGAGTAGGATTCCTGAT
GAAAACTGCCAGATTAACAGATATGGCCACTTTCAAGCCACCATCACAATTGTAGAGGGAAT
CTTAGAGGTTAACATCATCCAGATGACAGACGTCCTGATGCCGGTGCCATGGCCTGAAAGCT
CCCTAATAGACTTTGTCGTGACCTGCCAAGGGAGCATTCCCACGGAGGTCTGTACCATCATT
TCTGACCCCACCTGCGAGATCACCCAGAACACAGTCTGCAGCCCTGTGGATGTGGATGAGAT
GTGTCTGCTGACTGTGAGACGAACCTTCAATGGGTCTGGGACGTACTGTGTGAACCTCACCC
TGGGGGATGACACAAGCCTGGCTCTCACGAGCACCCTGATTTCTGTTCCTGACAGAGACCCA
GCCTCGCCTTTAAGGATGGCAAACAGTGCCCTGATCTCCGTTGGCTGCTTGGCCATATTTGT
CACTGTGATCTCCCTCTTGGTGTACAAAAAACACAAGGAATACAACCCAATAGAAAATAGTC
CTGGGAATGTGGTCAGAAGCAAAGGCCTGAGTGTCTTTCTCAACCGTGCAAAAGCCGTGTTC
TTCCCGGGAAACCAGGAAAAGGATCCGCTACTCAAAAACCAAGAATTTAAAGGAGTTTCTTA
AATTTCGACCTTGTTTCTGAAGCTCACTTTTCAGTGCCATTGATGTGAGATGTGCTGGAGTG
GCTATTAACCTTTTTTTCCTAAAGATTATTGTTAAATAGATATTGTGGTTTGGGGAAGTTGA
ATTTTTTATAGGTTAAATGTCATTTTAGAGATGGGGAGAGGGATTATACTGCAGGCAGCTTC
AGCCATGTTGTGAAACTGATAAAAGCAACTTAGCAAGGCTTCTTTTCATTATTTTTTATGTT
TCACTTATAAAGTCTTAGGTAACTAGTAGGATAGAAACACTGTGTCCCGAGAGTAAGGAGAG
AAGCTACTATTGATTAGAGCCTAACCCAGGTTAACTGCAAGAAGAGGCGGGATACTTTCAGC
TTTCCATGTAACTGTATGCATAAAGCCAATGTAGTCCAGTTTCTAAGATCATGTTCCAAGCTA
ACTGAATCCCACTTCAATACACACTCATGAACTCCTGATGGAACAATAACAGGCCCAAGCCT
GTGGTATGATGTGCACACTTGCTAGACTCAGAAAAAATACTACTCTCATAAATGGGTGGGAG
TATTTTGGTGACAACCTACTTTGCTTGGCTGAGTGAAGGAATGATATTCATATATTCATTTA
TTCCATGGACATTTAGTTAGTGCTTTTTATATACCAGGCATGATGCTGAGTGACACTCTTGT
GTATATTTCCAAATTTTTGTACAGTCGCTGCACATATTTGAAATCATATATTAAGACTTTCC
AAAGATGAGGTCCCTGGTTTTTCATGGCAACTTGATCAGTAAGGATTTCACCTCTGTTTGTA
ACTAAAACCATCTACTATATGTTAGACATGACATTCTTTTTCTCTCCTTCCTGAAAAATAAA
GTGTGGGAAGAGACA

FIGURE 42

></usr/seqdb2/sst/DNA/Dnaseqs.min/ss.DNA125214
><subunit 1 of 1, 572 aa, 1 stop
><MW: 63953, pI: 6.55, NX(S/T): 12
MECLYYFLGFLLLAARLPLDAAKRFHDVLGNERPSAYMREHNQLNGWSSDENDWNEKLYP
VWKRGDMRWKNSWKGGRVQAVLTSDSPALVGSNITFAVNLIFPRCQKEDANGNIVYEKNC
RNEAGLSADPYVYNWTAWSEDSDGENGTGQSHHNVFPDGKPFPHHPGWRRWNFIYVFHTL
GQYFQKLGRCSVRVSVNTANVTLGPQLMEVTVYRRHGRAYVPIAQVKDVYVVTDQIPVFV
TMFQKNDRNSSDETFLKDLPIMFDVLIHDPSHFLNYSTINYKWSFGDNTGLFVSTNHTVN
HTYVLNGTFSLNLTVKAAAPGPCPPPPPPPRPSKPTPSLATTLKSYDSNTPGPTGDNPLE
LSRIPDENCQINRYGHFQATITIVEGILEVNIIQMTDVLMPVPWPESSLIDFVVTCQGSI
PTEVCTIISDPTCEITQNTVCSPVDVDEMCLLTVRRTFNGSGTYCVNLTLGDDTSLALTS
TLISVPDRDPASPLRMANSALISVGCLAIFVTVISLLVYKKHKEYNPIENSPGNVVRSKG
LSVFLNRAKAVFFPGNQEKDPLLKNQEFKGVS

Important features of the protein:

Signal peptide:
Amino acids 1-21

Transmembrane domain:
Amino acids 496-516

N-glycosylation sites:
Amino acids 93-97;134-138;146-150;200-204;249-253;275-279;
296-300;300-304;306-310;312-316;459-463;467-471

N-myristoylation sites:
Amino acids 91-97;147-153;290-296;418-424

Prokaryotic membrane lipoprotein lipid attachment site:
Amino acids 496-507

Cell attachment sequence:
Amino acids 64-67

FIGURE 43

GCATAGATGAATGTATCAGTGGATGGATAGTTGGCTAGATGGGTGGGTTGGTGGATGAATGG
CAGAGCTTGCACCTGCCAGTCCATCTGACATCAAAGCCAGTGTCTCTAATGGTGACACCACC
CTCCTCTGCAGCAGGAGGCAGAGCTGTGGGATGAATGAGGTTCGCCAGGTCTCCCTTACCTA
TCCTGGGTCCCCAGCTCCTTCTCACTCTCTTCCCTTGCAGCCTCGAAGCGGAGGATCCCTGT
GTCCCAGCCGGGCATGGCCGACCCCCACCAGCTTTTCGATGACACAAGTTCAGCCCAGAGCC
GGGGCTATGGGGCCCAGCGGGCACCTGGTGGCCTGAGTTATCCTGCAGCCTCTCCCACGCCC
CATGCAGCCTTCCTGGCTGACCCGGTGTCCAACATGGCCATGGCCTATGGGAGCAGCCTGGC
CGCGCAGGGCAAGGAGCTGGTGGATAAGAACATCGACCGCTTCATCCCCATCACCAAGCTCA
AGTATTACTTTGCTGTGGACACCATGTATGTGGGCAGAAAGCTGGGCCTGCTGTTCTTCCCC
TACCTACACCAGGACTGGGAAGTGCAGTACCAACAGGACACCCCGGTGGCCCCCCGCTTTGAC
GTCAATGCCCCGGACCTCTACATTCCAGCAATGGCTTTCATCACCTACGTTTTGGTGGCTGG
TCTTGCGCTGGGGACCCAGGATAGGTTCTCCCCAGACCTCCTGGGGCTGCAAGCGAGCTCAG
CCCTGGCCTGGCTGACCCTGGAGGTGCTGGCCATCCTGCTCAGCCTCTATCTGGTCACTGTC
AACACCGACCTCACCACCATCGACCTGGTGGCCTTCTTGGGCTACAAATATGTCGGGATGAT
TGGCGGGGTCCTCATGGGCCTGCTCTTCGGGAAGATTGGCTACTACCTGGTGCTGGGCTGGT
GCTGCGTAGCCATCTTTGTGTTCATGATCCGGACGCTGCGGCTGAAGATCTTGGCAGACGCA
GCAGCTGAGGGGGTCCCGGTGCGTGGGGCCCGGAACCAGCTGCGCATGTACCTGACCATGGC
GGTGGCGGCGGCGCAGCCTATGCTCATGTACTGGCTCACCTTCCACCTGGTGCGGTGAGCGC
GCCCGCTGAACCTCCCGCTGCTGCTGCTGCTGCTGGGGGCCACTGTGGCCGCCGAACTCATC
TCCTGCCTGCAGGCCCCAAGGTCCACCCTGTCTGGCCACAGGCACCGCCTCCATCCCATGTC
CCGCCCAGCCCCGCCCCCAACCCAAGGTGCTGAGAGATCTCCAGCTGCACAGGCCACCGCCC
CAGGGCGTGGCCGCTGTTACAGAAACAATAAACCCTGATGGGCATGGCAAAAAAAAAAAAAA
AAAAAAAAAAAAAAAAAAAAAAAAAAAAAAAAAAAAAAAAAAAAAAAAAAAAAAAAAAAAAA
AAAAAGA

FIGURE 44

```
></usr/seqdb2/sst/DNA/Dnaseqs.min/ss.DNA125219
><subunit 1 of 1, 283 aa, 1 stop
><MW: 31175, pI: 7.51, NX(S/T): 0
MADPHQLFDDTSSAQSRGYGAQRAPGGLSYPAASPTPHAAFLADPVSNMAMAYGSSLAAQ
GKELVDKNIDRFIPITKLKYYFAVDTMYVGRKLGLLFFPYLHQDWEVQYQQDTPVAPRFD
VNAPDLYIPAMAFITYVLVAGLALGTQDRFSPDLLGLQASSALAWLTLEVLAILLSLYLV
TVNTDLTTIDLVAFLGYKYVGMIGGVLMGLLFGKIGYYLVLGWCCVAIFVFMIRTLRLKI
LADAAAEGVPVRGARNQLRMYLTMAVAAAQPMLMYWLTFHLVR
```

Important features of the protein:

Transmembrane domain:

Amino acids 126-142;164-179;215-233

N-myristoylation sites:

Amino acids 54-60;141-147;156-162;201-207;205-211;209-215

Amidation site:

Amino acids 89-93

FIGURE 45

GCTGAGCACCAACAGGAACTATTCCAGTGAAGAGCAAGTGCTGCCCGACCCAGGACCCTGTG
CCAGGCTGGCAGCCCTCCAGCTCCCTCCAGAGAGGAAACCTCTGTCTGGCTGAGGGTGGGAC
TAGCTGGGATGTCTCACTCCAGTTGCTCAGGTTCACCCAGGAAGCTCCTCCGTGGAGTGGCC
AGCCTGATTCTAGCCCTGTCCTCTCTGGCAGCACATGCCACACCTGCCTGGGCCTTCTGCTC
CCTGATGCTTGATGAGCCCCTGCCTCCTCAATGTTTCTCAAAGACAGACCCCCCTGAGGCCAGC
TTGAATGTGAAGACTGCTGAAGTCAGCTGGCTTCACTTGAGCTGCAGAAAAGGTGGCTGGGA
TGGCCCAGGTGCACCCAGAGGCCCCAGCCCTTTGGCTGCCTTTGGGTTGTGACTTGGGTTGT
CTCTGAGGCCCTGCCAGAGCTGGGCCTGCGGGTGGTGGGCGGTCCGACCTCGGGCAGTCAGT
GCTCCGCAGCCTCAGCACTGCATCCCAGACCCAGTGTCCTCAGAGGGAAGAGCCAGCCTCCC
TGCCTCATGGAACCAGGAGTCCCAAAAAGTCAGGAGCCTGGAGGCTCTGAAAGGAGCAGGGA
TTCCATAGTGCGTGAAGCTGAAATAGGCGCCCTCCTGGGGAGCCCCCAGCAAAACTGTTTTT
CATACCCACTCCCAGAACTGCCCCGCTCCAGCTCCAGCGCCAGCGCCAGCTGGTTGCCAGGC
GTCATTGGAGAGGCCTGGCTGCCCCAGGGGCAGCAGGGAGTGGTGGACCTGTATGGGCTGGC
AGGAGGCCATTGGCCATGCTGACAAGTGTCACCTGCCTTCCTAGCCTGGAGCCACCCCTCAG
GTGGCCTGCTTGCACCTCCTATCCGGAGGTAGCCTGCCCCACCTGTAGGCAGAGGGGGCTCT
TGCTTGAGGCCTGCACAGGAAGCAAGTATAGCCCCGGTGCCCCAGAGTGGGTTCCACTTAGC
CCTGGCGAGATGGCCTGTCCTGAGATCTCTGCTCCCAGACCCCACCATCTGGGGAGCACAGT
CCTTAGGCTGCCTGGTCCAGGAAGGGGGTGCGGCTCTGTCAGGAAACCTGGACTCTCAAGGC
CCACCAGCCTCTCCGTGAGTGTTAGAAATCACAGATACAGTATATACTTAATTACACTACTC
ACTACTCAAAAAAAAAAAAAAAAAAA

FIGURE 46

></usr/seqdb2/sst/DNA/Dnaseqs.min/ss.DNA128309
><subunit 1 of 1, 97 aa, 1 stop
><MW: 10112, pI: 8.64, NX(S/T): 0
MSHSSCSGSPRKLLRGVASLILALSSLAAHATPAWAFCSLMLDEPLPPQCFSKTDPPEAS
LNVKTAEVSWLHLSCRKGGWDGPGAPRGPSPLAAFGL

Important features of the protein:
Signal peptide:
Amino acids 1-31

FIGURE 47

TTCCGGGCCCTGGCGTCTCGTCTCCTTACCCTGGGGCTACCCTTGCCCGGTCCTACTGCCCG
CGGTTAACCCGCCGCGAGCCGCCTCTCCCCTCCCCGCCCGACTCAACCCTGCCCTCCCCCGT
GCTTTGCAGACGCCGCCCGGGGGCCCAGGCGGCTGATGCGTGTGGGCCTCGCGCTGATCTTG
GTGGGCCACGTGAACCTGCTGCTGGGGGCCGTGCTGCATGGCACCGTCCTGCGGCACGTGGC
CAATCCCCGCGGCGCTGTCACGCCGGAGTACACCGTAGCCAATGTCATCTCTGTCGGCTCGG
GGCTGCTGAGCGTTTCCGTGGGACTTGTGGCCCTCCTGGCGTCCAGGAACCTTCTTCGCCCT
CCACTGCACTGGGTCCTGCTGGCACTAGCTCTGGTGAACCTGCTCTTGTCCGTTGCCTGCTC
CCTGGGCCTCCTTCTTGCTGTGTCACTCACTGTGGCCAACGGTGGCCGCCGCCTTATTGCTG
ACTGCCACCCAGGACTGCTGGATCCTCTGGTACCACTGGATGAGGGGCCGGGACATACTGAC
TGCCCCTTTGACCCCACAAGAATCTATGATACAGCCTTGGCTCTCTGGATCCCTTCTTTGCT
CATGTCTGCAGGGGAGGCTGCTCTATCTGGTTACTGCTGTGTGGCTGCACTCACTCTACGTG
GAGTTGGGCCCTGCAGGAAGGACGGACTTCAGGGGCAGCTAGAGGAAATGACAGAGCTTGAA
TCTCCTAAATGTAAAAGGCAGGAAAATGAGCAGCTACTGGATCAAAATCAAGAAATCCGGGC
ATCACAGAGAAGTTGGGTTTAGGACAGGTGCTGTTCCGAGACTCAGTCCTAAAGGGTTTTTT
TTCCCACTAAGCAAGGGGCCCTGACCTCGGGATGAGATAACAAATTGTAATAAAGTAACTTC
TCTTTTCTTCTAAAAAAAAAAAAAAAAAAAAAAAAAAAAAAAAAAAAAAAAAAAAAAAAAAA

FIGURE 48

></usr/seqdb2/sst/DNA/Dnaseqs.min/ss.DNA129535
><subunit 1 of 1, 222 aa, 1 stop
><MW: 23566, pI: 6.70, NX(S/T): 0
MRVGLALILVGHVNLLLGAVLHGTVLRHVANPRGAVTPEYTVANVISVGSGLLSVSVGLV
ALLASRNLLRPPLHWVLLALALVNLLLSVACSLGLLLAVSLTVANGGRRLIADCHPGLLD
PLVPLDEGPGHTDCPFDPTRIYDTALALWIPSLLMSAGEAALSGYCCVAALTLRGVGPCR
KDGLQGQLEEMTELESPKCKRQENEQLLDQNQEIRASQRSWV

Important features of the protein:
Signal peptide:
Amino acids 1-18

Transmembrane domain:
Amino acids 44-60;76-96

N-myristoylation sites:
Amino acids 94-100;175-181

Amidation site:
Amino acids 106-110

Prokaryotic membrane lipoprotein lipid attachment site:
Amino acids 81-92

FIGURE 49

CGTCAGTCTAGAAGGATAAGAGAAAGAAAGTTAAGCAACTACAGGAAATGGCTTTGGGAG
TTCCAATATCAGTCTATCTTTTATTCAACGCAATGACAGCACTGACCGAAGAGGCAGCCG
TGACTGTAACACCTCCAATCACAGCCCAGCAAGCTGACAACATAGAAGGACCCATAGCCT
TGAAGTTCTCACACCTTTGCCTGGAAGATCATAACAGTTACTGCATCAACGGTGCTTGTG
CATTCCACCATGAGCTAGAGAAAGCCATCTGCAGGTGTTTTACTGGTTATACTGGAGAAA
GGTGTGAGCACTTGACTTTAACTTCATATGCTGTGGATTCTTATGAAAAATACATTGCAA
TTGGGATTGGTGTTGGATTACTATTAAGTGGTTTTCTTGTTATTTTTTACTGCTATATAA
GAAAGAGGTATGAAAAAGACAAAATATGAAGTCACTTCATATGCAATCGTTTGACAAATA
GTTATTCAGGCCCTATAATGTGTCAGGCACTGACATGTAAAATTTTTTTAATTAAAAAAG
AGCTGTAATCTGGCAAAAAGTTTCTATGTAATATTTTTCATGCCTTTTCTCATAAACCCA
GACGAGTGGTAAAAATTTGCCTTCAGTTGTAATAGGAGAGTTCAAACGTACAGTCTCCCT
TCAACCTATCTCTGTCTGCCCATATCAAAATTATAAATGAGGAGGACAGCAGGCCCCAAG
AAAGTAGGGACTAAGTATGTCTTGTTCAAAATTGTATATTCAGTGACTTACACTATGCCT
AGCACACAACACACACTGAGTAAATATTTGTTGAGTGAAATAAAATCAAGAAACAAGTAA
AAACTGA

FIGURE 50

></usr/seqdb2/sst/DNA/Dnaseqs.min/ss.DNA129549
><subunit 1 of 1, 133 aa, 1 stop
><MW: 14792, pI: 5.97, NX(S/T): 0
MALGVPISVYLLFNAMTALTEEAAVTVTPPITAQQADNIEGPIALKFSHLCLEDHNSYCI
NGACAFHHELEKAICRCFTGYTGERCEHLTLTSYAVDSYEKYIAIGIGVGLLLSGFLVIF
YCYIRKRYEKDKI

Important features of the protein:
Signal peptide:

1-20 (weak)

Transmembrane domain:

103-117

N-myristoylation site.
4-10;106-112;110-116

EGF-like domain cysteine pattern signature.
75-87

Integrins beta chain cysteine-rich domain proteins
66-88

FIGURE 51

GGCTCGAGCTTGGCTCTCAGACCATCCTGGTGGAAGAAACACTAGCAGTCTGCCCAATCTGA
ATGCAAATCCAGAATAATCTTTTCTTTTGTTGTTACACAGTTATGAGTGCAATTTTTAAATG
GCTGCTACTCTACAGCCTGCCTGCCTTATGCTTTCTCCTGGGCACGCAGGAAAGTGAGAGCT
TCCACTCCAAAGCAGAGATCCTAGTGACACTAAGTCAGGTAATAATCTCTCCAGCTGGACCT
CATGCACTCACATGGACAACACACTTCTCTCCTTCAGTGATCATCATCCTTGTACCATGTTG
GTGGCATGCTGTAATCGTGACTCAACATCCGGTTGCCAATTGCTATGTAACAAACCACCTCA
ACATTCAGTGGCTTGAATTGAAAGCAGGGTCTTGAAGAGATATTTGCACATTTCATCCTCCC
AGCAGCATTATTCACAACAGCCAATAGGCAGAAGCAACCCAATGTCCAACCATAGATGAGTG
GATAACCAAAATGTAGTCCATCCATACAATGAAATATGATTCAGCCTTAACAAGGAAGGAAG
TCCCGCCACGTGCTACAACATGGATGGACCTTGAGGACACTATGCTAAGTGAAGTAAGCCAG
GCACAAAAGGACAAATACTCTATGATTCCATTTTATAGGGTACCAAAGAGAATCAAACTCAC
AGAGATAGAAAGTAGACTGGGGTGGCCAGGGACTCGGGGAGAGAGGAAAGGGCAGTTATTGT
TTAAAAGGTACAGAGTTTCAGTTTGGGAAGATGAAAATGTTCTGGAAACGGTTAATGGTGAT
TTTACATTGTTTATGTTACCACGATTTGTAAAAGAGCAGCTGCGCTGAGAATGAGCATGCTT
GTCATTGGCAGCTCTCTGAGATTTTCAGTGCCTCTTACTGGCTTGTTAAGAAGACGGCAAAA
AAAAAAAAAAAAAAAAAAAAAAAAAAAAAAAAAAAAAAAAAAAAAAAAAAAA

FIGURE 52

></usr/seqdb2/sst/DNA/Dnaseqs.min/ss.DNA129580
><subunit 1 of 1, 114 aa, 1 stop
><MW: 12886, pI: 7.04, NX(S/T): 0
MQIQNNLFFCCYTVMSAIFKWLLLYSLPALCFLLGTQESESFHSKAEILVTLSQVIISPA
GPHALTWTTHFSPSVIIILVPCWWHAVIVTQHPVANCYVTNHLNIQWLELKAGS

Important features of the protein:
Signal peptide:
Amino acids 1-33

Transmembrane domain:
Amino acids 71-86

N-myristoylation site:
Amino acids 35-41

FIGURE 53

TTTTGAAATGGTTTATGACCTCTTCCCCACTTCCCCGCTTGCTTTGCTCATTAGTGTTCCTA
GGTGGCTGCTGGGTGACGGGCTTTTCATCATCTCTGATGTGGGCCAGTGCGAAAGAGCAGCT
GCAACATCTGTTTCTAATTGGGTCGTGCCTTTATAAATACTTCTTGCCTATTTGTCACATTG
CTTCCCTCCCACCCTGTCTTCCTTGGAGTACTGCAGAATCTGTAAGCGTCCCTGGAATGCAC
ACGTGGACCTTGTCATTCCCAAACAGACTTTCTGCTGGTCAGCACTTTGTAATGTTCGGCTG
TTACAGGCATTAGTCACTTGTGCTCAGAGAGAGACTGTGGTCTTTGGAAACTGAAGAAAATGTC
TTTTTTGTTGTTGTTAATTCTTGGCATCCAGTTAGATTTAACTTCTCAAGAGTTTACACAGA
CTTTTAGAAAAACATTCTGTCTCTAAGAAAAAAGTGCTCTAGCTTTGTACAGTTTTTGGATT
TTCACACTTGGTGGTTGTTTGCTGAAATGCTGTTTTGCTAGTGATTCCCCTCCTCCCCCTAT
CTGGGGTTGTAAGCAGCTCTGGGGCTCTGTTCACTTCGGATACCTGTTTCTGGGGACTGCTT
TTCAACAGCGTTTTTCCTAAGGGCATATGAGAAATTTAATTTCTGATGGAATGAAGGTGAAA
CTCTAGTCCCAGGTAAACCTGGGTAGGCTGTAGAGACAGAAAGGGGGCTGCAGGTCTAGGTG
GAAGAACGAGAACGAATGCAGCATGGTATTTCCAGGCCTTTTAGATTCGGCTTCATCCACAA
CCAATGTGAGTTCTTATCTGCAAAGCGGGCCTAAGTGTAATGGAGGGAAGGTGGGCCAGGCA
CCAGGGTCCTGGGTTCTCCCGCGCCTCACTCTGTCTCCACCTGGCCCATGCATAAAGAACAC
TAGTCAAGTAGCCATTGTACCTGTTTCCTTATCTGAAAATGAGAAGGTTGGAGAGTATGACT
TCTGTTGAAACAACAAGGCGCTTACAAATTTTGGTGAAGTCGAATGAGGGCAGCGTTAAGAG
AAATATCAAAGTTAGTCATTGGATTTCAGGGCTTAGGGATGGAAACCAGCTGGTAGTAGACT
GGTTGTAGTTATGTCCAAAGGGCAGAGTGGGAAAAATTTGGCCGAAAAGAGTGTGGTGGGTG
ACCAGCAAATGTTAGAGGTATACATCAGGGCACAGAGGAGAAAAGCTAACATGATACTGATG
ACTTCAAGTCTTCACTGTCCAATTCAGAGGATAGGGGAGGGTTTAAGCTGATTAAACAGTGG
GCTTTTTTTCTCCTGCAAGAGGGTGGAGGTCTATAACTGTGCAGATTTTATCAGATGCATGC
TAATACATGTTATTCTGGGGGACTCTCTTATACCTTGAAGTAGACATTGCTGCTATTTGCGT
GAAAAAAATAGGAGGACTTATTTGAATTGAGAATGGGGATAGGCTGAGTTCCACCGAGATGT
TGGCTTAGAGATGCCTGGGCCATGCTGTACAGTAGGAAGCCCAGCAGAGGAGATTGGGCTGT
GTGGGTCATGACAAAGGGAGTTGTTAGCTTATGGTTGGCTATTAAAGTCATGGGCAAGGATG
GGCAAGAAAAGTGTGTAAAATGAGCTGACAAAAGATAAATATGTTAATTA

FIGURE 54

></usr/seqdb2/sst/DNA/Dnaseqs.min/ss.DNA129794
><subunit 1 of 1, 102 aa, 1 stop
><MW: 11382, pI: 8.72, NX(S/T): 0
MTSSPLPRLLCSLVFLGGCWVTGFSSSLMWASAKEQLQHLFLIGSCLYKYFLPICHIASL
PPCLPWSTAESVSVPGMHTWTLSFPNRLSAGQHFVMFGCYRH

Important features of the protein:
Signal peptide:
Amino acids 1-21

N-myristoylation site:
Amino acids 18-24

Prokaryotic membrane lipoprotein lipid attachment sites:
Amino acids 9-20;36-47;
89-100

FIGURE 55

ACACTGGCCAAACACTCGCATCCCAGGGCGTCTCCGGCTGCTCCCATTGAGCTGTCTGCTCG
CTGTGCCCGCTGTGCCTGCTGTGCCCGCGCTGTCGCCGCTGCTACCGCGTCTGCTGGACGCG
GGAGACGCCAGCGAGCTGGTGATTGGAGCCCTGCGGAGAGCTCAAGCGCCCAGCTCTGCCCG
AGGAGCCCAGGCTGCCCCGTGAGTCCCATAGTTGCTGCAGGAGTGGAGCCATGAGCTGCGTC
CTGGGTGGTGTCATCCCCTTGGGGCTGCTGTTCCTGGTCTGCGGATCCCAAGGCTACCTCCT
GCCCAACGTCACTCTCTTAGAGGAGCTGCTCAGCAAATACCAGCACAACGAGTCTCACTCCC
GGGTCCGCAGAGCCATCCCCAGGGAGGACAAGGAGGAGATCCTCATGCTGCACAACAAGCTT
CGGGGCCAGGTGCAGCCTCAGGCCTCCAACATGGAGTACATGACCTGGGATGACGAACTGGA
GAAGTCTGCTGCAGCGTGGGCCAGTCAGTGCATCTGGGAGCACGGGCCCACCAGTCTGCTGG
TGTCCATCGGGCAGAACCTGGGCGCTCACTGGGGCAGGTATCGCTCTCCGGGGTTCCATGTG
CAGTCCTGGTATGACGAGGTGAAGGACTACACCTACCCCTACCCGAGCGAGTGCAACCCCTG
GTGTCCAGAGAGGTGCTCGGGGCCTATGTGCACGCACTACACACAGATAGTTTGGGCCACCA
CCAACAAGATCGGTTGTGCTGTGAACACCTGCCGGAAGATGACTGTCTGGGGAGAAGTTTGG
GAGAACGCGGTCTACTTTGTCTGCAATTATTCTCCAAAGGGGAACTGGATTGGAGAAGCCCC
CTACAAGAATGGCCGGCCCTGCTCTGAGTGCCCACCCAGCTATGGAGGCAGCTGCAGGAACA
ACTTGTGTTACCGAGAAGAAACCTACACTCCAAAACCTGAAACGGACGAGATGAATGAGGTG
GAAACGGCTCCCATTCCTGAAGAAAACCATGTTTGGCTCCAACCGAGGGTGATGAGACCCAC
CAAGCCCAAGAAAACCTCTGCGGTCAACTACATGACCCAAGTCGTCAGATGTGACACCAAGA
TGAAGGACAGGTGCAAAGGGTCCACGTGTAACAGGTACCAGTGCCCAGCAGGCTGCCTGAAC
CACAAGGCGAAGATCTTTGGAAGTCTGTTCTATGAAAGCTCGTCTAGCATATGCCGCGCCGC
CATCCACTACGGGATCCTGGATGACAAGGGAGGCCTGGTGGATATCACCAGGAACGGGAAGG
TCCCCTTCTTCGTGAAGTCTGAGAGACACGGCGTGCAGTCCCTCAGCAAATACAAACCTTCC
AGCTCATTCATGGTGTCAAAAGTGAAAGTGCAGGATTTGGACTGCTACACGACCGTTGCTCA
GCTGTGCCCGTTTGAAAAGCCAGCAACTCACTGCCCAAGAATCCATTGTCCGGCACACTGCA
AAGACGAACCTTCCTACTGGGCTCCGGTGTTTGGAACCAACATCTATGCAGATACCTCAAGC
ATCTGCAAGACAGCTGTGCACGCGGGAGTCATCAGCAACGAGAGTGGGGGTGACGTGGACGT
GATGCCCGTGGATAAAAAGAAGACCTACGTGGGCTCGCTCAGGAATGGAGTTCAGTCTGAAA
GCCTGGGGACTCCTCGGGATGGAAAGGCCTTCCGGATCTTTGCTGTCAGGCAGTGAATTTCC
AGCACCAGGGGAGAAGGGGCGTCTTCAGGAGGGCTTCGGGGTTTTGCTTTTATTTTTATTTT
GTCATTGCGGGGTATATGGAGAGTCA

FIGURE 56

```
></usr/seqdb2/sst/DNA/Dnaseqs.min/ss.DNA131590
><subunit 1 of 1, 497 aa, 1 stop
><MW: 55906, pI: 8.43, NX(S/T): 4
MSCVLGGVIPLGLLFLVCGSQGYLLPNVTLLEELLSKYQHNESHSRVRRAIPREDKEEIL
MLHNKLRGQVQPQASNMEYMTWDDELEKSAAAWASQCIWEHGPTSLLVSIGQNLGAHWGR
YRSPGFHVQSWYDEVKDYTYPYPSECNPWCPERCSGPMCTHYTQIVWATTNKIGCAVNTC
RKMTVWGEVWENAVYFVCNYSPKGNWIGEAPYKNGRPCSECPPSYGGSCRNNLCYREETY
TPKPETDEMNEVETAPIPEENHVWLQPRVMRPTKPKKTSAVNYMTQVVRCDTKMKDRCKG
STCNRYQCPAGCLNHKAKIFGSLFYESSSSICRAAIHYGILDDKGGLVDITRNGKVPFFV
KSERHGVQSLSKYKPSSSFMVSKVKVQDLDCYTTVAQLCPFEKPATHCPRIHCPAHCKDE
PSYWAPVFGTNIYADTSSICKTAVHAGVISNESGGDVDVMPVDKKKTYVGSLRNGVQSES
LGTPRDGKAFRIFAVRQ
```

Important features of the protein:

Signal peptide:
Amino acids 1-22

N-glycosylation sites:
Amino acids 27-31;41-45;451-455 cAMP- and cGMP-dependent protein kinase phosphorylation sites:
Amino acids 181-185;276-280;464-468

Tyrosine kinase phosphorylation site:
Amino acids 385-393

N-myristoylation sites:
Amino acids 111-117;115-121;174-180;204-210;227-233;300-306;
447-453;470-476

Extracellular proteins SCP/Tpx-1/Ag5/PR-1/Sc7 signature 2:
Amino acids 195-207

SCP-like extracellular protein:
Amino acids 56-208

FIGURE 57

GCACGAGGCCAAACACAGCAGCCTCAACATGAAGGTGGTTATGGTCCTCCTGCTTGCTGCCC
TCCCCCTTTACTGCTATGCAGGTTCTGGTTGCGTTCTTCTGGAGAGCGTCGTGGAAAAGACC
ATCGATCCATCGGTTTCTGTGGAGGAATACAAAGCAGATCTTCAGAGGTTCATCGACACTGA
GCAAACCGAAGCAGCTGTAGAGGAGTTCAAGGAGTGCTTCCTCAGCCAGAGCAATGAGACTC
TGGCCAACTTCCGAGTCATGGTGCATACGATATATGACAGCCTTTACTGTGCTGCGTATTAA
CTGTCACAAGAACTTTGGCTCAGAGGAATCCAGACGATGCTCACAACCCGACTGTGGACTGG
CAGAAATCTCAACTTTTCCTTTTGACTTTCCCCTTTGATCAGTAATATGGAAGACGTTGTTG
AAACCTGAAGTATAGTTAATTTAAATAAACCCACTGCAAGAAAAAAAAAAAA

FIGURE 58

```
></usr/seqdb2/sst/DNA/Dnaseqs.min/ss.DNA135173
><subunit 1 of 1, 93 aa, 1 stop
><MW: 10456, pI: 4.37, NX(S/T): 1
MKVVMVLLLAALPLYCYAGSGCVLLESVVEKTIDPSVSVEEYKADLQRFIDTEQTEAAVE
EFKECFLSQSNETLANFRVMVHTIYDSLYCAAY
```

Important features of the protein:
Signal peptide:
Amino acids 1-18

Prokaryotic membrane lipoprotein lipid attachment site:
Amino acids 12-23

FIGURE 59A

CAAGTCCGTTGAGGCTGCCAGGCGAGTCAGGTCTCTCTGGACCTCGCCTGACTCGGCTGGGC
TGTGCCTGAAATTGACCCAGCTCCACCATACTCCTTGATTATGAGAAAACAAGGAGTAAGCT
CAAAGCGGCTGCAATCTTCCGGCCGCAGCCAGTCTAAGGGGCGGCGCGGGGCCTCCCTCGCC
CGGGAGCCGGAGGTAGAGGAGGAGGTGGAAAAGTCGGTCCTAGGCGGCGGGAAACTGCCAAG
GGGCGCCTGGAGGTCCTCCCCGGGGAGGATCCAAAGTCTGAAAGAGCGAAAAGGCTTGGAGC
TAGAGGTGGTGGCCAAGACCTTTCTTCTCGGCCCCTTCCAGTTCGTCCGTAATTCCCTGGCG
CAGCTCCGGGAAAAGGTGCAGGAACTGCAGGCGCGGCGGTTCTCCAGCAGAACCACTCTCGG
CATCGCTGTCTTTGTGGCAATTTTACATTGGTTACATTTAGTAACACTTTTTGAAAATGATC
GTCATTTCTCTCACCTCTCATCTTTGGAACGGGAGATGACTTTTCGCACTGAAATGGGACTT
TATTATTCATACTTCAAGACCATTATTGAAGCACCTTCGTTTTTGGAAGGACTGTGGATGAT
TATGAATGACAGGCTTACTGAATATCCTCTTATAATTAATGCAATAAAACGCTTCCATCTTT
ATCCAGAGGTAATCATAGCCTCCTGGTATTGCACATTCATGGGAATAATGAATTTATTTGGA
CTAGAAACTAAGACCTGCTGGAATGTCACCAGAATAGAACCTCTTAATGAAGTTCAAAGCTG
TGAAGGATTGGGAGATCCTGCTTGCTTTTATGTTGGTGTAATCTTTATTTTAAATGGACTAA
TGATGGGATTGTTCTTCATGTATGGAGCATACCTGAGTGGGACTCAACTGGGAGGTCTTATT
ACAGTACTGTGCTTCTTTTTCAACCATGGAGAGGCCACCCGTGTGATGTGGACACCACCTCT
CCGTGAAAGTTTTTCCTATCCTTTCCTTGTACTTCAGATGTGTATTTTAACTTTGATTCTCA
GGACCTCAAGCAATGATAGAAGGCCCTTCATTGCACTCTGTCTTTCCAATGTTGCTTTTATG
CTTCCCTGGCAATTTGCTCAGTTTATACTTTTTACACAGATAGCATCATTATTTCCCATGTA
TGTTGTGGGATACATTGAACCAAGCAAATTTCAGAAGATCATTTATATGAACATGATTTCAGTT
ACCCTTAGTTTCATTTTGATGTTTGGAAATTCAATGTACTTATCTTCTTATTATTCTTCATC
TTTGTTAATGACGTGGGCAATAATTCTAAAGAGAAATGAAATTCAAAAACTGGGAGTATCTA
AACTCAACTTTTGGCTAATTCAAGGTAGTGCCTGGTGGTGTGGAACAATCATTTTGAAATTT
CTGACATCTAAAATCTTAGGCGTTTCAGACCACATTCGCCTGAGTGATCTTATAGCAGCCAG
AATCTTAAGGTATACAGATTTTGATACTTTAATATATACCTGTGCTCCCGAATTTGACTTCA
TGGAAAAAGCGACTCCGCTGAGATACACAAAGACATTATTGCTTCCAGTTGTTATGGTGATT
ACATGTTTTATCTTTAAAAAGACTGTTCGTGATATTTCATATGTTTTAGCTACAAACATTTA
TCTAAGAAAACAGCTCCTTGAACACAGTGAGCTGGCTTTTCACACATTGCAGTTGTTAGTGT
TTACTGCCCTTGCCATTTTAATTATGAGGCTAAAGATGTTTTTGACACCGCACATGTGTGTT
ATGGCTTCCTTGATATGCTCTCGACAGCTCTTTGGCTGGCTTTTTCGCAGAGTTCGTTTTGA
GAAGGTTATCTTTGGCATTTTAACAGTGATGTCAATACAAGGTTATGCAAACCTCCGTAATC
AATGGAGCATAATAGGAGAATTTAATAATTTGCCTCAGGAAGAACTTTTACAGTGGATCAAA
TACAGTACCACATCAGATGCTGTCTTTGCAGGTGCCATGCCTACAATGGCAAGCATCAAGCT
GTCTACACTTCATCCCATTGTGAATCATCCACATTACGAAGATGCAGACTTGAGGGCTCGGA
CAAAAATAGTTTATTCTACATATAGTCGAAAATCTGCCAAAGAAGTAAGAGATAAATTGTTG
GAGTTACATGTGAATTATTATGTTTTAGAAGAGGCATGGTGTGTTGTGAGAACTAAGCCTGG
TTGCAGTATGCTTGAAATCTGGGATGTGGAAGACCCTTCCAATGCAGCTAACCCTCCCTTAT
GTAGCGTCCTGCTCGAAGACGCCAGGCCTTACTTCACCACAGTATTTCAGAATAGTGTGTAC
AGAGTATTAAAGGTTAACTGAGAAGGATACTACCCATTTTACTATGGCACAATGCCGTGTGT
CAAAAACAATCACCCTTTGGCTTATTCACATTAATAAAAATCACAAGCTTTAATAACAGACA
CTTAAAAATAAGATAAAAATGGATTGGAAATTTTTCTGATTACTAAAAGGTAAATTACTTTT
CTGTTCATTGAATGTCAGCCTTATTAAGCTTGTCATATAAGTTATTAAATCATTCATGTCAT
ACTGCATAAACAAATGTTCATTTCAGAATTTTAAAGAGAAATGTATATAAAGAACMATGATT
TTAATAATCAGGGGTATGTAAGTCCTTTTTCATCCAACTAGGTGAATTGCTTCAGATTTTCT
CTAGTACCAGAGGGTACCTCCTCAAACTCTTTGAACCACTTAAGGCAGAAGAATGCAAGCTC
TGAAATGACATCCTTAAAATGCTGATACTGGTCACAGCCTCTTTACCTCTGTGAGGAAATTG
TAACAGTGTGTCTTTTAAGGTGTTTTTATTTTACCAGCCCTTAAGAAAGATCTCTAATACCT
TTTAATACTTTTTTTTAATAATTTCAAGTTGAAGTGTTTTTAAAAACACTTTGTTTTGTAAT
GTTTTGAATCTCTTGAGATGTGTTTACCCCACTAGATACATATTTGCCACTGGTTAGTTCTC
CATCTAAGCTCAAGAGGTTATTCATCTCTCTTTAGATTCCAGTGGCTTTTCTTTTAACATCC
AGGTAAAACAGAAACTGCTATGGTATACAACCAAGTTTTGGGGTTAAACATAATCAGAAAAG

FIGURE 59B

AAAATCCAGTTAAATTTATGAAGTGAGATTTTCAGATCCTAGATCTTGAATAAAGGAAAGGT
CTTTTCATCTTGATGGCCCCAAAGCTTGTTGGTCATGGTCTTTATTTCTGGCCACTATCTTC
TTAAATAATATATTTTTAAGCCCTCATTTATTTTTGGTTTTGGGTGAGGAAAGTCATGTTTT
CTAAGTCCTCTCCCCTAATAAAACCTACCCAACAATAGTGCTTTGAAAAGTGGTAGTTATCT
TGAAGATACTCTTGCCAAATGCAAAGATAAACATTCTTTTTGTCTGCTTTATAAATATGAAA
TATGCCAGATCTATAGTATTTTAATGTGCATCTACTTTAAATGAGTCATCTTGGGGTTTTTA
TAATTCCCTTATGTTCTTGCCCCTCTACACTTGAAATAACAAAATGCCTTAATTTTATGGAT
TAGTTCTCTTATAGTAGACAGGCAGCTATATGCAGCAAAACCAATAAAGTTATTTTTCAACT
TTCATAGTTGTAAAATATCTTATACCAGAATACAAAACAGCTAAGAAAACATGCCACATTTTAT
TTTAGCATTTTCAAATAATTTGTTTTTGGTGTAAGCACAGGATAAAAAAGGAGAGCGTCAAA
GAAAAGAGACATAACACCTAACATTCATAAAAATTAACAAAGTATATTTTGGATGATGTTTT
TACAGGAAATATTTTAAATAAGTTGGTAGAACTTTTAAAATGGTACTGTATTAGCTAATAAA
ATATTCAGTACAAATATATGTTTGGATTTATGCATTAAAAAACTAATAAAATTATTTCCAAC
TTTA

FIGURE 60

></usr/seqdb2/sst/DNA/Dnaseqs.min/ss.DNA138039
><subunit 1 of 1, 758 aa, 1 stop
><MW: 87354, pI: 9.36, NX(S/T): 1
MRKQGVSSKRLQSSGRSQSKGRRGASLAREPEVEEEVEKSVLGGGKLPRGAWRSSPGRIQ
SLKERKGLELEVVAKTFLLGPFQFVRNSLAQLREKVQELQARRFSSRTTLGIAVFVAILH
WLHLVTLFENDRHFSHLSSLEREMTFRTEMGLYYSYFKTIIEAPSFLEGLWMIMNDRLTE
YPLIINAIKRFHLYPEVIIASWYCTFMGIMNLFGLETKTCWNVTRIEPLNEVQSCEGLGD
PACFYVGVIFILNGLMMGLFFMYGAYLSGTQLGGLITVLCFFFNHGEATRVMWTPPLRES
FSYPFLVLQMCILTLILRTSSNDRRPFIALCLSNVAFMLPWQFAQFILFTQIASLFPMYV
VGYIEPSKFQKIIYMNMISVTLSFILMFGNSMYLSSYYSSSLLMTWAIILKRNEIQKLGV
SKLNFWLIQGSAWWCGTIILKFLTSKILGVSDHIRLSDLIAARILRYTDFDTLIYTCAPE
FDFMEKATPLRYTKTLLLPVVMVITCFIFKKTVRDISYVLATNIYLRKQLLEHSELAFHT
LQLLVFTALAILIMRLKMFLTPHMCVMASLICSRQLFGWLFRRVRFEKVIFGILTVMSIQ
GYANLRNQWSIIGEFNNLPQEELLQWIKYSTTSDAVFAGAMPTMASIKLSTLHPIVNHPH
YEDADLRARTKIVYSTYSRKSAKEVRDKLLELHVNYYVLEEAWCVVRTKPGCSMLEIWDV
EDPSNAANPPLCSVLLEDARPYFTTVFQNSVYRVLKVN

Important features of the protein:
Transmembrane domain:
Amino acids 109-124;197-213;241-260;266-283;302-315;336-356;
376-391;430-450;495-509;541-560;584-599;634-647

N-glycosylation site:
Amino acids 222-226 cAMP- and cGMP-dependent protein kinase phosphorylation site:
Amino acids 102-106

Tyrosine kinase phosphorylation site:
Amino acids 511-519

N-myristoylation sites:
Amino acids 24-30;50-56;151-157;254-260;264-270;269-275;
273-279;639-645

Amidation site:
Amino acids 20-24

FIGURE 61

GGCGCGGCCACATCCTTTAAATATGGTCTTTCTTGGGCGCGCGCGACAATGTGAGGAGTGGG
GTGGAGCGTGTGTGGTGTGTGGCTGCGGCCTGGGCAAGAGCCGCCGCGGACCATGAGCTGAG
TAAGTTCTGGAGGGATCCTGCCTCTTGGAGCCTTCGCAGCCAGGCAGCTGTGAACTGTGAGC
TAGAGTGAAGCAGAAATCTAGGAAGATGAGCTCCAAGATGGTCATAAGTGAACCAGGACTGA
ATTGGGATATTTCCCCCAAAAATGGCCTTAAGACATTTTTCTCTCGAGAAAATTATAAAGAT
CATTCCATGGCTCCAAGTTTAAAAGAACTACGTGTTTTATCCAACAGACGTATAGGAGAAAA
TTTGAATGCCTCAGCAAGTTCTGTAGAAAATGAGCCGGCAGTTAGTTCAGCAACTCAAGCAA
AGGAAAAAGTTAAAACCACAATTGGAATGGTTCTTCTTCCAAAACCAAGAGTTCCTTATCCT
CGTTTCTCTCGTTTCTCACAGAGAGAGCAGAGGAGTTATGTGGACTTGTTGGTTAAATACGC
AAAGATTCCTGCAAATTCCAAAGCTGTTGGAATAAATAAAAATGACTACTTGCAGTACTTGG
ATATGAAAAAACATGTGAACGAAGAAGTTACTGAGTTCCTAAAGTTTTTGCAGAATTCTGCA
AAGAAATGTGCGCAGGATTATAATATGCTTTCTGATGATGCCCGTCTCTTCACAGAGAAAAT
TTTAAGAGCTTGCATTGAACAAGTGAAAAAGTATTCAGAATTCTATACTCTCCACGAGGTCA
CCAGCTTAATGGGATTCTTCCCATTCAGAGTAGAGATGGGATTAAAGTTAGAAAAAACTCTT
CTCGCATTGGGCAGTGTAAAATATGTGAAAACAGTATTTCCCTCAATGCCTATAAAGTTGCAG
CTGTCAAAGGACGATATAGCTACCATTGAAACGTCAGAACAAACAGCTGAAGCTATGCATTA
TGATATTAGTAAAGATCCAAATGCAGAGAAGCTTGTTTCCAGATATCACCCTCAGATAGCTC
TAACTAGTCAGTCATTATTTACCTTATTAAATAATCATGGACCAACGTACAAGGAACAGTGG
GAAATTCCAGTGTGTATTCAAGTAATACCTGTTGCAGGTTCAAAACCAGTTAAAGTAATATA
TATTAATTCACCACTTCCCCAAAAGAAAATGACTATGAGAGAGAGAAATCAAATCTTTCATG
AAGTTCCATTAAAATTTATGATGTCCAAAAACACATCTGTTCCAGTCTCTGCAGTCTTTATG
GACAAACCTGAAGAGTTTATATCTGAAATGGACATGTCCTGTGAAGTCAACGAGTGCCGAAA
AATTGAGAGTCTTGAAAACTTGTATTTGGATTTTGATGATGATGTCACAGAACTTGAAACTT
TTGGAGTAACCACCACCAAAGTATCAAAATCACCAAGTCCAGCAAGTACTTCCACAGTACCT
AACATGACAGATGCTCCTACAGCCCCCAAAGCAGGAACTACAACTGTGGCACCAAGTGCACC
AGACATTTCTGCTAATTCTAGAAGTTTATCTCAGATTCTGATGGAACAATTGCAAAAGGAGA
AACAGCTGGTCACTGGTATGGATGGTGGCCCTGAGGAATGCAAAAATAAAGATGATCAGGGA
TTTGAATCATGTGAAAAGGTATCAAATTCTGACAAGCCTTTGATACAAGATAGTGACTTGAA
AACATCTGATGCCTTACAGTTAGAAAATTCTCAGGAAATTGAAACTTCTAATAAAAATGATA
TGACTATAGATATACTACATGCTGATGGTGAAAGACCTAATGTTCTAGAAAACCTAGACAAC
TCAAAGGAAAAGACTGTTGGATCAGAAGCAGCAAAAACTGAAGATACAGTTCTCTGCAGCAG
TGATACAGATGAGGAGTGTTTAATCATTGATACAGAATGTAAAAAAACCAGTTATAACAGTG
TTTAATTTAGATAAGTTTGAGGGAAAATAATCAGTAGGCAAGAGGAACATTTTTCCTGTAGT
AGCTAGAGTGCCTTGAAAAAATGTGTTGGCTATGTGAAGGAATATTTCAACTAAAATGGAAT
GGTATGCTTTTCACCCTTAAAGTTTGAGGAGGATCTTGATATGTTTTAACATTATCATGGCA
GGGAAATATATAAAGAAGAAAAATATTTTTACATTAAACCTTTTCTAAAAATTGTAAATAGA
AAAATAATTTGGTTTTTTATCAAGAACAACACTTATCGTTATGTATTGTGTTAGTTATATTG
CCAGTCTGTTGCGACTGACTCAAAAAGTTAAATGTTGCCACTGCTGAAGATGATTATGAGCA
TCGCAAACTTTGTTTCTGACCCATTTTGACAGTTTTTATATACTCCTTTAAAATGATGAATG
TTACAGGTTAATAAAGTTAATACCTTTAAA

FIGURE 62

></usr/seqdb2/sst/DNA/Dnaseqs.min/ss.DNA139540
><subunit 1 of 1, 592 aa, 1 stop
><MW: 66453, pI: 5.42, NX(S/T): 3
MSSKMVISEPGLNWDISPKNGLKTFFSRENYKDHSMAPSLKELRVLSNRRIGENLNASAS
SVENEPAVSSATQAKEKVKTTIGMVLLPKPRVPYPRFSRFSQREQRSYVDLLVKYAKIPA
NSKAVGINKNDYLQYLDMKKHVNEEVTEFLKFLQNSAKKCAQDYNMLSDDARLFTEKILR
ACIEQVKKYSEFYTLHEVTSLMGFFPFRVEMGLKLEKTLLALGSVKYVKTVFPSMPIKLQ
LSKDDIATIETSEQTAEAMHYDISKDPNAEKLVSRYHPQIALTSQSLFTLLNNHGPTYKE
QWEIPVCIQVIPVAGSKPVKVIYINSPLPQKKMTMRERNQIFHEVPLKFMMSKNTSVPVS
AVFMDKPEEFISEMDMSCEVNECRKIESLENLYLDFDDDVTELETFGVTTTKVSKSPSPA
STSTVPNMTDAPTAPKAGTTTVAPSAPDISANSRSLSQILMEQLQKEKQLVTGMDGGPEE
CKNKDDQGFESCEKVSNSDKPLIQDSDLKTSDALQLENSQEIETSNKNDMTIDILHADGE
RPNVLENLDNSKEKTVGSEAAKTEDTVLCSSDTDEECLIIDTECKKTSYNSV

Important features of the protein:
N-glycosylation sites:
Amino acids 56-60;354-358;427-431 cAMP- and cGMP-dependent protein kinase phosphorylation sites:
Amino acids 187-191;331-335;585-589

N-myristoylation sites:
Amino acids 126-132;407-413;557-563

FIGURE 63

TTTTTAACTTGAACTTCCAAGGCCACGTGCGTCTCCTGGCTCCTGCACGGACTGTGTGACTG
TCCCCGACAGCTTTCCTGTCTCGTCTCATGAGGGGTCCAGCACATGGCATTCTGGGTCGGCA
CCTGAAGTCCACCTCTATGAGACCCTCTGGGAGCGTGACGGGGCCTTGGCATGGGTCGGCCG
AGGCCCTTCTGTCCCAGGTCACTGGTGTGGTCGGCCCAGGCCCTCCTGTCCCACATCACCTG
TGTGGTCGGCCCAGGCCCTCCTGTCCCAGGTCACCGGTGTGGTCGGCCCAGGCCCTCCTGTC
CAGGTCCTCCTGTCCAGGTCACTGGTGTGGTCGGCCCAGGCCCTTCTGTCCCAGGTCACCTG
TGTGGTCGGCCCAGGGCCCTCCTGTACCATGTCACTGTTGAGGGGCTGGCTCTGGAAGAGGG
CAGGGACTTGGCATTGGTGGGGGCAGGGTTCCAAGGTGTGGCCTGTCAGCAGGAAGGGGCAG
GTGGCATGGGTCCAGGCGGGACTCAGGGCTGGGGTGCCACTGCTGGAGACTGTCCGGAGGCC
CCTCCAGGGCACCTTGCCATTGCCATTGTCGCTCATGGCCATCTGGTCCCGTTTCAGGGAAC
AAGAGGAGGATCAGATGCTGCGGGACATGATTGAGAAGCTGGGTGACTGGGCCGGGGATGCT
GAGGGCTGGGCTGGCTGGCTGGGTGGGCCGGGGATGCTGAGTGCTGGGCTGGCTGGCTGGGT
GGACCGGGCCTCCAGCTGGGGGTGGGGGGGGGCGGGTATCGGGTCCCCCCCTCAGCCTTGG
TGACAGGACAGGCAGGTTCACCCTGAGGGTGAGAGCTCCCTCCCGCCCCTAAGAGAGCCAGG
GGCAGCTGGTGACCGTGTGGTCATGGTGGGGACCAGCCCTCCGGGGCACCCAGTCGGGGCAG
GTTCTCACGTGGGAGGGCACAGGGCTTCCTGCAGGCTCGGAGGCCCAGGGCGGATTGTGGCC
AGTGGAAGGGAAGGATGTTTCTGGCAGGGGGACTTGTGTGGGCCACGGCTGTGCGGCTGCGG
CGTTGAGCACGGCCTCACTGTCCACCTGTCCCCTAGGCCTCCAGAGGAAGAAGTCCAAGTTC
CGCTTGTCCAAGATCTGGTCACCAAAAAGCAAAAGCAGCCCCTCCCAGTAGTAGCCAGTAGG
GCCGTGGGCTCGGCCCGGACCTGGCATCCGGACTTGGACTCGGGGCCATGGGCTTGGCCCGG
ACCCGGAACCCGGACTTGTACTCGGGGCCGTGGGCTCGGCCCGGACCCGGCATTCGGACTTG
GACTCGGGAAGGGCCTCCTGTCCCTACAAGGGGCATGTGGACAGCAGGGACCTGCGCTACCG
TCTGTGGTCTCAATAAAGAAACCGACCACATGGCCCCGGAAAAAAAAAAAAAAAAAAAAAAA
AAAAAAAAAAAAAAAAAAAAAAACA

FIGURE 64

```
><</usr/seqdb2/sst/DNA/Dnaseqs.min/ss.DNA139602
><subunit 1 of 1, 159 aa, 1 stop
><MW: 15900, pI: 8.07, NX(S/T): 0
MGRPRPFCPRSLVWSAQALLSHITCVVGPGPPVPGHRCGRPRPSCPGPPVQVTGVVGPGP
SVPGHLCGRPRALLYHVTVEGLALEEGRDLALVGAGFQGVACQQEGAGGMGPGGTQGWGA
TAGDCPEAPPGHLAIAIVAHGHLVPFQGTRGGSDAAGHD
```

Important features of the protein:
Signal peptide:
Amino acids 1-25

N-myristoylation sites:
Amino acids 109-115;113-119;119-125;148-154;151-157;152-158

FIGURE 65

GGCGACCACCGCCGCCTCCTCACCTGGCCATTGGTGCAGCCCGTTCCCGGCGGCGAGAGAAG
GCAGGCGCGCTCCTTGCGCCACGCCACACCGTCGGGCCCCCGTCGGGTCCCCCTCGGGCCGCA
ATGGTGGGCTCCGCGCGGCTGGGTCCGGCACTCTTGACCCCCTTTGTAACCACCGCGGCGGG
CACCCAGGGAGTTCGAGCAACGAAGTTGGTGACCTGCCCCGCTCCCAGGCAGTTTGCTGTTG
GGGCTTTCACGGCTGCTGGAAGGGCATGGCTGTTTGTCCCATCACTGGGCGCCAGCTTCTCA
AAGCTACGTTCACAGCAACGCAGTAGGGACTTTCGTGGCAGGCTTTTTTTAAGAGCTGAAAG
AAGGGCGGGAGGGTTTACGTCCTAGGGTGATGATTTCCTCACCAGACAGCGAAGTATCTATT
GGGAAACTCCAGGTGACCGCACCTCCTTCCGACAGTTCGCCCCGGGGCAAGTTTACCAGCTG
CGTCAGAAAGCAGGTTTGCAAAATCCTTGGAGAACGGCCTGAGCTAAGGACTGGGGTCAGGA
GGGTTTTAAACTCATTCTGATTTTCTTGCAATCATATCTCTTGAAAGTTTTTATATTTTCCC
CAATATTTTTCTGAGTTGCTATATCCAATGAAAACAATGCTGATGTAGAGGTCCACCAGCCA
ATGCTTTATTGGAAGTCAACGAATGAGACCGAGGGTGGCCCATAATCAATCTCGGCACGCGG
GAATGTGAACCTCTTCCAAGGTCTGGGCGAGTCCCTAGAGTTACGCAGATGAAGGACATTGG
CCCTCGAGAATCTCACACCAGCAAAGAAGAGCACAACGAAGCGCAAACTACTTATGATCATT
GTGGCTTTGGGCAAGTTGTTGTAGCTCCCAGCAACAATTTCTTCACCTGGAGTGCAGCAATA
AATGATACTGGTGCTGCAGGGCAGCTAATAAGCTTCTGAATAATATATGCAAAGTACTTGGC
ACCATGAGCAGAACTCAGTATACCGTCACTGAAGAAATAGCTTATTTAATGATTACACTTTT
CATATGTGCAAGTAAAAGTTTGACTTTTAGGGAGAGCCTCACCTACGGAATGTCTTTTTTAA
ATTTCTTTTTTAATTATACTTTAAGTTCTGGGATACATGTGCAGAACGTGCAGGTTTGTTAC
ACAGGTATACATGTGCCATGGTGGTTTGCAGCACCCATCAACCCTTCATCTAGGTTTTAAGC
TCCGCATGCATTAGTTATTTGTCCTAATGCTCTCCCTCCCCTTGTCCCCCACCCCCCAACAG
GCCTCAGGGTGTGATGTTCCCCTCCCTGGGTCCATATGTTCTCATTGTTCAACTCCCACTTA
TGATGAGAACATGCAGTGTTTGGTTTTCTGTTCCTGTGTTAGTTTGCTGAGAATGATGGTTT
CCAGCATCATCCACGTCCCTGCAAAGGACATGAATTCATTCTTTTTTATGGCTGCATGGTAT
TCCATGGTGTATATGTGCCACATTTTCTTCATCCAGTCTATCATTGATGGGCACTTGGGTTG
GTTCCAAGACTTTGTTATTGTGAACAGTGCTGCAATAAACATACGTTTGTATGTGTCAAAAA
AAAAAAAAAAAAAAAA

FIGURE 66

></usr/seqdb2/sst/DNA/Dnaseqs.min/ss.DNA139632
><subunit 1 of 1, 90 aa, 1 stop
><MW: 9586, pI: 12.18, NX(S/T): 0
MVGSARLGPALLTPFVTTAAGTQGVRATKLVTCPAPRQFAVGAFTAAGRAWLFVPSLGAS
FSKLRSQQRSRDFRGRLFLRAERRAGGFTS

Important features of the protein:
Signal peptide:
Amino acids 1-24

N-myristoylation sites:
Amino acids 24-30;42-48;58-64

FIGURE 67

CATGTCTAGACTGGGAGCCCTGGGTGGTGCCCGTGCCGGGCTGGGACTGTTGCTGGGTACCG
CCGCCGGCCTTGGATTCCTGTGCCTCCTTTACAGCCAGCGATGGAAACGGACCCAGCGTCAT
GGCCGCAGCCAGAGCCTGCCCAACTCCCTGGACTATACGCAGACTTCAGATCCCGGACGCCA
CGTGATGCTCCTGCGGGCTGTCCCAGGTGGGGCTGGAGATGCCTCAGTGCTGCCCAGCCTTC
CACGGGAAGGACAGGAGAAGGTGCTGGACCGCCTGGACTTTGTGCTGACCAGCCTTGTGGCG
CTGCGGCGGGAGGTGGAGGAGCTGAGAAGCAGCCTGCGAGGGCTTGCGGGGGAGATTGTTGG
GGAGGTCCGATGCCACATGGAAGAGAACCAGAGAGTGGCTCGGCGGCGAAGGTTTCCGTTTG
TCCGGGAGAGGAGTGACTCCACTGGCTCCAGCTCTGTCTACTTCACGGCCTCCTCGGGAGCC
ACGTTCACAGATGCTGAGAGTGAAGGGGGTTACACAACAGCCAATGCGGAGTCTGACAATGA
GCGGGACTCTGACAAAGAAAGTGAGGACGGGGAAGATGAAGTGAGCTGTGAGACTGTGAAGA
TGGGGAGAAAGGATTCTCTTGACTTGGAGGAAGAGGCAGCTTCAGGTGCCTCCAGTGCCCTG
GAGGCTGGAGGTTCCTCAGGCTTGGAGGATGTGCTGCCCCTCCTGCAGCAGGCCGACGAGCT
GCACAGGGGTGATGAGCAAGGCAAGCGGGAGGGCTTCCAGCTGCTGCTCAACAACAAGCTGG
TGTATGGAAGCCGGCAGGACTTTCTCTGGCGCCTGGCCCGAGCCTACAGTGACATGTGTGAG
CTCACTGAGGAGGTGAGCGAGAAGAAGTCATATGCCCTAGATGGAAAAGAAGAAGCAGAGGC
TGCTCTGGAGAAGGGGGATGAGAGTGCTGACTGTCACCTGTGGTATGCGGTGCTTTGTGGTC
AGCTGGCTGAGCATGAGAGCATCCAGAGGCGCATCCAGAGTGGCTTTAGCTTCAAGGAGCAT
GTGGACAAAGCCATTGCTCTCCAGCCAGAAAACCCCATGGCTCACTTTCTTCTTGGCAGGTG
GTGCTATCAGGTCTCTCACCTGAGCTGGCTAGAAAAAAAAACTGCTACAGCCTTGCTTGAAA
GCCCTCTCAGTGCCACTGTGGAAGATGCCCTCCAGAGCTTCCTAAAGGCTGAAGAACTACAG
CCAGGATTTTCCAAAGCAGGAAGGGTATATATTTCCAAGTGCTACAGAGAACTAGGGAAAAA
CTCTGAAGCTAGATGGTGGATGAAGTTGGCCCTGGAGCTGCCAGATGTCACGAAGGAGGATT
TGGCTATCCAGAAGGACCTGGAAGAACTGGAAGTCATTTTACGAGACTAACCACGTTTCACT
GGCCTTCATGACTTGATGCCACTATTTAAGGTGGGGGGGCGGGGAGGCTTTTTTCCTTAGAC
CTTGCTGAGATCAGGAAACCACACAAATCTGTCTCCTGGGTCTGACTGCTACCCACTACCAC
TCCCCATTAGTTAATTTATTCTAACCTCTAACCTAATCTAGAATTGGGGCAGTACTCATGGC
TTCCGTTTCTGTTGTTCTCTCCCTTGAGTAATCTCTTAAAAAAATCAAGATTCACACCTGCC
CCAGGATTACACATGGGTAGAGCCTGCAAGACCTGAGACCTTCCAATTGCTGGTGAGGTGGA
TGAACTTCAAAGCTATAGGAACAAAGCACATAACTTGTCACTTTAATCTTTTTCACTGACTA
ATAGGACTCAGTACATATAGTCTTAAGATCATACCTTACCTACCAAGGTAAAAAGAGGGATCA
GAGTGGCCCACAGACATTGCTTTCTTATCACCTATCATGTGAATTCTACCTGTATTCCTGGG
CTGGACCACTTGATAACTTCCAGTGTCCTGGCAGCTTTTGGAATGACAGCAGTGGTATGGGG
TTTATGATGCTATAAAACAATGTCTGAAAAGTTGCCTAGAATATATTTTGTTACAAACTTGA
AATAAACCAAATTTGATGTT

FIGURE 68

```
></usr/seqdb2/sst/DNA/Dnaseqs.min/ss.DNA139686
><subunit 1 of 1, 470 aa, 1 stop
><MW: 52118, pI: 5.06, NX(S/T): 0
MSRLGALGGARAGLGLLLGTAAGLGFLCLLYSQRWKRTQRHGRSQSLPNSLDYTQTSDPG
RHVMLLRAVPGGAGDASVLPSLPREGQEKVLDRLDFVLTSLVALRREVEELRSSLRGLAG
EIVGEVRCHMEENQRVARRRRFPFVRERSDSTGSSSVYFTASSGATFTDAESEGGYTTAN
AESDNERDSDKESEDGEDEVSCETVKMGRKDSLDLEEEAASGASSALEAGGSSGLEDVLP
LLQQADELHRGDEQGKREGFQLLLNNKLVYGSRQDFLWRLARAYSDMCELTEEVSEKKSY
ALDGKEEAEAALEKGDESADCHLWYAVLCGQLAEHESIQRRIQSGFSFKEHVDKAIALQP
ENPMAHFLLGRWCYQVSHLSWLEKKTATALLESPLSATVEDALQSFLKAEELQPGFSKAG
RVYISKCYRELGKNSEARWWMKLALELPDVTKEDLAIQKDLEELEVILRD
```

Important features of the protein:

Signal peptide:
Amino acids 1-32 cAMP- and cGMP-dependent protein kinase phosphorylation site:
Amino acids 209-213

N-myristoylation sites:
Amino acids 5-11;8-14;9-15;15-21;19-25;72-78;164-170;
174-180;222-228;230-236

Amidation sites:
Amino acids 207-211;254-258

Cell attachment sequence:
Amino acids 250-253

FIGURE 69

CCCACGCGTCCGAAACACTTTAAACCTGACCAGCTAAATGGATAAACCTAGCCTGCATAGCT
TTTAAACTGGGGTCTCATACAGCACAGGAGGCCTACTTGCTTCAAGAACTGAAAATCCAGAG
GATGAATTGCTTTATCTGGGAATGGCAAAAGCCAGCACAATAAGGAATGCCAGTTTGTATGG
GGCTACTAGCTCACATGCGGGATCAGAATGGTGTGAATGACAGCCGCACTGTGTCATGAAGG
TGGTGGTGGTTTCCGCACAAGAGACCAAATAAGAAGAAAGCTGAGAGAGGGGGGAAACGTTTTT
GGATGACAAAGGATGGGTTTCCATTTAATTACGCAGCTGAAAGGCATGAGTGTGGTGCTGGT
GCTACTTCCTACACTGCTGCTTGTTATGCTCACGGGTGCTCAGAGAGCTTGCCCAAAGAACT
GCAGATGTGATGGCAAAATTGTGTACTGTGAGTCTCATGCTTTCGCAGATATCCCTGAGAAC
ATTTCTGGAGGGTCACAAGGCTTATCATTAAGGTTCAACAGCATTCAGAAGCTCAAATCCAA
TCAGTTTGCCGGCCTTAACCAGCTTATATGGCTTTATCTTGACCATAATTACATTAGCTCAGTG
GATGAAGATGCATTTCAAGGGATCCGTAGACTGAAAGAATTAATTCTAAGCTCCAACAAAAT
TACTTATCTGCACAATAAAACATTTCACCCAGTTCCCAATCTCCGCAATCTGGACCTCTCCT
ACAATAAGCTTCAGACATTGCAATCTGAACAATTTAAAGGCCTTCGGAAACTCATCATTTTG
CACTTGAGATCTAACTCACTAAAGACTGTGCCCATAAGAGTTTTTCAAGACTGTCGGAATCT
TGATTTTTTGGATTTGGGTTACAATCGTCTTCGAAGCTTGTCCCGAAATGCATTTGCTGGCC
TCTTGAAGTTAAAGGAGCTCCACCTGGAGCACAACCAGTTTTCCAAGATCAACTTTGCTCAT
TTTCCACGTCTCTTCAACCTCCGCTCAATTTACTTACAATGGAACAGGATTCGCTCCATTAG
CCAAGGTTTGACATGGACTTGGAGTTCCTTACACAACTTGGATTTATCAGGGAATGACATCC
AAGGAATTGAGCCGGGCACATTTAAATGCCTCCCCAATTTACAAAAATTGAATTTGGATTCC
AACAAGCTCACCAATATCTCACAGGAAACTGTCAATGCGTGGATATCATTAATATCCATCAC
ATTGTCTGGAAATATGTGGGAATGCAGTCGGAGCATTTGTCCTTTATTTTATTGGCTTAAGA
ATTTCAAAGGAAATAAGGAAAGCACCATGATATGTGCGGGACCTAAGCACATCCAGGGTGAA
AAGGTTAGTGATGCAGTGGAAACATATAATATCTGTTCTGAAGTCCAGGTGGTCAACACAGA
AAGATCACACCTGGTGCCCCAAACTCCCCAGAAACCTCTGATTATCCCTAGACCTACCATCT
TCAAACCTGACGTCACCCAATCCACCTTTGAAACACCAAGCCCTTCCCCAGGGTTTCAGATT
CCTGGCGCAGAGCAAGAGTATGAGCATGTTTCATTTCACAAAATTATTGCCGGGAGTGTGGC
TCTCTTTCTCTCAGTGGCCATGATCCTCTTGGTGATCTATGTGTCTTGGAAACGCTACCCAG
CCAGCATGAAACAACTCCAGCAACACTCTCTTATGAAGAGGCGGCGGAAAAAGGCCAGAGAG
TCTGAAAGACAAATGAATTCCCCTTTACAGGAGTATTATGTGGACTACAAGCCTACAAACTC
TGAGACCATGGATATATCGGTTAATGGATCTGGGCCCTGCACATATACCATCTCTGGCTCCA
GGGAATGTGAGATGCCACACCACATGAAGCCCTTGCCATATTACAGCTATGACCAGCCTGTG
ATCGGGTACTGCCAGGCCCACCAGCCACTCCATGTCACCAAGGGCTATGAGACAGTGTCTCC
AGAGCAGGACGAAAGCCCCGGCCTGGAGCTGGGCCGAGACCACAGCTTCATCGCCACCATCG
CCAGGTCGGCAGCACCGGCCATCTACCTAGAGAGAATTGCAAACTAACGCTGAAGCCAACTC
CTCACTGGGGAGCTCCATGGGGGGGAGGGAGGGCCTTCATCTTAAAGGAGAATGGGTGTCCA
CAATCGCGCAATCGAGCAAGCTCATCGTTCCTGTTAAAACATTTATGGCATAGGGAAAAAAA
AAAAAAAAAAAAAA

FIGURE 70

></usr/seqdb2/sst/DNA/Dnaseqs.min/ss.DNA142392
><subunit 1 of 1, 590 aa, 1 stop
><MW: 67217, pI: 9.26, NX(S/T): 4
MGFHLITQLKGMSVVLVLLPTLLLVMLTGAQRACPKNCRCDGKIVYCESHAFADIPENIS
GGSQGLSLRFNSIQKLKSNQFAGLNQLIWLYLDHNYISSVDEDAFQGIRRLKELILSSNK
ITYLHNKTFHPVPNLRNLDLSYNKLQTLQSEQFKGLRKLIILHLRSNSLKTVPIRVFQDC
RNLDFLDLGYNRLRSLSRNAFAGLLKLKELHLEHNQFSKINFAHFPRLFNLRSIYLQWNR
IRSISQGLTWTWSSLHNLDLSGNDIQGIEPGTFKCLPNLQKLNLDSNKLTNISQETVNAW
ISLISITLSGNMWECSRSICPLFYWLKNFKGNKESTMICAGPKHIQGEKVSDAVETYNIC
SEVQVVNTERSHLVPQTPQKPLIIPRPTIFKPDVTQSTFETPSPSPGFQIPGAEQEYEHV
SFHKIIAGSVALFLSVAMILLVIYVSWKRYPASMKQLQQHSLMKRRRKKARESERQMNSP
LQEYYVDYKPTNSETMDISVNGSGPCTYTISGSRECEMPHHMKPLPYYSYDQPVIGYCQA
HQPLHVTKGYETVSPEQDESPGLELGRDHSFIATIARSAAPAIYLERIAN

Important features of the protein:
Signal peptide:
Amino acids 1-30

Transmembrane domain:
Amino acids 425-443

N-glycosylation sites:
Amino acids 58-62;126-130;291-295;501-505

Tyrosine kinase phosphorylation site:
Amino acids 136-143

N-myristoylation sites:
Amino acids 29-35;61-67;247-253;267-273;271-277;331-337;
502-508;512-518;562-568

Glycosyl hydrolases family:
Amino acids 310-319

FIGURE 71

TTCCAGTCAGAGTTAAGTTAAAACAGAAAAAAGGAAGATGGCAAGAATATTGTTACTTTTCC
TCCCGGGTCTTGTGGCTGTATGTGCTGTGCATGGAATATTTATGGACCGTCTAGCTTCCAAG
AAGCTCTGTGCAGATGATGAGTGTGTCTATACTATTTCTCTGGCTAGTGCTCAAGAAGATTA
TAATGCCCCGGACTGTAGATTCATTAACGTTAAAAAAGGGCAGCAGATCTATGTGTACTCAA
AGCTGGTAAAAGAAAATGGAGCTGGAGAATTTTGGGCTGGCAGTGTTTATGGTGATGGCCAG
GACGAGATGGGAGTCGTGGGTTATTTCCCCAGGAACTTGGTCAAGGAACAGCGTGTGTACCA
GGAAGCTACCAAGGAAGTTCCCACCACGGATATTGACTTCTTCTGCGAGTAATAAATTAGTT
AAAACTGCAAATAGAAAGAAAACACCAAAAATAAAGAAAAGAGCAAAAGTGGCCAAAAAATG
CATGTCTGTAATTTTGGACTGACGT

FIGURE 72

></usr/seqdb2/sst/DNA/Dnaseqs.min/ss.DNA143076
><subunit 1 of 1, 128 aa, 1 stop
><MW: 14332, pI: 4.83, NX(S/T): 0
MARILLLFLPGLVAVCAVHGIFMDRLASKKLCADDECVYTISLASAQEDYNAPDCRFINV
KKGQQIYVYSKLVKENGAGEFWAGSVYGDGQDEMGVVGYFPRNLVKEQRVYQEATKEVPT
TDIDFFCE

Important features of the protein:
Signal peptide:
Amino acids 1-14

N-myristoylation site:
Amino acids 84-90

FIGURE 73

CTCAGATTTGCCATGGAGAAATTTTCAGTCTCGGCAATCCTGCTTCTTGTGGCCATCTCTGG
TACTCTGGCCAAAGACACCACAGTCAAATCTGGATCCAAAAAGGACCCAAAGGACTCTCGAC
CCAAACTACCCCAGACCCTGTCCAGAGGTTGGGGAGATCAGCTCATCTGGACTCAGACTTAC
GAAGAAGCCTTATACAAATCCAAGACAAGCAACAGACCCTTGATGGTCATTCATCACTTGGA
CGAATGCCCGCACAGTCAAGCTTTAAAGAAAGTGTTTGCTGAAAATAAGGAGATCCAGAAATTG
GCAGAGCAGTTTGTTCTCCTCAACTTGATCTATGAAACAACTGACAAGCACCTTTCTCCTGA
TGGCCAGTACGTCCCCAGAATTGTGTTTGTGGACCCTTCCCTGACGGTGAGGGCAGACATCA
CCGGAAGATACTCAAACCGTCTCTACGCTTATGAACCTTCTGACACAGCTCTGTTGCACGAC
AACATGAAGAAAGCTCTCAAGTTGCTGAAGACAGAGTTGTAGAGTCAACTGTACAGTGCCTC
AGGAGCCGGGAAGGCAGAAGCACTGTGGACCTGCCGATGACATTACAGTTTAATGTTACAAC
AAATGTATTTTTTAAACACCCACGTGTGGGGAAACAATATTATTATCTACTACAGACACATG
ATTTTCTAGAAAATAAAGTCTTGTGAGAACTCCAAA

FIGURE 74

></usr/seqdb2/sst/DNA/Dnaseqs.min/ss.DNA143294
><subunit 1 of 1, 175 aa, 1 stop, 1 unknown
><MW: 19888.97, pI: 9.08, NX(S/T): 0
MEKFSVSAILLLVAISGTLAKDTTVKSGSKKDPKDSRPKLPQTLSRGWGDQLIWTQTYEE
ALYKSKTSNRPLMVIHHLDECPHSQALKKVFAENKEIQKLAEQFVLLNLIYETTDKHLSP
DGQYVPRIVFVDPSLTVRADITGRYSNRLYAYEPSDTALLHDNMKKALKLLKTEL

Important features of the protein:
Signal peptide:
Amino acids 1-20

FIGURE 75

GCCGGCGCCAGGGCAGGCGGGCGGCTGGCAGCTGTGGCGCCGACATGGCTGCGCTGGTGGAG
CCGCTGGGGCTGGAGCGGGACGTGTCCCGGGCGGTTGAGCTCCTCGAGCGGCTCCAGCGCAG
CGGGGAGCTGCCCCCGCAGAAGCTGCAGGCCCTCCAGCGAGTTCTGCAGAGCCGCTTCTGCT
CCGCTATCCGAGAGGTGTATGAGCAGCTTTATGACACGCTGGACATCACCGGCAGCGCCGAG
ATCCGAGCCCATGCCACAGCCAAGGCCACAGTGGCTGCCTTCACAGCCAGCGAGGGCCACGC
ACATCCCAGGGTAGTGGAGCTACCCAAGACGGATGAGGGCCTAGGCTTCAACATCATGGGTG
GCAAAGAGCAAAACTCGCCCATCTACATCTCCCGGGTCATCCCAGGGGGTGTGGCTGACCGC
CATGGAGGCCTCAAGCGTGGGGATCAACTGTTGTCGGTGAACGGTGTGAGCGTTGAGGGTGA
GCAGCATGAGAAGGCGGTGGAGCTGCTGAAGGCGGCCCAGGGCTCGGTGAAGCTGGTTGTCC
GTTACACACCGCGAGTGCTGGAGGAGATGGAGGCCCGGTTCGAGAAGATGCGCTCTGCCCGC
CGGCGCCAACAGCATCAGAGCTACTCGTCCTTGGAGTCTCGAGGTTGAAACCACAGATCTGG
ACGTTCACGTGCACTCTCTTCCTGTACAGTATTTATTGTTCCTGGCACTTTATTTAAAGATA
TTTGACCCTCAAAAAAAAAAAAAAAAAAAAAA

FIGURE 76

></usr/seqdb2/sst/DNA/Dnaseqs.min/ss.DNA143514
><subunit 1 of 1, 207 aa, 1 stop
><MW: 22896, pI: 8.93, NX(S/T): 0
MAALVEPLGLERDVSRAVELLERLQRSGELPPQKLQALQRVLQSRFCSAIREVYEQLYDT
LDITGSAEIRAHATAKATVAAFTASEGHAHPRVVELPKTDEGLGFNIMGGKEQNSPIYIS
RVIPGGVADRHGGLKRGDQLLSVNGVSVEGEQHEKAVELLKAAQGSVKLVVRYTPRVLEE
MEARFEKMRSARRRQQHQSYSSLESRG

Tyrosine kinase phosphorylation site:
Amino acids 51-59

N-myristoylation sites:
Amino acids 102-108;133-139

Cell attachment sequence:
Amino acids 136-139

PDZ domain (Also known as DHR or GLGF):
Amino acids 93-174

FIGURE 77

CTGTCAGCTGAGGATCCAGCCGAAAGAGGAGCCAGGCACTCAGGCCACCTGAGTCTACTCAC
CTGGACAACTGGAATCTGGCACCAATTCTAAACCACTCAGCTTCTCCGAGCTCACACCCCGG
AGATCACCTGAGGACCCGAGCCATTGATGGACTCGGACGAGACCGGGTTCGAGCACTCAGGA
CTGTGGGTTTCTGTGCTGGCTGGTCTGCTGGGAGCCTGCCAGGCACACCCCATCCCTGACTC
CAGTCCTCTCCTGCAATTCGGGGGCCAAGTCCGGCAGCGGTACCTCTACACAGATGATGCCC
AGCAGACAGAAGCCCACCTGGAGATCAGGGAGGATGGGACGGTGGGGGGCGCTGCTGACCAG
AGCCCCGAAAGTCTCCTGCAGCTGAAAGCCTTGAAGCCGGGAGTTATTCAAATCTTGGGAGT
CAAGACATCCAGGTTCCTGTGCCAGCGGCCAGATGGGGCCCTGTATGGATCGCTCCACTTTG
ACCCTGAGGCCTGCAGCTTCCGGGAGCTGCTTCTTGAGGACGGATACAATGTTTACCAGTCC
GAAGCCCACGGCCTCCCGCTGCACCTGCCAGGGAACAAGTCCCCACACCGGGACCCTGCACC
CCGAGGACCAGCTCGCTTCCTGCCACTACCAGGCCTGCCCCCCGCACTCCCGGAGCCACCCG
GAATCCTGGCCCCCCAGCCCCCCGATGTGGGCTCCTCGGACCCTCTGAGCATGGTGGGACCT
TCCCAGGGCCGAAGCCCCAGCTACGCTTCCTGAAGCCAGAGGCTGTTTACTATGACATCTCC
TCTTTATTTATTAGGTTATTTATCTTATTTATTTTTTTATTTTTCTTACTTGAGATAATAAAGA
GTTCCAGAGGAGAAAAAAAAAAAAAAAAAAAAAAAAAAAAAAAAAAAAAAAAAAAAAAAAAAA
AAAAAAG

FIGURE 78

></usr/seqdb2/sst/DNA/Dnaseqs.min/ss.DNA144841
><subunit 1 of 1, 208 aa, 1 stop
><MW: 22187, pI: 5.08, NX(S/T): 1
MDSDETGFEHSGLWVSVLAGLLGACQAHPIPDSSPLLQFGGQVRQRYLYTDDAQQTEAHL
EIREDGTVGGAADQSPESLLQLKALKPGVIQILGVKTSRFLCQRPDGALYGSLHFDPEAC
SFRELLLEDGYNVYQSEAHGLPLHLPGNKSPHRDPAPRGPARFLPLPGLPPALPEPPGIL
APQPPDVGSSDPLSMVGPSQGRSPSYAS

Important features of the protein:
Signal peptide:
Amino acids 1-27

N-myristoylation sites:
Amino acids 12-18;20-26;23-29;66-72;94-100;107-113;168-174

Prokaryotic membrane lipoprotein lipid attachment site:
Amino acids 15-26

HBGF/FGF family proteins:
Amino acids 57-73;80-131

FIGURE 79

AGTCCCAGACGGGCTTTTCCCAGAGAGCTAAAAGAGAAGGGCCAGAGAATGTCGTCCCAG
CCAGCAGGGAACCAGACCTCCCCCGGGGCCACAGAGGACTACTCCTATGGCAGCTGGTAC
ATCGATGAGCCCCAGGGGGGCGAGGAGCTCCAGCCAGAGGGGGAAGTGCCCTCCTGCCAC
ACCAGCATACCACCCGGCCTGTACCACGCCTGCCTGGCCTCGCTGTCAATCCTTGTGCTG
CTGCTCCTGGCCATGCTGGTGAGGCGCCGCCAGCTCTGGCCTGACTGTGTGCGTGGCAGG
CCCGGCCTGCCCAGCCCTGTGGATTTCTTGGCTGGGGACAGGCCCCGGGCAGTGCCTGCT
GCTGTTTTCATGGTCCTCCTGAGCTCCCTGTGTTTGCTGCTCCCCGACGAGGACGCATTG
CCCTTCCTGACTCTCGCCTCAGCACCCAGCCAAGATGGGAAAACTGAGGCTCCAAGAGGG
GCCTGGAAGATACTGGGACTGTTCTATTATGCTGCCCTCTACTACCCTCTGGCTGCCTGT
GCCACGGCTGGCCACACAGCTGCACACCTGCTCGGCAGCACGCTGTCCTGGGCCCACCTT
GGGGTCCAGGTCTGGCAGAGGGCAGAGTGTCCCCAGGTGCCCAAGATCTACAAGTACTAC
TCCCTGCTGGCCTCCCTGCCTCTCCTGCTGGGCCTCGGATTCCTGAGCCTTTGGTACCCT
GTGCAGCTGGTGAGAAGCTTCAGCCGTAGGACAGGAGCAGGCTCCAAGGGGCTGCAGAGC
AGCTACTCTGAGGAATATCTGAGGAACCTCCTTTGCAGGAAGAAGCTGGGAAGCAGCTAC
CACACCTCCAAGCATGGCTTCCTGTCCTGGGCCCGCGTCTGCTTGAGACACTGCATCTAC
ACTCCACAGCCAGGATTCCATCTCCCGCTGAAGCTGGTGCTTTCAGCTACACTGACAGGG
ACGGCCATTTACCAGGTGGCCCTGCTGCTGCTGGTGGGCGTGGTACCCACTATCCAGAAG
GTGAGGGCAGGGGTCACCACGGATGTCTCCTACCTGCTGGCCGGCTTTGGAATCGTGCTC
TCCGAGGACAAGCAGGAGGTGGTGGAGCTGGTGAAGCACCATCTGTGGGCTCTGGAAGTG
TGCTACATCTCAGCCTTGGTCTTGTCCTGCTTACTCACCTTCCTGGTCCTGATGCGCTCA
CTGGTGACACACAGGACCAACCTTCGAGCTCTGCACCGAGGAGCTGCCCTGGACTTGAGT
CCCTTGCATCGGAGTCCCCATCCCTCCCGCCAAGCCATATTCTGTTGGATGAGCTTCAGT
GCCTACCAGACAGCCTTTATCTGCCTTGGGCTCCTGGTGCAGCAGATCATCTTCTTCCTG
GGAACCACGGCCCTGGCCTTCCTGGTGCTCATGCCTGTGCTCCATGGCAGGAACCTCCTG
CTCTTCCGTTCCCTGGAGTCCTCGTGGCCCTTCTGGCTGACTTTGGCCCTGGCTGTGATC
CTGCAGAACATGGCAGCCCATTGGGTCTTCCTGGAGACTCATGATGGACACCCACAGCTG
ACCAACCGGCGAGTGCTCTATGCAGCCACCTTTCTTCTCTTCCCCCTCAATGTGCTGGTG
GGTGCCATGGTGGCCACCTGGCGAGTGCTCCTCTCTGCCCTCTACAACGCCATCCACCTT
GGCCAGATGGACCTCAGCCTGCTGCCACCGAGAGCCGCCACTCTCGACCCCGGCTACTAC
ACGTACCGAAACTTCTTGAAGATTGAAGTCAGCCAGTCGCATCCAGCCATGACAGCCTTC
TGCTCCCTGCTCCTGCAAGCGCAGAGCCTCCTACCCAGGACCATGGCAGCCCCCCAGGAC
AGCCTCAGACCAGGGGAGGAAGACGAAGGGATGCAGCTGCTACAGACAAAGGACTCCATG
GCCAAGGGAGCTAGGCCCGGGGCCAGCCGCGGCAGGGCTCGCTGGGGTCTGGCCTACACG
CTGCTGCACAACCCAACCCTGCAGGTCTTCCGCAAGACGGCCCTGTTGGGTGCCAATGGT
GCCCAGCCCTGAGGGCAGGGAAGGTCAACCCACCTGCCCATCTGTGCTGAGGCATGTTCC
TGCCTACCATCCTCCTCCCTCCCCGGCTCTCCTCCCAGCATCACACCAGCCATGCAGCCA
GCAGGTCCTCCGGATCACTGTGGTTGGGTGGAGGTCTGTCTGCACTGGGAGCCTCAGGAG
GGCTCTGCTCCACCCACTTGGCTATGGGAGAGCCAGCAGGGGTTCTGGAGAAAAAAACTG
GTGGGTTAGGGCCTTGGTCCAGGAGCCAGTTGAGCCAGGGCAGCCACATCCAGGCGTCTC
CCTACCCTGGCTCTGCCATCAGCCTTGAAGGGCCTCGATGAAGCCTTCTCTGGAACCACT
CCAGCCCAGCTCCACCTCAGCCTTGGCCTTCACGCTGTGGAAGCAGCCAAGGCACTTCCT
CACCCCCTCAGCGCCACGGACCTCTCTGGGGAGTGGCCGGAAAGCTCCCGGTCCTCTGGC
CTGCAGGGCAGCCCAAGTCATGACTCAGACCAGGTCCCACACTGAGCTGCCCACACTCGA
GAGCCAGATATTTTTGTAGTTTTTATGCCTTTGGCTATTATGAAAGAGGTTAGTGTGTTC
CCTGCAATAAACTTGTTCCTGAGAAAAAAAAAAAAAAAAAAAAAAAAAAAAAAAAAAAAA
AAAAAAAAAAAAAAAAAAAAAAAAAAAAAAAAA

FIGURE 80

Protein File:
MW: 73502.97, pI: 9.26
MSSQPAGNQTSPGATEDYSYGSWYIDEPQGGEELQPEGEVPSCHTSIPPGLYHACLASLS
ILVLLLLAMLVRRRQLWPDCVRGRPGLPSPVDFLAGDRPRAVPAAVFMVLLSSLCLLLPD
EDALPFLTLASAPSQDGKTEAPRGAWKILGLFYYAALYYPLAACATAGHTAAHLLGSTLS
WAHLGVQVWQRAECPQVPKIYKYYSLLASLPLLLGLGFLSLWYPVQLVRSFSRRTGAGSK
GLQSSYSEEYLRNLLCRKKLGSSYHTSKHGFLSWARVCLRHCIYTPQPGFHLPLKLVLSA
TLTGTAIYQVALLLLVGVVPTIQKVRAGVTTDVSYLLAGFGIVLSEDKQEVVELVKHHLW
ALEVCYISALVLSCLLTFLVLMRSLVTHRTNLRALHRGAALDLSPLHRSPHPSRQAIFCW
MSFSAYQTAFICLGLLVQQIIFFLGTTALAFLVLMPVLHGRNLLLFRSLESSWPFWLTLA
LAVILQNMAAHWVFLETHDGHPQLTNRRVLYAATFLLFPLNVLVGAMVATWRVLLSALYN
AIHLGQMDLSLLPPRAATLDPGYYTYRNFLKIEVSQSHPAMTAFCSLLLQAQSLLPRTMA
APQDSLRPGEEDEGMQLLQTKDSMAKGARPGASRGRARWGLAYTLLHNPTLQVFRKTALL
GANGAQP

Important features of the protein:

Transmembrane domains:
Amino acids 54-69;102-119;148-166;207-222;301-320;
364-380;431-451;474-489;512-531

N-glycosylation site:
Amino acids 8-12

N-myristoylation sites:
Amino acids 50-56;176-182;241-247;317-323;341-347;525-531;
627-633;631-637;640-646;661-667

Prokaryotic membrane lipoprotein lipid attachment site:
Amino acids 364-375

ATP/GTP-binding site motif A (P-loop):
Amino acids 132-140

FIGURE 81

AAAAAATACAGCAGGTGAAGGAGGTTGGAGAGTAGGGGGTGGAGGGCCCACGCAGCACTTGT
CCTTCACCCTGGAGGGGATCTGTTACATGCCCCAGATTGCTGGTCCCCTAGAAATGTTACTG
AGGCAGCCTCTGCATTTTTGCAGGGATTGTTTTCTACTGTTTGACATTCACGTAACCTCCTA
ACGCTGTCTGGGGAAGATGCTACCCCCTGCTCTCCCCGTCTTTCCTGCACTCTCAGCAATGG
GATGGGCTGACTGATGCCCTGTGGGCTGGAAAGCTGACCACAGTTGCTGCAGACCAGACCCC
CTCACATAGTGAGTGCTGGGCTGAGGAATCCAGGAGAGCCCGAGGGGGGACACTGAAGGTGT
ATCGTTGGCCCTGCCAGCTGCAAGTGAACTGCTTCTGATGAATTTTAATAGGGAGAAAGAAG
TATTTGCTAAGAATGGCAATCCTGACGCTCAGCCTTCAACTCATCTTGTTATTAATACCATC
AATATCCCATGAGGCTCATAAAACGAGTCTTTCTTCTTGGAAACATGACCAAGATTGGGCAA
ACGTCTCCAACATGACTTTCAGCAACGGAAAACTAAGAGTCAAAGGCATTTATTACCGGAAT
GCCGACATTTGCTCTCGACATCGCGTAACCTCAGCAGGCCTAACTCTGCAGGACCTTCAGCT
ATGGTGTAATTTGAGGTCAGTGGCCAGAGGACAGATCCCGTCTACATTATGAGTGAAGCGGAGA
GCTACTGCAGGGTTCTGAGCAGAGTCCTAATTTATATTTTAGAAGAATCATCATGGCTCCTA
GATTAGGAATAAAACGAAGGGGCCCAGGGATGGAAACGATGAGTCCAGTTGGGTTACTGCAA
AGATCCAGGCCAGAAATCCAGGCACAGTGGCACACACCTGAGTCCCAGATAATTCCACCTAC
TGGTCCTGCTCTGTGGCCTACTGGTCCGAGTCCAGCCCCGACTGATTTCTGGGCCTGTAATG
TCTAAAAACGCTCCCTGCTGATGTTTTGCAAGTGACTGTGTTACTTGAAGGCAGTTCCTAGG
ATAAACTAGTCGCTTTATCATTACAGAATCATTCACTGAGCATCAACTATGTAACCAGCATT
GGGTTGGGTGCCAGAGATCCAAAGCTAAGACACCAAAACCTGCTCTCCAGGAAACGAGAGGC
TGAGAA

FIGURE 82

></usr/seqdb2/sst/DNA/Dnaseqs.min/ss.DNA149995
><subunit 1 of 1, 95 aa, 1 stop
><MW: 10704, pI: 10.00, NX(S/T): 2
MAILTLSLQLILLLIPSISHEAHKTSLSSWKHDQDWANVSNMTFSNGKLRVKGIYYRNAD
ICSRHRVTSAGLTLQDLQLWCNLRSVARGQIPSTL

Important features of the protein:
Signal peptide:
Amino acids 1-19

N-glycosylation sites:
Amino acids 38-42;41-45

N-myristoylation site:
Amino acids 89-95

FIGURE 83

AATAGAAGTCCTCAGGACGGAGCAGAGGTGGCCGGCGGGCCCGGCTGACTGCGCCTCTGCTT
TCTTTCCATAACCTTTTCTTTCGGACTCGAATCACGGCTGCTGCGAAGGGTCTAGTTCCGGA
CACTAGGGTGCCCGAACGCGCTGATGCCCCGAGTGCTCGCAGGGCTTCCCGCTAACCATGCT
GCCGCCGCCGCGGCCCGCAGCTGCCTTGGCGCTGCCTGTGCTCCTGCTACTGCTGGTGGTGC
TGACGCCGCCCCCGACCGGCGCAAGGCCATCCCCAGGCCCAGATTACCTGCGGCGCGGCTGG
ATGCGGCTGCTAGCGGAGGGCGAGGGCTGCGCTCCCTGCCGGCCAGAAGAGTGCGCCGCGCC
GCGGGGCTGCCTGGCGGGCAGGGTGCGCGACGCGTGCGGCTGCTGCTGGGAATGCGCCAACC
TCGAGGGCCAGCTCTGCGACCTGGACCCCAGTGCTCACTTCTACGGGCACTGCGGCGAGCAG
CTTGAGTGCCGGCTGGACACAGGCGGCGACCTGAGCCGCGGAGAGGTGCCGGAACCTCTGTG
TGCCTGTCGTTCGCAGAGTCCGCTCTGCGGGTCCGACGGTCACACCTACTCCCAGATCTGCC
GCCTGCAGGAGGCGGCCCGCGCTCGGCCCGATGCCAACCTCACTGTGGCACACCCGGGGCCC
TGCGAATCGGGGCCCCAGATCGTGTCACATCCATATGACACTTGGAATGTGACAGGGCAGGA
TGTGATCTTTGGCTGTGAAGTGTTTGCCTACCCCATGGCCTCCATCGAGTGGAGGAAGGATG
GCTTGGACATCCAGCTGCCAGGGGATGACCCCCACATCTCTGTGCAGTTTAGGGGTGGACCC
CAGAGGTTTGAGGTGACTGGCTGGCTGCAGATCCAGGCTGTGCGTCCCAGTGATGAGGGCAC
TTACCGCTGCCTTGGCCGCAATGCCCTGGGTCAAGTGGAGGCCCCTGCTAGCTTGACAGTGC
TCACACCTGACCAGCTGAACTCTACAGGCATCCCCCAGCTGCGATCACTAAACCTGGTTCCT
GAGGAGGAGGCTGAGAGTGAAGAGAATGACGATTACTACTAGGTCCAGAGCTCTGGCCCATG
GGGGTGGGTGAGCGGCTATAGTGTTCATCCCTGCTCTTGAAAAGACCTGGAAAGGGGAGCAG
GGTCCCTTCATCGACTGCTTTCATGCTGTCAGTAGGGATGATCATGGGAGGCCTATTTGACT
CCAAGGTAGCAGTGTGGTAGGATAGAGACAAAAGCTGGAGGAGGGTAGGGAGAGAAGCTGAG
ACCAGGACCGGTGGGGTACAAAGGGGCCCATGCAGGAGATGCCCTGGCCAGTAGGACCTCCA
ACAGGTTGTTTCCCAGGCTGGGGTGGGGGCCTGAGCAGACACAGAGGTGCAGGCACCAGGAT
TCTCCACTTCTTCCAGCCCTGCTGGGCCACAGTTCTAACTGCCCTTCCTCCCAGGCCCTGGT
TCTTGCTATTTCCTGGTCCCCAACGTTTATCTAGCTTGTTTGCCCTTTCCCCAAACTCATCT
TCCAGAACTTTTCCCTCTCTCCTAAGCCCCAGTTGCACCTACTAACTGCAGTCCCTTTTGCT
GTCTGCCGTCTTTTGTACAAGAGAGAGAACAGCGGAGCATGACTTAGTTCAGTGCAGAGAGA
TTT

FIGURE 84

></usr/seqdb2/sst/DNA/Dnaseqs.min/ss.DNA167678
><subunit 1 of 1, 304 aa, 1 stop
><MW: 32945, pI: 4.69, NX(S/T): 3
MLPPPRPAAALALPVLLLLLVVLTPPPTGARPSPGPDYLRRGWMRLLAEGEGCAPCRPEE
CAAPRGCLAGRVRDACGCCWECANLEGQLCDLDPSAHFYGHCGEQLECRLDTGGDLSRGE
VPEPLCACRSQSPLCGSDGHTYSQICRLQEAARARPDANLTVAHPGPCESGPQIVSHPYD
TWNVTGQDVIFGCEVFAYPMASIEWRKDGLDIQLPGDDPHISVQFRGGPQRFEVTGWLQI
QAVRPSDEGTYRCLGRNALGQVEAPASLTVLTPDQLNSTGIPQLRSLNLVPEEEAESEEN
DDYY

Important features of the protein:
Signal peptide:
Amino acids 1-30

N-glycosylation sites:
Amino acids 159-163;183-187;277-281

Tyrosine kinase phosphorylation site:
Amino acids 244-252

N-myristoylation sites:
Amino acids 52-58;66-72;113-119;249-255

Kazal-type serine protease inhibitor domain:
Amino acids 121-168

Immunoglobulin domain:
Amino acids 186-255

Insulin-like growth factor binding proteins:
Amino acids 53-90

FIGURE 85

CAAAGCGGCGGCTGTCCGCGGTGCCGGCTGGGGGCGGAGAGGCGGCGGTGGGCTCCCTGGGG
TGTGTGAGCCCGGTGATGGAGCCGGGCCCGACAGCCGCGCAGCGGAGGTGTTCGTTGCCGCC
GTGGCTGCCGCTGGGGCTGCTGCTGTGGTCGGGGCTGGCCCTGGGCGCGCTCCCCTTCGGCA
GCAGTCCGCACAGGGTCTTCCACGACCTCCTGTCGGAGCAGCAGTTGCTGGAGGTGGAGGAC
TTGTCCCTGTCCCTCCTGCAGGGTGGAGGGCTGGGGCCTCTGTCGCTGCCCCCGGACCTGCC
GGATCTGGATCCTGAGTGCCGGGAGCTCCTGCTGGACTTCGCCAACAGCAGCGCAGAGCTGA
CAGGGTGTCTGGTGCGCAGCGCCCGGCCCGTGCGCCTCTGTCAGACCTGCTACCCCCTCTTC
CAACAGGTCGTCAGCAAGATGGACAACATCAGCCGAGCCGCGGGGAATACTTCAGAGAGTCAG
AGTTGTGCCAGAAGTCTCTTAATGGCAGATAGAATGCAAATAGTTGTGATTCTCTCAGAATT
TTTTAATACCACATGGCAGGAGGCAAATTGTGCAAATTGTTTAACAAACAACAGTGAAGAAT
TATCAAACAGCACAGTATATTTCCTTAATCTATTTAATCACACCCTGACCTGCTTTGAACAT
AACCTTCAGGGGAATGCACATAGTCTTTTACAGACAAAAAATTATTCAGAAGTATGCAAAAA
CTGCCGTGAAGCATACAAAACTCTGAGTAGTCTGTACAGTGAAATGCAAAAAATGAATGAAC
TTGAGAATAAGGCTGAACCTGGAACACATTTATGCATTGATGTGGAAGATGCAATGAACATC
ACTCGAAAACTATGGAGTCGAACTTTCAACTGTTCAGTCCCTTGCAGTGACACAGTGCCTGT
AATTGCTGTTTCTGTGTTCATTCTCTTTCTACCTGTTGTCTTCTACCTTAGTAGCTTTCTTC
ACTCAGAGCAAAAGAAACGCAAACTCATTCTGCCCAAACGTCTCAAGTCCAGTACCAGTTTT
GCAAATATTCAGGAAAATTCAAACTGAGACCTACAAAATGGAGAATTGACATATCACGTGAA
TGAATGGTGGAAGACACAACTTGGTTTCAGAAAGAAGATAAACTGTGATTTGACAAGTCAAG
CTCTTAAGAAATACAAGGACTTCAGATCCATTTTTAAATAAGAATTTTCGATTTTTCTTTCC
TTTTCCACTTCTTTCTAACAGATTTGGATATTTTTAATTTCCAG

FIGURE 86

></usr/seqdb2/sst/DNA/Dnaseqs.min/ss.DNA168028
><subunit 1 of 1, 334 aa, 1 stop
><MW: 37257, pI: 5.95, NX(S/T): 10
MEPGPTAAQRRCSLPPWLPLGLLLWSGLALGALPFGSSPHRVFHDLLSEQQLLEVEDLSL
SLLQGGGLGPLSLPPDLPDLDPECRELLLDFANSSAELTGCLVRSARPVRLCQTCYPLFQ
QVVSKMDNISRAAGNTSESQSCARSLLMADRMQIVVILSEFFNTTWQEANCANCLTNNSE
ELSNSTVYFLNLFNHTLTCFEHNLQGNAHSLLQTKNYSEVCKNCREAYKTLSSLYSEMQK
MNELENKAEPGTHLCIDVEDAMNITRKLWSRTFNCSVPCSDTVPVIAVSVFILFLPVVFY
LSSFLHSEQKKRKLILPKRLKSSTSFANIQENSN

Important features of the protein:
Signal peptide:
Amino acids 1-31

Transmembrane domain:
Amino acids 278-300

N-glycosylation sites:
Amino acids 93-97;128-132;135-139;163-167;177-181;
184-188;194-198;216-220;263-267;274-278 cAMP- and cGMP-dependent protein kinase phosphorylation site:
Amino acids 10-14

N-myristoylation sites:
Amino acids 27-33;206-212;251-257

Leucine zipper pattern:
Amino acids 190-212

FIGURE 87

ATGCTGGTAGCCGGCTTCCTGCTGGCGCTGCCGCCGAGCTGGGCCGCGGGCGCCCCCAGGGC
GGGCAGGCGCCCCGCGCGGCCGCGGGGCTGCGCGGACCGGCCGGAGGAGCTACTGGAGCAGC
TGTACGGGCGCCTGGCGGCCGGCGTGCTCAGTGCCTTCCACCACACGCTGCAGCTGGGGCCG
CGTGAGCAGGCGCGCAACGCGAGCTGCCCGGCAGGGGGCAGGCCCGGCGACCGCCGCTTCCG
GCCGCCCACCAACCTGCGCAGCGTGTCGCCCTGGGCCTACAGAATCTCCTACGACCCGGCGA
GGTACCCCAGGTACCTGCCTGAAGCCTACTGCCTGTGCCGGGGCTGCCTGACCGGGCTGTTC
GGCGAGGAGGACGTGCGCTTCCGCAGCGCCCCTGTCTACATGCCCACCGTCGTCCTGCGCCG
CACCCCCGCCTGCGCCGGCGGCCGTTCCGTCTACACCGAGGCCTACGTCACCATCCCCGTGG
GCTGCACCTGCGTCCCCGAGCCGGAGAAGGACGCAGACAGCATCAACTCCAGCATCGACAAA
CAGGGCGCCAAGCTCCTGCTGGGCCCCAACGACGCGCCCGCTGGCCCCTGAGGCCGGTCCTG
CCCCGGGAGGTCTCCCCGGCCCGCATCCCGAGGCGCCCAAGCTGGAGCCGCCTGGAGGGCTC
GGTCGGCGACCTCTGAAGAGAGTGCACCGAGCAAACCAAGTGCCGGAGCACCAGCGCCGCCT
TTCCATGGAGACTCGTAAGCAGCTTCATCTGACACGGGCATCCCTGGCTTGCTTTTAGCTAC
AAGCAAGCAGCGTGGCTGGAAGCTGATGGGAAACGACCCGGCACGGGCATCCTGTGTGCGGC
CCGCATGGAGGGTTTGGAAAAGTTCACGGAGGCTCCCTGAGGAGCCTCTCAGATCGGCTGCT
GCGGGTGCAGGGCGTGACTCACCGCTGGGTGCTTGCCAAAGAGATAGGGACGCATATGCTTT
TTAAAGCAATCTAAAAATAATAATAAGTATAGCGACTATATACCTACTTTTAAAATCAACTG
TTTTGAATAGAGGCAGAGCTATTTTATATTATCAAATGAGAGCTACTCTGTTACATTTCTTA
ACATATAAACATCGTTTTTTACTTCTTCTGGTAGAATTTTTTAAAGCATAATTGGAATCCTT
GGATAAATTTTGTAGCTGGTACACTCTGGCCTGGGTCTCTGAATTCAGCCTGTCACCGATGG
CTGACTGATGAAATGGACACGTCTCATCTGACCCACTCTTCCTTCCACTGAAGGTCTTCACG
GGCCTCCAGGTGGACCAAAGGGATGCACAGGCGGCTCGCATGCCCCAGGGCCAGCTAAGAGT
TCCAAAGATCTCAGATTTGGTTTTAGTCATGAATACATAAACAGTCTCAAACTCGCACAATT
TTTTCCCCCTTTTGAAAGCCACTGGGGCCAATTTGTGGTTAAGAGGTGGTGAGATAAGAAGT
GGAACGTGACATCTTTGCCAGTTGTCAGAAGAATCCAAGCAGGTATTGGCTTAGTTGTAAGG
GCTTTAGGATCAGGCTGAATATGAGGACAAAGTGGGCCACGTTAGCATCTGCAGAGATCAAT
CTGGAGGCTTCTGTTTCTGCATTCTGCCACGAGAGCTAGGTCCTTGATCTTTTCTTTAGATT
GAAAGTCTGTCTCTGAACACAATTATTTGTAAAAGTTAGTAGTTCTTTTTTAAATCATTAAA
AGAGGCTTGCTGAAGGAT

FIGURE 88

></usr/seqdb2/sst/DNA/Dnaseqs.min/ss.DNA173894
><subunit 1 of 1, 202 aa, 1 stop
><MW: 21879, pI: 9.30, NX(S/T): 2
MLVAGFLLALPPSWAAGAPRAGRRPARPRGCADRPEELLEQLYGRLAAGVLSAFHHTLQL
GPREQARNASCPAGGRPGDRRFRPPTNLRSVSPWAYRISYDPARYPRYLPEAYCLCRGCL
TGLFGEEDVRFRSAPVYMPTVVLRRTPACAGGRSVYTEAYVTIPVGCTCVPEPEKDADSI
NSSIDKQGAKLLLGPNDAPAGP

Important features of the protein:
Signal peptide:
Amino acids 1-15

N-glycosylation sites:
Amino acids 68-72;181-185

Tyrosine kinase phosphorylation site:
Amino acids 97-106

N-myristoylation sites:
Amino acids 17-23;49-55;74-80;118-124

Amidation site:
Amino acids 21-25

FIGURE 89

CCGGGGCCTCCGGAGAACGCTGTCCCATGAACGTGCGGGGAGCGGCCCCCGGCGTCCGCGCG
TCCCCGCGTCCCTGGCAATTCCCGACTTCCCAACGGCTTCCCGCTGGCAGCCCCGAAGCCGC
ACCATGTTCCGCCTCTGGTTGCTGCTGGCCGGGCTCTGCGGCCTCCTGGCGTCAAGACCCGGT
TTTCAAAATTCACTTCTACAGATCGTAATTCCAGAGAAAATCCAAACAAATACAAATGACAG
TTCAGAAATAGAATATGAACAAATATCCTATATTATTCCAATAGATGAGAAACTGTACACTG
TGCACCTTAAACAAAGATATTTTTTAGCAGATAATTTTATGATCTATTTGTACAATCAAGGA
TCTATGAATACTTATTCTTCAGATATTCAGACTCAATGCTACTATCAAGGAAATATTGAAGG
ATATCCAGATTCCATGGTCACACTCAGCACGTGCTCTGGACTAAGAGGAATACTGCAATTTG
AAAATGTTTCTTATGGAATTGAGCCTCTGGAATCTGCAGTTGAATTTCAGCATGTTCTTTAC
AAATTAAAGAATGAAGACAATGATATTGCAATTTTTATTGACAGAAGCCTGAAAGAACAACC
AATGGATGACAACATTTTTATAAGTGAAAAATCAGAACCAGCTGTTCCAGATTTATTTCCTC
TTTATCTAGAAATGCATATTGTGGTGGACAAAACTTTGTATGATTACTGGGGCTCTGATAGC
ATGATAGTAACAAATAAAGTCATCGAAATTGTTGGCCTTGCAAATTCAATGTTCACCCAATT
TAAAGTTACTATTGTGCTGTCATCATTGGAGTTATGGTCAGATGAAAATAAGATTTCTACAG
TTGGTGAGGCAGATGAATTATTGCAAAAATTTTTAGAATGGAAACAATCTTATCTTAACCTA
AGGCCTCATGATATTGCATATCTACTAATTTATATGGATTATCCTCGTTATTTGGGAGCAGT
GTTTCCTGGAACAATGTGTATTACTCGTTATTCTGCAGGAGTTGCATTGTACCCCAAGGAGA
TAACTCTGGAGGCATTTGCAGTTATTGTCACCCAGATGCTGGCACTCAGTCTGGGAATATCA
TATGACGACCCAAAGAAATGTCAATGTTCAGAATCCACCTGTATAATGAATCCAGAAGTTGT
GCAATCCAATGGTGTGAAGACTTTTAGCAGTTGCAGTTTGAGGAGCTTTCAAAATTTCATTT
CAAATGTGGGTGTCAAATGTCTTCAGAATAAGCCACAAATGCAAAAAAAATCTCCGAAACCA
GTCTGTGGCAATGGCAGATTGGAGGGAAATGAAATCTGTGATTGTGGTACTGAGGCTCAATG
TGGACCTGCAAGCTGTTGTGATTTTCGAACTTGTGTACTGAAAGACGGAGCAAAATGTTATA
AAGGACTGTGCTGCAAAGACTGTCAAATTTTACAATCAGGCGTTGAATGTAGGCCGAAAGCA
CATCCTGAATGTGACATCGCTGAAAATTGTAATGGAAGCTCACCAGAATGTGGTCCTGACAT
AACTTTAATCAATGGACTTTCATGCAAAAATAATAAGTTTATTTGTTATGACGGAGACTGCC
ATGATCTCGATGCACGTTGTGAGAGTGTATTTGGAAAAGGTTCAAGAAATGCTCCATTTGCC
TGCTATGAAGAAATACAATCTCAATCAGACAGATTTGGGAACTGTGGTAGGGATAGAAATAA
CAAATATGTGTTCTGTGGATGGAGGAATCTTATATGTGGAAGATTAGTTTGTACCTACCCTA
CTCGAAAGCCTTTCCATCAAGAAAATGGTGATGTGATTTATGCTTTCGTACGAGATTCTGTA
TGCATAACTGTAGACTACAAATTGCCTCGAACAGTTCCAGATCCACTGGCTGTCAAAAATGG
CTCTCAGTGTGATATTGGGAGGGTTTGTGTAAATCGTGAATGTGTAGAATCAAGGATAATTAAG
GCTTCAGCACATGTTTGTTCACAACAGTGTTCTGGACATGGAGTGTGTGATTCCAGAAACAA
GTGCCATTGTTCGCCAGGCTATAAGCCTCCAAACTGCCAAATACGTTCCAAAGGATTTTCCA
TATTTCCTGAGGAAGATATGGGTTCAATCATGGAAAGAGCATCTGGGAAGACTGAAAACACC
TGGCTTCTAGGTTTCCTCATTGCTCTTCCTATTCTCATTGTAACAACCGCAATAGTTTTGGC
AAGGAAACAGTTGAAAAAGTGGTTCGCCAAGGAAGAGGAATTCCCAAGTAGCGAATCTAAAT
CGGAAGGTAGCACACAGACATATGCCAGCCAATCCAGCTCAGAAGGCAGCACTCAGACATAT
GCCAGCCAAACCAGATCAGAAAGCAGCAGTCAAGCTGATACTAGCAAATCCAAATCAGAAGA
TAGTGCTGAAGCATATACTAGCAGATCCAAATCACAGGACAGTACCCAAACACAAAGCAGTA
GTAACTAGTGATTCCTTCAGAAGGCAACGGATAACATCGAGAGTCTCGCTAAGAAATGAAAA
TTCTGTCTTTCCTTCCGTGGTCACAGCTGAAAGAAACAATAAATTGAGTGTGGATC

FIGURE 90

></usr/seqdb2/sst/DNA/Dnaseqs.min/ss.DNA176775
><subunit 1 of 1, 787 aa, 1 stop
><MW: 87934, pI: 5.49, NX(S/T): 4
MFRLWLLLAGLCGLLASRPGFQNSLLQIVIPEKIQTNTNDSSEIEYEQISYIIPIDEKLY
TVHLKQRYFLADNFMIYLYNQGSMNTYSSDIQTQCYYQGNIEGYPDSMVTLSTCSGLRGI
LQFENVSYGIEPLESAVEFQHVLYKLKNEDNDIAIFIDRSLKEQPMDDNIFISEKSEPAV
PDLFPLYLEMHIVVDKTLYDYWGSDSMIVTNKVIEIVGLANSMFTQFKVTIVLSSLELWS
DENKISTVGEADELLQKFLEWKQSYLNLRPHDIAYLLIYMDYPRYLGAVFPGTMCITRYS
AGVALYPKEITLEAFAVIVTQMLALSLGISYDDPKKCQCSESTCIMNPEVVQSNGVKTFS
SCSLRSFQNFISNVGVKCLQNKPQMQKKSPKPVCGNGRLEGNEICDCGTEAQCGPASCCD
FRTCVLKDGAKCYKGLCCKDCQILQSGVECRPKAHPECDIAENCNGSSPECGPDITLING
LSCKNNKFICYDGDCHDLDARCESVFGKGSRNAPFACYEEIQSQSDRFGNCGRDRNNKYV
FCGWRNLICGRLVCTYPTRKPFHQENGDVIYAFVRDSVCITVDYKLPRTVPDPLAVKNGS
QCDIGRVCVNRECVESRIIKASAHVCSQQCSGHGVCDSRNKCHCSPGYKPPNCQIRSKGF
SIFPEEDMGSIMERASGKTENTWLLGFLIALPILIVTTAIVLARKQLKKWFAKEEEFPSS
ESKSEGSTQTYASQSSSEGSTQTYASQTRSESSSQADTSKSKSEDSAEAYTSRSKSQDST
QTQSSSN

Important features of the protein:
Signal peptide:
Amino acids 1-16

Transmembrane domain:
Amino acids 309-326;681-705

N-glycosylation sites:
Amino acids 39-43;125-129;465-469;598-602

Glycosaminoglycan attachment site:
Amino acids 631-635

Tyrosine kinase phosphorylation site:
Amino acids 269-276

N-myristoylation sites:
Amino acids 13-19;82-88;99-105;218-224;401-407;634-640;
726-732;739-745

EGF-like domain proteins:
Amino acids 642-654

Disintegrins proteins:
Amino acids 400-407;422-472;403-453;467-517;634-684

Reprolysin (M12B) family zinc metalloprotease:
Amino acids 186-383

Reprolysin family propeptide:
Amino acids 63-176

FIGURE 91

CACCAGACAGCACTCCAGCACTCTGTTTGGGGGGCATTCGAAACAGCAAAATCACTCATAAA
AGGCAAAAAATTGCAAAAAAAAATAGTAATAACCAGCATGGCACTAAATAGACCATGAAAAG
ACATGTGTGTGCAGTATGAAAATTGAGACAGGAAGGCAGAGTGTCAGCTTGTTCCACCTCAG
CTGGGAATGTGCATCAGGCAACTCAAGTTTTTCACCACGGCATGTGTCTGTGAATGTCCGCA
AAACATTCTCTCTCCCCAGCCTTCATGTGTTAACCTGGGGATGATGTGGACCTGGGCACTGTGG
ATGCTCCCTTCACTCTGCAAATTCAGCCTGGCAGCTCTGCCAGCTAAGCCTGAGAACATTTC
CTGTGTCTACTACTATAGGAAAAATTTAACCTGCACTTGGAGTCCAGGAAAGGAAACCAGTT
ATACCCAGTACACAGTTAAGAGAACTTACGCTTTTGGAGAAAAACATGATAATTGTACAACC
AATAGTTCTACAAGTGAAAATCGTGCTTCGTGCTCTTTTTTCCTTCCAAGAATAACGATCCC
AGATAATTATACCATTGAGGTGGAAGCTGAAAATGGAGATGGTGTAATTAAATCTCATATGA
CATACTGGAGATTAGAGAACATAGCGAAAACTGAACCACCTAAGATTTTCCGTGTGAAACCA
GTTTTGGGCATCAAACGAATGATTCAAATTGAATGGATAAAGCCTGAGTTGGCGCCTGTTTC
ATCTGATTTAAAATACACACTTCGATTCAGGACAGTCAACAGTACCAGCTGGATGGAAGTCA
ACTTCGCTAAGAACCGTAAGGATAAAAACCAAACGTACAACCTCACGGGGCTGCAGCCTTTT
ACAGAATATGTCATAGCTCTGCGATGTGCGGTCAAGGAGTCAAAGTTCTGGAGTGACTGGAG
CCAAGAAAAAATGGGAATGACTGAGGAAGAAGCTCCATGTGGCCTGGAACTGTGGAGAGTCC
TGAAACCAGCTGAGGCGGATGGAAGAAGGCCAGTGCGGTTGTTATGGAAGAAGGCAAGAGGA
GCCCCAGTCCTAGAGAAAACACTTGGCTACAACATATGGTACTATCCAGAAAGCAACACTAA
CCTCACAGAAACAATGAACACTACTAACCAGCAGCTTGAACTGCATCTGGGAGGCGAGAGCT
TTTGGGTGTCTATGATTTCTTATAATTCTCTTGGGAAGTCTCCAGTGGCCACCCTGAGGATT
CCAGCTATTCAAGAAAAATCATTTCAGTGCATTGAGGTCATGCAGGCCTGCGTTGCTGAGGA
CCAGCTAGTGGTGAAGTGGCAAAGCTCTGCTCTAGACGTGAACACTTGGATGATTGAATGGT
TTCCGGATGTGGACTCAGAGCCCACCACCCTTTCCTGGGAATCTGTGTCTCAGGCCACGAAC
TGGACGATCCAGCAAGATAAATTAAAACCTTTCTGGTGCTATAACATCTCTGTGTATCCAAT
GTTGCATGACAAAGTTGGCGAGCCATATTCCATCCAGGCTTATGCCAAAGAAGGCGTTCCAT
CAGAAGGTCCTGAGACCAAGGTGGAGAACATTGGCGTGAAGACGGTCACGATCACATGGAAA
GAGATTCCCAAGAGTGAGAGAAAGGGTATCATCTGCAACTACACCATCTTTTACCAAGCTGA
AGGTGGAAAAGGATTCTGTAAGCACGCCCATAGCGAAGTGGAAAAAAACCCCAAGCCCCAGA
TAGATGCTATGGATAGACCTGTTGTAGGCATGGCTCCCCCATCTCATTGTGACTTGCAACCT
GGCATGAATCACTTAGCTTCTTTAAATCTCTCTGAAAATGGGGCCAAGAGCACCCACCTTTT
GGGGTTTTGGGGGTTAAATGAGAGTGAAGTGACAGTACCTGAGAGGAGAGTCCTGAGGAAAT
GGAAGGAGTTGTTATAATTTGTCCTGGTTAGGCCCTGAATTGACCTCCCGGGAGCTCCCCGA
CCATCATTCCCAGGAATGGCGTGCCTGGCTTAAAGAGTGAGGAGGAACAGACCCTGTCACCA
TGACTTCTACTGCCCCTGCCAAATCATGCTTTTGTTTTTCAGTCCACCTTATCTCCTGACATCT
TAAATACTGGGCAAGGCTTGGATTCTTGCTTAGGCTAAATAATTTTTTCTTATGGTAAAATA
CACGTAAAATATTTTTCCAGTTTAAACATTTGAAAGTGTACAATTTAGTGGCATTAGAAGCA
TTCACAATATTGTGCAACCATCACCACTATTTCCAGAACTCTTCTATTTCTGCCCAAATAGA
AGCCCTATACCCATTCATTAGTCACTCCCCATTCCTCTCCTCCCACAGCCCCTGGCAACTAC
CAAACTGCTTTGTGTCTCTATGGATTGCCTATTTTGGATATTTCATATACATAGAATCATAA
ANTAAAAAAAAAAAAAAAAAAAA

FIGURE 92

></usr/seqdb2/sst/DNA/Dnaseqs.min/ss.DNA177313
><subunit 1 of 1, 582 aa, 1 stop
><MW: 66605, pI: 8.14, NX(S/T): 15
MCIRQLKFFTTACVCECPQNILSPQPSCVNLGMMWTWALWMLPSLCKFSLAALPAKPENI
SCVYYYRKNLTCTWSPGKETSYTQYTVKRTYAFGEKHDNCTTNSSTSENRASCSFFLPRI
TIPDNYTIEVEAENGDGVIKSHMTYWRLENIAKTEPPKIFRVKPVLGIKRMIQIEWIKPE
LAPVSSDLKYTLRFRTVNSTSWMEVNFAKNRKDKNQTYNLTGLQPFTEYVIALRCAVKES
KFWSDWSQEKMGMTEEEAPCGLELWRVLKPAEADGRRPVRLLWKKARGAPVLEKTLGYNI
WYYPESNTNLTETMNTTNQQLELHLGGESFWVSMISYNSLGKSPVATLRIPAIQEKSFQC
IEVMQACVAEDQLVVKWQSSALDVNTWMIEWFPDVDSEPTTLSWESVSQATNWTIQQDKL
KPFWCYNISVYPMLHDKVGEPYSIQAYAKEGVPSEGPETKVENIGVKTVTITWKEIPKSE
RKGIICNYTIFYQAEGGKGFCKHAHSEVEKNPKPQIDAMDRPVVGMAPPSHCDLQPGMNH
LASLNLSENGAKSTHLLGFWGLNESEVTVPERRVLRKWKELL

Important features of the protein:
Signal peptide:
Amino acids 1-46

N-glycosylation sites:
Amino acids 59-63;69-73;99-103;103-107;125-129;198-202;
215-219;219-223;309-313;315-319;412-416;
427-431;487-491;545-549;563-567

N-myristoylation sites:
Amino acids 32-38;137-143;483-489;550-556;561-567

Amidation site:
Amino acids 274-278

Growth factor and cytokines receptors family signature 1:
Amino acids 62-75

Fibronectin type III domain:
Amino acids 54-144;154-247

FIGURE 93

ATTCTCCTAGAGCATCTTTGGAAGCATGAGGCCACGATGCTGCATCTTGGCTCTTGTCTGCT
GGATAACAGTCTTCCTCCTCCAGTGTTCAAAAGGAACTACAGACGCTCCTGTTGGCTCAGGA
CTGTGGCTGTGCCAGCCGACACCCAGGTGTGGGAACAAGATCTACAACCCTTCAGAGCAGTG
CTGTTATGATGATGCCATCTTATCCTTAAAGGAGACCCGCCGCTGTGGCTCCACCTGCACCT
TCTGGCCCTGCTTTGAGCTCTGCTGTCCCGAGTCTTTTGGCCCCCAGCAGAAGTTTCTTGTG
AAGTTGAGGGTTCTGGGTATGAAGTCTCAGTGTCACTTATCTCCCATCTCCCGGAGCTGTAC
CAGGAACAGGAGGCACGTCCTGTACCCATAAAAACCCCAGGCTCCACTGGCAGACGGCAGAC
AAGGGGAGAAGAGACGAAGCAGCTGGACATCGGAGACTACAGTTGAACTTCGGAGAGAAGCA
ACTTGACTTCAGAGGGATGGCTCAATGACATAGCTTTGGAGAGGAGCCCAGCTGGGGATGGC
CAGACTTCAGGGGAAGAATGCCTTCCTGCTTCATCCCCTTTCCAGCTCCCCTTCCCGCTGAG
AGCCACTTTCATCGGCAATAAAATCCCCCACATTTACCATCT

FIGURE 94

</usr/seqdb2/sst/DNA/Dnaseqs.min/ss.DNA57700
<subunit 1 of 1, 125 aa, 1 stop
<MW: 14198, pI: 9.01, NX(S/T): 1
MRPRCCILALVCWITVFLLQCSKGTTDAPVGSGLWLCQPTPRCGNKIYNPSEQCCYDDAI
LSLKETRRCGSTCTFWPCFELCCPESFGPQQKFLVKLRVLGMKSQCHLSPISRSCTRNRR
HVLYP

Important features:
Signal peptide:
Amino acids 1-21

N-myristoylation sites:
Amino acids 33-39;70-76

Anaphylatoxin domain proteins:
Amino acids 50-60

FIGURE 95

GCATTTTTGTCTGTGCTCCCTGATCTTCAGGTCACCACCATGAAGTTCTTAGCAGTCCTGGT
ACTCTTGGGAGTTTCCATCTTTCTGGTCTCTGCCCAGAATCCGACAACAGCTGCTCCAGCTG
ACACGTATCCAGCTACTGGTCCTGCTGATGATGAAGCCCCTGATGCTGAAACCACTGCTGCT
GCAACCACTGCGACCACTGCTGCTCCTACCACTGCAACCACCGCTGCTTCTACCACTGCTCG
TAAAGACATTCCAGTTTTACCCAAATGGGTTGGGGATCTCCCGAATGGTAGAGTGTGTCCCT
GAGATGGAATCAGCTTGAGTCTTCTGCAATTGGTCACAACTATTCATGCTTCCTGTGATTTC
ATCCAACTACTTACCTTGCCTACGATATCCCCTTTATCTCTAATCAGTTTATTTTCTTTCAA
ATAAAAAATAACTATGAGCAACATAAAAAAAAAAAAA

FIGURE 96

</usr/seqdb2/sst/DNA/Dnaseqs.min/ss.DNA62872
<subunit 1 of 1, 90 aa, 1 stop
<MW: 9039, pI: 4.37, NX(S/T): 1
MKFLAVLVLLGVSIFLVSAQNPTTAAPADTYPATGPADDEAPDAETTAAATTATTAAPTT
ATTAASTTARKDIPVLPKWVGDLPNGRVCP

Important features:
Signal peptide:
Amino acids 1-19

FIGURE 97

GGACTCTGAAGGTCCCAAGCAGCTGCTGAGGCCCCCAAGGAAGTGGTTCCAACCTTGGACCC
CTAGGGGTCTGGATTTGCTGGTTAACAAGATAACCTGAGGGCAGGACCCCATAGGGGAATGC
TACCTCCTGCCCTTCCACCTGCCCTGGTGTTCACGGTGGCCTGGTCCCTCCTTGCCGAGAGA
GTGTCCTGGGTCAGGGACGCAGAGGACGCTCACAGACTCCAGCCCTTTGTTACCGAGAGGAC
ACTTGGCAAGGTCCAGCGATGGTCCGGAGTCCACACACAGACTGGCGGCAGGGCAGGAGGGG
GACAGTTCTGTTGTGCTTGGTTGGACAGTAAGAGGGTCTTGGCCAGTCCAGGGTGGGGGGCG
GCAAACTCCATAAAGAACCAGAGGGTCTGGGCCCCGGCCACAGAGTCATCTGCCCAGCTCCT
CTGCTGCTGGCCAGTGGGAGTGGCACGAGGTGGGGCTTTGTGCCAGTAAAACCACAGGCTGG
ATTTGCCTGCGGGCCATGGTCCCTGTCTAGGGCAGCAATTCTCAACCTTCTTGCTCTCAGGA
CCCCAAAGAGCTTTCATTGTATCTATTGATTTTTACCACATTAGCAATTAAAACTGAGAAAT
GGGCCGGGCACGGTGGCTCACGCCTGTAATCCCAGCACTTTGGGAGGCCGAGGCGGGTGGAT
CACCTGAGATCAGGAGTTCAAGACCAGCCTGGCCAACATGGTGAAACCTTGTCTACTAAAAA
TACAAAAAATTAGCCAGGCACAGTGGTGTGCACTGGTAGTCCCAGTTACTCGGGAGGCTGAG
GCAGGAAAATCGCTTGAACCCAGGAGGCGGACGTTGCGGTGAGCCGAGATCGCGCCGCTGAT
TCCAGCCTGGGCGACAAGAGTGAGACTCCATCTCACACA

FIGURE 98

</usr/seqdb2/sst/DNA/Dnaseqs.min/ss.DNA62876
<subunit 1 of 1, 120 aa, 1 stop
<MW: 12925, pI: 9.46, NX(S/T): 0
MLPPALPPALVFTVAWSLLAERVSWVRDAEDAHRLQPFVTERTLGKVQRWSGVHTQTGGR
AGGGQFCCAWLDSKRVLASPGWGAANSIKNQRVWAPATESSAQLLCCWPVGVARGGALCQ

Important features:
Signal peptide:
Amino acids 1-17

N-myristoylation sites:
Amino acids 58-64;63-69;64-70;83-89;111-117;115-121

FIGURE 99

AATTTTTCACCAGAGTAAACTTGAGAAACCAACTGGACCTTGAGTATTGTACATTTTGCCTC
GTGGACCCAAAGGTAGCAATCTGAAACATGAGGAGTACGATTCTACTGTTTTGTCTTCTAGG
ATCAACTCGGTCATTACCACAGCTCAAACCTGCTTTGGGACTCCCTCCCACAAAACTGGCTC
CGGATCAGGGAACACTACCAAACCAACAGCAGTCAAATCAGGTCTTTCCTTCTTTAAGTCTG
ATACCATTAACACAGATGCTCACACTGGGGCCAGATCTGCATCTGTTAAATCCTGCTGCAGG
AATGACACCTGGTACCCAGACCCACCCATTGACCCTGGGAGGGTTGAATGTACAACAGCAAC
TGCACCCACATGTGTTACCAATTTTTGTCACACAACTTGGAGCCCAGGGCACTATCCTAAGC
TCAGAGGAATTGCCACAAATCTTCACGAGCCTCATCATCCATTCCTTGTTCCCGGGAGGCAT
CCTGCCCACCAGTCAGGCAGGGGCTAATCCAGATGTCCAGGATGGAAGCCTTCCAGCAGGAG
GAGCAGGTGTAAATCCTGCCACCCAGGGAACCCCAGCAGGCCGCCTCCCAACTCCCAGTGGC
ACAGATGACGACTTTGCAGTGACCACCCCTGCAGGCATCCAAAGGAGCACACATGCCATCGA
GGAAGCCACCACAGAATCAGCAAATGGAATTCAGTAAGCTGTTTCAAATTTTTTCAACTAAG
CTGCCTCGAATTTGGTGATACATGTGAATCTTTATCATTGATTATATTATGGAATAGATTGA
GACACATTGGATAGTCTTAGAAGAAATTAATTCTTAATTTACCTGAAAATATTCTTGAAATTT
CAGAAAATATGTTCTATGTAGAGAATCCCAACTTTTAAAAACAATAATTCAATGGATAAATC
TGTCTTTGAAATATAACATTATGCTGCCTGGATGATATGCATATTAAAACATATTTGGAAAA
CTGGAAAAAAAAAAAAAAAAAAAAAAAAAAAAAAAAAAAAAAAAAAAAAAAAAAAAAAAAAAAA
AAAAAAAAAAAAAAAAAA

FIGURE 100

```
></usr/seqdb2/sst/DNA/Dnaseqs.min/ss.DNA66660
><subunit 1 of 1, 209 aa, 1 stop
><MW: 21588, pI: 5.50, NX(S/T): 0
MRSTILLFCLLGSTRSLPQLKPALGLPPTKLAPDQGTLPNQQQSNQVFPSLSLIPLTQML
TLGPDLHLLNPAAGMTPGTQTHPLTLGGLNVQQQLHPHVLPIFVTQLGAQGTILSSEELP
QIFTSLIIHSLFPGGILPTSQAGANPDVQDGSLPAGGAGVNPATQGTPAGRLPTPSGTDD
DFAVTTPAGIQRSTHAIEEATTESANGIQ
```

Important features of the protein:

Signal peptide:

Amino acids 1-16

Leucine zipper patterns:

Amino acids 10-32;17-39

N-myristoylation sites:

Amino acids 12-18;25-31;36-42;74-80;108-114;111-117;
135-141;151-157;159-165;166-172;189-195

FIGURE 101

GGGGTCTCCCTCAGGGCCGGGAGGCACAGCGGTCCCTGCTTGCTGAAGGGCTGGATGTACGC
ATCCGCAGGTTCCCGCGGACTTGGGGGCGCCCGCTGAGCCCCGGCGCCCGCAGAAGACTTGT
GTTTGCCTCCTGCAGCCTCAACCCGGAGGGCAGCGAGGGCCTACCACCATGATCACTGGTGT
GTTCAGCATGCGCTTGTGGACCCCAGTGGGCGTCCTGACCTCGCTGGCGTACTGCCTGCACC
AGCGGCGGGTGGCCCTGGCCGAGCTGCAGGAGGCCGATGGCCAGTGTCCGGTCGACCGCAGC
CTGCTGAAGTTGAAAATGGTGCAGGTCGTGTTTCGACACGGGGCTCGGAGTCCTCTCAAGCC
GCTCCCGCTGGAGGAGCAGGTAGAGTGGAACCCCCAGCTATTAGAGGTCCCACCCCAAACTC
AGTTTGATTACACAGTCACCAATCTAGCTGGTGGTCCGAAACCATATTCTCCTTACGACTCT
CAATACCATGAGACCACCCTGAAGGGGGGCATGTTTGCTGGGCAGCTGACCAAGGTGGGCAT
GCAGCAAATGTTTGCCTTGGGAGAGAGACTGAGGAAGAACTATGTGGAAGACATTCCCTTTC
TTTCACCAACCTTCAACCCACAGGAGGTCTTTATTCGTTCCACTAACATTTTTCGGAATCTG
GAGTCCACCCGTTGTTTGCTGGCTGGGCTTTTCCAGTGTCAGAAAGAAGGACCCATCATCAT
CCACACTGATGAAGCAGATTCAGAAGTCTTGTATCCCAACTACCAAAGCTGCTGGAGCCTGA
GGCAGAGAACCAGAGGCCGGAGGCAGACTGCCTCTTTACAGCCAGGAATCTCAGAGGATTTG
AAAAAGGTGAAGGACAGGATGGGCATTGACAGTAGTGATAAAGTGGACTTCTTCATCCTCCT
GGACAACGTGGCTGCCGAGCAGGCACACAACCTCCCAAGCTGCCCCATGCTGAAGAGATTTG
CACGGATGATCGAACAGAGAGCTGTGGACACATCCTTGTACATACTGCCCAAGGAAGACAGG
GAAAGTCTTCAGATGGCAGTAGGCCCATTCCTCCACATCCTAGAGAGCAACCTGCTGAAAGC
CATGGACTCTGCCACTGCCCCCGACAAGATCAGAAAGCTGTATCTCTATGCGGCTCATGATG
TGACCTTCATACCGCTCTTAATGACCCTGGGGATTTTTGACCACAAATGGCCACCGTTTGCT
GTTGACCTGACCATGGAACTTTACCAGCACCTGGAATCTAAGGAGTGGTTTGTGCAGCTCTA
TTACCACGGGAAGGAGCAGGTGCCGAGAGGTTGCCCTGATGGGCTCTGCCCGCTGGACATGT
TCTTGAATGCCATGTCAGTTTATACCTTAAGCCCAGAAAAATACCATGCACTCTGCTCTCAA
ACTCAGGTGATGGAAGTTGGAAATGAAGAGTAACTGATTTATAAAAGCAGGATGTGTTGATT
TTAAAATAAAGTGCCTTTATACAATG

FIGURE 102

MITGVFSMRLWTPVGVLTSLAYCLHQRRVALAELQEADGQCPVDRSLLKLKMVQVVFRHGARSPLKPLPLEEQV
EWNPQLLEVPPQTQFDYTVTNLAGGPKPYSPYDSQYHETTLKGGMFAGQLTKVGMQQMFALGERLRKNYVEDIP
FLSPTFNPQEVFIRSTNIFRNLESTRCLLAGLFQCQKEGPIIIHTDEADSEVLYPNYQSCWSLRQRTRGRRQTA
SLQPGISEDLKKVKDRMGIDSSDKVDFFILLDNVAAEQAHNLPSCPMLKRFARMIEQRAVDTSLYILPKEDRES
LQMAVGPFLHILESNLLKAMDSATAPDKIRKLYLYAAHDVTFIPLLMTLGIFDHKWPPFAVDLTMELYQHLESK
EWFVQLYYHGKEQVPRGCPDGLCPLDMFLNAMSVYTLSPEKYHALCSQTQVMEVGNEE

Important features:
Signal sequence:
amino acids 1-23 cAMP- and cGMP-dependent protein kinase phosphorylation site.
amino acids 218-222

Casein kinase II phosphorylation site.
amino acids 87-91, 104-108, 320-324

Tyrosine kinase phosphorylation site.
amino acids 280-288

N-myristoylation site.
amino acids 15-21, 117-123, 118-124, 179-185, 240-246, 387-393

Amidation site.
amino acids 216-220

Leucine zipper pattern.
amino acids 10-32

Histidine acid phosphatases phosphohistidine signature.
amino acids 50-65

FIGURE 103

GGGGCGGGTGGACGCGGACTCGAACGCAGTTGCTTCGGGACCCAGGACCCCCTCGGGCCCGA
CCCGCCAGGAAAGACTGAGGCCGCGGCCTGCCCCGCCCGGCTCCCTGCGCCGCCGCCGCCTC
CCGGGACAGAAGATGTGCTCCAGGGTCCCTCTGCTGCTGCCGCTGCTCCTGCTACTGGCCCT
GGGGCCTGGGGTGCAGGGCTGCCCATCCGGCTGCCAGTGCAGCCAGCCACAGACAGTCTTCT
GCACTGCCCGCCAGGGGACCACGGTGCCCCGAGACGTGCCACCCGACACGGTGGGGCTGTAC
GTCTTTGAGAACGGCATCACCATGCTCGACGCAAGCAGCTTTGCCGGCCTGCCGGGCCTGCA
GCTCCTGGACCTGTCACAGAACCAGATCGCCAGCCTGCGCCTGCCCCGCCTGCTGCTGCTGG
ACCTCAGCCACAACAGCCTCCTGGCCCTGGAGCCCGGCATCCTGGACACTGCCAACGTGGAG
GCGCTGCGGCTGGCTGGTCTGGGGCTGCAGCAGCTGGACGAGGGGCTCTTCAGCCGCTTGCG
CAACCTCCACGACCTGGATGTGTCCGACAACCAGCTGGAGCGAGTGCCACCTGTGATCCGAG
GCCTCCGGGGCCTGACGCGCCTGCGGCTGGCCGGCAACACCCGCATTGCCCAGCTGCGGCCC
GAGGACCTGGCCGGCCTGGCTGCCCTGCAGGAGCTGGATGTGAGCAACCTAAGCCTGCAGGC
CCTGCCTGGCGACCTCTCGGGCCTCTTCCCCCGCCTGCGGCTGCTGGCAGCTGCCCGCAACC
CCTTCAACTGCGTGTGCCCCCTGAGCTGGTTTGGCCCCTGGGTGCGCGAGAGCCACGTCACA
CTGGCCAGCCCTGAGGAGACGCGCTGCCACTTCCCGCCCAAGAACGCTGGCCGGCTGCTCCT
GGAGCTTGACTACGCCGACTTTGGCTGCCCAGCCACCACCACCACAGCCACAGTGCCCACCA
CGAGGCCCGTGGTGCGGGAGCCCACAGCCTTGTCTTCTAGCTTGGCTCCTACCTGGCTTAGC
CCCACAGCGCCGGCCACTGAGGCCCCCAGCCCGCCCTCCACTGCCCCACCGACTGTAGGGCC
TGTCCCCCAGCCCCAGGACTGCCCACCGTCCACCTGCCTCAATGGGGGCACATGCCACCTGG
GGACACGGCACCACCTGGCGTGCTTGTGCCCCGAAGGCTTCACGGGCCTGTACTGTGAGAGC
CAGATGGGGCAGGGGACACGGCCCAGCCCTACACCAGTCACGCCGAGGCCACCACGGTCCCT
GACCCTGGGCATCGAGCCGGTGAGCCCCACCTCCCTGCGCGTGGGGCTGCAGCGCTACCTCC
AGGGGAGCTCCGTGCAGCTCAGGAGCCTCCGTCTCACCTATCGCAACCTATCGGGCCCTGAT
AAGCGGCTGGTGACGCTGCGACTGCCTGCCTCGCTCGCTGAGTACACGGTCACCCAGCTGCG
GCCCAACGCCACTTACTCCGTCTGTGTCATGCCTTTGGGGCCCGGGCGGGTGCCGGAGGGCG
AGGAGGCCTGCGGGGAGGCCCATACACCCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGC
CGCGCTGGCTGCGGTGGGGGCAGCCTACTGTGTGCGGCGGGGGCGGGCCATGGCAGCAGCGG
CTCAGGACAAAGGGCAGGTGGGGCCAGGGGCTGGGCCCCTGGAACTGGAGGGAGTGAAGGTC
CCCTTGGAGCCAGGCCCGAAGGCAACAGAGGGCGGTGGAGAGGCCCTGCCCAGCGGGTCTGA
GTGTGAGGTGCCACTCATGGGCTTCCCAGGGCCTGGCCTCCAGTCACCCCTCCACGCAAAGC
CCTACATCTAAGCCAGAGAGAGACAGGGCAGCTGGGGCCGGGCTCTCAGCCAGTGAGATGGC
CAGCCCCCTCCTGCTGCCACACCACGTAAGTTCTCAGTCCCAACCTCGGGGATGTGTGCAGA
CAGGGCTGTGTGACCACAGCTGGGCCCTGTTCCCTCTGGACCTCGGTCTCCTCATCTGTGAG
ATGCTGTGGCCCAGCTGACGAGCCCTAACGTCCCCAGAACCGAGTGCCTATGAGGACAGTGT
CCGCCCTGCCCTCCGCAACGTGCAGTCCCTGGGCACGGCGGGCCCTGCCATGTGCTGGTAAC
GCATGCCTGGGCCCTGCTGGGCTCTCCCACTCCAGGCGGACCCTGGGGGCCAGTGAAGGAAG
CTCCCGGAAAGAGCAGAGGGAGAGCGGGTAGGCGGCTCTGTGACTCTAGTCTTGGCCCCAGG
AAGCGAAGGAACAAAAGAAACTGGAAAGGAAGATGCTTTAGGAACATGTTTTGCTTTTTTAA
AATATATATATATTTATAAGAGATCCTTTCCCATTTATTCTGGGAAGATGTTTTTCAAACTC
AGAGACAAGGACTTTGGTTTTTGTAAGACAAACGATGATATGAAGGCCTTTTGTAAGAAAAA
ATAAAAAAAAAAA

FIGURE 104

</usr/seqdb2/sst/DNA/Dnaseqs.min/ss.DNA44804
<subunit 1 of 1, 598 aa, 1 stop
<MW: 63030, pI: 7.24, NX(S/T): 3
MCSRVPLLLPLLLLLALGPGVQGCPSGCQCSQPQTVFCTARQGTTVPRDVPPDTVGLYVFEN
GITMLDASSFAGLPGLQLLDLSQNQIASLRLPRLLLLDLSHNSLLALEPGILDTANVEALRL
AGLGLQQLDEGLFSRLRNLHDLDVSDNQLERVPPVIRGLRGLTRLRLAGNTRIAQLRPEDLA
GLAALQELDVSNLSLQALPGDLSGLFPRLRLLAAARNPFNCVCPLSWFGPWVRESHVTLASP
EETRCHFPPKNAGRLLLELDYADFGCPATTTTATVPTTRPVVREPTALSSSLAPTWLSPTAP
ATEAPSPPSTAPPTVGPVPQPQDCPPSTCLNGGTCHLGTRHHLACLCPEGFTGLYCESQMGQ
GTRPSPTPVTPRPPRSLTLGIEPVSPTSLRVGLQRYLQGSSVQLRSLRLTYRNLSGPDKRLV
TLRLPASLAEYTVTQLRPNATYSVCVMPLGPGRVPEGEEACGEAHTPPAVHSNHAPVTQARE
GNLPLLIAPALAAVLLAALAAVGAAYCVRRGRAMAAAAQDKGQVGPGAGPLELEGVKVPLEP
GPKATEGGGEALPSGSECEVPLMGFPGPGLQSPLHAKPYI

Signal sequence.
amino acids 1-23
Transmembrane domain.
amino acids 501-522
N-glycosylation sites.
amino acids 198-202, 425-429, 453-457
Tyrosine kinase phosphorylation site.
amino acids 262-270
N-myristoylation sites.
amino acids 23-29, 27-33, 112-118, 273-279, 519-525, 565-571
Prokaryotic membrane lipoprotein lipid attachment site.
amino acids 14-25
EGF-like domain cysteine pattern signature.
amino acids 355-367
Leucine zipper pattern.
amino acids 122-144, 194-216

FIGURE 105

CCCACGCGTCCGAAGGCAGACAAAGGTTCATTTGTAAAGAAGCTCCTTCCAGCACCTCCTCT
CTTCTCCTTTTGCCCAAACTCACCCAGTGAGTGTGAGCATTTAAGAAGCATCCTCTGCCAAG
ACCAAAAGGAAAGAAGAAAAAGGGCCAAAAGCCAAAATGAAACTGATGGTACTTGTTTTCAC
CATTGGGCTAACTTTGCTGCTAGGAGTTCAAGCCATGCCTGCAAATCGCCTCTCTTGCTACA
GAAAGATACTAAAAGATCACAACTGTCACAACCTTCCGGAAGGAGTAGCTGACCTGACACAG
ATTGATGTCAATGTCCAGGATCATTTCTGGGATGGGAAGGGATGTGAGATGATCTGTTACTG
CAACTTCAGCGAATTGCTCTGCTGCCCAAAAGACGTTTTCTTTGGACCAAAGATCTCTTTCG
TGATTCCTTGCAACAATCAATGAGAATCTTCATGTATTCTGGAGAACACCATTCCTGATTTC
CCACAAACTGCACTACATCAGTATAACTGCATTTCTAGTTTCTATATAGTGCAATAGAGCAT
AGATTCTATAAATTCTTACTTGTCTAAGACAAGTAAATCTGTGTTAAACAAGTAGTAATAAA
AGTTAATTCAATCTAAAAAAAAAAAAA

FIGURE 106

</usr/seqdb2/sst/DNA/Dnaseqs.min/ss.DNA52758
<subunit 1 of 1, 98 aa, 1 stop
<MW: 11081, pI: 6.68, NX(S/T): 1
MKLMVLVFTIGLTLLLGVQAMPANRLSCYRKILKDHNCHNLPEGVADLTQIDVNVQDHFW
DGKGCEMICYCNFSELLCCPKDVFFGPKISFVIPCNNQ

Important features:
Signal peptide:
Amino acids 1-20

N-glycosylation site:
Amino acids 72-76

Tyrosine kinase phosphorylation site:
Amino acids 63-71

FIGURE 107

AGTGACTGCAGCCTTCCTAGATCCCCTCCACTCGGTTTCTCTCTTTGCAGGAGCACCGGCAG
CACCAGTGTGTGAGGGGAGCAGGCAGCGGTCCTAGCCAGTTCCTTGATCCTGCCAGACCACC
CAGCCCCCGGCACAGAGCTGCTCCACAGGCACCATGAGGATCATGCTGCTATTCACAGCCAT
CCTGGCCTTCAGCCTAGCTCAGAGCTTTGGGGCTGTCTGTAAGGAGCCACAGGAGGAGGTGG
TTCCTGGCGGGGGCCGCAGCAAGAGGGATCCAGATCTCTACCAGCTGCTCCAGAGACTCTTC
AAAAGCCACTCATCTCTGGAGGGATTGCTCAAAGCCCTGAGCCAGGCTAGCACAGATCCTAA
GGAATCAACATCTCCCGAGAAACGTGACATGCATGACTTCTTTGTGGGACTTATGGGCAAGA
GGAGCGTCCAGCCAGAGGGAAAGACAGGACCTTTCTTACCTTCAGTGAGGGTTCCTCGGCCC
CTTCATCCCAATCAGCTTGGATCCACAGGAAAGTCTTCCCTGGGAACAGAGGAGCAGAGACC
TTTATAAGACTCTCCTACGGATGTGAATCAAGAGAACGTCCCCAGCTTTGGCATCCTCAAGTA
TCCCCCGAGAGCAGAATAGGTACTCCACTTCCGGACTCCTGGACTGCATTAGGAAGACCTCT
TTCCCTGTCCCAATCCCCAGGTGCGCACGCTCCTGTTACCCTTTCTCTTCCCTGTTCTTGTA
ACATTCTTGTGCTTTGACTCCTTCTCCATCTTTTCTACCTGACCCTGGTGTGGAAACTGCAT
AGTGAATATCCCCAACCCCAATGGGCATTGACTGTAGAATACCCTAGAGTTCCTGTAGTGTC
CTACATTAAAAATATAATGTCTCTCTCTATTCCTCAACAATAAAGGATTTTTGCATATGAAA
AAAAAAAAAAAAAAAAAAAAAAAAAAAAAAAAAAAAAAAAAA

FIGURE 108

</usr/seqdb2/sst/DNA/Dnaseqs.min/ss.DNA59849
<subunit 1 of 1, 135 aa, 1 stop
<MW: 14833, pI: 9.78, NX(S/T): 0
MRIMLLFTAILAFSLAQSFGAVCKEPQEEVVPGGGRSKRDPDLYQLLQRLFKSHSSLEGL
LKALSQASTDPKESTSPEKRDMHDFFVGLMGKRSVQPEGKTGPFLPSVRVPRPLHPNQLG
STGKSSLGTEEQRPL

Important features:
Signal peptide:
Amino acids 1-18

Tyrosine kinase phosphorylation site:
Amino acids 36-45

N-myristoylation sites:
Amino acids 33-39;59-65

Amidation site:
Amino acids 90-94

Leucine zipper pattern:
Amino acids 43-65

Tachykinin family signature:
Amino acids 86-92

FIGURE 109

GCGGCCACACGCAGCTAGCCGGAGCCCGGACCAGGCGCCTGTGCCTCCTCCTCGTCCCTCGC
CGCGTCCGCGAAGCCTGGAGCCGGCGGGAGCCCCGCGCTCGCCATGTCGGGCGAGCTCAGCA
ACAGGTTCCAAGGAGGGAAGGCGTTCGGCTTGCTCAAAGCCCGGCAGGAGAGGAGGCTGGCC
GAGATCAACCGGGAGTTTCTGTGTGACCAGAAGTACAGTGATGAAGAGAACCTTCCAGAAAA
GCTCACAGCCTTCAAAGAGAAGTACATGGAGTTTGACCTGAACAATGAAGGCGAGATTGACC
TGATGTCTTTAAAGAGGATGATGGAGAAGCTTGGTGTCCCCAAGACCCACCTGGAGATGAAG
AAGATGATCTCAGAGGTGACAGGAGGGGTCAGTGACACTATATCCTACCGAGACTTTGTGAA
CATGATGCTGGGGAAACGGTCGGCTGTCCTCAAGTTAGTCATGATGTTTGAAGGAAAAGCCA
ACGAGAGCAGCCCCAAGCCAGTTGGCCCCCCTCCAGAGAGAGACATTGCTAGCCTGCCCTGA
GGACCCCGCCTGGACTCCCCAGCCTTCCCACCCCATACCTCCCTCCCGATCTTGCTGCCCTT
CTTGACACACTGTGATCTCTCTCTCTCTCATTTGTTTGGTCATTGAGGGTTTGTTTGTGTTT
TCATCAATGTCTTTGTAAAGCACAAATTATCTGCCTTAAAGGGGCTCTGGGTCGGGGAATCC
TGAGCCTTGGGTCCCCTCCCTCTCTTCTTCCCTCCTTCCCCGCTCCCTGTGCAGAAGGGCTG
ATATCAAACCAAAAACTAGAGGGGGCAGGGCCAGGGCAGGGAGGCTTCCAGCCTGTGTTCCC
CTCACTTGGAGGAACCAGCACTCTCCATCCTTTCAGAAAGTCTCCAAGCCAAGTTCAGGCTC
ACTGACCTGGCTCTGACGAGGACCCCAGGCCACTCTGAGAAGACCTTGGAGTAGGGACAAGG
CTGCAGGGCCTCTTTCGGGTTTCCTTGGACAGTGCCATGGTTCCAGTGCTCTGGTGTCACCC
AGGACACAGCCACTCGGGGCCCCGCTGCCCCAGCTGATCCCCACTCATTCCACACCTCTTCT
CATCCTCAGTGATGTGAAGGTGGGAAGGAAAGGAGCTTGGCATTGGGAGCCCTTCAAGAAGG
TACCAGAAGGAACCCTCCAGTCCTGCTCTCTGGCCACACCTGTGCAGGCAGCTGAGAGGCAG
CGTGCAGCCCTACTGTCCCTTACTGGGGCAGCAGAGGGCTTCGGAGGCAGAAGTGAGGCCTG
GGGTTTGGGGGGAAAGGTCAGCTCAGTGCTGTTCCACCTTTTAGGGAGGATACTGAGGGGAC
CAGGATGGGAGAATGAGGAGTAAAATGCTCACGGCAAAGTCAGCAGCACTGGTAAGCCAAGA
CTGAGAAATACAAGGTTGCTTGTCTGACCCCAATCTGCTTGAAAAAAAAAAAAAAAAAAA

FIGURE 110

MSGELSNRFQGGKAFGLLKARQERRLAEINREFLCDQKYSDEENLPEKLTAFKEKYMEFDLN
NEGEIDLMSLKRMMEKLGVPKTHLEMKKMISEVTGGVSDTISYRDFVNMMLGKRSAVLKLVM
MFEGKANESSPKPVGPPPERDIASLP

FIGURE 111

TAAAACAGCTACAATATTCCAGGGCCAGTCACTTGCCATTTCTCATAACAGCGTCAGAGAGA
AAGAACTGACTGAAACGTTTGAGATGAAGAAAGTTCTCCTCCTGATCACAGCCATCTTGGCA
GTGGCTGTTGGTTTCCCAGTCTCTCAAGACCAGGAACGAGAAAAAAGAAGTATCAGTGACAG
CGATGAATTAGCTTCAGGGTTTTTTGTGTTCCCTTACCCATATCCATTTCGCCCACTTCCAC
CAATTCCATTTCCAAGATTTCCATGGTTTAGACGTAATTTTCCTATTCCAATACCTGAATCT
GCCCCTACAACTCCCCTTCCTAGCGAAAAGTAAACAAGAAGGATAAGTCACGATAAACCTGG
TCACCTGAAATTGAAATTGAGCCACTTCCTTGAAGAATCAAAATTCCTGTTAATAAAAGAAA
AACAAATGTAATTGAAATAGCACACAGCATTCTCTAGTCAATATCTTTAGTGATCTTCTTTA
ATAAACATGAAAGCAAAGATTTTGGTTTCTTAATTTCCACA

FIGURE 112

></usr/seqdb2/sst/DNA/Dnaseqs.min/ss.DNA71290
><subunit 1 of 1, 85 aa, 1 stop
><MW: 9700, pI: 9.55, NX(S/T): 0
MKKVLLLITAILAVAVGFPVSQDQEREKRSISDSDELASGFFVFPYPYPFRPLPPIPFPR
FPWFRRNFPIPIPESAPTTPLPSEK

Important features of the protein:
Signal peptide:
Amino acids 1-17

Homologous region to B3-hordein:
Amino acids 47-85

FIGURE 113

CTCCTCTTAACATACTTGCAGCTAAAACTAAATATTGCTGCTTGGGGACCTCCTTCTAGCCT
TAAATTTCAGCTCATCACCTTCACCTGCCTTGGTCATGGCTCTGCTATTCTCCTTGATCCTT
GCCATTTGCACCAGACCTGGATTCCTAGCGTCTCCATCTGGAGTGCGGCTGGTGGGGGGCCT
CCACCGCTGTGAAGGGCGGGTGGAGGTGGAACAGAAAGGCCAGTGGGGCACCGTGTGTGATG
ACGGCTGGGACATTAAGGACGTGGCTGTGTTGTGCCGGGAGCTGGGCTGTGGAGCTGCCAGC
GGAACCCCTAGTGGTATTTTGTATGAGCCACCAGCAGAAAAAGAGCAAAAGGTCCTCATCCA
ATCAGTCAGTTGCACAGGAACAGAAGATACATTGGCTCAGTGTGAGCAAGAAGAAGTTTATG
ATTGTTCACATGATGAAGATGCTGGGGCATCGTGTGAGAACCCAGAGAGCTCTTTCTCCCCA
GTCCCAGAGGGTGTCAGGCTGGCTGACGGCCCTGGGCATTGCAAGGGACGCGTGGAAGTGAA
GCACCAGAACCAGTGGTATACCGTGTGCCAGACAGGCTGGAGCCTCCGGGCCGCAAAGGTGG
TGTGCCGGCAGCTGGGATGTGGGAGGGCTGTACTGACTCAAAAACGCTGCAACAAGCATGCC
TATGGCCGAAAACCCATCTGGCTGAGCCAGATGTCATGCTCAGGACGAGAAGCAACCCTTCA
GGATTGCCCTTCTGGGCCTTGGGGGAAGAACACCTGCAACCATGATGAAGACACGTGGGTCG
AATGTGAAGATCCCTTTGACTTGAGACTAGTAGGAGGAGACAACCTCTGCTCTGGGCGACTG
GAGGTGCTGCACAAGGGCGTATGGGGCTCTGTCTGTGATGACAACTGGGGAGAAAAGGAGGA
CCAGGTGGTATGCAAGCAACTGGGCTGTGGGAAGTCCCTCTCTCCCTCCTTCAGAGACCGGA
AATGCTATGGCCCTGGGGTTGGCCGCATCTGGCTGGATAATGTTCGTTGCTCAGGGGAGGAG
CAGTCCCTGGAGCAGTGCCAGCACAGATTTTGGGGGTTTCACGACTGCACCCACCAGGAAGA
TGTGGCTGTCATCTGCTCAGTGTAGGTGGGCATCATCTAATCTGTTGAGTGCCTGAATAGAA
GAAAAACACAGAAGAAGGGAGCATTTACTGTCTACATGACTGCATGGGATGAACACTGATCT
TCTTCTGCCCTTGGACTGGGACTTATACTTGGTGCCCCTGATTCTCAGGCCTTCAGAGTTGG
ATCAGAACTTACAACATCAGGTCTAGTTCTCAGGCCATCAGACATAGTTTGGAACTACATCA
CCACCTTTCCTATGTCTCCACATTGCACACAGCAGATTCCCAGCCTCCATAATTGTGTGTAT
CAACTACTTAAATACATTCTCACACACACACACACACACACACACACACACACACACACATA
CACCATTTGTCCTGTTTCTCTGAAGAACTCTGACAAAATACAGATTTTGGTACTGAAAGAGA
TTCTAGAGGAACGGAATTTTAAGGATAAATTTTCTGAATTGGTTATGGGGTTTCTGAAATTG
GCTCTATAATCTAATTAGATATAAAATTCTGGTAACTTTATTTACAATAATAAAGATAGCAC
TATGTGTTCAAA

FIGURE 114

MALLFSLILAICTRPGFLASPSGVRLVGGLHRCEGRVEVEQKGQWGTVCDDGWDIKDVAVLC
RELGCGAASGTPSGILYEPPAEKEQKVLIQSVSCTGTEDTLAQCEQEEVYDCSHDEDAGASC
ENPESSFSPVPEGVRLADGPGHCKGRVEVKHQNQWYTVCQTGWSLRAAKVVCRQLGCGRAVL
TQKRCNKHAYGRKPIWLSQMSCSGREATLQDCPSGPWGKNTCNHDEDTWVECEDPFDLRLVG
GDNLCSGRLEVLHKGVWGSVCDDNWGEKEDQVVCKQLGCGKSLSPSFRDRKCYGPGVGRIWL
DNVRCSGEEQSLEQCQHRFWGFHDCTHQEDVAVICSV

Signal sequence:
amino acids 1-15

Casein kinase II phosphorylation site.
amino acids 47-51, 97-101, 115-119, 209-213, 214-218, 234-238, 267-271, 294-298, 316-320, 336-340

N-myristoylation site.
amino acids 29-35, 43-49, 66-72, 68-74, 72-78, 98-104, 137-143, 180-186, 263-269, 286-292

Amidation site.
amino acids 196-200

Speract receptor repeated domain signature.
amino acids 29-67, 249-287

FIGURE 115

CATTTCCAACAAGAGCACTGGCCAAGTCAGCTTCTTCTGAGAGAGTCTCTAGAAGACATGAT
GCTACACTCAGCTTTGGGTCTCTGCCTCTTACTCGTCACAGTTTCTTCCAACCTTGCCATTG
CAATAAAAAAGGAAAAGAGGCCTCCTCAGACACTCTCAAGAGGATGGGGAGATGACATCACT
TGGGTACAAACTTATGAAGAAGGTCTCTTTTATGCTCAAAAAAGTAAGAAGCCATTAATGGT
TATTCATCACCTGGAGGATTGTCAATACTCTCAAGCACTAAAGAAAGTATTTGCCCAAAATG
AAGAAATACAAGAAATGGCTCAGAATAAGTTCATCATGCTAAACCTTATGCATGAAACCACT
GATAAGAATTTATCACCTGATGGGCAATATGTGCCTAGAATCATGTTTGTAGACCCTTCTTT
AACAGTTAGAGCTGACATAGCTGGAAGATACTCTAACAGATTGTACACATATGAGCCTCGGG
ATTTACCCCTATTGATAGAAAACATGAAGAAAGCATTAAGACTTATTCAGTCAGAGCTATAA
GAGATGATGGAAAAAAGCCTTCACTTCAAAGAAGTCAAATTTCATGAAGAAAACCTCTGGCA
CATTGACAAATACTAAATGTGCAAGTATATAGATTTTGTAATATTACTATTTAGTTTTTTTA
ATGTGTTTGCAATAGTCTTATTAAAATAAATGTTTTTTAAATCTGA

FIGURE 116

</usr/seqdb2/sst/DNA/Dnaseqs.min/ss.DNA64896
<subunit 1 of 1, 166 aa, 1 stop
<MW: 19171, pI: 8.26, NX(S/T): 1
MMLHSALGLCLLLVTVSSNLAIAIKKEKRPPQTLSRGWGDDITWVQTYEEGLFYAQKSKK
PLMVIHHLEDCQYSQALKKVFAQNEEIQEMAQNKFIMLNLMHETTDKNLSPDGQYVPRIM
FVDPSLTVRADIAGRYSNRLYTYEPRDLPLLIENMKKALRLIQSEL

Important features:
Signal peptide:
Amino acids 1-23

N-myristoylation site:
Amino acids 51-57

FIGURE 117

CCTGGAGCCGGAAGCGCGGCTGCAGCAGGGCGAGGCTCCAGGTGGGGTCGGTTCCGCATCCA
GCCTAGCGTGTCCACGATGCGGCTGGGCTCCGGGACTTTCGCTACCTGTTGCGTAGCGATCG
AGGTGCTAGGGATCGCGGTCTTCCTTCGGGGATTCTTCCCGGCTCCCGTTCGTTCCTCTGCC
AGAGCGGAACACGGAGCGGAGCCCCCAGCGCCCGAACCCTCGGCTGGAGCCAGTTCTAACTG
GACCACGCTGCCACCACCTCTCTTCAGTAAAGTTGTTATTGTTCTGATAGATGCCTTGAGAG
ATGATTTTGTGTTTGGGTCAAAGGGTGTGAAATTTATGCCCTACACAACTTACCTTGTGGAA
AAAGGAGCATCTCACAGTTTTGTGGCTGAAGCAAAGCCACCTACAGTTACTATGCCTCGAAT
CAAGGCATTGATGACGGGGAGCCTTCCTGGCTTTGTCGACGTCATCAGGAACCTCAATTCTC
CTGCACTGCTGGAAGACAGTGTGATAAGACAAGCAAAAGCAGCTGGAAAAAGAATAGTCTTT
TATGGAGATGAAACCTGGGTTAAATTATTCCCAAAGCATTTTGTGGAATATGATGGAACAAC
CTCATTTTTCGTGTCAGATTACACAGAGGTGGATAATAATGTCACGAGGCATTTGGATAAAG
TATTAAAAAGAGGAGATTGGGACATATTAATCCTCCACTACCTGGGGCTGGACCACATTGGC
CACATTTCAGGGCCCAACAGCCCCCTGATTGGGCAGAAGCTGAGCGAGATGGACAGCGTGCT
GATGAAGATCCACACCTCACTGCAGTCGAAGGAGAGAGAGACGCCTTTACCCAATTTGCTGG
TTCTTTGTGGTGACCATGGCATGTCTGAAACAGGAAGTCACGGGGCCTCCTCCACCGAGGAG
GTGAATACACCTCTGATTTTAATCAGTTCTGCGTTTGAAAGGAAACCCGGTGATATCCGACA
TCCAAAGCACGTCCAATAGACGGATGTGGCTGCGACACTGGCGATAGCACTTGGCTTACCGA
TTCCAAAAGACAGTGTAGGGAGCCTCCTATTCCCAGTTGTGGAAGGAAGACCAATGAGAGAG
CAGTTGAGATTTTTACATTTGAATACAGTGCAGCTTAGTAAACTGTTGCAAGAGAATGTGCC
GTCATATGAAAAAGATCCTGGGTTTGAGCAGTTTAAAATGTCAGAAAGATTGCATGGGAACT
GGATCAGACTGTACTTGGAGGAAAAGCATTCAGAAGTCCTATTCAACCTGGGCTCCAAGGTT
CTCAGGCAGTACCTGGATGCTCTGAAGACGCTGAGCTTGTCCCTGAGTGCACAAGTGGCCCA
GTTCTCACCCTGCTCCTGCTCAGCGTCCCACAGGCACTGCACAGAAAGGCTGAGCTGGAAGTC
CCACTGTCATCTCCTGGGTTTTCTCTGCTCTTTTATTTGGTGATCCTGGTTCTTTCGGCCGT
TCACGTCATTGTGTGCACCTCAGCTGAAAGTTCGTGCTACTTCTGTGGCCTCTCGTGGCTGG
CGGCAGGCTGCCTTTCGTTTACCAGACTCTGGTTGAACACCTGGTGTGTGCCAAGTGCTGGC
AGTGCCCTGGACAGGGGGCCTCAGGGAAGGACGTGGAGCAGCCTTATCCCAGGCCTCTGGGT
GTCCCGACACAGGTGTTCACATCTGTGCTGTCAGGTCAGATGCCTCAGTTCTTGGAAAGCTA
GGTTCCTGCGACTGTTACCAAGGTGATTGTAAAGAGCTGGCGGTCACAGAGGAACAAGCCCC
CCAGCTGAGGGGGTGTGTGAATCGGACAGCCTCCCAGCAGAGGTGTGGGAGCTGCAGCTGAG
GGAAGAAGAGACAATCGGCCTGGACACTCAGGAGGGTCAAAAGGAGACTTGGTCGCACCACT
CATCCTGCCACCCCCAGAATGCATCCTGCCTCATCAGGTCCAGATTTCTTTCCAAGGCGGAC
GTTTTCTGTTGGAATTCTTAGTCCTTGGCCTCGGACACCTTCATTCGTTAGCTGGGGAGTGG
TGGTGAGGCAGTGAAGAAGAGGCGGATGGTCACACTCAGATCCACAGAGCCCAGGATCAAGG
GACCCACTGCAGTGGCAGCAGGACTGTTGGGCCCCCACCCCAACCCTGCACAGCCCTCATCC
CCTCTTGGCTTGAGCCGTCAGAGGCCCTGTGCTGAGTGTCTGACCGAGACACTCACAGCTTT
GTCATCAGGGCACAGGCTTCCTCGGAGCCAGGATGATCTGTGCCACGCTTGCACCTCGGGCC
CATCTGGGCTCATGCTCTCTCTCCTGCTATTGAATTAGTACCTAGCTGCACACAGTATGTAG
TTACCAAAAGAATAAACGGCAATAATTGAGAAAAAAAA

FIGURE 118

></usr/seqdb2/sst/DNA/Dnaseqs.min/ss.DNA84920
><subunit 1 of 1, 310 aa, 1 stop
><MW: 33875, pI: 7.08, NX(S/T): 2
MRLGSGTFATCCVAIEVLGIAVFLRGFFPAPVRSSARAEHGAEPPAPEPSAGASSNWTTL
PPPLFSKVVIVLIDALRDDFVFGSKGVKFMPYTTYLVEKGASHSFVAEAKPPTVTMPRIK
ALMTGSLPGFVDVIRNLNSPALLEDSVIRQAKAAGKRIVFYGDETWVKLFPKHFVEYDGT
TSFFVSDYTEVDNNVTRHLDKVLKRGDWDILILHYLGLDHIGHISGPNSPLIGQKLSEMD
SVLMKIHTSLQSKERETPLPNLLVLCGDHGMSETGSHGASSTEEVNTPLILISSAFERKP
GDIRHPKHVQ

Important features of the protein:
Signal peptide:
Amino acids 1-34

Transmembrane domain:
Amino acids 58-76

N-glycosylation sites:
Amino acids 56-60;194-198

N-myristoylation sites:
Amino acids 6-12;52-58;100-106;125-131;233-239;270-276;
275-281;278-284

Amidation site:
Amino acids 154-158

Cell attachment sequence:
Amino acids 205-208

FIGURE 119

GCCCACGCGTCCGATGGCGTTCACGTTCGCGGCCTTCTGCTACATGCTGGCGCTGCTGCTCA
CTGCCGCGCTCATCTTCTTCGCCATTTGGCACATTATAGCATTTGATGAGCTGAAGACTGAT
TACAAGAATCCTATAGACCAGTGTAATACCCTGAATCCCCTTGTACTCCCAGAGTACCTCAT
CCACGCTTTCTTCTGTGTCATGTTTCTTTGTGCAGCAGAGTGGCTTACACTGGGTCTCAATA
TGCCCCTCTTGGCATATCATATTTGGAGGTATATGAGTAGACCAGTGATGAGTGGCCCAGGA
CTCTATGACCCTACAACCATCATGAATGCAGATATTCTAGCATATTGTCAGAAGGAAGGATGG
TGCAAATTAGCTTTTTATCTTCTAGCATTTTTTTACTACCTATATGGCATGATCTATGTTTT
GGTGAGCTCTTAGAACAACACACAGAAGAATTGGTCCAGTTAAGTGCATGCAAAAAGCCACC
AAATGAAGGGATTCTATCCAGCAAGATCCTGTCCAAGAGTAGCCTGTGGAATCTGATCAGTT
ACTTTAAAAAATGACTCCTTATTTTTTAAATGTTTCCACATTTTTGCTTGTGGAAAGACTGT
TTTCATATGTTATACTCAGATAAAGATTTTAAATGGTATTACGTATAAATTAATATAAAATG
ATTACCTCTGGTGTTGACAGGTTTGAACTTGCACTTCTTAAGGAACAGCCATAATCCTCTGA
ATGATGCATTAATTACTGACTGTCCTAGTACATTGGAAGCTTTTGTTTATAGGAACTTGTAG
GGCTCATTTTGGTTTCATTGAAACAGTATCTAATTATAAATTAGCTGTAGATATCAGGTGCT
TCTGATGAAGTGAAAATGTATATCTGACTAGTGGGAAACTTCATGGGTTTCCTCATCTGTCA
TGTCGATGATTATATATGGATACATTTACAAAAATAAAAAGCGGGAATTTTCCCTTCGCTTG
AATATTATCCCTGTATATTGCATGAATGAGAGATTTCCCATATTTCCATCAGAGTAATAAAT
ATACTTGCTTTAATTCTTAAGCATAAGTAAACATGATATAAAAATATATGCTGAATTACTTG
TGAAGAATGCATTTAAAGCTATTTTAAATGTGTTTTTATTTGTAAGACATTACTTATTAAGA
AATTGGTTATTATGCTTACTGTTCTAATCTGGTGGTAAAGGTATTCTTAAGAATTTGCAGGT
ACTACAGATTTTCAAAACTGAATGAGAGAAAATTGTATAACCATCCTGCTGTTCCTTTAGTG
CAATACAATAAAACTCTGAAATTAAGACTC

FIGURE 120

</usr/seqdb2/sst/DNA/Dnaseqs.min/ss.DNA23330
<subunit 1 of 1, 144 aa, 1 stop
<MW: 16699, pI: 5.60, NX(S/T): 0
MAFTFAAFCYMLALLLTAALIFFAIWHIIAFDELKTDYKNPIDQCNTLNPLVLPEYLIHA
FFCVMFLCAAEWLTLGLNMPLLAYHIWRYMSRPVMSGPGLYDPTTIMNADILAYCQKEGW
CKLAFYLLAFFYYLYGMIYVLVSS

Important features:
Signal peptide:
Amino acids 1-20

Type II transmembrane domain:
Amino acids 11-31

Other transmembrane domain:
Amino acids 57-77;123-143

Glycosaminoglycan attachment site:
Amino acids 96-100

FIGURE 121

CGGACGCGTGGGCGGACGCGTGGGCGGCCCACGGCGCCCGCGGGCTGGGGCGGTCGCTTCTT
CCTTCTCCGTGGCCTACGAGGGTCCCCAGCCTGGGTAAAGATGGCCCCATGGCCCCCGAAGG
GCCTAGTCCCAGCTGTGCTCTGGGGCCTCAGCCTCTTCCTCAACCTCCCAGGACCTATCTGG
CTCCAGCCCTCTCCACCTCCCCAGTCTTCTCCCCCGCCTCAGCCCCATCCGTGTCATACCTG
CCGGGGACTGGTTGACAGCTTTAACAAGGGCCTGGAGAGAACCATCCGGGACAACTTTGGAG
GTGGAAACACTGCCTGGGAGGAAGAGAATTTGTCCAAATACAAAGACAGTGAGACCCGCCTG
GTAGAGGTGCTGGAGGGTGTGTGCAGCAAGTCAGACTTCGAGTGCCACCGCCTGCTGGAGCT
GAGTGAGGAGCTGGTGGAGAGCTGGTGGTTTCACAAGCAGCAGGAGGCCCCGGACCTCTTCC
AGTGGCTGTGCTCAGATTCCCTGAAGCTCTGCTGCCCCGCAGGCACCTTCGGGCCCTCCTGC
CTTCCCTGTCCTGGGGGAACAGAGAGGCCCTGCGGTGGCTACGGGCAGTGTGAAGGAGAAGG
GACACGAGGGGGCAGCGGGCACTGTGACTGCCAAGCCGGCTACGGGGGTGAGGCCTGTGGCC
AGTGTGGCCTTGGCTACTTTGAGGCAGAACGCAACGCCAGCCATCTGGTATGTTCGGCTTGT
TTTGGCCCCTGTGCCCGATGCTCAGGACCTGAGGAATCAAACTGTTTGCAATGCAAGAAGGG
CTGGGCCCTGCATCACCTCAAGTGTGTAGACATTGATGAGTGTGGCACAGAGGGAGCCAACT
GTGGAGCTGACCAATTCTGCGTGAACACTGAGGGCTCCTATGAGTGCCGAGACTGTGCCAAG
GCCTGCCTAGGCTGCATGGGGGCAGGGCCAGGTCGCTGTAAGAAGTGTAGCCCTGGCTATCA
GCAGGTGGGCTCCAAGTGTCTCGATGTGGATGAGTGTGAGACAGAGGTGTGTCCGGGAGAGA
ACAAGCAGTGTGAAAACACCGAGGGCGGTTATCGCTGCATCTGTGCCGAGGGCTACAAGCAG
ATGGAAGGCATCTGTGTGAAGGAGCAGATCCCAGAGTCAGCAGGCTTCTTCTCAGAGATGAC
AGAAGACGAGTTGGTGGTGCTGCAGCAGATGTTCTTTGGCATCATCATCTGTGCACTGGCCA
CGCTGGCTGCTAAGGGCGACTTGGTGTTCACCGCCATCTTCATTGGGGCTGTGGCGGCCATG
ACTGGCTACTGGTTGTCAGAGCGCAGTGACCGTGTGCTGGAGGGCTTCATCAAGGGCAGATA
ATCGCGGCCACCACCTGTAGGACCTCCTCCCACCCACGCTGCCCCCAGAGCTTGGGCTGCCC
TCCTGCTGGACACTCAGGACAGCTTGGTTTATTTTTGAGAGTGGGGTAAGCACCCCTACCTG
CCTTACAGAGCAGCCCAGGTACCCAGGCCCGGGCAGACAAGGCCCCTGGGGTAAAAAGTAGC
CCTGAAGGTGGATACCATGAGCTCTTCACCTGGCGGGGACTGGCAGGCTTCACAATGTGTGA
ATTTCAAAAGTTTTTCCTTAATGGTGGCTGCTAGAGCTTTGGCCCCTGCTTAGGATTAGGTG
GTCCTCACAGGGGTGGGGCCATCACAGCTCCCTCCTGCCAGCTGCATGCTGCCAGTTCCTGT
TCTGTGTTCACCACATCCCCACACCCCATTGCCACTTATTTATTCATCTCAGGAAATAAAGA
AAGGTCTTGGAAAGTTAAAAAAAAAAAAAAAAAAAAAAAA

FIGURE 122

MAPWPPKGLVPAVLWGLSLFLNLPGPIWLQPSPPPQSSPPPQPHPCHTCRGLVDSFNKGLER
TIRDNFGGGNTAWEEENLSKYKDSETRLVEVLEGVCSKSDFECHRLLELSEELVESWWFHKQ
QEAPDLFQWLCSDSLKLCCPAGTFGPSCLPCPGGTERPCGGYGQCEGEGTRGGSGHCDCQAG
YGGEACGQCGLGYFEAERNASHLVCSACFGPCARCSGPEESNCLQCKKGWALHHLKCVDIDE
CGTEGANCGADQFCVNTEGSYECRDCAKACLGCMGAGPGRCKKCSPGYQQVGSKCLDVDECE
TEVCPGENKQCENTEGGYRCICAEGYKQMEGICVKEQIPESAGFFSEMTEDELVVLQQMFFG
IIICALATLAAKGDLVFTAIFIGAVAAMTGYWLSERSDRVLEGFIKGR

Important features:
Signal peptide:

Amino acids 1-29

Transmembrane domain:

Amino acids 342-392

N-glycosylation sites:

Amino acids 79-83;205-209 cAMP- and cGMP-dependent protein kinase phosphorylation site:
Amino acids 290-294

Aspartic acid and asparagine hydroxylation site:
Amino acids 321-333

EGF-like domain cysteine pattern signature:
Amino acids 181-193

FIGURE 123

GCAAGCCAAGGCGCTGTTTGAGAAGGTGAAGAAGTTCCGGACCCATGTGGAGGAGGGGGACATTGTGTACCGCC
TCTACATGCGGCAGACCATCATCAAGGTGATCAAGTTCATCCTCATCATCTGCTACACCGTCTACTACGTGCAC
AACATCAAGTTCGACGTGGACTGCACCGTGGACATTGAGAGCCTGACGGGCTACCGCACCTACCGCTGTGCCCA
CCCCCTGGCCACACTCTTCAAGATCCTGGCGTCCTTCTACATCAGCCTAGTCATCTTCTACGGCCTCATCTGCA
TGTACACACTGTGGTGGATGCTACGGCGCTCCCTCAAGAAGTACTCGTTTGAGTCGATCCGTGAGGAGAGCAGC
TACAGCGACATCCCCGACGTCAAGAACGACTTCGCCTTCATGCTGCACCTCATTGACCAATACGACCCGCTCTA
CTCCAAGCGCTTCGCCGTCTTCCTGTCGGAGGTGAGTGAGAACAAGCTGCGGCAGCTGAACCTCAACAACGAGT
GGACGCTGGACAAGCTCCGGCAGCGGCTCACCAAGAACGCGCAGGACAAGCTGGAGCTGCACCTGTTCATGCTC
AGTGGCATCCCTGACACTGTGTTTGACCTGGTGGAGCTGGAGGTCCTCAAGCTGGAGCTGATCCCCGACGTGAC
CATCCCGCCCAGCATTGCCCAGCTCACGGGCCTCAAGGAGCTGTGGCTCTACCACACAGCGGCCAAGATTGAAG
CGCCTGCGCTGGCCTTCCTGCGCGAGAACCTGCGGGCGCTGCACATCAAGTTCACCGACATCAAGGAGATCCCG
CTGTGGATCTATAGCCTGAAGACACTGGAGGAGCTGCACCTGACGGGCAACCTGAGCGCGGAGAACAACCGCTA
CATCGTCATCGACGGGCTGCGGGAGCTCAAACGCCTCAAGGTGCTGCGGCTCAAGAGCAACCTAAGCAAGCTGC
CACAGGTGGTCACAGATGTGGGCGTGCACCTGCAGAAGCTGTCCATCAACAATGAGGGCACCAAGCTCATCGTC
CTCAACAGCCTCAAGAAGATGGCGAACCTGACTGAGCTGGAGCTGATCCGCTGCGACCTGGAGCGCATCCCCCA
CTCCATCTTCAGCCTCCACAACCTGCAGGAGATTGACCTCAAGGACAACAACCTCAAGACCATCGAGGAGATCA
TCAGCTTCCAGCACCTGCACCGCCTCACCTGCCTTAAGCTGTGGTACAACCACATCGCCTACATCCCCATCCAG
ATCGGCAACCTCACCAACCTGGAGCGCCTCTACCTGAACCGCAACAAGATCGAGAAGATCCCCACCCAGCTCTT
CTACTGCCGCAAGCTGCGCTACCTGGACCTCAGCCACAACAACCTGACCTTCCTCCCTGCCGACATCGGCCTCC
TGCAGAACCTCCAGAACCTAGCCATCACGGCCAACCGGATCGAGACGCTCCCTCCGGAGCTCTTCCAGTGCCGG
AAGCTGCGGGCCCTGCACCTGGGCAACAACGTGCTGCAGTCACTGCCCTCCAGGGTGGGCGAGCTGACCAACCT
GACGCAGATCGAGCTGCGGGGCAACCGGCTGGAGTGCCTGCCTGTGGAGCTGGGCGAGTGCCCACTGCTCAAGC
GCAGCGGCTTGGTGGTGGAGGAGGACCTGTTCAACACACTGCCACCCGAGGTGAAGGAGCGGCTGTGGAGGGCT
GACAAGGAGCAGGCCTGAGCGAGGCCGGCCCAGCACAGCAAGCAGCAGGACCGCTGCCCAGTCCTCAGGCCCGG
AGGGGCAGGCCTAGCTTCTCCCAGAACTCCCGGACAGCCAGGACAGCCTCGCGGCTGGGCAGGAGCCTGGGGCC
GCTTGTGAGTCAGGCCAGAGCGAGAGGACAGTATCTGTGGGGCTGGCCCCTTTTCTCCCTCTGAGACTCACGTC
CCCCAGGGCAAGTGCTTGTGGAGGAGAGCAAGTCTCAAGAGCGCAGTATTTGGATAATCAGGGTCTCCTCCCTG
GAGGCCAGCTCTGCCCCAGGGGCTGAGCTGCCACCAGAGGTCCTGGGACCCTCACTTTAGTTCTTGGTATTTAT
TTTTCTCCATCTCCCACCTCCTTCATCCAGATAACTTATACATTCCCAAGAAAGTTCAGCCCAGATGGAAGGTG
TTCAGGGAAAGGTGGGCTGCCTTTTCCCCTTGTCCTTATTTAGCGATGCCGCCGGGCATTTAACACCCACCTGG
ACTTCAGCAGAGTGGTCCGGGGCGAACCAGCCATGGGACGGTCACCCAGCAGTGCCGGGCTGGGCTCTGCGGTG
CGGTCCACGGGAGAGCAGGCCTCCAGCTGGAAAGGCCAGGCCTGGAGCTTGCCTCTTCAGTTTTTGTGGCAGTT
TTAGTTTTTTGTTTTTTTTTTTTTAATCAAAAAACAATTTTTTTTAAAAAAAAGCTTTGAAAATGGATGGTTT
GGGTATTAAAAAGAAAAAAAAAACTTAAAAAAAAAAAGACACTAACGGCCAGTGAGTTGGAGTCTCAGGGCAGG
GTGGCAGTTTCCCTTGAGCAAAGCAGCCAGACGTTGAACTGTGTTTCCTTTCCCTGGGCGCAGGGTGCAGGGTG
TCTTCCGGATCTGGTGTGACCTTGGTCCAGGAGTTCTATTTGTTCCTGGGGAGGGAGGTTTTTTTGTTTGTTTT
TTGGGTTTTTTTGGTGTCTTGTTTTCTTTCTCCTCCATGTGTCTTGGCAGGCACTCATTTCTGTGGCTGTCGGC
CAGAGGGAATGTTCTGGAGCTGCCAAGGAGGGAGGAGACTCGGGTTGGCTAATCCCCGGATGAACGGTGCTCCA
TTCGCACCTCCCCTCCTCGTGCCTGCCCTGCCTCTCCACGCACAGTGTTAAGGAGCCAAGAGGAGCCACTTCGC
CCAGACTTTGTTTCCCCACCTCCTGCGGCATGGGTGTGTCCAGTGCCACCGCTGGCCTCCGCTGCTTCCATCAG
CCCTGTCGCCACCTGGTCCTTCATGAAGAGCAGACACTTAGAGGCTGGTCGGGAATGGGGAGGTCGCCCCTGGG
AGGGCAGGCGTTGGTTCCAAGCCGGTTCCCGTCCCTGGCGCCTGGAGTGCACACAGCCCAGTCGGCACCTGGTG
GCTGGAAGCCAACCTGCTTTAGATCACTCGGGTCCCCACCTTAGAAGGGTCCCCGCCTTAGATCAATCACGTGG
ACACTAAGGCACGTTTTAGAGTCTCTTGTCTTAATGATTATGTCCATCCGTCTGTCCGTCCATTTGTGTTTTCT
GCGTCGTGTCATTGGATATAATCCTCAGAAATAATGCACACTAGCCTCTGACAACCATGAAGCAAAAATCCGTT
ACATGTGGGTCTGAACTTGTAGACTCGGTCACAGTATCAAATAAAATCTATAACAGAAAAAAAAAAAAAAA

FIGURE 124

MRQTIIKVIKFILIICYTVYYVHNIKFDVDCTVDIESLTGYRTYRCAHPLATLFKILASFYI
SLVIFYGLICMYTLWWMLRRSLKKYSFESIREESSYSDIPDVKNDFAFMLHLIDQYDPLYSK
RFAVFLSEVSENKLRQLNLNNEWTLDKLRQRLTKNAQDKLELHLFMLSGIPDTVFDLVELEV
LKLELIPDVTIPPSIAQLTGLKELWLYHTAAKIEAPALAFLRENLRALHIKFTDIKEIPLWI
YSLKTLEELHLTGNLSAENNRYIVIDGLRELKRLKVLRLKSNLSKLPQVVTDVGVHLQKLSI
NNEGTKLIVLNSLKKMANLTELELIRCDLERIPHSIFSLHNLQEIDLKDNNLKTIEEIISFQ
HLHRLTCLKLWYNHIAYIPIQIGNLTNLERLYLNRNKIEKIPTQLFYCRKLRYLDLSHNNLT
FLPADIGLLQNLQNLAITANRIETLPPELFQCRKLRALHLGNNVLQSLPSRVGELTNLTQIE
LRGNRLECLPVELGECPLLKRSGLVVEEDLFNTLPPEVKERLWRADKEQA

Transmembrane domain:
amino acids 51-75 (type II)

N-glycosylation site.
amino acids 262-266, 290-294, 328-332, 396-400, 432-436, 491-495 cAMP- and cGMP-dependent protein kinase phosphorylation site.
amino acids 85-89

Casein kinase II phosphorylation site.
amino acids 91-95, 97-101, 177-181, 253-257, 330-334, 364-368, 398-402, 493-497

N-myristoylation site.
amino acids 173-179, 261-267, 395-401, 441-447

FIGURE 125

GTTGTGTCCTTCAGCAAAACAGTGGATTTAAATCTCCTTGCACAAGCTTGAGAGCAACACAA
TCTATCAGGAAAGAAAGAAAGAAAAAAACCGAACCTGACAAAAAAGAAGAAAAAGAAGAAGA
AAAAAAATCATGAAAACCATCCAGCCAAAAATGCACAATTCTATCTCTTGGGCAATCTTCAC
GGGGCTGGCTGCTCTGTGTCTCTTCCAAGGAGTGCCCGTGCGCAGCGGAGATGCCACCTTCC
CCAAAGCTATGGACAACGTGACGGTCCGGCAGGGGGAGAGCGCCACCCTCAGGTGCACTATT
GACAACCGGGTCACCCGGGTGGCCTGGCTAAACCGCAGCACCATCCTCTATGCTGGGAATGA
CAAGTGGTGCCTGGATCCTCGCGTGGTCCTTCTGAGCAACACCCAAACGCAGTACAGCATCG
AGATCCAGAACGTGGATGTGTATGACGAGGGCCCTTACACCTGCTCGGTGCAGACAGACAAC
CACCCAAAGACCTCTAGGGTCCACCTCATTGTGCAAGTATCTCCCAAAATTGTAGAGATTTC
TTCAGATATCTCCATTAATGAAGGGAACAATATTAGCCTCACCTGCATAGCAACTGGTAGAC
CAGAGCCTACGGTTACTTGGAGACACATCTCTCCCAAAGCGGTTGGCTTTGTGAGTGAAGAC
GAATACTTGGAAATTCAGGGCATCACCCGGGAGCAGTCAGGGGACTACGAGTGCAGTGCCTC
CAATGACGTGGCCGCGCCCGTGGTACGGAGAGTAAAGGTCACCGTGAACTATCCACCATACA
TTTCAGAAGCCAAGGGTACAGGTGTCCCCGTGGGACAAAAGGGGACACTGCAGTGTGAAGCC
TCAGCAGTCCCCTCAGCAGAATTCCAGTGGTACAAGGATGACAAAAGACTGATTGAAGGAAA
GAAAGGGGTGAAAGTGGAAAACAGACCTTTCCTCTCAAAACTCATCTTCTTCAATGTCTCTG
AACATGACTATGGGAACTACACTTGCGTGGCCTCCAACAAGCTGGGCCACACCAATGCCAGC
ATCATGCTATTTGGTCCAGGCGCCGTCAGCGAGGTGAGCAACGGCACGTCGAGGAGGGCAGG
CTGCGTCTGGCTGCTGCCTCTTCTGGTCTTGCACCTGCTTCTCAAATTTTGATGTGAGTGCC
ACTTCCCCACCCGGGAAAGGCTGCCGCCACCACCACCACCAACACAACAGCAATGGCAACAC
CGACAGCAACCAATCAGATATATACAAATGAAATTAGAAGAAACACAGCCTCATGGGACAGA
AATTTGAGGGAGGGGAACAAAGAATACTTTGGGGGGAAAAGAGTTTTAAAAAAGAAATTGAA
AATTGCCTTGCAGATATTTAGGTACAATGGAGTTTTCTTTTCCCAAACGGGAAGAACACAGC
ACACCCGGCTTGGACCCACTGCAAGCTGCATCGTGCAACCTCTTTGGTGCCAGTGTGGGCAA
GGGCTCAGCCTCTCTGCCCACAGAGTGCCCCCACGTGGAACATTCTGGAGCTGGCCATCCCA
AATTCAATCAGTCCATAGAGACGAACAGAATGAGACCTTCCGGCCCAAGCGTGGCGCTGCGG
GCACTTTGGTAGACTGTGCCACCACGGCGTGTGTTGTGAAACGTGAAATAAAAAGAGCAAAA
AAAAA

FIGURE 126

MKTIQPKMHNSISWAIFTGLAALCLFQGVPVRSGDATFPKAMDNVTVRQGESATLRCTIDNR
VTRVAWLNRSTILYAGNDKWCLDPRVVLLSNTQTQYSIEIQNVDVYDEGPYTCSVQTDNHPK
TSRVHLIVQVSPKIVEISSDISINEGNNISLTCIATGRPEPTVTWRHISPKAVGFVSEDEYL
EIQGITREQSGDYECSASNDVAAPVVRRVKVTVNYPPYISEAKGTGVPVGQKGTLQCEASAV
PSAEFQWYKDDKRLIEGKKGVKVENRPFLSKLIFFNVSEHDYGNYTCVASNKLGHTNASIML
FGPGAVSEVSNGTSRRAGCVWLLPLLVLHLLLKF

Important features:
Signal peptide:
amino acids 1-28

FIGURE 127

GGCGCCGGTGCACCGGGCGGGCTGAGCGCCTCCTGCGGCCCGGCCTGCGCGCCCCGGCCCGCCGCGCCGCCCAC
GCCCCAACCCCGGCCCGCGCCCCCTAGCCCCCGCCCGGGCCCGCGCCCGCGCCCGCGCCCAGGTGAGCGCTCCG
CCCGCCGCGAGGCCCCGCCCCGGCCCGCCCCCGCCCCGCCCCGGCCGGCGGGGGAACCGGGCGGATTCCTCGCG
CGTCAAACCACCTGATCCCATAAAACATTCATCCTCCCGGCGGCCCGCGCTGCGAGCGCCCCGCCAGTCCGCGC
CGCCGCCGCCCTCGCCCTGTGCGCCCTGCGCGCCCTGCGCACCCGCGGCCCGAGCCCAGCCAGAGCCGGGCGGA
GCGGAGCGCGCCGAGCCTCGTCCCGCGGCCGGGCCGGGGCCGGGCCGTAGCGGCGGCGCCTGGATGCGGACCCG
GCCGCGGGGAGACGGGCGCCCGCCCCGAAACGACTTTCAGTCCCCGACGCGCCCCGCCCAACCCCTACGATGAA
GAGGGCGTCCGCTGGAGGGAGCCGGCTGCTGGCATGGGTGCTGTGGCTGCAGGCCTGGCAGGTGGCAGCCCCAT
GCCCAGGTGCCTGCGTATGCTACAATGAGCCCAAGGTGACGACAAGCTGCCCCCAGCAGGGCCTGCAGGCTGTG
CCCGTGGGCATCCCTGCTGCCAGCCAGCGCATCTTCCTGCACGGCAACCGCATCTCGCATGTGCCAGCTGCCAG
CTTCCGTGCCTGCCGCAACCTCACCATCCTGTGGCTGCACTCGAATGTGCTGGCCCGAATTGATGCGGCTGCCT
TCACTGGCCTGGCCCTCCTGGAGCAGCTGGACCTCAGCGATAATGCACAGCTCCGGTCTGTGGACCCTGCCACA
TTCCACGGCCTGGGCCGCCTACACACGCTGCACCTGGACCGCTGCGGCCTGCAGGAGCTGGGCCCGGGGCTGTT
CCGCGGCCTGGCTGCCCTGCAGTACCTCTACCTGCAGGACAACGCGCTGCAGGCACTGCCTGATGACACCTTCC
GCGACCTGGGCAACCTCACACACCTCTTCCTGCACGGCAACCGCATCTCCAGCGTGCCCGAGCGCGCCTTCCGT
GGGCTGCACAGCCTCGACCGTCTCCTACTGCACCAGAACCGCGTGGCCCATGTGCACCCGCATGCCTTCCGTGA
CCTTGGCCGCCTCATGACACTCTATCTGTTTGCCAACAATCTATCAGCGCTGCCCACTGAGGCCCTGGCCCCCC
TGCGTGCCCTGCAGTACCTGAGGCTCAACGACAACCCCTGGGTGTGTGACTGCCGGGCACGCCCACTCTGGGCC
TGGCTGCAGAAGTTCCGCGGCTCCTCCTCCGAGGTGCCCTGCAGCCTCCCGCAACGCCTGGCTGGCCGTGACCT
CAAACGCCTAGCTGCCAATGACCTGCAGGGCTGCGCTGTGGCCACCGGCCCTTACCATCCCATCTGGACCGGCA
GGGCCACCGATGAGGAGCCGCTGGGGCTTCCCAAGTGCTGCCAGCCAGATGCCGCTGACAAGGCCTCAGTACTG
GAGCCTGGAAGACCAGCTTCGGCAGGCAATGCGCTGAAGGGACGCGTGCCGCCCGGTGACAGCCCGCCGGGCAA
CGGCTCTGGCCCACGGCACATCAATGACTCACCCTTTGGGACTCTGCCTGGCTCTGCTGAGCCCCCGCTCACTG
CAGTGCGGCCCGAGGGCTCCGAGCCACCAGGGTTCCCCACCTCGGGCCCTCGCCGGAGGCCAGGCTGTTCACGC
AAGAACCGCACCCGCAGCCACTGCCGTCTGGGCCAGGCAGGCAGCGGGGGTGGCGGGACTGGTGACTCAGAAGG
CTCAGGTGCCCTACCCAGCCTCACCTGCAGCCTCACCCCCCTGGGCCTGGCGCTGGTGCTGTGGACAGTGCTTG
GGCCCTGCTGACCCCCAGCGGACACAAGAGCGTGCTCAGCAGCCAGGTGTGTGTACATACGGGGTCTCTCTCCA
CGCCGCCAAGCCAGCCGGGCGGCCGACCCCTGGGGCAGGCCAGGCCAGGTCCTCCCTGATGGACGCCTGCCGCC
CGCCACCCCCATCTCCACCCCATCATGTTTACAGGGTTCGGCGGCAGCGTTTGTTCCAGAACGCCGCCTCCCAC
CCAGATCGCGGTATATAGAGATATGCATTTTATTTTACTTGTGTAAAAATATCGGACGACGTGGAATAAAGAGC
TCTTTTCTTAAAAAAA

FIGURE 128

MKRASAGGSRLLAWVLWLQAWQVAAPCPGACVCYNEPKVTTSCPQQGLQAVPVGIPAASQRIFLHGNRISHVPA
ASFRACRNLTILWLHSNVLARIDAAAFTGLALLEQLDLSDNAQLRSVDPATFHGLGRLHTLHLDRCGLQELGPG
LFRGLAALQYLYLQDNALQALPDDTFRDLGNLTHLFLHGNRISSVPERAFRGLHSLDRLLLHQNRVAHVHPHAF
RDLGRLMTLYLFANNLSALPTEALAPLRALQYLRLNDNPWVCDCRARPLWAWLQKFRGSSSEVPCSLPQRLAGR
DLKRLAANDLQGCAVATGPYHPIWTGRATDEEPLGLPKCCQPDAADKASVLEPGRPASAGNALKGRVPPGDSPP
GNGSGPRHINDSPFGTLPGSAEPPLTAVRPEGSEPPGFPTSGPRRRPGCSRKNRTRSHCRLGQAGSGGGGTGDS
EGSGALPSLTCSLTPLGLALVLWTVLGPC

Important features:
Signal peptide:
amino acids 1-26

Leucine zipper pattern.
amino acids 135-156

Glycosaminoglycan attachment site.
amino acids 436-439

N-glycosylation site.
amino acids 82-85, 179-183, 237-240, 372-375 and 423-426

VWFC domain
amino acids 411-425

FIGURE 129

GCGCCGGGAGCCCATCTGCCCCCAGGGGCACGGGGCGCGGGGCCGGCTCCCGCCCGGCACATGGCTGCAGCCAC
CTCGCGCGCACCCCGAGGCGCCGCGCCCAGCTCGCCCGAGGTCCGTCGGAGGCGCCCGGCCGCCCCGGAGCCAA
GCAGCAACTGAGCGGGGAAGCGCCCGCGTCCGGGGATCGGGATGTCCCTCCTCCTTCTCCTCTTGCTAGTTTCC
TACTATGTTGGAACCTTGGGGACTCACACTGAGATCAAGAGAGTGGCAGAGGAAAAGGTCACTTTGCCCTGCCA
CCATCAACTGGGGCTTCCAGAAAAAGACACTCTGGATATTGAATGGCTGCTCACCGATAATGAAGGGAACCAAA
AAGTGGTGATCACTTACTCCAGTCGTCATGTCTACAATAACTTGACTGAGGAACAGAAGGGCCGAGTGGCCTTT
GCTTCCAATTTCCTGGCAGGAGATGCCTCCTTGCAGATTGAACCTCTGAAGCCCAGTGATGAGGGCCGGTACAC
CTGTAAGGTTAAGAATTCAGGGCGCTACGTGTGGAGCCATGTCATCTTAAAAGTCTTAGTGAGACCATCCAAGC
CCAAGTGTGAGTTGGAAGGAGAGCTGACAGAAGGAAGTGACCTGACTTTGCAGTGTGAGTCATCCTCTGGCACA
GAGCCCATTGTGTATTACTGGCAGCGAATCCGAGAGAAAGAGGGAGAGGATGAACGTCTGCCTCCCAAATCTAG
GATTGACTACAACCACCCTGGACGAGTTCTGCTGCAGAATCTTACCATGTCCTACTCTGGACTGTACCAGTGCA
CAGCAGGCAACGAAGCTGGGAAGGAAAGCTGTGTGGTGCGAGTAACTGTACAGTATGTACAAAGCATCGGCATG
GTTGCAGGAGCAGTGACAGGCATAGTGGCTGGAGCCCTGCTGATTTTCCTCTTGGTGTGGCTGCTAATCCGAAG
GAAAGACAAAGAAAGATATGAGGAAGAAGAGAGACCTAATGAAATTCGAGAAGATGCTGAAGCTCCAAAAGCCC
GTCTTGTGAAACCCAGCTCCTCTTCCTCAGGCTCTCGGAGCTCACGCTCTGGTTCTTCCTCCACTCGCTCCACA
GCAAATAGTGCCTCACGCAGCCAGCGGACACTGTCAACTGACGCAGCACCCCAGCCAGGGCTGGCCACCCAGGC
ATACAGCCTAGTGGGGCCAGAGGTGAGAGGTTCTGAACCAAAGAAAGTCCACCATGCTAATCTGACCAAAGCAG
AAACCACACCCAGCATGATCCCCAGCCAGAGCAGAGCCTTCCAAACGGTCTGAATTACAATGGACTTGACTCCC
ACGCTTTCCTAGGAGTCAGGGTCTTTGGACTCTTCTCGTCATTGGAGCTCAAGTCACCAGCCACACAACCAGAT
GAGAGGTCATCTAAGTAGCAGTGAGCATTGCACGGAACAGATTCAGATGAGCATTTTCCTTATACAATACCAAA
CAAGCAAAAGGATGTAAGCTGATTCATCTGTAAAAAGGCATCTTATTGTGCCTTTAGACCAGAGTAAGGGAAAG
CAGGAGTCCAAATCTATTTGTTGACCAGGACCTGTGGTGAGAAGGTTGGGGAAAGGTGAGGTGAATATACCTAA
AACTTTTAATGTGGGATATTTTGTATCAGTGCTTTGATTCACAATTTTCAAGAGGAAATGGGATGCTGTTTGTA
AATTTTCTATGCATTTCTGCAAACTTATTGGATTATTAGTTATTCAGACAGTCAAGCAGAACCCACAGCCTTAT
TACACCTGTCTACACCATGTACTGAGCTAACCACTTCTAAGAAACTCCAAAAAAGGAAACATGTGTCTTCTATT
CTGACTTAACTTCATTTGTCATAAGGTTTGGATATTAATTTCAAGGGGAGTTGAAATAGTGGGAGATGGAGAAG
AGTGAATGAGTTTCTCCCACTCTATACTAATCTCACTATTTGTATTGAGCCCAAAATAACTATGAAAGGAGACA
AAAATTTGTGACAAAGGATTGTGAAGAGCTTTCCATCTTCATGATGTTATGAGGATTGTTGACAAACATTAGAA
ATATATAATGGAGCAATTGTGGATTTCCCCTCAAATCAGATGCCTCTAAGGACTTTCCTGCTAGATATTTCTGG
AAGGAGAAAATACAACATGTCATTTATCAACGTCCTTAGAAAGAATTCTTCTAGAGAAAAAGGGATCTAGGAAT
GCTGAAAGATTACCCAACATACCATTATAGTCTCTTCTTTCTGAGAAAATGTGAAACCAGAATTGCAAGACTGG
GTGGACTAGAAAGGGAGATTAGATCAGTTTTCTCTTAATATGTCAAGGAAGGTAGCCGGGCATGGTGCCAGGCA
CCTGTAGGAAAATCCAGCAGGTGGAGGTTGCAGTGAGCCGAGATTATGCCATTGCACTCCAGCCTGGGTGACAG
AGCGGGACTCCGTCTC

FIGURE 130

MSLLLLLLLVSYYVGTLGTHTEIKRVAEEKVTLPCHHQLGLPEKDTLDIEWLLTDNEGNQKVVITYSSRHVYNN
LTEEQKGRVAFASNFLAGDASLQIEPLKPSDEGRYTCKVKNSGRYVWSHVILKVLVRPSKPKCELEGELTEGSD
LTLQCESSSGTEPIVYYWQRIREKEGEDERLPPKSRIDYNHPGRVLLQNLTMSYSGLYQCTAGNEAGKESCVVR
VTVQYVQSIGMVAGAVTGIVAGALLIFLLVWLLIRRKDKERYEEEERPNEIREDAEAPKARLVKPSSSSSGSRS
SRSGSSSTRSTANSASRSQRTLSTDAAPQPGLATQAYSLVGPEVRGSEPKKVHHANLTKAETTPSMIPSQSRAFQTV

Important freatures:
Signal sequence:
amino acids 1-16

Transmembrane domain:
amino acids 232-251

FIGURE 131

GGAAGTCCACGGGGAGCTTGGATGCCAAAGGGAGGACGGCTGGGTCCTCTGGAGAGGACTAC
TCACTGGCATATTTCTGAGGTATCTGTAGAATAACCACAGCCTCAGATACTGGGGACTTTAC
AGTCCCACAGAACCGTCCTCCCAGGAAGCTGAATCCAGCAAGAACAATGGAGGCCAGCGGGA
AGCTCATTTGCAGACAAAGGCAAGTCCTTTTTTCCTTTCTCCTTTTGGGCTTATCTCTGGCG
GGCGCGGCGGAACCTAGAAGCTATTCTGTGGTGGAGGAAACTGAGGGCAGCTCCTTTGTCAC
CAATTTAGCAAAGGACCTGGGTCTGGAGCAGAGGGAATTCTCCAGGCGGGGGGTTAGGGTTG
TTTCCAGAGGGAACAAACTACATTTGCAGCTCAATCAGGAGACCGCGGATTTGTTGCTAAAT
GAGAAATTGGACCGTGAGGATCTGTGCGGTCACACAGAGCCCTGTGTGCTACGTTTCCAAGT
GTTGCTAGAGAGTCCCTTCGAGTTTTTTCAAGCTGAGCTGCAAGTAATAGACATAAACGACC
ACTCTCCAGTATTTCTGGACAAACAAATGTTGGTGAAAGTATCAGAGAGCAGTCCTCCTGGG
ACTACGTTTCCTCTGAAGAATGCCGAAGACTTAGATGTAGGCCAAAACAATATTGAGAACTA
TATAATCAGCCCCAACTCCTATTTTCGGGTCCTCACCCGCAAACGCAGTGATGGCAGGAAAT
ACCCAGAGCTGGTGCTGGACAAAGCGCTGGACCGAGAGGAAGAAGCTGAGCTCAGGTTAACA
CTCACAGCACTGGATGGTGGCTCTCCGCCCAGATCTGGCACTGCTCAGGTCTACATCGAAGT
CCTGGATGTCAACGATAATGCCCCTGAATTTGAGCAGCCTTTCTATAGAGTGCAGATCTCTG
AGGACAGTCCGGTAGGCTTCCTGGTTGTGAAGGTCTCTGCCACGGATGTAGACACAGGAGTC
AACGGAGAGATTTCCTATTCACTTTTCCAAGCTTCAGAAGAGATTGGCAAAACCTTTAAGAT
CAATCCCTTGACAGGAGAAATTGAACTAAAAAAACAACTCGATTTCGAAAAACTTCAGTCCT
ATGAAGTCAATATTGAGGCAAGAGATGCTGGAACCTTTTCTGGAAAATGCACCGTTCTGATT
CAAGTGATAGATGTGAACGACCATGCCCCAGAAGTTACCATGTCTGCATTTACCAGCCCAAT
ACCTGAGAACGCGCCTGAAACTGTGGTTGCACTTTTCAGTGTTTCAGATCTTGATTCAGGAG
AAAATGGGAAAATTAGTTGCTCCATTCAGGAGGATCTACCCTTCCTCCTGAAATCCGCGGAA
AACTTTTACACCCTACTAACGGAGAGACCACTAGACAGAGAAAGCAGAGCGGAATACAACAT
CACTATCACTGTCACTGACTTGGGGACCCCTATGCTGATAACACAGCTCAATATGACCGTGC
TGATCGCCGATGTCAATGACAACGCTCCCGCCTTCACCCAAACCTCCTACACCCTGTTCGTC
CGCGAGAACAACAGCCCCGCCCTGCACATCCGCAGCGTCAGCGCTACAGACAGAGACTCAGG
CACCAACGCCCAGGTCACCTACTCGCTGCTGCCGCCCCAGGACCCGCACCTGCCCCTCACAT
CCCTGGTCTCCATCAACGCGGACAACGGCCACCTGTTCGCCCTCAGGTCTCTGGACTACGAG
GCCCTGCAGGGGTTCCAGTTCCGCGTGGGCGCTTCAGACCACGGCTCCCCGGCGCTGAGCAG
CGAGGCGCTGGTGCGCGTGGTGGTGCTGGACGCCAACGACAACTCGCCCTTCGTGCTGTACC
CGCTGCAGAACGGCTCCGCGCCCTGCACCGAGCTGGTGCCCCGGGCGGCCGAGCCGGGCTAC
CTGGTGACCAAGGTGGTGGCGGTGGACGGCGACTCGGGCCAGAACGCCTGGCTGTCGTACCA
GCTGCTCAAGGCCACGGAGCTCGGTCTGTTCGGCGTGTGGGCGCACAATGGCGAGGTGCGCA
CCGCCAGGCTGCTGAGCGAGCGCGACGCGGCCAAGCACAGGCTGGTGGTGCTGGTCAAGGAC
AATGGCGAGCCTCCGCGCTCGGCCACCGCCACGCTGCACGTGCTCCTGGTGGACGGCTTCTC
CCAGCCCTACCTGCCTCTCCCGGAGGCGGCCCCGACCCAGGCCCAGGCCGACTTGCTCACCG
TCTACCTGGTGGTGGCGTTGGCCTCGGTGTCTTCGCTCTTCCTCTTTTCGGTGCTCCTGTTC
GTGGCGGTGCGGCTGTGTAGGAGGAGCAGGGCGGCCTCGGTGGGTCGCTGCTTGGTGCCCGA
GGGCCCCCTTCCAGGGCATCTTGTGGACATGAGCGGCACCAGGACCCTATCCCAGAGCTACC
AGTATGAGGTGTGTCTGGCAGGAGGCTCAGGGACCAATGAGTTCAAGTTCCTGAAGCCGATT
ATCCCCAACTTCCCTCCCCAGTGCCCTGGGAAAGAAATACAAGGAAATTCTACCTTCCCCAA
TAACTTTGGGTTCAATATTCAGTGACCATAGTTGACTTTTACATTCCATAGGTATTTTATTT
TGTGGCATTTCCATGCCAATGTTTATTTCCCCCAATTTGTGTGTATGTAATATTGTACGGAT
TTACTCTTGATTTTTCTCATGTTCTTTCTCCCTTTGTTTTAAAGTGAACATTTACCTTTATT
CCTGGTTCTT

FIGURE 132

</usr/seqdb2/sst/DNA/Dnaseqs.min/ss.DNA48314
<subunit 1 of 1, 798 aa, 1 stop
<MW: 87552, pI: 4.84, NX(S/T): 5
MEASGKLICRQRQVLFSFLLLGLSLAGAAEPRSYSVVEETEGSSFVTNLAKDLGLEQREFSR
RGVRVVSRGNKLHLQLNQETADLLLNEKLDREDLCGHTEPCVLRFQVLLESPFEFFQAELQV
IDINDHSPVFLDKQMLVKVSESSPPGTTFPLKNAEDLDVGQNNIENYIISPNSYFRVLTRKR
SDGRKYPELVLDKALDREEEAELRLTLTALDGGSPPRSGTAQVYIEVLDVNDNAPEFEQPFY
RVQISEDSPVGFLVVKVSATDVDTGVNGEISYSLFQASEEIGKTFKINPLTGEIELKKQLDF
EKLQSYEVNIEARDAGTFSGKCTVLIQVIDVNDHAPEVTMSAFTSPIPENAPETVVALFSVS
DLDSGENGKISCSIQEDLPFLLKSAENFYTLLTERPLDRESRAEYNITITVTDLGTPMLITQ
LNMTVLIADVNDNAPAFTQTSYTLFVRENNSPALHIRSVSATDRDSGTNAQVTYSLLPPQDP
HLPLTSLVSINADNGHLFALRSLDYEALQGFQFRVGASDHGSPALSSEALVRVVVLDANDNS
PFVLYPLQNGSAPCTELVPRAAEPGYLVTKVVAVDGDSGQNAWLSYQLLKATELGLFGVWAH
NGEVRTARLLSERDAAKHRLVVLVKDNGEPPRSATATLHVLLVDGFSQPYLPLPEAAPTQAQ
ADLLTVYLVVALASVSSLFLFSVLLFVAVRLCRRSRAASVGRCLVPEGPLPGHLVDMSGTRT
LSQSYQYEVCLAGGSGTNEFKFLKPIIPNFPPQCPGKEIQGNSTFPNNFGFNIQ

Important features:
Signal peptide:
amino acids 1-26

Transmembrane domain:
amino acids 685-712

Cadherins extracellular repeated domain signature.
amino acids 122-132, 231-241, 336-346, 439-449 and 549-559

ATP/GTP-binding site motif A (P-loop).
amino acids 285-292

N-glycosylation site.
amino acids 418-421, 436-439, 567-570 and 786-789

FIGURE 133

GGAAGGGGAGGAGCAGGCCACACAGGCACAGGCCGGTGAGGGACCTGCCCAGACCTGGAGGGTCTCGCTCTGTC
ACACAGGCTGGAGTGCAGTGGTGTGATCTTGGCTCATCGTAACCTCCACCTCCCGGGTTCAAGTGATTCTCATG
CCTCAGCCTCCCGAGTAGCTGGGATTACAGGTGGTGACTTCCAAGAGTGACTCCGTCGGAGGAAAATGACTCCC
CAGTCGCTGCTGCAGACGACACTGTTCCTGCTGAGTCTGCTCTTCCTGGTCCAAGGTGCCCACGGCAGGGGCCA
CAGGGAAGACTTTCGCTTCTGCAGCCAGCGGAACCAGACACACAGGAGCAGCCTCCACTACAAACCCACACCAG
ACCTGCGCATCTCCATCGAGAACTCCGAAGAGGCCCTCACAGTCCATGCCCCTTTCCCTGCAGCCCACCCTGCT
TCCCGATCCTTCCCTGACCCCAGGGGCCTCTACCACTTCTGCCTCTACTGGAACCGACATGCTGGGAGATTACA
TCTTCTCTATGGCAAGCGTGACTTCTTGCTGAGTGACAAAGCCTCTAGCCTCCTCTGCTTCCAGCACCAGGAGG
AGAGCCTGGCTCAGGGCCCCCCGCTGTTAGCCACTTCTGTCACCTCCTGGTGGAGCCCTCAGAACATCAGCCTG
CCCAGTGCCGCCAGCTTCACCTTCTCCTTCCACAGTCCTCCCCACACGGCCGCTCACAATGCCTCGGTGGACAT
GTGCGAGCTCAAAAGGGACCTCCAGCTGCTCAGCCAGTTCCTGAAGCATCCCCAGAAGGCCTCAAGGAGGCCCT
CGGCTGCCCCCGCCAGCCAGCAGTTGCAGAGCCTGGAGTCGAAACTGACCTCTGTGAGATTCATGGGGGACATG
GTGTCCTTCGAGGAGGACCGGATCAACGCCACGGTGTGGAAGCTCCAGCCCACAGCCGGCCTCCAGGACCTGCA
CATCCACTCCCGGCAGGAGGAGGAGCAGAGCGAGATCATGGAGTACTCGGTGCTGCTGCCTCGAACACTCTTCC
AGAGGACGAAAGGCCGGAGCGGGGAGGCTGAGAAGAGACTCCTCCTGGTGGACTTCAGCAGCCAAGCCCTGTTC
CAGGACAAGAATTCCAGCCAAGTCCTGGGTGAGAAGGTCTTGGGGATTGTGGTACAGAACACCAAAGTAGCCAA
CCTCACGGAGCCCGTGGTGCTCACTTTCCAGCACCAGCTACAGCCGAAGAATGTGACTCTGCAATGTGTGTTCT
GGGTTGAAGACCCCACATTGAGCAGCCCGGGGCATTGGAGCAGTGCTGGGTGTGAGACCGTCAGGAGAGAAACC
CAAACATCCTGCTTCTGCAACCACTTGACCTACTTTGCAGTGCTGATGGTCTCCTCGGTGGAGGTGGACGCCGT
GCACAAGCACTACCTGAGCCTCCTCTCCTACGTGGGCTGTGTCGTCTCTGCCCTGGCCTGCCTTGTCACCATTG
CCGCCTACCTCTGCTCCAGGGTGCCCCTGCCGTGCAGGAGGAAACCTCGGGACTACACCATCAAGGTGCACATG
AACCTGCTGCTGGCCGTCTTCCTGCTGGACACGAGCTTCCTGCTCAGCGAGCCGGTGGCCCTGACAGGCTCTGA
GGCTGGCTGCCGAGCCAGTGCCATCTTCCTGCACTTCTCCCTGCTCACCTGCCTTTCCTGGATGGGCCTCGAGG
GGTACAACCTCTACCGACTCGTGGTGGAGGTCTTTGGCACCTATGTCCCTGGCTACCTACTCAAGCTGAGCGCC
ATGGGCTGGGGCTTCCCCATCTTTCTGGTGACGCTGGTGGCCCTGGTGGATGTGGACAACTATGGCCCCATCAT
CTTGGCTGTGCATAGGACTCCAGAGGGCGTCATCTACCCTTCCATGTGCTGGATCCGGGACTCCCTGGTCAGCT
ACATCACCAACCTGGGCCTCTTCAGCCTGGTGTTTCTGTTCAACATGGCCATGCTAGCCACCATGGTGGTGCAG
ATCCTGCGGCTGCGCCCCCACACCCAAAAGTGGTCACATGTGCTGACACTGCTGGGCCTCAGCCTGGTCCTTGG
CCTGCCCTGGGCCTTGATCTTCTTCTCCTTTGCTTCTGGCACCTTCCAGCTTGTCGTCCTCTACCTTTTCAGCA
TCATCACCTCCTTCCAAGGCTTCCTCATCTTCATCTGGTACTGGTCCATGCGGCTGCAGGCCCGGGGTGGCCCC
TCCCCTCTGAAGAGCAACTCAGACAGCGCCAGGCTCCCCATCAGCTCGGGCAGCACCTCGTCCAGCCGCATCTA
GGCCTCCAGCCCACCTGCCCATGTGATGAAGCAGAGATGCGGCCTCGTCGCACACTGCCTGTGGCCCCCGAGCC
AGGCCCAGCCCCAGGCCAGTCAGCCGCAGACTTTGGAAAGCCCAACGACCATGGAGAGATGGGCCGTTGCCATG
GTGGACGGACTCCCGGGCTGGGCTTTTGAATTGGCCTTGGGGACTACTCGGCTCTCACTCAGCTCCCACGGGAC
TCAGAAGTGCGCCGCCATGCTGCCTAGGGTACTGTCCCCACATCTGTCCCAACCCAGCTGGAGGCCTGGTCTCT
CCTTACAACCCCTGGGCCCAGCCCTCATTGCTGGGGGCCAGGCCTTGGATCTTGAGGGTCTGGCACATCCTTAA
TCCTGTGCCCCTGCCTGGGACAGAAATGTGGCTCCAGTTGCTCTGTCTCTCGTGGTCACCCTGAGGGCACTCTG
CATCCTCTGTCATTTTAACCTCAGGTGGCACCCAGGGCGAATGGGGCCCAGGGCAGACCTTCAGGGCCAGAGCC
CTGGCGGAGGAGAGGCCCTTTGCCAGGAGCACAGCAGCAGCTCGCCTACCTCTGAGCCCAGGCCCCCTCCCTCC
CTCAGCCCCCCAGTCCTCCCTCCATCTTCCCTGGGGTTCTCCTCCTCTCCCAGGGCCTCCTTGCTCCTTCGTTC
ACAGCTGGGGGTCCCCGATTCCAATGCTGTTTTTTGGGGAGTGGTTTCCAGGAGCTGCCTGGTGTCTGCTGTAA
ATGTTTGTCTACTGCACAAGCCTCGGCCTGCCCCTGAGCCAGGCTCGGTACCGATGCGTGGGCTGGGCTAGGTC
CCTCTGTCCATCTGGGCCTTTGTATGAGCTGCATTGCCCTTGCTCACCCTGACCAAGCACACGCCTCAGAGGGG
CCCTCAGCCTCTCCTGAAGCCCTCTTGTGGCAAGAACTGTGGACCATGCCAGTCCCGTCTGGTTTCCATCCCAC
CACTCCAAGGACTGAGACTGACCTCCTCTGGTGACACTGGCCTAGAGCCTGACACTCTCCTAAGAGGTTCTCTC
CAAGCCCCCAAATAGCTCCAGGCGCCCTCGGCCGCCCATCATGGTTAATTCTGTCCAACAAACACACACGGGTA
GATTGCTGGCCTGTTCTAGGTGGTAGGGACACAGATGACCGACCTGGTCACTCCTCCTGCCAACATTCAGTCTG
GTATGTGAGGCGTGCGTGAAGCAAGAACTCCTGGAGCTACAGGGACAGGGAGCCATCATTCCTGCCTGGGAATC
CTGGAAGACTTCCTGCAGGAGTCAGCGTTCAATCTTGACCTTGAAGATGGGAAGGATGTTCTTTTTACGTACCA
ATTCTTTTGTCTTTTGATATTAAAAAGAAGTACATGTTCATTGTAGAGAATTTGGAAACTGTAGAAGAGAATCA
AGAAGAAAAATAAAAATCAGCTGTTGTAATCGCCTAGCAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAA

FIGURE 134

MTPQSLLQTTLFLLSLLFLVQGAHGRGHREDFRFCSQRNQTHRSSLHYKPTPDLRISIENSE
EALTVHAPFPAAHPASRSFPDPRGLYHFCLYWNRHAGRLHLLYGKRDFLLSDKASSLLCFQH
QEESLAQGPPLLATSVTSWWSPQNISLPSAASFTFSFHSPPHTAAHNASVDMCELKRDLQLL
SQFLKHPQKASRRPSAAPASQQLQSLESKLTSVRFMGDMVSFEEDRINATVWKLQPTAGLQD
LHIHSRQEEEQSEIMEYSVLLPRTLFQRTKGRSGEAEKRLLLVDFSSQALFQDKNSSQVLGE
KVLGIVVQNTKVANLTEPVVLTFQHQLQPKNVTLQCVFWVEDPTLSSPGHWSSAGCETVRRE
TQTSCFCNHLTYFAVLMVSSVEVDAVHKHYLSLLSYVGCVVSALACLVTIAAYLCSRVPLPC
RRKPRDYTIKVHMNLLLAVFLLDTSFLLSEPVALTGSEAGCRASAIFLHFSLLTCLSWMGLE
GYNLYRLVVEVFGTYVPGYLLKLSAMGWGFPIFLVTLVALVDVDNYGPIILAVHRTPEGVIY
PSMCWIRDSLVSYITNLGLFSLVFLFNMAMLATMVVQILRLRPHTQKWSHVLTLLGLSLVLG
LPWALIFFSFASGTFQLVVLYLFSIITSFQGFLIFIWYWSMRLQARGGPSPLKSNSDSARLP
ISSGSTSSSRI

Important features:
Signal peptide:
amino acids 1-25
Putative transmembrane domains:
amino acids 382-398, 402-420, 445-468, 473-491, 519-537, 568-590 and 634-657
Microbodies C-terminal targeting signal.
amino acids 691-693
cAMP- and cGMP-dependent protein kinase phosphorylation sites.
amino acids 198-201 and 370-373
N-glycosylation sites.
amino acids 39-42, 148-151, 171-174, 234-237, 303-306, 324-327 and 341-344
G-protein coupled receptors family 2 proteins
amino acids 475-504

FIGURE 135

GCCTAGCCAGGCCAAGAATGCAATTGCCCCGGTGGTGGGAGCTGGGAGACCCCTGTGCTTGGACGGGACAGGGTCGG
GGGACACGCAGGATGAGCCCCGCGACCACTGGCACATTCTTGCTGACAGTGTACAGTATTTTCTCCAAGGTACA
CTCCGATCGGAATGTATACCCATCAGCAGGTGTCCTCTTTGTTCATGTTTTGGAAAGAGAATATTTTAAGGGGG
AATTTCCACCTTACCCAAAACCTGGCGAGATTAGTAATGATCCCATAACATTTAATACAAATTTAATGGGTTAC
CCAGACCGACCTGGATGGCTTCGATATATCCAAAGGACACCATATAGTGATGGAGTCCTATATGGGTCCCCAAC
AGCTGAAAATGTGGGGAAGCCAACAATCATTGAGATAACTGCCTACAACAGGCGCACCTTTGAGACTGCAAGGC
ATAATTTGATAATTAATATAATGTCTGCAGAAGACTTCCCGTTGCCATATCAAGCAGAATTCTTCATTAAGAAT
ATGAATGTAGAAGAAATGTTGGCCAGTGAGGTTCTTGGAGACTTTCTTGGCGCAGTGAAAAATGTGTGGCAGCC
AGAGCGCCTGAACGCCATAAACATCACATCGGCCCTAGACAGGGGTGGCAGGGTGCCACTTCCCATTAATGACC
TGAAGGAGGGCGTTTATGTCATGGTTGGTGCAGATGTCCCGTTTTCTTCTTGTTTACGAGAAGTTGAAAATCCA
CAGAATCAATTGAGATGTAGTCAAGAAATGGAGCCTGTAATAACATGTGATAAAAAATTTCGTACTCAATTTTA
CATTGACTGGTGCAAAATTTCATTGGTTGATAAAACAAAGCAAGTGTCCACCTATCAGGAAGTGATTCGTGGAG
AGGGGATTTTACCTGATGGTGGAGAATACAAACCCCCTTCTGATTCTTTGAAAAGCAGAGACTATTACACCGAT
TTCCTAATTACACTGGCTGTGCCCTCGGCAGTGGCACTGGTCCTTTTTCTAATACTTGCTTATATCATGTGCTG
CCGACGGGAAGGCGTGGAAAAGAGAAACATGCAAACACCAGACATCCAACTGGTCCATCACAGTGCTATTCAGA
AATCTACCAAGGAGCTTCGAGACATGTCCAAGAATAGAGAGATAGCATGGCCCCTGTCAACGCTTCCTGTGTTC
CACCCTGTGACTGGGGAAATCATACCTCCTTTACACACAGACAACTATGATAGCACAAACATGCCATTGATGCA
AACGCAGCAGAACTTGCCACATCAGACTCAGATTCCCCAACAGCAGACTACAGGTAAATGGTATCCCTGAAGAA
AGAAAACTGACTGAAGCAATGAATTTATAATCAGACAATATAGCAGTTACATCACATTTCTTTTCTCTTCCAAT
AATGCATGAGCTTTTCTGGCATATGTTATGCATGTTGGCAGTATTAAGTGTATACCAAATAATACAACATAACT
TTCATTTTACTAATGTATTTTTTTGTACTTAAAGCATTTTTGACAATTTGTAAAACATTGATGACTTTATATTT
GTTACAATAAAAGTTGATCTTTAAAATAAATATTATTAATGAAGCCTAAAAAAAAAAA

FIGURE 136

MQLPRWWELGDPCAWTGQGRGTRRMSPATTGTFLLTVYSIFSKVHSDRNVYPSAGVLFVHVLEREYFKGEFPPY
PKPGEISNDPITFNTNLMGYPDRPGWLRYIQRTPYSDGVLYGSPTAENVGKPTIIEITAYNRRTFETARHNLII
NIMSAEDFPLPYQAEFFIKNMNVEEMLASEVLGDFLGAVKNVWQPERLNAINITSALDRGGRVPLPINDLKEGV
YVMVGADVPFSSCLREVENPQNQLRCSQEMEPVITCDKKFRTQFYIDWCKISLVDKTKQVSTYQEVIRGEGILP
DGGEYKPPSDSLKSRDYYTDFLITLAVPSAVALVLFLILAYIMCCRREGVEKRNMQTPDIQLVHHSAIQKSTKE
LRDMSKNREIAWPLSTLPVFHPVTGEIIPPLHTDNYDSTNMPLMQTQQNLPHQTQIPQQQTTGKWYP signal sequence:
Amino acids 1-46 transmembrane domain:
Amino acids 319-338

N-glycosylation site:
Amino acids 200-204 cAMP- and cGMP-dependent protein kinase phosphorylation site:
Amino acids 23-27

Tyrosine kinase phosphorylation site:
Amino acids 43-52

N-myristoylation sites:
Amino acids 17-23;112-118;116-122;

185-191

FIGURE 137

CAGAAGAGGGGGCTAGCTAGCTGTCTCTGCGGACCAGGGAGACCCCCGCGCCCCCCCGGTGT
GAGGCGGCCTCACAGGGCCGGGTGGGCTGGCGAGCCGACGCGGCGGCGGAGGAGGCTGTGAG
GAGTGTGTGGAACAGGACCCGGGACAGAGGAACCATGGCTCCGCAGAACCTGAGCACCTTTT
GCCTGTTGCTGCTATACCTCATCGGGGCGGTGATTGCCGGACGAGATTTCTATAAGATCTTG
GGGGTGCCTCGAAGTGCCTCTATAAAGGATATTAAAAAGGCCTATAGGAAACTAGCCCTGCA
GCTTCATCCCGACCGGAACCCTGATGATCCACAAGCCCAGGAGAAATTCCAGGATCTGGGTG
CTGCTTATGAGGTTCTGTCAGATAGTGAGAAACGGAAACAGTACGATACTTATGGTGAAGAA
GGATTAAAAGATGGTCATCAGAGCTCCCATGGAGACATTTTTTCACACTTCTTTGGGGATTT
TGGTTTCATGTTTGGAGGAACCCCTCGTCAGCAAGACAGAAATATTCCAAGAGGAAGTGATA
TTATTGTAGATCTAGAAGTCACTTTGGAAGAAGTATATGCAGGAAATTTTGTGGAAGTAGTT
AGAAACAAACCTGTGGCAAGGCAGGCTCCTGGCAAACGGAAGTGCAATTGTCGGCAAGAGAT
GCGGACCACCCAGCTGGGCCCTGGGCGCTTCCAAATGACCCAGGAGGTGGTCTGCGACGAAT
GCCCTAATGTCAAACTAGTGAATGAAGAACGAACGCTGGAAGTAGAAATAGAGCCTGGGGTG
AGAGACGGCATGGAGTACCCCTTTATTGGAGAAGGTGAGCCTCACGTGGATGGGGAGCCTGG
AGATTTACGGTTCCGAATCAAAGTTGTCAAGCACCCAATATTTGAAAGGAGAGGAGATGATT
TGTACACAAATGTGACAATCTCATTAGTTGAGTCACTGGTTGGCTTTGAGATGGATATTACT
CACTTGGATGGTCACAAGGTACATATTTCCCGGGATAAGATCACCAGGCCAGGAGCGAAGCT
ATGGAAGAAAGGGGAAGGGCTCCCCAACTTTGACAACAACAATATCAAGGGCTCTTTGATAA
TCACTTTTGATGTGGATTTTCCAAAAGAACAGTTAACAGAGGAAGCGAGAGAAGGTATCAAA
CAGCTACTGAAACAAGGGTCAGTGCAGAAGGTATACAATGGACTGCAAGGATATTGAGAGTG
AATAAAATTGGACTTTGTTTAAAATAAGTGAATAAGCGATATTTATTATCTGCAAGGTTTTT
TTGTGTGTGTTTTTGTTTTTATTTTCAATATGCAAGTTAGGCTTAATTTTTTTATCTAATGA
TCATCATGAAATGAATAAGAGGGCTTAAGAATTTGTCCATTTGCATTCGGAAAAGAATGACC
AGCAAAAGGTTTACTAATACCTCTCCCTTTGGGGATTTAATGTCTGGTGCTGCCGCCTGAGT
TTCAAGAATTAAAGCTGCAAGAGGACTCCAGGAGCAAAAGAAACACAATATAGAGGGTTGGA
GTTGTTAGCAATTTCATTCAAAATGCCAACTGGAGAAGTCTGTTTTTAAATACATTTTGTTG
TTATTTTTA

FIGURE 138

MAPQNLSTFCLLLLYLIGAVIAGRDFYKILGVPRSASIKDIKKAYRKLALQLHPDRNPDDPQAQEKFQDLGAAY
EVLSDSEKRKQYDTYGEEGLKDGHQSSHGDIFSHFFGDFGFMFGGTPRQQDRNIPRGSDIIVDLEVTLEEVYAG
NFVEVVRNKPVARQAPGKRKCNCRQEMRTTQLGPGRFQMTQEVVCDECPNVKLVNEERTLEVEIEPGVRDGMEY
PFIGEGEPHVDGEPGDLRFRIKVVKHPIFERRGDDLYTNVTISLVESLVGFEMDITHLDGHKVHISRDKITRPG
AKLWKKGEGLPNFDNNNIKGSLIITFDVDFPKEQLTEEAREGIKQLLKQGSVQKVYNGLQGY

Important features:
Signal peptide:
amino acids 1-22

Cell attachment sequence.
amino acids 254-257

Nt-dnaJ domain signature.
amino acids 67-87

Homologous region to Nt-dnaJ domain proteins.
amino acids 26-58

N-glycosylation site.
amino acids 5-9, 261-265

Tyrosine kinase phosphorylation site.
amino acids 253-260

N-myristoylation site.
amino acids 18-24, 31-37, 93-99, 215-221

Amidation site.
amino acids 164-168

FIGURE 139

CCAGTCTGTCGCCACCTCACTTGGTGTCTGCTGTCCCCGCCAGGCAAGCCTGGGGTGAGAGC
ACAGAGGAGTGGGCCGGGACCATGCGGGGGACGCGGCTGGCGCTCCTGGCGCTGGTGCTGGC
TGCCTGCGGAGAGCTGGCGCCGGCCCTGCGCTGCTACGTCTGTCCGGAGCCCACAGGAGTGT
CGGACTGTGTCACCATCGCCACCTGCACCACCAACGAAACCATGTGCAAGACCACACTCTAC
TCCCGGGAGATAGTGTACCCCTTCCAGGGGGACTCCACGGTGACCAAGTCCTGTGCCAGCAA
GTGTAAGCCCTCGGATGTGGATGGCATCGGCCAGACCCTGCCCGTGTCCTGCTGCAATACTG
AGCTGTGCAATGTAGACGGGGCGCCCGCTCTGAACAGCCTCCACTGCGGGGCCCTCACGCTC
CTCCCACTCTTGAGCCTCCGACTGTAGAGTCCCCGCCCACCCCCATGGCCCTATGCGGCCCA
GCCCCGAATGCCTTGAAGAAGTGCCCCCTGCACCAGGAAAAAAAAAAAAAAAAA

FIGURE 140

</usr/seqdb2/sst/DNA/Dnaseqs.min/ss.DNA56405
<subunit 1 of 1, 125 aa, 1 stop
<MW: 13115, pI: 5.90, NX(S/T): 1
MRGTRLALLALVLAACGELAPALRCYVCPEPTGVSDCVTIATCTTNETMCKTTLYSREIVYP
FQGDSTVTKSCASKCKPSDVDGIGQTLPVSCCNTELCNVDGAPALNSLHCGALTLLPLLSLRL

Important features:
Signal peptide:
amino acids 1-17

N-glycosylation site.
amino acids 46-49

FIGURE 141

GGCGCCGCGTAGGCCCGGGAGGCCGGGCCGGCCGGGCTGCGAGCGCCTGCCCCATGCGCCGC
CGCCTCTCCGCACGATGTTCCCCTCGCGGAGGAAAGCGGCGCAGCTGCCCTGGGAGGACGGC
AGGTCCGGGTTGCTCTCCGGCGGCCTCCCTCGGAAGTGTTCCGTCTTCCACCTGTTCGTGGC
CTGCCTCTCGCTGGGCTTCTTCTCCCTACTCTGGCTGCAGCTCAGCTGCTCTGGGGACGTGG
CCCGGGCAGTCAGGGGACAAGGGCAGGAGACCTCGGGCCCTCCCCGTGCCTGCCCCCCAGAG
CCGCCCCCTGAGCACTGGGAAGAAGACGCATCCTGGGGCCCCCACCGCCTGGCAGTGCTGGT
GCCCTTCCGCGAACGCTTCGAGGAGCTCCTGGTCTTCGTGCCCCACATGCGCCGCTTCCTGA
GCAGGAAGAAGATCCGGCACCACATCTACGTGCTCAACCAGGTGGACCACTTCAGGTTCAAC
CGGGCAGCGCTCATCAACGTGGGCTTCCTGGAGAGCAGCAACAGCACGGACTACATTGCCAT
GCACGACGTTGACCTGCTCCCTCTCAACGAGGAGCTGGACTATGGCTTTCCTGAGGCTGGGC
CCTTCCACGTGGCCTCCCCGGAGCTCCACCCTCTCTACCACTACAAGACCTATGTCGGCGGC
ATCCTGCTGCTCTCCAAGCAGCACTACCGGCTGTGCAATGGGATGTCCAACCGCTTCTGGGG
CTGGGGCCGCGAGGACGACGAGTTCTACCGGCGCATTAAGGGAGCTGGGCTCCAGCTTTTCC
GCCCCTCGGGAATCACAACTGGGTACAAGACATTTCGCCACCTGCATGACCCAGCCTGGCGG
AAGAGGGACCAGAAGCGCATCGCAGCTCAAAAACAGGAGCAGTTCAAGGTGGACAGGGAGGG
AGGCCTGAACACTGTGAAGTACCATGTGGCTTCCCGCACTGCCCTGTCTGTGGGCGGGGCCC
CCTGCACTGTCCTCAACATCATGTTGGACTGTGACAAGACCGCCACACCCTGGTGCACATTC
AGCTGAGCTGGATGGACAGTGAGGAAGCCTGTACCTACAGGCCATATTGCTCAGGCTCAGGA
CAAGGCCTCAGGTCGTGGGCCCAGCTCTGACAGGATGTGGAGTGGCCAGGACCAAGACAGCA
AGCTACGCAATTGCAGCCACCCGGCCGCCAAGGCAGGCTTGGGCTGGGCCAGGACACGTGGG
GTGCCTGGGACGCTGCTTGCCATGCACAGTGATCAGAGAGAGGCTGGGGTGTGTCCTGTCCG
GGACCCCCCCTGCCTTCCTGGTCACCCTACTCTGACCTCCTTCACGTGCCCAGGCCTGTGGG
TAGTGGGGAGGGCTGAACAGGACAACCTCTCATCACCCTACTCTGACCTCCTTCACGTGCCC
AGGCCTGTGGGTAGTGGGGAGGGCTGAACAGGACAACCTCTCATCACCCCCAAAAAAAAAAA
AAAAAAAAAAAAAAAAAAAAAAAAAAAAAAAAAAAAA

FIGURE 142

></usr/seqdb2/sst/DNA/Dnaseqs.min/ss.DNA56531
><subunit 1 of 1, 327 aa, 1 stop
><MW: 37406, pI: 9.30, NX(S/T): 1
MFPSRRKAAQLPWEDGRSGLLSGGLPRKCSVFHLFVACLSLGFFSLLWLQLSCSGDVARAVR
GQGQETSGPPRACPPEPPPEHWEEDASWGPHRLAVLVPFRERFEELLVFVPHMRRFLSRKKI
RHHIYVLNQVDHFRFNRAALINVGFLESSNSTDYIAMHDVDLLPLNEELDYGFPEAGPFHVA
SPELHPLYHYKTYVGGILLLSKQHYRLCNGMSNRFWGWGREDDEFYRRIKGAGLQLFRPSGI
TTGYKTFRHLHDPAWRKRDQKRIAAQKQEQFKVDREGGLNTVKYHVASRTALSVGGAPCTVL
NIMLDCDKTATPWCTFS

Signal peptide:
amino acids 1-42

Transmembrane domain:
amino acids 29-49 (type II)

N-glycosylation site.
amino acids 154-158 cAMP- and cGMP-dependent protein kinase phosphorylation site.
amino acids 27-31

Tyrosine kinase phosphorylation site.
amino acids 226-233

N-myristoylation site.
amino acids 19-25, 65-71, 247-253, 285-291, 303-309, 304-310

FIGURE 143

GTGGGATTTATTTGAGTGCAAGATCGTTTTCTCAGTGGTGGTGGAAGTTGCCTCATCGCAGGCAGATGTTGGGG
CTTTGTCCGAACAGCTCCCCTCTGCCAGCTTCTGTAGATAAGGGTTAAAAACTAATATTTATATGACAGAAGAA
AAAGATGTCATTCCGTAAAGTAAACATCATCATCTTGGTCCTGGCTGTTGCTCTCTTCTTACTGGTTTTGCACC
ATAACTTCCTCAGCTTGAGCAGTTTGTTAAGGAATGAGGTTACAGATTCAGGAATTGTAGGGCCTCAACCTATA
GACTTTGTCCCAAATGCTCTCCGACATGCAGTAGATGGGAGACAAGAGGAGATTCCTGTGGTCATCGCTGCATC
TGAAGACAGGCTTGGGGGGGCCATTGCAGCTATAAACAGCATTCAGCACAACACTCGCTCCAATGTGATTTTCT
ACATTGTTACTCTCAACAATACAGCAGACCATCTCCGGTCCTGGCTCAACAGTGATTCCCTGAAAAGCATCAGA
TACAAAATTGTCAATTTTGACCCTAAACTTTTGGAAGGAAAAGTAAAGGAGGATCCTGACCAGGGGGAATCCAT
GAAACCTTTAACCTTTGCAAGGTTCTACTTGCCAATTCTGGTTCCCAGCGCAAAGAAGGCCATATACATGGATG
ATGATGTAATTGTGCAAGGTGATATTCTTGCCCTTTACAATACAGCACTGAAGCCAGGACATGCAGCTGCATTT
TCAGAAGATTGTGATTCAGCCTCTACTAAAGTTGTCATCCGTGGAGCAGGAAACCAGTACAATTACATTGGCTA
TCTTGACTATAAAAAGGAAAGAATTCGTAAGCTTTCCATGAAAGCCAGCACTTGCTCATTTAATCCTGGAGTTT
TTGTTGCAAACCTGACGGAATGGAAACGACAGAATATAACTAACCAACTGGAAAAATGGATGAAACTCAATGTA
GAAGAGGGACTGTATAGCAGAACCCTGGCTGGTAGCATCACAACACCTCCTCTGCTTATCGTATTTTATCAACA
GCACTCTACCATCGATCCTATGTGGAATGTCCGCCACCTTGGTTCCAGTGCTGGAAAACGATATTCACCTCAGT
TTGTAAAGGCTGCCAAGTTACTCCATTGGAATGGACATTTGAAGCCATGGGGAAGGACTGCTTCATATACTGAT
GTTTGGGAAAAATGGTATATTCCAGACCCAACAGGCAAATTCAACCTAATCCGAAGATATACCGAGATCTCAAA
CATAAAGTGAAACAGAATTTGAACTGTAAGCAAGCATTTCTCAGGAAGTCCTGGAAGATAGCATGCATGGGAAG
TAACAGTTGCTAGGCTTCAATGCCTATCGGTAGCAAGCCATGGAAAAAGATGTGTCAGCTAGGTAAAGATGACA
AACTGCCCTGTCTGGCAGTCAGCTTCCCAGACAGACTATAGACTATAAATATGTCTCCATCTGCCTTACCAAGT
GTTTTCTTACTACAATGCTGAATGACTGGAAAGAAGAACTGATATGGCTAGTTCAGCTAGCTGGTACAGATAAT
TCAAAACTGCTGTTGGTTTTAATTTTGTAACCTGTGGCCTGATCTGTAAATAAAACTTACATTTTTC

FIGURE 144

MSFRKVNIIILVLAVALFLLVLHHNFLSLSSLLRNEVTDSGIVGPQPIDFVPNALRHAVDGR
QEEIPVVIAASEDRLGGAIAAINSIQHNTRSNVIFYIVTLNNTADHLRSWLNSDSLKSIRYK
IVNFDPKLLEGKVKEDPDQGESMKPLTFARFYLPILVPSAKKAIYMDDDVIVQGDILALYNT
ALKPGHAAAFSEDCDSASTKVVIRGAGNQYNYIGYLDYKKERIRKLSMKASTCSFNPGVFVA
NLTEWKRQNITNQLEKWMKLNVEEGLYSRTLAGSITTPPLLIVFYQQHSTIDPMWNVRHLGS
SAGKRYSPQFVKAAKLLHWNGHLKPWGRTASYTDVWEKWYIPDPTGKFNLIRRYTEISNIK

FIGURE 145

AAACTTGACGCCATGAAGATCCCGGTCCTTCCTGCCGTGGTGCTCCTCTCCCTCCTGGTGCT
CCACTCTGCCCAGGGAGCCACCCTGGGTGGTCCTGAGGAAGAAAGCACCATTGAGAATTATG
CGTCACGACCCGAGGCCTTTAACACCCCGTTCCTGAACATCGACAAATTGCGATCTGCGTTT
AAGGCTGATGAGTTCCTGAACTGGCACGCCCTCTTTGAGTCTATCAAAAGGAAACTTCCTTT
CCTCAACTGGGATGCCTTTCCTAAGCTGAAAGGACTGAGGAGCGCAACTCCTGATGCCCAGT
GACCATGACCTCCACTGGAAGAGGGGGCTAGCGTGAGCGCTGATTCTCAACCTACCATAACT
CTTTCCTGCCTCAGGAACTCCAATAAAACATTTTCCATCCAAA

FIGURE 146

MKIPVLPAVVLLSLLVLHSAQGATLGGPEEESTIENYASRPEAFNTPFLNIDKLRSAFKADE
FLNWHALFESIKRKLPFLNWDAFPKLKGLRSATPDAQ

FIGURE 147

CCTCTGTCCACTGCTTTCGTGAAGACAAGATGAAGTTCACAATTGTCTTTGCTGGACTTCTT
GGAGTCTTTCTAGCTCCTGCCCTAGCTAACTATAATATCAACGTCAATGATGACAACAACAA
TGCTGGAAGTGGGCAGCAGTCAGTGAGTGTCAACAATGAACACAATGTGGCCAATGTTGACA
ATAACAACGGATGGGACTCCTGGAATTCCATCTGGGATTATGGAAATGGCTTTGCTGCAACC
AGACTCTTTCAAAAGAAGACATGCATTGTGCACAAAATGAACAAGGAAGTCATGCCCTCCAT
TCAATCCCTTGATGCACTGGTCAAGGAAAAGAAGCTTCAGGGTAAGGGACCAGGAGGACCAC
CTCCCAAGGGCCTGATGTACTCAGTCAACCCAAACAAAGTCGATGACCTGAGCAAGTTCGGA
AAAAACATTGCAAACATGTGTCGTGGGATTCCAACATACATGGCTGAGGAGATGCAAGAGGC
AAGCCTGTTTTTTTACTCAGGAACGTGCTACACGACCAGTGTACTATGGATTGTGGACATTT
CCTTCTGTGGAGACACGGTGGAGAACTAAACAATTTTTTAAAGCCACTATGGATTTAGTCAT
CTGAATATGCTGTGCAGAAAAAATATGGGCTCCAGTGGTTTTTACCATGTCATTCTGAAATT
TTTCTCTACTAGTTATGTTTGATTTCTTTAAGTTTCAATAAAATCATTTAGCATTGAAAAAAA

FIGURE 148

MKFTIVFAGLLGVFLAPALANYNINVNDDNNNAGSGQQSVSVNNEHNVANVDNNNGWDSWNS
IWDYGNGFAATRLFQKKTCIVHKMNKEVMPSIQSLDALVKEKKLQGKGPGGPPPKGLMYSVN
PNKVDDLSKFGKNIANMCRGIPTYMAEEMQEASLFFYSGTCYTTSVLWIVDISFCGDTVEN

Signal Peptide:
amino acids 1-20

N-myristoylation Sites:
amino acids 67-72, 118-123, 163-168

Flavodoxin protein homology:
amino acids 156-174

FIGURE 149

GGCACGAGCCAGGAACTAGGAGGTTCTCACTGCCCGAGCAGAGGCCCTACACCCACCGAGGC
ATGGGGCTCCCTGGGCTGTTCTGCTTGGCCGTGCTGGCTGCCAGCAGCTTCTCCAAGGCACG
GGAGGAAGAAATTACCCCTGTGGTCTCCATTGCCTACAAAGTCCTGGAAGTTTTCCCCAAAG
GCCGCTGGGTGCTCATAACCTGCTGTGCACCCCAGCCACCACCGCCCATCACCTATTCCCTC
TGTGGAACCAAGAACATCAAGGTGGCCAAGAAGGTGGTGAAGACCCACGAGCCGGCCTCCTT
CAACCTCAACGTCACACTCAAGTCCAGTCCAGACCTGCTCACCTACTTCTGCCGGGCGTCCT
CCACCTCAGGTGCCCATGTGGACAGTGCCAGGCTACAGATGCACTGGGAGCTGTGGTCCAAG
CCAGTGTCTGAGCTGCGGGCCAACTTCACTCTGCAGGACAGAGGGGCAGGCCCCAGGGTGGA
GATGATCTGCCAGGCGTCCTCGGGCAGCCCACCTATCACCAACAGCCTGATCGGGAAGGATG
GGCAGGTCCACCTGCAGCAGAGACCATGCCACAGGCAGCCTGCCAACTTCTCCTTCCTGCCG
AGCCAGACATCGGACTGGTTCTGGTGCCAGGCTGCAAACAACGCCAATGTCCAGCACAGCGC
CCTCACAGTGGTGCCCCCAGGTGGTGACCAGAAGATGGAGGACTGGCAGGGTCCCCTGGAGA
GCCCCATCCTTGCCTTGCCGCTCTACAGGAGCACCCGCCGTCTGAGTGAAGAGGAGTTTGGG
GGGTTCAGGATAGGGAATGGGGAGGTCAGAGGACGCAAAGCAGCAGCCATGTAGAATGAACC
GTCCAGAGAGCCAAGCACGGCAGAGGACTGCAGGCCATCAGCGTGCACTGTTCGTATTTGGA
GTTCATGCAAAATGAGTGTGTTTTAGCTGCTCTTGCCACAAAAAAAAAAAAAAAAAAAAAAA

FIGURE 150

MGLPGLFCLAVLAASSFSKAREEEITPVVSIAYKVLEVFPKGRWVLITCCAPQPPPPITYSL
CGTKNIKVAKKVVKTHEPASFNLNVTLKSSPDLLTYFCRASSTSGAHVDSARLQMHWELWSK
PVSELRANFTLQDRGAGPRVEMICQASSGSPPITNSLIGKDGQVHLQQRPCHRQPANFSFLP
SQTSDWFWCQAANNANVQHSALTVVPPGGDQKMEDWQGPLESPILALPLYRSTRRLSEEEFG
GFRIGNGEVRGRKAAAM

Signal Peptide:
amino acids 1-18

N-glycosylation Sites:
amino acids 86-89, 132-135, 181-184

FIGURE 151

GCGTGGGGATGTCTAGGAGCTCGAAGGTGGTGCTGGGCCTCTCGGTGCTGCTGACGGCGGCC
ACAGTGGCCGGCGTACATGTGAAGCAGCAGTGGGACCAGCAGAGGCTTCGTGACGGAGTTAT
CAGAGACATTGAGAGGCAAATTCGGAAAAAAGAAAACATTCGTCTTTTGGGAGAACAGATTA
TTTTGACTGAGCAACTTGAAGCAGAAAGAGAGAAGATGTTATTGGCAAAAGGATCTCAAAAA
TCATGACTTGAATGTGAAATATCTGTTGGACAGACAACACGAGTTTGTGTGTGTGTGTTGAT
GGAGAGTAGCTTAGTAGTATCTTCATCTTTTTTTTTGGTCACTGTCCTTTTAAACTTGATCA
AATAAAGGACAGTGGGTCATATAAGTTACTGCTTTCAGGGTCCCTTATATCTGAATAAAGGA
GTGTGGGCAGACACTTTTTGGAAGAGTCTGTCTGGGTGATCCTGGTAGAAGCCCCATTAGGG
TCACTGTCCAGTGCTTAGGGTTGTTACTGAGAAGCACTGCCGAGCTTGTGAGAAGGAAGGGA
TGGATAGTAGCATCCACCTGAGTAGTCTGATCAGTCGGCATGATGACGAAGCCACGAGAACA
TCGACCTCAGAAGGACTGGAGGAAGGTGAAGTGGAGGGAGAGACGCTCCTGATCGTCGAATCC

FIGURE 152

MSRSSKVVLGLSVLLTAATVAGVHVKQQWDQQRLRDGVIRDIERQIRKKENIRLLGEQIILT
EQLEAEREKMLLAKGSQKS

FIGURE 153

AATGTGAGAGGGGCTGATGGAAGCTGATAGGCAGGACTGGAGTGTTAGCACCAGTACTGGAT
GTGACAGCAGGCAGAGGAGCACTTAGCAGCTTATTCAGTGTCCGATTCTGATTCCGGCAAGG
ATCCAAGCATGGAATGCTGCCGTCGGGCAACTCCTGGCACACTGCTCCTCTTTCTGGCTTTC
CTGCTCCTGAGTTCCAGGACCGCACGCTCCGAGGAGGACCGGGACGGCCTATGGGATGCCTG
GGGCCCATGGAGTGAATGCTCACGCACCTGCGGGGGAGGGGCCTCCTACTCTCTGAGGCGCT
GCCTGAGCAGCAAGAGCTGTGAAGGAAGAAATATCCGATACAGAACATGCAGTAATGTGGAC
TGCCCACCAGAAGCAGGTGATTTCCGAGCTCAGCAATGCTCAGCTCATAATGATGTCAAGCA
CCATGGCCAGTTTTATGAATGGCTTCCTGTGTCTAATGACCCTGACAACCCATGTTCACTCA
AGTGCCAAGCCAAAGGAACAACCCTGGTTGTTGAACTAGCACCTAAGGTCTTAGATGGTACG
CGTTGCTATACAGAATCTTTGGATATGTGCATCAGTGGTTTATGCCAAATTGTTGGCTGCGA
TCACCAGCTGGGAAGCACCGTCAAGGAAGATAACTGTGGGGTCTGCAACGGAGATGGGTCCA
CCTGCCGGCTGGTCCGAGGGCAGTATAAATCCCAGCTCTCCGCAACCAAATCGGATGATACT
GTGGTTGCACTTCCCTATGGAAGTAGACATATTCGCCTTGTCTTAAAAGGTCCTGATCACTT
ATATCTGGAAACCAAAACCCTCCAGGGGACTAAAGGTGAAAACAGTCTCAGCTCCACAGGAA
CTTTCCTTGTGGACAATTCTAGTGTGGACTTCCAGAAATTTCCAGACAAAGAGATACTGAGA
ATGGCTGGACCACTCACAGCAGATTTCATTGTCAAGATTCGTAACTCGGGCTCCGCTGACAG
TACAGTCCAGTTCATCTTCTATCAACCCATCATCCACCGATGGAGGGAGACGGATTTCTTTC
CTTGCTCAGCAACCTGTGGAGGAGGTTATCAGCTGACATCGGCTGAGTGCTACGATCTGAGG
AGCAACCGTGTGGTTGCTGACCAATACTGTCACTATTACCCAGAGAACATCAAACCCAAACC
CAAGCTTCAGGAGTGCAACTTGGATCCTTGTCCAGCCAGTGACGGATACAAGCAGATCATGC
CTTATGACCTCTACCATCCCCTTCCTCGGTGGGAGGCCACCCCATGGACCGCGTGCTCCTCC
TCGTGTGGGGGGGGCATCCAGAGCCGGGCAGTTTCCTGTGTGGAGGAGGACATCCAGGGGCA
TGTCACTTCAGTGGAAGAGTGGAAATGCATGTACACCCCTAAGATGCCCATCGCGCAGCCCT
GCAACATTTTTGACTGCCCTAAATGGCTGGCACAGGAGTGGTCTCCGTGCACAGTGACATGT
GCCCAGGGCCTCAGATACCGTGTGGTCCTCTGCATCGACCATCGAGGAATGCACACAGGAGG
CTGTAGCCCAAAAACAAAGCCCCACATAAAAGAGGAATGCATCGTACCCACTCCCTGCTATA
AACCCAAAGAGAAACTTCCAGTCGAGGCCAAGTTGCCATGGTTCAAACAAGCTCAAGAGCTA
GAAGAAGGAGCTGCTGTGTCAGAGGAGCCCTCGTAAGTTGTAAAAGCACAGACTGTTCTATA
TTTGAAACTGTTTTGTTTAAAGAAAGCAGTGTCTCACTGGTTGTAGCTTTCATGGGTTCTGA
ACTAAGTGTAATCATCTCACCAAAGCTTTTTGGCTCTCAAATTAAAGATTGATTAGTTTCAA
AAAAAAAAA

FIGURE 154

</usr/seqdb2/sst/DNA/Dnaseqs.min/ss.DNA58847
<subunit 1 of 1, 525 aa, 1 stop
<MW: 58416, pI: 6.62, NX(S/T): 1
MECCRRATPGTLLLFLAFLLLSSRTARSEEDRDGLWDAWGPWSECSRTCGGGASYSLRRCLS
SKSCEGRNIRYRTCSNVDCPPEAGDFRAQQCSAHNDVKHHGQFYEWLPVSNDPDNPCSLKCQ
AKGTTLVVELAPKVLDGTRCYTESLDMCISGLCQIVGCDHQLGSTVKEDNCGVCNGDGSTCR
LVRGQYKSQLSATKSDDTVVALPYGSRHIRLVLKGPDHLYLETKTLQGTKGENSLSSTGTFL
VDNSSVDFQKFPDKEILRMAGPLTADFIVKIRNSGSADSTVQFIFYQPIIHRWRETDFFPCS
ATCGGGYQLTSAECYDLRSNRVVADQYCHYYPENIKPKPKLQECNLDPCPASDGYKQIMPYD
LYHPLPRWEATPWTACSSSCGGGIQSRAVSCVEEDIQGHVTSVEEWKCMYTPKMPIAQPCNI
FDCPKWLAQEWSPCTVTCGQGLRYRVVLCIDHRGMHTGGCSPKTKPHIKEECIVPTPCYKPK
EKLPVEAKLPWFKQAQELEEGAAVSEEPS

Important features:
Signal peptide:
amino acids 1-25

N-glycosylation site.
amino acids 251-254

Thrombospondin 1
amino acids 385-399 von Willebrand factor type C domain proteins
amino acids 385-399, 445-459 and 42-56

FIGURE 155

GTGGACTCTGAGAAGCCCAGGCAGTTGAGGACAGGAGAGAGAAGGCTGCAGACCCAGAGGGAGGGAGGACAGGG
AGTCGGAAGGAGGAGGACAGAGGAGGGCACAGAGACGCAGAGCAAGGGCGGCAAGGAGGAGACCCTGGTGGGAG
GAAGACACTCTGGAGAGAGAGGGGGCTGGGCAGAGATGAAGTTCCAGGGGCCCCTGGCCTGCCTCCTGCTGGCC
CTCTGCCTGGGCAGTGGGGAGGCTGGCCCCCTGCAGAGCGGAGAGGAAAGCACTGGGACAAATATTGGGGAGGC
CCTTGGACATGGCCTGGGAGACGCCCTGAGCGAAGGGGTGGGAAAGGCCATTGGCAAAGAGGCCGGAGGGGCAG
CTGGCTCTAAAGTCAGTGAGGCCCTTGGCCAAGGGACCAGAGAAGCAGTTGGCACTGGAGTCAGGCAGGTTCCA
GGCTTTGGCGCAGCAGATGCTTTGGGCAACAGGGTCGGGGAAGCAGCCCATGCTCTGGGAAACACTGGGCACGA
GATTGGCAGACAGGCAGAAGATGTCATTCGACACGGAGCAGATGCTGTCCGCGGCTCCTGGCAGGGGGTGCCTG
GCCACAGTGGTGCTTGGGAAACTTCTGGAGGCCATGGCATCTTTGGCTCTCAAGGTGGCCTTGGAGGCCAGGGC
CAGGGCAATCCTGGAGGTCTGGGGACTCCGTGGGTCCACGGATACCCCGGAAACTCAGCAGGCAGCTTTGGAAT
GAATCCTCAGGGAGCTCCCTGGGGTCAAGGAGGCAATGGAGGGCCACCAAACTTTGGGACCAACACTCAGGGAG
CTGTGGCCCAGCCTGGCTATGGTTCAGTGAGAGCCAGCAACCAGAATGAAGGGTGCACGAATCCCCCACCATCT
GGCTCAGGTGGAGGCTCCAGCAACTCTGGGGGAGGCAGCGGCTCACAGTCGGGCAGCAGTGGCAGTGGCAGCAA
TGGTGACAACAACAATGGCAGCAGCAGTGGTGGCAGCAGCAGTGGCAGCAGCAGTGGCAGCAGCAGTGGCGGCA
GCAGTGGCGGCAGCAGTGGTGGCAGCAGTGGCAACAGTGGTGGCAGCAGAGGTGACAGCGGCAGTGAGTCCTCC
TGGGGATCCAGCACCGGCTCCTCCTCCGGCAACCACGGTGGGAGCGGCGGAGGAAATGGACATAAACCCGGGTG
TGAAAAGCCAGGGAATGAAGCCCGCGGGAGCGGGGAATCTGGGATTCAGGGCTTCAGAGGACAGGGAGTTTCCA
GCAACATGAGGGAAATAAGCAAAGAGGGCAATCGCCTCCTTGGAGGCTCTGGAGACAATTATCGGGGGCAAGGG
TCGAGCTGGGGCAGTGGAGGAGGTGACGCTGTTGGTGGAGTCAATACTGTGAACTCTGAGACGTCTCCTGGGAT
GTTTAACTTTGACACTTTCTGGAAGAATTTTAAATCCAAGCTGGGTTTCATCAACTGGGATGCCATAAACAAGG
ACCAGAGAAGCTCTCGCATCCCGTGACCTCCAGACAAGGAGCCACCAGATTGGATGGGAGCCCCCACACTCCCT
CCTTAAAACACCACCCTCTCATCACTAATCTCAGCCCTTGCCCTTGAAATAAACCTTAGCTGCCCCACAAAAAA
AAAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAA

FIGURE 156

></usr/seqdb2/sst/DNA/Dnaseqs.min/ss.DNA59212
><subunit 1 of 1, 440 aa, 1 stop
><MW: 42208, pI: 6.36, NX(S/T): 1
MKFQGPLACLLLALCLGSGEAGPLQSGEESTGTNIGEALGHGLGDALSEGVGKAIGKEAGGA
AGSKVSEALGQGTREAVGTGVRQVPGFGAADALGNRVGEAAHALGNTGHEIGRQAEDVIRHG
ADAVRGSWQGVPGHSGAWETSGGHGIFGSQGGLGGQGQGNPGGLGTPWVHGYPGNSAGSFGM
NPQGAPWGQGGNGGPPNFGTNTQGAVAQPGYGSVRASNQNEGCTNPPPSGSGGGSSNSGGGS
GSQSGSSGSGSNGDNNNGSSSGGSSSGSSSGSSSGGSSGGSSGGSSGNSGGSRGDSGSESSW
GSSTGSSSGNHGGSGGGNGHKPGCEKPGNEARGSGESGIQGFRGQGVSSNMREISKEGNRLL
GGSGDNYRGQGSSWGSGGGDAVGGVNTVNSETSPGMFNFDTFWKNFKSKLGFINWDAINKDQ
RSSRIP

Signal peptide:
amino acids 1-21

N-glycosylation site.
amino acids 265-269

Glycosaminoglycan attachment site.
amino acids 235-239, 237-241, 244-248, 255-259, 324-328, 388-392

Casein kinase II phosphorylation site.
amino acids 26-30, 109-113, 259-263, 300-304, 304-308

N-myristoylation site.
amino acids 17-23, 32-38, 42-48, 50-56, 60-66, 61-67, 64-70, 74-80, 90-96, 96-102, 130-136, 140-146, 149-155, 152-158, 155-161, 159-165, 163-169, 178-184, 190-196, 194-200, 199-205, 218-224, 236-242, 238-244, 239-245, 240-246, 245-251, 246-252, 249-252, 253-259, 256-262, 266-272, 270-276, 271-277, 275-281, 279-285, 283-289, 284-290, 287-293, 288-294, 291-297, 292-298, 295-301, 298-304, 305-311, 311-317, 315-321, 319-325, 322-328, 323-329, 325-331, 343-349, 354-360, 356-362, 374-380, 381-387, 383-389, 387-393, 389-395, 395-401

Cell attachment sequence.
amino acids 301-304

FIGURE 157

CCCACGCGTCCGCCCACGCGTCCGCCCACGCGTCCGCCCACGCGTCCGCCCACGCGTCCGCCCACGCGTCCGCC
CACGCGTCCGGTGCAAGCTCGCGCCGCACACTGCCTGGTGGAGGGAAGGAGCCCGGGCGCCTCTCGCCGCTCCC
CGCGCCGCCGTCCGCACCTCCCCACCGCCCGCCGCCCGCCGCCCGCCGCCCGCAAAGCATGAGTGAGCCCGCTC
TCTGCAGCTGCCCGGGGCGCGAATGGCAGGCTGTTTCCGCGGAGTAAAAGGTGGCGCCGGTCAGTGGTCGTTTC
CAATGACGGACATTAACCAGACTGTCAGATCCTGGGGAGTCGCGAGCCCCGAGTTTGGAGTTTTTTCCCCCCAC
AACGTCACAGTCCGAACTGCAGAGGGAAAGGAAGGCGGCAGGAAGGCGAAGCTCGGGCTCCGGCACGTAGTTGG
GAAACTTGCGGGTCCTAGAAGTCGCCTCCCCGCCTTGCCGGCCGCCCTTGCAGCCCCGAGCCGAGCAGCAAAGT
GAGACATTGTGCGCCTGCCAGATCCGCCGGCCGCGGACCGGGGCTGCCTCGGAAACACAGAGGGGTCTTCTCTC
GCCCTGCATATAATTAGCCTGCACACAAAGGGAGCAGCTGAATGGAGGTTGTCACTCTCTGGAAAAGGATTTCT
GACCGAGCGCTTCCAATGGACATTCTCCAGTCTCTCTGGAAAGATTCTCGCTAATGGATTTCCTGCTGCTCGGT
CTCTGTCTATACTGGCTGCTGAGGAGGCCCTCGGGGGTGGTCTTGTGTCTGCTGGGGGCCTGCTTTCAGATGCT
GCCCGCCGCCCCCAGCGGGTGCCCGCAGCTGTGCCGGTGCGAGGGGCGGCTGCTGTACTGCGAGGCGCTCAACC
TCACCGAGGCGCCCCACAACCTGTCCGGCCTGCTGGGCTTGTCCCTGCGCTACAACAGCCTCTCGGAGCTGCGC
GCCGGCCAGTTCACGGGGTTAATGCAGCTCACGTGGCTCTATCTGGATCACAATCACATCTGCTCCGTGCAGGG
GGACGCCTTTCAGAAACTGCGCCGAGTTAAGGAACTCACGCTGAGTTCCAACCAGATCACCCAACTGCCCAACA
CCACCTTCCGGCCCATGCCCAACCTGCGCAGCGTGGACCTCTCGTACAACAAGCTGCAGGCGCTCGCGCCCGAC
CTCTTCCACGGGCTGCGGAAGCTCACCACGCTGCATATGCGGGCCAACGCCATCCAGTTTGTGCCCGTGCGCAT
CTTCCAGGACTGCCGCAGCCTCAAGTTTCTCGACATCGGATACAATCAGCTCAAGAGTCTGGCGCGCAACTCTT
TCGCCGGCTTGTTTAAGCTCACCGAGCTGCACCTCGAGCACAACGACTTGGTCAAGGTGAACTTCGCCCACTTC
CCGCGCCTCATCTCCCTGCACTCGCTCTGCCTGCGGAGGAACAAGGTGGCCATTGTGGTCAGCTCGCTGGACTG
GGTTTGGAACCTGGAGAAAATGGACTTGTCGGGCAACGAGATCGAGTACATGGAGCCCCATGTGTTCGAGACCG
TGCCGCACCTGCAGTCCCTGCAGCTGGACTCCAACCGCCTCACCTACATCGAGCCCCGGATCCTCAACTCTTGG
AAGTCCCTGACAAGCATCACCCTGGCCGGGAACCTGTGGGATTGCGGGCGCAACGTGTGTGCCCTAGCCTCGTG
GCTCAGCAACTTCCAGGGGCGCTACGATGGCAACTTGCAGTGCGCCAGCCCGGAGTACGCACAGGGCGAGGACG
TCCTGGACGCCGTGTACGCCTTCCACCTGTGCGAGGATGGGGCCGAGCCCACCAGCGGCCACCTGCTCTCGGCC
GTCACCAACCGCAGTGATCTGGGGCCCCCTGCCAGCTCGGCCACCACGCTCGCGGACGGCGGGGAGGGGCAGCA
CGACGGCACATTCGAGCCTGCCACCGTGGCTCTTCCAGGCGGCGAGCACGCCGAGAACGCCGTGCAGATCCACA
AGGTGGTCACGGGCACCATGGCCCTCATCTTCTCCTTCCTCATCGTGGTCCTGGTGCTCTACGTGTCCTGGAAG
TGTTTCCCAGCCAGCCTCAGGCAGCTCAGACAGTGCTTTGTCACGCAGCGCAGGAAGCAAAAGCAGAAACAGAC
CATGCATCAGATGGCTGCCATGTCTGCCCAGGAATACTACGTTGATTACAAACCGAACCACATTGAGGGAGCCC
TGGTGATCATCAACGAGTATGGCTCGTGTACCTGCCACCAGCAGCCCGCGAGGGAATGCGAGGTGTGATTGTCC
CAGTGGCTCTCAACCCATGCGCTACCAAATACGCCTGGGCAGCCGGGACGGGCCGGCGGGCACCAGGCTGGGGT
CTCCTTGTCTGTGCTCTGATATGCTCCTTGACTGAAACTTTAAGGGGATCTCTCCCAGAGACTTGACATTTTAG
CTTTATTGTGTCTTAAAAACAAAAGCGAATTAAAACACAACAAAAAACCCCACCCCACAACCTTCAGGACAGTC
TATCTTAAATTTCATATGAGAACTCCTTCCTCCCTTTGAAGATCTGTCCATATTCAGGAATCTGAGAGTGTAAA
AAAGGTGGCCATAAGACAGAGAGAGAATAATCGTGCTTTGTTTTATGCTACTCCTCCCACCCTGCCCATGATTA
AACATCATGTATGTAGAAGATCTTAAGTCCATACGCATTTCATGAAGAACCATTGGAAAGAGGAATCTGCAATC
TGGGAGCTTAAGAGCAAATGATGACCATAGAAAGCTATGTTCTTACTTTGTGTGTGTGTCTGTATGTTTCTGCG
TTGTGTGTCTTTGTAGGCAAGCAAACGTTGTCTACACAAACGGGAATTTAGCTCACATCATTTCATGCCCCTGT
GCCTCTAGCTCTGGAGATTGGTGGGGGGAGGTGGGGGGAAACGGCAGGAATAAGGGAAAGTGGTAGTTTTAACT
AAGGTTTTGTAACACTTGAAATCTTTTCTTTCTCAAATTAATTATCTTTAAGCTTCAAGAAACTTGCTCTGACC
CCTCTAAGCAAACTACTAAGCATTTAAAAGAGAATCTAATTTTTAAAGGTGTAGCACCTTTTTTTTTATTCTTC
CCACAGAGGGTGCTAATCTCATTATGCTGTGCTATCTGAAAAGAACTTAAGGCCACAATTCACGTCTCGTCCTG
GGCATTGTGATGGATTGACCCTCCATTTGCAGTACCTTCCCAGCTGATTAAAGTTCAGCAGTGGTATTGAGGTT
TTTCGAATATTTATATAGAAAAAAAGTCTTTTCACATGACAAATGACACTCTCACACCAGTCTTAGCCCTAGTA
GTTTTTTAGGTTGGACCAGAGGAAGCAGGTTAAATGAGACCTGTCCTCTGCTGCACTCAGAAAAAATAGGCAGT
CCCTGATGCTCAGATCTTAGCCTTGATATTAATAGTTGAGACCACCTACCCACAATGCAGCCTATACTCCCAAG
ACTACAAAGTTACCATCGCAAAGGAAAGGTTATTCCAGTAAAAGGAAATAGTTTTCTCAACCATTTAAAAATAT
TCTTCTGAACTCATCAAAGTAGAAGAGCCCCCAACCTTTTCTCTCTGCCTTCAAGAAGGCAGACATTTGGTATG
ATTTAGCATCAACAACACATTTATGAGTATATGTAAGTAATCAGAGGGGCAAATGCCACTTGTTATTCCTCCCA
AGTTTTCCAAGCAAGTACACACAGATCTCTGGTAGGATTAGGGGCCACTTGTGTTTCCGGCTTATTTTAGTCGA
CTTGTCAGCAAGTTTGATGCCTAGTCTATCTGACATGGCCCAGTAGAACAGGGCATTGATGGATCACATGAGAT
GGTAGAAGGAACATCATCACATACCCCTCTCACAGAGAAAATTATCAAAGAACCAGAAATTATATCTGTTTTGG
AGCAAGAGTGTCATAATGTTTCAGGGTAGTCAAAATAAACATAAATTATCTCCTCTAGATGAGTGGCGATGTTG
GCTGATTTGGGTCTGCCATTGACAGAATGTCAAATAAAAAGGAATTAGCTAGAATATGACCATTAAATGTGCTT
CTGAAATATATTTTGAGATAGGTTTAGAATGTCA

FIGURE 158

MDFLLLGLCLYWLLRRPSGVVLCLLGACFQMLPAAPSGCPQLCRCEGRLLYCEALNLTEAPHNLSGLLGLSLRY
NSLSELRAGQFTGLMQLTWLYLDHNHICSVQGDAFQKLRRVKELTLSSNQITQLPNTTFRPMPNLRSVDLSYNK
LQALAPDLFHGLRKLTTLHMRANAIQFVPVRIFQDCRSLKFLDIGYNQLKSLARNSFAGLFKLTELHLEHNDLV
KVNFAHFPRLISLHSLCLRRNKVAIVVSSLDWVWNLEKMDLSGNEIEYMEPHVFETVPHLQSLQLDSNRLTYIE
PRILNSWKSLTSITLAGNLWDCGRNVCALASWLSNFQGRYDGNLQCASPEYAQGEDVLDAVYAFHLCEDGAEPT
SGHLLSAVTNRSDLGPPASSATTLADGGEGQHDGTFEPATVALPGGEHAENAVQIHKVVTGTMALIFSFLIVVL
VLYVSWKCFPASLRQLRQCFVTQRRKQKQKQTMHQMAAMSAQEYYVDYKPNHIEGALVIINEYGSCTCHQQPAR
ECEV

FIGURE 159

CAGAGAGGAGGCTTTGGGAATTGTCCAGCAGAAACAGAGAAGTCTGAGGTGGTGTCAAGACA
AAAGATGCTTCAGCTTTGGAAACTTGTTCTCCTGTGCGGCGTGCTCACTGGGACCTCAGAGTCT
CTTCTTGACAATCTTGGCAATGACCTAAGCAATGTCGTGGATAAGCTGGAACCTGTTCTTCA
CGAGGGACTTGAGACAGTTGACAATACTCTTAAAGGCATCCTTGAGAAACTGAAGGTCGACC
TAGGAGTGCTTCAGAAATCCAGTGCTTGGCAACTGGCCAAGCAGAAGGCCCAGGAAGCTGAG
AAATTGCTGAACAATGTCATTTCTAAGCTGCTTCCAACTAACACGGACATTTTTGGGTTGAA
AATCAGCAACTCCCTCATCCTGGATGTCAAAGCTGAACCGATCGATGATGGCAAAGGCCTTA
ACCTGAGCTTCCCTGTCACCGCGAATGTCACTGTGGCCGGGCCCATCATTGGCCAGATTATC
AACCTGAAAGCCTCCTTGGACCTCCTGACCGCAGTCACAATTGAAACTGATCCCCAGACACA
CCAGCCTGTTGCCGTCCTGGGAGAATGCGCCAGTGACCCAACCAGCATCTCACTTTCCTTGC
TGGACAAACACAGCCAAATCATCAACAAGTTCGTGAATAGCGTGATCAACACGCTGAAAAGC
ACTGTATCCTCCCTGCTGCAGAAGGAGATATGTCCACTGATCCGCATCTTCATCCACTCCCT
GGATGTGAATGTCATTCAGCAGGTCGTCGATAATCCTCAGCACAAAACCCAGCTGCAAACCC
TCATCTGAAGAGGACGAATGAGGAGGACCACTGTGGTGCATGCTGATTGGTTCCCAGTGGCT
TGCCCCACCCCCTTATAGCATCTCCCTCCAGGAAGCTGCTGCCACCACCTAACCAGCGTGAA
AGCCTGAGTCCCACCAGAAGGACCTTCCCAGATACCCCTTCTCCTCACAGTCAGAACAGCAG
CCTCTACACATGTTGTCCTGCCCCTGGCAATAAAGGCCCATTTCTGCACCCTTAA

FIGURE 160

></usr/seqdb2/sst/DNA/Dnaseqs.min/ss.DNA59622
><subunit 1 of 1, 249 aa, 1 stop
><MW: 27011, pI: 5.48, NX(S/T): 2
MLQLWKLVLLCGVLTGTSESLLDNLGNDLSNVVDKLEPVLHEGLETVDNTLKGILEKLKV
DLGVLQKSSAWQLAKQKAQEAEKLLNNVISKLLPTNTDIFGLKISNSLILDVKAEPIDDG
KGLNLSFPVTANVTVAGPIIGQIINLKASLDLLTAVTIETDPQTHQPVAVLGECASDPTS
ISLSLLDKHSQIINKFVNSVINTLKSTVSSLLQKEICPLIRIFIHSLDVNVIQQVVDNPQ
HKTQLQTLI

Important features:
Signal peptide:
Amino acids 1-15

N-glycosylation sites:
Amino acids 124-128;132-136

N-myristoylation sites:
Amino acids 12-18;16-22;26-32;101-107;122-128;141-147

Leucine zipper pattern:
Amino acids 44-66

FIGURE 161

CAGCCACAGACGGGTCATGAGCGCGGTATTACTGCTGGCCCTCCTGGGGTTCATCCTCCCAC
TGCCAGGAGTGCAGGCGCTGCTCTGCCAGTTTGGGACAGTTCAGCATGTGTGGAAGGTGTCC
GACCTACCCCGGCAATGGACCCCTAAGAACACCAGCTGCGACAGCGGCTTGGGGTGCCAGGA
CACGTTGATGCTCATTGAGAGCGGACCCCAAGTGAGCCTGGTGCTCTCCAAGGGCTGCACGG
AGGCCAAGGACCAGGAGCCCCGCGTCACTGAGCACCGGATGGGCCCCGGCCTCTCCCTGATC
TCCTACACCTTCGTGTGCCGCCAGGAGGACTTCTGCAACAACCTCGTTAACTCCCTCCCGCT
TTGGGCCCCACAGCCCCCAGCAGACCCAGGATCCTTGAGGTGCCCAGTCTGCTTGTCTATGG
AAGGCTGTCTGGAGGGGACAACAGAAGAGATCTGCCCCAAGGGGACCACACACTGTTATGAT
GGCCTCCTCAGGCTCAGGGGAGGAGGCATCTTCTCCAATCTGAGAGTCCAGGGATGCATGCC
CCAGCCAGGTTGCAACCTGCTCAATGGGACACAGGAAATTGGGCCCGTGGGTATGACTGAGA
ACTGCAATAGGAAAGATTTTCTGACCTGTCATCGGGGGACCACCATTATGACACACGGAAAC
TTGGCTCAAGAACCCACTGATTGGACCACATCGAATACCGAGATGTGCGAGGTGGGGCAGGT
GTGTCAGGAGACGCTGCTGCTCATAGATGTAGGACTCACATCAACCCTGGTGGGGACAAAAG
GCTGCAGCACTGTTGGGGCTCAAAATTCCCAGAAGACCACCATCCACTCAGCCCCTCCTGGG
GTGCTTGTGGCCTCCTATACCCACTTCTGCTCCTCGGACCTGTGCAATAGTGCCAGCAGCAG
CAGCGTTCTGCTGAACTCCCTCCCTCCTCAAGCTGCCCCTGTCCCAGGAGACCGGCAGTGTC
CTACCTGTGTGCAGCCCCTTGGAACCTGTTCAAGTGGCTCCCCCCGAATGACCTGCCCCAGG
GGCGCCACTCATTGTTATGATGGGTACATTCATCTCTCAGGAGGTGGGCTGTCCACCAAAAT
GAGCATTCAGGGCTGCGTGGCCCAACCTTCCAGCTTCTTGTTGAACCACACCAGACAAATCG
GGATCTTCTCTGCGCGTGAGAAGCGTGATGTGCAGCCTCCTGCCTCTCAGCATGAGGGAGGT
GGGGCTGAGGGCCTGGAGTCTCTCACTTGGGGGGTGGGGCTGGCACTGGCCCCAGCGCTGTG
GTGGGGAGTGGTTTGCCCTTCCTGCTAACTCTATTACCCCCACGATTCTTCACCGCTGCTGA
CCACCCACACTCAACCTCCCTCTGACCTCATAACCTAATGGCCTTGGACACCAGATTCTTTC
CCATTCTGTCCATGAATCATCTTCCCCACACACAATCATTCATATCTACTCACCTAACAGCA
ACACTGGGGAGAGCCTGGAGCATCCGGACTTGCCCTATGGGAGAGGGGACGCTGGAGGAGTG
GCTGCATGTATCTGATAATACAGACCCTGTCCTTTCA

FIGURE 162

></usr/seqdb2/sst/DNA/Dnaseqs.min/ss.DNA59847
><subunit 1 of 1, 437 aa, 1 stop
><MW: 46363, pI: 6.22, NX(S/T): 3
MSAVLLLALLGFILPLPGVQALLCQFGTVQHVWKVSDLPRQWTPKNTSCDSGLGCQDTLM
LIESGPQVSLVLSKGCTEAKDQEPRVTEHRMGPGLSLISYTFVCRQEDFCNNLVNSLPLW
APQPPADPGSLRCPVCLSMEGCLEGTTEEICPKGTTHCYDGLLRLRGGGIFSNLRVQGCM
PQPGCNLLNGTQEIGPVGMTENCNRKDFLTCHRGTTIMTHGNLAQEPTDWTTSNTEMCEV
GQVCQETLLLIDVGLTSTLVGTKGCSTVGAQNSQKTTIHSAPPGVLVASYTHFCSSDLCN
SASSSSVLLNSLPPQAAPVPGDRQCPTCVQPLGTCSSGSPRMTCPRGATHCYDGYIHLSG
GGLSTKMSIQGCVAQPSSFLLNHTRQIGIFSAREKRDVQPPASQHEGGGAEGLESLTWGV
GLALAPALWWGVVCPSC

Important features of the protein:
Signal peptide:
Amino acids 1-15

Transmembrane domain:
Amino acids 243-260

N-glycosylation sites:
Amino acids 46-50;189-193;382-386

Glycosaminoglycan attachment sites:
Amino acids 51-55;359-363

N-myristoylation sites:
Amino acids 54-60;75-81;141-147;154-160;168-174;169-175;
198-204;254-260;261-267;269-275;284-290;333-339
347-353;360-366;361-367;388-394;408-414;419-425

FIGURE 163

GAGGATTTGCCACAGCAGCGGATAGAGCAGGAGAGCACCACCGGAGCCCTTGAGACATCCTTGAGAAGAGCCAC
AGCATAAGAGACTGCCCTGCTTGGTGTTTTGCAGGATGATGGTGGCCCTTCGAGGAGCTTCTGCATTGCTGGTT
CTGTTCCTTGCAGCTTTTCTGCCCCCGCCGCAGTGTACCCAGGACCCAGCCATGGTGCATTACATCTACCAGCG
CTTTCGAGTCTTGGAGCAAGGGCTGGAAAAATGTACCCAAGCAACGAGGGCATACATTCAAGAATTCCAAGAGT
TCTCAAAAAATATATCTGTCATGCTGGGAAGATGTCAGACCTACACAAGTGAGTACAAGAGTGCAGTGGGTAAC
TTGGCACTGAGAGTTGAACGTGCCCAACGGGAGATTGACTACATACAATACCTTCGAGAGGCTGACGAGTGCAT
CGTATCAGAGGACAAGACACTGGCAGAAATGTTGCTCCAAGAAGCTGAAGAAGAGAAAAAGATCCGGACTCTGC
TGAATGCAAGCTGTGACAACATGCTGATGGGCATAAAGTCTTTGAAAATAGTGAAGAAGATGATGGACACACAT
GGCTCTTGGATGAAAGATGCTGTCTATAACTCTCCAAAGGTGTACTTATTAATTGGATCCAGAAACAACACTGT
TTGGGAATTTGCAAACATACGGGCATTCATGGAGGATAACACCAAGCCAGCTCCCCGGAAGCAAATCCTAACAC
TTTCCTGGCAGGGAACAGGCCAAGTGATCTACAAAGGTTTTCTATTTTTTCATAACCAAGCAACTTCTAATGAG
ATAATCAAATATAACCTGCAGAAGAGGACTGTGGAAGATCGAATGCTGCTCCCAGGAGGGGTAGGCCGAGCATT
GGTTTACCAGCACTCCCCCTCAACTTACATTGACCTGGCTGTGGATGAGCATGGGCTCTGGGCCATCCACTCTG
GGCCAGGCACCCATAGCCATTTGGTTCTCACAAAGATTGAGCCGGGCACACTGGGAGTGGAGCATTCATGGGAT
ACCCCATGCAGAAGCCAGGATGCTGAAGCCTCATTCCTCTTGTGTGGGGTTCTCTATGTGGTCTACAGTACTGG
GGGCCAGGGCCCTCATCGCATCACCTGCATCTATGATCCACTGGGCACTATCAGTGAGGAGGACTTGCCCAACT
TGTTCTTCCCCAAGAGACCAAGAAGTCACTCCATGATCCATTACAACCCCAGAGATAAGCAGCTCTATGCCTGG
AATGAAGGAAACCAGATCATTTACAAACTCCAGACAAAGAGAAAGCTGCCTCTGAAGTAATGCATTACAGCTGT
GAGAAAGAGCACTGTGGCTTTGGCAGCTGTTCTACAGGACAGTGAGGCTATAGCCCCTTCACAATATAGTATCC
CTCTAATCACACACAGGAAGAGTGTGTAGAAGTGGAAATACGTATGCCTCCTTTCCCAAATGTCACTGCCTTAG
GTATCTTCCAAGAGCTTAGATGAGAGCATATCATCAGGAAAGTTTCAACAATGTCCATTACTCCCCCAAACCTC
CTGGCTCTCAAGGATGACCACATTCTGATACAGCCTACTTCAAGCCTTTTGTTTTACTGCTCCCCAGCATTTAC
TGTAACTCTGCCATCTTCCCTCCCACAATTAGAGTTGTATGCCAGCCCCTAATATTCACCACTGGCTTTTCTCT
CCCCTGGCCTTTGCTGAAGCTCTTCCCTCTTTTTCAAATGTCTATTGATATTCTCCCATTTTCACTGCCCAACT
AAAATACTATTAATATTTCTTTCTTTTCTTTTCTTTTTTTTGAGACAAGGTCTCACTATGTTGCCCAGGCTGGT
CTCAAACTCCAGAGCTCAAGAGATCCTCCTGCCTCAGCCTCCTAAGTACCTGGGATTACAGGCATGTGCCACCA
CACCTGGCTTAAAATACTATTTCTTATTGAGGTTTAACCTCTATTTCCCCTAGCCCTGTCCTTCCACTAAGCTT
GGTAGATGTAATAATAAAGTGAAAATATTAACATTTGAATATCGCTTTCCAGGTGTGGAGTGTTTGCACATCAT
TGAATTCTCGTTTCACCTTTGTGAAACATGCACAAGTCTTTACAGCTGTCATTCTAGAGTTTAGGTGAGTAACA
CAATTACAAAGTGAAAGATACAGCTAGAAAATACTACAAATCCCATAGTTTTTCCATTGCCCAAGGAAGCATCA
AATACGTATGTTTGTTCACCTACTCTTATAGTCAATGCGTTCATCGTTTCAGCCTAAAAATAATAGTCTGTCCC
TTTAGCCAGTTTTCATGTCTGCACAAGACCTTTCAATAGGCCTTTCAAATGATAATTCCTCCAGAAAACCAGTC
TAAGGGTGAGGACCCCAACTCTAGCCTCCTCTTGTCTTGCTGTCCTCTGTTTCTCTCTTTCTGCTTTAAATTCA
ATAAAAGTGACACTGAGCAAAAAAAAAAAAAAA

FIGURE 164

MMVALRGASALLVLFLAAFLPPPQCTQDPAMVHYIYQRFRVLEQGLEKCTQATRAYIQEFQEFSKNISVMLGRC
QTYTSEYKSAVGNLALRVERAQREIDYIQYLREADECIVSEDKTLAEMLLQEAEEEKKIRTLLNASCDNMLMGI
KSLKIVKKMMDTHGSWMKDAVYNSPKVYLLIGSRNNTVWEFANIRAFMEDNTKPAPRKQILTLSWQGTGQVIYK
GFLFFHNQATSNEIIKYNLQKRTVEDRMLLPGGVGRALVYQHSPSTYIDLAVDEHGLWAIHSGPGTHSHLVLTK
IEPGTLGVEHSWDTPCRSQDAEASFLLCGVLYVVYSTGGQGPHRITCIYDPLGTISEEDLPNLFFPKRPRSHSM
IHYNPRDKQLYAWNEGNQIIYKLQTKRKLPLK

FIGURE 165

TGGCCTCCCCAGCTTGCCAGGCACAAGGCTGAGCGGGAGGAAGCGAGAGGCATCTAAGCAGGCAGTGTTTTGCC
TTCACCCCAAGTGACCATGAGAGGTGCCACGCGAGTCTCAATCATGCTCCTCCTAGTAACTGTGTCTGACTGTG
CTGTGATCACAGGGGCCTGTGAGCGGGATGTCCAGTGTGGGGCAGGCACCTGCTGTGCCATCAGCCTGTGGCTT
CGAGGGCTGCGGATGTGCACCCCGCTGGGGCGGGAAGGCGAGGAGTGCCACCCCGGCAGCCACAAGGTCCCCTT
CTTCAGGAAACGCAAGCACCACACCTGTCCTTGCTTGCCCAACCTGCTGTGCTCCAGGTTCCCGGACGGCAGGT
ACCGCTGCTCCATGGACTTGAAGAACATCAATTTTTAGGCGCTTGCCTGGTCTCAGGATACCCACCATCCTTTT
CCTGAGCACAGCCTGGATTTTTATTTCTGCCATGAAACCCAGCTCCCATGACTCTCCCAGTCCCTACACTGACT
ACCCTGATCTCTCTTGTCTAGTACGCACATATGCACACAGGCAGACATACCTCCCATCATGACATGGTCCCCAG
GCTGGCCTGAGGATGTCACAGCTTGAGGCTGTGGTGTGAAAGGTGGCCAGCCTGGTTCTCTTCCCTGCTCAGGC
TGCCAGAGAGGTGGTAAATGGCAGAAAGGACATTCCCCCTCCCCTCCCCAGGTGACCTGCTCTCTTTCCTGGGC
CCTGCCCCTCTCCCCACATGTATCCCTCGGTCTGAATTAGACATTCCTGGGCACAGGCTCTTGGGTGCATTGCT
CAGAGTCCCAGGTCCTGGCCTGACCCTCAGGCCCTTCACGTGAGGTCTGTGAGGACCAATTTGTGGGTAGTTCA
TCTTCCCTCGATTGGTTAACTCCTTAGTTTCAGACCACAGACTCAAGATTGGCTCTTCCCAGAGGGCAGCAGAC
AGTCACCCCAAGGCAGGTGTAGGGAGCCCAGGGAGGCCAATCAGCCCCCTGAAGACTCTGGTCCCAGTCAGCCT
GTGGCTTGTGGCCTGTGACCTGTGACCTTCTGCCAGAATTGTCATGCCTCTGAGGCCCCCTCTTACCACACTTT
ACCAGTTAACCACTGAAGCCCCCAATTCCCACAGCTTTTCCATTAAAATGCAAATGGTGGTGGTTCAATCTAAT
CTGATATTGACATATTAGAAGGCAATTAGGGTGTTTCCTTAAACAACTCCTTTCCAAGGATCAGCCCTGAGAGC
AGGTTGGTGACTTTGAGGAGGGCAGTCCTCTGTCCAGATTGGGGTGGGAGCAAGGGACAGGGAGCAGGGCAGGG
GCTGAAAGGGGCACTGATTCAGACCAGGGAGGCAACTACACACCAACATGCTGGCTTTAGAATAAAAGCACCAA
CTGAAAAAA

FIGURE 166

MRGATRVSIMLLLVTVSDCAVITGACERDVQCGAGTCCAISLWLRGLRMCTPLGREGEECHPGSHKVPFFRKRK
HHTCPCLPNLLCSRFPDGRYRCSMDLKNINF

Important feratures:
Signal peptide:
amino acids 1-19

Tyrosine kinase phosphorylation site:
amino acids 88-95

N-myristoylation sites:
amino acids 33-39, 35-41, 46-52

FIGURE 167

AACTCAAACTCCTCTCTCTGGGAAAACGCGGTGCTTGCTCCTCCCGGAGTGGCCTTGGCAGGGTGTTGGAGCCC
TCGGTCTGCCCCGTCCGGTCTCTGGGGCCAAGGCTGGGTTTCCCTCATGTATGGCAAGAGCTCTACTCGTGCGG
TGCTTCTTCTCCTTGGCATACAGCTCACAGCTCTTTGGCCTATAGCAGCTGTGGAAATTTATACCTCCCGGGTG
CTGGAGGCTGTTAATGGGACAGATGCTCGGTTAAAATGCACTTTCTCCAGCTTTGCCCCTGTGGGTGATGCTCT
AACAGTGACCTGGAATTTTCGTCCTCTAGACGGGGGACCTGAGCAGTTTGTATTCTACTACCACATAGATCCCT
TCCAACCCATGAGTGGGCGGTTTAAGGACCGGGTGTCTTGGGATGGGAATCCTGAGCGGTACGATGCCTCCATC
CTTCTCTGGAAACTGCAGTTCGACGACAATGGGACATACACCTGCCAGGTGAAGAACCCACCTGATGTTGATGG
GGTGATAGGGGAGATCCGGCTCAGCGTCGTGCACACTGTACGCTTCTCTGAGATCCACTTCCTGGCTCTGGCCA
TTGGCTCTGCCTGTGCACTGATGATCATAATAGTAATTGTAGTGGTCCTCTTCCAGCATTACCGGAAAAAGCGA
TGGGCCGAAAGAGCTCATAAAGTGGTGGAGATAAAATCAAAAGAAGAGGAAAGGCTCAACCAAGAGAAAAAGGT
CTCTGTTTATTTAGAAGACACAGACTAACAATTTTAGATGGAAGCTGAGATGATTTCCAAGAACAAGAACCCTA
GTATTTCTTGAAGTTAATGGAAACTTTTCTTTGGCTTTTCCAGTTGTGACCCGTTTTCCAACCAGTTCTGCAGC
ATATTAGATTCTAGACAAGCAACACCCCTCTGGAGCCAGCACAGTGCTCCTCCATATCACCAGTCATACACAGC
CTCATTATTAAGGTCTTATTTAATTTCAGAGTGTAAATTTTTTCAAGTGCTCATTAGGTTTTATAAACAAGAAG
CTACATTTTTGCCCTTAAGACACTACTTACAGTGTTATGACTTGTATACACATATATTGGTATCAAAGGGGATA
AAAGCCAATTTGTCTGTTACATTTCCTTTCACGTATTTCTTTTAGCAGCACTTCTGCTACTAAAGTTAATGTGT
TTACTCTCTTTCCTTCCCACATTCTCAATTAAAAGGTGAGCTAAGCCTCCTCGGTGTTTCTGATTAACAGTAAA
TCCTAAATTCAAACTGTTAAATGACATTTTTATTTTTATGTCTCTCCTTAACTATGAGACACATCTTGTTTTAC
TGAATTTCTTTCAATATTCCAGGTGATAGATTTTTGTCG

FIGURE 168

MYGKSSTRAVLLLLGIQLTALWPIAAVEIYTSRVLEAVNGTDARLKCTFSSFAPVGDALTVTWNFRPLDGGPEQ
FVFYYHIDPFQPMSGRFKDRVSWDGNPERYDASILLWKLQFDDNGTYTCQVKNPPDVDGVIGEIRLSVVHTVRF
SEIHFLALAIGSACALMIIIVIVVVLFQHYRKKRWAERAHKVVEIKSKEEERLNQEKKVSVYLEDTD

FIGURE 169

GAGCGAACATGGCAGCGCGTTGGCGGTTTTGGTGTGTCTCTGTGACCATGGTGGTGGCGCTG
CTCATCGTTTGCGACGTTCCCTCAGCCTCTGCCCAAAGAAAGAAGGAGATGGTGTTATCTGA
AAAGGTTAGTCAGCTGATGGAATGGACTAACAAAAGACCTGTAATAAGAATGAATGGAGACA
AGTTCCGTCGCCTTGTGAAAGCCCCACCGAGAAATTACTCCGTTATCGTCATGTTCACTGCT
CTCCAACTGCATAGACAGTGTGTCGTTTGCAAGCAAGCTGATGAAGAATTCCAGATCCTGGC
AAACTCCTGGCGATACTCCAGTGCATTCACCAACAGGATATTTTTTGCCATGGTGGATTTTG
ATGAAGGCTCTGATGTATTTCAGATGCTAAACATGAATTCAGCTCCAACTTTCATCAACTTT
CCTGCAAAAGGGAAACCCAAACGGGGTGATACATATGAGTTACAGGTGCGGGGTTTTTCAGC
TGAGCAGATTGCCCGGTGGATCGCCGACAGAACTGATGTCAATATTAGAGTGATTAGACCCC
CAAATTATGCTGGTCCCCTTATGTTGGGATTGCTTTTGGCTGTTATTGGTGGACTTGTGTAT
CTTCGAAGAAGTAATATGGAATTTCTCTTTAATAAAACTGGATGGGCTTTTGCAGCTTTGTG
TTTTGTGCTTGCTATGACATCTGGTCAAATGTGGAACCATATAAGAGGACCACCATATGCCC
ATAAGAATCCCCACACGGGACATGTGAATTATATCCATGGAAGCAGTCAAGCCCAGTTTGTA
GCTGAAACACACATTGTTCTTCTGTTTAATGGTGGAGTTACCTTAGGAATGGTGCTTTTATG
TGAAGCTGCTACCTCTGACATGGATATTGGAAAGCGAAAGATAATGTGTGTGGCTGGTATTG
GACTTGTTGTATTATTCTTCAGTTGGATGCTCTCTATTTTTAGATCTAAATATCATGGCTAC
CCATACAGCTTTCTGATGAGTTAAAAAGGTCCCAGAGATATATAGACACTGGAGTACTGGAA
ATTGAAAAACGAAAATCGTGTGTGTTTGAAAAGAAGAATGCAACTTGTATATTTTGTATTAC
CTCTTTTTTTCAAGTGATTTAAATAGTTAATCATTTAACCAAAGAAGATGTGTAGTGCCTTA
ACAAGCAATCCTCTGTCAAAATCTGAGGTATTTGAAAATAATTATCCTCTTAACCTTCTCTT
CCCAGTGAACTTTATGGAACATTTAATTTAGTACAATTAAGTATATTATAAAAATTGTAAAA
CTACTACTTTGTTTTAGTTAGAACAAAGCTCAAAACTACTTTAGTTAACTTGGTCATCTGAT
TTTATATTGCCTTATCCAAAGATGGGGAAAGTAAGTCCTGACCAGGTGTTCCCACATATGCC
TGTTACAGATAACTACATTAGGAATTCATTCTTAGCTTCTTCATCTTTGTGTGGATGTGTAT
ACTTTACGCATCTTTCCTTTTGAGTAGAGAAATTATGTGTGTCATGTGGTCTTCTGAAAATG
GAACACCATTCTTCAGAGCACACGTCTAGCCCTCAGCAAGACAGTTGTTTCTCCTCCTCCTT
GCATATTTCCTACTGCGCTCCAGCCTGAGTGATAGAGTGAGACTCTGTCTCAAAAAAAAGTA
TCTCTAAATACAGGATTATAATTTCTGCTTGAGTATGGTGTTAACTACCTTGTATTTAGAAA
GATTTCAGATTCATTCCATCTCCTTAGTTTTCTTTTAAGGTGACCCATCTGTGATAAAAATA
TAGCTTAGTGCTAAAATCAGTGTAACTTATACATGGCCTAAAATGTTTCTACAAATTAGAGT
TTGTCACTTATTCCATTTGTACCTAAGAGAAAAATAGGCTCAGTTAGAAAAGGACTCCCTGG
CCAGGCGCAGTGACTTACGCCTGTAATCTCAGCACTTTGGGAGGCCAAGGCAGGCAGATCAC
GAGGTCAGGAGTTCGAGACCATCCTGGCCAACATGGTGAAACCCCGTCTCTACTAAAAATAT
AAAAATTAGCTGGGTGTGGTGGCAGGAGCCTGTAATCCCAGCTACACAGGAGGCTGAGGCAC
GAGAATCACTTGAACTCAGGAGATGGAGGTTTCAGTGAGCCGAGATCACGCCACTGCACTCC
AGCCTGGCAACAGAGCGAGACTCCATCTCAAAAAAAAAAAAAA

FIGURE 170

MAARWRFWCVSVTMVVALLIVCDVPSASAQRKKEMVLSEKVSQLMEWTNKRPVIRMNGDKFR
RLVKAPPRNYSVIVMFTALQLHRQCVVCKQADEEFQILANSWRYSSAFTNRIFFAMVDFDEG
SDVFQMLNMNSAPTFINFPAKGKPKRGDTYELQVRGFSAEQIARWIADRTDVNIRVIRPPNY
AGPLMLGLLLAVIGGLVYLRRSNMEFLFNKTGWAFAALCFVLAMTSGQMWNHIRGPPYAHKN
PHTGHVNYIHGSSQAQFVAETHIVLLFNGGVTLGMVLLCEAATSDMDIGKRKIMCVAGIGLV
VLFFSWMLSIFRSKYHGYPYSFLMS

Signal peptide:
amino acids 1-29

Transmembrane domains:
amino acids 183-205, 217-237, 217-287, 301-321

FIGURE 171

CTCCACTGCAACCACCCAGAGCCATGGCTCCCCGAGGCTGCATCGTAGCTGTCTTTGCCATTTTCTGCATCTCC
AGGCTCCTCTGCTCACACGGAGCCCCAGTGGCCCCCATGACTCCTTACCTGATGCTGTGCCAGCCACACAAGAG
ATGTGGGGACAAGTTCTACGACCCCCTGCAGCACTGTTGCTATGATGATGCCGTCGTGCCCTTGGCCAGGACCC
AGACGTGTGGAAACTGCACCTTCAGAGTCTGCTTTGAGCAGTGCTGCCCCTGGACCTTCATGGTGAAGCTGATA
AACCAGAACTGCGACTCAGCCCGGACCTCGGATGACAGGCTTTGTCGCAGTGTCAGCTAATGGAACATCAGGGG
AACGATGACTCCTGGATTCTCCTTCCTGGGTGGGCCTGGAGAAAGAGGCTGGTGTTACCTGAGATCTGGGATGC
TGAGTGGCTGTTTGGGGGCCAGAGAAACACACACTCAACTGCCCACTTCATTCTGTGACCTGTCTGAGGCCCAC
CCTGCAGCTGCCCTGAGGAGGCCCACAGGTCCCCTTCTAGAATTCTGGACAGCATGAGATGCGTGTGCTGATGG
GGGCCCAGGGACTCTGAACCCTCCTGATGACCCCTATGGCCAACATCAACCCGGCACCACCCCAAGGCTGGCTG
GGGAACCCTTCACCCTTCTGTGAGATTTTCCATCATCTCAAGTTCTCTTCTATCCAGGAGCAAAGCACAGGATC
ATAATAAATTTATGTACTTTATAAATGAAAA

FIGURE 172

MAPRGCIVAVFAIFCISRLLCSHGAPVAPMTPYLMLCQPHKRCGDKFYDPLQHCCYDDAVVPLARTQTCGNCTF
RVCFEQCCPWTFMVKLINQNCDSARTSDDRLCRSVS

Important features:
Signal peptide:
amino acids 1-24

FIGURE 173

GGGGGCGGGTGCCTGGAGCACGGCGCTGGGGCCGCCCGCAGCGCTCACTCGCTCGCACTCAG
TCGCGGGAGGCTTCCCCGCGCCGGCCGCGTCCCGCCCGCTCCCCGGCACCAGAAGTTCCTCT
GCGCGTCCGACGGCGACATGGGCGTCCCCACGGCCCTGGAGGCCGGCAGCTGGCGCTGGGGA
TCCCTGCTCTTCGCTCTCTTCCTGGCTGCGTCCCTAGGTCCGGTGGCAGCCTTCAAGGTCGC
CACGCCGTATTCCCTGTATGTCTGTCCCGAGGGGCAGAACGTCACCCTCACCTGCAGGCTCT
TGGGCCCTGTGGACAAAGGGCACGATGTGACCTTCTACAAGACGTGGTACCGCAGCTCGAGG
GGCGAGGTGCAGACCTGCTCAGAGCGCCGGCCCATCCGCAACCTCACGTTCCAGGACCTTCA
CCTGCACCATGGAGGCCACCAGGCTGCCAACACCAGCCACGACCTGGCTCAGCGCCACGGGC
TGGAGTCGGCCTCCGACCACCATGGCAACTTCTCCATCACCATGCGCAACCTGACCCTGCTG
GATAGCGGCCTCTACTGCTGCCTGGTGGTGGAGATCAGGCACCACCACTCGGAGCACAGGGT
CCATGGTGCCATGGAGCTGCAGGTGCAGACAGGCAAAGATGCACCATCCAACTGTGTGGTGT
ACCCATCCTCCTCCCAGGATAGTGAAAACATCACGGCTGCAGCCCTGGCTACGGGTGCCTGC
ATCGTAGGAATCCTCTGCCTCCCCCTCATCCTGCTCCTGGTCTACAAGCAAAGGCAGGCAGC
CTCCAACCGCCGTGCCCAGGAGCTGGTGCGGATGGACAGCAACATTCAAGGGATTGAAAACC
CCGGCTTTGAAGCCTCACCACCTGCCCAGGGGATACCCGAGGCCAAAGTCAGGCACCCCCTG
TCCTATGTGGCCCAGCGGCAGCCTTCTGAGTCTGGGCGGCATCTGCTTTCGGAGCCCAGCAC
CCCCCTGTCTCCTCCAGGCCCCGGAGACGTCTTCTTCCCATCCCTGGACCCTGTCCCTGACT
CTCCAAACTTTGAGGTCATCTAGCCCAGCTGGGGGACAGTGGGCTGTTGTGGCTGGGTCTGG
GGCAGGTGCATTTGAGCCAGGGCTGGCTCTGTGAGTGGCCTCCTTGGCCTCGGCCCTGGTTC
CCTCCCTCCTGCTCTGGGCTCAGATACTGTGACATCCCAGAAGCCCAGCCCCTCAACCCCTC
TGGATGCTACATGGGGATGCTGGACGGCTCAGCCCCTGTTCCAAGGATTTTGGGGTGCTGAG
ATTCTCCCCTAGAGACCTGAAATTCACCAGCTACAGATGCCAAATGACTTACATCTTAAGAA
GTCTCAGAACGTCCAGCCCTTCAGCAGCTCTCGTTCTGAGACATGAGCCTTGGGATGTGGCA
GCATCAGTGGGACAAGATGGACACTGGGCCACCCTCCCAGGCACCAGACACAGGGCACGGTG
GAGAGACTTCTCCCCCGTGGCCGCCTTGGCTCCCCCGTTTTGCCCGAGGCTGCTCTTCTGTC
AGACTTCCTCTTTGTACCACAGTGGCTCTGGGGCCAGGCCTGCCTGCCCACTGGCCATCGCC
ACCTTCCCCAGCTGCCTCCTACCAGCAGTTTCTCTGAAGATCTGTCAACAGGTTAAGTCAAT
CTGGGGCTTCCACTGCCTGCATTCCAGTCCCCAGAGCTTGGTGGTCCCGAAACGGGAAGTAC
ATATTGGGGCATGGTGGCCTCCGTGAGCAAATGGTGTCTTGGGCAATCTGAGGCCAGGACAG
ATGTTGCCCCACCCACTGGAGATGGTGCTGAGGGAGGTGGGTGGGGCCTTCTGGGAAGGTGA
GTGGAGAGGGGCACCTGCCCCCCGCCCTCCCCATCCCCTACTCCCACTGCTCAGCGCGGGCC
ATTGCAAGGGTGCCACACAATGTCTTGTCCACCCTGGGACACTTCTGAGTATGAAGCGGGAT
GCTATTAAAAACTACATGGGGAAAAAAAAAAAAAAAAAAAAAAAAAAAAAAAAAAAAAAAAGA

FIGURE 174

></usr/seqdb2/sst/DNA/Dnaseqs.min/ss.DNA64897
><subunit 1 of 1, 311 aa, 1 stop
><MW: 33908, pI: 6.87, NX(S/T): 6
MGVPTALEAGSWRWGSLLFALFLAASLGPVAAFKVATPYSLYVCPEGQNVTLTCRLLGPVDK
GHDVTFYKTWYRSSRGEVQTCSERRPIRNLTFQDLHLHHGGHQAANTSHDLAQRHGLESASD
HHGNFSITMRNLTLLDSGLYCCLVVEIRHHHSEHRVHGAMELQVQTGKDAPSNCVVYPSSSQ
DSENITAAALATGACIVGILCLPLILLLVYKQRQAASNRRAQELVRMDSNIQGIENPGFEAS
PPAQGIPEAKVRHPLSYVAQRQPSESGRHLLSEPSTPLSPPGPGDVFFPSLDPVPDSPNFEVI

Signal peptide:
amino acids 1-28

Transmembrane domain:
amino acids 190-216

FIGURE 175

CTAGCCTGCGCCAAGGGGTAGTGAGACCGCGCGGCAACAGCTTGCGGCTGCGGGGAGCTCCCGTGGGCGCTCCG
CTGGCTGTGCAGGCGGCCATGGATTCCTTGCGGAAAATGCTGATCTCAGTCGCAATGCTGGGCGCAGGGGCTGG
CGTGGGCTACGCGCTCCTCGTTATCGTGACCCCGGGAGAGCGGCGGAAGCAGGAAATGCTAAAGGAGATGCCAC
TGCAGGACCCAAGGAGCAGGGAGGAGGCGGCCAGGACCCAGCAGCTATTGCTGGCCACTCTGCAGGAGGCAGCG
ACCACGCAGGAGAACGTGGCCTGGAGGAAGAACTGGATGGTTGGCGGCGAAGGCGGCGCCAGCGGGAGGTCACC
GTGAGACCGGACTTGCCTCCGTGGGCGCCGGACCTTGGCTTGGGCGCAGGAATCCGAGGCAGCCTTTCTCCTTC
GTGGGCCCAGCGGAGAGTCCGGACCGAGATACCATGCCAGGACTCTCCGGGGTCCTGTGAGCTGCCGTCGGGTG
AGCACGTTTCCCCCAAACCCTGGACTGACTGCTTTAAGGTCCGCAAGGCGGGCCAGGGCCGAGACGCGAGTCGG
ATGTGGTGAACTGAAAGAACCAATAAAATCATGTTCCTCCAAAAAAAAAAAAAAAAAAAAAAAAAAAAAAAAA
AAAAAAAAAAAAAAAAAAAAAAAAAAA

FIGURE 176

MDSLRKMLISVAMLGAGAGVGYALLVIVTPGERRKQEMLKEMPLQDPRSREEAARTQQLLLATLQEAATTQENV
AWRKNWMVGGEGGASGRSP

Important features:
Signal peptide:
amino acids 1-18

FIGURE 177

GCCAGGCAGGTGGGCCTCAGGAGGTGCCTCCAGGCGGCCAGTGGGCCTGAGGCCCCAGCAAG
GGCTAGGGTCCATCTCCAGTCCCAGGACACAGCAGCGGCCACCATGGCCACGCCTGGGCTCC
AGCAGCATCAGAGCAGCCCCTGTGGTTGGCAGCAAAGTTCAGCTTGGCTGGGCCCGCTGTGA
GGGGCTTCGCGCTACGCCCTGCGGTGTCCCGAGGGCTGAGGTCTCCTCATCTTCTCCCTAGC
AGTGGATGAGCAACCCAACGGGGGCCCGGGGAGGGGAACTGGCCCCGAGGGAGAGGAACCCC
AAAGCCACATCTGTAGCCAGGATGAGCAGTGTGAATCCAGGCAGCCCCCAGGACCGGGGAGG
CACAGGTGGCCCCCACCACCCGGAGGAGCAGCTCCTGCCCCTGTCCGGGGGATGACTGATTC
TCCTCCGCCAGGCCACCCAGAGGAGAAGGCCACCCCGCCTGGAGGCACAGGCCATGAGGGGC
TCTCAGGAGGTGCTGCTGATGTGGCTTCTGGTGTTGGCAGTGGGCGGCACAGAGCACGCCTA
CCGGCCCGGCCGTAGGGTGTGTGCTGTCCGGGCTCACGGGGACCCTGTCTCCGAGTCGTTCG
TGCAGCGTGTGTACCAGCCCTTCCTCACCACCTGCGACGGGCACCGGGCCTGCAGCACCTAC
CGAACCATCTATAGGACCGCCTACCGCCGCAGCCCTGGGCTGGCCCCTGCCAGGCCTCGCTA
CGCGTGCTGCCCCGGCTGGAAGAGGACCAGCGGGCTTCCTGGGGCCTGTGGAGCAGCAATAT
GCCAGCCGCCATGCCGGAACGGAGGGAGCTGTGTCCAGCCTGGCCGCTGCCGCTGCCCTGCA
GGATGGCGGGGTGACACTTGCCAGTCAGATGTGGATGAATGCAGTGCTAGGAGGGGCGGCTG
TCCCCAGCGCTGCATCAACACCGCCGGCAGTTACTGGTGCCAGTGTTGGGAGGGGCACAGCC
TGTCTGCAGACGGTACACTCTGTGTGCCCAAGGGAGGGCCCCCCAGGGTGGCCCCCAACCCG
ACAGGAGTGGACAGTGCAATGAAGGAAGAAGTGCAGAGGCTGCAGTCCAGGGTGGACCTGCT
GGAGGAGAAGCTGCAGCTGGTGCTGGCCCCACTGCACAGCCTGGCCTCGCAGGCACTGGAGC
ATGGGCTCCCGGACCCCGGCAGCCTCCTGGTGCACTCCTTCCAGCAGCTCGGCCGCATCGAC
TCCCTGAGCGAGCAGATTTCCTTCCTGGAGGAGCAGCTGGGGTCCTGCTCCTGCAAGAAAGA
CTCGTGACTGCCCAGCGCTCCAGGCTGGACTGAGCCCCTCACGCCGCCCTGCAGCCCCCATG
CCCCTGCCCAACATGCTGGGGGTCCAGAAGCCACCTCGGGGTGACTGAGCGGAAGGCCAGGC
AGGGCCTTCCTCCTCTTCCTCCTCCCCTTCCTCGGGAGGCTCCCCAGACCCTGGCATGGGAT
GGGCTGGGATCTTCTCTGTGAATCCACCCCTGGCTACCCCCACCCTGGCTACCCCAACGGCA
TCCCAAGGCCAGGTGGACCCTCAGCTGAGGGAAGGTACGAGCTCCCTGCTGGAGCCTGGGAC
CCATGGCACAGGCCAGGCAGCCCGGAGGCTGGGTGGGGCCTCAGTGGGGGCTGCTGCCTGAC
CCCCAGCACAATAAAAATGAAACGTG

FIGURE 178

MRGSQEVLLMWLLVLAVGGTEHAYRPGRRVCAVRAHGDPVSESFVQRVYQPFLTTCDGHRAC
STYRTIYRTAYRRSPGLAPARPRYACCPGWKRTSGLPGACGAAICQPPCRNGGSCVQPGRCR
CPAGWRGDTCQSDVDECSARRGGCPQRCINTAGSYWCQCWEGHSLSADGTLCVPKGGPPRVA
PNPTGVDSAMKEEVQRLQSRVDLLEEKLQLVLAPLHSLASQALEHGLPDPGSLLVHSFQQLG
RIDSLSEQISFLEEQLGSCSCKKDS

Signal sequence:
1-19

FIGURE 179

GACAGCTGTGTCTCGATGGAGTAGACTCTCAGAACAGCGCAGTTTGCCCTCCGCTCACGCAG
AGCCTCTCCGTGGCTTCCGCACCTTGAGCATTAGGCCAGTTCTCCTCTTCTCTCTAATCCAT
CCGTCACCTCTCCTGTCATCCGTTTCCATGCCGTGAGGTCCATTCACAGAACACATCCATGG
CTCTCATGCTCAGTTTGGTTCTGAGTCTCCTCAAGCTGGGATCAGGGCAGTGGCAGGTGTTT
GGGCCAGACAAGCCTGTCCAGGCCTTGGTGGGGGAGGACGCAGCATTCTCCTGTTTCCTGTC
TCCTAAGACCAATGCAGAGGCCATGGAAGTGCGGTTCTTCAGGGGCCAGTTCTCTAGCGTGG
TCCACCTCTACAGGGACGGGAAGGACCAGCCATTTATGCAGATGCCACAGTATCAAGGCAGG
ACAAAACTGGTGAAGGATTCTATTGCGGAGGGGCGCATCTCTCTGAGGCTGGAAAACATTAC
TGTGTTGGATGCTGGCCTCTATGGGTGCAGGATTAGTTCCCAGTCTTACTACCAGAAGGCCA
TCTGGGAGCTACAGGTGTCAGCACTGGGCTCAGTTCCTCTCATTTCCATCACGGGATATGTT
GATAGAGACATCCAGCTACTCTGTCAGTCCTCGGGCTGGTTCCCCCGGCCCACAGCGAAGTG
GAAAGGTCCACAAGGACAGGATTTGTCCACAGACTCCAGGACAAACAGAGACATGCATGGCC
TGTTTGATGTGGAGATCTCTCTGACCGTCCAAGAGAACGCCGGGAGCATATCCTGTTCCATG
CGGCATGCTCATCTGAGCCGAGAGGTGGAATCCAGGGTACAGATAGGAGATACCTTTTTCGA
GCCTATATCGTGGCACCTGGCTACCAAAGTACTGGGAATACTCTGCTGTGGCCTATTTTTTG
GCATTGTTGGACTGAAGATTTTCTTCTCCAAATTCCAGTGGAAAATCCAGGCGGAACTGGAC
TGGAGAAGAAAGCACGGACAGGCAGAATTGAGAGACGCCCGGAAACACGCAGTGGAGGTGAC
TCTGGATCCAGAGACGGCTCACCCGAAGCTCTGCGTTTCTGATCTGAAAACTGTAACCCATA
GAAAAGCTCCCCAGGAGGTGCCTCACTCTGAGAAGAGATTTACAAGGAAGAGTGTGGTGGCT
TCTCAGAGTTTCCAAGCAGGGAAACATTACTGGGAGGTGGACGGAGGACACAATAAAAGGTG
GCGCGTGGGAGTGTGCCGGGATGATGTGGACAGGAGGAAGGAGTACGTGACTTTGTCTCCCG
ATCATGGGTACTGGGTCCTCAGACTGAATGGAGAACATTTGTATTTCACATTAAATCCCCGT
TTTATCAGCGTCTTCCCCAGGACCCCACCTACAAAAATAGGGGTCTTCCTGGACTATGAGTG
TGGGACCATCTCCTTCTTCAACATAAATGACCAGTCCCTTATTTATACCCTGACATGTCGGT
TTGAAGGCTTATTGAGGCCCTACATTGAGTATCCGTCCTATAATGAGCAAAATGGAACTCCC
ATAGTCATCTGCCCAGTCACCCAGGAATCAGAGAAAGAGGCCTCTTGGCAAAGGGCCTCTGC
AATCCCAGAGACAAGCAACAGTGAGTCCTCCTCACAGGCAACCACGCCCTTCCTCCCCAGGG
GTGAAATGTAGGATGAATCACATCCCACATTCTTCTTTAGGGATATTAAGGTCTCTCTCCCA
GATCCAAAGTCCCGCAGCAGCCGGCCAAGGTGGCTTCCAGATGAAGGGGGACTGGCCTGTCC
ACATGGGAGTCAGGTGTCATGGCTGCCCTGAGCTGGGAGGGAAGAAGGCTGACATTACATTT
AGTTTGCTCTCACTCCATCTGGCTAAGTGATCTTGAAATACCACCTCTCAGGTGAAGAACCG
TCAGGAATTCCCATCTCACAGGCTGTGGTGTAGATTAAGTAGACAAGGAATGTGAATAATGC
TTAGATCTTATTGATGACAGAGTGTATCCTAATGGTTTGTTCATTATATTACACTTTCAGTA
AAAAAA

FIGURE 180

MALMLSLVLSLLKLGSGQWQVFGPDKPVQALVGEDAAFSCFLSPKTNAEAMEVRFFRGQFSS
VVHLYRDGKDQPFMQMPQYQGRTKLVKDSIAEGRISLRLENITVLDAGLYGCRISSQSYYQK
AIWELQVSALGSVPLISITGYVDRDIQLLCQSSGWFPRPTAKWKGPQGQDLSTDSRTNRDMH
GLFDVEISLTVQENAGSISCSMRHAHLSREVESRVQIGDTFFEPISWHLATKVLGILCCGLF
FGIVGLKIFFSKFQWKIQAELDWRRKHGQAELRDARKHAVEVTLDPETAHPKLCVSDLKTVT
HRKAPQEVPHSEKRFTRKSVVASQSFQAGKHYWEVDGGHNKRWRVGVCRDDVDRRKEYVTLS
PDHGYWVLRLNGEHLYFTLNPRFISVFPRTPPTKIGVFLDYECGTISFFNINDQSLIYTLTC
RFEGLLRPYIEYPSYNEQNGTPIVICPVTQESEKEASWQRASAIPETSNSESSSQATTPFLP
RGEM

Signal peptide:
amino acids 1-17

Transmembrane domain:
amino acids 239-255

FIGURE 181

GCGATGGTGCGCCCGGTGGCGGTGGCGGCGGCGGTTGCGGAGGCTTCCTTGGTCGGATTGCAACCAGGAGAAGA
TGACTGACCAACCGACTGGCTGAATGAATGAATGGCGGAGCCGAGCGCGCCATGAGGAGCCTGCCGAGCCTGGG
CGGCCTCGCCCTGTTGTGCTGCGCCGCCGCCGCCGCCGCCGTCGCCTCAGCCGCCTCGGCGGGGAATGTCACCG
GTGGCGGCGGGGCCGCGGGGCAGGTGGACGCGTCGCCGGGCCCCGGGTTGCGGGGCGAGCCCAGCCACCCCTTC
CCTAGGGCGACGGCTCCCACGGCCCAGGCCCCGAGGACCGGGCCCCCGCGCGCCACCGTCCACCGACCCCTGGC
TGCGACTTCTCCAGCCCAGTCCCCGGAGACCACCCCTCTTTGGGCGACTGCTGGACCCTCTTCCACCACCTTTC
AGGCGCCGCTCGGCCCCTCGCCGACCACCCCTCCGGCGGCGGAACGCACTTCGACCACCTCTCAGGCGCCGACC
AGACCCGCGCCGACCACCCTTTCGACGACCACTGGCCCGGCGCCGACCACCCCTGTAGCGACCACCGTACCGGC
GCCCACGACTCCCCGGACCCCGACCCCCGATCTCCCCAGCAGCAGCAACAGCAGCGTCCTCCCCACCCCACCTG
CCACCGAGGCCCCCTCTTCGCCTCCTCCAGAGTATGTATGTAACTGCTCTGTGGTTGGAAGCCTGAATGTGAAT
CGCTGCAACCAGACCACAGGGCAGTGTGAGTGTCGGCCAGGTTATCAGGGGCTTCACTGTGAAACCTGCAAAGA
GGGCTTTTACCTAAATTACACTTCTGGGCTCTGTCAGCCATGTGACTGTAGTCCACATGGAGCTCTCAGCATAC
CGTGCAACAGGTAAGCAACAGAGGGTGGAACTGAAGTTTATTTTATTTTAGCAAGGGAAAAAAAAAGGCTGCTA
CTCTCAAGGACCATACTGGTTTAAACAAAGGAGGATGAGGGTCATAGATTTACAAAATATTTTATATACTTTTA
TTCTCTTACTTTATATGTTATATTTAATGTCAGGATTTAAAAACATCTAATTTACTGATTTAGTTCTTCAAAAG
CACTAGAGTCGCCAATTTTTCTCTGGGATAATTTCTGTAAATTTCATGGGAAAAAATTATTGAAGAATAAATCT
GCTTTCTGGAAGGGCTTTCAGGCATGAAACCTGCTAGGAGGTTTAGAAATGTTCTTATGTTTATTAATATACCA
TTGGAGTTTGAGGAAATTTGTTGTTTGGTTTATTTTTCTCTCTAATCAAAATTCTACATTTGTTTCTTTGGACA
TCTAAAGCTTAACCTGGGGGTACCCTAATTTATTTAACTAGTGGTAAGTAGACTGGTTTTACTCTATTTACCAG
TACATTTTTGAGACCAAAAGTAGATTAAGCAGGAATTATCTTTAAACTATTATGTTATTTGGAGGTAATTTAAT
CTAGTGGAATAATGTACTGTTATCTAAGCATTTGCCTTGTACTGCACTGAAAGTAATTATTCTTTGACCTTATG
TGAGGCACTTGGCTTTTTGTGGACCCCAAGTCAAAAAACTGAAGAGACAGTATTAAATAATGAAAAAAATAATG
ACAGGTTATACTCAGTGTAACCTGGGTATAACCCAAGATCTGCTGCCACTTACGAGCTGTGTTCCTTGGGCAAG
TAATTTCCTTTCACTGAGCTTGTTTCTTCTCAAGGTTGTTGTGAAGATTAAATGAGTTGATATATATAAAATGC
CTAGCACATGTCACTCAATAAATTCTGGTTTGTTTTAATTTCAAAGGAATATTATGGACTGAAATGAGAGAACA
TGTTTTAAGAACTTTTAGCTCCTTGACAAAGAAGTGCTTTATACTTTAGCACTAAATATTTTAAATGCTTTATA
AATGATATTATACTGTTATGGAATATTGTATCATATTGTAGTTTATTAAAAATGTAGAAGAGGCTGGGCGCGGT
GGCTCACGCCTGTAATCCTAGCACTTTGGGAGGCCAAGGCGGGTGGATCACTTGAGGCCAGGAGTTCTAGATGA
GCCTGGCCAGCACAGTGAAACCCCGTCTCTACTAAAAATACAAACAAATTAGCTGGGCGTGGTGGCACACACCT
GTAGTCCCAGCTACTCGGGAGGCTGAGGCAGGAGAATCGGTTGAACCCGGGAGGTGGAGGTTGCAGTGAGCTGA
GATCGCGCCACTGCACTCCAGCCTGGTGAGAGAGGGAGACTCTGTCTTAAAAAAAAAAAAAAAAAAAAAAAAAA

FIGURE 182

></usr/seqdb2/sst/DNA/Dnaseqs.min/ss.DNA64952
><subunit 1 of 1, 258 aa, 1 stop
><MW: 25716, pI: 8.13, NX(S/T): 5
MRSLPSLGGLALLCCAAAAAAVASAASAGNVTGGGGAAGQVDASPGPGLRGEPSHPFPRATA
PTAQAPRTGPPRATVHRPLAATSPAQSPETTPLWATAGPSSTTFQAPLGPSPTTPPAAERTS
TTSQAPTRPAPTTLSTTTGPAPTTPVATTVPAPTTPRTPTPDLPSSSNSSVLPTPPATEAPS
SPPPEYVCNCSVVGSLNVNRCNQTTGQCECRPGYQGLHCETCKEGFYLNYTSGLCQPCDCSP
HGALSIPCNR

Important features of the protein:
Signal peptide:
amino acids 1-25

N-glycosylation sites.
amino acids 30-33, 172-175, 195-198, 208-211, 235-238

EGF-like domain cysteine pattern signature.
amino acids 214-226.

FIGURE 183

TGCGGCGCAGTGTAGACCTGGGAGGATGGGCGGCCTGCTGCTGGCTGCTTTTCTGGCTTTGGTCTCGGTGCCCA
GGGCCCAGGCCGTGTGGTTGGGAAGACTGGACCCTGAGCAGCTTCTTGGGCCCTGGTACGTGCTTGCGGTGGCC
TCCCGGGAAAAGGGCTTTGCCATGGAGAAGGACATGAAGAACGTCGTGGGGGTGGTGGTGACCCTCACTCCAGA
AAACAACCTGCGGACGCTGTCCTCTCAGCACGGGCTGGGAGGGTGTGACCAGAGTGTCATGGACCTGATAAAGC
GAAACTCCGGATGGGTGTTTGAGAATCCCTCAATAGGCGTGCTGGAGCTCTGGGTGCTGGCCACCAACTTCAGA
GACTATGCCATCATCTTCACTCAGCTGGAGTTCGGGGACGAGCCCTTCAACACCGTGGAGCTGTACAGTCTGAC
GGAGACAGCCAGCCAGGAGGCCATGGGGCTCTTCACCAAGTGGAGCAGGAGCCTGGGCTTCCTGTCACAGTAGC
AGGCCCAGCTGCAGAAGGACCTCACCTGTGCTCACAAGATCCTTCTGTGAGTGCTGCGTCCCCAGTAGGGATGG
CGCCCACAGGGTCCTGTGACCTCGGCCAGTGTCCACCCACCTCGCTCAGCGGCTCCCGGGGCCCAGCACCAGCT
CAGAATAAAGCGATTCCACAGCA

FIGURE 184

MGGLLLAAFLALVSVPRAQAVWLGRLDPEQLLGPWYVLAVASREKGFAMEKDMKNVVGVVVTLTPENNLRTLSS
QHGLGGCDQSVMDLIKRNSGWVFENPSIGVLELWVLATNFRDYAIIFTQLEFGDEPFNTVELYSLTETASQEAM
GLFTKWSRSLGFLSQ

Important features:
Signal peptide:
amino acids 1-20

FIGURE 185

GTTCCGCAGATGCAGAGGTTGAGGTGGCTGCGGGACTGGAAGTCATCGGGCAGAGGTCTCACAGCAGCCAAGGA
ACCTGGGGCCCGCTCCTCCCCCCTCCAGGCCATGAGGATTCTGCAGTTAATCCTGCTTGCTCTGGCAACAGGGC
TTGTAGGGGGAGAGACCAGGATCATCAAGGGGTTCGAGTGCAAGCCTCACTCCCAGCCCTGGCAGGCAGCCCTG
TTCGAGAAGACGCGGCTACTCTGTGGGGCGACGCTCATCGCCCCCAGATGGCTCCTGACAGCAGCCCACTGCCT
CAAGCCCCGCTACATAGTTCACCTGGGGCAGCACAACCTCCAGAAGGAGGAGGGCTGTGAGCAGACCCGGACAG
CCACTGAGTCCTTCCCCCACCCCGGCTTCAACAACAGCCTCCCCAACAAAGACCACCGCAATGACATCATGCTG
GTGAAGATGGCATCGCCAGTCTCCATCACCTGGGCTGTGCGACCCCTCACCCTCTCCTCACGCTGTGTCACTGC
TGGCACCAGCTGCCTCATTTCCGGCTGGGGCAGCACGTCCAGCCCCCAGTTACGCCTGCCTCACACCTTGCGAT
GCGCCAACATCACCATCATTGAGCACCAGAAGTGTGAGAACGCCTACCCCGGCAACATCACAGACACCATGGTG
TGTGCCAGCGTGCAGGAAGGGGGCAAGGACTCCTGCCAGGGTGACTCCGGGGGCCCTCTGGTCTGTAACCAGTC
TCTTCAAGGCATTATCTCCTGGGGCCAGGATCCGTGTGCGATCACCCGAAAGCCTGGTGTCTACACGAAAGTCT
GCAAATATGTGGACTGGATCCAGGAGACGATGAAGAACAATTAGACTGGACCCACCCACCACAGCCCATCACCC
TCCATTTCCACTTGGTGTTTGGTTCCTGTTCACTCTGTTAATAAGAAACCCTAAGCCAAGACCCTCTACGAACA
TTCTTTGGGCCTCCTGGACTACAGGAGATGCTGTCACTTAATAATCAACCTGGGGTTCGAAATCAGTGAGACCT
GGATTCAAATTCTGCCTTGAAATATTGTGACTCTGGGAATGACAACACCTGGTTTGTTCTCTGTTGTATCCCCA
GCCCCAAAGACAGCTCCTGGCCATATATCAAGGTTTCAATAAATATTTGCTAAATGAAAAAAAAAAAAAAAAAA
AAAAAAAAAAAAAAAAAAAAA

FIGURE 186

MRILQLILLALATGLVGGETRIIKGFECKPHSQPWQAALFEKTRLLCGATLIAPRWLLTAAHCLKPRYIVHLGQ
HNLQKEEGCEQTRTATESFPHPGFNNSLPNKDHRNDIMLVKMASPVSITWAVRPLTLSSRCVTAGTSCLISGWG
STSSPQLRLPHTLRCANITIIEHQKCENAYPGNITDTMVCASVQEGGKDSCQGDSGGPLVCNQSLQGIISWGQD
PCAITRKPGVYTKVCKYVDWIQETMKNN

Important features:
Signal peptide:
amino acids 1-18

Serine proteases, trypsin family, histidine active site.
amino acids 58-63

N-glycosylation sites.
amino acids 99-102, 165-168, 181-184, 210-213

Glycosaminoglycan attachment site.
amino acids 145-148

Kringle domain proteins.
amino acids 197-209, 47-64

Serine proteases, trypsin family, histidine protein
amino acids 199-209, 47-63, 220-243

Apple domain proteins
amino acids 222-249, 189-222

FIGURE 187

GCTCAAGTGCCCTGCCTTGCCCCACCCAGCCCAGCCTGGCCAGAGCCCCCTGGAGAAGGAGC
TCTCTTCTTGCTTGGCAGCTGGACCAAGGGAGCCAGTCTTGGGCGCTGGAGGGCCTGTCCTG
ACCATGGTCCCTGCCTGGCTGTGGCTGCTTTGTGTCTCCGTCCCCCAGGCTCTCCCCAAGGC
CCAGCCTGCAGAGCTGTCTGTGGAAGTTCCAGAAAACTATGGTGGAAATTTCCCTTTATACC
TGACCAAGTTGCCGCTGCCCCGTGAGGGGGCTGAAGGCCAGATCGTGCTGTCAGGGGACTCA
GGCAAGGCAACTGAGGGCCCATTTGCTATGGATCCAGATTCTGGCTTCCTGCTGGTGACCAG
GGCCCTGGACCGAGAGGAGCAGGCAGAGTACCAGCTACAGGTCACCCTGGAGATGCAGGATG
GACATGTCTTGTGGGGTCCACAGCCTGTGCTTGTGCACGTGAAGGATGAGAATGACCAGGTG
CCCCATTTCTCTCAAGCCATCTACAGAGCTCGGCTGAGCCGGGGTACCAGGCCTGGCATCCC
CTTCCTCTTCCTTGAGGCTTCAGACCGGGATGAGCCAGGCACAGCCAACTCGGATCTTCGAT
TCCACATCCTGAGCCAGGCTCCAGCCCAGCCTTCCCCAGACATGTTCCAGCTGGAGCCTCGG
CTGGGGGCTCTGGCCCTCAGCCCCAAGGGGAGCACCAGCCTTGACCACGCCCTGGAGAGGAC
CTACCAGCTGTTGGTACAGGTCAAGGACATGGGTGACCAGGCCTCAGGCCACCAGGCCACTG
CCACCGTGGAAGTCTCCATCATAGAGAGCACCTGGGTGTCCCTAGAGCCTATCCACCTGGCA
GAGAATCTCAAAGTCCTATACCCGCACCACATGGCCCAGGTACACTGGAGTGGGGGTGATGT
GCACTATCACCTGGAGAGCCATCCCCCGGGACCCTTTGAAGTGAATGCAGAGGGAAACCTCT
ACGTGACCAGAGAGCTGGACAGAGAAGCCCAGGCTGAGTACCTGCTCCAGGTGCGGGCTCAG
AATTCCCATGGCGAGGACTATGCGGCCCCTCTGGAGCTGCACGTGCTGGTGATGGATGAGAA
TGACAACGTGCCTATCTGCCCTCCCCGTGACCCCACAGTCAGCATCCCTGAGCTCAGTCCAC
CAGGTACTGAAGTGACTAGACTGTCAGCAGAGGATGCAGATGCCCCCGGCTCCCCCAATTCC
CACGTTGTGTATCAGCTCCTGAGCCCTGAGCCTGAGGATGGGGTAGAGGGGAGAGCCTTCCA
GGTGGACCCCACTTCAGGCAGTGTGACGCTGGGGGTGCTCCCACTCCGAGCAGGCCAGAACA
TCCTGCTTCTGGTGCTGGCCATGGACCTGGCAGGCGCAGAGGGTGGCTTCAGCAGCACGTGT
GAAGTCGAAGTCGCAGTCACAGATATCAATGATCACGCCCCTGAGTTCATCACTTCCCAGAT
TGGGCCTATAAGCCTCCCTGAGGATGTGGAGCCCGGGACTCTGGTGGCCATGCTAACAGCCA
TTGATGCTGACCTCGAGCCCGCCTTCCGCCTCATGGATTTTGCCATTGAGAGGGGAGACACA
GAAGGGACTTTTGGCCTGGATTGGGAGCCAGACTCTGGGCATGTTAGACTCAGACTCTGCAA
GAACCTCAGTTATGAGGCAGCTCCAAGTCATGAGGTGGTGGTGGTGGTGCAGAGTGTGGCGA
AGCTGGTGGGGCCAGGCCCAGGCCCTGGAGCCACCGCCACGGTGACTGTGCTAGTGGAGAGA
GTGATGCCACCCCCCAAGTTGGACCAGGAGAGCTACGAGGCCAGTGTCCCCATCAGTGCCCC
AGCCGGCTCTTTCCTGCTGACCATCCAGCCCTCCGACCCCATCAGCCGAACCCTCAGGTTCT
CCCTAGTCAATGACTCAGAGGGCTGGCTCTGCATTGAGAAATTCTCCGGGGAGGTGCACACC
GCCCAGTCCCTGCAGGGCGCCCAGCCTGGGGACACCTACACGGTGCTTGTGGAGGCCCAGGA
TACAGCCCTGACTCTTGCCCCTGTGCCCTCCCAATACCTCTGCACACCCCGCCAAGACCATG
GCTTGATCGTGAGTGGACCCACCAAGGACCCCGATCTGGCCAGTGGGCACGGTCCCTACAGC
TTCACCCTTGGTCCCAACCCCACGGTGCAACGGGATTGGCGCCTCCAGACTCTCAATGGTTC
CCATGCCTACCTCACCTTGGCCCTGCATTGGGTGGAGCCACGTGAACACATAATCCCCGTGG
TGGTCAGCCACAATGCCCAGATGTGGCAGCTCCTGGTTCCAGTGATCGTGTGTCGCTGCAAC
GTGGAGGGGCAGTGCATGCGCAAGGTGGGCCGCATGAAGGGCATGCCCACGAAGCTGTCGGC
AGTGGGCATCCTTGTAGGCACCCTGGTAGCAATAGGAATCTTCCTCATCCTCATTTTCACCC
ACTGGACCATGTCAAGGAAGAAGGACCCGGATCAACCAGCAGACAGCGTGCCCCTGAAGGCG
ACTGTCTGAATGGCCCAGGCAGCTCTAGCTGGGAGCTTGGCCTCTGGCTCCATCTGAGTCCC
CTGGGAGAGAGCCCAGCACCCAAGATCCAGCAGGGGACAGGACAGAGTAGAAGCCCCTCCAT
CTGCCCTGGGGTGGAGGCACCATCACCATCACCAGGCATGTCTGCAGAGCCTGGACACCAAC
TTTATGGACTGCCCATGGGAGTGCTCCAAATGTCAGGGTGTTTGCCCAATAATAAAGCCCCA
GAGAACTGGGCTGGGCCCTATGGGAAAAAAAAAAAAAAAAAAAAAAAAAAAAAAAAAAAAG

FIGURE 188

MVPAWLWLLCVSVPQALPKAQPAELSVEVPENYGGNFPLYLTKLPLPREGAEGQIVLSGDSG
KATEGPFAMDPDSGFLLVTRALDREEQAEYQLQVTLEMQDGHVLWGPQPVLVHVKDENDQVP
HFSQAIYRARLSRGTRPGIPFLFLEASDRDEPGTANSDLRFHILSQAPAQPSPDMFQLEPRL
GALALSPKGSTSLDHALERTYQLLVQVKDMGDQASGHQATATVEVSIIESTWVSLEPIHLAE
NLKVLYPHHMAQVHWSGGDVHYHLESHPPGPFEVNAEGNLYVTRELDREAQAEYLLQVRAQN
SHGEDYAAPLELHVLVMDENDNVPICPPRDPTVSIPELSPPGTEVTRLSAEDADAPGSPNSH
VVYQLLSPEPEDGVEGRAFQVDPTSGSVTLGVLPLRAGQNILLLVLAMDLAGAEGGFSSTCE
VEVAVTDINDHAPEFITSQIGPISLPEDVEPGTLVAMLTAIDADLEPAFRLMDFAIERGDTE
GTFGLDWEPDSGHVRLRLCKNLSYEAAPSHEVVVVVQSVAKLVGPGPGPGATATVTVLVERV
MPPPKLDQESYEASVPISAPAGSFLLTIQPSDPISRTLRFSLVNDSEGWLCIEKFSGEVHTA
QSLQGAQPGDTYTVLVEAQDTALTLAPVPSQYLCTPRQDHGLIVSGPSKDPDLASGHGPYSF
TLGPNPTVQRDWRLQTLNGSHAYLTLALHWVEPREHIIPVVVSHNAQMWQLLVRVIVCRCNV
EGQCMRKVGRMKGMPTKLSAVGILVGTLVAIGIFLILIFTHWTMSRKKDPDQPADSVPLKATV

Signal peptide:
amino acids 1-18

Transmembrane domain:
amino acids 762-784

FIGURE 189

GACTTTGCTTGAATGTTTACATTTTCTGCTCGCTGTCCTACATATCACAATATAGTGTTCACGTTTTGTTAAAA
CTTTGGGGTGTCAGGAGTTGAGCTTGCTCAGCAAGCCAGCATGGCTAGGATGAGCTTTGTTATAGCAGCTTGCC
AATTGGTGCTGGGCCTACTAATGACTTCATTAACCGAGTCTTCCATACAGAATAGTGAGTGTCCACAACTTTGC
GTATGTGAAATTCGTCCCTGGTTTACCCCACAGTCAACTTACAGAGAAGCCACCACTGTTGATTGCAATGACCT
CCGCTTAACAAGGATTCCCAGTAACCTCTCTAGTGACACACAAGTGCTTCTCTTACAGAGCAATAACATCGCGA
AGACTGTGGATGAGCTGCAGCAGCTTTTCAACTTGACTGAACTAGATTTCTCCCAAAACAACTTTACTAACATT
AAGGAGGTCGGGCTGGCAAACCTAACCCAGCTCACAACGCTGCATTTGGAGGAAAATCAGATTACCGAGATGAC
TGATTACTGTCTACAAGACCTCAGCAACCTTCAAGAACTCTACATCAACCACAACCAAATTAGCACTATTTCTG
CTCATGCTTTTGCAGGCTTAAAAAATCTATTAAGGCTCCACCTGAACTCCAACAAATTGAAAGTTATTGATAGT
CGCTGGTTTGATTCTACACCCAACCTGGAAATTCTCATGATCGGAGAAAACCCTGTGATTGGAATTCTGGATAT
GAACTTCAAACCCCTCGCAAATTTGAGAAGCTTAGTTTTGGCAGGAATGTATCTCACTGATATTCCTGGAAATG
CTTTGGTGGGTCTGGATAGCCTTGAGAGCCTGTCTTTTTATGATAACAAACTGGTTAAAGTCCCTCAACTTGCC
CTGCAAAAAGTTCCAAATTTGAAATTCTTAGACCTCAACAAAAACCCCATTCACAAAATCCAAGAAGGGGACTT
CAAAAATATGCTTCGGTTAAAAGAACTGGGAATCAACAATATGGGCGAGCTCGTTTCTGTCGACCGCTATGCCC
TGGATAACTTGCCTGAACTCACAAAGCTGGAAGCCACCAATAACCCTAAACTCTCTTACATCCACCGCTTGGCT
TTCCGAAGTGTCCCTGCTCTGGAAAGCTTGATGCTGAACAACAATGCCTTGAATGCCATTTACCAAAAGACAGT
CGAATCCCTCCCCAATCTGCGTGAGATCAGTATCCATAGCAATCCCCTCAGGTGTGACTGTGTGATCCACTGGA
TTAACTCCAACAAAACCAACATCCGCTTCATGGAGCCCCTGTCCATGTTCTGTGCCATGCCGCCCGAATATAAA
GGGCACCAGGTGAAGGAAGTTTTAATCCAGGATTCGAGTGAACAGTGCCTCCCAATGATATCTCACGACAGCTT
CCCAAATCGTTTAAACGTGGATATCGGCACGACGGTTTTCCTAGACTGTCGAGCCATGGCTGAGCCAGAACCTG
AAATTTACTGGGTCACTCCCATTGGAAATAAGATAACTGTGGAAACCCTTTCAGATAAATACAAGCTAAGTAGC
GAAGGTACCTTGGAAATATCTAACATACAAATTGAAGACTCAGGAAGATACACATGTGTTGCCCAGAATGTCCA
AGGGGCAGACACTCGGGTGGCAACAATTAAGGTTAACGGGACCCTTCTGGATGGTACCCAGGTGCTAAAAATAT
ACGTCAAGCAGACAGAATCCCATTCCATCTTAGTGTCCTGGAAAGTTAATTCCAATGTCATGACGTCAAACTTA
AAATGGTCGTCTGCCACCATGAAGATTGATAACCCTCACATAACATATACTGCCAGGGTCCCAGTCGATGTCCA
TGAATACAACCTAACGCATCTGCAGCCTTCCACAGATTATGAAGTGTGTCTCACAGTGTCCAATATTCATCAGC
AGACTCAAAAGTCATGCGTAAATGTCACAACCAAAAATGCCGCCTTCGCAGTGGACATCTCTGATCAAGAAACC
AGTACAGCCCTTGCTGCAGTAATGGGGTCTATGTTTGCCGTCATTAGCCTTGCGTCCATTGCTGTGTACTTTGC
CAAAAGATTTAAGAGAAAAAACTACCACCACTCATTAAAAAAGTATATGCAAAAAACCTCTTCAATCCCACTAA
ATGAGCTGTACCCACCACTCATTAACCTCTGGGAAGGTGACAGCGAGAAAGACAAAGATGGTTCTGCAGACACC
AAGCCAACCCAGGTCGACACATCCAGAAGCTATTACATGTGGTAACTCAGAGGATATTTTGCTTCTGGTAGTAA
GGAGCACAAAGACGTTTTTGCTTTATTCTGCAAAAGTGAACAAGTTGAAGACTTTTGTATTTTTGACTTTGCTA
GTTTGTGGCAGAGTGGAGAGGACGGGTGGATATTTCAAATTTTTTTAGTATAGCGTATCGCAAGGGTTTGACAC
GGCTGCCAGCGACTCTAGGCTTCCAGTCTGTGTTTGGTTTTTATTCTTATCATTATTATGATTGTTATTATATT
ATTATTTTATTTTAGTTGTTGTGCTAAACTCAATAATGCTGTTCTAACTACAGTGCTCAATAAAATGATTAATG
ACAGGAAAAAAAAAAAAAAAAAAAAAAAAAAAAAAAAAAAAAAAAAAAAAAAAAAAAAAAAAAAAAAAAAAAAA
AAAA

FIGURE 190

MARMSFVIAACQLVLGLLMTSLTESSIQNSECPQLCVCEIRPWFTPQSTYREATTVDCNDLRLTRIPSNLSSDT
QVLLLQSNNIAKTVDELQQLFNLTELDFSQNNFTNIKEVGLANLTQLTTLHLEENQITEMTDYCLQDLSNLQEL
YINHNQISTISAHAFAGLKNLLRLHLNSNKLKVIDSRWFDSTPNLEILMIGENPVIGILDMNFKPLANLRSLVL
AGMYLTDIPGNALVGLDSLESLSFYDNKLVKVPQLALQKVPNLKFLDLNKNPIHKIQEGDFKNMLRLKELGINN
MGELVSVDRYALDNLPELTKLEATNNPKLSYIHRLAFRSVPALESLMLNNNALNAIYQKTVESLPNLREISIHS
NPLRCDCVIHWINSNKTNIRFMEPLSMFCAMPPEYKGHQVKEVLIQDSSEQCLPMISHDSFPNRLNVDIGTTVF
LDCRAMAEPEPEIYWVTPIGNKITVETLSDKYKLSSEGTLEISNIQIEDSGRYTCVAQNVQGADTRVATIKVNG
TLLDGTQVLKIYVKQTESHSILVSWKVNSNVMTSNLKWSSATMKIDNPHITYTARVPVDVHEYNLTHLQPSTDY
EVCLTVSNIHQQTQKSCVNVTTKNAAFAVDISDQETSTALAAVMGSMFAVISLASIAVYFAKRFKRKNYHHSLK
KYMQKTSSIPLNELYPPLINLWEGDSEKDKDGSADTKPTQVDTSRSYYMW

Important features:
Signal peptide:

Amino acids 1-25

Transmembrane domain:

Amino acids 508-530

N-glycosylation sites:

Amino acids 69-73;96-100;106-110;117-121;385-389;517-521;
582-586;611-615

Tyrosine kinase phosphorylation site:

Amino acids 573-582

N-myristoylation sites:

Amino acids 16-22;224-230;464-470;637-643;698-704

FIGURE 191

GGGAGAGAGGATAAATAGCAGCGTGGCTTCCCTGGCTCCTCTCTGCATCCTTCCCGACCTTC
CCAGCAATATGCATCTTGCACGTCTGGTCGGCTCCTGCTCCCTCCTTCTGCTACTGGGGGCC
CTGTCTGGATGGGCGGCCAGCGATGACCCCATTGAGAAGGTCATTGAAGGGATCAACCGAGG
GCTGAGCAATGCAGAGAGAGAGGTGGGCAAGGCCCTGGATGGCATCAACAGTGGAATCACGC
ATGCCGGAAGGGAAGTGGAGAAGGTTTTCAACGGACTTAGCAACATGGGGAGCCACACCGGC
AAGGAGTTGGACAAAGGCGTCCAGGGGCTCAACCACGGCATGGACAAGGTTGCCCATGAGAT
CAACCATGGTATTGGACAAGCAGGAAAGGAAGCAGAGAAGCTTGGCCATGGGGTCAACAACG
CTGCTGGACAGGCCGGGAAGGAAGCAGACAAAGCGGTCCAAGGGTTCCACACTGGGGTCCAC
CAGGCTGGGAAGGAAGCAGAGAAACTTGGCCAAGGGGTCAACCATGCTGCTGACCAGGCTGG
AAAGGAAGTGGAGAAGCTTGGCCAAGGTGCCCACCATGCTGCTGGCCAGGCCGGGAAGGAGC
TGCAGAATGCTCATAATGGGGTCAACCAAGCCAGCAAGGAGGCCAACCAGCTGCTGAATGGC
AACCATCAAAGCGGATCTTCCAGCCATCAAGGAGGGGCCACAACCACGCCGTTAGCCTCTGG
GGCCTCAGTCAACACGCCTTTCATCAACCTTCCCGCCCTGTGGAGGAGCGTCGCCAACATCA
TGCCCTAAACTGGCATCCGGCCTTGCTGGGAGAATAATGTCGCCGTTGTCACATCAGCTGAC
ATGACCTGGAGGGGTTGGGGGTGGGGGACAGGTTTCTGAAATCCCTGAAGGGGGTTGTACTG
GGATTTGTGAATAAACTTGATACACCA

FIGURE 192

></usr/seqdb2/sst/DNA/Dnaseqs.min/ss.DNA66675
><subunit 1 of 1, 247 aa, 1 stop
><MW: 25335, pI: 7.00, NX(S/T): 0
MHLARLVGSCSLLLLLGALSGWAASDDPIEKVIEGINRGLSNAEREVGKALDGINSGITHAG
REVEKVFNGLSNMGSHTGKELDKGVQGLNHGMDKVAHEINHGIGQAGKEAEKLGHGVNNAAG
QAGKEADKAVQGFHTGVHQAGKEAEKLGQGVNHAADQAGKEVEKLGQGAHHAAGQAGKELQN
AHNGVNQASKEANQLLNGNHQSGSSSHQGGATTTPLASGASVNTPFINLPALWRSVANIMP

Important features of the protein:
Signal peptide:
amino acids 1-25

Homologous region to circumsporozoite (CS) repeats:
amino acids 35-225

FIGURE 193

GAAGTAGAGGTGTTGTGCTGAGCGGCGCTCGGCGAACTGTGTGGACCGTCTGCTGGGACTCC
GGCCCTGCGTCCGCTCAGCCCCGTGGCCCCGCGCACCTACTGCCATGGAGACGCGGCCTCGT
CTCGGGGCCACCTGTTTGCTGGGCTTCAGTTTCCTGCTCCTCGTCATCTCTTCTGATGGACA
TAATGGGCTTGGAAAGGGTTTTGGAGATCATATTCATTGGAGGACACTGGAAGATGGGAAGA
AAGAAGCAGCTGCCAGTGGACTGCCCCTGATGGTGATTATTCATAAATCCTGGTGTGGAGCT
TGCAAAGCTCTAAAGCCCAAATTTGCAGAATCTACGGAAATTTCAGAACTCTCCCATAATTT
TGTTATGGTAAATCTTGAGGATGAAGAGGAACCCAAAGATGAAGATTTCAGCCCTGACGGGG
GTTATATTCCACGAATCCTTTTTCTGGATCCCAGTGGCAAGGTGCATCCTGAAATCATCAAT
GAGAATGGAAACCCCAGCTACAAGTATTTTTATGTCAGTGCCGAGCAAGTTGTTCAGGGGAT
GAAGGAAGCTCAGGAAAGGCTGACGGGTGATGCCTTCAGAAAGAAACATCTTGAAGATGAAT
TGTAACATGAATGTGCCCCTTCTTTCATCAGAGTTAGTGTTCTGGAAGGAAAGCAGCAGGGA
AGGGAATATTGAGGAATCATCTAGAACAATTAAGCCGACCAGGAAACCTCATTCCTACCTAC
ACTGGAAGGAGCGCTCTCACTGTGGAAGAGTTCTGCTAACAGAAGCTGGTCTGCATGTTTGT
GGATCCAGCGGAGAGTGGCAGACTTTCTTCTCCTTTTCCCTCTCACCTAAATGTCAACTTGT
CATTGAATGTAAAGAATGAAACCTTCTGACACAAAA

FIGURE 194

></usr/seqdb2/sst/DNA/Dnaseqs.min/ss.DNA67300
><subunit 1 of 1, 172 aa, 1 stop
><MW: 19206, pI: 5.36, NX(S/T): 1
METRPRLGATCLLGFSFLLLVISSDGHNGLGKGFGDHIHWRTLEDGKKEAAASGLPLMVI
IHKSWCGACKALKPKFAESTEISELSHNFVMVNLEDEEEPKDEDFSPDGGYIPRILFLDP
SGKVHPEIINENGNPSYKYFYVSAEQVVQGMKEAQERLTGDAFRKKHLEDEL

Important features of the protein:
Signal peptide:
Amino acids 1-23

Thioredoxin family proteins:
Amino acids 58-75

N-myristoylation sites:
Amino acids 29-35;67-73;150-156

Amidation site:
Amino acid 45-49

FIGURE 195

CGGCTCGAGTGCAGCTGTGGGGAGATTTCAGTGCATTGCCTCCCCTGGGTGCTCTTCATCTTGGATTTGAAAGT
TGAGAGCAGCATGTTTTGCCCACTGAAACTCATCCTGCTGCCAGTGTTACTGGATTATTCCTTGGGCCTGAATG
ACTTGAATGTTTCCCCGCCTGAGCTAACAGTCCATGTGGGTGATTCAGCTCTGATGGGATGTGTTTTCCAGAGC
ACAGAAGACAAATGTATATTCAAGATAGACTGGACTCTGTCACCAGGAGAGCACGCCAAGGACGAATATGTGCT
ATACTATTACTCCAATCTCAGTGTGCCTATTGGGCGCTTCCAGAACCGCGTACACTTGATGGGGGACATCTTAT
GCAATGATGGCTCTCTCCTGCTCCAAGATGTGCAAGAGGCTGACCAGGGAACCTATATCTGTGAAATCCGCCTC
AAAGGGGAGAGCCAGGTGTTCAAGAAGGCGGTGGTACTGCATGTGCTTCCAGAGGAGCCCAAAGAGCTCATGGT
CCATGTGGGTGGATTGATTCAGATGGGATGTGTTTTCCAGAGCACAGAAGTGAAACACGTGACCAAGGTAGAAT
GGATATTTTCAGGACGGCGCGCAAAGGAGGAGATTGTATTTCGTTACTACCACAAACTCAGGATGTCTGTGGAG
TACTCCCAGAGCTGGGGCCACTTCCAGAATCGTGTGAACCTGGTGGGGGACATTTTCCGCAATGACGGTTCCAT
CATGCTTCAAGGAGTGAGGGAGTCAGATGGAGGAAACTACACCTGCAGTATCCACCTAGGGAACCTGGTGTTCA
AGAAAACCATTGTGCTGCATGTCAGCCCGGAAGAGCCTCGAACACTGGTGACCCCGGCAGCCCTGAGGCCTCTG
GTCTTGGGTGGTAATCAGTTGGTGATCATTGTGGGAATTGTCTGTGCCACAATCCTGCTGCTCCCTGTTCTGAT
ATTGATCGTGAAGAAGACCTGTGGAAATAAGAGTTCAGTGAATTCTACAGTCTTGGTGAAGAACACGAAGAAGA
CTAATCCAGAGATAAAAGAAAAACCCTGCCATTTTGAAAGATGTGAAGGGGAGAAACACATTTACTCCCCAATA
ATTGTACGGGAGGTGATCGAGGAAGAAGAACCAAGTGAAAAATCAGAGGCCACCTACATGACCATGCACCCAGT
TTGGCCTTCTCTGAGGTCAGATCGGAACAACTCACTTGAAAAAAAGTCAGGTGGGGGAATGCCAAAAACACAGC
AAGCCTTTTGAGAAGAATGGAGAGTCCCTTCATCTCAGCAGCGGTGGAGACTCTCTCCTGTGTGTGTCCTGGGC
CACTCTACCAGTGATTTCAGACTCCCGCTCTCCCAGCTGTCCTCCTGTCTCATTGTTTGGTCAATACACTGAAG
ATGGAGAATTTGGAGCCTGGCAGAGAGACTGGACAGCTCTGGAGGAACAGGCCTGCTGAGGGGAGGGGAGCATG
GACTTGGCCTCTGGAGTGGGACACTGGCCCTGGGAACCAGGCTGAGCTGAGTGGCCTCAAACCCCCCGTTGGAT
CAGACCCTCCTGTGGGCAGGGTTCTTAGTGGATGAGTTACTGGGAAGAATCAGAGATAAAAACCAACCCAAATCAA

FIGURE 196

MFCPLKLILLPVLLDYSLGLNDLNVSPPELTVHVGDSALMGCVFQSTEDKCIFKIDWTLSPGEHAKDEYVLYYY
SNLSVPIGRFQNRVHLMGDILCNDGSLLLQDVQEADQGTYICEIRLKGESQVFKKAVVLHVLPEEPKELMVHVG
GLIQMGCVFQSTEVKHVTKVEWIFSGRRAKEEIVFRYYHKLRMSVEYSQSWGHFQNRVNLVGDIFRNDGSIMLQ
GVRESDGGNYTCSIHLGNLVFKKTIVLHVSPEEPRTLVTPAALRPLVLGGNQLVIIVGIVCATILLLPVLILIV
KKTCGNKSSVNSTVLVKNTKKTNPEIKEKPCHFERCEGEKHIYSPIIVREVIEEEEPSEKSEATYMTMHPVWPS
LRSDRNNSLEKKSGGGMPKTQQAF

FIGURE 197

CGCCATGGCCGGGCTATCCCGCGGGTCCGCGCGCGCACTGCTCGCCGCCCTGCTGGCGTCGACG
CTGTTGGCGCTGCTCGTGTCGCCCGCGCGGGGTCGCGGCGGCCGGGACCACGGGGACTGGGA
CGAGGCCTCCCGGCTGCCGCCGCTACCACCCCGCGAGGACGCGGCGCGCGTGGCCCGCTTCG
TGACGCACGTCTCCGACTGGGGCGCTCTGGCCACCATCTCCACGCTGGAGGCGGTGCGCGGC
CGGCCCTTCGCCGACGTCCTCTCGCTCAGCGACGGGCCCCCGGGCGCGGGCAGCGGCGTGCC
CTATTTCTACCTGAGCCCGCTGCAGCTCTCCGTGAGCAACCTGCAGGAGAATCCATATGCTA
CACTGACCATGACTTTGGCACAGACCAACTTCTGCAAGAAACATGGATTTGATCCACAAAGT
CCCCTTTGTGTTCACATAATGCTGTCAGGAACTGTGACCAAGGTGAATGAAACAGAAATGGA
TATTGCAAAGCATTCGTTATTCATTCGACACCCTGAGATGAAAACCTGGCCTTCCAGCCATA
ATTGGTTCTTTGCTAAGTTGAATATAACCAATATCTGGGTCCTGGACTACTTTGGTGGACCA
AAAATCGTGACACCAGAAGAATATTATAATGTCACAGTTCAGTGAAGCAGACTGTGGTGAAT
TTAGCAACACTTATGAAGTTTCTTAAAGTGGCTCATACACACTTAAAAGGCTTAATGTTTCT
CTGGAAAGCGTCCCAGAATATTAGCCAGTTTTCTGTC

FIGURE 198

></usr/seqdb2/sst/DNA/Dnaseqs.min/ss.DNA71269
><subunit 1 of 1, 220 aa, 1 stop
><MW: 24075, pI: 7.67, NX(S/T): 3
MAGLSRGSARALLAALLASTLLALLVSPARGRGGRDHGDWDEASRLPPLPPREDAARVAR
FVTHVSDWGALATISTLEAVRGRPFADVLSLSDGPPGAGSGVPYFYLSPLQLSVSNLQEN
PYATLTMTLAQTNFCKKHGFDPQSPLCVHIMLSGTVTKVNETEMDIAKHSLFIRHPEMKT
WPSSHNWFFAKLNITNIWVLDYFGGPKIVTPEEYYNVTVQ

Important features of the protein:
Transmembrane domain:
Amino acids
11-29

N-glycosylation sites:
Amino acids
160-164;193-197;216-220

N-myristoylation sites:
Amino acids
3-9;7-13;69-75;97-103

FIGURE 199

TCGCCATGGCCTCTGCCGGAATGCAGATCCTGGGAGTCGTCCTGACACTGCTGGGCTGGGTG
AATGGCCTGGTCTCCTGTGCCCTGCCCATGTGGAAGGTGACCGCTTTCATCGGCAACAGCAT
CGTGGTGGCCCAGGTGGTGTGGGAGGGCCTGTGGATGTCCTGCGTGGTGCAGAGCACCGGCC
AGATGCAGTGCAAGGTGTACGACTCACTGCTGGCGCTGCCACAGGACCTGCAGGCTGCACGT
GCCCTCTGTGTCATCGCCCTCCTTGTGGCCCTGTTCGGCTTGCTGGTCTACCTTGCTGGGGC
CAAGTGTACCACCTGTGTGGAGGAGAAGGATTCCAAGGCCCGCCTGGTGCTCACCTCTGGGA
TTGTCTTTGTCATCTCAGGGGTCCTGACGCTAATCCCCGTGTGCTGGACGGCGCATGCCATC
ATCCGGGACTTCTATAACCCCCTGGTGGCTGAGGCCCAAAAGCGGGAGCTGGGGGCCTCCCT
CTACTTGGGCTGGGCGGCCTCAGGCCTTTTGTTGCTGGGTGGGGGGTTGCTGTGCTGCACTT
GCCCCTCGGGGGGGTCCCAGGGCCCCAGCCATTACATGGCCCGCTACTCAACATCTGCCCCT
GCCATCTCTCGGGGGCCCTCTGAGTACCCTACCAAGAATTACGTCTGACGTGGAGGGGAATG
GGGGCTCCGCTGGCGCTAGAGCCATCCAGAAGTGGCAGTGCCCAACAGCTTTGGGATGGGTT
CGTACCTTTTGTTTCTGCCTCCTGCTATTTTTCTTTTGACTGAGGATATTTAAAATTCATTT
GAAAACTGAGCCAAGGTGTTGACTCAGACTCTCACTTAGGCTCTGCTGTTTCTCACCCTTGG
ATGATGGAGCCAAAGAGGGGATGCTTTGAGATTCTGGATCTTGACATGCCCATCTTAGAAGC
CAGTCAAGCTATGGAACTAATGCGGAGGCTGCTTGCTGTGCTGGCTTTGCAACAAGACAGAC
TGTCCCCAAGAGTTCCTGCTGCTGCTGGGGGCTGGGCTTCCCTAGATGTCACTGGACAGCTG
CCCCCCATCCTACTCAGGTCTCTGGAGCTCCTCTCTTCACCCCTGGAAAAACAAATCATCTG
TTAACAAAGGACTGCCCACCTCCGGAACTTCTGACCTCTGTTTCCTCCGTCCTGATAAGACG
TCCACCCCCCAGGGCCAGGTCCCAGCTATGTAGACCCCCGCCCCCACCTCCAACACTGCACC
CTTCTGCCCTGCCCCCCTCGTCTCACCCCCTTTACACTCACATTTTTATCAAATAAAGCATG
TTTTGTTAGTGCA

FIGURE 200

></usr/seqdb2/sst/DNA/Dnaseqs.min/ss.DNA73736
><subunit 1 of 1, 220 aa, 1 stop
><MW: 23292, pI: 8.43, NX(S/T): 0
MASAGMQILGVVLTLLGWVNGLVSCALPMWKVTAFIGNSIVVAQVVWEGLWMSCVVQSTGQM
QCKVYDSLLALPQDLQAARALCVIALLVALFGLLVYLAGAKCTTCVEEKDSKARLVLTSGIV
FVISGVLTLIPVCWTAHAIIRDFYNPLVAEAQKRELGASLYLGWAASGLLLLGGGLLCCTCP
SGGSQGPSHYMARYSTSAPAISRGPSEYPTKNYV

Transmembrane domains:
amino acids 8-30 (type II), 82-102, 121-140, 166-186

FIGURE 201

AGTGACAATCTCAGAGCAGCTTCTACACCACAGCCATTTCCAGCATGAAGATCACTGGGGGTCTCCTTCTGCTC
TGTACAGTGGTCTATTTCTGTAGCAGCTCAGAAGCTGCTAGTCTGTCTCCAAAAAAAGTGGACTGCAGCATTTA
CAAGAAGTATCCAGTGGTGGCCATCCCCTGCCCCATCACATACCTACCAGTTTGTGGTTCTGACTACATCACCT
ATGGGAATGAATGTCACTTGTGTACCGAGAGCTTGAAAAGTAATGGAAGAGTTCAGTTTCTTCACGATGGAAGT
TGCTAAATTCTCCATGGACATAGAGAGAAAGGAATGATATTCTCATCATCATCTTCATCATCCCAGGCTCTGAC
TGAGTTTCTTTCAGTTTTACTGATGTTCTGGGTGGGGGACAGAGCCAGATTCAGAGTAATCTTGACTGAATGGA
GAAAGTTTCTGTGCTACCCCTACAAACCCATGCCTCACTGACAGACCAGCATTTTTTTTTTAACACGTCAATAA
AAAAATAATCTCCCAGA

FIGURE 202

MKITGGLLLLCTVVYFCSSSEAASLSPKKVDCSIYKKYPVVAIPCPITYLPVCGSDYITYGNECHLCTESLKSN
GRVQFLHDGSC

Important features:
Signal peptide:
amino acids 1-19

FIGURE 203

CGACGATGCTACGCGCGCCCGGCTGCCTCCTCCGGACCTCCGTAGCGCCTGCCGCGGCCCTGGCTGCGGCGCTG
CTCTCGTCGCTTGCGCGCTGCTCTCTTCTAGAGCCGAGGGACCCGGTGGCCTCGTCGCTCAGCCCCTATTTCGG
CACCAAGACTCGCTACGAGGATGTCAACCCCGTGCTATTGTCGGGCCCCGAGGCTCCGTGGCGGGACCCTGAGC
TGCTGGAGGGGACCTGCACCCCGGTGCAGCTGGTCGCCCTCATTCGCCACGGCACCCGCTACCCCACGGTCAAA
CAGATCCGCAAGCTGAGGCAGCTGCACGGGTTGCTGCAGGCCCGCGGGTCCAGGGATGGCGGGGCTAGTAGTAC
CGGCAGCCGCGACCTGGGTGCAGCGCTGGCCGACTGGCCTTTGTGGTACGCGGACTGGATGGACGGGCAGCTAG
TAGAGAAGGGACGGCAGGATATGCGACAGCTGGCGCTGCGTCTGGCCTCGCTCTTCCCGGCCCTTTTCAGCCGT
GAGAACTACGGCCGCCTGCGGCTCATCACCAGTTCCAAGCACCGCTGCATGGATAGCAGCGCCGCCTTCCTGCA
GGGGCTGTGGCAGCACTACCACCCTGGCTTGCCGCCGCCGGACGTCGCAGATATGGAGTTTGGACCTCCAACAG
TTAATGATAAACTAATGAGATTTTTTGATCACTGTGAGAAGTTTTTAACTGAAGTAGAAAAAAATGCTACAGCT
CTTTATCACGTGGAAGCCTTCAAAACTGGACCAGAAATGCAGAACATTTTAAAAAAAGTTGCAGCTACTTTGCA
AGTGCCAGTAAATGATTTAAATGCAGATTTAATTCAAGTAGCCTTTTTCACCTGTTCATTTGACCTGGCAATTA
AAGGTGTTAAATCTCCTTGGTGTGATGTTTTTGACATAGATGATGCAAAGGTATTAGAATATTTAAATGATCTG
AAACAATATTGGAAAAGAGGATATGGGTATACTATTAACAGTCGATCCAGCTGCACCTTGTTTCAGGATATCTT
TCAGCACTTGGACAAAGCAGTTGAACAGAAACAAAGGTCTCAGCCAATTTCTTCTCCAGTCATCCTCCAGTTTG
GTCATGCAGAGACTCTTCTTCCACTGCTTTCTCTCATGGGCTACTTCAAAGACAAGGAACCCCTAACAGCGTAC
AATTACAAAAAACAAATGCATCGGAAGTTCCGAAGTGGTCTCATTGTACCTTATGCCTCGAACCTGATATTTGT
GCTTTACCACTGTGAAAATGCTAAGACTCCTAAAGAACAATTCCGAGTGCAGATGTTATTAAATGAAAAGGTGT
TACCTTTGGCTTACTCACAAGAAACTGTTTCATTTTATGAAGATCTGAAGAACCACTACAAGGACATCCTTCAG
AGTTGTCAAACCAGTGAAGAATGTGAATTAGCAAGGGCTAACAGTACATCTGATGAACTATGAGTAACTGAAGA
ACATTTTTAATTCTTTAGGAATCTGCAATGAGTGATTACATGCTTGTAATAGGTAGGCAATTCCTTGATTACAG
GAAGCTTTTATATTACTTGAGTATTTCTGTCTTTTCACAGAAAAACATTGGGTTTCTCTCTGGGTTTGGACATG
AAATGTAAGAAAAGATTTTTCACTGGAGCAGCTCTCTTAAGGAGAAACAAATCTATTTAGAGAAACAGCTGGCC
CTGCAAATGTTTACAGAAATGAAATTCTTCCTACTTATATAAGAAATCTCACACTGAGATAGAATTGTGATTTC
ATAATAACACTTGAAAAGTGCTGGAGTAACAAAATATCTCAGTTGGACCATCCTTAACTTGATTGAACTGTCTA
GGAACTTTACAGATTGTTCTGCAGTTCTCTCTTCTTTTCCTCAGGTAGGACAGCTCTAGCATTTTCTTAATCAG
GAATATTGTGGTAAGCTGGGAGTATCACTCTGGAAGAAAGTAACATCTCCAGATGAGAATTTGAAACAAGAAAC
AGAGTGTTGTAAAAGGACACCTTCACTGAAGCAAGTCGGAAAGTACAATGAAAATAAATATTTTTGGTATTTAT
TTATGAAATATTTGAACATTTTTTCAATAATTCCTTTTTACTTCTAGGAAGTCTCAAAAGACCATCTTAAATTA
TTATATGTTTGGACAATTAGCAACAAGTCAGATAGTTAGAATCGAAGTTTTTCAAATCCATTGCTTAGCTAACT
TTTTCATTCTGTCACTTGGCTTCGATTTTTATATTTTCCTATTATATGAAATGTATCTTTTGGTTGTTTGATTT
TTCTTTCTTTCTTTGTAAATAGTTCTGAGTTCTGTCAAATGCCGTGAAAGTATTTGCTATAATAAAGAAAATTC
TTGTGACTTTAAAAAAAAA

FIGURE 204

MLRAPGCLLRTSVAPAAALAAALLSSLARCSLLEPRDPVASSLSPYFGTKTRYEDVNPVLLSGPEAPWRDPELL
EGTCTPVQLVALIRHGTRYPTVKQIRKLRQLHGLLQARGSRDGGASSTGSRDLGAALADWPLWYADWMDGQLVE
KGRQDMRQLALRLASLFPALFSRENYGRLRLITSSKHRCMDSSAAFLQGLWQHYHPGLPPPDVADMEFGPPTVN
DKLMRFFDHCEKFLTEVEKNATALYHVEAFKTGPEMQNILKKVAATLQVPVNDLNADLIQVAFFTCSFDLAIKG
VKSPWCDVFDIDDAKVLEYLNDLKQYWKRGYGYTINSRSSCTLFQDIFQHLDKAVEQKQRSQPISSPVILQFGH
AETLLPLLSLMGYFKDKEPLTAYNYKKQMHRKFRSGLIVPYASNLIFVLYHCENAKTPKEQFRVQMLLNEKVLP
LAYSQETVSFYEDLKNHYKDILQSCQTSEECELARANSTSDEL

Important features:

Signal sequence
amino acids 1-30

N-glycosylation sites.
amino acids 242-246, 481-485

N-myristoylation sites.
amino acids 107-113, 113-119, 117-123, 118-124, 128-134

Endoplasmic reticulum targeting sequence.
amino acids 484-489

FIGURE 205

GCGACGCGCGGCGGGGCGGCGAGAGGAAACGCGGCGCCGGGCCGGGCCCGGCCCTGGAGATG
GTCCCCGGCGCCGCGGGCTGGTGTTGTCTCGTGCTCTGGCTCCCCGCGTGCGTCGCGGCCCA
CGGCTTCCGTATCCATGATTATTTGTACTTTCAAGTGCTGAGTCCTGGGGACATTCGATACA
TCTTCACAGCCACACCTGCCAAGGACTTTGGTGGTATCTTTCACACAAGGTATGAGCAGATT
CACCTTGTCCCCGCTGAACCTCCAGAGGCCTGCGGGGAACTCAGCAACGGTTTCTTCATCCA
GGACCAGATTGCTCTGGTGGAGAGCGGGGGCTGCTCCTTCCTCTCCAAGACTCGGGTGGTCC
AGGAGCACGGCGGGCGGGCGGTGATCATCTCTGACAACGCAGTTGACAATGACAGCTTCTAC
GTGGAGATGATCCAGGACAGTACCCAGCGCACAGCTGACATCCCCGCCCTCTTCCTGCTCGG
CCGAGACGGCTACATGATCCGCCGCTCTCTGGAACAGCATGGGCTGCCATGGGCCATCATTT
CCATCCCAGTCAATGTCACCAGCATCCCCACCTTTGAGCTGCTGCAACCGCCCTGGACCTTC
TGGTAGAAGAGTTTGTCCCACATTCCAGCCATAAGTGACTCTGAGCTGGGAAGGGGAAACCC
AGGAATTTTGCTACTTGGAATTTGGAGATAGCATCTGGGGACAAGTGGAGCCAGGTAGAGGA
AAAGGGTTTGGGCGTTGCTAGGCTGAAAGGGAAGCCACACCACTGGCCTTCCCTTCCCCAGG
GCCCCCAAGGGTGTCTCATGCTACAAGAAGAGGCAAGAGACAGGCCCCAGGGCTTCTGGCTA
GAACCCGAAACAAAAGGAGCTGAAGGCAGGTGGCCTGAGAGCCATCTGTGACCTGTCACACT
CACCTGGCTCCAGCCTCCCCTACCCAGGGTCTCTGCACAGTGACCTTCACAGCAGTTGTTGG
AGTGGTTTAAAGAGCTGGTGTTTGGGGACTCAATAAACCCTCACTGACTTTTTAGCAATAAA
GCTTCTCATCAGGGTTGCAAAAAAAAAAAAAAAAAAAAAAAAAAA

FIGURE 206

></usr/seqdb2/sst/DNA/Dnaseqs.min/ss.DNA76532
><subunit 1 of 1, 188 aa, 1 stop
><MW: 21042, pI: 5.36, NX(S/T): 2
MVPGAAGWCCLVLWLPACVAAHGFRIHDYLYFQVLSPGDIRYIFTATPAKDFGGIFHTRYEQ
IHLVPAEPPEACGELSNGFFIQDQIALVERGGCSFLSKTRVVQEHGGRAVIISDNAVDNDSF
YVEMIQDSTQRTADIPALFLLGRDGYMIRRSLEQHGLPWAIISIPVNVTSIPTFELLQPPWTFW

Signal peptide:
amino acids 1-20

FIGURE 207

CTCGCTTCTTCCTTCTGGATGGGGGCCCAGGGGGCCCAGGAGAGTATAAAGGCGATGTGGAG
GGTGCCCGGCACAACCAGACGCCCAGTCACAGGCGAGAGCCCTGGGATGCACCGGCCAGAGG
CCATGCTGCTGCTGCTCACGCTTGCCCTCCTGGGGGGCCCCACCTGGGCAGGGAAGATGTAT
GGCCCTGGAGGAGGCAAGTATTTCAGCACCACTGAAGACTACGACCATGAAATCACAGGGCT
GCGGGTGTCTGTAGGTCTTCTCCTGGTGAAAAGTGTCCAGGTGAAACTTGGAGACTCCTGGG
ACGTGAAACTGGGAGCCTTAGGTGGGAATACCCAGGAAGTCACCCTGCAGCCAGGCGAATAC
ATCACAAAAGTCTTTGTCGCCTTCCAAGCTTTCCTCCGGGGTATGGTCATGTACACCAGCAA
GGACCGCTATTTCTATTTTGGGAAGCTTGATGGCCAGATCTCCTCTGCCTACCCCAGCCAAG
AGGGGCAGGTGCTGGTGGGCATCTATGGCCAGTATCAACTCCTTGGCATCAAGAGCATTGGC
TTTGAATGGAATTATCCACTAGAGGAGCCGACCACTGAGCCACCAGTTAATCTCACATACTC
AGCAAACTCACCCGTGGGTCGCTAGGGTGGGGTATGGGGCCATCCGAGCTGAGGCCATCTGT
GTGGTGGTGGCTGATGGTACTGGAGTAACTGAGTCGGGACGCTGAATCTGAATCCACCAATA
AATAAAGCTTCTGCAGAAAA

FIGURE 208

></usr/seqdb2/sst/DNA/Dnaseqs.min/ss.DNA76541
><subunit 1 of 1, 178 aa, 1 stop
><MW: 19600, pI: 5.89, NX(S/T): 1
MHRPEAMLLLLTLALLGGPTWAGKMYGPGGGKYFSTTEDYDHEITGLRVSVGLLLVKSVQVK
LGDSWDVKLGALGGNTQEVTLQPGEYITKVFVAFQAFLRGMVMYTSKDRYFYFGKLDGQISS
AYPSQEGQVLVGIYGQYQLLGIKSIGFEWNYPLEEPTTEPPVNLTYSANSPVGR

Signal peptide:
amino acids 1-22

FIGURE 209

GGAGAATGGAGAGAGCAGTGAGAGTGGAGTCCGGGGTCCTGGTCGGGGTGGTCTGTCTGCTCCTGGCATGCCCT
GCCACAGCCACTGGGCCCGAAGTTGCTCAGCCTGAAGTAGACACCACCCTGGGTCGTGTGCGAGGCCGGCAGGT
GGGCGTGAAGGGCACAGACCGCCTTGTGAATGTCTTTCTGGGCATTCCATTTGCCCAGCCGCCACTGGGCCCTG
ACCGGTTCTCAGCCCCACACCCAGCACAGCCCTGGGAGGGTGTGCGGGATGCCAGCACTGCGCCCCCAATGTGC
CTACAAGACGTGGAGAGCATGAACAGCAGCAGATTTGTCCTCAACGGAAAACAGCAGATCTTCTCCGTTTCAGA
GGACTGCCTGGTCCTCAACGTCTATAGCCCAGCTGAGGTCCCCGCAGGGTCCGGTAGGCCGGTCATGGTATGGG
TCCATGGAGGCGCTCTGATAACTGGCGCTGCCACCTCCTACGATGGATCAGCTCTGGCTGCCTATGGGGATGTG
GTCGTGGTTACAGTCCAGTACCGCCTTGGGGTCCTTGGCTTCTTCAGCACTCGAGATGAGCATGCACCTGGCAA
CCAGGGCTTCCTAGATGTGGTAGCTGCTTTGCGCTGGGTGCAAGAAAACATCGCCCCCTTCGGGGGTGACCTCA
ACTGTGTCACTGTCTTTGGTGGATCTGCCGGTGGGAGCATCATCTCTGGCCTGGTCCTGTCCCCAGTGGCTGCA
GGGCTGTTCCACAGAGCCATCACACAGAGTGGGGTCATCACCACCCCAGGGATCATCGACTCTCACCCTTGGCC
CCTAGCTCAGAAAATCGCAAACACCTTGGCCTGCAGCTCCAGCTCCCCGGCTGAGATGGTGCAGTGCCTTCAGC
AGAAAGAAGGAGAAGAGCTGGTCCTTAGCAAGAAGCTGAAAAATACTATCTATCCTCTCACCGTTGATGGCACT
GTCTTCCCCAAAAGCCCCAAGGAACTCCTGAAGGAGAAGCCCTTCCACTCTGTGCCCTTCCTCATGGGTGTCAA
CAACCATGAGTTCAGCTGGCTCATCCCCAGGGGCTGGGGTCTCCTGGATACAATGGAGCAGATGAGCCGGGAGG
ACATGCTGGCCATCTCAACACCCGTCTTGACCAGTCTGGATGTGCCCCCTGAGATGATGCCCACCGTCATAGAT
GAATACCTAGGAAGCAACTCGGACGCACAAGCCAAATGCCAGGCGTTCCAGGAATTCATGGGTGACGTATTCAT
CAATGTTCCCACCGTCAGTTTTTCAAGATACCTTCGAGATTCTGGAAGCCCTGTCTTTTTCTATGAGTTCCAGC
ATCGACCCAGTTCTTTTGCGAAGATCAAACCTGCCTGGGTGAAGGCTGATCATGGGGCCGAGGGTGCTTTTGTG
TTCGGAGGTCCCTTCCTCATGGACGAGAGCTCCCGCCTGGCCTTTCCAGAGGCCACAGAGGAGGAGAAGCAGCT
AAGCCTCACCATGATGGCCCAGTGGACCCACTTTGCCCGGACAGGGGACCCCAATAGCAAGGCTCTGCCTCCTT
GGCCCCAATTCAACCAGGCGGAACAATATCTGGAGATCAACCCAGTGCCACGGGCCGGACAGAAGTTCAGGGAG
GCCTGGATGCAGTTCTGGTCAGAGACGCTCCCCAGCAAGATACAACAGTGGCACCAGAAGCAGAAGAACAGGAA
GGCCCAGGAGGACCTCTGAGGCCAGGCCTGAACCTTCTTGGCTGGGGCAAACCACTCTTCAAGTGGTGGCAGAG
TCCCAGCACGGCAGCCCGCCTCTCCCCCTGCTGAGACTTTAATCTCCACCAGCCCTTAAAGTGTCGGCCGCTCT
GTGACTGGAGTTATGCTCTTTTGAAATGTCACAAGGCCGCCTCCCACCTCTGGGGCATTGTACAAGTTCTTCCC
TCTCCCTGAAGTGCCTTTCCTGCTTTCTTCGTGGTAGGTTCTAGCACATTCCTCTAGCTTCCTGGAGGACTCAC
TCCCCAGGAAGCCTTCCCTGCCTTCTCTGGGCCGTGCGGCCCCGAGTCTGCGTCCATTAGAGCACAGTCCACCC
GAGGCTAGCACCGTGTCTGTGTCTGTCTCCCCCTCAGAGGAGCTCTCTCAAAATGGGGATTAGCCTAACCCCAC
TCTGTCACCCACACCAGGATCGGGTGGGACCTGGAGCTAGGGGGTGTTTGCTGAGTGAGTGAGTGAAACACAGA
ATATGGGAATGGCAGCTGCTGAACTTGAACCCAGAGCCTTCAGGTGCCAAAGCCATACTCAGGCCCCCACCGAC
ATTGTCCACCCTGGCCAGAAGGGTGCATGCCAATGGCAGAGACCTGGGATGGGAGAAGTCCTGGGGCGCCAGGG
GATCCAGCCTAGAGCAGACCTTAGCCCCTGACTAAGGCCTCAGACTAGGGCGGGAGGGGTCTCCTCCTCTCTGC
TGCCCAGTCCTGGCCCCTGCACAAGACAACAGAATCCATCAGGGCCATGAGTGTCACCCAGACCTGACCCTCAC
CAATTCCAGCCCCTGACCCTCAGGACGCTGGATGCCAGCTCCCAGCCCCAGTGCCGGGTCCTCCCTCCCTTCCT
GGCTTGGGGAGACCAGTTTCTGGGGAGCTTCCAAGAGCACCCACCAAGACACAGCAGGACAGGCCAGGGGAGGG
CATCTGGACCAGGGCATCCGTCGGGCTATTGTCACAGAGAAAAGAAGAGACCCACCCACTCGGGCTGCAAAAGG
TGAAAAGCACCAAGAGGTTTTCAGATGGAAGTGAGAGGTGACAGTGTGCTGGCAGCCCTCACAGCCCTCGCTTG
CTCTCCCTGCCGCCTCTGCCTGGGCTCCCACTTTGGCAGCACTTGAGGAGCCCTTCAACCCGCCGCTGCACTGT
AGGAGCCCCTTTCTGGGCTGGCCAAGGCCGGAGCCAGCTCCCTCAGCTTGCGGGGAGGTGCGGAGGGAGAGGGG
CGGGCAGGAACCGGGGCTGCGCGCAGCGCTTGCGGGCCAGAGTGAGTTCCGGGTGGGCGTGGGCTCGGCGGGGC
CCCACTCAGAGCAGCTGGCCGGCCCCAGGCAGTGAGGGCCTTAGCACCTGGGCCAGCAGCTGCTGTGCTCGATT
TCTCGCTGGGCCTTAGCTGCCTCCCCGCGGGGCAGGGCTCGGGACCTGCAGCCCTCCATGCCTGACCCTCCCCC
CACCCCCCGTGGGCTCCTGTGCGGCCGGAGCCTCCCCAAGGAGCGCCGCCCCCTGCTCCACAGCGCCCAGTCCC
ATCGACCACCCAAGGGCTGAGGAGTGCGGGTGCACAGCGCGGGACTGGCAGGCAGCTCCACCTGCTGCCCCAGT
GCTGGATCCACTGGGTGAAGCCAGCTGGGCTCCTGAGTCTGGTGGGGACTTGGAGAACCTTTATGTCTAGCTAA
GGGATTGTAAATACACCGATGGGCACTCTGTATCTAGCTCAAGGTTTGTAAACACACCAATCAGCACCCTGTGT
CTAGCTCAGTGTTTGTGAATGCACCAATCCACACTCTGTATCTGGCTACTCTGGTGGGGACTTGGAGAACCTTT
GTGTCCACACTCTGTATCTAGCTAATCTAGTGGGGATGTGGAGAACCTTTGTGTCTAGCTCAGGGATCGTAAAC
GCACCAATCAGCACCCTGTCAAAACAGACCACTTGACTCTCTGTAAAATGGACCAATCAGCAGGATGTGGGTGG
GGCGAGACAAGAGAATAAAAGCAGGCTGCCTGAGCCAGCAGTGACAACCCCCCTCGGGTCCCCTCCCACGCCGT
GGAAGCTTTGTTCTTTCCCTCTTTGCAATAAATCTTGCTACTGCCCAAAA

FIGURE 210

MERAVRVESGVLVGVVCLLLACPATATGPEVAQPEVDTTLGRVRGRQVGVKGTDRLVNVFLGIPFAQPPLGPDR
FSAPHPAQPWEGVRDASTAPPMCLQDVESMNSSRFVLNGKQQIFSVSEDCLVLNVYSPAEVPAGSGRPVMVWVH
GGALITGAATSYDGSALAAYGDVVVVTVQYRLGVLGFFSTGDEHAPGNQGFLDVVAALRWVQENIAPFGGDLNC
VTVFGGSAGGSIISGLVLSPVAAGLFHRAITQSGVITTPGIIDSHPWPLAQKIANTLACSSSSPAEMVQCLQQK
EGEELVLSKKLKNTIYPLTVDGTVFPKSPKELLKEKPFHSVPFLMGVNNHEFSWLIPRGWGLLDTMEQMSREDM
LAISTPVLTSLDVPPEMMPTVIDEYLGSNSDAQAKCQAFQEFMGDVFINVPTVSFSRYLRDSGSPVFFYEFQHR
PSSFAKIKPAWVKADHGAEGAFVFGGPFLMDESSRLAFPEATEEEKQLSLTMMAQWTHFARTGDPNSKALPPWP
QFNQAEQYLEINPVPRAGQKFREAWMQFWSETLPSKIQQWHQKQKNRKAQEDL

Important features:
Signal peptide:
amino acids 1-27

Transmembrane domain:
amino acids 226-245

N-glycosylation site.
amino acids 105-109

N-myristoylation sites.
amino acids 10-16, 49-55, 62-68, 86-92, 150-156, 155-161, 162-168, 217-223, 227-233, 228-234, 232-238, 262-268, 357-363, 461-467

Prokaryotic membrane lipoprotein lipid attachment site.
amino acids 12-23

Carboxylesterases type-B serine active site.
amino acids 216-232

FIGURE 211

AACTTCTACATGGGCCTCCTGCTGCTGGTGCTCTTCCTCAGCCTCCTGCCGGTGGCCTACAC
CATCATGTCCCTCCCACCCTCCTTTGACTGCGGGCCGTTCAGGTGCAGAGTCTCAGTTGCCC
GGGAGCACCTCCCCTCCCGAGGCAGTCTGCTCAGAGGGCCTCGGCCCAGAATTCCAGTTCTG
GTTTCATGCCAGCCTGTAAAAGGCCATGGAACTTTGGGTGAATCACCGATGCCATTTAAGAG
GGTTTTCTGCCAGGATGGAAATGTTAGGTCGTTCTGTGTCTGCGCTGTTCATTTCAGTAGCC
ACCAGCCACCTGTGGCCGTTGAGTGCTTGAAATGAGGAACTGAGAAAATTAATTTCTCATGT
ATTTTTCTCATTTATTTATTAATTTTTAACTGATAGTTGTACATATTTGGGGGTACATGTGA
TATTTGGATACATGTATACAATATATAATGATCAAATCAGGGTAACTGGGATATCCATCACA
TCAAACATTTATTTTTTATTCTTTTTAGACAGAGTCTCACTCTGTCACCCAGGCTGGAGTGC
AGTGGTGCCATCTCAGCTTACTGCAACCTCTGCCTGCCAGGTTCAAGCGATTCTCATGCCTC
CACCTCCCAAGTAGCTGGGACTACAGGCATGCACCACAATGCCCAACTAATTTTTGTATTTT
TAGTAGAGACGGGGTTTTGCCATGTTGCCCAGGCTGGCCTTGAACTCCTGGCCTCAAACAAT
CCACTTGCCTCGGCCTCCCAAAGTGTTATGATTACAGGCGTGAGCCACCGTGCCTGGCCTAA
ACATTTATCTTTTCTTTGTGTTGGGAACTTTGAAATTATACAATGAATTATTGTTAACTGTC
ATCTCCCTGCTGTGCTATGGAACACTGGGACTTCTTCCCTCTATCTAACTGTATATTTGTAC
CAGTTAACCAACCGTACTTCATCCCCACTCCTCTCTATCCTTCCCAACCTCTGATCACCTCA
TTCTACTCTCTACCTCCATGAGATCCACTTTTTTAGCTCCCACATGTGAGTAAGAAAATGCA
ATATTTGTCTTTCTGTGCCTGGCTTATTTCACTTAACATAATGACTTCCTGTTCCATCCATG
TTGCTGCAAATGACAGGATTTCGTTCTTAATTTCAATTAAAATAACCACACATGGCAAAAA

FIGURE 212

MGLLLLVLFLSLLPVAYTIMSLPPSFDCGPFRCRVSVAREHLPSRGSLLRGPRPRIPVLVSC
QPVKGHGTLGESPMPFKRVFCQDGNVRSFCVCAVHFSSHQPPVAVECLK

Important features of the protein:
Signal peptide:
amino acids 1-18

N-myristoylation site.
amino acids 86-92

Zinc carboxypeptidases, zinc-binding region 2 signature.
amino acids 68-79

FIGURE 213

AGGGCCCGCGGGTGGAGAGAGCGACGCCCGAGGGGATGGCGGCAGCGTCCCGGAGCGCCTCT
GGCTGGGCGCTACTGCTGCTGGTGGCACTTTGGCAGCAGCGCGCGGCCGGCTCCGGCGTCTT
CCAGCTGCAGCTGCAGGAGTTCATCAACGAGCGCGGCGTACTGGCCAGTGGGCGGCCTTGCG
AGCCCGGCTGCCGGACTTTCTTCCGCGTCTGCCTTAAGCACTTCCAGGCGGTCGTCTCGCCC
GGACCCTGCACCTTCGGGACCGTCTCCACGCCGGTATTGGGCACCAACTCCTTCGCTGTCCG
GGACGACAGTAGCGGCGGGGGGCGCAACCCTCTCCAACTGCCCTTCAATTTCACCTGGCCGG
GTACCTTCTCGCTCATCATCGAAGCTTGGCACGCGCCAGGAGACGACCTGCGGCCAGAGGCC
TTGCCACCAGATGCACTCATCAGCAAGATCGCCATCCAGGGCTCCCTAGCTGTGGGTCAGAA
CTGGTTATTGGATGAGCAAACCAGCACCCTCACAAGGCTGCGCTACTCTTACCGGGTCATCT
GCAGTGACAACTACTATGGAGACAACTGCTCCCGCCTGTGCAAGAAGCGCAATGACCACTTC
GGCCACTATGTGTGCCAGCCAGATGGCAACTTGTCCTGCCTGCCCGGTTGGACTGGGGAATA
TTGCCAACAGCCTATCTGTCTTTCGGGCTGTCATGAACAGAATGGCTACTGCAGCAAGCCAG
CAGAGTGCCTCTGCCGCCCAGGCTGGCAGGGCCGGCTGTGTAACGAATGCATCCCCCACAAT
GGCTGTCGCCACGGCACCTGCAGCACTCCCTGGCAATGTACTTGTGATGAGGGCTGGGGAGG
CCTGTTTTGTGACCAAGATCTCAACTACTGCACCCACCACTCCCCATGCAAGAATGGGGCAA
CGTGCTCCAACAGTGGGCAGCGAAGCTACACCTGCACCTGTCGCCCAGGCTACACTGGTGTG
GACTGTGAGCTGGAGCTCAGCGAGTGTGACAGCAACCCCTGTCGCAATGGAGGCAGCTGTAA
GGACCAGGAGGATGGCTACCACTGCCTGTGTCCTCCGGGCTACTATGGCCTGCACTGTGAAC
ACAGCACCTTGAGCTGCGCCGACTCCCCCTGCTTCAATGGGGGCTCCTGCCGGGAGCGCAAC
CAGGGGGCCAACTATGCTTGTGAATGTCCCCCCAACTTCACCGGCTCCAACTGCGAGAAGAA
AGTGGACAGGTGCACCAGCAACCCCTGTGCCAACGGGGGACAGTGCCTGAACCGAGGTCCAA
GCCGCATGTGCCGCTGCCGTCCTGGATTCACGGGCACCTACTGTGAACTCCACGTCAGCGAC
TGTGCCCGTAACCCTTGCGCCCACGGTGGCACTTGCCATGACCTGGAGAATGGGCTCATGTG
CACCTGCCCTGCCGGCTTCTCTGGCCGACGCTGTGAGGTGCGGACATCCATCGATGCCTGTG
CCTCGAGTCCCTGCTTCAACAGGGCCACCTGCTACACCGACCTCTCCACAGACACCTTTGTG
TGCAACTGCCCTTATGGCTTTGTGGGCAGCCGCTGCGAGTTCCCCGTGGGCTTGCCGCCCAG
CTTCCCCTGGGTGGCCGTCTCGCTGGGTGTGGGGCTGGCAGTGCTGCTGGTACTGCTGGGCA
TGGTGGCAGTGGCTGTGCGGCAGCTGCGGCTTCGACGGCCGGACGACGGCAGCAGGGAAGCC
ATGAACAACTTGTCGGACTTCCAGAAGGACAACCTGATTCCTGCCGCCCAGCTTAAAAACAC
AAACCAGAAGAAGGAGCTGGAAGTGGACTGTGGCCTGGACAAGTCCAACTGTGGCAAACAGC
AAAACCACACATTGGACTATAATCTGGCCCCAGGGCCCCTGGGGCGGGGGACCATGCCAGGA
AAGTTTCCCCACAGTGACAAGAGCTTAGGAGAGAAGGCGCCACTGCGGTTACACAGTGAAAA
GCCAGAGTGTCGGATATCAGCGATATGCTCCCCCAGGGACTCCATGTACCAGTCTGTGTGTT
TGATATCAGAGGAGAGGAATGAATGTGTCATTGCCACGGAGGTATAAGGCAGGAGCCTACCT
GGACATCCCTGCTCAGCCCCGCGGCTGGACCTTCCTTCTGCATTGTTTACA

FIGURE 214

MAAASRSASGWALLLLVALWQQRAAGSGVFQLQLQEFINERGVLASGRPCEPGCRTFFRVCL
KHFQAVVSPGPCTFGTVSTPVLGTNSFAVRDDSSGGGRNPLQLPFNFTWPGTFSLIIEAWHA
PGDDLRPEALPPDALISKIAIQGSLAVGQNWLLDEQTSTLTRLRYSYRVICSDNYYGDNCSR
LCKKRNDHFGHYVCQPDGNLSCLPGWTGEYCQQPICLSGCHEQNGYCSKPAECLCRPGWQGR
LCNECIPHNGCRHGTCSTPWQCTCDEGWGGLFCDQDLNYCTHHSPCKNGATCSNSGQRSYTC
TCRPGYTGVDCELELSECDSNPCRNGGSCKDQEDGYHCLCPPGYYGLHCEHSTLSCADSPCF
NGGSCRERNQGANYACECPPNFTGSNCEKKVDRCTSNPCANGGQCLNRGPSRMCRCRPGFTG
TYCELHVSDCARNPCAHGGTCHDLENGLMCTCPAGFSGRRCEVRTSIDACASSPCFNRATCY
TDLSTDTFVCNCPYGFVGSRCEFPVGLPPSFPWVAVSLGVGLAVLLVLLGMVAVAVRQLRLR
RPDDGSREAMNNLSDFQKDNLIPAAQLKNTNQKKELEVDCGLDKSNCGKQQNHTLDYNLAPG
PLGRCTMPGKFPHSDKSLGEKAPLRLHSEKPECRISAICSPRDSMYQSVCLISEERNECVIA
TEV

Important features of the protein:
Signal peptide:
amino acids 1-26
Transmembrane domain:
amino acids 530-552
N-glycosylation sites.
amino acids 108-112, 183-187, 205-209, 393-397, 570-574, 610-614
Glycosaminoglycan attachment site.
amino acids 96-100
Tyrosine kinase phosphorylation site.
amino acids 340-347
N-myristoylation sites.
amino acids 42-48, 204-210, 258-264, 277-283, 297-303, 383-389, 415-421, 461-467, 522-528, 535-541, 563-569, 599-605, 625-631
Amidation site.
amino acids 471-475
Aspartic acid and asparagine hydroxylation site.
amino acids 339-351
EGF-like domain cysteine pattern signature.
amino acids 173-185, 206-218, 239-251, 270-282, 310-322, 348-360, 388-400, 426-438, 464-476, 506-518
Calcium-binding EGF-like:
amino acids 224-245, 255-276, 295-316, 333-354, 373-394, 411-432, 449-470

FIGURE 215

CGCGAGGCGCGGGGAGCCTGGGACCAGGAGCGAGAGCCGCCTACCTGCAGCCGCCGCCCACG
GCACGGCAGCCACCATGGCGCTCCTGCTGTGCTTCGTGCTCCTGTGCGGAGTAGTGGATTTC
GCCAGAAGTTTGAGTATCACTACTCCTGAAGAGATGATTGAAAAAGCCAAAGGGGAAACTGC
CTATCTGCCATGCAAATTTACGCTTAGTCCCGAAGACCAGGGACCGCTGGACATCGAGTGGC
TGATATCACCAGCTGATAATCAGAAGGTGGATCAAGTGATTATTTTATATTCTGGAGACAAA
ATTTATGATGACTACTATCCAGATCTGAAAGGCCGAGTACATTTTACGAGTAATGATCTCAA
ATCTGGTGATGCATCAATAAATGTAACGAATTTACAACTGTCAGATATTGGCACATATCAGT
GCAAAGTGAAAAAAGCTCCTGGTGTTGCAAATAAGAAGATTCATCTGGTAGTTCTTGTTAAG
CCTTCAGGTGCGAGATGTTACGTTGATGGATCTGAAGAAATTGGAAGTGACTTTAACATAAA
ATGTGAACCAAAAGAAGGTTCACTTCCATTACAGTATGAGTGGCAAAAATTGTCTGACTCAC
AGAAAATGCCCACTTCATGGTTAGCAGAAATGACTTCATCTGTTATATCTGTAAAAAATGCC
TCTTCTGAGTACTCTGGGACATACAGCTGTACAGTCAGAAACAGAGTGGGCTCTGATCAGTG
CCTGTTGCGTCTAAACGTTGTCCCTCCTTCAAATAAAGCTGGACTAATTGCAGGAGCCATTA
TAGGAACTTTGCTTGCTCTAGCGCTCATTGGTCTTATCATCTTTTGCTGTCGTAAAAAGCGC
AGAGAAGAAAAATATGAAAAGGAAGTTCATCACGATATCAGGGAAGATGTGCCACCTCCAAA
GAGCCGTACGTCCACTGCCAGAAGCTACATCGGCAGTAATCATTCATCCCTGGGGTCCATGT
CTCCTTCCAACATGGAAGGATATTCCAAGACTCAGTATAACCAAGTACCAAGTGAAGACTTT
GAACGCACTCCTCAGAGTCCGACTCTCCCACCTGCTAAGTTCAAGTACCCTTACAAGACTGA
TGGAATTACAGTTGTATAAATATGGACTACTGAAGAATCTGAAGTATTGTATTATTTGACTT
TATTTTAGGCCTCTAGTAAAGACTTAAATGTTTTTTAAAAAAAGCACAAGGCACAGAGATTA
GAGCAGCTGTAAGAACACATCTACTTTATGCAATGGCATTAGACATGTAAGTCAGATGTCAT
GTCAAAATTAGTACGAGCCAAATTCTTTGTTAAAAAACCCTATGTATAGTGACACTGATAGT
TAAAAGATGTTTTATTATATTTTCAATAACTACCACTAACAAATTTTTAACTTTTCATATGC
ATATTCTGATATGTGGTCTTTTAGGAAAAGTATGGTTAATAGTTGATTTTTCAAAGGAAATT
TTAAAATTCTTACGTTCTGTTTAATGTTTTTGCTATTTAGTTAAATACATTGAAGGGAAATA
CCCGTTCTTTTCCCCTTTTATGCACACAACAGAAACACGCGTTGTCATGCCTCAAACTATTT
TTTATTTGCAACTACATGATTTCACACAATTCTCTTAAACAACGACATAAAATAGATTTCCT
TGTATATAAATAACTTACATACGCTCCATAAAGTAAATTCTCAAAGGTGCTAGAACAAATCG
TCCACTTCTACAGTGTTCTCGTATCCAACAGAGTTGATGCACAATATATAAATACTCAAGTC
CAATATTAAAAACTTAGGCACTTGACTAACTTTAATAAAATTTCTCAAACTATATCAATATC
TAAAGTGCATATATTTTTTAAGAAAGATTATTCTCAATAACTTCTATAAAAATAAGTTTGAT
GGTTTGGCCCATCTAACTTCACTACTATTAGTAAGAACTTTTAACTTTTAATGTGTAGTAAG
GTTTATTCTACCTTTTTCTCAACATGACACCAACACAATCAAAAACGAAGTTAGTGAGGTGC
TAACATGTGAGGATTAATCCAGTGATTCCGGTCACAATGCATTCCAGGAGGAGGTACCCATG
TCACTGGAATTGGGCGATATGGTTTATTTTTTCTTCCCTGATTTGGATAACCAAATGGAACA
GGAGGAGGATAGTGATTCTGATGGCCATTCCCTCGATACATTCCTGGCTTTTTTCTGGGCAA
AGGGTGCCACATTGGAAGAGGTGGAAATATAAGTTCTGAAATCTGTAGGGAAGAGAACACAT
TAAGTTAATTCAAAGGAAAAAATCATCATCTATGTTCCAGATTTCTCATTAAAGACAAAGTT
ACCCACAACACTGAGATCACATCTAAGTGACACTCCTATTGTCAGGTCTAAATACATTAAAA
ACCTCATGTGTAATAGGCGTATAATGTATAACAGGTGACCAATGTTTTCTGAATGCATAAAG
AAATGAATAAACTCAAACACAGTACTTCCTAAACAACTTCAACCAAAAAAGACCAAAACATG
GAACGAATGGAAGCTTGTAAGGACATGCTTGTTTTAGTCCAGTGGTTTCCACAGCTGGCTAA
GCCAGGAGTCACTTGGAGGCTTTTAAATACAAAACATTGGAGCTGGAGGCCATTATCCTTAG
CAAACTAATGCAGAAACAGAAAATCAACTACCGCATGTTCTCACTTATAAGTGGGAGGTAAT
GATAAGAACTTATGAACACAAAGAAGGAAACAATAGACATTGGAGTCTATTTGAGAGGGGAG
GGTGGGAGAAGGAAAAGGAGCAGAAAAGATAACTATTGAGTACTGCCTTCACACCTGGGTGA
TGAAATAATATGTACAACAAATCCCTGTGACACATGTTTACCTATGGAACAAACCTTCATGT
GTATCCCTAAACCTAAAATAAAAGTTAAAAAAAAAAAAAARAAAAAAAAAAAAAAAAAAAAAA
AAAAAAAAAAAAAAAAAAAAAAAAAAAAAAAAAAAAAAAAAAAAAAAAAAAAAAAAAAAAAAA
AAAAAAAAAAAAAAAAAAAAAA

FIGURE 216

></usr/seqdb2/sst/DNA/Dnaseqs.full/ss.DNA82361
><subunit 1 of 1, 352 aa, 1 stop
><MW: 38938, pI: 7.86, NX(S/T): 3
MALLLCFVLLCGVVDFARSLSITTPEEMIEKAKGETAYLPCKFTLSPEDQGPLDIEWLISPA
DNQKVDQVIILYSGDKIYDDYYPDLKGRVHFTSNDLKSGDASINVTNLQLSDIGTYQCKVKK
APGVANKKIHLVVLVKPSGARCYVDGSEEIGSDFKIKCEPKEGSLPLQYEWQKLSDSQKMPT
SWLAEMTSSVISVKNASSEYSGTYSCTVRNRVGSDQCLLRLNVVPPSNKAGLIAGAIIGTLL
ALALIGLIIFCCRKKRREEKYEKEVHHDIREDVPPPKSRTSTARSYIGSNHSSLGSMSPSNM
EGYSKTQYNQVPSEDFERTPQSPTLPPAKFKYPYKTDGITVV

Signal sequence.
amino acids 1-19

Transmembrane domain:
amino acids 236-257

N-glycosylation sites.
amino acids 106-110, 201-205, 298-302

Tyrosine kinase phosphorylation sites.
amino acids 31-39, 78-85, 262-270

N-myristoylation sites.
amino acids 116-122, 208-214, 219-225, 237-243, 241-247, 245-251, 296-302

Myelin P0 protein.
amino acids 96-125

FIGURE 217

GATGGCGCAGCCACAGCTTCTGTGAGATTCGATTTCTCCCCAGTTCCCCTGTGGGTCTGAGG
GGACCAGAAGGGTGAGCTACGTTGGCTTTCTGGAAGGGGAGGCTATATGCGTCAATTCCCCA
AAACAAGTTTTGACATTTCCCCTGAAATGTCATTCTCTATCTATTCACTGCAAGTGCCTGCT
GTTCCAGGCCTTACCTGCTGGGCACTAACGGCGGAGCCAGGATGGGGACAGAATAAAGGAGC
CACGACCTGTGCCACCAACTCGCACTCAGACTCTGAACTCAGACCTGAAATCTTCTCTTCAC
GGGAGGCTTGGCAGTTTTTCTTACTCCTGTGGTCTCCAGATTTCAGGCCTAAGATGAAAGCC
TCTAGTCTTGCCTTCAGCCTTCTCTCTGCTGCGTTTTATCTCCTATGGACTCCTTCCACTGG
ACTGAAGACACTCAATTTGGGAAGCTGTGTGATCGCCACAAACCTTCAGGAAATACGAAATG
GATTTTCTGAGATACGGGGCAGTGTGCAAGCCAAAGATGGAAACATTGACATCAGAATCTTA
AGGAGGACTGAGTCTTTGCAAGACACAAAGCCTGCGAATCGATGCTGCCTCCTGCGCCATTT
GCTAAGACTCTATCTGGACAGGGTATTTAAAAACTACCAGACCCCTGACCATTATACTCTCC
GGAAGATCAGCAGCCTCGCCAATTCCTTTCTTACCATCAAGAAGGACCTCCGGCTCTCTCAT
GCCCACATGACATGCCATTGTGGGGAGGAAGCAATGAAGAAATACAGCCAGATTCTGAGTCA
CTTTGAAAAGCTGGAACCTCAGGCAGCAGTTGTGAAGGCTTTGGGGGAACTAGACATTCTTC
TGCAATGGATGGAGGAGACAGAATAGGAGGAAAGTGATGCTGCTGCTAAGAATATTCGAGGT
CAAGAGCTCCAGTCTTCAATACCTGCAGAGGAGGCATGACCCCAAACCACCATCTCTTTACT
GTACTAGTCTTGTGCTGGTCACAGTGTATCTTATTTATGCATTACTTGCTTCCTTGCATGAT
TGTCTTTATGCATCCCCAATCTTAATTGAGACCATACTTGTATAAGATTTTTGTAATATCTT
TCTGCTATTGGATATATTTATTAGTTAATATATTTATTTATTTTTTGCTATTTAATGTATTT
ATTTTTTTACTTGGACATGAAACTTTAAAAAAATTCACAGATTATATTTATAACCTGACTAG
AGCAGGTGATGTATTTTTATACAGTAAAAAAAAAAAACCTTGTAAATTCTAGAAGAGTGGCT
AGGGGGGTTATTCATTTGTATTCAACTAAGGACATATTTACTCATGCTGATGCTCTGTGAGA
TATTTGAAATTGAACCAATGACTACTTAGGATGGGTTGTGGAATAAGTTTTGATGTGGAATT
GCACATCTACCTTACAATTACTGACCATCCCCAGTAGACTCCCCAGTCCCATAATTGTGTAT
CTTCCAGCCAGGAATCCTACACGGCCAGCATGTATTTCTACAAATAAAGTTTTCTTTGCATA
CCAAAAAAAAAAAAAAAAAAA

FIGURE 218

></usr/seqdb2/sst/DNA/Dnaseqs.min/ss.DNA83500

MKASSLAFSLLSAAFYLLWTPSTGLKTLNLGSCVIATNLQEIRNGFSEIRGSVQAKDGN
IDIRILRRTESLQDTKPANRCCLLRHLLRLYLDRVFKNYQTPDHYTLRKISSLANSFLT
IKKDLRLSHAHMTCHCGEEAMKKYSQILSHFEKLEPQAAVVKALGELDILLQWMEETE

FIGURE 219

CGCGGAGCCCTGCGCTGGGAGGTGCACGGTGTGCACGCTGGACTGGACCCCCATGCAACCCC
GCGCCCTGCGCCTTAACCAGGACTGCTCCGCGCGCCCCTGAGCCTCGGGCTCCGGCCCGGAC
CTGCAGCCTCCCAGGTGGCTGGGAAGAACTCTCCAACAATAAATACATTTGATAAGAAAGATG
GCTTTAAAAGTGCTACTAGAACAAGAGAAAACGTTTTTCACTCTTTTAGTATTACTAGGCT
ATTTGTCATGTAAAGTGACTTGTGAATCAGGAGACTGTAGACAGCAAGAATTCAGGGATCGG
TCTGGAAACTGTGTTCCCTGCAACCAGTGTGGGCCAGGCATGGAGTTGTCTAAGGAATGTGG
CTTCGGCTATGGGGAGGATGCACAGTGTGTGACGTGCCGGCTGCACAGGTTCAAGGAGGACT
GGGGCTTCCAGAAATGCAAGCCCTGTCTGGACTGCGCAGTGGTGAACCGCTTTCAGAAGGCA
AATTGTTCAGCCACCAGTGATGCCATCTGCGGGGACTGCTTGCCAGGATTTTATAGGAAGAC
GAAACTTGTCGGCTTTCAAGACATGGAGTGTGTGCCTTGTGGAGACCCTCCTCCTCCTTACG
AACCGCACTGTGCCAGCAAGGTCAACCTCGTGAAGATCGCGTCCACGGCCTCCAGCCCACGG
GACACGGCGCTGGCTGCCGTTATCTGCAGCGCTCTGGCCACCGTCCTGCTGGCCCTGCTCAT
CCTCTGTGTCATCTATTGTAAGAGACAGTTTATGGAGAAGAAACCCAGCTGGTCTCTGCGGT
CGCAGGACATTCAGTACAACGGCTCTGAGCTGTCGTGTTTTGACAGACCTCAGCTCCACGAA
TATGCCCACAGAGCCTGCTGCCAGTGCCGCCGTGACTCAGTGCAGACCTGCGGGCCGGTGCG
CTTGCTCCCATCCATGTGCTGTGAGGAGGCCTGCAGCCCCAACCCGGCGACTCTTGGTTGTG
GGGTGCATTCTGCAGCCAGTCTTCAGGCAAGAAACGCAGGCCCAGCCGGGGAGATGGTGCCG
ACTTTCTTCGGATCCCTCACGCAGTCCATCTGTGGCGAGTTTTCAGATGCCTGGCCTCTGAT
GCAGAATCCCATGGGTGGTGACAACATCTCTTTTTGTGACTCTTATCCTGAACTCACTGGAG
AAGACATTCATTCTCTCAATCCAGAACTTGAAAGCTCAACGTCTTTGGATTCAAATAGCAGT
CAAGATTTGGTTGGTGGGGCTGTTCCAGTCCAGTCTCATTCTGAAAACTTTACAGCAGCTAC
TGATTTATCTAGATATAACAACACACTGGTAGAATCAGCATCAACTCAGGATGCACTAACTA
TGAGAAGCCAGCTAGATCAGGAGAGTGGCGCTGTCATCCACCCAGCCACTCAGACGTCCCTC
CAGGAAGCTTAAAGAACCTGCTTCTTTCTGCAGTAGAAGCGTGTGCTGGAACCCAAAGAGTA
CTCCTTTGTTAGGCTTATGGACTGAGCAGTCTGGACCTTGCATGGCTTCTGGGGCAAAAATA
AATCTGAACCAAACTGACGGCATTTGAAGCCTTTCAGCCAGTTGCTTCTGAGCCAGACCAGC
TGTAAGCTGAAACCTCAATGAATAACAAGAAAAGACTCCAGGCCGACTCATGATACTCTGCA
TCTTTCCTACATGAGAAGCTTCTCTGCCACAAAAGTGACTTCAAAGACTGATGGGTTGAGCT
GGCAGCCTATGAGATTGTGGACATATAACAAGAAACAGAAATGCCCTCATGCTTATTTTCAT
GGTGATTGTGGTTTTACAAGACTGAAGACCCAGAGTATACTTTTTCTTTCCAGAAATAATTT
CATACCGCCTATGAAATATCAGATAAATTACCTTAGCTTTTATGTAGAATGGGTTCAAAAGT
GAGTGTTTCTATTTGAGAAGGACACTTTTTCATCATCTAAACTGATTCGCATAGGTGGTTAG
AATGGCCCTCATATTGCCTGCCTAAATCTTGGGTTTATTAGATGAAGTTTACTGAATCAGAG
GAATCAGACAGAGGAGGATAGCTCTTTCCAGAATCCACACTTCTGACCTCAGCCTCGGTCTC
ATGAACACCCGCTGATCTCAGGAGAACACCTGGGCTAGGGAATGTGGTCGAGAAAGGGCAGC
CCATTGCCCAGAATTAACACATATTGTAGAGACTTGTATGCAAAGGTTGGCATATTTATATG
AAAATTAGTTGCTATAGAAACATTTGTTGCATCTGTCCCTCTGCCTGAGCTTAGAAGGTTAT
AGAAAAAGGGTATTTATAAACATAAATGACCTTTTACTTGCATTGTATCTTATACTAAAGGC
TTTAGAAATTACAACATATCAGGTTCCCCTACTACTGAAGTAGCCTTCCGTGAGAACACACC
ACATGTTAGGACTAGAAGAAAATGCACAATTTGTAGGGGTTTGGATGAAGCAGCTGTAACTG
CCCTAGTGTAGTTTGACCAGGACATTGTCGTGCTCCTTCCAATTGTGTAAGATTAGTTAGCA
CATCATCTCCTACTTTAGCCATCCGGTGTTGGATTTAAGAGGACGGTGCTTCTTTCTATTAA
AGTGCTCCATCCCCTACCATCTACACATTAGCATTGTCTCTAGAGCTAAGACAGAAATTAAC
CCCGTTCAGTCACAAAGCAGGGAATGGTTCATTTACTCTTAATCTTTATGCCCTGGAGAAGA
CCTACTTGAACAGGGCATATTTTTTAGACTTCTGAACATCAGTATGTTCGAGGGTACTATGA
TATTTTGGTTTGGAATTGCCCTGCCCAAGTCACTGTCTTTTAACTTTTAAACTGAATATTAA
AATGTATCTGTCTTTCCT

FIGURE 220

></usr/seqdb2/sst/DNA/Dnaseqs.min/ss.DNA84210
><subunit 1 of 1, 417 aa, 1 stop
><MW: 45305, pI: 5.12, NX(S/T): 6
MALKVLLEQEKTFFTLLVLLGYLSCKVTCESGDCRQQEFRDRSGNCVPCNQCGPGMELSK
ECGFGYGEDAQCVTCRLHRFKEDWGFQKCKPCLDCAVVNRFQKANCSATSDAICGDCLPG
FYRKTKLVGFQDMECVPCGDPPPPYEPHCASKVNLVKIASTASSPRDTALAAVICSALAT
VLLALLILCVIYCKRQFMEKKPSWSLRSQDIQYNGSELSCFDRPQLHEYAHRACCQCRRD
SVQTCGPVRLLPSMCCEEACSPNPATLGCGVHSAASLQARNAGPAGEMVPTFFGSLTQSI
CGEFSDAWPLMQNPMGGDNISFCDSYPELTGEDIHSLNPELESSTSLDSNSSQDLVGGAV
PVQSHSENFTAATDLSRYNNTLVESASTQDALTMRSQLDQESGAVIHPATQTSLQEA

Important features of the protein:
Signal peptide:
Amino acids
1-25

Transmembrane domain:
Amino acids
169-192

N-glycosylation sites:
Amino acids
105-109;214-218;319-323;350-354;368-372;379-383 cAMP- and cGMP-dependent protein kinase phosphorylation sites:
Amino acids
200-204;238-242

Tyrosine kinase phosphorylation site:
Amino acids
207-214

N-myristoylation sites:
Amino acids
55-61;215-221;270-276

Prokaryotic membrane lipoprotein lipid attachment site:
Amino acids
259-270

TNFR/NGFR family cysteine-rich region proteins:
Amino acids
89-96

FIGURE 221

CTAGAGAGTATAGGGCAGAAGGATGGCAGATGAGTGACTCCACATCCAGAGCTGCCTCCCTT
TAATCCAGGATCCTGTCCTTCCTGTCCTGTAGGAGTGCCTGTTGCCAGTGTGGGGTGAGACA
AGTTTGTCCCACAGGGCTGTCTGAGCAGATAAGATTAAGGGCTGGGTCTGTGCTCAATTAAC
TCCTGTGGGCACGGGGGCTGGGAAGAGCAAAGTCAGCGGTGCCTACAGTCAGCACCATGCTG
GGCCTGCCGTGGAAGGGAGGTCTGTCCTGGGCGCTGCTGCTGCTTCTCTTAGGCTCCCAGAT
CCTGCTGATCTATGCCTGGCATTTCCACGAGCAAAGGGACTGTGATGAACACAATGTCATGG
CTCGTTACCTCCCTGCCACAGTGGAGTTTGCTGTCCACACATTCAACCAACAGAGCAAGGAC
TACTATGCCTACAGACTGGGGCACATCTTGAATTCCTGGAAGGAGCAGGTGGAGTCCAAGAC
TGTATTCTCAATGGAGCTACTGCTGGGGAGAACTAGGTGTGGGAAATTTGAAGACGACATTG
ACAACTGCCATTTCCAAGAAAGCACAGAGCTGAACAATACTTTCACCTGCTTCTTCACCATC
AGCACCAGGCCCTGGATGACTCAGTTCAGCCTCCTGAACAAGACCTGCTTGGAGGGATTCCA
CTGAGTGAAACCCACTCACAGGCTTGTCCATGTGCTGCTCCCACATTCCGTGGACATCAGCA
CTACTCTCCTGAGGACTCTTCAGTGGCTGAGCAGCTTTGGACTTGTTTGTTATCCTATTTTG
CATGTGTTTGAGATCTCAGATCAGTGTTTTAGAAAATCCACACATCTTGAGCCTAATCATGT
AGTGTAGATCATTAAACATCAGCATTTTAAGAAAAAAAAAAAAAAAAAAAAAAAAAAAAAAA
AAAAAAAAAAAAAAAAAAAAAAAAAAAAAAAA

FIGURE 222

MLGLPWKGGLSWALLLLLLGSQILLIYAWHFHEQRDCDEHNVMARYLPATVEFAVHTFNQQS
KDYYAYRLGHILNSWKEQVESKTVFSMELLLGRTRCGKFEDDIDNCHFQESTELNNTFTCFF
TISTRPWMTQFSLLNKTCLEGFH

Important features of the protein:
Signal péptide:
amino acids 1-25

N-glycosylation sites.
amino acids 117-121, 139-143

N-myristoylation site.
amino acids 9-15

FIGURE 223

AATCGGCTGATTCTGCATCTGGAAACTGCCTTCATCTTGAAAGAAAAGCTCCAGGTCCCT
TCTCCAGCCACCCAGCCCCAAGATGGTGATGCTGCTGCTGCTGCTTTCCGCACTGGCTGG
CCTCTTCGGTGCGGCAGAGGGACAAGCATTTCATCTTGGGAAGTGCCCCAATCCTCCGGT
GCAGGAGAATTTTGACGTGAATAAGTATCTCGGAAGATGGTACGAAATTGAGAAGATCCC
AACAACCTTTGAGAATGGACGCTGCATCCAGGCCAACTACTCACTAATGGAAAACGGAAA
GATCAAAGTGTTAAACCAGGAGTTGAGAGCTGATGGAACTGTGAATCAAATCGAAGGTGA
AGCCACCCCAGTTAACCTCACAGAGCCTGCCAAGCTGGAAGTTAAGTTTTCCTGGTTTAT
GCCATCGGCACCGTACTGGATCCTGGCCACCGACTATGAGAACTATGCCCTCGTGTATTC
CTGTACCTGCATCATCCAACTTTTTCACGTGGATTTTGCTTGGATCTTGGCAAGAAACCC
TAATCTCCCTCCAGAAACAGTGGACTCTCTAAAAAATATCCTGACTTCTAATAACATTGA
TGTCAAGAAAATGACGGTCACAGACCAGGTGAACTGCCCCAAGCTCTCGTAACCAGGTTC
TACAGGGAGGCTGCACCCACTCCATGTTACTTCTGCTTCGCTTTCCCCTACCCCACCCCC
CCCCCATAAAGACAAACCAATCAACCACGACAAAGGAAGTTGACCTGAACATGTAACCAT
GCCCTACCCTGTTACCTTGCTAGCTGCAAAATAAACTTGTTGCTGACCTGCTGTGCTCGC
AAAAAA

FIGURE 224

MVMLLLLLSALAGLFGAAEGQAFHLGKCPNPPVQENFDVNKYLGRWYEIEKIPTTFENG
RCIQANYSLMENGKIKVLNQELRADGTVNQIEGEATPVNLTEPAKLEVKFSWFMPSAPY
WILATDYENYALVYSCTCIIQLFHVDFAWILARNPNLPPETVDSLKNILTSNNIDVKKM
TVTDQVNCPKLS

Signal sequence
1-16

N-glycosylation site.

65-68
98-101 cAMP- and cGMP-dependent protein kinase phosphorylation site.

175-178

N-myristoylation site.

13-18
16-21

Lipocalin proteins.

36-47
120-130

Lipocalin / cytosolic fatty-acid binding proteins

41-185

FIGURE 225

GGGTGATTGAACTAAACCTTCGCCGCACCGAGTTTGCAGTACGGCCGTCACCCGCACCGCTG
CCTGCTTGCGGTTGGAGAAATCAAGGCCCTACCGGGCCTCCGTAGTCACCTCTCTATAGTGG
GCGTGGCCGAGGCCGGGGTGACCCTGCCGGAGCCTCCGCTGCCAGCGACATGTTCAAGGTAA
TTCAGAGGTCCGTGGGGCCAGCCAGCCTGAGCTTGCTCACCTTCAAAGTCTATGCAGCACCA
AAAAAGGACTCACCTCCCAAAAATTCCGTGAAGGTTGATGAGCTTTCACTCTACTCAGTTCC
TGAGGGTCAATCGAAGTATGTGGAGGAGGCAAGGAGCCAGCTTGAAGAAAGCATCTCACAGC
TCCGACACTATTGCGAGCCATACACAACCTGGTGTCAGGAAACGTACTCCCAAACTAAGCCC
AAGATGCAAAGTTTGGTTCAATGGGGGTTAGACAGCTATGACTATCTCCAAAATGCACCTCC
TGGATTTTTTCCGAGACTTGGTGTTATTGGTTTTGCTGGCCTTATTGGACTCCTTTTGGCTA
GAGGTTCAAAAATAAAGAAGCTAGTGTATCCGCCTGGTTTCATGGGATTAGCTGCCTCCCTC
TATTATCCACAACAAGCCATCGTGTTTGCCCAGGTCAGTGGGGAGAGATTATATGACTGGGG
TTTACGAGGATATATAGTCATAGAAGATTTGTGGAAGGAGAACTTTCAAAAGCCAGGAAATG
TGAAGAATTCACCTGGAACTAAGTAGAAAACTCCATGCTCTGCCATCTTAATCAGTTATAGG
TAAACATTGGAAACTCCATAGAATAAATCAGTATTTCTACAGAAAAATGGCATAGAAGTCAG
TATTGAATGTATTAAATTGGCTTTCTTCTTCAGGAAAAACTAGACCAGACCTCTGTTATCTT
CTGTGAAATCATCCTACAAGCAAACTAACCTGGAATCCCTTCACCTAGAGATAATGTACAAG
CCTTAGAACTCCTCATTCTCATGTTGCTATTTATGTACCTAATTAAAACCCAAGTTTAAAAA
AAAAAAAAAAAAAAAAAAAAAAAAAAAAAAAAAA

FIGURE 226

MFKVIQRSVGPASLSLLTFKVYAAPKKDSPPKNSVKVDELSLYSVPEGQSKYVEEARSQLEE
SISQLRHYCEPYTTWCQETYSQTKPKMQSLVQWGLDSYDYLQNAPPGFFPRLGVIGFAGLIG
LLLARGSKIKKLVYPPGFMGLAASLYYPQQAIVFAQVSGERLYDWGLRGYIVIEDLWKENFQ
KPGNVKNSPGTK

Important features:
Signal peptide:
Amino acids 1-23

Transmembrane domain:
Amino acids 111-130 cAMP- and cGMP-dependent protein kinase phosphorylation site:
Amino acids 26-30

Tyrosine kinase phosphorylation site:
Amino acids 36-44

N-myristoylation sites:
Amino acids 124-130;144-150;189-195

FIGURE 227

CACCGGAGGGCACGCAGCTGACGGAGCTGCGCTGCGTTCGCCTCGTTTGCCTCGCGCCCTCC
ACTGGAGCTGTTCGCGCCTCCCGGCTCCCACCGCAGCCCACCCGGCAGAGGAGTCGCTACCA
GCGCCCAGTGCGCTCTGTCAGTCCGCAAACTCCTTGCCGCCCGCCCCGGGCTGGGCACCAAA
TACCAGGCTACCATGGTCTACAAGACTCTCTTCGCTCTTTGCATCTTAACTGCAGGATGGAG
GGTACAGAGTCTGCCTACATCAGCTCCTTTGTCTGTTTCTCTTCCGACAAACATTGTACCAC
CGACCACCATCTGGACTAGCTCTCCACAAAACACTGATGCAGACACTGCCTCCCCATCCAAC
GGCACTCACAACAACTCGGTGCTCCCAGTTACAGCATCAGCCCCAACATCTCTGCTTCCTAA
GAACATTTCCATAGAGTCCAGAGAAGAGGAGATCACCAGCCCAGGTTCGAATTGGGAAGGCA
CAAACACAGACCCCTCACCTTCTGGGTTCTCGTCAACAAGCGGTGGAGTCCACTTAACAACC
ACGTTGGAGGAACACAGCTCGGGCACTCCTGAAGCAGGCGTGGCAGCTACACTGTCGCAGTC
CGCTGCTGAGCCTCCCACACTCATCTCCCCTCAAGCTCCAGCCTCATCACCCTCATCCCTAT
CAACCTCACCACCTGAGGTCTTTTCTGCCTCCGTTACTACCAACCATAGCTCCACTGTGACC
AGCACCCAACCCACTGGAGCTCCAACTGCACCAGAGTCCCCGACAGAGGAGTCCAGCTCTGA
CCACACACCCACTTCACATGCCACAGCTGAGCCAGTGCCCCAGGAGAAAACACCCCCAACAA
CTGTGTCAGGCAAAGTGATGTGTGAGCTCATAGACATGGAGACCACCACCACCTTTCCCAGG
GTGATCATGCAGGAAGTAGAACATGCATTAAGTTCAGGCAGCATCGCCGCCATTACCGTGAC
AGTCATTGCCGTGGTGCTGCTGGTGTTTGGAGTTGCAGCCTACCTAAAAATCAGGCATTCCT
CCTATGGAAGACTTTTGGACGACCATGACTACGGGTCCTGGGGAAACTACAACAACCCTCTG
TACGATGACTCCTAACAATGGAATATGGCCTGGGATGAGGATTAACTGTTCTTTATTTATAA
GTGCTTATCCAGTAGAATTAATAAGTACCTGATGCGCATTGAACGACAATCTTAAGCCCTGT
TTTGTTGGTATGGTTGTTTTTGTTTTCCTCCCTCTCCTCTGGCTGCTACAACTTCCCCTTTC
TGGTACAAGAAGAACCATTCTTTAAAGGTGAGTGGAGGCTGATTTGCAGCTGAAGTGGGCCA
GCCTTGCACCAGCCAGGCCAGACCACCATGGTGAAGGCTTCTTTCCCCACTGCAGGACCCAC
TTTGAGAAGGATCGAGGAGGAGGATTTGGGTTGTTTTGTTAGGGGTTACTTTCAGGGGAACA
TTTCATTTGTGTTATTTCTTAAACTTCTATTTAGGAAATTACATTAAGTATTAATGAGGGGA
AAGGAAATGAGCTCTACGAGGATTTCACCTTGCATGGGAGAGAGCAGGGTTTTCTCAGATTC
CTTTTTAATCTCTATTTATCTGGTTGTTTCTGACAGGATGCTGCCTGCTTGGCTCTACGAGC
TGGAAAGCAGCTTCTTAGCTGCCTAATTAATGAAAGATGAAAATAGGAAGTGCCCTGGAGGG
GGCCAGCAGGTCACGGGGCAGAATCTCTCAGGTTGCTGTGGGATCTCAGTGTGCCCCTACCT
GTTCTCCCCTCCAGGCCACCTGTCTCTGTAAAGGATGTCTGCTCTGTTCAAAAGGCAGCTGG
GATCCCAGCCCACAAGTGATCAGCAGAGTTGCATTTCCAAAGAAAAAGGCTATGAGATGAGC
TGAGTTATAGAGAGAAAGGGAGAGGCATGTACGGTGTGGGGAAGTGGAAGAGAAGCTGGCGG
GGGAGAAGGAGGCTAACCTGCACTGAGTACTTCATTAGGACAAGTGAGAATCAGCTATTGAT
AATGGCCAGAGATATCCACAGCTTGGAGGAGCCCAGAGACTGTTTGCTTTATACCCACACAG
CAACTGGTCCACTGCTTTACTGTCTGTTGGATAATGGCTGTAAAATGTTTAAAAAC

FIGURE 228

MVYKTLFALCILTAGWRVQSLPTSAPLSVSLPTNIVPPTTIWTSSPQNTDADTASPSNGTHN
NSVLPVTASAPTSLLPKNISIESREEEITSPGSNWEGTNTDPSPSGFSSTSGGVHLTTTLEE
HSSGTPEAGVAATLSQSAAEPPTLISPQAPASSPSSLSTSPPEVFSASVTTNHSSTVTSTQP
TGAPTAPESPTEESSSDHTPTSHATAEPVPQEKTPPTTVSGKVMCELIDMETTTTFPRVIMQ
EVEHALSSGSIAAITVTVIAVVLLVFGVAAYLKIRHSSYGRLLDDHDYGSWGNYNNPLYDDS

Important features of the protein:
Signal peptide:
amino acids 1-20

Transmembrane domain:
amino acids 258-278

N-glycosylation sites.
amino acids 58-61, 62-65, 80-83, 176-179

Casein kinase II phosphorylation sites.
amino acids 49-52, 85-88, 95-98, 100-103, 120-123, 121-124, 141-144, 164-167, 191-194, 195-198, 200-203

Tyrosine kinase phosphorylation site.
amino acids 289-296

N-myristoylation sites.
amino acids 59-64, 115-120, 128-133, 133-138, 257-262, 297-302

FIGURE 229

CTCCTGCACTAGGCTCTCAGCCAGGGATGATGCGCTGCTGCCGCCGCCGCTGCTGCTGCCGG
CAACCACCCCATGCCCTGAGGCCGTTGCTGTTGCTGCCCCTCGTCCTTTTACCTCCCCTGGC
AGCAGCTGCAGCGGGCCCAAACCGATGTGACACCATATACCAGGGCTTCGCCGAGTGTCTCA
TCCGCTTGGGGGACAGCATGGGCCGCGGAGGCGAGCTGGAGACCATCTGCAGGTCTTGGAAT
GACTTCCATGCCTGTGCCTCTCAGGTCCTGTCAGGCTGTCCGGAGGAGGCAGCTGCAGTGTG
GGAATCACTACAGCAAGAAGCTCGCCAGGCCCCCCGTCCGAATAACTTGCACACTCTGTGCG
GTGCCCCGGTGCATGTTCGGGAGCGCGGCACAGGCTCCGAAACCAACCAGGAGACGCTGCGG
GCTACAGCGCCTGCACTCCCCATGGCCCCTGCGCCCCCACTGCTGGCGGCTGCTCTGGCTCTG
GCCTACCTCCTGAGGCCTCTGGCCTAGCTTGTTGGGTTGGGTAGCAGCGCCCGTACCTCCAG
CCCTGCTCTGGCGGTGGTTGTCCAGGCTCTGCAGAGCGCAGCAGGGCTTTTCATTAAAGGTA
TTTATATTTGTA

FIGURE 230

></usr/seqdb2/sst/DNA/Dnaseqs.min/ss.DNA92265
><subunit 1 of 1, 165 aa, 1 stop
><MW: 17786, pI: 8.43, NX(S/T): 0
MMRCCRRRCCCRQPPHALRPLLLLPLVLLPPLAAAAAGPNRCDTIYQGFAECLIRLGDSM
GRGGELETICRSWNDFHACASQVLSGCPEEAAAVWESLQQEARQAPRPNNLHTLCGAPVH
VRERGTGSETNQETLRATAPALPMAPAPPLLAAALALAYLLRPLA

Important features of the protein:
Signal peptide:
Amino acids 1-35

Transmembrane domain:
Amino acids 141-157

N-myristoylation site:
Amino acids 127-133

Prokaryotic membrane lipoprotein lipid attachment site:
Amino acids 77-88

FIGURE 231

AAGTACTTGTGTCCGGGTGGTGGACTGGATTAGCTGCGGAGCCCTGGAAGCTGCCTGTCCTT
CTCCCTGTGCTTAACCAGAGGTGCCCATGGGTTGGACAATGAGGCTGGTCACAGCAGCACTG
TTACTGGGTCTCATGATGGTGGTCACTGGAGACGAGGATGAGAACAGCCCGTGTGCCCATGA
GGCCCTCTTGGACGAGGACACCCTCTTTTGCCAGGGCCTTGAAGTTTTCTACCCAGAGTTGG
GGAACATTGGCTGCAAGGTTGTTCCTGATTGTAACAACTACAGACAGAAGATCACCTCCTGG
ATGGAGCCGATAGTCAAGTTCCCGGGGGCCGTGGACGGCGCAACCTATATCCTGGTGATGGT
GGATCCAGATGCCCCTAGCAGAGCAGAACCCAGACAGAGATTCTGGAGACATTGGCTGGTAA
CAGATATCAAGGGCGCCGACCTGAAGAAAGGGAAGATTCAGGGCCAGGAGTTATCAGCCTAC
CAGGCTCCCTCCCCACCGGCACACAGTGGCTTCCATCGCTACCAGTTCTTTGTCTATCTTCA
GGAAGGAAAAGTCATCTCTCTCCTTCCCAAGGAAAACAAAACTCGAGGCTCTTGGAAAATGG
ACAGATTTCTGAACCGCTTCCACCTGGGCGAACCTGAAGCAAGCACCCAGTTCATGACCCAG
AACTACCAGGACTCACCAACCCTCCAGGCTCCCAGAGGAAGGGCCAGCGAGCCCAAGCACAA
AACCAGGCAGAGATAGCTGCCTGCTAGATAGCCGGCTTTGCCATCCGGGCATGTGGCCACAC
TGCTCACCACCGACGATGTGGGTATGGAACCCCCTCTGGATACAGAACCCCTTCTTTTCCAA
ATTAAAAAAAAAAAATCATCAAA

FIGURE 232

></usr/seqdb2/sst/DNA/Dnaseqs.min/ss.DNA92274
><subunit 1 of 1, 223 aa, 1 stop
><MW: 25402, pI: 8.14, NX(S/T): 1
MGWTMRLVTAALLLGLMMVVTGDEDENSPCAHEALLDEDTLFCQGLEVFYPELGNIGCKVVP
DCNNYRQKITSWMEPIVKFPGAVDGATYILVMVDPDAPSRAEPRQRFWRHWLVTDIKGADLK
KGKIQGQELSAYQAPSPPAHSGFHRYQFFVYLQEGKVISLLPKENKTRGSWKMDRFLNRFHL
GEPEASTQFMTQNYQDSPTLQAPRGRASEPKHKTRQR

Important features of the protein:
Signal peptide:
amino acids 1-22

N-glycosylation site.
amino acids 169-173

Tyrosine kinase phosphorylation site.
amino acids 59-68

N-myristoylation sites.
amino acids 54-60, 83-89, 130-136

Phosphatidylethanolamine signature.
amino acids 113-157

FIGURE 233

AAGGAGCAGCCCGCAAGCACCAAGTGAGAGGCATGAAGTTACAGTGTGTTTCCCTTTGGCTC
CTGGGTACAATACTGATATTGTGCTCAGTAGACAACCACGGTCTCAGGAGATGTCTGATTTC
CACAGACATGCACCATATAGAAGAGAGTTTCCAAGAAATCAAAAGAGCCATCCAAGCTAAGG
ACACCTTCCCAAATGTCACTATCCTGTCCACATTGGAGACTCTGCAGATCATTAAGCCCTTA
GATGTGTGCTGCGTGACCAAGAACCTCCTGGCGTTCTACGTGGACAGGGTGTTCAAGGATCA
TCAGGAGCCAAACCCCAAAATCTTGAGAAAAATCAGCAGCATTGCCAACTCTTTCCTCTACA
TGCAGAAAACTCTGCGGCAATGTCAGGAACAGAGGCAGTGTCACTGCAGGCAGGAAGCCACC
AATGCCACCAGAGTCATCCATGACAACTATGATCAGCTGGAGGTCCACGCTGCTGCCATTAA
ATCCCTGGGAGAGCTCGACGTCTTTCTAGCCTGGATTAATAAGAATCATGAAGTAATGTTCT
CAGCTTGATGACAAGGAACCTGTATAGTGATCCAGGGATGAACACCCCCTGTGCGGTTTACT
GTGGGAGACAGCCCACCTTGAAGGGGAAGGAGATGGGGAAGGCCCCTTGCAGCTGAAAGTCC
CACTGGCTGGCCTCAGGCTGTCTTATTCCGCTTGAAAATAGGCAAAAAGTCTACTGTGGTAT
TTGTAATAAACTCTATCTGCTGAAAGGGCCTGCAGGCCATCCTGGGAGTAAAGGGCTGCCTT
CCCATCTAATTTATTGTAAAGTCATATAGTCCATGTCTGTGATGTGAGCCAAGTGATATCCT
GTAGTACACATTGTACTGAGTGGTTTTTCTGAATAAATTCCATATTTTACCTATGA

FIGURE 234

></usr/seqdb2/sst/DNA/Dnaseqs.full/ss.DNA92282
><subunit 1 of 1, 177 aa, 1 stop
><MW: 20452, pI: 8.00, NX(S/T): 2
MKLQCVSLWLLGTILILCSVDNHGLRRCLISTDMHHIEESFQEIKRAIQAKDTFPNVTILST
LETLQIIKPLDVCCVTKNLLAFYVDRVFKDHQEPNPKILRKISSIANSFLYMQKTLRQCQEQ
RQCHCRQEATNATRVIHDNYDQLEVHAAAIKSLGELDVFLAWINKNHEVMFSA

Signal sequence:
amino acids 1-18

N-glycosylation sites.
amino acids 56-60, 135-139 cAMP- and cGMP-dependent protein kinase phosphorylation site.
amino acids 102-106

N-myristoylation site.
amino acids 24-30

Actinin-type actin-binding domain signature 1.
amino acids 159-169

FIGURE 235

GCCCGGGCGGCTGCCCTTGGGTGCTCCCTTCCCTGCCCGACACCCAGACCGACCTTGACCGC
CCACCTGGCAGGAGCAGGACAGGACGGCCGGACGCGGCCATGGCCGAGCTCCCGGGGCCCTT
TCTCTGCGGGGCCCTGCTAGGCTTCCTGTGCCTGAGTGGGCTGGCCGTGGAGGTGAAGGTAC
CCACAGAGCCGCTGAGCACGCCCCTGGGGAAGACAGCCGAGCTGACCTGCACCTACAGCACG
TCGGTGGGAGACAGCTTCGCCCTGGAGTGGAGCTTTGTGCAGCCTGGGAAACCCATCTCTGA
GTCCCATCCAATCCTGTACTTCACCAATGGCCATCTGTATCCAACTGGTTCTAAGTCAAAGC
GGGTCAGCCTGCTTCAGAACCCCCCCACAGTGGGGGTGGCCACACTGAAACTGACTGACGTC
CACCCCTCAGATACTGGAACCTACCTCTGCCAAGTCAACAACCCACCAGATTTCTACACCAA
TGGGTTGGGGCTAATCAACCTTACTGTGCTGGTTCCCCCCAGTAATCCCTTATGCAGTCAGA
GTGGACAAACCTCTGTGGGAGGCTCTACTGCACTGAGATGCAGCTCTTCCGAGGGGGCTCCT
AAGCCAGTGTACAACTGGGTGCGTCTTGGAACTTTTCCTACACCTTCTCCTGGCAGCATGGT
TCAAGATGAGGTGTCTGGCCAGCTCATTCTCACCAACCTCTCCCTGACCTCCTCGGGCACCT
ACCGCTGTGTGGCCACCAACCAGATGGGCAGTGCATCCTGTGAGCTGACCCTCTCTGTGACC
GAACCCTCCCAAGGCCGAGTGGCCGGAGCTCTGATTGGGGTGCTCCTGGGCGTGCTGTTGCT
GTCAGTTGCTGCGTTCTGCCTGGTCAGGTTCCAGAAAGAGAGGGGGAAGAAGCCCAAGGAGA
CATATGGGGGTAGTGACCTTCGGGAGGATGCCATCGCTCCTGGGATCTCTGAGCACACTTGT
ATGAGGGCTGATTCTAGCAAGGGGTTCCTGGAAAGACCCTCGTCTGCCAGCACCGTGACGAC
CACCAAGTCCAAGCTCCCTATGGTCGTGTGACTTCTCCCGATCCCTGAGGGCGGTGAGGGGG
AATATCAATAATTAAAGTCTGTGGGTACCCTTNAAAAAAAAAAAA

FIGURE 236

></usr/seqdb2/sst/DNA/Dnaseqs.min/ss.DNA108760
><subunit 1 of 1, 327 aa, 1 stop
><MW: 34348, pI: 7.88, NX(S/T): 2
MAELPGPFLCGALLGFLCLSGLAVEVKVPTEPLSTPLGKTAELTCTYSTSVGDSFALEWS
FVQPGKPISESHPILYFTNGHLYPTGSKSKRVSLLQNPPTVGVATLKLTDVHPSDTGTYL
CQVNNPPDFYTNGLGLINLTVLVPPSNPLCSQSGQTSVGGSTALRCSSSEGAPKPVYNWV
RLGTFPTPSPGSMVQDEVSGQLILTNLSLTSSGTYRCVATNQMGSASCELTLSVTEPSQG
RVAGALIGVLLGVLLLSVAAFCLVRFQKERGKKPKETYGGSDLREDAIAPGISEHTCMRA
DSSKGFLERPSSASTVTTTKSKLPMVV

Important features of the protein:
Signal peptide:
Amino acids 1-20

Transmembrane domain:
Amino acids 242-260

N-glycosylation sites:
Amino acids 138-142;206-210 cAMP- and cGMP-dependent protein kinase phosphorylation site:
Amino acids 90-94

N-myristoylation sites:
Amino acids 11-17;117-123;159-165;213-219;224-230;244-250;
248-254

Amidation site:
Amino acids 270-274

Prokaryotic membrane lipoprotein lipid attachment site:
Amino acids 218-229

FIGURE 237

GGATGCAGCAGAGAGGAGCAGCTGGAAGCCGTGGCTGCGCTCTCTTCCCTCTGCTGGGCG
TCCTGTTCTTCCAGGGTGTTTATATCGTCTTTTCCTTGGAGATTCGTGCAGATGCCCATG
TCCGAGGTTATGTTGGAGAAAAGATCAAGTTGAAATGCACTTTCAAGTCAACTTCAGATG
TCACTGACAAGCTTACTATAGACTGGACATATCGCCCTCCCAGCAGCAGCCACACAGTAT
CAATATTTCATTATCAGTCTTTCCAGTACCCAACCACAGCAGGCACATTTCGGGATCGGA
TTTCCTGGGTTGGAAATGTATACAAAGGGGATGCATCTATAAGTATAAGCAACCCTACCA
TAAAGGACAATGGGACATTCAGCTGTGCTGTGAAGAATCCCCCAGATGTGCACCATAATA
TTCCCATGACAGAGCTAACAGTCACAGAAAGGGGTTTTGGCACCATGCTTTCCTCTGTGG
CCCTTCTTTCCATCCTTGTCTTTGTGCCCTCAGCCGTGGTGGTTGCTCTGCTGCTGGTGA
GAATGGGGAGGAAGGCTGCTGGGCTGAAGAAGAGGAGCAGGTCTGGCTATAAGAAGTCAT
CTATTGAGGTTTCCGATGACACTGATCAGGAGGAGGAAGAGGCGTGTATGGCGAGGCTTT
GTGTCCGTTGCGCTGAGTGCCTGGATTCAGACTATGAAGAGACATATTGATGAAAGTCTG
TATGACACAAGAAGAGTCACCTAAAGACAGGAAACATCCCATTCCACTGGCAGCTAAAGC
CTGTCAGAGAAAGTGGAGCTGGCCTGGACCATAGCGATGGACAATCCTGGAGATCATCAG
TAAAGACTTTAGGAACCACTTATTTATTGAATAAATGTTCTTGTTGTATTTATAAACTGT
TCAGGAAGTCTCATAAGAGACTCATGACTTCCCCTTTCAATGAATTATGCTGTAATTGAA
TGAAGAAATTCTTTTCCTGAGCA

FIGURE 238

MQQRGAAGSRGCALFPLLGVLFFQGVYIVFSLEIRADAHVRGYVGEKIKLKCTFKSTSD
VTDKLTIDWTYRPPSSSHTVSIFHYQSFQYPTTAGTFRDRISWVGNVYKGDASISISNP
TIKDNGTFSCAVKNPPDVHHNIPMTELTVTERGFGTMLSSVALLSILVFVPSAVVVALL
LVRMGRKAAGLKKRSRSGYKKSSIEVSDDTDQEEEEACMARLCVRCAECLDSDYEETY

Transmembrane domain
11-30
157-177

N-glycosylation site
123-127 cAMP- and cGMP-dependent protein kinase phosphorylation site
189-193
197-201

Tyrosine kinase phosphorylation site
63-71

N-myristoylation site
5-11
8-14
124-130
153-159

Amidation site
181-185

FIGURE 239

CAGGCGGGCCCCCGCGCGGCAGGGCCCTGGACCCGCGCGGCTCCCGGGGATGGTGAGCAAGGCGCTGCTGCGCC
TCGTGTCTGCCGTCAACCGCAGGAGGATGAAGCTGCTGCTGGGCATCGCCTTGCTGGCCTACGTCGCCTCTGTT
TGGGGCAACTTCGTTAATATGAGGTCTATCCAGGAAAATGGTGAACTAAAAATTGAAAGCAAGATTGAAGAGAT
GGTTGAACCACTAAGAGAGAAAATCAGAGATTTAGAAAAAAGCTTTACCCAGAAATACCCACCAGTAAAGTTTT
TATCAGAAAAGGATCGGAAAAGAATTTTGATAACAGGAGGCGCAGGGTTCGTGGGCTCCCATCTAACTGACAAA
CTCATGATGGACGGCCACGAGGTGACCGTGGTGGACAATTTCTTCACGGGCAGGAAGAGAAACGTGGAGCACTG
GATCGGACATGAGAACTTCGAGTTGATTAACCACGACGTGGTGGAGCCCCTCTACATCGAGGTTGACCAGATAT
ACCATCTGGCATCTCCAGCCTCCCCTCCAAACTACATGTATAATCCTATCAAGACATTAAAGACCAATACGATT
GGGACATTAAACATGTTGGGGCTGGCAAAACGAGTCGGTGCCCGTCTGCTCCTGGCCTCCACATCGGAGGTGTA
TGGAGATCCTGAAGTCCACCCTCAAAGTGAGGATTACTGGGGCCACGTGAATCCAATAGGACCTCGGGCCTGCT
ACGATGAAGGCAAACGTGTTGCAGAGACCATGTGCTATGCCTACATGAAGCAGGAAGGCGTGGAAGTGCGAGTG
GCCAGAATCTTCAACACCTTTGGGCCACGCATGCACATCAACGATGGGCGAGTAGTCAGCAACTTCATCCTGCA
GGCGCTCCAGGGGGAGCCACTCACGGTATACGGATCCGGGTCTCAGACAAGGGCGTTCCAGTACGTCAGCGATC
TAGTGAATGGCCTCGTGGCTCTCATGAACAGCAACGTCAGCAGCCCGGTCAACCTGGGGAACCCAGAAGAACAC
ACAATCCTAGAATTTGCTCAGTTAATTAAAAACCTTGTTGGTAGCGGAAGTGAAATTCAGTTTCTCTCCGAAGC
CCAGGATGACCCACAGAAAAGAAAACCAGACATCAAAAAAGCAAAGCTGATGCTGGGGTGGGAGCCCGTGGTCC
CGCTGGAGGAAGGTTTAAACAAAGCAATTCACTACTTCCGTAAAGAACTCGAGTACCAGGCAAATAATCAGTAC
ATCCCCAAACCAAAGCCTGCCAGAATAAAGAAAGGACGGACTCGCCACAGCTGAACTCCTCACTTTTAGGACAC
AAGACTACCATTGTACACTTGATGGGATGTATTTTTGGCTTTTTTTTGTTGTCGTTTAAAGAAAGACTTTAACA
GGTGTCATGAAGAACAAACTGGAATTTCATTCTGAAGCTTGCTTTAATGAAATGGATGTGCCTAAAAGCTCCCC
TCAAAAAACTGCAGATTTTGCCTTGCACTTTTTGAATCTCTCTTTTTATGTAAAATAGCGTAGATGCATCTCTG
CGTATTTTCAAGTTTTTTTATCTTGCTGTGAGAGCATATGTTGTGACTGTCGTTGACAGTTTTATTTACTGGTT
TCTTTGTGAAGCTGAAAAGGAACATTAAGCGGGACAAAAAATGCCGATTTTATTTATAAAAGTGGGTACTTAAT
AAATGAGTCGTTATACTATGCATAAAGAAAAATCCTAGCAGTATTGTCAGGTGGTGGTGCGCCGGCATTGATTT
TAGGGCAGATAAAAGAATTCTGTGTGAGAGCTTTATGTTTCTCTTTTAATTCAGAGTTTTTCCAAGGTCTACTT
TTGAGTTGCAAACTTGACTTTGAAATATTCCTGTTGGTCATGATCAAGGATATTTGAAATCACTACTGTGTTTT
GCTGCGTATCTGGGGCGGGGGCAGGTTGGGGGGCACAAAGTTAACATATTCTTGGTTAACCATGGTTAAATATG
CTATTTTAATAAAATATTGAAACTCA

FIGURE 240

MVSKALLRLVSAVNRRRMKLLLGIALLAYVASVWGNFVNMRSIQENGELKIESKIEEMVEPL
REKIRDLEKSFTQKYPPVKFLSEKDRKRILITGGAGFVGSHLTDKLMMDGHEVTVVDNFFTG
RKRNVEHWIGHENFELINHDVVEPLYIEVDQIYHLASPASPPNYMYNPIKTLKTNTIGTLNM
LGLAKRVGARLLLASTSEVYGDPEVHPQSEDYWGHVNPIGPRACYDEGKRVAETMCYAYMKQ
EGVEVRVARIFNTFGPRMHMNDGRVVSNFILQALQGEPLTVYGSGSQTRAFQYVSDLVNGLV
ALMNSNVSSPVNLGNPEEHTILEFAQLIKNLVGSGSEIQFLSEAQDDPQKRKPDIKKAKLML
GWEPVVPLEEGLNKAIHYFRKELEYQANNQYIPKPKPARIKKGRTRHS

Important features:
Signal peptide:
amino acids 1-32

N-glycosylation site:
amino acids 316-320

Tyrosine kinase phosphorylation site:
amino acids 235-244

N-myristoylation sites:
amino acids 35-41,101-107,383-389

Amidation sites:
amino acids 123-127,233-237

FIGURE 241

GCCCGGTGGAGAATTAGGTGCTGCTGGGAGCTCCTGCCTCCCACAGGATTCCAGCTGCAGGG
AGCCTCAGGGACTCTGGGCCGCACGGAGTTGGGGGCATTCCCCAGAGAGCGTCGCCATGGTC
TGCAGGGAGCAGTTATCAAAGAATCAGGTCAAGTGGGTGTTTGCCGGCATTACCTGTGTGTC
TGTGGTGGTCATTGCCGCAATAGTCCTTGCCATCACCCTGCGGCGGCCAGGCTGTGAGCTGG
AGGCCTGCAGCCCTGATGCCGACATGCTGGACTACCTGCTGAGCCTGGGCCAGATCAGCCGG
CGAGATGCCTTGGAGGTCACCTGGTACCACGCAGCCAACAGCAAGAAAGCCATGACAGCTGC
CCTGAACAGCAACATCACAGTCCTGGAGGCTGACGTCAATGTAGAAGGGCTCGGCACAGCCA
ATGAGACAGGAGTTCCCATCATGGCACACCCCCCCACTATCTACAGTGACAACACACTGGAG
CAGTGGCTGGACGCTGTGCTGGGCTCTTCCCAAAAGGGCATCAAACTGGACTTCAAGAACAT
CAAGGCAGTGGGCCCCTCCCTGGACCTCCTGCGGCAGCTGACAGAGGAAGGCAAAGTCCGGC
GGCCCATATGGATCAACGCTGACATCTTAAAGGGCCCCAACATGCTCATCTCAACTGAGGTC
AATGCCACACAGTTCCTGGCCCTGGTCCAGGAGAAGTATCCCAAGGCTACCCTATCTCCAGG
CTGGACCACCTTCTACATGTCCACGTCCCCAAACAGGACGTACACCCAAGCCATGGTGGAGA
AGATGCACGAGCTGGTGGGAGGAGTGCCCCAGAGGGTCACCTTCCCTGTACGGTCTTCCATG
GTGCGGGCTGCCTGGCCCCACTTCAGCTGGCTGCTGAGCCAATCTGAGAGGTACAGCCTGAC
GCTGTGGCAGGCTGCCTCGGACCCCATGTCGGTGGAAGATCTGCTCTACGTCCGGGATAACA
CTGCTGTCCACCAAGTCTACTATGACATCTTTGAGCCTCTCCTGTCACAGTTCAAGCAGCTG
GCCTTGAATGCCACACGGAAACCAATGTACTACACGGGAGGCAGCCTGATCCCTCTTCTCCA
GCTGCCTGGGGATGACGGTCTGAATGTGGAGTGGCTGGTTCCTGACGTCCAGGGCAGCGGTA
AAACAGCAACAATGACCCTCCCAGACACAGAAGGCATGATCCTGCTGAACACTGGCCTCGAG
GGAACTGTGGCTGAAAACCCCGTGCCCATTGTTCATACTCCAAGTGGCAACATCCTGACGCT
GGAGTCCTGCCTGCAGCAGCTGGCCACACATCCCGGACACTGGGGCATCCATTTGCAAATAG
TGGAGCCCGCAGCCCTCCGGCCATCCCTGGCCTTGCTGGCACGCCTCTCCAGCCTTGGCCTC
TTGCATTGGCCTGTGTGGGTTGGGGCCAAAATCTCCCACGGGAGTTTTTCGGTCCCCGGCCA
TGTGGCTGGCAGAGAGCTGCTTACAGCTGTGGCTGAGGTCTTCCCCCACGTGACTGTGGCAC
CAGGCTGGCCTGAGGAGGTGCTGGGCAGTGGCTACAGGGAACAGCTGCTCACAGATATGCTA
GAGTTGTGCCAGGGGCTCTGGCAACCTGTGTCCTTCCAGATGCAGGCCATGCTGCTGGGCCA
CAGCACAGCTGGAGCCATAGGCAGGCTGCTGGCATCCTCCCCCCGGGCCACCGTCACAGTGGAG
CACAACCCAGCTGGGGGCGACTATGCCTCTGTGAGGACAGCATTGCTGGCAGCTAGGGCTGT
GGACAGGACCCGAGTCTACTACAGGCTACCCCAGGGCTACCACAAGGACTTGCTGGCTCATG
TTGGTAGAAACTGAGCACCCAGGGGTGGTGGGCCAGCGGACCTCAGGGCGGAGGCTTCCCAC
GGGGAGGCAGGAAGAAATAAAGGTCTTTGGCTTTCTCCAGGCAAAAAAAAAAAAAAAAAAAA
AAAAAAAAAAAAAAAAAAAAAAAAAAAAAAAAAAAAAAAAAG

FIGURE 242

></usr/seqdb2/sst/DNA/Dnaseqs.min/ss.DNA119514
><subunit 1 of 1, 585 aa, 1 stop
><MW: 64056, pI: 6.58, NX(S/T): 5
MVCREQLSKNQVKWVFAGITCVSVVVIAAIVLAITLRRPGCELEACSPDADMLDYLLSLG
QISRRDALEVTWYHAANSKKAMTAALNSNITVLEADVNVEGLGTANETGVPIMAHPPTIY
SDNTLEQWLDAVLGSSQKGIKLDFKNIKAVGPSLDLLRQLTEEGKVRRPIWINADILKGP
NMLISTEVNATQFLALVQEKYPKATLSPGWTTFYMSTSPNRTYTQAMVEKMHELVGGVPQ
RVTFPVRSSMVRAAWPHFSWLLSQSERYSLTLWQAASDPMSVEDLLYVRDNTAVHQVYYD
IFEPLLSQFKQLALNATRKPMYYTGGSLIPLLQLPGDDGLNVEWLVPDVQGSGKTATMTL
PDTEGMILLNTGLEGTVAENPVPIVHTPSGNILTLESCLQQLATHPGHWGIHLQIVEPAA
LRPSLALLARLSSLGLLHWPVWVGAKISHGSFSVPGHVAGRELLTAVAEVFPHVTVAPGW
PEEVLGSGYREQLLTDMLELCQGLWQPVSFQMQAMLLGHSTAGAIGRLLASSPRATVTVE
HNPAGGDYASVRTALLAARAVDRTRVYYRLPQGYHKDLLAHVGRN

Important features of the protein:
Transmembrane domain:
Amino acids 18-37 (Possible type II)

N-glycosylation sites:
Amino acids 89-93;106-110;189-193;220-224;315-319

Tyrosine kinase phosphorylation site:
Amino acids 65-74

N-myristoylation sites:
Amino acids 101-107;351-357;372-378;390-396;444-450;545-551

Aminotransferases class-V pyridoxal-phosphate attachment site:
Amino acids 312-330

FIGURE 243

CTTCAGAACAGGTTCTCCTTCCCCAGTCACCAGTTGCTCGAGTTAGAATTGTCTGCAATGGC
CGCCCTGCAGAAATCTGTGAGCTCTTTCCTTATGGGGACCCTGGCCACCAGCTGCCTCCTTC
TCTTGGCCCTCTTGGTACAGGGAGGAGCAGCTGCGCCCATCAGCTCCCACTGCAGGCTTGAC
AAGTCCAACTTCCAGCAGCCCTATATCACCAACCGCACCTTCATGCTGGCTAAGGAGGCTAG
CTTGGCTGATAACAACACAGACGTTCGTCTCATTGGGGAGAAACTGTTCCACGGAGTCAGTA
TGAGTGAGCGCTGCTATCTGATGAAGCAGGTGCTGAACTTCACCCTTGAAGAAGTGCTGTTC
CCTCAATCTGATAGGTTCCAGCCTTATATGCAGGAGGTGGTGCCCTTCCTGGCCAGGCTCAG
CAACAGGCTAAGCACATGTCATATTGAAGGTGATGACCTGCATATCCAGAGGAATGTGCAAA
AGCTGAAGGACACAGTGAAAAAGCTTGGAGAGAGTGGAGAGATCAAAGCAATTGGAGAACTG
GATTTGCTGTTTATGTCTCTGAGAAATGCCTGCATTTGACCAGAGCAAAGCTGAAAAATGAA
TAACTAACCCCCTTTCCCTGCTAGAAATAACAATTAGATGCCCCAAAGCGATTTTTTTTAAC
CAAAAGGAAGATGGGAAGCCAAACTCCATCATGATGGGTGGATTCCAAATGAACCCCTGCGT
TAGTTACAAAGGAAACCAATGCCACTTTTGTTTATAAGACCAGAAGGTAGACTTTCTAAGCA
TAGATATTTATTGATAACATTTCATTGTAACTGGTGTTCTATACACAGAAAACAATTTATTT
TTTAAATAATTGTCTTTTTCCATAAAAAAGATTACTTTCCATTCCTTTAGGGGAAAAAACCC
CTAAATAGCTTCATGTTTCCATAATCAGTACTTTATATTTATAAATGTATTTATTATTATTA
TAAGACTGCATTTTATTTATATCATTTTATTAATATGGATTTATTTATAGAAACATCATTCG
ATATTGCTACTTGAGTGTAAGGCTAATATTGATATTTATGACAATAATTATAGAGCTATAAC
ATGTTTATTTGACCTCAATAAACACTTGGATATCCC

FIGURE 244

MAALQKSVSSFLMGTLATSCLLLLALLVQGGAAAPISSHCRLDKSNFQQPYITNRTFMLAKE
ASLADNNTDVRLIGEKLFHGVSMSERCYLMKQVLNFTLEEVLFPQSDRFQPYMQEVVPFLAR
LSNRLSTCHIEGDDLHIQRNVQKLKDTVKKLGESGEIKAIGELDLLFMSLRNACI

Important features of the protein:
Signal peptide:
amino acids 1-33

N-glycosylation sites.
amino acids 54-58, 68-72, 97-101

N-myristoylation sites.
amino acids 14-20, 82-88

Prokaryotic membrane lipoprotein lipid attachment site.
amino acids 10-21

POLYNUCLEOTIDE OVEREXPRESSED IN TUMORS

Matter enclosed in heavy brackets [ ] appears in the original patent but forms no part of this reissue specification; matter printed in italics indicates the additions made by reissue.

RELATED APPLICATIONS

This is a continuation application claiming priority under 35 USC §120 to U.S. Ser. No. 10/119,480 filed Apr. 9, 2002, which is a continuation under 35 USC §120 of international application PCT/US01/21066 filed Jun. 29, 2001, which is a continuation-in-part of international application PCT/US01/17800 filed Jun. 1, 2001.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF THE INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 10 nucleotides in length, alternatively at least about 15 nucleotides in length, alternatively at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, E. coli, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

In yet other embodiments, the present invention is directed to methods of using the PRO polypeptides of the present invention for a variety of uses based upon the functional biological assay data presented in the Examples below.

BRIEF DESCRIPTION OF THE DRAWINGS

FIGS. 1A–1B show a nucleotide sequence (SEQ ID NO:1) of a native sequence PRO6004 cDNA, wherein SEQ ID NO:1 is a clone designated herein as "DNA92259".

FIG. 2 shows the amino acid sequence (SEQ ID NO:2) derived from the coding sequence of SEQ ID NO:1 shown in FIGS. 1A–1B.

FIG. 3 shows a nucleotide sequence (SEQ ID NO:3) of a native sequence PRO4981 cDNA, wherein SEQ ID NO:3 is a clone designated herein as "DNA94849-2960".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO7174 cDNA, wherein SEQ ID NO:5 is a clone designated herein as "DNA96883-2745".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO5778 cDNA, wherein SEQ ID NO:7 is a clone designated herein as "DNA96894-2675".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO4332 cDNA, wherein SEQ ID NO:9 is a clone designated herein as "DNA100272-2969".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO9799 cDNA, wherein SEQ ID NO:11 is a clone designated herein as "DNA108696-2966".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO9909 cDNA, wherein SEQ ID NO:13 is a clone designated herein as "DNA117935-2801".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO9917 cDNA, wherein SEQ ID NO:15 is a clone designated herein as "DNA119474-2803".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO9771 cDNA, wherein SEQ ID NO:17 is a clone designated herein as "DNA119498-2965".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO9877 cDNA, wherein SEQ ID NO:19 is a clone designated herein as "DNA119502-2789".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO9903 cDNA, wherein SEQ ID NO:21 is a clone designated herein as "DNA119516-2797".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO9830 cDNA, wherein SEQ ID NO:23 is a clone designated herein as "DNA119530-2968".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO7155 cDNA, wherein SEQ ID NO:25 is a clone designated herein as "DNA121772-2741".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO9862 cDNA, wherein SEQ ID NO:27 is a clone designated herein as "DNA125148-2782".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO9882 cDNA, wherein SEQ ID NO:29 is a clone designated herein as "DNA125150-2793".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO9864 cDNA, wherein SEQ ID NO:31 is a clone designated herein as "DNA125151-2784".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO10013 cDNA, wherein SEQ ID NO:33 is a clone designated herein as "DNA125181-2804".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO9885 cDNA, wherein SEQ ID NO:35 is a clone designated herein as "DNA125192-2794".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO9879 cDNA, wherein SEQ ID NO:37 is a clone designated herein as "DNA125196-2792".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO10111 cDNA, wherein SEQ ID NO:39 is a clone designated herein as "DNA125200-2810".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO9925 cDNA, wherein SEQ ID NO:41 is a clone designated herein as "DNA125214-2814".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO9905 cDNA, wherein SEQ ID NO:43 is a clone designated herein as "DNA125219-2799".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO10276 cDNA, wherein SEQ ID NO:45 is a clone designated herein as "DNA128309-2825".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO9898 cDNA, wherein SEQ ID NO:47 is a clone designated herein as "DNA129535-2796".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO9904 cDNA, wherein SEQ ID NO:49 is a clone designated herein as "DNA129549-2798".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO19632 cDNA, wherein SEQ ID NO:51 is a clone designated herein as "DNA129580-2863".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO19672 cDNA, wherein SEQ ID NO:53 is a clone designated herein as "DNA129794-2967".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO9783 cDNA, wherein SEQ ID NO:55 is a clone designated herein as "DNA131590-2962".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO10112 cDNA, wherein SEQ ID NO:57 is a clone designated herein as "DNA135173-2811".

FIG. 58 shows the amino acid sequence (SEQ ID NO:58) derived from the coding sequence of SEQ ID NO:57 shown in FIG. 57.

FIGS. 59A–59B show a nucleotide sequence (SEQ ID NO:59) of a native sequence PRO10284 cDNA, wherein SEQ ID NO:59 is a clone designated herein as "DNA138039-2828".

FIG. 60 shows the amino acid sequence (SEQ ID NO:60) derived from the coding sequence of SEQ ID NO:59 shown in FIGS. 59A–59B.

FIG. 61 shows a nucleotide sequence (SEQ ID NO:61) of a native sequence PRO10100 cDNA, wherein SEQ ID NO:61 is a clone designated herein as "DNA139540-2807".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO19628 cDNA, wherein SEQ ID NO:63 is a clone designated herein as "DNA139602-2859".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO19684 cDNA, wherein SEQ ID NO:65 is a clone designated herein as "DNA139632-2880".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO10274 cDNA, wherein SEQ ID NO:67 is a clone designated herein as "DNA139686-2823".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO9907 cDNA, wherein SEQ ID NO:69 is a clone designated herein as "DNA142392-2800".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO9873 cDNA, wherein SEQ ID NO:71 is a clone designated herein as "DNA143076-2787".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO10201 cDNA, wherein SEQ ID NO:73 is a clone designated herein as "DNA143294-2818".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO10200 cDNA, wherein SEQ ID NO:75 is a clone designated herein as "DNA143514-2817".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO10196 cDNA, wherein SEQ ID NO:77 is a clone designated herein as "DNA144841-2816".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO10282 cDNA, wherein SEQ ID NO:79 is a clone designated herein as "DNA148380-2827".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO19650 cDNA, wherein SEQ ID NO:81 is a clone designated herein as "DNA149995-2871".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO21184 cDNA, wherein SEQ ID NO:83 is a clone designated herein as "DNA167678-2963".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO21201 cDNA, wherein SEQ ID NO:85 is a clone designated herein as "DNA168028-2956".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO21175 cDNA, wherein SEQ ID NO:87 is a clone designated herein as "DNA173894-2947".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO21340 cDNA, wherein SEQ ID NO:89 is a clone designated herein as "DNA176775-2957".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO21384cDNA, wherein SEQ ID NO:91 is a clone designated herein as "DNA177313-2982".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO982 cDNA, wherein SEQ ID NO:93 is a clone designated herein as "DNA57700-1408".

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO1160 cDNA, wherein SEQ ID NO:95 is a clone designated herein as "DNA62872-1509".

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO1187 cDNA, wherein SEQ ID NO:97 is a clone designated herein as "DNA62876-1517".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO1329 cDNA, wherein SEQ ID NO:99 is a clone designated herein as "DNA66660-1585".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO231 cDNA, wherein SEQ ID NO:101 is a clone designated herein as "DNA34434-1139".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO357 cDNA, wherein SEQ ID NO:103 is a clone designated herein as "DNA44804-1248".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO725 cDNA, wherein SEQ ID NO:105 is a clone designated herein as "DNA52758-1399".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO1155 cDNA, wherein SEQ ID NO:107 is a clone designated herein as "DNA59849-1504".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO1306 cDNA, wherein SEQ ID NO:109 is a clone designated herein as "DNA65410-1569".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO1419 cDNA, wherein SEQ ID NO:111 is a clone designated herein as "DNA71290-1630".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO229 cDNA, wherein SEQ ID NO:113 is a clone designated herein as "DNA33100-1159".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO1272 cDNA, wherein SEQ ID NO:115 is a clone designated herein as "DNA64896-1539".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO4405 cDNA, wherein SEQ ID NO:117 is a clone designated herein as "DNA84920-2614".

FIG. 118 shows the amino acid sequence (SEQ ID NO:118) derived from the coding sequence of SEQ ID NO:117 shown in FIG. 117.

FIG. 119 shows a nucleotide sequence (SEQ ID NO:119) of a native sequence PRO181 cDNA, wherein SEQ ID NO:119 is a clone designated herein as "DNA23330-1390".

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO214 cDNA, wherein SEQ ID NO:121 is a clone designated herein as "DNA32286-1191".

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO247 cDNA, wherein SEQ ID NO:123 is a clone designated herein as "DNA35673-1201".

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO337 cDNA, wherein SEQ ID NO:125 is a clone designated herein as "DNA43316-1237".

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO526 cDNA, wherein SEQ ID NO:127 is a clone designated herein as "DNA44184-1319".

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO363 cDNA, wherein SEQ ID NO:129 is a clone designated herein as "DNA45419-1252".

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO531 cDNA, wherein SEQ ID NO:131 is a clone designated herein as "DNA48314-1320".

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO1083 cDNA, wherein SEQ ID NO:133 is a clone designated herein as "DNA50921-1458".

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO840 cDNA, wherein SEQ ID NO:135 is a clone designated herein as "DNA53987".

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO1080 cDNA, wherein SEQ ID NO:137 is a clone designated herein as "DNA56047-1456".

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO788 cDNA, wherein SEQ ID NO:139 is a clone designated herein as "DNA56405-1357".

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO1478 cDNA, wherein SEQ ID NO:141 is a clone designated herein as "DNA56531-1648".

FIG. 142 shows the amino acid sequence (SEQ ID NO:142) derived from the coding sequence of SEQ ID NO:141 shown in FIG. 141.

FIG. 143 shows a nucleotide sequence (SEQ ID NO:143) of a native sequence PRO1134 cDNA, wherein SEQ ID NO:143 is a clone designated herein as "DNA56865-1491".

FIG. 144 shows the amino acid sequence (SEQ ID NO:144) derived from the coding sequence of SEQ ID NO:143 shown in FIG. 143.

FIG. 145 shows a nucleotide sequence (SEQ ID NO:145) of a native sequence PRO826 cDNA, wherein SEQ ID NO:145 is a clone designated herein as "DNA57694-1341".

FIG. 146 shows the amino acid sequence (SEQ ID NO:146) derived from the coding sequence of SEQ ID NO:145 shown in FIG. 145.

FIG. 147 shows a nucleotide sequence (SEQ ID NO:147) of a native sequence PRO1005 cDNA, wherein SEQ ID NO:147 is a clone designated herein as "DNA57708-1411".

FIG. 148 shows the amino acid sequence (SEQ ID NO:148) derived from the coding sequence of SEQ ID NO:147 shown in FIG. 147.

FIG. 149 shows a nucleotide sequence (SEQ ID NO:149) of a native sequence PRO809 cDNA, wherein SEQ ID NO:149 is a clone designated herein as "DNA57836-1338".

FIG. 150 shows the amino acid sequence (SEQ ID NO:150) derived from the coding sequence of SEQ ID NO:149 shown in FIG. 149.

FIG. 151 shows a nucleotide sequence (SEQ ID NO:151) of a native sequence PRO1194 cDNA, wherein SEQ ID NO:151 is a clone designated herein as "DNA57841-1522".

FIG. 152 shows the amino acid sequence (SEQ ID NO:152) derived from the coding sequence of SEQ ID NO:151 shown in FIG. 151.

FIG. 153 shows a nucleotide sequence (SEQ ID NO:153) of a native sequence PRO1071 cDNA, wherein SEQ ID NO:153 is a clone designated herein as "DNA58847-1383".

FIG. 154 shows the amino acid sequence (SEQ ID NO:154) derived from the coding sequence of SEQ ID NO:153 shown in FIG. 153.

FIG. 155 shows a nucleotide sequence (SEQ ID NO:155) of a native sequence PRO1411 cDNA, wherein SEQ ID NO:155 is a clone designated herein as "DNA59212-1627".

FIG. 156 shows the amino acid sequence (SEQ ID NO:156) derived from the coding sequence of SEQ ID NO:155 shown in FIG. 155.

FIG. 157 shows a nucleotide sequence (SEQ ID NO:157) of a native sequence PRO1309 cDNA, wherein SEQ ID NO:157 is a clone designated herein as "DNA59588-1571".

FIG. 158 shows the amino acid sequence (SEQ ID NO:158) derived from the coding sequence of SEQ ID NO:157 shown in FIG. 157.

FIG. 159 shows a nucleotide sequence (SEQ ID NO:159) of a native sequence PRO1025 cDNA, wherein SEQ ID NO:159 is a clone designated herein as "DNA59622-1334".

FIG. 160 shows the amino acid sequence (SEQ ID NO:160) derived from the coding sequence of SEQ ID NO:159 shown in FIG. 159.

FIG. 161 shows a nucleotide sequence (SEQ ID NO:161) of a native sequence PRO1181 cDNA. wherein SEQ ID NO:161 is a clone designated herein as "DNA59847-2510".

FIG. 162 shows the amino acid sequence (SEQ ID NO:162) derived from the coding sequence of SEQ ID NO:161 shown in FIG. 161.

FIG. 163 shows a nucleotide sequence (SEQ ID NO:163) of a native sequence PRO1126 cDNA, wherein SEQ ID NO:163 is a clone designated herein as "DNA60615-1483".

FIG. 164 shows the amino acid sequence (SEQ ID NO:164) derived from the coding sequence of SEQ ID NO:163 shown in FIG. 163.

FIG. 165 shows a nucleotide sequence (SEQ ID NO:165) of a native sequence PRO1186 cDNA, wherein SEQ ID NO:165 is a clone designated herein as "DNA60621-1516".

FIG. 166 shows the amino acid sequence (SEQ ID NO:166) derived from the coding sequence of SEQ ID NO:165 shown in FIG. 165.

FIG. 167 shows a nucleotide sequence (SEQ ID NO:167) of a native sequence PRO1192 cDNA, wherein SEQ ID NO:167 is a clone designated herein as "DNA62814-1521".

FIG. 168 shows the amino acid sequence (SEQ ID NO:168) derived from the coding sequence of SEQ ID NO:167 shown in FIG. 167.

FIG. 169 shows a nucleotide sequence (SEQ ID NO:169) of a native sequence PRO1244 cDNA, wherein SEQ ID NO:169 is a clone designated herein as "DNA64883-1526".

FIG. 170 shows the amino acid sequence (SEQ ID NO:170) derived from the coding sequence of SEQ ID NO:169 shown in FIG. 169.

FIG. 171 shows a nucleotide sequence (SEQ ID NO:171) of a native sequence PRO1274 cDNA, wherein SEQ ID NO:171 is a clone designated herein as "DNA64889-1541".

FIG. 172 shows the amino acid sequence (SEQ ID NO:172) derived from the coding sequence of SEQ ID NO:171 shown in FIG. 171.

FIG. 173 shows a nucleotide sequence (SEQ ID NO:173) of a native sequence PRO1412 cDNA, wherein SEQ ID NO:173 is a clone designated herein as "DNA64897-1628".

FIG. 174 shows the amino acid sequence (SEQ ID NO:174) derived from the coding sequence of SEQ ID NO:173 shown in FIG. 173.

FIG. 175 shows a nucleotide sequence (SEQ ID NO:175) of a native sequence PRO1286 cDNA, wherein SEQ ID NO:175 is a clone designated herein as "DNA64903-1553".

FIG. 176 shows the amino acid sequence (SEQ ID NO:176) derived from the coding sequence of SEQ ID NO:175 shown in FIG. 175.

FIG. 177 shows a nucleotide sequence (SEQ ID NO:177) of a native sequence PRO1330 cDNA, wherein SEQ ID NO:177 is a clone designated herein as "DNA64907-1163-1".

FIG. 178 shows the amino acid sequence (SEQ ID NO:178) derived from the coding sequence of SEQ ID NO:177 shown in FIG. 177.

FIG. 179 shows a nucleotide sequence (SEQ ID NO:179) of a native sequence PRO1347 cDNA, wherein SEQ ID NO:179 is a clone designated herein as "DNA64950-1590".

FIG. 180 shows the amino acid sequence (SEQ ID NO:180) derived from the coding sequence of SEQ ID NO:179 shown in FIG. 179.

FIG. 181 shows a nucleotide sequence (SEQ ID NO:181) of a native sequence PRO1305 cDNA, wherein SEQ ID NO:181 is a clone designated herein as "DNA64952-1568".

FIG. 182 shows the amino acid sequence (SEQ ID NO:182) derived from the coding sequence of SEQ ID NO:181 shown in FIG. 181.

FIG. 183 shows a nucleotide sequence (SEQ ID NO:183) of a native sequence PRO1273 cDNA, wherein SEQ ID NO:183 is a clone designated herein as "DNA65402-1540".

FIG. 184 shows the amino acid sequence (SEQ ID NO:184) derived from the coding sequence of SEQ ID NO:183 shown in FIG. 183.

FIG. 185 shows a nucleotide sequence (SEQ ID NO:185) of a native sequence PRO1279 cDNA, wherein SEQ ID NO:185 is a clone designated herein as "DNA65405-1547".

FIG. 186 shows the amino acid sequence (SEQ ID NO:186) derived from the coding sequence of SEQ ID NO:185 shown in FIG. 185.

FIG. 187 shows a nucleotide sequence (SEQ ID NO:187) of a native sequence PRO1340 cDNA, wherein SEQ ID NO:187 is a clone designated herein as "DNA66663-1598".

FIG. 188 shows the amino acid sequence (SEQ ID NO:188) derived from the coding sequence of SEQ ID NO:187 shown in FIG. 187.

FIG. 189 shows a nucleotide sequence (SEQ ID NO:189) of a native sequence PRO1338 cDNA, wherein SEQ ID NO:189 is a clone designated herein as "DNA66667".

FIG. 190 shows the amino acid sequence (SEQ ID NO:190) derived from the coding sequence of SEQ ID NO:189 shown in FIG. 189.

FIG. 191 shows a nucleotide sequence (SEQ ID NO:191) of a native sequence PRO1343 cDNA, wherein SEQ ID NO:191 is a clone designated herein as "DNA66675-1587".

FIG. 192 shows the amino acid sequence (SEQ ID NO:192) derived from the coding sequence of SEQ ID NO:191 shown in FIG. 191.

FIG. 193 shows a nucleotide sequence (SEQ ID NO:193) of a native sequence PRO1376 cDNA, wherein SEQ ID NO:193 is a clone designated herein as "DNA67300-1605".

FIG. 194 shows the amino acid sequence (SEQ ID NO:194) derived from the coding sequence of SEQ ID NO:193 shown in FIG. 193.

FIG. 195 shows a nucleotide sequence (SEQ ID NO:195) of a native sequence PRO1387 cDNA, wherein SEQ ID NO:195 is a clone designated herein as "DNA68872-1620".

FIG. 196 shows the amino acid sequence (SEQ ID NO:196) derived from the coding sequence of SEQ ID NO:195 shown in FIG. 195.

FIG. 197 shows a nucleotide sequence (SEQ ID NO:197) of a native sequence PRO1409 cDNA, wherein SEQ ID NO:197 is a clone designated herein as "DNA71269-1621".

FIG. 198 shows the amino acid sequence (SEQ ID NO:198) derived from the coding sequence of SEQ ID NO:197 shown in FIG. 197.

FIG. 199 shows a nucleotide sequence (SEQ ID NO:199) of a native sequence PRO1488 cDNA, wherein SEQ ID NO:199 is a clone designated herein as "DNA73736-1657".

FIG. 200 shows the amino acid sequence (SEQ ID NO:200) derived from the coding sequence of SEQ ID NO:199 shown in FIG. 199.

FIG. 201 shows a nucleotide sequence (SEQ ID NO:201) of a native sequence PRO1474 cDNA, wherein SEQ ID NO:201 is a clone designated herein as "DNA73739-1645".

FIG. 202 shows the amino acid sequence (SEQ ID NO:202) derived from the coding sequence of SEQ ID NO:201 shown in FIG. 201.

FIG. 203 shows a nucleotide sequence (SEQ ID NO:203) of a native sequence PRO1917 cDNA, wherein SEQ ID NO:203 is a clone designated herein as "DNA76400-2528".

FIG. 204 shows the amino acid sequence (SEQ ID NO:204) derived from the coding sequence of SEQ ID NO:203 shown in FIG. 203.

FIG. 205 shows a nucleotide sequence (SEQ ID NO:205) of a native sequence PRO1760 cDNA, wherein SEQ ID NO:205 is a clone designated herein as "DNA76532-1702".

FIG. 206 shows the amino acid sequence (SEQ ID NO:206) derived from the coding sequence of SEQ ID NO:205 shown in FIG. 205.

FIG. 207 shows a nucleotide sequence (SEQ ID NO:207) of a native sequence PRO1567 cDNA, wherein SEQ ID NO:207 is a clone designated herein as "DNA76541-1675".

FIG. 208 shows the amino acid sequence (SEQ ID NO:208) derived from the coding sequence of SEQ ID NO:207 shown in FIG. 207.

FIG. 209 shows a nucleotide sequence (SEQ ID NO:209) of a native sequence PRO1887 cDNA, wherein SEQ ID NO:209 is a clone designated herein as "DNA79862-2522".

FIG. 210 shows the amino acid sequence (SEQ ID NO:210) derived from the coding sequence of SEQ ID NO:209 shown in FIG. 209.

FIG. 211 shows a nucleotide sequence (SEQ ID NO:211) of a native sequence PRO1928 cDNA, wherein SEQ ID NO:211 is a clone designated herein as "DNA81754-2532".

FIG. 212 shows the amino acid sequence (SEQ ID NO:212) derived from the coding sequence of SEQ ID NO:211 shown in FIG. 211.

FIG. 213 shows a nucleotide sequence (SEQ ID NO:213) of a native sequence PRO4341 cDNA, wherein SEQ ID NO:213 is a clone designated herein as "DNA81761-2583".

FIG. 214 shows the amino acid sequence (SEQ ID NO:214) derived from the coding sequence of SEQ ID NO:213 shown in FIG. 213.

FIG. 215 shows a nucleotide sequence (SEQ ID NO:215) of a native sequence PRO5723 cDNA, wherein SEQ ID NO:215 is a clone designated herein as "DNA82361".

FIG. 216 shows the amino acid sequence (SEQ ID NO:216) derived from the coding sequence of SEQ ID NO:215 shown in FIG. 215.

FIG. 217 shows a nucleotide sequence (SEQ ID NO:217) of a native sequence PRO1801 cDNA, wherein SEQ ID NO:217 is a clone designated herein as "DNA83500-2506".

FIG. 218 shows the amino acid sequence (SEQ ID NO:218) derived from the coding sequence of SEQ ID NO:217 shown in FIG. 217.

FIG. 219 shows a nucleotide sequence (SEQ ID NO:219) of a native sequence PRO4333 cDNA, wherein SEQ ID NO:219 is a clone designated herein as "DNA84210-2576".

FIG. 220 shows the amino acid sequence (SEQ ID NO:220) derived from the coding sequence of SEQ ID NO:219 shown in FIG. 219.

FIG. 221 shows a nucleotide sequence (SEQ ID NO:221) of a native sequence PRO3543 cDNA, wherein SEQ ID NO:221 is a clone designated herein as "DNA86571-2551".

FIG. 222 shows the amino acid sequence (SEQ ID NO:222) derived from the coding sequence of SEQ ID NO:221 shown in FIG. 221.

FIG. 223 shows a nucleotide sequence (SEQ ID NO:223) of a native sequence PRO3444 cDNA, wherein SEQ ID NO:223 is a clone designated herein as "DNA87997".

FIG. 224 shows the amino acid sequence (SEQ ID NO:224) derived from the coding sequence of SEQ ID NO:223 shown in FIG. 223.

FIG. 225 shows a nucleotide sequence (SEQ ID NO:225) of a native sequence PRO4302 cDNA, wherein SEQ ID NO:225 is a clone designated herein as "DNA92218-2554".

FIG. 226 shows the amino acid sequence (SEQ ID NO:226) derived from the coding sequence of SEQ ID NO:225 shown in FIG. 225.

FIG. 227 shows a nucleotide sequence (SEQ ID NO:227) of a native sequence PRO4322 cDNA, wherein SEQ ID NO:227 is a clone designated herein as "DNA92223-2567".

FIG. 228 shows the amino acid sequence (SEQ ID NO:228) derived from the coding sequence of SEQ ID NO:227 shown in FIG. 227.

FIG. 229 shows a nucleotide sequence (SEQ ID NO:229) of a native sequence PRO5725 cDNA, wherein SEQ ID NO:229 is a clone designated herein as "DNA92265-2669".

FIG. 230 shows the amino acid sequence (SEQ ID NO:230) derived from the coding sequence of SEQ ID NO:229 shown in FIG. 229.

FIG. 231 shows a nucleotide sequence (SEQ ID NO:231) of a native sequence PRO4408 cDNA, wherein SEQ ID NO:231 is a clone designated herein as "DNA92274-2617".

FIG. 232 shows the amino acid sequence (SEQ ID NO:232) derived from the coding sequence of SEQ ID NO:231 shown in FIG. 231.

FIG. 233 shows a nucleotide sequence (SEQ ID NO:233) of a native sequence PRO9940 cDNA, wherein SEQ ID NO:223 is a clone designated herein as "DNA92282".

FIG. 234 shows the amino acid sequence (SEQ ID NO:234) derived from the coding sequence of SEQ ID NO:233 shown in FIG. 233.

FIG. 235 shows a nucleotide sequence (SEQ ID NO:235) of a native sequence PRO7154 cDNA, wherein SEQ ID NO:235 is a clone designated herein as "DNA108760-2740".

FIG. 236 shows the amino acid sequence (SEQ ID NO:236) derived from the coding sequence of SEQ ID NO:235 shown in FIG. 235.

FIG. 237 shows a nucleotide sequence (SEQ ID NO:237) of a native sequence PRO7425 cDNA, wherein SEQ ID NO:237 is a clone designated herein as "DNA108792-2753".

FIG. 238 shows the amino acid sequence (SEQ ID NO:238) derived from the coding sequence of SEQ ID NO:237 shown in FIG. 237.

FIG. 239 shows a nucleotide sequence (SEQ ID NO:239) of a native sequence PRO6079 cDNA, wherein SEQ ID NO:239 is a clone designated herein as "DNA111750-2706".

FIG. 240 shows the amino acid sequence (SEQ ID NO:240) derived from the coding sequence of SEQ ID NO:239 shown in FIG. 239.

FIG. 241 shows a nucleotide sequence (SEQ ID NO:241) of a native sequence PRO9836 cDNA, wherein SEQ ID NO:241 is a clone designated herein as "DNA119514-2772".

FIG. 242 shows the amino acid sequence (SEQ ID NO:242) derived from the coding sequence of SEQ ID NO:241 shown in FIG. 241.

FIG. 243 shows a nucleotide sequence (SEQ ID NO:243) of a native sequence PRO10096 cDNA, wherein SEQ ID NO:243 is a clone designated herein as "DNA125185-2806".

FIG. 244 shows the amino acid sequence (SEQ ID NO:244) derived from the coding sequence of SEQ ID NO:243 shown in FIG. 243.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention-individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1–6 (1997) and von Heinje et al., Nucl. Acids. Res. 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., Nucleic Acids Res. 25:3389–3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., Nucleic Acids Res. 25:3389–3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic gents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., Protein Eng. 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$–$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequence of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444–6448 (1993).

An "isolated" antibody is one which has been identified and separated and/or recovered from a component of its natural environment Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a polypeptide disclosed herein or an agonist or antagonist thereof is an amount sufficient to carry out a specifically stated purpose. An "effective amount" may be determined empirically and in a routine manner, in relation to the stated purpose.

Table 1

```
/*
 *
 * C-C increased from 12 to 15
 * Z is average of EQ
 * B is average of ND
 * match with stop is _M; stop-stop = 0; J (joker) match = 0
 */
#define  _M      -8        /* value of a match with a stop */

int      _day[26][26] = {
/*     A  B  C  D  E  F  G  H  I  J  K  L  M  N  O  P  Q  R  S  T  U  V  W  X  Y  Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M,_M, 0,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
 */
#include <stdio.h>
#include <ctype.h>

#define  MAXJMP        16      /* max jumps in a diag */
#define  MAXGAP        24      /* don't continue to penalize gaps larger than this */
#define  JMPS          1024    /* max jmps in an path */
#define  MX            4       /* save if there's at least MX-1 bases since last jmp */

#define  DMAT          3       /* value of matching bases */
#define  DMIS          0       /* penalty for mismatched bases */
#define  DINS0         8       /* penalty for a gap */
#define  DINS1         1       /* penalty per base */
#define  PINS0         8       /* penalty for a gap */
#define  PINS1         4       /* penalty per residue */

struct jmp {
        short           n[MAXJMP];      /* size of jmp (neg for dely) */
        unsigned short  x[MAXJMP];      /* base no. of jmp in seq x */
};                                      /* limits seq to 2^16 -1 */

struct diag {
        int             score;          /* score at last jmp */
        long            offset;         /* offset of prev block */
        short           ijmp;           /* current jmp index */
        struct jmp      jp;             /* list of jmps */
};

struct path {
        int     spc;            /* number of leading spaces */
        short   n[JMPS];/* size of jmp (gap) */
        int     x[JMPS];/* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */

char            *calloc(), *malloc(), *index(), *strcpy();
char            *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"

static	_dbval[26] = {
	1,14,2,13,0,0,4,11,0,0,12,0,3,15,0,0,0,5,6,8,8,7,9,0,10,0
};

static	_pbval[26] = {
	1, 2|(1<<('D'-'A'))|(1<<('N'-'A')), 4, 8, 16, 32, 64,
	128, 256, 0xFFFFFFFF, 1<<10, 1<<11, 1<<12, 1<<13, 1<<14,
	1<<15, 1<<16, 1<<17, 1<<18, 1<<19, 1<<20, 1<<21, 1<<22,
	1<<23, 1<<24, 1<<25|(1<<('E'-'A'))|(1<<('Q'-'A'))
};

main(ac, av)
	int	ac;
	char	*av[];
{
	prog = av[0];
	if (ac != 3) {
		fprintf(stderr, "usage: %s file1 file2\n", prog);
		fprintf(stderr, "where file1 and file2 are two dna or two protein sequences.\n");
		fprintf(stderr, "The sequences can be in upper- or lower-case\n");
		fprintf(stderr, "Any lines beginning with ';' or '<' are ignored\n");
		fprintf(stderr, "Output is in the file \"align.out\"\n");
		exit(1);
	}
	namex[0] = av[1];
	namex[1] = av[2];
	seqx[0] = getseq(namex[0], &len0);
	seqx[1] = getseq(namex[1], &len1);
	xbm = (dna)? _dbval : _pbval;

	endgaps = 0;		/* 1 to penalize endgaps */
	ofile = "align.out";	/* output file */

	nw();		/* fill in the matrix, get the possible jmps */
	readjmps();	/* get the actual jmps */
	print();	/* print stats, alignment */

	cleanup(0);	/* unlink any tmp files */
}
```

main

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                    nw
{
        char            *px, *py;       /* seqs and ptrs */
        int             *ndely, *dely;  /* keep track of dely */
        int             ndelx, delx;    /* keep track of delx */
        int             *tmp;           /* for swapping row0, row1 */
        int             mis;            /* score for each type */
        int             ins0, ins1;     /* insertion penalties */
        register        id;             /* diagonal index */
        register        ij;             /* jmp index */
        register        *col0, *col1;   /* score for curr, last row */
        register        xx, yy;         /* index into seqs */

        dx = (struct diag *)g_calloc("to get diags", len0+len1+1, sizeof(struct diag));

        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;

        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;

        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

        /* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

        /* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

        /* pick the maximum score; we're favoring
         * mis over any del and delx over dely
         */
```

Table 1 (cont')

...nw

```
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                         */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
}
(void) free((char *)ndely);
(void) free((char *)dely);
(void) free((char *)col0);
(void) free((char *)col1);                    }
```

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */

#include "nw.h"

#define SPC     3
#define P_LINE  256     /* maximum output line */
#define P_SPC   3       /* space between name or num and seq */

extern  _day[26][26];
int     olen;           /* set output line length */
FILE    *fx;            /* output file */

print()                                                                  print
{
        int     lx, ly, firstgap, lastgap;      /* overlap */

        if ((fx = fopen(ofile, "w")) == 0) {
                fprintf(stderr, "%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) { /* trailing gap in y */
                lastgap = dmax0 - (len0 - 1);
                ly -= lastgap;
        }
        getmat(lx, ly, firstgap, lastgap);
        pr_align();
}
```

Table 1 (cont')

```
/*
 * trace back the best path, count matches
 */
static
getmat(lx, ly, firstgap, lastgap)                                   getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1,

        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "< %d match%s in an overlap of %d: %.2f percent similarity\n",
                nm, (nm == 1)? "" : "es", lx, pct);
```

Table 1 (cont')

```
        fprintf(fx, "<gaps in first sequence: %d", gapx);                    ...getmat
        if (gapx) {
                (void) sprintf(outx, " (%d %s%s)",
                        ngapx, (dna)? "base":"residue", (ngapx == 1)? "":"s");
                fprintf(fx,"%s", outx);

        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}

static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
 * print alignment of described in struct path pp[]
 */
static
pr_align()                                                                   pr_align
{
        int             nn;     /* char count */
        int             more;
        register        i;

        for (i = 0, lmax = 0; i < 2; i++) {
                nn = stripname(namex[i]);
                if (nn > lmax)
                        lmax = nn;

                nc[i] = 1;
                ni[i] = 1;
                siz[i] = ij[i] = 0;
                ps[i] = seqx[i];
                po[i] = out[i];                 }
```

Table 1 (cont')

...pr_align

```
for (nn = nm = 0, more = 1; more; ) {
        for (i = more = 0; i < 2; i++) {
                /*
                 * do we have more of this sequence?
                 */
                if (!*ps[i])
                        continue;

                more++;

                if (pp[i].spc) {        /* leading space */
                        *po[i]++ = ' ';
                        pp[i].spc--;
                }
                else if (siz[i]) {      /* in a gap */
                        *po[i]++ = '-';
                        siz[i]--;
                }
                else {                  /* we're putting a seq element
                                         */
                        *po[i] = *ps[i];
                        if (islower(*ps[i]))
                                *ps[i] = toupper(*ps[i]);
                        po[i]++;
                        ps[i]++;

                        /*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}

/*
 * dump a block of lines, including numbers, stars: pr_align()
 */
static
dumpblock()
{
        register  i;

        for (i = 0; i < 2; i++)
                *po[i]-- = '\0';
```

dumpblock

Table 1 (cont')

...dumpblock

```
	(void) putc('\n', fx);
	for (i = 0; i < 2; i++) {
		if (*out[i] && (*out[i] != ' ' || *(po[i]) != ' ')) {
			if (i == 0)
				nums(i);
			if (i == 0 && *out[1])
				stars();
			putline(i);
			if (i == 0 && *out[1])
				fprintf(fx, star);
			if (i == 1)
				nums(i);
		}
	}
}

/*
 * put out a number line: dumpblock()
 */
static
nums(ix)
	int	ix;	/* index in out[] holding seq line */
{
	char		nline[P_LINE];
	register	i, j;
	register char	*pn, *px, *py;

	for (pn = nline, i = 0; i < lmax+P_SPC; i++, pn++)
		*pn = ' ';
	for (i = nc[ix], py = out[ix]; *py; py++, pn++) {
		if (*py == ' ' || *py == '-')
			*pn = ' ';
		else {
			if (i%10 == 0 || (i == 1 && nc[ix] != 1)) {
				j = (i < 0)? -i : i;
				for (px = pn; j; j /= 10, px--)
					*px = j%10 + '0';
				if (i < 0)
					*px = '-';
			}
			else
				*pn = ' ';
			i++;
		}
	}
	*pn = '\0';
	nc[ix] = i;
	for (pn = nline; *pn; pn++)
		(void) putc(*pn, fx);
	(void) putc('\n', fx);
}

/*
 * put out a line (name, [num], seq, [num]): dumpblock()
 */
static
putline(ix)
	int	ix;		{
```

nums putline

Table 1 (cont')

...putline

```
        int                     i;
        register char           *px;

        for (px = namex[ix], i = 0; *px && *px != ':'; px++, i++)
                (void) putc(*px, fx);
        for (; i < lmax+P_SPC; i++)
                (void) putc(' ', fx);

        /* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}


/*
 * put a line of stars (seqs always in out[0], out[1]): dumpblock()
 */
static
stars()
{
        int                     i;
        register char           *p0, *p1, cx, *px;

        if (!*out[0] || (*out[0] == ' ' && *(po[0]) == ' ') ||
           !*out[1] || (*out[1] == ' ' && *(po[1]) == ' '))
                return;
        px = star;
        for (i = lmax+P_SPC; i; i--)
                *px++ = ' ';

        for (p0 = out[0], p1 = out[1]; *p0 && *p1; p0++, p1++) {
                if (isalpha(*p0) && isalpha(*p1)) {

                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

stars

Table 1 (cont')

stripname

```
/*
 * strip path or prefix from pn, return len: pr_align()
 */
static
stripname(pn)
        char    *pn;    /* file name (may be path) */
{
        register char   *px, *py;

        py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
#include "nw.h"
#include <sys/file.h>

char    *jname = "/tmp/homgXXXXXX";             /* tmp file for jmps */
FILE    *fj;

int     cleanup();                              /* cleanup tmp file */
long    lseek();

/*
 * remove any tmp file if we blow
 */
cleanup(i)                                                          cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                   getseq
        char    *file;  /* file name */
        int     *len;   /* seq len */
{
        char            line[1024], *pseq;
        register char   *px, *py;
        int             natgc, tlen;
        FILE            *fp;

        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
        py = pseq + 4;
        *len = tlen;
        rewind(fp);

        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}

char    *
g_calloc(msg, nx, sz)
        char    *msg;           /* program, calling routine */
        int     nx, sz;         /* number and size of elements */
{
        char            *px, *calloc();

        if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
 * get final jmps from dx[] or tmp file, set pp[], reset dmax: main()
 */
readjmps()
{
        int             fd = -1;
        int             siz, i0, i1;
        register  i, j, xx;

        if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

g_calloc readjmps

Table 1 (cont')

...readjmps

```
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {                  /* gap in second seq */
                                pp[1].n[i1] = -siz;
                                xx += siz;
                                /* id = xx - yy + len1 - 1
                                 */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {  /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }

        /* reverse the order of jmps
         */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;
        }
        if (fd >= 0)
                (void) close(fd);
        if (fj) {
                (void) unlink(jname);
                fj = 0;
                offset = 0;
        }                                       }
```

Table 1 (cont')

writejmps

```
/*
 * write a filled jmp struct offset of the prev one (if any): nw()
 */
writejmps(ix)
        int     ix;
{
        char    *mktemp();

        if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; glu; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6): 547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; an α-tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc., 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding PRO is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases.

Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et at., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456–457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527–537 (1990) and Mansour et al., Nature, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5772 (ATCC 53,635). Other suitable prokaryotic host cells include Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA; E. coli W3110 strain 9E4, which has the complete genotype tonA ptr3; E. coli W3110 strain 27C7 (ATCC 55,244), which has the complete genotype tonA ptr3 phoA E15 (argF-lac)169 degP ompT kan$^r$; E. coli W3110 strain 37D6, which has the complete genotype tonA ptr3 phoA E15 (argF-lac)169 degP ompT rbs7 ilvG kan$^r$; E. coli W3110 strain 40B4, which is strain 37D6 with a non-kanamycin resistant degP deletion mutation; and an E. coli strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. Saccharomyces cerevisiae is a commonly used lower eukaryotic host microorganism. Others include Schizosaccharomyces pombe (Beach and Nurse, Nature, 290: 140 [1981]; EP 139,383 published 2 May 1985); Kluyveromyces hosts (U.S. Pat. No. 4,943,529; Fleer et al., Bio/Technology, 9:968–975 (1991)) such as, e.g., K. lactis (MW98-8C, CBS683, CBS4574; Louvencourt et al., J. Bacteriol., 154(2):737–742 [1983]), K. fragilis (ATCC 12,424), K. bulgaricus (ATCC 16,045), K. wickeramii (ATCC 24,178), K. waltii (ATCC 56,500), K. drosophilarum (ATCC 36,906; Van den Berg et al., Bio/Technology, 8:135 (1990)), K. thermotolerans, and K. manrianus; yarrowia (EP 402,226); Pichia pastoris (EP 183,070; Sreekrishna et al., J. Basic Microbiol., 28:265–278 [1988]); Candida; Trichoderma reesia (EP 244,234); Neurospora crassa (Case et at., Proc. Natl. Acad. Sci. USA, 76:5259–5263 [1979]); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991), and Aspergillus hosts such as A. nidulans (Ballance et al., Biochem. Biophvs. Res. Conmun., 112:284–289 [1983]; Tilburn et al., Gene, 26:205–221 [1983]; Yelton et al., Proc. Natl. Acad. Sci. USA, 81: 1470–1474 [1984]) and A. niger (Kelly and Hynes, EMBO J., 4:475–479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, The Biochemistry of Methylotrophs, 269 (1982).

Suitable host cells for the expression of glycosylated PRO are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader alpha factor leader (including Saccharomyces and Kluyveromyces α-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trpl gene present in the yeast plasmid YRp7 [Stinchcomb et al., Nature, 282:39 (1979); Kingsman et al., Gene, 7:141 (1979); Tschemper et al., Gene, 10:157 (1980)). The trpl gene provides a selection marker for a mutant strain of yeast lacking the ability to grow in tryptophan, for example, ATCC No. 44076 or PEP4 1[Jones, Genetics, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21–25 (1983)]. Promoters for use in bacterial systems also will contain a Shine-Dalgarno (S. D.) sequence operably linked to the DNA encoding PRO.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., Nature, 293: 620–625 (1981); Mantei et al., Nature, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knockout" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429–4432 (1987); and Wagner et al., Proc. Natl. Acad. Sci. USA 87, 3410–3414 (1990). For review of gene marking and gene therapy protocols see Anderson et al., Science 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumim, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for be determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN), interleukin-2, and MN rgp120. Johnson et al., Nat. Med., 2:795–799 (1996); Yasuda, Biomed. Ther., 27:1221–1223 (1993); Hora et al., Bio/Technology. 8:755–758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245–246 (1989); Chien et al., Proc. Natl. Acad. Sci. USA, 88:9578–9582 (1991)) as disclosed by Chevray and Nathans, Proc. Natl. Acad. Sci. USA, 89: 5789–5793 (1991). Many transcriptional activators, such as yeast GALA, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GALA, and another, in which candidate activating proteins are fused to the activation domain. The expression of a GAL1-lacZ reporter gene under control of a GALA-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res. 6:3073 (1979); Cooney et al., Science, 241: 456(1988); Dervanet al., Science, 251:1360(1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology, 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polygonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyenet al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368, 812–13 (1994); Fishwild et al., Nature Biotechnology 14, 845–51 (1996); Neuberger, Nature Biotechnology 14, 826 (1996); Lonberg and Huszar, Intern. Rev. Immunol. 1365–93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217–225 (1992) describe the production of a fully humanized bispecific antibody $F(ab')_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity may also be prepared using heterobifunctional cross-linkers as described in Wolff et al. Cancer Research, 53: 2560–2565 (1993). Alternatively, an antibody can be engineered that has dual Fc regions and may thereby have enhanced complement lysis and ADCC capabilities. See Stevenson et al., Anti-Cancer Drug Design, 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco el al., Proc. Natl. Acad. Sci. USA, 90: 7889–7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13: 1014 (1974); Pain et al., J. Immunol. Meth., 40:219 (1981); and Nygren, J. Histochem. and Cytochem., 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., Methods in Enzymology 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., Current Protocols in Molecular Biology, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278–1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500–1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, $MAL^+$, $SUC^+$, $GAL^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., Nucl. Acid. Res., 20:1425 (1992). Transformed cells were then inoculated from agar into YEPD complex media broth (100 ml) and grown overnight at 30° C. The YEPD broth was prepared as described in Kaiser et al., Methods in Yeast Genetics, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., Methods in Yeast Genetics, Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., Anal. Biochem., 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

5'-TGTAAAACGACGGCCAGT
TAAATAGACCTGCAATTATTAATCT-3' (SEQ ID NO:245)

The sequence of reverse oligonucleotide 2 was:

5'-CAGGAAACAGCTATGACC
ACCTGCACACCTGCAAATCCATT-3' (SEQ ID NO:246)

PCR was then performed as follows:

| | | | |
|---|---|---|---|
| a. | | Denature | 92° C., 5 minutes |
| b. | 3 cycles of: | Denature | 92° C., 30 seconds |
| | | Anneal | 59° C., 30 seconds |
| | | Extend | 72° C., 60 seconds |
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110–2209, USA (ATCC) as shown in Table 7 below.

TABLE 7

| Material | ATCC Dep. No. | Deposit Date |
|---|---|---|
| DNA94849-2960 | PTA-2306 | Jul. 25, 2000 |
| DNA96883-2745 | PTA-544 | Aug. 17, 1999 |
| DNA96894-2675 | PTA-260 | Jun. 22, 1999 |
| DNA100272-2969 | PTA-2299 | Jul. 25, 2000 |
| DNA108696-2966 | PTA-2315 | Aug. 1, 2000 |
| DNA117935-2801 | PTA-1088 | Dec. 22, 1999 |
| DNA119474-2803 | PTA-1097 | Dec. 22, 1999 |

TABLE 7-continued

| Material | ATCC Dep. No. | Deposit Date |
|---|---|---|
| DNA119498-2965 | PTA-2298 | Jul. 25, 2000 |
| DNA119502-2789 | PTA-1082 | Dec. 22, 1999 |
| DNA119516-2797 | PTA-1083 | Dec. 22, 1999 |
| DNA119530-2968 | PTA-2396 | Aug. 8, 2000 |
| DNA121772-2741 | PTA-1030 | Dec. 7, 1999 |
| DNA125148-2782 | PTA-955 | Nov. 16, 1999 |
| DNA125150-2793 | PTA-1085 | Dec. 22, 1999 |
| DNA121151-2784 | PTA-1029 | Dec. 7, 1999 |
| DNA125181-2804 | PTA-1096 | Dec. 22, 1999 |
| DNA125192-2794 | PTA-1086 | Dec. 22, 1999 |
| DNA125196-2792 | PTA-1091 | Dec. 22, 1999 |
| DNA125200-2810 | PTA-1186 | Jan. 11, 2000 |
| DNA125214-2814 | PTA-1270 | Feb. 2, 2000 |
| DNA125219-2799 | PTA-1084 | Dec. 22, 1999 |
| DNA128309-2825 | PTA-1340 | Feb. 8, 2000 |
| DNA129535-2796 | PTA-1087 | Dec. 22, 1999 |
| DNA129549-2798 | PTA-1099 | Dec. 22, 1999 |
| DNA129580-2863 | PTA-1584 | Mar. 28, 2000 |
| DNA129794-2967 | PTA-2305 | Jul. 25, 2000 |
| DNA131590-2962 | PTA-2297 | Jul. 25, 2000 |
| DNA135173-2811 | PTA-1184 | Jan. 11, 2000 |
| DNA138039-2828 | PTA-1343 | Feb. 8, 2000 |
| DNA139540-2807 | PTA-1187 | Jan. 11, 2000 |
| DNA139602-2859 | PTA-1588 | Mar. 28, 2000 |
| DNA139632-2880 | PTA-1629 | Apr. 4, 2000 |
| DNA139686-2823 | PTA-1264 | Feb. 2, 2000 |
| DNA142392-2800 | PTA-1092 | Dec. 22, 1999 |
| DNA143076-2787 | PTA-1028 | Dec. 7, 1999 |
| DNA143294-2818 | PTA-1182 | Jan. 11, 2000 |
| DNA143514-2817 | PTA-1266 | Feb. 2, 2000 |
| DNA144841-2816 | PTA-1188 | Jan. 11, 2000 |
| DNA148380-2827 | PTA-1181 | Jan. 11, 2000 |
| DNA149995-2871 | PTA-1971 | May 31, 2000 |
| DNA167678-2963 | PTA-2302 | Jul. 25, 2000 |
| DNA168028-2956 | PTA-2304 | Jul. 25, 2000 |
| DNA173894-2947 | PTA-2108 | Jun. 20, 2000 |
| DNA176775-2957 | PTA-2303 | Jul. 25, 2000 |
| DNA177313-2982 | PTA-2251 | Jul. 19, 2000 |
| DNA57700-1408 | 203583 | Jan. 12, 1999 |
| DNA62872-1509 | 203100 | Aug. 4, 1998 |
| DNA62876-1517 | 203095 | Aug. 4, 1998 |
| DNA66660-1585 | 203279 | Sep. 22, 1998 |
| DNA34434-1139 | 209252 | Sep. 16, 1997 |
| DNA44804-1248 | 209527 | Dec. 10, 1997 |
| DNA52758-1399 | 209773 | Apr. 14, 1998 |
| DNA59849-1504 | 209986 | Jun. 16, 1998 |
| DNA65410-1569 | 203231 | Sep. 15, 1998 |
| DNA71290-1630 | 203275 | Sep. 22, 1998 |
| DNA33100-1159 | 209377 | Oct. 16, 1997 |
| DNA64896-1539 | 203238 | Sep. 9, 1998 |
| DNA84920-2614 | 203966 | Apr. 27, 1999 |
| DNA23330-1390 | 209775 | Apr. 14, 1998 |
| DNA32286-1191 | 209385 | Oct. 16, 1997 |
| DNA35673-1201 | 209418 | Oct. 28, 1997 |
| DNA43316-1237 | 209487 | Nov. 21, 1997 |
| DNA44184-1319 | 209704 | Mar. 26, 1998 |
| DNA45419-1252 | 209616 | Feb. 5, 1998 |
| DNA48314-1320 | 209702 | Mar. 26, 1998 |
| DNA50921-1458 | 209859 | May 12, 1998 |
| DNA53987 | 209858 | May 12, 1998 |
| DNA56047-1456 | 209948 | Jun. 9, 1998 |
| DNA56405-1357 | 209849 | May 6, 1998 |
| DNA56531-1648 | 203286 | Sep. 29, 1998 |
| DNA56865-1491 | 203022 | Jun. 23, 1998 |
| DNA57694-1341 | 203017 | Jun. 23, 1998 |
| DNA57708-1411 | 203021 | Jun. 23, 1998 |
| DNA57836-1338 | 203025 | Jun. 23, 1998 |
| DNA57841-1522 | 203458 | Nov. 3, 1998 |
| DNA58847-1383 | 209879 | May 20, 1998 |
| DNA59212-1627 | 203245 | Sep. 9, 1998 |
| DNA59588-1571 | 203106 | Aug. 11, 1998 |
| DNA59622-1334 | 209984 | Jun. 16, 1998 |
| DNA59847-2510 | 203576 | Jan. 12, 1999 |
| DNA60615-1483 | 209880 | Jun. 16, 1998 |
| DNA60621-1516 | 203091 | Aug. 4, 1998 |
| DNA62814-1521 | 203093 | Aug. 4, 1998 |
| DNA64883-1526 | 203253 | Sep. 9, 1998 |

TABLE 7-continued

| Material | ATCC Dep. No. | Deposit Date |
|---|---|---|
| DNA64889-1541 | 203250 | Sep. 9, 1998 |
| DNA64897-1628 | 203216 | Sep. 15, 1998 |
| DNA64903-1553 | 203223 | Sep. 15, 1998 |
| DNA64907-1163-1 | 203242 | Sep. 9, 1998 |
| DNA64950-1590 | 203224 | Sep. 15, 1998 |
| DNA64952-1568 | 203222 | Sep. 15, 1998 |
| DNA65402-1540 | 203252 | Sep. 9, 1998 |
| DNA65405-1547 | 203476 | Nov. 17, 1998 |
| DNA66663-1598 | 203268 | Sep. 22, 1998 |
| DNA66667 | 203267 | Sep. 22, 1998 |
| DNA66675-1587 | 203282 | Sep. 22, 1998 |
| DNA67300-1605 | 203163 | Aug. 25, 1998 |
| DNA68872-1620 | 203160 | Aug. 25, 1998 |
| DNA71269-1621 | 203284 | Sep. 22, 1998 |
| DNA73736-1657 | 203466 | Nov. 17, 1998 |
| DNA73739-1645 | 203270 | Sep. 22, 1998 |
| DNA76400-2528 | 203573 | Jan. 12, 1999 |
| DNA76532-1702 | 203473 | Nov. 17, 1998 |
| DNA76541-1675 | 203409 | Oct. 27, 1998 |
| DNA79862-2522 | 203550 | Dec. 22, 1998 |
| DNA81754-2532 | 203542 | Dec. 15, 1998 |
| DNA81761-2583 | 203862 | Mar. 23, 1999 |
| DNA83500-2506 | 203391 | Oct. 29, 1998 |
| DNA84210-2576 | 203818 | Mar. 2, 1999 |
| DNA86571-2551 | 203660 | Feb. 9, 1999 |
| DNA92218-2554 | 203834 | Mar. 9, 1999 |
| DNA92223-2567 | 203851 | Mar. 16, 1999 |
| DNA92265-2669 | PTA-256 | Jun. 22, 1999 |
| DNA92274-2617 | 203971 | Apr. 27, 1999 |
| DNA108760-2740 | PTA-548 | Aug. 17, 1999 |
| DNA108792-2753 | PTA-617 | Aug. 31, 1999 |
| DNA111750-2706 | PTA-489 | Aug. 3, 1999 |
| DNA119514-2772 | PTA-946 | Nov. 9, 1999 |
| DNA125185-2806 | PTA-1031 | Dec. 7, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Isolation of cDNA Clones Encoding Human PRO6004, PRO5723, PRO3444, and PRO9940

DNA molecules encoding the PRO840, PRO1338, PRO6004, PRO5723, PRO3444, and PRO9940 polypeptides shown in the accompanying figures were obtained through GenBank.

Example 6

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 7

Expression of PRO in E. coli

This example illustrates preparation of an unglycosylated form of PRO by recombinant expression in E. coli.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in E. coli in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH_4)_2SO_4$, 0.71 g sodium citratee·2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 8

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., Cell, 31:543 (1982)] and dissolved in 500 μl of 1 mM Tris-HCl 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0. 14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 9

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 10

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into Spodoptera frugiperda ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., Baculovirus expression vectors: A Laboratory Manual, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., Nature, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$, with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 11

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 12

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 13

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the-aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 14

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, Bio/Technology, 9: 19–21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, Biochemistry, 31:7796–7801 (1992) or which act as inhibitors, agonists, or antagonists of native peptides as shown by Athauda et al., J. Biochem., 113: 742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 15

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control= DME+5% serum+/−PDGF at 500 ng/ml; negative control= protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1×pen strep+1X fungizone. Assay Media=low glucose DMEM+5% FBS.

The following polypeptides tested positive in this assay: PRO982, PRO1160, PRO1187, and PRO1329.

Example 16

Chondrocyte Re-differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articulary cartilage of metacarpophalangeal joints of 4–6 month old female pigs. The isolated cells are then seeded at 25,000 cells/cm$^2$ in Ham F-12 containing 10% FBS and 4 μg/ml gentamycin. The culture media is changed every third day and the cells are then seeded in 96 well plates at 5,000 cells/well in 100 μl of the same media without serum and 100 μl of the test PRO polypeptide, 5 nM staurosporin (positive control) or medium alone (negative control) is added to give a final volume of 200 μl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO357.

Example 17

Identification of PRO Polypeptides that Stimulate TNF-α Release in Human Blood (Assay 128)

This assay shows that certain PRO polypeptides of the present invention act to stimulate the release of TNF-α in human blood. PRO polypeptides testing positive in this assay are useful for, among other things, research purposes where stimulation of the release of TNF-α would be desired and for the therapeutic treatment of conditions wherein enhanced TNF-α release would be beneficial. Specifically, 200 μl of human blood supplemented with 50 mM Hepes buffer (pH 7.2) is aliquoted per well in a 96 well test plate. To each well is then added 300 μl of either the test PRO polypeptide in 50 mM Hepes buffer (at various concentrations) or 50 mM Hepes buffer alone (negative control) and the plates are incubated at 37° C. for 6 hours. The samples are then centrifuged and 50 μl of plasma is collected from each well and tested for the presence of TNF-α by ELISA assay. A positive in the assay is a higher amount of TNF-α in the PRO polypeptide treated samples as compared to the negative control samples.

The following PRO polypeptides tested positive in this assay: PRO231; PRO357, PRO725, PRO1155, PRO1306, and PRO1419.

Example 18

Promotion of Chondrocyte Redifferentiation (Assay 129)

This assay is designed to determine whether PRO polypeptides of the present invention show the ability to induce the proliferation and/or redifferentiation of chondrocytes in culture. PRO polypeptides testing positive in this assay would be expected to be useful for the therapeutic treatment of various bone and/or cartilage disorders such as, for example, sports injuries and arthritis.

Porcine chondrocytes are isolated by overnight collagenase digestion of articular cartilage of the metacarpophalangeal joint of 4–6 month old female pigs. The isolated cells are then seeded at 25,000 cells/cm$^2$ in Ham F-12 containing 10% FBS and 4 μg/ml gentamycin. The culture media is changed every third day. On day 12, the cells are seeded in 96 well plates at 5,000 cells/well in 100 μl of the same media without serum and 100 μl of either serum-free medium (negative control), staurosporin (final concentration of 5 nM; positive control) or the test PRO polypeptide are added to give a final volume of 200 μl/well. After 5 days at 37° C., 22 μl of media comtaining 100 μg/ml Hoechst 33342 and 50 μg/ml 5-CFDA is added to each well and incubated for an additional 10 minutes at 37° C. A picture of the green fluorescence is taken for each well and the differentiation state of the chondrocytes is calculated by morphometric analysis. A positive result in the assay is obtained when the >50% of the PRO polypeptide treated cells are differentiated (compared to the background obtained by the negative control).

The following PRO polypeptides tested positive in this assay: PRO229, PRO1272, and PRO4405.

Example 19

Normal Human Dermal Fibroblast Proliferation (Assay 141)

This assay is designed to determine whether PRO polypeptides of the present invention show the ability to induce proliferation of human dermal fibroblast cells in culture and, therefore, function as useful growth factors.

On day 0, human dermal fibroblast cells (from cell lines, maximum of 12–14 passages) were plated in 96-well plates at 1000 cells/well per 100 microliter and incubated overnight in complete media [fibroblast growth media (FGM, Clonetics), plus supplements: insulin, human epithelial growth factor (hEGF), gentamicin (GA-1000), and fetal bovine serum (FBS, Clonetics)]. On day 1, complete media was replaced by basal media [FGM plus 1% FBS] and addition of PRO polypeptides at 1%, 0.1% and 0.01%. On day 7, an assessment of cell proliferation was performed by Alamar Blue assay followed by Crystal Violet. Results are expressed as % of the cell growth observed with control buffer.

The following PRO polypeptides stimulated normal human dermal fibroblast proliferation in this assay: PRO982, PRO357, PRO725, PRO1306, PRO1419, PRO214, PRO247, PRO337, PRO526, PRO363, PRO531, PRO1083, PRO840, PRO1080, PRO1478, PRO1134, PRO826, PRO1005, PRO809, PRO1071, PRO1411, PRO1309, PRO1025, PRO1181, PRO1126, PRO1186, PRO1192, PRO1244, PRO1274, PRO1412, PRO1286, PRO1330, PRO1347, PRO1305, PRO1273, PRO1279, PRO1340, PRO1338, PRO1343, PRO1376, PRO1387, PRO1409, PRO1474, PRO1917, PRO1760, PRO1567, PRO1887, PRO1928, PRO4341, PRO1801, PRO4333, PRO3543, PRO3444, PRO4322, PRO9940, PRO6079, PRO9836 and PRO10096.

The following PRO polypeptides inhibited normal human dermal fibroblast proliferation in this assay: PRO181, PRO229, PRO788, PRO1194, PRO1272, PRO1488, PRO4302, PRO4408, PRO5723, PRO5725, PRO7154, and PRO7425.

Example 20

Microarray Analysis to Detect Overexpression of PRO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, cancerous tumors derived from various human tissues were studied for PRO polypeptide-encoding gene expression relative to non-cancerous human tissue in an attempt to identify those PRO polypeptides which are overexpressed in cancerous tumors. Cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described PRO polypeptide-encoding nucleic acid sequences were used in the creation of the microarray and RNA from a panel of nine different tumor tissues (listed below) were used for the hybridization thereto. A value based upon the normalized ratio:experimental ratio was designated as a "cutoff ratio". Only values that were above this cutoff ratio were determined to be significant. Table 8 below shows the results of these experiments, demonstrating that various PRO polypeptides of the present invention are significantly overexpressed in various human tumor tissues, as compared to a non-cancerous human tissue control or other human tumor tissues. As described above, these data demonstrate that the PRO polypeptides of the present invention are useful not only as diagnostic markers for the presence of one or more cancerous tumors, but also serve as therapeutic targets for the treatment of those tumors.

TABLE 8

| Molecule | is overexpressed in: | as compared to normal control: |
|---|---|---|
| PRO6004 | colon tumor | universal normal control |
| PRO4981 | colon tumor | universal normal control |
| PRO4981 | lung tumor | universal normal control |
| PRO7174 | colon tumor | universal normal control |
| PRO5778 | lung tumor | universal normal control |
| PRO5778 | breast tumor | universal normal control |
| PRO5778 | liver tumor | universal normal control |
| PRO4332 | colon tumor | universal normal control |
| PRO9799 | colon tumor | universal normal control |
| PRO9909 | colon tumor | universal normal control |
| PRO9917 | colon tumor | universal normal control |
| PRO9917 | lung tumor | universal normal control |
| PRO9917 | breast tumor | universal normal control |
| PRO9771 | colon tumor | universal normal control |
| PRO9877 | colon tumor | universal normal control |
| PRO9903 | colon tumor | universal normal control |
| PRO9830 | colon tumor | universal normal control |
| PRO7155 | colon tumor | universal normal control |
| PRO7155 | lung tumor | universal normal control |
| PRO7155 | prostate tumor | universal normal control |
| PRO9862 | colon tumor | universal normal control |

TABLE 8-continued

| Molecule | is overexpressed in: | as compared to normal control: |
|---|---|---|
| PRO9882 | colon tumor | universal normal control |
| PRO9864 | colon tumor | universal normal control |
| PRO10013 | colon tumor | universal normal control |
| PRO9885 | colon tumor | universal normal control |
| PRO9879 | colon tumor | universal normal control |
| PRO10111 | colon tumor | universal normal control |
| PRO10111 | rectal tumor | universal normal control |
| PRO9925 | breast tumor | universal normal control |
| PRO9925 | rectal tumor | universal normal control |
| PRO9925 | colon tumor | universal normal control |
| PRO9925 | lung tumor | universal normal control |
| PRO9905 | colon tumor | universal normal control |
| PRO10276 | colon tumor | universal normal control |
| PRO9898 | colon tumor | universal normal control |
| PRO9904 | colon tumor | universal normal control |
| PRO19632 | colon tumor | universal normal control |
| PRO19672 | colon tumor | universal normal control |
| PRO9783 | colon tumor | universal normal control |
| PRO9783 | lung tumor | universal normal control |
| PRO9783 | breast tumor | universal normal control |
| PRO9783 | prostate tumor | universal normal control |
| PRO9783 | rectal tumor | universal normal control |
| PRO10112 | colon tumor | universal normal control |
| PRO10284 | colon tumor | universal normal control |
| PRO10100 | colon tumor | universal normal control |
| PRO19628 | colon tumor | universal normal control |
| PRO19684 | colon tumor | universal normal control |
| PRO10274 | colon tumor | universal normal control |
| PRO9907 | colon tumor | universal normal control |
| PRO9873 | colon tumor | universal normal control |
| PRO10201 | colon tumor | universal normal control |
| PRO10200 | colon tumor | universal normal control |
| PRO10196 | colon tumor | universal normal control |
| PRO10282 | lung tumor | universal normal control |
| PRO10282 | breast tumor | universal normal control |
| PRO10282 | colon tumor | universal normal control |
| PRO10282 | rectal tumor | universal normal control |
| PRO19650 | colon tumor | universal normal control |
| PRO21184 | lung tumor | universal normal control |
| PRO21184 | breast tumor | universal normal control |
| PRO21184 | colon tumor | universal normal control |
| PRO21201 | breast tumor | universal normal control |
| PRO21201 | colon tumor | universal normal control |
| PRO21175 | breast tumor | universal normal control |
| PRO21175 | colon tumor | universal normal control |
| PRO21175 | lung tumor | universal normal control |
| PRO21340 | colon tumor | universal normal control |
| PRO21340 | prostate tumor | universal normal control |
| PRO21384 | colon tumor | universal normal control |
| PRO21384 | lung tumor | universal normal control |
| PRO21384 | breast tumor | universal normal control |

Example 21

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200–600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results.

(1) the DNA94849-2960 molecule is significantly expressed in the following tissues: cartilage, testis, colon tumor, heart, placenta, bone marrow, adrenal gland, prostate, spleen aortic endothelial cells and uterus, and not significantly expressed in the following tissues: HUVEC.

(2) the DNA100272-2969 molecule is significantly expressed in cartilage, testis, human umblilical vein endothelial cells (HUVEC), colon tumor, heart, placenta, bone marrow, adrenal gland, prostate, spleen and aortic endothelial cells; and not significantly expressed in uterus. Among a panel of normal and tumor cells examined, the DNA100272-2969 was found to be expressed in normal esophagus, esophageal tumor, normal stomach, stomach tumor, normal kidney, kidney tumor, normal lung, lung tumor, normal rectum, rectal tumor, normal liver and liver tumor.

(3) the DNA108696-2966 molecule is highly expressed in prostate and also expressed in testis, bone marrow and spleen. The DNA108696-2966 molecule is expressed in normal stomach, but not expressed in stomach tumor. The DNA108696-2966 molecule is not expressed in normal kidney, kidney tumor, normal lung, or lung tumor. The DNA108696-2966 molecule is highly expressed in normal rectum, lower expression in rectal tumor. The DNA108696-2966 molecule is not expressed in normal liver or liver tumor. The DNA108696-2966 molecule is not expressed in normal esophagus, esophagial tumor, cartilage, HUVEC, colon tumor, heart, placenta, adrenal gland, aortic endothelial cells and uterus.

(4) the DNA119498-2965 molecule is significantly expressed in the following tissues: highly expressed in aortic endothelial cells, and also significantly expressed in cartilage, testis, HUVEC, colon tumor, heart, placenta, bone marrow, adrenal galnd, prostate and spleen. It is not significantly expressed in uterus.

(5) the DNA119530-2968 molecule is expressed in the following tissues: normal esophagus and not expressed in the following tissues: esophageal tumors, stomach tumors, normal stomach, normal kidney, kidney tumor, normal lung, lung tumor, normal rectum, rectal tumors, normal liver or liver tumors.

(6) the DNA129794-2967 molecule is significantly expressed in testis and adrenal gland; and not significantly expressed in cartilage, human umblilical vein endothelial cells (HUVEC), colon tumor, heart, placenta, bone marrow, prostate, spleen, aortic endothelial cells and uterus.

(7) the DNA131590-2962 molecule is significantly expressed in the following tissues: bone marrow, adrenal gland, prostate, spleen, uterus, cartilage, testis, colon tumor, heart, and placenta, and not significantly expressed in the following tissues: HUVEC, and aortic endothelial cells.

(8) the DNA149995-2871 molecule is highly expressed in testis, and adrenal gland; expressed in cartilage, human umblilical vein endothelial cells (HUVEC), colon tumor, heart, prostate and uterus; weakly expressed in bone marrow, spleen and aortic endothelial cells; and not significantly expressed in placenta.

(9) the DNA167678-2963 molecule is significantly expressed in the following tissues: normal esophagus, esophagial tumor, highly expressed in normal stomach, stomach tumor, highly expressed in normal kidney, kidney tumor, expressed in lung, lung tumor, normal rectum, rectal tumor, weakly expressed in normal liver, and not significantly expressed in liver tumor.

(10) the DNA168028-2956 molecule is highly expressed in bone marrow; expressed in testis, human umblilical vein endothelial cells (HUVEC), colon tumor, heart, placenta, adrenal gland, prostate, spleen, aortic endothelial cells and uterus; and is weakly expressed in cartilage. Among a panel of normal and tumor samples examined, the DNA168028-2956 was found to be expressed in stomach tumor, normal kidney, kidney tumor, lung tumor, normal rectum and rectal tumor; and not expressed in normal esophagus, esophageal tumor, normal stomach, normal lung, normal liver and liver tumor.

(11) the DNA176775-2957 molecule is highly expressed in testis; expressed in cartilage and prostate; weakly expressed in adrenal gland, spleen and uterus; and not significantly expressed in human umblilical vein endothelial cells (HUVEC), colon tumor, heart, placenta, bone marrow and aortic endothelial cells.

(12) the DNA177313-2982 molecule is significantly expressed in prostate and aortic endothelial cells; and not significantly expressed in cartilage, testis, human umbilical vein endothelial cells (HUVEC), colon tumor, heart, placenta, bone marrow, adrenal gland, spleen and uterus. Among a panel of normal and tumor cells, the DNA177313-2982 molecule was found to be expressed in esophageal tumor but not in normal esophagus, normal stomach, stomach tumor, normal kidney, kidney tumor, normal lung, lung tumor, normal rectum, rectal tumor, normal liver and liver tumor.

SEQUENCE LISTING

```
<160> NUMBER OF SEQ ID NOS: 246

<210> SEQ ID NO 1
<211> LENGTH: 4834
<212> TYPE: DNA
<213> ORGANISM: Homo sapiens
<220> FEATURE:
<221> NAME/KEY: Unsure
<222> LOCATION: 3784
<223> OTHER INFORMATION: Unknown base

<400> SEQUENCE: 1
```

-continued

```
gcagccctag cagggatgga catgatgctg ttggtgcagg gtgcttgttg      50
ctcgaaccag tggctggcgg cggtgctcct cagcctgtgc tgcctgctac     100
cctcctgcct cccggctgga cagagtgtgg acttcccctg ggcggccgtg     150
gacaacatga tggtcagaaa aggggacacg gcggtgctta ggtgttattt     200
ggaagatgga gcttcaaagg gtgcctggct gaaccggtca agtattattt     250
ttgcgggagg tgataagtgg tcagtggatc ctcgagtttc aatttcaaca     300
ttgaataaaa gggactacag cctccagata cagaatgtag atgtgacaga     350
tgatggccca tacacgtgtt ctgttcagac tcaacataca cccagaacaa     400
tgcaggtgca tctaactgtg caagttcctc ctaagatata tgacatctca     450
aatgatatga ccgtcaatga aggaaccaac gtcactctta cttgtttggc     500
cactgggaaa ccagagcctt ccatttcttg gcgacacatc tccccatcag     550
caaaaccatt tgaaaatgga caatatttgg acatttatgg aattacaagg     600
gaccaggctg gggaatatga atgcagtgcg gaaaatgatg tgtcattccc     650
agatgtgagg aaagtaaaag ttgttgtcaa ctttgctcct actattcagg     700
aaattaaatc tggcaccgtg acccccggac gcagtggcct gataagatgt     750
gaaggtgcag gtgtgccgcc tccagccttt gaatggtaca aaggagagaa     800
gaagctcttc aatggccaac aaggaattat tattcaaaat tttagcacaa     850
gatccattct cactgttacc aacgtgacac aggagcactt cggcaattat     900
acttgtgtgg ctgccaacaa gctaggcaca accaatgcga gcctgcctct     950
taaccctcca agtacagccc agtatggaat taccgggagc gctgatgttc    1000
ttttctcctg ctggtacctt gtgttgacac tgtcctcttt caccagcata    1050
ttctacctga agaatgccat tctacaataa attcaaagac ccataaaagg    1100
cttttaagga ttctctgaaa gtgctgatgg ctggatccaa tctggtacag    1150
tttgttaaaa gcagcgtggg atataatcag cagtgcttac atggggatga    1200
tcgccttctg tagaattgct cattatgtaa atactttaat tctactcttt    1250
tttgattagc tacattacct tgtgaagcag tacacattgt cctttttta     1300
agacgtgaaa gctctgaaat tacttttaga ggatattaat tgtgatttca    1350
tgtttgtaat ctacaacttt tcaaaagcat tcagtcatgg tctgctaggt    1400
tgcaggctgt agtttacaaa aacgaatatt gcagtgaata tgtgattctt    1450
taaggctgca atacaagcat tcagttccct gtttcaataa gagtcaatcc    1500
acatttacaa agatgcattt ttttcttttt tgataaaaaa gcaaataata    1550
ttgccttcag attatttctt caaaatataa cacatatcta gatttttctg    1600
ctcgcatgat attcaggttt caggaatgag ccttgtaata taactggctg    1650
tgcagctctg cttctctttc ctgtaagttc agcatgggtg tgccttcata    1700
caataatatt tttctctttg tctccaacta atataaaatg ttttgctaaa    1750
tcttacaatt tgaaagtaaa aataaaccag agtgatcaag ttaaaccata    1800
cactatctct aagtaacgaa ggagctattg gactgtaaaa atctcttcct    1850
gcactgacaa tggggtttga gaattttgcc ccacactaac tcagttcttg    1900
tgatgagaga caatttaata acagtatagt aaatatacca tatgatttct    1950
```

-continued

```
ttagttgtag ctaaatgtta gatccaccgt gggaaatcat tccctttaaa    2000
atgacagcac agtccactca aaggattgcc tagcaataca gcatcttttc    2050
ctttcactag tccaagccaa aaattttaag atgatttgtc agaaagggca    2100
caaagtccta tcacctaata ttacaagagt tggtaagcgc tcatcattaa    2150
ttttattttg tggcagctaa gttagtatga cagaggcagt gctcctgtgg    2200
acaggagcat tttgcatatt ttccatctga aagtatcact cagttgatag    2250
tctggaatgc atgttatata ttttaaaact tccaaaatat attataacaa    2300
acattctata tcggtatgta gcagaccaat ctctaaaata gctaattctt    2350
caataaaatc tttctatata gccatttcag tgcaaacaag taaaatcaaa    2400
aaagaccatc ctttattttt ccttacatga tatatgtaag atgcgatcaa    2450
ataaagacaa aacaccagtg atgagaatat cttaagataa gtaattatca    2500
aattattgtg aatgttaaat tatttctact ataaagaagc aaaactacat    2550
ttttgaagga aaatgctgtt actctaacat taatttacag gaatagtttg    2600
atggtttcac tctttactaa agaaaggcca tcaccttgaa agccatttta    2650
caggtttgat gaagttacca atttcagtac acctaaattt ctacaaatag    2700
tccccttta caagttgtaa caacaaagac cctataataa aattagatac    2750
aagaaatttt gcagtggtta tacatatttg agatatctag tatgttgccc    2800
tagcagggat ggcttaaaaa ctgtgatttt ttttcttcaa gtaaaactta    2850
gtcccaaagt acatcataaa tcaattttaa ttagaaaaat gaatcttaaa    2900
tgaggggaca taagtatact ctttccacaa aatggcaata ataaggcata    2950
aagctagtaa atctactaac tgtaataaat gtatgacatt attttgattg    3000
atacattaaa aaagagtttt tagaacaaat atggcattta actttattat    3050
ttatttgctt ttaagaaata ttctttgtgg aattgttgaa taaactataa    3100
aatattattt tgtattgcag ctttaaagtg gcacactcca taataatcta    3150
cttactagaa atagtggtgc taccacaaaa aatgttaacc atcagtacca    3200
ttgtttggga gaaagaaaca gatcaagaat gcatattatt cagtgaccgc    3250
tttcctagag ttaaaatacc tcctctttgt aaggtttgta ggtaaattga    3300
ggtataaact atggatgaac caaataatta gttcaaagtg ttgtcatgat    3350
tccaaatttg tggagtctgg tgtttttacc atagaatgtg acagaagtac    3400
agtcatagct cagtagctat atgtatttgc ctttatgtta gaagagactt    3450
tcttgagtga catttttaaa tagaggaggt attcactatg tttttctgta    3500
tcacagcagc attcctagtc cttaggccct cggacagagt gaaatcatga    3550
gtatttatga gttcaatatt gtcaaataag gctacagtat ttgctttttt    3600
gtgtgaatgt attgcatata atgttcaagt agatgatttt acatttatgg    3650
acatataaaa tgtctgatta ccccatttta tcagtcctga ctgtacaaga    3700
ttgttgcaat ttcagaatag cagttttata aattgattta tcttttaatc    3750
tataacaatt tgtgttagct gttcatttca ggantatatt ttctacaagt    3800
tccacttgtg ggactccttt tgttgcccct atttttttt aaagaaggaa    3850
gaaagaaaaa taagtagcag tttaaaaatg agaatggaga gaaaagaaaa    3900
agaatgaaaa ggaaaggcag taaagaggga aaaaaaagga aggatggaag    3950
```

-continued

```
gaatgaagga aggaagggag gaaggggaga aggtaggaag aaagaaagga          4000

tgagagggaa ggaagaatca gagtattagg gtagttaact tacacatttg          4050

cattcttagt ttaactgcaa gtggtgtaac tatgtttttc aatgatcgca          4100

tttgaaacat aagtcctatt ataccattaa gttcctatta tgcagcaatt          4150

atataataaa aagtactgcc caagttatag taatgtgggt gtttttgaga          4200

cactaaaaga tttgagaggg agaatttcaa acttaaagcc acttttgggg          4250

ggtttataac ttaactgaaa aattaatgct tcatcataac atttaagcta          4300

tatctagaaa gtagactgga gaactgagaa aattacccag gtaattcagg          4350

gaaaaaaaaa aatatatata tatataaata cccctacatt tgaagtcaga          4400

aaactctgaa aaactgaatt atcaaagtca atcatctata atgatcaaat          4450

ttactgaaca attgttaatt tatccattgt gcttagcttt gtgacacagc          4500

caaaagttac ctatttaatc ttttcaataa aaattgtttt ttgaaatcca          4550

gaaatgattt aaaaagaggt caggttttta actatttatt gaagtatgtg          4600

gatgtacagt atttcaatag atatgaatat gaataaatgg tatgccttaa          4650

gattctttga atatgtattt actttaaaga ctggaaaaag ctcttcctgt          4700

cttttagtaa aacatccata tttcataacc tgatgtaaaa tatgttgtac          4750

tgtttccaat aggtgaatat aaactcagtt tatcaattaa aaaaaaaaaa          4800

aaaaaaaaaa aaaaaaaaaa aaaaaaaaaa  aaaa                          4834
```

<210> SEQ ID NO 2
<211> LENGTH: 354
<212> TYPE: PRT
<213> ORGANISM: Homo sapiens

<400> SEQUENCE: 2

```
Met Asp Met Met Leu Leu Val Gln Gly Ala Cys Cys Ser Asn Gln
  1               5                  10                  15

Trp Leu Ala Ala Val Leu Leu Ser Leu Cys Cys Leu Leu Pro Ser
                 20                  25                  30

Cys Leu Pro Ala Gly Gln Ser Val Asp Phe Pro Trp Ala Ala Val
                 35                  40                  45

Asp Asn Met Met Val Arg Lys Gly Asp Thr Ala Val Leu Arg Cys
                 50                  55                  60

Tyr Leu Glu Asp Gly Ala Ser Lys Gly Ala Trp Leu Asn Arg Ser
                 65                  70                  75

Ser Ile Ile Phe Ala Gly Gly Asp Lys Trp Ser Val Asp Pro Arg
                 80                  85                  90

Val Ser Ile Ser Thr Leu Asn Lys Arg Asp Tyr Ser Leu Gln Ile
                 95                 100                 105

Gln Asn Val Asp Val Thr Asp Asp Gly Pro Tyr Thr Cys Ser Val
                110                 115                 120

Gln Thr Gln His Thr Pro Arg Thr Met Gln Val His Leu Thr Val
                125                 130                 135

Gln Val Pro Pro Lys Ile Tyr Asp Ile Ser Asn Asp Met Thr Val
                140                 145                 150

Asn Glu Gly Thr Asn Val Thr Leu Thr Cys Leu Ala Thr Gly Lys
                155                 160                 165

Pro Glu Pro Ser Ile Ser Trp Arg His Ile Ser Pro Ser Ala Lys
```

-continued

```
                170                 175                 180

Pro Phe Glu Asn Gly Gln Tyr Leu Asp Ile Tyr Gly Ile Thr Arg
                185                 190                 195

Asp Gln Ala Gly Glu Tyr Glu Cys Ser Ala Glu Asn Asp Val Ser
                200                 205                 210

Phe Pro Asp Val Arg Lys Val Lys Val Val Val Asn Phe Ala Pro
                215                 220                 225

Thr Ile Gln Glu Ile Lys Ser Gly Thr Val Thr Pro Gly Arg Ser
                230                 235                 240

Gly Leu Ile Arg Cys Glu Gly Ala Gly Val Pro Pro Pro Ala Phe
                245                 250                 255

Glu Trp Tyr Lys Gly Glu Lys Lys Leu Phe Asn Gly Gln Gln Gly
                260                 265                 270

Ile Ile Ile Gln Asn Phe Ser Thr Arg Ser Ile Leu Thr Val Thr
                275                 280                 285

Asn Val Thr Gln Glu His Phe Gly Asn Tyr Thr Cys Val Ala Ala
                290                 295                 300

Asn Lys Leu Gly Thr Thr Asn Ala Ser Leu Pro Leu Asn Pro Pro
                305                 310                 315

Ser Thr Ala Gln Tyr Gly Ile Thr Gly Ser Ala Asp Val Leu Phe
                320                 325                 330

Ser Cys Trp Tyr Leu Val Leu Thr Leu Ser Ser Phe Thr Ser Ile
                335                 340                 345

Phe Tyr Leu Lys Asn Ala Ile Leu Gln
                350


<210> SEQ ID NO 3
<211> LENGTH: 2506
<212> TYPE: DNA
<213> ORGANISM: Homo sapiens

<400> SEQUENCE: 3

cactgcccgt ccgctcttca gcagccggtc gcgggcggtg gaaaagcgag          50

tgaagagagc gcgacggcgg cggcggcggc ggcgcagcta ttgctggacg         100

gccagtggga gagcgaggcc tgagcctctg cgtctaggat caaaatggtt         150

tcaatcccag aatactatga aggcaagaac gtcctcctca caggagctac         200

cggttttcta gggaaggtgc ttctggaaaa gttgctgagg tcttgtccta         250

aggtgaattc agtatatgtt ttggtgaggc agaaagctgg acagacacca         300

caagagcgag tggaagaagt ccttagtggc aagctttttg acagattgag         350

agatgaaaat ccagatttta gagagaaaat tatagcaatc aacagcgaac         400

tcacccaacc taaactggct ctcagtgaag aagataaaga ggtgatcata         450

gattctacca atattatatt ccactgtgca gctacagtaa ggtttaatga         500

aaatttaaga gatgctgttc agttaaatgt gattgcaacg cgacagctta         550

ttctccttgc acaacaaatg aagaatctgg aagtgttcat gcatgtatca         600

acagcatatg cctactgtaa tcgcaagcat attgatgaag tagtctatcc         650

accacctgtg gatcccaaga agctgattga ttctttagag tggatggatg         700

atggcctagt aaatgatatc acgccaaaat tgataggaga cagacctaat         750

acatacatat acacaaaagc attggcagaa tatgttgtac aacaagaagg         800

agcaaaacta aatgtggcaa ttgtaaggcc atcgattgtt ggtgccagtt         850
```

-continued

```
ggaaagaacc ttttccagga tggattgata actttaatgg accaagtggt      900
ctctttattg cggcagggaa aggaattctt cgaacaatac gtgcctccaa      950
caatgccctt gcagatcttg ttcctgtaga tgtagttgtc aacatgagtc     1000
ttgcggcagc ctggtattcc ggagttaata gaccaagaaa catcatggtg     1050
tataattgta caacaggcag cactaatcct ttccactggg gtgaagttga     1100
gtaccatgta atttccactt tcaagaggaa tcctctcgaa caggccttca     1150
gacggcccaa tgtaaatcta acctccaatc atcttttata tcattactgg     1200
attgctgtaa gccataaggc cccagcattc ctgtatgata tctacctcag     1250
gatgactgga agaagcccaa ggatgatgaa aacaataact cgtcttcaca     1300
aagctatggt gtttcttgaa tatttcacaa gtaattcttg ggtttggaat     1350
actgagaatg tcaatatgtt aatgaatcaa ctaaaccctg aagataaaaa     1400
gaccttcaat attgatgtac ggcagttaca ttgggcagaa tatatagaga     1450
actactgctt gggaactaag aagtacgtat tgaatgaaga aatgtctggc     1500
ctccctgcag ccagaaaaca tctgaacaag ttgcggaata tacgttatgg     1550
ttttaatact atccttgtga tcctcatctg gcgcattttt attgcaagat     1600
cacaaatggc aagaaatatc tggtactttg tggttagtct gtgttacaag     1650
tttttgtcat acttccgagc atccagcact atgagatact gaagaccaag     1700
gattcagcat tagaacatct atacatatgg tgatctaaat gtacaaaatg     1750
taaaatgtat aagtcatctc actttttgtc aagacattaa accatcttag     1800
atcggagtgt gaagtaaatt atggtatatt ttatgtaaca ttttaatgtt     1850
tatgctcata aaacttagtg aacacactgt gttatgccag ctcaaatcta     1900
cagtagccac caaaaccatg acttaatatt ttgagcccta gaagaaaggg     1950
gtgtgctgag gacaagagtg gggaaatagg aacactgacc agtataactg     2000
tgcaattctg gaacatatta attaaaataa tatgccttaa catatagtga     2050
atttctaatt ctaatgttca gtgcaatgga agacatttat ttggacagta     2100
tactagcaaa gttggtagat atttgattct tcattttttg ttttttttcat    2150
tagttgaagt gggttttagt tttgtttaaa attataacca gcgtattttc     2200
acatcattct gtaagttaaa tgatatcaaa catgaaagag atgttctcat     2250
ttttcttttt ctgattaaac gtctgatgca tatcattttt ctataagtaa     2300
tcagttgctt ttaaaatcag aaggctatat tattctaatg accctattcg     2350
atctaaatgg gtttgagaat ccatatcagc aacatacgtg ttttttgaca     2400
gaaagtgaaa acaaattccg taaaactgtt agtatcaaaa agaataggaa     2450
tacagttttc ttttccacat tatgatcaaa taaaaatctt gtgagattgt     2500
taaaaa                                                     2506
```

<210> SEQ ID NO 4
<211> LENGTH: 515
<212> TYPE: PRT
<213> ORGANISM: Homo sapiens

<400> SEQUENCE: 4

```
Met Val Ser Ile Pro Glu Tyr Tyr Glu Gly Lys Asn Val Leu Leu
  1               5                  10                  15
```

-continued

```
Thr Gly Ala Thr Gly Phe Leu Gly Lys Val Leu Leu Glu Lys Leu
                20                  25                  30

Leu Arg Ser Cys Pro Lys Val Asn Ser Val Tyr Val Leu Val Arg
                35                  40                  45

Gln Lys Ala Gly Gln Thr Pro Gln Glu Arg Val Glu Glu Val Leu
                50                  55                  60

Ser Gly Lys Leu Phe Asp Arg Leu Arg Asp Glu Asn Pro Asp Phe
                65                  70                  75

Arg Glu Lys Ile Ile Ala Ile Asn Ser Glu Leu Thr Gln Pro Lys
                80                  85                  90

Leu Ala Leu Ser Glu Glu Asp Lys Glu Val Ile Ile Asp Ser Thr
                95                 100                 105

Asn Ile Ile Phe His Cys Ala Ala Thr Val Arg Phe Asn Glu Asn
               110                 115                 120

Leu Arg Asp Ala Val Gln Leu Asn Val Ile Ala Thr Arg Gln Leu
               125                 130                 135

Ile Leu Leu Ala Gln Gln Met Lys Asn Leu Glu Val Phe Met His
               140                 145                 150

Val Ser Thr Ala Tyr Ala Tyr Cys Asn Arg Lys His Ile Asp Glu
               155                 160                 165

Val Val Tyr Pro Pro Pro Val Asp Pro Lys Lys Leu Ile Asp Ser
               170                 175                 180

Leu Glu Trp Met Asp Asp Gly Leu Val Asn Asp Ile Thr Pro Lys
               185                 190                 195

Leu Ile Gly Asp Arg Pro Asn Thr Tyr Ile Tyr Thr Lys Ala Leu
               200                 205                 210

Ala Glu Tyr Val Val Gln Gln Glu Gly Ala Lys Leu Asn Val Ala
               215                 220                 225

Ile Val Arg Pro Ser Ile Val Gly Ala Ser Trp Lys Glu Pro Phe
               230                 235                 240

Pro Gly Trp Ile Asp Asn Phe Asn Gly Pro Ser Gly Leu Phe Ile
               245                 250                 255

Ala Ala Gly Lys Gly Ile Leu Arg Thr Ile Arg Ala Ser Asn Asn
               260                 265                 270

Ala Leu Ala Asp Leu Val Pro Val Asp Val Val Val Asn Met Ser
               275                 280                 285

Leu Ala Ala Ala Trp Tyr Ser Gly Val Asn Arg Pro Arg Asn Ile
               290                 295                 300

Met Val Tyr Asn Cys Thr Thr Gly Ser Thr Asn Pro Phe His Trp
               305                 310                 315

Gly Glu Val Glu Tyr His Val Ile Ser Thr Phe Lys Arg Asn Pro
               320                 325                 330

Leu Glu Gln Ala Phe Arg Arg Pro Asn Val Asn Leu Thr Ser Asn
               335                 340                 345

His Leu Leu Tyr His Tyr Trp Ile Ala Val Ser His Lys Ala Pro
               350                 355                 360

Ala Phe Leu Tyr Asp Ile Tyr Leu Arg Met Thr Gly Arg Ser Pro
               365                 370                 375

Arg Met Met Lys Thr Ile Thr Arg Leu His Lys Ala Met Val Phe
               380                 385                 390

Leu Glu Tyr Phe Thr Ser Asn Ser Trp Val Trp Asn Thr Glu Asn
               395                 400                 405
```

-continued

```
Val Asn Met Leu Met Asn Gln Leu Asn Pro Glu Asp Lys Lys Thr
                410                 415                 420

Phe Asn Ile Asp Val Arg Gln Leu His Trp Ala Glu Tyr Ile Glu
                425                 430                 435

Asn Tyr Cys Leu Gly Thr Lys Lys Tyr Val Leu Asn Glu Glu Met
                440                 445                 450

Ser Gly Leu Pro Ala Ala Arg Lys His Leu Asn Lys Leu Arg Asn
                455                 460                 465

Ile Arg Tyr Gly Phe Asn Thr Ile Leu Val Ile Leu Ile Trp Arg
                470                 475                 480

Ile Phe Ile Ala Arg Ser Gln Met Ala Arg Asn Ile Trp Tyr Phe
                485                 490                 495

Val Val Ser Leu Cys Tyr Lys Phe Leu Ser Tyr Phe Arg Ala Ser
                500                 505                 510

Ser Thr Met Arg Tyr
                515


<210> SEQ ID NO 5
<211> LENGTH: 1759
<212> TYPE: DNA
<213> ORGANISM: Homo sapiens

<400> SEQUENCE: 5

cgatgccggc ggtcagtggt ccaggtccct tattctgcct tctcctcctg          50

ctcctggacc cccacagccc tgagacgggg tgtcctcctc tacgcaggtt         100

tgagtacaag ctcagcttca aaggcccaag gctggcattg cctggggctg         150

gaataccctt ctggagccat catggagacg ccatcctggg cctggaggaa         200

gtgcggctga cgccatccat gaggaaccgg agtggcgccg tgtggagcag         250

ggcctctgtc cccttctctg cctgggaagt agaggtgcag atgagggtga         300

cgggactggg gcgccgggga gcccagggca tggccgtgtg gtacacccgg         350

ggcaggggcc atgtaggctc tgtccttggg gggctggctt cgtgggacgg         400

catcgggatc ttctttgact ctccggcaga ggatactcag gacagtcctg         450

ccatccgtgt gctggccagc gacgggcaca tcccctctga gcagcctggg         500

gatggagcta gccaagggct gggctcctgt cattgggact tccggaaccg         550

gccacactcc ttcagagcac ggatcaccta ctgggggcag aggctgcgca         600

tgtccttgaa cagtggcctc actcccagtg atccaggtga gttctgtgtg         650

gatgtggggc ccctgctttt ggtccctgga ggtttctttg gggtctcagc         700

agccaccggc accctggcag gtgaggatcc cactggacag gttccccctc         750

agcccttcct ggagatgcag cagctccgcc tggcgaggca gctggaaggg         800

ctgtgggcaa ggctgggctt gggcaccagg gaggatgtaa ctccaaaatc         850

agactctgaa gctcaaggag aaggggaaag gctctttgac ctggaggaga         900

cgctgggcag acaccgccgg atcctgcagg ctctgcgggg tctctccaag         950

cagctggccc aggctgagag acaatggaag aagcagctgg ggcccccagg        1000

ccaagccagg cctgacggag gctgggccct ggatgcttcc tgccagattc        1050

catccacccc agggaggggt ggccacctct ccatgtcact caataaggac        1100

tctgccaagg tcggtgccct gctccatgga cagtggactc tgctccaggc        1150

cctgcaagag atgagggatg cagctgtccg catggctgca gaagcccagg        1200
```

-continued

```
tctcctacct gcctgtgggc attgagcatc atttcttaga gctggaccac          1250

atcctgggcc tcctgcagga ggagcttcgg ggcccggcga aggcagcagc          1300

caaggccccc cgcccacctg gccagccccc aagggcctcc tcgtgcctgc          1350

agcctggcat cttcctgttc tacctcctca ttcagactgt aggcttcttc          1400

ggctacgtgc acttcaggca ggagctgaac aagagccttc aggagtgtct          1450

gtccacaggc agccttcctc tgggtcctgc accacacacc cccagggccc          1500

tggggattct gaggaggcag cctctccctg ccagcatgcc tgcctgaccc          1550

acctcagagc ctgctttgca tcactgggaa gcaggcagtg tcttgggtgg          1600

gggcttggtc agtatcctct ccgtctgggt gcccagctcc cacgcacacc          1650

tgagctttcg gcatgctccc acctcgttaa aggtgatttc cctctcccca          1700

aaaaaaaaaa aaaaaaaaaa aaaaaaaaaa aaaaaaaaaa aaaaaaaaaa          1750

aaaaaaaaa                                                       1759
```

<210> SEQ ID NO 6
<211> LENGTH: 514
<212> TYPE: PRT
<213> ORGANISM: Homo sapiens

<400> SEQUENCE: 6

```
Met Pro Ala Val Ser Gly Pro Gly Pro Leu Phe Cys Leu Leu Leu
  1               5                  10                  15

Leu Leu Leu Asp Pro His Ser Pro Glu Thr Gly Cys Pro Pro Leu
                 20                  25                  30

Arg Arg Phe Glu Tyr Lys Leu Ser Phe Lys Gly Pro Arg Leu Ala
                 35                  40                  45

Leu Pro Gly Ala Gly Ile Pro Phe Trp Ser His His Gly Asp Ala
                 50                  55                  60

Ile Leu Gly Leu Glu Glu Val Arg Leu Thr Pro Ser Met Arg Asn
                 65                  70                  75

Arg Ser Gly Ala Val Trp Ser Arg Ala Ser Val Pro Phe Ser Ala
                 80                  85                  90

Trp Glu Val Glu Val Gln Met Arg Val Thr Gly Leu Gly Arg Arg
                 95                 100                 105

Gly Ala Gln Gly Met Ala Val Trp Tyr Thr Arg Gly Arg Gly His
                110                 115                 120

Val Gly Ser Val Leu Gly Gly Leu Ala Ser Trp Asp Gly Ile Gly
                125                 130                 135

Ile Phe Phe Asp Ser Pro Ala Glu Asp Thr Gln Asp Ser Pro Ala
                140                 145                 150

Ile Arg Val Leu Ala Ser Asp Gly His Ile Pro Ser Glu Gln Pro
                155                 160                 165

Gly Asp Gly Ala Ser Gln Gly Leu Gly Ser Cys His Trp Asp Phe
                170                 175                 180

Arg Asn Arg Pro His Ser Phe Arg Ala Arg Ile Thr Tyr Trp Gly
                185                 190                 195

Gln Arg Leu Arg Met Ser Leu Asn Ser Gly Leu Thr Pro Ser Asp
                200                 205                 210

Pro Gly Glu Phe Cys Val Asp Val Gly Pro Leu Leu Leu Val Pro
                215                 220                 225

Gly Gly Phe Phe Gly Val Ser Ala Ala Thr Gly Thr Leu Ala Gly
```

-continued

```
                230                 235                 240

Glu Asp Pro Thr Gly Gln Val Pro Pro Gln Pro Phe Leu Glu Met
                245                 250                 255

Gln Gln Leu Arg Leu Ala Arg Gln Leu Glu Gly Leu Trp Ala Arg
                260                 265                 270

Leu Gly Leu Gly Thr Arg Glu Asp Val Thr Pro Lys Ser Asp Ser
                275                 280                 285

Glu Ala Gln Gly Glu Gly Glu Arg Leu Phe Asp Leu Glu Glu Thr
                290                 295                 300

Leu Gly Arg His Arg Arg Ile Leu Gln Ala Leu Arg Gly Leu Ser
                305                 310                 315

Lys Gln Leu Ala Gln Ala Glu Arg Gln Trp Lys Lys Gln Leu Gly
                320                 325                 330

Pro Pro Gly Gln Ala Arg Pro Asp Gly Gly Trp Ala Leu Asp Ala
                335                 340                 345

Ser Cys Gln Ile Pro Ser Thr Pro Gly Arg Gly Gly His Leu Ser
                350                 355                 360

Met Ser Leu Asn Lys Asp Ser Ala Lys Val Gly Ala Leu Leu His
                365                 370                 375

Gly Gln Trp Thr Leu Leu Gln Ala Leu Gln Glu Met Arg Asp Ala
                380                 385                 390

Ala Val Arg Met Ala Ala Glu Ala Gln Val Ser Tyr Leu Pro Val
                395                 400                 405

Gly Ile Glu His His Phe Leu Glu Leu Asp His Ile Leu Gly Leu
                410                 415                 420

Leu Gln Glu Glu Leu Arg Gly Pro Ala Lys Ala Ala Ala Lys Ala
                425                 430                 435

Pro Arg Pro Pro Gly Gln Pro Pro Arg Ala Ser Ser Cys Leu Gln
                440                 445                 450

Pro Gly Ile Phe Leu Phe Tyr Leu Leu Ile Gln Thr Val Gly Phe
                455                 460                 465

Phe Gly Tyr Val His Phe Arg Gln Glu Leu Asn Lys Ser Leu Gln
                470                 475                 480

Glu Cys Leu Ser Thr Gly Ser Leu Pro Leu Gly Pro Ala Pro His
                485                 490                 495

Thr Pro Arg Ala Leu Gly Ile Leu Arg Arg Gln Pro Leu Pro Ala
                500                 505                 510

Ser Met Pro Ala


<210> SEQ ID NO 7
<211> LENGTH: 3010
<212> TYPE: DNA
<213> ORGANISM: Homo sapiens

<400> SEQUENCE: 7

gcccccagca tggcttggca gggctggccc gcggcgtggc agtgggtcgc                50

cggctgctgg ctcctcctcg tccttgtcct cgtcctactt gtgagccccc               100

gcggctgccg agcgcggcgg ggcctccgcg gtctgctcat ggcgcacagc               150

cagcggctgc tcttccgaat cgggtacagc ctgtacaccc gcacctggct               200

cgggtacctc ttctaccgac agcagctgcg cagggctcgg aatcgctacc               250

ctaaaggcca ctcgaaaacc cagccccgcc tcttcaatgg agtgaaggtg               300

cttcccatcc ctgtcctctc ggacaactac agctacctca tcatcgacac               350
```

-continued

```
ccaggcccag ctggctgtgg ctgtggaccc ttcagaccct cgggctgtgc     400
aggcttccat tgaaaaggaa ggggtcacct tggtcgccat tctgtgtact     450
cacaagcact gggaccacag tggagggaac cgtgacctca gccggcggca     500
ccgggactgt cgggtgtacg ggagccctca ggacggcatc ccctacctca     550
cccatcccct gtgtcatcaa gatgtggtca gcgtgggacg gcttcagatc     600
cgggccctgg ctacacctgg ccacacacaa ggccatctgg tctacctact     650
ggatggggag ccctacaagg gtccctcctg cctcttctca ggggacctgc     700
tcttcctctc tggctgtggg cggacctttg agggcaatgc agagaccatg     750
ctgagctcac tggacactgt gctggggcta ggggatgaca cccttctgtg     800
gcctggtcat gagtatgcag aggagaacct gggctttgca ggtgtggtgg     850
agcccgagaa cctggcccgg gagaggaaga tgcagtgggt gcagcggcag     900
cggctggagc gcaagggcac gtgcccatct accctgggag aggagcgctc     950
ctacaacccg ttcctgagaa cccactgcct ggcgctacag gaggctctgg    1000
ggccggggcc gggccccact ggggatgatg actactcccg ggcccagctc    1050
ctggaagagc tccgccggct gaaggatatg cacaagagca agtgatgccc    1100
ccagcgcccc cagcccagcc cactccccgc atggggaggc cgccaccacc    1150
aacacctcat catccttctc atcgctaaca ccaccacctc catcggcacc    1200
caagcgggca tcatcccccc acactgctca ggggagggga gggatcaggc    1250
gatgagactg tgaggccaaa agaagggggc ctgttggagg ctgggaaccc    1300
cgcagcgcga ggctgcctca tcaacggcaa gaggaaagga ggggtctcgg    1350
gacatctcca gaccctacca actgggaggg tcccctcctc cttccctact    1400
cctgggacgg cagcaaggac atgggggctg ctgttagctt ctccgtcagg    1450
aggcctcatc tcactgtagc cctggaaccc agggtccatc ttgcccttcc    1500
cccatccatg gttgggaaag aagctcagcc cctcacagtg gcctcaagtg    1550
tgatgcctta caaaagcacc actcagatgg gcagctggac tctggtgtcc    1600
tgagactctg ccctcttccc acagcctccc tgccccaccc atccctgcaa    1650
agccattttt cagacagagc cattcctaag aacactgaag ggctggaatg    1700
ctggctggcc actctctgcc tcagtggcct ccctacagcc tggaagaagg    1750
agggtcctga ttgccaagga aacctcctca ttgggctaag gagacactgg    1800
agtctggagt gtggagcccc acagtcttgc aggtcacatg ctctccttgc    1850
acatctggcc tggttgtacc cactggcctc tgcctctgcc ctgggccaaa    1900
agggcccctc cttgccaggg gagagacagc cacggtcctc tttggccgat    1950
gctgtattct cattttggcc cttgttctta ggcccgtctg cccgccctcc    2000
tccatctaac ctttcctgtt ttatccgcag ccctttttctt ctttgagtta    2050
gtaaagattt attctgtaac ctgacactca tctggccctt tgcagtttgc    2100
cagccatatt cccatgtgat ttcccactgg atccaggccc ccatccggct    2150
ggcaggaggg ggctctgacg tacaggttgg aaatcagaag tctgtgagag    2200
cgcgggagtg catggcagct ctgggtccca gacctggccc gacccctctg    2250
cttcacctcc agctctgctg ctcctctact cttgggtcga gatccctttg    2300
```

-continued

```
gagccacagc gaggaaccct gtggtcctca ggcaggtgta ccttgagtca          2350

gccaggagcc ctcttttcct gtgtcaaagc ctgccctcgg gctctgctca          2400

cctctggtga ccctccaaga tgcccctgcc ctcagtttcc cctcatgatc          2450

tggcctctgc ccccttctct agccacagcc tctagtacac tttagcaata          2500

ccaccagact agttagagtt ccccactcac caagcaagac atgcagtttc          2550

atgcctctgt gccttcgctc atgctgtttc ttccgactgg aatgccttcc          2600

cctgctcctc ctgccttgtc tgcctggcaa gttcatctct cacgatcccc          2650

tcaaaggccc cctcctccag gaaggcaacc cctgtgcccc tcccctccag          2700

gctacctctg cactttgtca atgcttctct tgtggcactt atcacactgt          2750

attttacttg tttacatgtt tgtctcccct tctagactgt gaatccttaa          2800

gggcatggac tgtatcttat gcatctctgt atttctgcgc ctagcacggt          2850

gcctagcaca cagtaggcgc tcaataaatg ttgaatgaat gaaaaaaaaa          2900

aaaaaaaaaa aaaaaaaaaa aaaaaaaaaa aaaaaaaaaa aaaaaaaaaa          2950

aaaaaaaaaa aaaaaaaaaa aaaaaaaaaa aaaaaaaaaa aaaaaaaaaa          3000

aaaaaaaaaa                                                      3010
```

<210> SEQ ID NO 8
<211> LENGTH: 361
<212> TYPE: PRT
<213> ORGANISM: Homo sapiens

<400> SEQUENCE: 8

```
Met Ala Trp Gln Gly Trp Pro Ala Ala Trp Gln Trp Val Ala Gly
  1               5                  10                  15

Cys Trp Leu Leu Leu Val Leu Val Leu Val Leu Leu Val Ser Pro
                 20                  25                  30

Arg Gly Cys Arg Ala Arg Arg Gly Leu Arg Gly Leu Leu Met Ala
                 35                  40                  45

His Ser Gln Arg Leu Leu Phe Arg Ile Gly Tyr Ser Leu Tyr Thr
                 50                  55                  60

Arg Thr Trp Leu Gly Tyr Leu Phe Tyr Arg Gln Gln Leu Arg Arg
                 65                  70                  75

Ala Arg Asn Arg Tyr Pro Lys Gly His Ser Lys Thr Gln Pro Arg
                 80                  85                  90

Leu Phe Asn Gly Val Lys Val Leu Pro Ile Pro Val Leu Ser Asp
                 95                 100                 105

Asn Tyr Ser Tyr Leu Ile Ile Asp Thr Gln Ala Gln Leu Ala Val
                110                 115                 120

Ala Val Asp Pro Ser Asp Pro Arg Ala Val Gln Ala Ser Ile Glu
                125                 130                 135

Lys Glu Gly Val Thr Leu Val Ala Ile Leu Cys Thr His Lys His
                140                 145                 150

Trp Asp His Ser Gly Gly Asn Arg Asp Leu Ser Arg Arg His Arg
                155                 160                 165

Asp Cys Arg Val Tyr Gly Ser Pro Gln Asp Gly Ile Pro Tyr Leu
                170                 175                 180

Thr His Pro Leu Cys His Gln Asp Val Val Ser Val Gly Arg Leu
                185                 190                 195

Gln Ile Arg Ala Leu Ala Thr Pro Gly His Thr Gln Gly His Leu
                200                 205                 210
```

-continued

```
Val Tyr Leu Leu Asp Gly Glu Pro Tyr Lys Gly Pro Ser Cys Leu
                215                 220                 225

Phe Ser Gly Asp Leu Leu Phe Leu Ser Gly Cys Gly Arg Thr Phe
                230                 235                 240

Glu Gly Asn Ala Glu Thr Met Leu Ser Ser Leu Asp Thr Val Leu
                245                 250                 255

Gly Leu Gly Asp Asp Thr Leu Leu Trp Pro Gly His Glu Tyr Ala
                260                 265                 270

Glu Glu Asn Leu Gly Phe Ala Gly Val Val Glu Pro Glu Asn Leu
                275                 280                 285

Ala Arg Glu Arg Lys Met Gln Trp Val Gln Arg Gln Arg Leu Glu
                290                 295                 300

Arg Lys Gly Thr Cys Pro Ser Thr Leu Gly Glu Glu Arg Ser Tyr
                305                 310                 315

Asn Pro Phe Leu Arg Thr His Cys Leu Ala Leu Gln Glu Ala Leu
                320                 325                 330

Gly Pro Gly Pro Gly Pro Thr Gly Asp Asp Asp Tyr Ser Arg Ala
                335                 340                 345

Gln Leu Leu Glu Glu Leu Arg Arg Leu Lys Asp Met His Lys Ser
                350                 355                 360

Lys


<210> SEQ ID NO 9
<211> LENGTH: 872
<212> TYPE: DNA
<213> ORGANISM: Homo sapiens

<400> SEQUENCE: 9

gctgacaatc cccttgacgt tctatcccgg aagctccacc tggggcccaa                50

tgttgggcgt gatgttcctc gcctgtctct gcctggaaaa ctggtcttcc               100

caagctccac tggcagccac ttctccatgt tgggcatcgg agacatcgtt               150

atgcctggtc tcctactatg ctttgtcctt cgctatgaca actacaaaaa               200

gcaagccagt ggggactcct gtggggcccc tggacctgcc aacatctccg               250

ggcgcatgca gaaggtctcc tactctcact gcaccctcat cggatacttt               300

gtaggcctgc tcactgctac tgtggcgtct cgcattcacc gggccgccca               350

gcccgccctt ctctatttgg tgccatttac tttattgcca ctcctcacga               400

tggcctattt aaagggcgac ctccggcgga tgtggtctga gcctttccac               450

tccaagtcca gcagctcccg attcctggaa gtatgatgga tcacgtggaa               500

agtgaccaga tggccgtcat agtccttttc tctcaactca tggtttgttt               550

cctcttagag ctggcctggt actcagaaat gtacctgtgt ttaaggaact               600

gccgtgtgac tggatttggc attgaaaggg agctcgtttg caggagagag               650

gtgctggagc cctgtttggt tccttctctt cctgcggatg tagaggtggg               700

gccccttcca agagggacag gcctctcccc agcgcgcctt cctcccacgt               750

ttttatggat ctgcaccaga ctgttacctt ctgggggaga tggagatttg               800

actgtttaaa aactgaaaac agcgaggagt ctttctagaa cttttgaaca               850

ctaaaaggat gaaaaaatta  gc                                            872


<210> SEQ ID NO 10
```

-continued

<211> LENGTH: 108
<212> TYPE: PRT
<213> ORGANISM: Homo sapiens

<400> SEQUENCE: 10

Met Met Asp His Val Glu Ser Asp Gln Met Ala Val Ile Val Leu
1 5 10 15

Phe Ser Gln Leu Met Val Cys Phe Leu Leu Glu Leu Ala Trp Tyr
20 25 30

Ser Glu Met Tyr Leu Cys Leu Arg Asn Cys Arg Val Thr Gly Phe
35 40 45

Gly Ile Glu Arg Glu Leu Val Cys Arg Arg Glu Val Leu Glu Pro
50 55 60

Cys Leu Val Pro Ser Leu Pro Ala Asp Val Glu Val Gly Pro Leu
65 70 75

Pro Arg Gly Thr Gly Leu Ser Pro Ala Arg Leu Pro Pro Thr Phe
80 85 90

Leu Trp Ile Cys Thr Arg Leu Leu Pro Ser Gly Gly Asp Gly Asp
95 100 105

Leu Thr Val

<210> SEQ ID NO 11
<211> LENGTH: 1739
<212> TYPE: DNA
<213> ORGANISM: Homo sapiens

<400> SEQUENCE: 11 tcgcacactg gtggcttcag aagaaattct caacacctag ctcgccagag 50 agtctatgta tgggattgaa caatctgtaa actaaaggat cctaatcatg 100 aaaataagta tgataaatta taagtcacta ttggcactgt tgtttatatt 150 agcctcctgg atcattttta cagttttcca gaactccaca aaggtttggt 200 ctgctctaaa cttatccatc tccctccatt actggaacaa ctccacaaag 250 tccttattcc ctaaaacacc actgatatca ttaaagccac taacagagac 300 tgaactcaga ataaaggaaa tcatagagaa actagatcag cagatcccac 350 ccagaccttt cacccacgtg aacaccacca ccagcgccac acatagcaca 400 gccaccatcc tcaaccctcg agatacgtac tgcaggggag accagctgca 450 catcctgctg gaggtgaggg accacttggg acgcaggaag caatatggcg 500 gggatttcct gagggccagg atgtcttccc cagcgctgat ggcaggtgct 550 tcaggaaagg tgactgactt caacaacggc acctacctgg tcagcttcac 600 tctgttctgg gagggccagg tctctctgtc tctgctgctc atccacccca 650 gtgaaggggt gtcagctctc tggagtgcaa ggaaccaagg ctatgacagg 700 gtgatcttca ctggccagtt tgtcaatggc acttcccaag tccactctga 750 atgtggcctg atcctaaaca caaatgctga attgtgccag tacctggaca 800 acagagacca agaaggcttc tactgtgtga ggcctcaaca catgccctgt 850 gctgcactca ctcacatgta ttctaagaac aagaaagttt cttatcttag 900 caaacaagaa aagagcctct ttgaaaggtc aaatgtgggt gtagagatta 950 tggaaaaatt caatacaatt agtgtctcca aatgcaacaa agaaacagtt 1000 gcaatgaaag agaaatgcaa gtttggaatg acatccacaa tccccagtgg 1050

-continued

```
gcatgtctgg agaaacacat ggaatcctgt ctcctgtagt ttggctacag          1100

tcaaaatgaa ggaatgcctg agaggaaaac tcatatacct aatgggagat          1150

tccacgatcc gccagtggat ggaatacttc aaagccagta tcaacacact          1200

gaagtcagtg gatctgcatg aatctggaaa attgcaacac cagcttgctg          1250

tggatttgga taggaacatc aacatccagt ggcaaaaata ttgttatccc          1300

ttgataggat caatgaccta ttcagtcaaa gagatggagt acctcacccg          1350

ggccattgac agaactggag gagaaaaaaa tactgtcatt gttatttccc          1400

tgggccagca tttcagaccc tttcccattg atgtttttat ccgaagggcc          1450

ctcaatgtcc acaaagccat tcagcatctt cttctgagaa gcccagacac          1500

tatggttatc atcaaaacag aaaacatcag ggagatgtac aatgatgcag          1550

aaagatttag tgactttcat ggttacattc aatatctcat cataaaggac          1600

attttccagg atctcagtgt gagtatcatt gatgcctggg atataacaat          1650

tgcatatggc acaaataatg tacacccacc tcaacatgta gtcggaaatc          1700

agattaatat attattaaac tatatttgtt  aaataacaa                     1739
```

<210> SEQ ID NO 12
<211> LENGTH: 544
<212> TYPE: PRT
<213> ORGANISM: Homo sapiens

<400> SEQUENCE: 12

```
Met Lys Ile Ser Met Ile Asn Tyr Lys Ser Leu Leu Ala Leu Leu
  1               5                  10                  15

Phe Ile Leu Ala Ser Trp Ile Ile Phe Thr Val Phe Gln Asn Ser
                 20                  25                  30

Thr Lys Val Trp Ser Ala Leu Asn Leu Ser Ile Ser Leu His Tyr
                 35                  40                  45

Trp Asn Asn Ser Thr Lys Ser Leu Phe Pro Lys Thr Pro Leu Ile
                 50                  55                  60

Ser Leu Lys Pro Leu Thr Glu Thr Glu Leu Arg Ile Lys Glu Ile
                 65                  70                  75

Ile Glu Lys Leu Asp Gln Gln Ile Pro Pro Arg Pro Phe Thr His
                 80                  85                  90

Val Asn Thr Thr Thr Ser Ala Thr His Ser Thr Ala Thr Ile Leu
                 95                 100                 105

Asn Pro Arg Asp Thr Tyr Cys Arg Gly Asp Gln Leu His Ile Leu
                110                 115                 120

Leu Glu Val Arg Asp His Leu Gly Arg Arg Lys Gln Tyr Gly Gly
                125                 130                 135

Asp Phe Leu Arg Ala Arg Met Ser Ser Pro Ala Leu Met Ala Gly
                140                 145                 150

Ala Ser Gly Lys Val Thr Asp Phe Asn Asn Gly Thr Tyr Leu Val
                155                 160                 165

Ser Phe Thr Leu Phe Trp Glu Gly Gln Val Ser Leu Ser Leu Leu
                170                 175                 180

Leu Ile His Pro Ser Glu Gly Val Ser Ala Leu Trp Ser Ala Arg
                185                 190                 195

Asn Gln Gly Tyr Asp Arg Val Ile Phe Thr Gly Gln Phe Val Asn
                200                 205                 210

Gly Thr Ser Gln Val His Ser Glu Cys Gly Leu Ile Leu Asn Thr
```

-continued

```
                215                 220                 225

Asn Ala Glu Leu Cys Gln Tyr Leu Asp Asn Arg Asp Gln Glu Gly
                230                 235                 240

Phe Tyr Cys Val Arg Pro Gln His Met Pro Cys Ala Ala Leu Thr
                245                 250                 255

His Met Tyr Ser Lys Asn Lys Lys Val Ser Tyr Leu Ser Lys Gln
                260                 265                 270

Glu Lys Ser Leu Phe Glu Arg Ser Asn Val Gly Val Glu Ile Met
                275                 280                 285

Glu Lys Phe Asn Thr Ile Ser Val Ser Lys Cys Asn Lys Glu Thr
                290                 295                 300

Val Ala Met Lys Glu Lys Cys Lys Phe Gly Met Thr Ser Thr Ile
                305                 310                 315

Pro Ser Gly His Val Trp Arg Asn Thr Trp Asn Pro Val Ser Cys
                320                 325                 330

Ser Leu Ala Thr Val Lys Met Lys Glu Cys Leu Arg Gly Lys Leu
                335                 340                 345

Ile Tyr Leu Met Gly Asp Ser Thr Ile Arg Gln Trp Met Glu Tyr
                350                 355                 360

Phe Lys Ala Ser Ile Asn Thr Leu Lys Ser Val Asp Leu His Glu
                365                 370                 375

Ser Gly Lys Leu Gln His Gln Leu Ala Val Asp Leu Asp Arg Asn
                380                 385                 390

Ile Asn Ile Gln Trp Gln Lys Tyr Cys Tyr Pro Leu Ile Gly Ser
                395                 400                 405

Met Thr Tyr Ser Val Lys Glu Met Glu Tyr Leu Thr Arg Ala Ile
                410                 415                 420

Asp Arg Thr Gly Gly Glu Lys Asn Thr Val Ile Val Ile Ser Leu
                425                 430                 435

Gly Gln His Phe Arg Pro Phe Pro Ile Asp Val Phe Ile Arg Arg
                440                 445                 450

Ala Leu Asn Val His Lys Ala Ile Gln His Leu Leu Leu Arg Ser
                455                 460                 465

Pro Asp Thr Met Val Ile Ile Lys Thr Glu Asn Ile Arg Glu Met
                470                 475                 480

Tyr Asn Asp Ala Glu Arg Phe Ser Asp Phe His Gly Tyr Ile Gln
                485                 490                 495

Tyr Leu Ile Ile Lys Asp Ile Phe Gln Asp Leu Ser Val Ser Ile
                500                 505                 510

Ile Asp Ala Trp Asp Ile Thr Ile Ala Tyr Gly Thr Asn Asn Val
                515                 520                 525

His Pro Pro Gln His Val Val Gly Asn Gln Ile Asn Ile Leu Leu
                530                 535                 540

Asn Tyr Ile Cys


<210> SEQ ID NO 13
<211> LENGTH: 1893
<212> TYPE: DNA
<213> ORGANISM: Homo sapiens

<400> SEQUENCE: 13

gcaaagagaa gactgaaaga caaacctggg tgcagccaga gaggtccaga                50

tagatgagct tgtggcatcc attccccaag ttcagcctag ggactccacg               100
```

-continued

```
taccccagct gggtctcatt gttccagaac tgcattagtt aagattaccc      150
agacttggat ttcaaaggaa tactttcatt gttccgtctg taacacgaag      200
taattggggc cagctggatg tcaggatgcg tgtggttacc attgtaatct      250
tgctctgctt ttgcaaagcg gctgagctgc gcaaagcaag cccaggcagt      300
gtgagaagcc gagtgaatca tggccgggcg ggtggaggcc ggagaggctc      350
caacccggtc aaacgctacg caccaggcct cccgtgtgac gtgtacacat      400
atctccatga gaaatactta gattgtcaag aaagaaaatt agtttatgtg      450
ctgcctggtt ggcctcagga tttgctgcac atgctgctag caagaaacaa      500
gatccgcaca ttgaagaaca acatgttttc caagtttaaa aagctgaaaa      550
gcctggatct gcagcagaat gagatctcta aaattgagag tgaggcgttc      600
tttggtttaa acaaactcac caccctctta ctgcagcaca accagatcaa      650
agtcttgacg gaggaagtgt tcatttacac acctctcttg agctacctgc      700
gtctttatga caacccctgg cactgtactt gtgagataga aacgcttatt      750
tcaatgttgc agattcccag gaaccggaat ttggggaact acgccaagtg      800
tgaaagtcca caagaacaaa aaaataaaaa actgcggcag ataaaatctg      850
aacagttgtg taatgaagaa aaggaacaat tggacccgaa accccaagtg      900
tcagggagac ccccagtcat caagcctgag gtggactcaa ctttttgcca      950
caattatgtg tttcccatac aaacactgga ctgcaaaagg aaagagttga     1000
aaaaagtgcc aaacaacatc cctccagata ttgttaaact tgacttgtca     1050
tacaataaaa tcaaccaact tcgacccaag gaatttgaag atgttcatga     1100
gctgaagaaa ttaaacctca gcagcaatgg cattgaattc atcgatcctg     1150
ccgctttttt agggctcaca catttagaag aattagattt atcaaacaac     1200
agtctgcaaa actttgacta tggcgtatta gaagacttgt atttttttgaa    1250
actcttgtgg ctcagagata acccttggag atgtgactac aacattcact     1300
acctctacta ctggttaaag caccactaca atgtccattt taatggcctg     1350
gaatgcaaaa cgcctgaaga atacaaagga tggtctgtgg gaaaatatat     1400
tagaagttac tatgaagaat gccccaaaga caagttacca gcatatcctg     1450
agtcatttga ccaagacaca gaagatgatg aatgggaaaa aaaacataga     1500
gatcacaccg caaagaagca aagcgtaata attactatag taggataagg     1550
tagaaattgt tctgattgta attagttttg tattttctat actggtgtta     1600
gaaaacatat gtttacattt gattaactgt gttgcctatt tatgcagggt     1650
aatccagcta aaggaagctt tctttaatta taagtattat tgtgactatt     1700
atagtaatca agagaatgct atcatcctgc ttgcctgtcc atttgtggaa     1750
cagcatctgg tgatatgcaa ttccacactg gtaacctgca gcagttgggt     1800
cctaatgatg gcattagact ttcataatgt cctgtataaa tgtttttact     1850
gcttttagaa aataaagaaa aaaaacttgg ttcatgttta  aaa           1893
```

<210> SEQ ID NO 14
<211> LENGTH: 440
<212> TYPE: PRT
<213> ORGANISM: Homo sapiens

<400> SEQUENCE: 14

-continued

```
Met Arg Val Val Thr Ile Val Ile Leu Leu Cys Phe Cys Lys Ala
  1               5                  10                  15

Ala Glu Leu Arg Lys Ala Ser Pro Gly Ser Val Arg Ser Arg Val
                 20                  25                  30

Asn His Gly Arg Ala Gly Gly Gly Arg Arg Gly Ser Asn Pro Val
                 35                  40                  45

Lys Arg Tyr Ala Pro Gly Leu Pro Cys Asp Val Tyr Thr Tyr Leu
                 50                  55                  60

His Glu Lys Tyr Leu Asp Cys Gln Glu Arg Lys Leu Val Tyr Val
                 65                  70                  75

Leu Pro Gly Trp Pro Gln Asp Leu Leu His Met Leu Leu Ala Arg
                 80                  85                  90

Asn Lys Ile Arg Thr Leu Lys Asn Asn Met Phe Ser Lys Phe Lys
                 95                 100                 105

Lys Leu Lys Ser Leu Asp Leu Gln Gln Asn Glu Ile Ser Lys Ile
                110                 115                 120

Glu Ser Glu Ala Phe Phe Gly Leu Asn Lys Leu Thr Thr Leu Leu
                125                 130                 135

Leu Gln His Asn Gln Ile Lys Val Leu Thr Glu Glu Val Phe Ile
                140                 145                 150

Tyr Thr Pro Leu Leu Ser Tyr Leu Arg Leu Tyr Asp Asn Pro Trp
                155                 160                 165

His Cys Thr Cys Glu Ile Glu Thr Leu Ile Ser Met Leu Gln Ile
                170                 175                 180

Pro Arg Asn Arg Asn Leu Gly Asn Tyr Ala Lys Cys Glu Ser Pro
                185                 190                 195

Gln Glu Gln Lys Asn Lys Lys Leu Arg Gln Ile Lys Ser Glu Gln
                200                 205                 210

Leu Cys Asn Glu Glu Lys Glu Gln Leu Asp Pro Lys Pro Gln Val
                215                 220                 225

Ser Gly Arg Pro Pro Val Ile Lys Pro Glu Val Asp Ser Thr Phe
                230                 235                 240

Cys His Asn Tyr Val Phe Pro Ile Gln Thr Leu Asp Cys Lys Arg
                245                 250                 255

Lys Glu Leu Lys Lys Val Pro Asn Asn Ile Pro Pro Asp Ile Val
                260                 265                 270

Lys Leu Asp Leu Ser Tyr Asn Lys Ile Asn Gln Leu Arg Pro Lys
                275                 280                 285

Glu Phe Glu Asp Val His Glu Leu Lys Lys Leu Asn Leu Ser Ser
                290                 295                 300

Asn Gly Ile Glu Phe Ile Asp Pro Ala Ala Phe Leu Gly Leu Thr
                305                 310                 315

His Leu Glu Glu Leu Asp Leu Ser Asn Asn Ser Leu Gln Asn Phe
                320                 325                 330

Asp Tyr Gly Val Leu Glu Asp Leu Tyr Phe Leu Lys Leu Leu Trp
                335                 340                 345

Leu Arg Asp Asn Pro Trp Arg Cys Asp Tyr Asn Ile His Tyr Leu
                350                 355                 360

Tyr Tyr Trp Leu Lys His His Tyr Asn Val His Phe Asn Gly Leu
                365                 370                 375

Glu Cys Lys Thr Pro Glu Glu Tyr Lys Gly Trp Ser Val Gly Lys
                380                 385                 390
```

-continued

```
Tyr Ile Arg Ser Tyr Tyr Glu Glu Cys Pro Lys Asp Lys Leu Pro
                395                 400                 405

Ala Tyr Pro Glu Ser Phe Asp Gln Asp Thr Glu Asp Asp Glu Trp
                410                 415                 420

Glu Lys Lys His Arg Asp His Thr Ala Lys Lys Gln Ser Val Ile
                425                 430                 435

Ile Thr Ile Val Gly
                440


<210> SEQ ID NO 15
<211> LENGTH: 1524
<212> TYPE: DNA
<213> ORGANISM: Homo sapiens

<400> SEQUENCE: 15

gcggcagcag cgcgggcccc agcagcctcg gcagccacag ccgctgcagc                50

cggggcagcc tccgctgctg tcgcctcctc tgatgcgctt gccctctccc               100

ggccccggga ctccgggaga atgtgggtcc taggcatcgc ggcaactttt               150

tgcggattgt tcttgcttcc aggctttgcg ctgcaaatcc agtgctacca               200

gtgtgaagaa ttccagctga acaacgactg ctcctccccc gagttcattg               250

tgaattgcac ggtgaacgtt caagacatgt gtcagaaaga agtgatggag               300

caaagtgccg ggatcatgta ccgcaagtcc tgtgcatcat cagcggcctg               350

tctcatcgcc tctgccgggt accagtcctt ctgctcccca gggaaactga               400

actcagtttg catcagctgc tgcaacaccc ctctttgtaa cgggccaagg               450

cccaagaaaa ggggaagttc tgcctcggcc ctcaggccag ggctccgcac               500

caccatcctg ttcctcaaat tagccctctt ctcggcacac tgctgaagct               550

gaaggagatg ccaccccctc ctgcattgtt cttccagccc tcgcccccaa               600

ccccccacct ccctgagtga gtttcttctg ggtgtccttt tattctgggt               650

agggagcggg agtccgtgtt ctcttttgtt cctgtgcaaa taatgaaaga               700

gctcggtaaa gcattctgaa taaattcagc ctgactgaat tttcagtatg               750

tacttgaagg aaggaggtgg agtgaaagtt cacccccatg tctgtgtaac               800

cggagtcaag gccaggctgg cagagtcagt ccttagaagt cactgaggtg               850

ggcatctgcc ttttgtaaag cctccagtgt ccattccatc cctgatgggg               900

gcatagtttg agactgcaga gtgagagtga cgttttctta gggctggagg               950

gccagttccc actcaaggct ccctcgcttg acattcaaac ttcatgctcc              1000

tgaaaaccat tctctgcagc agaattggct ggtttcgcgc ctgagttggg              1050

ctctagtgac tcgagactca atgactggga cttagactgg ggctcggcct              1100

cgctctgaaa agtgcttaag aaaatcttct cagttctcct tgcagaggac              1150

tggcgccggg acgcgaagag caacgggcgc tgcacaaagc gggcgctgtc              1200

ggtggtggag tgcgcatgta cgcgcaggcg cttctcgtgg ttggcgtgct              1250

gcagcgacag gcggcagcac agcacctgca cgaacacccg ccgaaactgc              1300

tgcgaggaca ccgtgtacag gagcgggttg atgaccgagc tgaggtagaa              1350

aaacgtctcc gagaagggga ggaggatcat gtacgcccgg aagtaggacc              1400

tcgtccagtc gtgcttgggt ttggccgcag ccatgatcct ccgaatctgg              1450

ttgggcatcc agcatacggc caatgtcaca acaatcagcc ctgggcagac              1500
```

acgagcagga gggagagaca gaga 1524

<210> SEQ ID NO 16
<211> LENGTH: 141
<212> TYPE: PRT
<213> ORGANISM: Homo sapiens

<400> SEQUENCE: 16

Met Trp Val Leu Gly Ile Ala Ala Thr Phe Cys Gly Leu Phe Leu
1 5 10 15

Leu Pro Gly Phe Ala Leu Gln Ile Gln Cys Tyr Gln Cys Glu Glu
20 25 30

Phe Gln Leu Asn Asn Asp Cys Ser Ser Pro Glu Phe Ile Val Asn
35 40 45

Cys Thr Val Asn Val Gln Asp Met Cys Gln Lys Glu Val Met Glu
50 55 60

Gln Ser Ala Gly Ile Met Tyr Arg Lys Ser Cys Ala Ser Ser Ala
65 70 75

Ala Cys Leu Ile Ala Ser Ala Gly Tyr Gln Ser Phe Cys Ser Pro
80 85 90

Gly Lys Leu Asn Ser Val Cys Ile Ser Cys Cys Asn Thr Pro Leu
95 100 105

Cys Asn Gly Pro Arg Pro Lys Lys Arg Gly Ser Ser Ala Ser Ala
110 115 120

Leu Arg Pro Gly Leu Arg Thr Thr Ile Leu Phe Leu Lys Leu Ala
125 130 135

Leu Phe Ser Ala His Cys
140

<210> SEQ ID NO 17
<211> LENGTH: 1402
<212> TYPE: DNA
<213> ORGANISM: Homo sapiens

<400> SEQUENCE: 17 cgcaaagccg ccctcggggc gctcatggcg ggacgcctcc tgggaaaggc 50 tttagccgcg gtgtctctct ctctggcctt ggcctctgtg actatcaggt 100 cctcgcgctg ccgcggcatc caggcgttca gaaactcgtt ttcatcttct 150 tggtttcatc ttaataccaa cgtcatgtct ggttctaatg gttccaaaga 200 aaattctcac aataaggctc ggacgtctcc ttacccaggt tcaaaagttg 250 aacgaagcca ggttcctaat gagaaagtgg gctggcttgt tgagtggcaa 300 gactataagc ctgtggaata cactgcagtc tctgtcttgg ctggacccag 350 gtgggcagat cctcagatca gtgaaagtaa tttttctccc aagtttaacg 400 aaaaggatgg gcatgttgag agaaagagca agaatggcct gtatgagatt 450 gaaaatggaa gaccgagaaa tcctgcagga cggactggac tggtgggccg 500 ggggcttttg gggcgatggg gcccaaatca cgctgcagat cccattataa 550 ccagatggaa aagggatagc agtggaaata aaatcatgca tcctgtttct 600 gggaagcata tcttacaatt tgttgcaata aaaaggaaag actgtggaga 650 atgggcaatc ccagggggga tggtggatcc aggagagaag attagtgcca 700 cactgaaaag agaatttggt gaggaagctc tcaactcctt acagaaaacc 750

-continued

```
agtgctgaga agagagaaat agaggaaaag ttgcacaaac tcttcagcca          800

agaccaccta gtgatatata agggatatgt tgatgatcct cgaaacactg          850

ataatgcatg gatggagaca gaagctgtga actaccatga cgaaacaggt          900

gagataatgg ataatcttat gctagaagct ggagatgatg ctggaaaagt          950

gaaatgggtg gacatcaatg ataaactgaa gctttatgcc agtcactctc         1000

aattcatcaa acttgtggct gagaaacgag atgcacactg gagcgaggac         1050

tctgaagctg actgccatgc gttgtagctg atggtctccg tgtaagccaa         1100

aggcccacag aggagcatat actgaaaaga aggcagtatc acagaattta         1150

tactataaaa agggcagggt aggccacttg gcctatttac tttcaaaaca         1200

atttgcattt agagtgtttc gcatcagaat aacatgagta agatgaactg         1250

gaacacaaaa ttttcagctc tttggtcaaa aggaatataa gtaatcatat         1300

tttgtatgta ttcgatttaa gcatggctta aattaaattt aaacaactaa         1350

tgctctttga agaatcataa tcagaataaa gataaattct tgatcagcta         1400

ta                                                             1402
```

<210> SEQ ID NO 18
<211> LENGTH: 350
<212> TYPE: PRT
<213> ORGANISM: Homo sapiens

<400> SEQUENCE: 18

```
Met Ala Gly Arg Leu Leu Gly Lys Ala Leu Ala Ala Val Ser Leu
  1               5                  10                  15

Ser Leu Ala Leu Ala Ser Val Thr Ile Arg Ser Ser Arg Cys Arg
                 20                  25                  30

Gly Ile Gln Ala Phe Arg Asn Ser Phe Ser Ser Ser Trp Phe His
                 35                  40                  45

Leu Asn Thr Asn Val Met Ser Gly Ser Asn Gly Ser Lys Glu Asn
                 50                  55                  60

Ser His Asn Lys Ala Arg Thr Ser Pro Tyr Pro Gly Ser Lys Val
                 65                  70                  75

Glu Arg Ser Gln Val Pro Asn Glu Lys Val Gly Trp Leu Val Glu
                 80                  85                  90

Trp Gln Asp Tyr Lys Pro Val Glu Tyr Thr Ala Val Ser Val Leu
                 95                 100                 105

Ala Gly Pro Arg Trp Ala Asp Pro Gln Ile Ser Glu Ser Asn Phe
                110                 115                 120

Ser Pro Lys Phe Asn Glu Lys Asp Gly His Val Glu Arg Lys Ser
                125                 130                 135

Lys Asn Gly Leu Tyr Glu Ile Glu Asn Gly Arg Pro Arg Asn Pro
                140                 145                 150

Ala Gly Arg Thr Gly Leu Val Gly Arg Gly Leu Leu Gly Arg Trp
                155                 160                 165

Gly Pro Asn His Ala Ala Asp Pro Ile Ile Thr Arg Trp Lys Arg
                170                 175                 180

Asp Ser Ser Gly Asn Lys Ile Met His Pro Val Ser Gly Lys His
                185                 190                 195

Ile Leu Gln Phe Val Ala Ile Lys Arg Lys Asp Cys Gly Glu Trp
                200                 205                 210

Ala Ile Pro Gly Gly Met Val Asp Pro Gly Glu Lys Ile Ser Ala
```

-continued

```
                215                 220                 225

Thr Leu Lys Arg Glu Phe Gly Glu Glu Ala Leu Asn Ser Leu Gln
                230                 235                 240

Lys Thr Ser Ala Glu Lys Arg Glu Ile Glu Glu Lys Leu His Lys
                245                 250                 255

Leu Phe Ser Gln Asp His Leu Val Ile Tyr Lys Gly Tyr Val Asp
                260                 265                 270

Asp Pro Arg Asn Thr Asp Asn Ala Trp Met Glu Thr Glu Ala Val
                275                 280                 285

Asn Tyr His Asp Glu Thr Gly Glu Ile Met Asp Asn Leu Met Leu
                290                 295                 300

Glu Ala Gly Asp Asp Ala Gly Lys Val Lys Trp Val Asp Ile Asn
                305                 310                 315

Asp Lys Leu Lys Leu Tyr Ala Ser His Ser Gln Phe Ile Lys Leu
                320                 325                 330

Val Ala Glu Lys Arg Asp Ala His Trp Ser Glu Asp Ser Glu Ala
                335                 340                 345

Asp Cys His Ala Leu
                350


<210> SEQ ID NO 19
<211> LENGTH: 2138
<212> TYPE: DNA
<213> ORGANISM: Homo sapiens

<400> SEQUENCE: 19

cgagggctcc tgctggtact gtgttcgctg ctgcacagca aggccctgcc                50

acccaccttc aggccatgca gccatgttcc gggagcccta attgcacaga               100

agcccatggg gagctccaga ctggcagccc tgctcctgcc tctcctcctc               150

atagtcatcg acctctctga ctctgctggg attggctttc gccacctgcc               200

ccactggaac acccgctgtc ctctggcctc ccacacggat gacagtttca               250

ctggaagttc tgcctatatc ccttgccgca cctggtgggc cctcttctcc               300

acaaagcctt ggtgtgtgcg agtctggcac tgttcccgct gtttgtgcca               350

gcatctgctg tcaggtggct caggtcttca acggggcctc ttccacctcc               400

tggtgcagaa atccaaaaag tcttccacat tcaagttcta taggagacac               450

aagatgccag cacctgctca gaggaagctg ctgcctcgtc gtcacctgtc               500

tgagaagagc catcacattt ccatcccctc cccagacatc tcccacaagg               550

gacttcgctc taaaaggacc caaccttcgg atccagagac atgggaaagt               600

cttcccagat tggactcaca aaggcatgga ggacccgagt tctcctttga               650

tttgctgcct gaggcccggg ctattcgggt gaccatatct tcaggccctg               700

aggtcagcgt gcgtctttgt caccagtggg cactggagtg tgaagagctg               750

agcagtccct atgatgtcca gaaaattgtg tctgggggcc acactgtaga               800

gctgccttat gaattccttc tgccctgtct gtgcatagag gcatcctacc               850

tgcaagagga cactgtgagg cgcaaaaaat gtcccttcca gagctggcca               900

gaagcctatg gctcggactt ctggaagtca gtgcacttca ctgactacag               950

ccagcacact cagatggtca tggccctgac actccgctgc ccactgaagc              1000

tggaagctgc cctctgccag aggcacgact ggcataccct ttgcaaagac              1050
```

-continued

```
ctcccgaatg ccacggctcg agagtcagat gggtggtatg ttttggagaa          1100

ggtggacctg cacccccagc tctgcttcaa gttctctttt ggaaacagca          1150

gccatgttga atgcccccac cagactgggt ctctcacatc ctggaatgta          1200

agcatggata cccaagccca gcagctgatt cttcacttct cctcaagaat          1250

gcatgccacc ttcagtgctg cctggagcct cccaggcttg gggcaggaca          1300

ctttggtgcc ccccgtgtac actgtcagcc aggcccgggg ctcaagccca          1350

gtgtcactag acctcatcat tcccttcctg aggccagggt gctgtgtcct          1400

ggtgtggcgg tcagatgtcc agtttgcctg gaagcacctc ttgtgtccag          1450

atgtctctta cagacacctg gggctcttga tcctggcact gctggccctc          1500

ctcaccctac tgggtgttgt tctggccctc acctgccggc gcccacagtc          1550

aggcccgggc ccagcgcggc cagtgctcct cctgcacgcg gcggactcgg          1600

aggcgcagcg gcgcctggtg ggagcgctgg ctgaactgct acgggcagcg          1650

ctgggcggcg ggcgcgacgt gatcgtggac ctgtgggagg ggaggcacgt          1700

ggcgcgcgtg ggcccgctgc cgtggctctg ggcggcgcgg acgcgcgtag          1750

cgcgggagca gggcactgtg ctgctgctgt ggagcggcgc cgaccttcgc          1800

ccggtcagcg gccccgaccc ccgcgccgcg cccctgctcg ccctgctcca          1850

cgctgccccg cgcccgctgc tgctgctcgc ttacttcagt cgcctctgcg          1900

ccaagggcga catccccccg ccgctgcgcg ccctgccgcg ctaccgcctg          1950

ctgcgcgacc tgccgcgtct gctgcgggcg ctggacgcgc ggcctttcgc          2000

agaggccacc agctggggcc gccttggggc gcggcagcgc aggcagagcc          2050

gcctagagct gtgcagccgg cttgaacgag aggccgcccg acttgcagac          2100

ctaggttgag cagagctcca ccgcagtccc  gggtgtct                      2138
```

<210> SEQ ID NO 20
<211> LENGTH: 667
<212> TYPE: PRT
<213> ORGANISM: Homo sapiens

<400> SEQUENCE: 20

```
Met Gly Ser Ser Arg Leu Ala Ala Leu Leu Leu Pro Leu Leu Leu
  1               5                  10                  15

Ile Val Ile Asp Leu Ser Asp Ser Ala Gly Ile Gly Phe Arg His
                 20                  25                  30

Leu Pro His Trp Asn Thr Arg Cys Pro Leu Ala Ser His Thr Asp
                 35                  40                  45

Asp Ser Phe Thr Gly Ser Ser Ala Tyr Ile Pro Cys Arg Thr Trp
                 50                  55                  60

Trp Ala Leu Phe Ser Thr Lys Pro Trp Cys Val Arg Val Trp His
                 65                  70                  75

Cys Ser Arg Cys Leu Cys Gln His Leu Leu Ser Gly Gly Ser Gly
                 80                  85                  90

Leu Gln Arg Gly Leu Phe His Leu Leu Val Gln Lys Ser Lys Lys
                 95                 100                 105

Ser Ser Thr Phe Lys Phe Tyr Arg Arg His Lys Met Pro Ala Pro
                110                 115                 120

Ala Gln Arg Lys Leu Leu Pro Arg Arg His Leu Ser Glu Lys Ser
                125                 130                 135
```

-continued

```
His His Ile Ser Ile Pro Ser Pro Asp Ile Ser His Lys Gly Leu
                140                 145                 150

Arg Ser Lys Arg Thr Gln Pro Ser Asp Pro Glu Thr Trp Glu Ser
                155                 160                 165

Leu Pro Arg Leu Asp Ser Gln Arg His Gly Gly Pro Glu Phe Ser
                170                 175                 180

Phe Asp Leu Leu Pro Glu Ala Arg Ala Ile Arg Val Thr Ile Ser
                185                 190                 195

Ser Gly Pro Glu Val Ser Val Arg Leu Cys His Gln Trp Ala Leu
                200                 205                 210

Glu Cys Glu Glu Leu Ser Ser Pro Tyr Asp Val Gln Lys Ile Val
                215                 220                 225

Ser Gly Gly His Thr Val Glu Leu Pro Tyr Glu Phe Leu Leu Pro
                230                 235                 240

Cys Leu Cys Ile Glu Ala Ser Tyr Leu Gln Glu Asp Thr Val Arg
                245                 250                 255

Arg Lys Lys Cys Pro Phe Gln Ser Trp Pro Glu Ala Tyr Gly Ser
                260                 265                 270

Asp Phe Trp Lys Ser Val His Phe Thr Asp Tyr Ser Gln His Thr
                275                 280                 285

Gln Met Val Met Ala Leu Thr Leu Arg Cys Pro Leu Lys Leu Glu
                290                 295                 300

Ala Ala Leu Cys Gln Arg His Asp Trp His Thr Leu Cys Lys Asp
                305                 310                 315

Leu Pro Asn Ala Thr Ala Arg Glu Ser Asp Gly Trp Tyr Val Leu
                320                 325                 330

Glu Lys Val Asp Leu His Pro Gln Leu Cys Phe Lys Phe Ser Phe
                335                 340                 345

Gly Asn Ser Ser His Val Glu Cys Pro His Gln Thr Gly Ser Leu
                350                 355                 360

Thr Ser Trp Asn Val Ser Met Asp Thr Gln Ala Gln Gln Leu Ile
                365                 370                 375

Leu His Phe Ser Ser Arg Met His Ala Thr Phe Ser Ala Ala Trp
                380                 385                 390

Ser Leu Pro Gly Leu Gly Gln Asp Thr Leu Val Pro Pro Val Tyr
                395                 400                 405

Thr Val Ser Gln Ala Arg Gly Ser Ser Pro Val Ser Leu Asp Leu
                410                 415                 420

Ile Ile Pro Phe Leu Arg Pro Gly Cys Cys Val Leu Val Trp Arg
                425                 430                 435

Ser Asp Val Gln Phe Ala Trp Lys His Leu Leu Cys Pro Asp Val
                440                 445                 450

Ser Tyr Arg His Leu Gly Leu Leu Ile Leu Ala Leu Leu Ala Leu
                455                 460                 465

Leu Thr Leu Leu Gly Val Val Leu Ala Leu Thr Cys Arg Arg Pro
                470                 475                 480

Gln Ser Gly Pro Gly Pro Ala Arg Pro Val Leu Leu Leu His Ala
                485                 490                 495

Ala Asp Ser Glu Ala Gln Arg Arg Leu Val Gly Ala Leu Ala Glu
                500                 505                 510

Leu Leu Arg Ala Ala Leu Gly Gly Gly Arg Asp Val Ile Val Asp
                515                 520                 525

Leu Trp Glu Gly Arg His Val Ala Arg Val Gly Pro Leu Pro Trp
```

-continued

```
                530                 535                 540

Leu Trp Ala Ala Arg Thr Arg Val Ala Arg Glu Gln Gly Thr Val
                545                 550                 555

Leu Leu Leu Trp Ser Gly Ala Asp Leu Arg Pro Val Ser Gly Pro
                560                 565                 570

Asp Pro Arg Ala Ala Pro Leu Leu Ala Leu Leu His Ala Ala Pro
                575                 580                 585

Arg Pro Leu Leu Leu Leu Ala Tyr Phe Ser Arg Leu Cys Ala Lys
                590                 595                 600

Gly Asp Ile Pro Pro Pro Leu Arg Ala Leu Pro Arg Tyr Arg Leu
                605                 610                 615

Leu Arg Asp Leu Pro Arg Leu Leu Arg Ala Leu Asp Ala Arg Pro
                620                 625                 630

Phe Ala Glu Ala Thr Ser Trp Gly Arg Leu Gly Ala Arg Gln Arg
                635                 640                 645

Arg Gln Ser Arg Leu Glu Leu Cys Ser Arg Leu Glu Arg Glu Ala
                650                 655                 660

Ala Arg Leu Ala Asp Leu Gly
                665


<210> SEQ ID NO 21
<211> LENGTH: 2714
<212> TYPE: DNA
<213> ORGANISM: Homo sapiens

<400> SEQUENCE: 21

cggctcgagg ccctttgtga gggctgtgag ctgcgcctga cggtggcacc                50

atgagcagct caggtggggc gcccggggcg tccgccagct ctgcgccgcc               100

cgcgcaggaa gagggcatga cgtggtggta ccgctggctg tgtcgcctgt               150

ctggggtgct gggggcagtc tcttgcgcga tctctggcct cttcaactgc               200

atcaccatcc accctctgaa catcgcggcc ggcgtgtgga tgatcatgaa               250

tgccttcatc ttgttgctgt gtgaggcgcc cttctgctgc cagttcatcg               300

agtttgcaaa cacagtggcg gagaaggtgg accggctgcg ctcctggcag               350

aaggctgtct tctactgcgg gatggcggtc gttcccatcg tcatcagcct               400

gaccctgacc acgctgctgg gcaacgccat cgcctttgct acgggggtgc               450

tgtacggact ctctgctctg ggcaaaaagg gcgatgcgat ctcctatgcc               500

aggatccagc agcagaggca gcaggcggat gaggagaagc tcgcggagac               550

cctggagggg gagctgtgaa gggctgggcg cccctccctc cctgtcccct               600

cttctggctc tgtgtgggtc caagtgaggc ctggactgtc cacgctgagg               650

cacagcctgg agaggggcct ttgcacgtgt ccctacacct ggagtcctct               700

gctcctttct ccagactggc ttaagccagg agccactggc tgctggtgtg               750

agggtctggg ctgctggact tgaggcagag cctgcagcag ctgtgtggac               800

actacccagc cctactcctc tgctgggtgg gtctgcagat ctcacaccac               850

agacagggct gcctgtgacc tgctgtgacc tgggagcagc ttcccctgga               900

gatgctggtc ctggcttgag gggaggggca agtgggaccc tgccacctgg               950

gcactgagca gagggacctc ccccagctct cttagcaggt ggagccccag              1000

ggcctgggac agcctgccgc tgccagcaac ctcccactgc tgcctagggt              1050
```

-continued

```
gcagcgccca ctgtcaccct gccttctgaa gaagcccaca gggctcctaa          1100
ggtgcacccc ggtacctgga actgcagcct tggcagtgac tggacagctg          1150
ggtgggggat gctccctgct ggccctggga accttggaca ggccacctca          1200
aggcccctcg gctgcccctc ctccctgggc ctgctggggc ccctaggttc          1250
tacccatcac cccccgcccc tgctggcctt ggtgctaagg aagtggggag          1300
agcaggctct ccctggcacc gagggtgccc accctctccc tggtgtggcc          1350
ccgtcaacat cagccacagc ccagccccat tagtgggtta gtgggtctga          1400
cctcagcccc actcaggtgc tcctgctggc ctgcccaagc cctgccctca          1450
gggagcttct gccttttaag aactgggcag aggccacagt cacctcccca          1500
cacagagctg tccccactgc cctgggtgcc aggctgtccg gagccaggcc          1550
tacccaggga ggatgcagag agctggtgcc caggatgtgc acccccatat          1600
tccctctgcc ctgtggcctc agcccgctgg cctctctgac cgtgaggctg          1650
gctctcagcc atcgggcagg tgcctggtca ggcctggctt agcccaggtg          1700
gggcttggca gaagcgggcg ggtgtggaag atattccatc tggggccaac          1750
cccaggctgg gcctgcgctg agcttctgga gcgcaggtac tgggtcttgc          1800
taagtgaact gtttcccagg aacacctctc gggcccatct gcgtctgagg          1850
ctgggagtgg catctgaggc cgggagtggc atctgaggcc aggagtggca          1900
ggctggtggg ctgggcgtgg ggttttctgg gccctgccca gtactgccct          1950
ggggacttgg tgggctcctg ggtcagcagc atcccacccc tgggagtctg          2000
gccagctgag ccccagggtg gcaggggcat tatagcctgg tggacatgtg          2050
ccttcagggt tcctccgggg ccaccttcct caggccagtg ctgggttcaa          2100
agggctgtgt gtgtgtgtgt ttgtgtgtgt atgtatatgt gtgtgggtgc          2150
acacatctgt cccatgtatg cagtgagacc tgtctacctc ccacaaggag          2200
caagggctct gcccgccctc tgctcattcc tacccaggta gtgggacccc          2250
gggccccctt ctgcctggct tgcctgcttc tgccctttcc agaggggtct          2300
cactgacagc cagagacagc aggagaaggg ttggctgtgg atcaaggaag          2350
gctgcccctg taccctgtgg ggaaatggtg ggtgcatggc tggatgcaga          2400
ggtggaaggc cctgggccac aggcgagagt gggcgtgtca cctgtcccag          2450
gttcccagca agtctgcagc tgtgcagtcc tggggtccct gaccctgtcg          2500
cccagggggc gtgctgtcca gcaggggccc tgccttgcaa ggaacgtctc          2550
tccggcggct gggccgctcc tgcctggtct gggctgtgtg tggcgccctt          2600
tcctccttgt ttgttcctct gtgttctgtg tgcgtcttaa gcaataaagc          2650
gtggccgtgg gaaaaaaaaa aaaaaaaaaa aaaaaaaaaa aaaaaaaaaa          2700
aaaaaaaaaa  aaaa                                                2714
```

<210> SEQ ID NO 22
<211> LENGTH: 172
<212> TYPE: PRT
<213> ORGANISM: Homo sapiens

<400> SEQUENCE: 22

```
Met Ser Ser Ser Gly Gly Ala Pro Gly Ala Ser Ala Ser Ser Ala
  1               5                  10                  15
```

-continued

```
Pro Pro Ala Gln Glu Glu Gly Met Thr Trp Trp Tyr Arg Trp Leu
                20                  25                  30

Cys Arg Leu Ser Gly Val Leu Gly Ala Val Ser Cys Ala Ile Ser
                35                  40                  45

Gly Leu Phe Asn Cys Ile Thr Ile His Pro Leu Asn Ile Ala Ala
                50                  55                  60

Gly Val Trp Met Ile Met Asn Ala Phe Ile Leu Leu Leu Cys Glu
                65                  70                  75

Ala Pro Phe Cys Cys Gln Phe Ile Glu Phe Ala Asn Thr Val Ala
                80                  85                  90

Glu Lys Val Asp Arg Leu Arg Ser Trp Gln Lys Ala Val Phe Tyr
                95                 100                 105

Cys Gly Met Ala Val Val Pro Ile Val Ile Ser Leu Thr Leu Thr
               110                 115                 120

Thr Leu Leu Gly Asn Ala Ile Ala Phe Ala Thr Gly Val Leu Tyr
               125                 130                 135

Gly Leu Ser Ala Leu Gly Lys Lys Gly Asp Ala Ile Ser Tyr Ala
               140                 145                 150

Arg Ile Gln Gln Gln Arg Gln Gln Ala Asp Glu Glu Lys Leu Ala
               155                 160                 165

Glu Thr Leu Glu Gly Glu Leu
               170


<210> SEQ ID NO 23
<211> LENGTH: 888
<212> TYPE: DNA
<213> ORGANISM: Homo sapiens

<400> SEQUENCE: 23

gtgaaacacc catggtttta tgctctattt ctcttttcct catcttcttc                50

cacatcctct ttctgaatgt atcaaactac ttccttgaag tggggcacca               100

ggagggccac tccagtctcc aatgcaggga ctcaggggca gggatctctg               150

agaaagtggc catctcgtta ttaaagctct gtcctctgct tccctctcac               200

ctcagaagca gcccgtttat tcaacagagc tccaggttgc cagctagggg               250

ttttcgggac catagaccaa gcaaccccga gagactgagt actgacctgc               300

agttgttcca gaaactctgc tgggaattag gttgtgacct agaagtgaac               350

tgacactaac agtgagaagg cagggtaaga atgcagtcta gagcgcaacc               400

tttctccact agacttgtaa gtaatttaag tgaatcctgt ccccctgggg               450

ttctatcctg gctggctctg ctggtgaact tgactggcca gcatagggca               500

cttgatgaga ccctggaatg ctgaggccag ttgggcagca agctttcacc               550

tcatccttct gcccatctat ccagccattc aaacattcat tcgcctgaag               600

acatttatca agctcctgca atgggtcagg catctgctag gcactgggga               650

cacagagctc acagtctcct ggagggggtg agagatgact gacaggtggt               700

ctgtggtgca gtgtgacctg ggaatgcaca cagtactgtg gaaacacggg               750

agaggcatct agcacaacct gagagggcca ggggaggctt cctggcaggt               800

ttccctttaa ccatcttaag ggaaagaggc actaggtagg aaaataaagg               850

gacagtggtg tcccagacag agggcactct  acatggaa                           888


<210> SEQ ID NO 24
```

-continued

<211> LENGTH: 113
<212> TYPE: PRT
<213> ORGANISM: Homo sapiens

<400> SEQUENCE: 24

Met Val Leu Cys Ser Ile Ser Leu Phe Leu Ile Phe Phe His Ile
1 5 10 15

Leu Phe Leu Asn Val Ser Asn Tyr Phe Leu Glu Val Gly His Gln
20 25 30

Glu Gly His Ser Ser Leu Gln Cys Arg Asp Ser Gly Ala Gly Ile
35 40 45

Ser Glu Lys Val Ala Ile Ser Leu Leu Lys Leu Cys Pro Leu Leu
50 55 60

Pro Ser His Leu Arg Ser Ser Pro Phe Ile Gln Gln Ser Ser Arg
65 70 75

Leu Pro Ala Arg Gly Phe Arg Asp His Arg Pro Ser Asn Pro Glu
80 85 90

Arg Leu Ser Thr Asp Leu Gln Leu Phe Gln Lys Leu Cys Trp Glu
95 100 105

Leu Gly Cys Asp Leu Glu Val Asn
110

<210> SEQ ID NO 25
<211> LENGTH: 2534
<212> TYPE: DNA
<213> ORGANISM: Homo sapiens

<400> SEQUENCE: 25 cgggctccgc gcggtcccac ttcccggctc ccttcgcctc caggatgcgc 50 tgagccctac aacaccccca gcggccgccg gctcccccac gaggtgtgaa 100 tgacagaggt ggtgccatcc agcgcgctca gcgaggtcag cctgcgcctc 150 ctctgccacg atgacataga cactgtgaag cacctgtgtg gcgactggtt 200 ccccatcgag tacccagact catggtatcg tgatatcaca tccaacaaga 250 agttcttttc ccttgctgca acctacagag gtgccattgt gggaatgata 300 gtagctgaaa ttaagaacag gaccaaaata cataaagagg atggagatat 350 tctagcaacc aacttctctg ttgacacaca agtcgcgtac atcctaagtc 400 tgggcgtcgt gaaagagttc aggaagcacg gcataggttc cctcttactt 450 gaaagtttaa aggatcacat atcaaccacc gcccaggacc actgcaaagc 500 catttacctg catgtcctca ccaccaacaa cacagcaata aacttctatg 550 aaaacagaga cttcaagcag caccactatc tcccctatta ctactccatt 600 cgaggggtcc tcaaagatgg cttcacctat gtcctctaca tcaacggcgg 650 gcaccctccc tggacgattt tggactacat ccagcacctg ggctctgcac 700 tagccagcct gagcccctgc tccattccgc acagagtcta ccgccaggcc 750 cacagcctgc tctgcagctt cctgccatgg tcgggcatct cttccaagag 800 tggcatcgag tacagccgga ccatgtgatg tcggctgggc agccgccacc 850 aggccccacc cttcagccgc ccgcagagcc cgccttcctg tccatctgac 900 cccttctgtt ttctgcaagg agctgccagc catctaactg ggctcgtcgg 950 cctgccccag ctgcaggccc ggtgctacac gggctcggga acagaacatc 1000 gtgggcatgc gcagagcatg cccatccgtg gcaggctctt cagctcccct 1050

-continued

```
ccctgcttct ggaaacctct gcctgctgcc ctggccctgc ccccctgcgc          1100

atgcaccatc cccagggctg acccagtgtg gctgcattca ctgggagggg          1150

cctgccctca ctgggcctct cccactccgc tgcctgttct tgcagctcct          1200

tcctggaaag ctggagggga ctttctcctg caagggagga acgcaagtat          1250

tatggacaca cttgaccgta aaggcacagg agcctcggaa caagggggcg          1300

caataaaggg aatggcccgt ccccttccag aaccagccca aagaagcctg          1350

gggggtgagg agtggccccc actcctccat gaggggctga tgaggggtgg          1400

gcagcctggg ggaggctttc ctcgcaagca cagagctctg aggctcagcc          1450

ccctggcaca ggcggtcacg catcaggacg gttcctactc ctcagcacct          1500

tccgtgcagt taccagtgcc ctgggaggtc acactgcccg tcggaccttg          1550

gcatgctcca ttcagctgac ctgctgagga caggcatcgc cgagactcct          1600

tgggtcctcc ccgccctccc tcatgctgcc acaagctgct gctccaaggc          1650

ctggccacat gcagacagga ggaagctgag ctcgacatta ggcctcaagg          1700

ctgccatctg tcttgtaggg cctggccttg tgggcagggg gcagtcctgt          1750

gccttgtggg ccctcagcct ctgagggcag agatgctgtc agtgccgcag          1800

gtgcatcaca tacttctagc atcctctcca ccctgcattc caaatgctgc          1850

ttgctgcctg ccctgccctc cgatgcaggg gtggggtggg gggcggagtc          1900

ccgcccagca tagctgcagt gtcacaaagc catggcagag ggtcctagcg          1950

gcgccaccct gccccagcct gaggaggagg gagagggagg aacaaccctg          2000

ggcagacggg gtctcaggga cctgtgtcct tccgcctcca gagctgccca          2050

gccacgggct ctcagggtgc tggggcagcc ccaggtcccc tcttgaactc          2100

agctggggcc aggggccctc agaatgaagg caggcaccag gcaggagcag          2150

catccccctc cttgacggtg ctggcaggag ggccgcgcca tgctgactgc          2200

ttgaacctct gctgacctga cagtgctggc gggagggccg caccatgctg          2250

actgcctgaa tctctgctga ggctgcctgc ctgccgggcc cagctcagcg          2300

ccctctccac tgcgaatcag tggcgatcat gtgatttcta tttctgcccc          2350

acagggtaag ggacgagtct tctggaaggc tctgccatgg acatttgtcc          2400

tcgggctcag aggccccacc ctgccccaca cctgccccta atcactgcag          2450

tgtccagccc agtgttgaac agattgtagc gttctgtctc attacgagca          2500

aataaataga ctttcattgg gaaaaaaaaa  aaaa                          2534
```

<210> SEQ ID NO 26
<211> LENGTH: 242
<212> TYPE: PRT
<213> ORGANISM: Homo sapiens

<400> SEQUENCE: 26

```
Met Thr Glu Val Val Pro Ser Ser Ala Leu Ser Glu Val Ser Leu
  1               5                  10                  15

Arg Leu Leu Cys His Asp Asp Ile Asp Thr Val Lys His Leu Cys
                 20                  25                  30

Gly Asp Trp Phe Pro Ile Glu Tyr Pro Asp Ser Trp Tyr Arg Asp
                 35                  40                  45

Ile Thr Ser Asn Lys Lys Phe Phe Ser Leu Ala Ala Thr Tyr Arg
```

-continued

```
                50                  55                  60

Gly Ala Ile Val Gly Met Ile Val Ala Glu Ile Lys Asn Arg Thr
                65                  70                  75

Lys Ile His Lys Glu Asp Gly Asp Ile Leu Ala Thr Asn Phe Ser
                80                  85                  90

Val Asp Thr Gln Val Ala Tyr Ile Leu Ser Leu Gly Val Val Lys
                95                 100                 105

Glu Phe Arg Lys His Gly Ile Gly Ser Leu Leu Leu Glu Ser Leu
               110                 115                 120

Lys Asp His Ile Ser Thr Thr Ala Gln Asp His Cys Lys Ala Ile
               125                 130                 135

Tyr Leu His Val Leu Thr Thr Asn Asn Thr Ala Ile Asn Phe Tyr
               140                 145                 150

Glu Asn Arg Asp Phe Lys Gln His His Tyr Leu Pro Tyr Tyr Tyr
               155                 160                 165

Ser Ile Arg Gly Val Leu Lys Asp Gly Phe Thr Tyr Val Leu Tyr
               170                 175                 180

Ile Asn Gly Gly His Pro Pro Trp Thr Ile Leu Asp Tyr Ile Gln
               185                 190                 195

His Leu Gly Ser Ala Leu Ala Ser Leu Ser Pro Cys Ser Ile Pro
               200                 205                 210

His Arg Val Tyr Arg Gln Ala His Ser Leu Leu Cys Ser Phe Leu
               215                 220                 225

Pro Trp Ser Gly Ile Ser Ser Lys Ser Gly Ile Glu Tyr Ser Arg
               230                 235                 240

Thr Met


<210> SEQ ID NO 27
<211> LENGTH: 991
<212> TYPE: DNA
<213> ORGANISM: Homo sapiens

<400> SEQUENCE: 27

gttgggcagc agccacccgc tcacctccat ccccaggact tagagggacg          50

cagggcgttg ggaacagagg acactccagg cgctgaccct gggaggccag         100

gaccagggcc aaagtcccgt gggcaagagg agtcctcaga ggtccttcat         150

tcagcggttc cgggaggtct gggaagccca cggcctggct ggggcagggt         200

caacgccgcc aggccgccat ggtcctgtgc tggctgctgc ttctggtgat         250

ggctctgccc ccaggcacga cgggcgtcaa ggactgcgtc ttctgtgagc         300

tcaccgactc catgcagtgt cctggtacct acatgcactg tggcgatgac         350

gaggactgct tcacaggcca cggggtcgcc ccgggcactg gtccggtcat         400

caacaaaggc tgcctgcgag ccaccagctg cggccttgag gaacccgtca         450

gctacagggg cgtcacctac agcctcacca ccaactgctg caccggccgc         500

ctgtgtaaca gagccccgag cagccagaca gtgggggcca ccaccagcct         550

ggcactgggg ctgggtatgc tgcttcctcc acgtttgctg tgaccaacag         600

ggaggacagg gcctgggact gttctcccag atccgccact ccccatgtcc         650

ccatgtcctt cccccactaa atggccagag aggccctgga caacctcttg         700

cggccctggc ttcatccctt ctaaggctgt ccaccaggag cccggtgcta         750

ggggaagcat ccccaggcct gactgagcgg caggggagca cggcccgtgg         800
```

-continued

```
gtttgattgt attactctgt tccactggtt ctaagacgca gagcttctca              850

catctcaatc aggatgcttc tctccattgg tagcacttta gagtccatga              900

aatatggtaa aaaatatata tatatcataa taaatgacag ctgatgttca              950

tgggggaaaa aaaaaaaaaa aaaaaaaaaa aaaaaaaaaa  a                      991


<210> SEQ ID NO 28
<211> LENGTH: 124
<212> TYPE: PRT
<213> ORGANISM: Homo sapiens

<400> SEQUENCE: 28

Met Val Leu Cys Trp Leu Leu Leu Leu Val Met Ala Leu Pro Pro
  1               5                  10                  15

Gly Thr Thr Gly Val Lys Asp Cys Val Phe Cys Glu Leu Thr Asp
                 20                  25                  30

Ser Met Gln Cys Pro Gly Thr Tyr Met His Cys Gly Asp Asp Glu
                 35                  40                  45

Asp Cys Phe Thr Gly His Gly Val Ala Pro Gly Thr Gly Pro Val
                 50                  55                  60

Ile Asn Lys Gly Cys Leu Arg Ala Thr Ser Cys Gly Leu Glu Glu
                 65                  70                  75

Pro Val Ser Tyr Arg Gly Val Thr Tyr Ser Leu Thr Thr Asn Cys
                 80                  85                  90

Cys Thr Gly Arg Leu Cys Asn Arg Ala Pro Ser Ser Gln Thr Val
                 95                 100                 105

Gly Ala Thr Thr Ser Leu Ala Leu Gly Leu Gly Met Leu Leu Pro
                110                 115                 120

Pro Arg Leu Leu


<210> SEQ ID NO 29
<211> LENGTH: 2020
<212> TYPE: DNA
<213> ORGANISM: Homo sapiens

<400> SEQUENCE: 29

ggcattttga aagcccagtg ttgcccaggg ggcatctcct ttgtgtttat               50

gagagacctg cattctccct ggctcagttc tctcaggctc tccagagctc              100

aggacctctg agaagaatgg agccctcctg gcttcaggaa ctcatggctc              150

acccccttctt gctgctgatc ctcctctgca tgtctctgct gctgtttcag              200

gtaatcaggt tgtaccagag gaggagatgg atgatcagag ccctgcacct              250

gtttcctgca ccccctgccc actggttcta tggccacaag gagttttacc              300

cagtaaagga gtttgaggtg tatcataagc tgatggaaaa atacccatgt              350

gctgttccct tgtgggttgg acccttttacg atgttcttca gtgtccatga              400

cccagactat gccaagattc tcctgaaaag acaagatccc aaaagtgctg              450

ttagccacaa aatccttgaa tcctgggttg gtcgaggact tgtgaccctg              500

gatggttcta aatggaaaaa gcaccgccag attgtgaaac ctggcttcaa              550

catcagcatt ctgaaaatat tcatcaccat gatgtctgag agtgttcgga              600

tgatgctgaa caaatgggag gaacacattg cccaaaactc acgtctggag              650

ctctttcaac atgtctccct gatgaccctg gacagcatca tgaagtgtgc              700
```

-continued

```
cttcagccac cagggcagca tccagttgga cagtaccctg gactcatacc          750

tgaaagcagt gttcaacctt agcaaaatct ccaaccagcg catgaacaat          800

tttctacatc acaacgacct ggttttcaaa ttcagctctc aaggccaaat          850

cttttctaaa tttaaccaag aacttcatca gttcacagag aaagtaatcc          900

aggaccggaa ggagtctctt aaggataagc taaaacaaga tactactcag          950

aaaaggcgct gggattttct ggacatactt ttgagtgcca aaagcgaaaa         1000

caccaaagat ttctctgaag cagatctcca ggctgaagtg aaaacgttca         1050

tgtttgcagg acatgacacc acatccagtg ctatctcctg gatcctttac         1100

tgcttggcaa agtaccctga gcatcagcag agatgccgag atgaaatcag         1150

ggaactccta ggggatgggt cttctattac ctgggaacac ctgagccaga         1200

tgccttacac cacgatgtgc atcaaggaat gcctccgcct ctacgcaccg         1250

gtagtaaaca tatcccggtt actcgacaaa cccatcacct ttccagatgg         1300

acgctcctta cctgcaggaa taactgtgtt tatcaatatt tgggctcttc         1350

accacaaccc ctatttctgg gaagaccctc aggtctttaa ccccttgaga         1400

ttctccaggg aaaattctga aaaaatacat ccctatgcct tcataccatt         1450

ctcagctgga ttaaggaact gcattgggca gcattttgcc ataattgagt         1500

gtaaagtggc agtggcatta actctgctcc gcttcaagct ggctccagac         1550

cactcaaggc ctccccagcc tgttcgtcaa gttgtcctca agtccaagaa         1600

tggaatccat gtgtttgcaa aaaaagtttg ctaattttaa gtcctttcgt         1650

ataagaatta atgagacaat tttcctacca aaggaagaac aaaaggataa         1700

atataataca aaatatatgt atatggttgt ttgacaaatt atataactta         1750

ggatacttct gactggtttt gacatccatt aacagtaatt ttaatttctt         1800

tgctgtatct ggtgaaaccc acaaaaacac ctgaaaaaac tcaagctgac         1850

ttccactgcg aagggaaatt attggtttgt gtaactagtg gtagagtggc         1900

tttcaagcat agtttgatca aaactccact cagtatctgc attactttta         1950

tctctgcaaa tatctgcatg atagctttat tctcagttat ctttccccat         2000

aataaaaaat atctgccaaa                                          2020
```

```
<210> SEQ ID NO 30
<211> LENGTH: 505
<212> TYPE: PRT
<213> ORGANISM: Homo sapiens

<400> SEQUENCE: 30

Met Glu Pro Ser Trp Leu Gln Glu Leu Met Ala His Pro Phe Leu
  1               5                  10                  15

Leu Leu Ile Leu Leu Cys Met Ser Leu Leu Leu Phe Gln Val Ile
                 20                  25                  30

Arg Leu Tyr Gln Arg Arg Arg Trp Met Ile Arg Ala Leu His Leu
                 35                  40                  45

Phe Pro Ala Pro Pro Ala His Trp Phe Tyr Gly His Lys Glu Phe
                 50                  55                  60

Tyr Pro Val Lys Glu Phe Glu Val Tyr His Lys Leu Met Glu Lys
                 65                  70                  75

Tyr Pro Cys Ala Val Pro Leu Trp Val Gly Pro Phe Thr Met Phe
                 80                  85                  90
```

-continued

```
Phe Ser Val His Asp Pro Asp Tyr Ala Lys Ile Leu Leu Lys Arg
                 95                 100                 105

Gln Asp Pro Lys Ser Ala Val Ser His Lys Ile Leu Glu Ser Trp
                110                 115                 120

Val Gly Arg Gly Leu Val Thr Leu Asp Gly Ser Lys Trp Lys Lys
                125                 130                 135

His Arg Gln Ile Val Lys Pro Gly Phe Asn Ile Ser Ile Leu Lys
                140                 145                 150

Ile Phe Ile Thr Met Met Ser Glu Ser Val Arg Met Met Leu Asn
                155                 160                 165

Lys Trp Glu Glu His Ile Ala Gln Asn Ser Arg Leu Glu Leu Phe
                170                 175                 180

Gln His Val Ser Leu Met Thr Leu Asp Ser Ile Met Lys Cys Ala
                185                 190                 195

Phe Ser His Gln Gly Ser Ile Gln Leu Asp Ser Thr Leu Asp Ser
                200                 205                 210

Tyr Leu Lys Ala Val Phe Asn Leu Ser Lys Ile Ser Asn Gln Arg
                215                 220                 225

Met Asn Asn Phe Leu His His Asn Asp Leu Val Phe Lys Phe Ser
                230                 235                 240

Ser Gln Gly Gln Ile Phe Ser Lys Phe Asn Gln Glu Leu His Gln
                245                 250                 255

Phe Thr Glu Lys Val Ile Gln Asp Arg Lys Glu Ser Leu Lys Asp
                260                 265                 270

Lys Leu Lys Gln Asp Thr Thr Gln Lys Arg Arg Trp Asp Phe Leu
                275                 280                 285

Asp Ile Leu Leu Ser Ala Lys Ser Glu Asn Thr Lys Asp Phe Ser
                290                 295                 300

Glu Ala Asp Leu Gln Ala Glu Val Lys Thr Phe Met Phe Ala Gly
                305                 310                 315

His Asp Thr Thr Ser Ser Ala Ile Ser Trp Ile Leu Tyr Cys Leu
                320                 325                 330

Ala Lys Tyr Pro Glu His Gln Gln Arg Cys Arg Asp Glu Ile Arg
                335                 340                 345

Glu Leu Leu Gly Asp Gly Ser Ser Ile Thr Trp Glu His Leu Ser
                350                 355                 360

Gln Met Pro Tyr Thr Thr Met Cys Ile Lys Glu Cys Leu Arg Leu
                365                 370                 375

Tyr Ala Pro Val Val Asn Ile Ser Arg Leu Leu Asp Lys Pro Ile
                380                 385                 390

Thr Phe Pro Asp Gly Arg Ser Leu Pro Ala Gly Ile Thr Val Phe
                395                 400                 405

Ile Asn Ile Trp Ala Leu His His Asn Pro Tyr Phe Trp Glu Asp
                410                 415                 420

Pro Gln Val Phe Asn Pro Leu Arg Phe Ser Arg Glu Asn Ser Glu
                425                 430                 435

Lys Ile His Pro Tyr Ala Phe Ile Pro Phe Ser Ala Gly Leu Arg
                440                 445                 450

Asn Cys Ile Gly Gln His Phe Ala Ile Ile Glu Cys Lys Val Ala
                455                 460                 465

Val Ala Leu Thr Leu Leu Arg Phe Lys Leu Ala Pro Asp His Ser
                470                 475                 480
```

-continued

```
Arg Pro Pro Gln Pro Val Arg Gln Val Val Leu Lys Ser Lys Asn
                485                 490                 495

Gly Ile His Val Phe Ala Lys Lys Val Cys
                500                 505


<210> SEQ ID NO 31
<211> LENGTH: 1118
<212> TYPE: DNA
<213> ORGANISM: Homo sapiens

<400> SEQUENCE: 31

tccgctgtcg cccagtcccg gccgctggcg ggaactgacc tggagcaagc                50

aggaccttcc ctcccacctc tcccgcctgg cctccgcggg agtcccctac               100

gatcccgctc agcagtgggg cactcgctga ggacagcgag tcctgggagt               150

gagcccaagg ccacccctgg ccagcccagg agagatagcc agggcaggcc               200

cagcagcccg aggccaggct ctggccacgg cggtctccga catggagaga               250

cattgtctgc tttttatcct gttaacctgt cttcggtggt tgtgccacga               300

cattccccag ggttcaggtg cccggtggcc gagggtcagt ccagtggtag               350

agccttgctc tcctaggctc atcctgctgg cggtcctcct gcttctgctg               400

tgtggtgtca cagctggttg tgtccggttc tgctgcctcc ggaagcaggc               450

acaggcccag ccacatctgc caccagcacg gcagccctgc gacgtggcag               500

tcatccctat ggacagtgac agccctgtac acagcactgt gacctcctac               550

agctccgtgc agtacccact gggcatgcgg ttgcccctgc cctttgggga               600

gctggacctg gactccacgg ctcctcctgc ctacagcctg tacaccccgg               650

agcctccacc ctcctacgat gaagctgtca agatggccaa gcccagagag               700

gaaggaccag cactctccca gaaacccagc cctctccttg gggcctcggg               750

cctagagacc actccagtgc cccaggagtc gggccccaat actcaactac               800

caccttgtag ccctggtgcc ccttgaagga ggtaggagaa cggaccagag               850

cttggagaac taatgcttgg agccaagggc cccagcccac cccaccgtcc               900

cacacattgc tgtggcccca acctcggtgc catgttacac cggcccctgg               950

cgtcacccac taggcaggct gctgctttca gcctcagccc ctggcccagc              1000

cccagcaggc cctcagcctg gaagaggccc cttgggccta agcctcgggt              1050

gggagctcag ggccacctgt gacgtctgca tcttcttgga gagagaataa              1100

agtttgtatt  taagtggt                                                 1118


<210> SEQ ID NO 32
<211> LENGTH: 194
<212> TYPE: PRT
<213> ORGANISM: Homo sapiens

<400> SEQUENCE: 32

Met Glu Arg His Cys Leu Leu Phe Ile Leu Leu Thr Cys Leu Arg
  1               5                  10                  15

Trp Leu Cys His Asp Ile Pro Gln Gly Ser Gly Ala Arg Trp Pro
                20                  25                  30

Arg Val Ser Pro Val Val Glu Pro Cys Ser Pro Arg Leu Ile Leu
                35                  40                  45

Leu Ala Val Leu Leu Leu Leu Leu Cys Gly Val Thr Ala Gly Cys
                50                  55                  60
```

-continued

```
Val Arg Phe Cys Cys Leu Arg Lys Gln Ala Gln Ala Gln Pro His
                65                  70                  75

Leu Pro Pro Ala Arg Gln Pro Cys Asp Val Ala Val Ile Pro Met
                80                  85                  90

Asp Ser Asp Ser Pro Val His Ser Thr Val Thr Ser Tyr Ser Ser
                95                 100                 105

Val Gln Tyr Pro Leu Gly Met Arg Leu Pro Leu Pro Phe Gly Glu
               110                 115                 120

Leu Asp Leu Asp Ser Thr Ala Pro Pro Ala Tyr Ser Leu Tyr Thr
               125                 130                 135

Pro Glu Pro Pro Pro Ser Tyr Asp Glu Ala Val Lys Met Ala Lys
               140                 145                 150

Pro Arg Glu Glu Gly Pro Ala Leu Ser Gln Lys Pro Ser Pro Leu
               155                 160                 165

Leu Gly Ala Ser Gly Leu Glu Thr Thr Pro Val Pro Gln Glu Ser
               170                 175                 180

Gly Pro Asn Thr Gln Leu Pro Pro Cys Ser Pro Gly Ala Pro
               185                 190


<210> SEQ ID NO 33
<211> LENGTH: 1976
<212> TYPE: DNA
<213> ORGANISM: Homo sapiens

<400> SEQUENCE: 33

ccttgcttgg tgcttggcac acacaaatcc agtgggctac acaggttttc          50

cagaagcccc acgaggtggt aatggtgctg ctgattcaga ccctgggggc         100

cctcatgccc tcgctgccct cctgcctcag caacggcgtg gagagggcag         150

ggcccgagca ggagctcacc aggctgctgg agttctacga cgccaccgcc         200

cacttcgcca agggcttgga gatggcactg ctcccccacc tacatgaaca         250

caatctggta aaagtcacgg agctggtgga tgctgtgtat gatccataca         300

aaccctacca gctgaagtat ggcgacatgg aagagagcaa cctcctcatc         350

cagatgagtg ctgtgcctct ggagcatggg gaagtgattg actgtgtgca         400

ggagctgagc cactccgtga acaagctgtt tggtctggcg tctgcagccg         450

ttgacagatg cgtcagattc accaatggcc tggggacctg cggcctgttg         500

tcagccctga aatccctctt tgccaagtat gtgtctgatt tcaccagcac         550

tctccagtcc atacgaaaga agtgcaaact ggaccacatt cctcccaact         600

ccctcttcca ggaagattgg acggcttttc agaactccat taggataata         650

gccacctgtg gagagctttt gcggcattgt ggggacttcg agcagcagct         700

agccaacagg attttgtcca cagctgggaa gtatctatct gattcctgca         750

gcccccggag cctggctggt tttcaggaga gcatcttgac agacaagaag         800

aactctgcca agaacccatg gcaagaatat aattacctcc agaaagataa         850

ccctgctgaa tatgccagtt taatggaaat actttatacc cttaaggaaa         900

aagggtcaag caaccacaac ctgctggctg cacctcgagc agcgctgact         950

cggcttaacc agcaggccca ccagctggct ttcgattccg tgttcctgcg        1000

catcaaacaa cagctgttgc ttatttcgaa gatggacagc tggaatacgg        1050

ctggcatcgg agaaaccctc acagatgaac tgcccgcctt tagtctcacc        1100
```

-continued

```
cctctcgagt acatcagcaa catcgggcag tacatcatgt ccctcccct          1150

gaatcttgag ccatttgtga ctcaggagga ctctgcctta gagttggcat         1200

tgcacgctgg aaagctgcca tttcctcctg agcaggggga tgaattgccc         1250

gagctggaca acatggctga caactggctg ggctcgatcg ccagagccac         1300

aatgcagacc tactgtgatg cgatcctaca gatccctgag ctgagcccac         1350

actctgccaa gcagctggcc actgacatcg actatctgat caacgtgatg         1400

gatgccctgg gcctgcagcc gtcccgcacc ctccagcaca tcgtgacgct         1450

actgaagacc aggcctgagg actatagaca ggtcagcaaa ggcctgcccc         1500

gtcgcctggc caccaccgtg gccaccatgc ggagtgtgaa ttactgaccc         1550

caccacacac cggaccacca agagagccag ggctgctgtt tcgtgactca         1600

ccagcacaga tttgctcaga aactctgccc aagattgggc agaagttact         1650

ttaaaaagac ttggttcagc tggtcacggt ggctcacgcc tgtaatccca         1700

gcactttggg aggccaagcc agatggatca tgaggccagg agttcgagac         1750

cagcctgacc aacatggtga aaccccatct ctactaaaaa tacaaaaatt         1800

aacagcagag cgagactctg tctcaaaaaa aaaaaaaaaa agacttggtt         1850

catttgtata atcaaaaaga gttgtaaatt aaagatgtat tatttatcag         1900

agaagacttt ttagataatt tttttaaagg atcagatctt gaaaatggaa         1950

taaataacta ctgtgaaatg  caaaaa                                  1976
```

```
<210> SEQ ID NO 34
<211> LENGTH: 491
<212> TYPE: PRT
<213> ORGANISM: Homo sapiens

<400> SEQUENCE: 34

Met Val Leu Leu Ile Gln Thr Leu Gly Ala Leu Met Pro Ser Leu
  1               5                  10                  15

Pro Ser Cys Leu Ser Asn Gly Val Glu Arg Ala Gly Pro Glu Gln
                 20                  25                  30

Glu Leu Thr Arg Leu Leu Glu Phe Tyr Asp Ala Thr Ala His Phe
                 35                  40                  45

Ala Lys Gly Leu Glu Met Ala Leu Leu Pro His Leu His Glu His
                 50                  55                  60

Asn Leu Val Lys Val Thr Glu Leu Val Asp Ala Val Tyr Asp Pro
                 65                  70                  75

Tyr Lys Pro Tyr Gln Leu Lys Tyr Gly Asp Met Glu Glu Ser Asn
                 80                  85                  90

Leu Leu Ile Gln Met Ser Ala Val Pro Leu Glu His Gly Glu Val
                 95                 100                 105

Ile Asp Cys Val Gln Glu Leu Ser His Ser Val Asn Lys Leu Phe
                110                 115                 120

Gly Leu Ala Ser Ala Ala Val Asp Arg Cys Val Arg Phe Thr Asn
                125                 130                 135

Gly Leu Gly Thr Cys Gly Leu Leu Ser Ala Leu Lys Ser Leu Phe
                140                 145                 150

Ala Lys Tyr Val Ser Asp Phe Thr Ser Thr Leu Gln Ser Ile Arg
                155                 160                 165

Lys Lys Cys Lys Leu Asp His Ile Pro Pro Asn Ser Leu Phe Gln
```

-continued

```
                170                 175                 180

Glu Asp Trp Thr Ala Phe Gln Asn Ser Ile Arg Ile Ile Ala Thr
                185                 190                 195

Cys Gly Glu Leu Leu Arg His Cys Gly Asp Phe Glu Gln Gln Leu
                200                 205                 210

Ala Asn Arg Ile Leu Ser Thr Ala Gly Lys Tyr Leu Ser Asp Ser
                215                 220                 225

Cys Ser Pro Arg Ser Leu Ala Gly Phe Gln Glu Ser Ile Leu Thr
                230                 235                 240

Asp Lys Lys Asn Ser Ala Lys Asn Pro Trp Gln Glu Tyr Asn Tyr
                245                 250                 255

Leu Gln Lys Asp Asn Pro Ala Glu Tyr Ala Ser Leu Met Glu Ile
                260                 265                 270

Leu Tyr Thr Leu Lys Glu Lys Gly Ser Ser Asn His Asn Leu Leu
                275                 280                 285

Ala Ala Pro Arg Ala Ala Leu Thr Arg Leu Asn Gln Gln Ala His
                290                 295                 300

Gln Leu Ala Phe Asp Ser Val Phe Leu Arg Ile Lys Gln Gln Leu
                305                 310                 315

Leu Leu Ile Ser Lys Met Asp Ser Trp Asn Thr Ala Gly Ile Gly
                320                 325                 330

Glu Thr Leu Thr Asp Glu Leu Pro Ala Phe Ser Leu Thr Pro Leu
                335                 340                 345

Glu Tyr Ile Ser Asn Ile Gly Gln Tyr Ile Met Ser Leu Pro Leu
                350                 355                 360

Asn Leu Glu Pro Phe Val Thr Gln Glu Asp Ser Ala Leu Glu Leu
                365                 370                 375

Ala Leu His Ala Gly Lys Leu Pro Phe Pro Pro Glu Gln Gly Asp
                380                 385                 390

Glu Leu Pro Glu Leu Asp Asn Met Ala Asp Asn Trp Leu Gly Ser
                395                 400                 405

Ile Ala Arg Ala Thr Met Gln Thr Tyr Cys Asp Ala Ile Leu Gln
                410                 415                 420

Ile Pro Glu Leu Ser Pro His Ser Ala Lys Gln Leu Ala Thr Asp
                425                 430                 435

Ile Asp Tyr Leu Ile Asn Val Met Asp Ala Leu Gly Leu Gln Pro
                440                 445                 450

Ser Arg Thr Leu Gln His Ile Val Thr Leu Leu Lys Thr Arg Pro
                455                 460                 465

Glu Asp Tyr Arg Gln Val Ser Lys Gly Leu Pro Arg Arg Leu Ala
                470                 475                 480

Thr Thr Val Ala Thr Met Arg Ser Val Asn Tyr
                485                 490


<210> SEQ ID NO 35
<211> LENGTH: 1227
<212> TYPE: DNA
<213> ORGANISM: Homo sapiens

<400> SEQUENCE: 35

gcaagtgcca ccatgctagt gtgatttgga cttcagtaaa agttagtttg                50

cttccttccc gttgtcccat ctcactcctg ggccacccat ggggctgctg               100

gtagctggtg tgtggctgct gctggactgt gtggcagtcc atccatctgt               150
```

-continued

```
cagcagccac tgcgggccta cttgctgggt gcccagcacc gcactcacca          200

ctgcaggcgt ggccaggagc gtgagatccc cagagcccat ggccagtgag          250

aggcggccag ggataggtac ccagggaatg ccacaggagt ttgctgggct          300

cacggagctc tttcactggt cagagaggag tgtgtgtagg agaggacttc          350

tacttggtgt tgaaggacag atggggtttg gctgggagag aggaggaatg          400

tgggcgggcc ttataggcag gcgagaaggt gagagccaag gccctctgtg          450

ggcagggcga ggtggcgtgt tgaggagact cgtccagctg ggcagaggct          500

catgttgagg gatgaggcag agctgggggga ggagggagcc cagaaatggc         550

aggtccttga atgcaggttt ggaagcaggg acgccctgtg agggtacaga          600

gtctgggctg ttaccttctg tggcttttgc tagaaggtga gatgtcaggg          650

aggaagacag gactccagga tgtctcctgt ctctctctgg aaaaaggagg          700

tgggcccctt tctcagcagt cagctgctgt ttttgaggtc ttctccatgg          750

ataatccacg gtgttggaag tggttaaggt aatggatcct catgggctta          800

ccataaaaat atctggaggc tggaccattt tccttaaaac gttataaaag          850

ctggaattga atgccatcgg tgtcacccct gggaagtgtg ctttctcttg          900

agctcttttg gccccgagat agcagtcact ccatagtttc gtgaagacca          950

gcctggtgtt gcctggtttt ctgccattag ggagcagcta gaggtcttcc         1000

agtagctcct gtgtaaagtg atgaaagaaa agggctgggt gctgactgct         1050

cctggagaaa agcaacacac tcccaaagtc ttaattgcct gcttccaggg         1100

agctgtggtg gtttcccttg ggcagggcac acgccccagt ggttgactta         1150

ataaggatac attttaatca gaggacaaaa atgtgccctg acttgatttc         1200

cgcatgggct tccagcatgg  tcaaagg                                 1227
```

<210> SEQ ID NO 36
<211> LENGTH: 139
<212> TYPE: PRT
<213> ORGANISM: Homo sapiens

<400> SEQUENCE: 36

```
Met Gly Leu Leu Val Ala Gly Val Trp Leu Leu Leu Asp Cys Val
  1               5                  10                  15

Ala Val His Pro Ser Val Ser Ser His Cys Gly Pro Thr Cys Trp
                 20                  25                  30

Val Pro Ser Thr Ala Leu Thr Thr Ala Gly Val Ala Arg Ser Val
                 35                  40                  45

Arg Ser Pro Glu Pro Met Ala Ser Glu Arg Arg Pro Gly Ile Gly
                 50                  55                  60

Thr Gln Gly Met Pro Gln Glu Phe Ala Gly Leu Thr Glu Leu Phe
                 65                  70                  75

His Trp Ser Glu Arg Ser Val Cys Arg Arg Gly Leu Leu Leu Gly
                 80                  85                  90

Val Glu Gly Gln Met Gly Phe Gly Trp Glu Arg Gly Gly Met Trp
                 95                 100                 105

Ala Gly Leu Ile Gly Arg Arg Glu Gly Glu Ser Gln Gly Pro Leu
                110                 115                 120

Trp Ala Gly Arg Gly Gly Val Leu Arg Arg Leu Val Gln Leu Gly
                125                 130                 135
```

-continued

Arg Gly Ser Cys

<210> SEQ ID NO 37
<211> LENGTH: 1225
<212> TYPE: DNA
<213> ORGANISM: Homo sapiens

<400> SEQUENCE: 37 ggccaggaat ggggtccccg ggcatggtgc tgggcctcct ggtgcagatc 50 tgggccctgc aagaagcctc aagcctgagc gtgcagcagg ggcccaactt 100 gctgcaggtg aggcagggca gtcaggcgac cctggtctgc caggtggacc 150 aggccacagc ctgggaacgg ctccgtgtta agtggacaaa ggatggggcc 200 atcctgtgtc aaccgtacat caccaacggc agcctcagcc tgggggtctg 250 cgggccccag ggacggctct cctggcaggc acccagccat ctcaccctgc 300 agctggaccc tgtgagcctc aaccacagcg gggcgtacgt gtgctgggcg 350 gccgtagaga ttcctgagtt ggaggaggct gagggcaaca taacaaggct 400 ctttgtggac ccagatgacc ccacacagaa cagaaaccgg atcgcaagct 450 tcccaggatt cctcttcgtg ctgctggggg tgggaagcat gggtgtggct 500 gcgatcgtgt ggggtgcctg gttctggggc cgccgcagct gccagcaaag 550 ggactcagga aatgcattct acagcaacgt cctataccgg ccccgggggg 600 ccccaaagaa gagtgaggac tgctctggag aggggaagga ccagaggggc 650 cagagcattt attcaacctc cttcccgcaa ccggcccccc gccagccgca 700 cctggcgtca agaccctgcc ccagcccgag accctgcccc agccccaggc 750 ccggccaccc cgtctctatg gtcagggtct ctcctagacc aagccccacc 800 cagcagccga ggccaaaagg gttccccaaa gtgggagagg agtgagagat 850 cccaggagac ctcaacagga ccccacccat aggtacacac aaaaaagggg 900 ggatcgaggc cagacacggt ggctcacgcc tgtaatccca gcagtttggg 950 aagccgaggc gggtggaaca cttgaggtca ggggtttgag accagcctgg 1000 cttgaacctg ggaggcggag gttgcagtga gccgagattg cgccactgca 1050 ctccagcctg ggcgacagag tgagactccg tctcaaaaaa aaaacaaaaa 1100 gcaggaggat tgggagcctg tcagccccat cctgagaccc cgtcctcatt 1150 tctgtaatga tggatctcgc tcccactttc ccccaagaac ctaataaagg 1200 cttgtgaaga aaaaaaaaaa aaaaa 1225

<210> SEQ ID NO 38
<211> LENGTH: 278
<212> TYPE: PRT
<213> ORGANISM: Homo sapiens

<400> SEQUENCE: 38

Met Gly Ser Pro Gly Met Val Leu Gly Leu Leu Val Gln Ile Trp
1 5 10 15

Ala Leu Gln Glu Ala Ser Ser Leu Ser Val Gln Gln Gly Pro Asn
20 25 30

Leu Leu Gln Val Arg Gln Gly Ser Gln Ala Thr Leu Val Cys Gln
35 40 45

Val Asp Gln Ala Thr Ala Trp Glu Arg Leu Arg Val Lys Trp Thr
50 55 60

-continued

```
Lys Asp Gly Ala Ile Leu Cys Gln Pro Tyr Ile Thr Asn Gly Ser
                65                  70                  75

Leu Ser Leu Gly Val Cys Gly Pro Gln Gly Arg Leu Ser Trp Gln
                80                  85                  90

Ala Pro Ser His Leu Thr Leu Gln Leu Asp Pro Val Ser Leu Asn
                95                 100                 105

His Ser Gly Ala Tyr Val Cys Trp Ala Ala Val Glu Ile Pro Glu
               110                 115                 120

Leu Glu Glu Ala Glu Gly Asn Ile Thr Arg Leu Phe Val Asp Pro
               125                 130                 135

Asp Asp Pro Thr Gln Asn Arg Asn Arg Ile Ala Ser Phe Pro Gly
               140                 145                 150

Phe Leu Phe Val Leu Leu Gly Val Gly Ser Met Gly Val Ala Ala
               155                 160                 165

Ile Val Trp Gly Ala Trp Phe Trp Gly Arg Arg Ser Cys Gln Gln
               170                 175                 180

Arg Asp Ser Gly Asn Ala Phe Tyr Ser Asn Val Leu Tyr Arg Pro
               185                 190                 195

Arg Gly Ala Pro Lys Lys Ser Glu Asp Cys Ser Gly Glu Gly Lys
               200                 205                 210

Asp Gln Arg Gly Gln Ser Ile Tyr Ser Thr Ser Phe Pro Gln Pro
               215                 220                 225

Ala Pro Arg Gln Pro His Leu Ala Ser Arg Pro Cys Pro Ser Pro
               230                 235                 240

Arg Pro Cys Pro Ser Pro Arg Pro Gly His Pro Val Ser Met Val
               245                 250                 255

Arg Val Ser Pro Arg Pro Ser Pro Thr Gln Gln Pro Arg Pro Lys
               260                 265                 270

Gly Phe Pro Lys Val Gly Glu Glu
               275


<210> SEQ ID NO 39
<211> LENGTH: 1837
<212> TYPE: DNA
<213> ORGANISM: Homo sapiens

<400> SEQUENCE: 39

accagcagaa ggctgggagt ctgtagtttg ttcctgctgc caggctccac          50

tgaggggaac ggggacctgt ctgaagagaa gatgcccctg ctgacactct         100

acctgctcct cttctggctc tcaggctact ccattgccac tcaaatcacc         150

ggtccaacaa cagtgaatgg cttggagcgg ggctccttga ccgtgcagtg         200

tgtttacaga tcaggctggg agacctactt gaagtggtgg tgtcgaggag         250

ctatttggcg tgactgcaag atccttgtta aaaccagtgg gtcagagcag         300

gaggtgaaga gggaccgggt gtccatcaag gacaatcaga aaaaccgcac         350

gttcactgtg accatggagg atctcatgaa aactgatgct gacacttact         400

ggtgtggaat tgagaaaact ggaaatgacc ttggggtcac agttcaagtg         450

accattgacc cagcaccagt cacccaagaa gaaactagca gctccccaac         500

tctgaccggc caccacttgg acaacaggca caagctcctg aagctcagtg         550

tcctcctgcc cctcatcttc accatattgc tgctgctttt ggtggccgcc         600

tcactcttgg cttggaggat gatgaagtac cagcagaaag cagccgggat         650
```

-continued

```
gtccccagag caggtactgc agcccctgga gggcgacctc tgctatgcag              700

acctgaccct gcagctggcc ggaacctccc cgcgaaaggc taccacgaag              750

ctttcctctg cccaggttga ccaggtggaa gtggaatatg tcaccatggc              800

ttccttgccg aaggaggaca tttcctatgc atctctgacc ttgggtgctg              850

aggatcagga accgacctac tgcaacatgg gccacctcag tagccacctc              900

cccggcaggg gccctgagga gcccacggaa tacagcacca tcagcaggcc              950

ttagcctgca ctccaggctc cttcttggac cccaggctgt gagcacactc             1000

ctgcctcatc gaccgtctgc cccctgctcc cctcatcagg accaacccgg             1050

ggactggtgc ctctgcctga tcagccagca ttgcccctag ctctgggttg             1100

ggcttggggc caagtctcag ggggcttcta ggagttgggg ttttctaaac             1150

gtcccctcct ctcctacata gttgaggagg gggctaggga tatgctctgg             1200

ggctttcatg ggaatgatga agatgataat gagaaaaatg ttatcattat             1250

tatcatgaag taccattatc ataatacaat gaacctttat ttattgccta             1300

ccacatgtta tgggctgaat aatggccccc aaagatatct gtgtcctaat             1350

cctcagaact tgtgactgtt accttctgtg gcagaaaggg acagtgcaga             1400

tgtatgtaag ttaaggactt tgagatagag aggttattct tgctgattca             1450

ggtgggccca aaatatcacc acaagggtcc tcataagaaa gaggccagaa             1500

ggtcaaagag gtagagacaa agtgatgatg gaagtggacg tgggtgtgac             1550

gtgagcaggg gccatgaatg ccgcagcctt cagatgccag aaagggaaag             1600

gaatggattc ccctgcctgg agcctccaaa agaaaccagc cctgcccacg             1650

ccttgacttg agcccattga aactgatctt gagctcctgg cctccagaat             1700

tgcaggagaa taaatttgtg ttgtttttaa tgaaaaaaaa aaaaaaaaaa             1750

aaaaaaaaaa aaaaaaaaaa aaaaaaaaaa aaaaaaaaaa aaaaaaaaaa             1800

aaaaaaaaaa aaaaaaaaaa aaaaaaaaaa  aaaaaag                          1837
```

```
<210> SEQ ID NO 40
<211> LENGTH: 290
<212> TYPE: PRT
<213> ORGANISM: Homo sapiens

<400> SEQUENCE: 40

Met Pro Leu Leu Thr Leu Tyr Leu Leu Leu Phe Trp Leu Ser Gly
  1               5                  10                  15

Tyr Ser Ile Ala Thr Gln Ile Thr Gly Pro Thr Thr Val Asn Gly
                 20                  25                  30

Leu Glu Arg Gly Ser Leu Thr Val Gln Cys Val Tyr Arg Ser Gly
                 35                  40                  45

Trp Glu Thr Tyr Leu Lys Trp Trp Cys Arg Gly Ala Ile Trp Arg
                 50                  55                  60

Asp Cys Lys Ile Leu Val Lys Thr Ser Gly Ser Glu Gln Glu Val
                 65                  70                  75

Lys Arg Asp Arg Val Ser Ile Lys Asp Asn Gln Lys Asn Arg Thr
                 80                  85                  90

Phe Thr Val Thr Met Glu Asp Leu Met Lys Thr Asp Ala Asp Thr
                 95                 100                 105

Tyr Trp Cys Gly Ile Glu Lys Thr Gly Asn Asp Leu Gly Val Thr
```

-continued

```
                110                 115                 120

Val Gln Val Thr Ile Asp Pro Ala Pro Val Thr Gln Glu Glu Thr
                125                 130                 135

Ser Ser Ser Pro Thr Leu Thr Gly His His Leu Asp Asn Arg His
                140                 145                 150

Lys Leu Leu Lys Leu Ser Val Leu Leu Pro Leu Ile Phe Thr Ile
                155                 160                 165

Leu Leu Leu Leu Leu Val Ala Ala Ser Leu Leu Ala Trp Arg Met
                170                 175                 180

Met Lys Tyr Gln Gln Lys Ala Ala Gly Met Ser Pro Glu Gln Val
                185                 190                 195

Leu Gln Pro Leu Glu Gly Asp Leu Cys Tyr Ala Asp Leu Thr Leu
                200                 205                 210

Gln Leu Ala Gly Thr Ser Pro Arg Lys Ala Thr Thr Lys Leu Ser
                215                 220                 225

Ser Ala Gln Val Asp Gln Val Glu Val Glu Tyr Val Thr Met Ala
                230                 235                 240

Ser Leu Pro Lys Glu Asp Ile Ser Tyr Ala Ser Leu Thr Leu Gly
                245                 250                 255

Ala Glu Asp Gln Glu Pro Thr Tyr Cys Asn Met Gly His Leu Ser
                260                 265                 270

Ser His Leu Pro Gly Arg Gly Pro Glu Glu Pro Thr Glu Tyr Ser
                275                 280                 285

Thr Ile Ser Arg Pro
                290


<210> SEQ ID NO 41
<211> LENGTH: 2683
<212> TYPE: DNA
<213> ORGANISM: Homo sapiens

<400> SEQUENCE: 41

aagaacactg ttgctcttgg tggacgggcc cagaggaatt cagagttaaa                50

ccttgagtgc ctgcgtccgt gagaattcag catggaatgt ctctactatt               100

tcctgggatt tctgctcctg gctgcaagat tgccacttga tgccgccaaa               150

cgatttcatg atgtgctggg caatgaaaga ccttctgctt acatgaggga               200

gcacaatcaa ttaaatggct ggtcttctga tgaaaatgac tggaatgaaa               250

aactctaccc agtgtggaag cggggagaca tgaggtggaa aaactcctgg               300

aagggaggcc gtgtgcaggc ggtcctgacc agtgactcac cagccctcgt               350

gggctcaaat ataacatttg cggtgaacct gatattccct agatgccaaa               400

aggaagatgc caatggcaac atagtctatg agaagaactg cagaaatgag               450

gctggtttat ctgctgatcc gtatgtttac aactggacag catggtcaga               500

ggacagtgac ggggaaaatg gcaccggcca aagccatcat aacgtcttcc               550

ctgatgggaa accttttcct caccaccccg gatggagaag atggaatttc               600

atctacgtct tccacacact tggtcagtat ttccagaaat tgggacgatg               650

ttcagtgaga gtttctgtga acacagccaa tgtgacactt gggcctcaac               700

tcatggaagt gactgtctac agaagacatg gacgggcata tgttcccatc               750

gcacaagtga aagatgtgta cgtggtaaca gatcagattc ctgtgtttgt               800

gactatgttc cagaagaacg atcgaaattc atccgacgaa accttcctca               850
```

-continued

```
aagatctccc cattatgttt gatgtcctga ttcatgatcc tagccacttc      900
ctcaattatt ctaccattaa ctacaagtgg agcttcgggg ataatactgg      950
cctgtttgtt tccaccaatc atactgtgaa tcacacgtat gtgctcaatg     1000
gaaccttcag ccttaacctc actgtgaaag ctgcagcacc aggaccttgt     1050
ccgccaccgc caccaccacc cagaccttca aaacccaccc cttctttagc     1100
aactactcta aaatcttatg attcaaacac cccaggacct actggtgaca     1150
acccccctgga gctgagtagg attcctgatg aaaactgcca gattaacaga    1200
tatggccact ttcaagccac catcacaatt gtagagggaa tcttagaggt     1250
taacatcatc cagatgacag acgtcctgat gccggtgcca tggcctgaaa     1300
gctccctaat agactttgtc gtgacctgcc aagggagcat tcccacggag     1350
gtctgtacca tcatttctga ccccacctgc gagatcaccc agaacacagt     1400
ctgcagccct gtggatgtgg atgagatgtg tctgctgact gtgagacgaa     1450
ccttcaatgg gtctgggacg tactgtgtga acctcaccct gggggatgac     1500
acaagcctgg ctctcacgag caccctgatt tctgttcctg acagagaccc     1550
agcctcgcct ttaaggatgg caaacagtgc cctgatctcc gttggctgct     1600
tggccatatt tgtcactgtg atctccctct tggtgtacaa aaaacacaag     1650
gaatacaacc caatagaaaa tagtcctggg aatgtggtca gaagcaaagg     1700
cctgagtgtc tttctcaacc gtgcaaaagc cgtgttcttc ccgggaaacc     1750
aggaaaagga tccgctactc aaaaaccaag aatttaaagg agtttcttaa     1800
atttcgacct tgtttctgaa gctcactttt cagtgccatt gatgtgagat     1850
gtgctggagt ggctattaac ctttttttcc taaagattat tgttaaatag     1900
atattgtggt ttggggaagt tgaatttttt ataggttaaa tgtcatttta     1950
gagatgggga gagggattat actgcaggca gcttcagcca tgttgtgaaa     2000
ctgataaaag caacttagca aggcttcttt tcattatttt ttatgtttca     2050
cttataaagt cttaggtaac tagtaggata gaaacactgt gtcccgagag     2100
taaggagaga agctactatt gattagagcc taacccaggt taactgcaag     2150
aagaggcggg atactttcag ctttccatgt aactgtatgc ataaagccaa     2200
tgtagtccag tttctaagat catgttccaa gctaactgaa tcccacttca     2250
atacacactc atgaactcct gatggaacaa taacaggccc aagcctgtgg     2300
tatgatgtgc acacttgcta gactcagaaa aaatactact ctcataaatg     2350
ggtgggagta ttttggtgac aacctacttt gcttggctga gtgaaggaat     2400
gatattcata tattcattta ttccatggac atttagttag tgctttttat     2450
ataccaggca tgatgctgag tgacactctt gtgtatattt ccaaattttt     2500
gtacagtcgc tgcacatatt tgaaatcata tattaagact ttccaaagat     2550
gaggtccctg gtttttcatg gcaacttgat cagtaaggat ttcacctctg     2600
tttgtaacta aaaccatcta ctatatgtta gacatgacat tctttttctc     2650
tccttcctga aaaataaagt gtgggaagag  aca                      2683
```

<210> SEQ ID NO 42
<211> LENGTH: 572
<212> TYPE: PRT

-continued

<213> ORGANISM: Homo sapiens

<400> SEQUENCE: 42

```
Met Glu Cys Leu Tyr Tyr Phe Leu Gly Phe Leu Leu Leu Ala Ala
  1               5                  10                  15

Arg Leu Pro Leu Asp Ala Ala Lys Arg Phe His Asp Val Leu Gly
                 20                  25                  30

Asn Glu Arg Pro Ser Ala Tyr Met Arg Glu His Asn Gln Leu Asn
                 35                  40                  45

Gly Trp Ser Ser Asp Glu Asn Asp Trp Asn Glu Lys Leu Tyr Pro
                 50                  55                  60

Val Trp Lys Arg Gly Asp Met Arg Trp Lys Asn Ser Trp Lys Gly
                 65                  70                  75

Gly Arg Val Gln Ala Val Leu Thr Ser Asp Ser Pro Ala Leu Val
                 80                  85                  90

Gly Ser Asn Ile Thr Phe Ala Val Asn Leu Ile Phe Pro Arg Cys
                 95                 100                 105

Gln Lys Glu Asp Ala Asn Gly Asn Ile Val Tyr Glu Lys Asn Cys
                110                 115                 120

Arg Asn Glu Ala Gly Leu Ser Ala Asp Pro Tyr Val Tyr Asn Trp
                125                 130                 135

Thr Ala Trp Ser Glu Asp Ser Asp Gly Glu Asn Gly Thr Gly Gln
                140                 145                 150

Ser His His Asn Val Phe Pro Asp Gly Lys Pro Phe Pro His His
                155                 160                 165

Pro Gly Trp Arg Arg Trp Asn Phe Ile Tyr Val Phe His Thr Leu
                170                 175                 180

Gly Gln Tyr Phe Gln Lys Leu Gly Arg Cys Ser Val Arg Val Ser
                185                 190                 195

Val Asn Thr Ala Asn Val Thr Leu Gly Pro Gln Leu Met Glu Val
                200                 205                 210

Thr Val Tyr Arg Arg His Gly Arg Ala Tyr Val Pro Ile Ala Gln
                215                 220                 225

Val Lys Asp Val Tyr Val Val Thr Asp Gln Ile Pro Val Phe Val
                230                 235                 240

Thr Met Phe Gln Lys Asn Asp Arg Asn Ser Ser Asp Glu Thr Phe
                245                 250                 255

Leu Lys Asp Leu Pro Ile Met Phe Asp Val Leu Ile His Asp Pro
                260                 265                 270

Ser His Phe Leu Asn Tyr Ser Thr Ile Asn Tyr Lys Trp Ser Phe
                275                 280                 285

Gly Asp Asn Thr Gly Leu Phe Val Ser Thr Asn His Thr Val Asn
                290                 295                 300

His Thr Tyr Val Leu Asn Gly Thr Phe Ser Leu Asn Leu Thr Val
                305                 310                 315

Lys Ala Ala Ala Pro Gly Pro Cys Pro Pro Pro Pro Pro Pro Pro
                320                 325                 330

Arg Pro Ser Lys Pro Thr Pro Ser Leu Ala Thr Thr Leu Lys Ser
                335                 340                 345

Tyr Asp Ser Asn Thr Pro Gly Pro Thr Gly Asp Asn Pro Leu Glu
                350                 355                 360

Leu Ser Arg Ile Pro Asp Glu Asn Cys Gln Ile Asn Arg Tyr Gly
                365                 370                 375
```

-continued

```
His Phe Gln Ala Thr Ile Thr Ile Val Glu Gly Ile Leu Glu Val
                380                 385                 390

Asn Ile Ile Gln Met Thr Asp Val Leu Met Pro Val Pro Trp Pro
                395                 400                 405

Glu Ser Ser Leu Ile Asp Phe Val Val Thr Cys Gln Gly Ser Ile
                410                 415                 420

Pro Thr Glu Val Cys Thr Ile Ile Ser Asp Pro Thr Cys Glu Ile
                425                 430                 435

Thr Gln Asn Thr Val Cys Ser Pro Val Asp Val Asp Glu Met Cys
                440                 445                 450

Leu Leu Thr Val Arg Arg Thr Phe Asn Gly Ser Gly Thr Tyr Cys
                455                 460                 465

Val Asn Leu Thr Leu Gly Asp Asp Thr Ser Leu Ala Leu Thr Ser
                470                 475                 480

Thr Leu Ile Ser Val Pro Asp Arg Asp Pro Ala Ser Pro Leu Arg
                485                 490                 495

Met Ala Asn Ser Ala Leu Ile Ser Val Gly Cys Leu Ala Ile Phe
                500                 505                 510

Val Thr Val Ile Ser Leu Leu Val Tyr Lys Lys His Lys Glu Tyr
                515                 520                 525

Asn Pro Ile Glu Asn Ser Pro Gly Asn Val Val Arg Ser Lys Gly
                530                 535                 540

Leu Ser Val Phe Leu Asn Arg Ala Lys Ala Val Phe Phe Pro Gly
                545                 550                 555

Asn Gln Glu Lys Asp Pro Leu Leu Lys Asn Gln Glu Phe Lys Gly
                560                 565                 570

Val Ser


<210> SEQ ID NO 43
<211> LENGTH: 1434
<212> TYPE: DNA
<213> ORGANISM: Homo sapiens

<400> SEQUENCE: 43

gcatagatga atgtatcagt ggatggatag ttggctagat gggtgggttg                50

gtggatgaat ggcagagctt gcacctgcca gtccatctga catcaaagcc               100

agtgtctcta atggtgacac caccctcctc tgcagcagga ggcagagctg               150

tgggatgaat gaggttcgcc aggtctccct tacctatcct gggtccccag               200

ctccttctca ctctcttccc ttgcagcctc gaagcggagg atccctgtgt               250

cccagccggg catggccgac ccccaccagc ttttcgatga cacaagttca               300

gcccagagcc ggggctatgg ggcccagcgg gcacctggtg gcctgagtta               350

tcctgcagcc tctcccacgc cccatgcagc cttcctggct gacccggtgt               400

ccaacatggc catggcctat gggagcagcc tggccgcgca gggcaaggag               450

ctggtggata agaacatcga ccgcttcatc cccatcacca agctcaagta               500

ttactttgct gtggacacca tgtatgtggg cagaaagctg ggcctgctgt               550

tcttccccta cctacaccag gactgggaag tgcagtacca acaggacacc               600

ccggtggccc cccgctttga cgtcaatgcc ccggacctct acattccagc               650

aatggctttc atcacctacg ttttggtggc tggtcttgcg ctggggaccc               700

aggataggtt ctccccagac ctcctggggc tgcaagcgag ctcagccctg               750
```

-continued

```
gcctggctga ccctggaggt gctggccatc ctgctcagcc tctatctggt              800

cactgtcaac accgacctca ccaccatcga cctggtggcc ttcttgggct              850

acaaatatgt cgggatgatt ggcggggtcc tcatgggcct gctcttcggg              900

aagattggct actacctggt gctgggctgg tgctgcgtag ccatctttgt              950

gttcatgatc cggacgctgc ggctgaagat cttggcagac gcagcagctg             1000

agggggtccc ggtgcgtggg gcccggaacc agctgcgcat gtacctgacc             1050

atggcggtgg cggcggcgca gcctatgctc atgtactggc tcaccttcca             1100

cctggtgcgg tgagcgcgcc cgctgaacct cccgctgctg ctgctgctgc             1150

tgggggccac tgtggccgcc gaactcatct cctgcctgca ggccccaagg             1200

tccaccctgt ctggccacag gcaccgcctc catcccatgt cccgcccagc             1250

cccgccccca acccaaggtg ctgagagatc tccagctgca caggccaccg             1300

ccccagggcg tggccgctgt tacagaaaca ataaaccctg atgggcatgg             1350

caaaaaaaaa aaaaaaaaaa aaaaaaaaaa aaaaaaaaaa aaaaaaaaaa             1400

aaaaaaaaaa aaaaaaaaaa aaaaaaaaaa  aaga                             1434
```

<210> SEQ ID NO 44
<211> LENGTH: 283
<212> TYPE: PRT
<213> ORGANISM: Homo sapiens

<400> SEQUENCE: 44

```
Met Ala Asp Pro His Gln Leu Phe Asp Asp Thr Ser Ser Ala Gln
  1               5                  10                  15

Ser Arg Gly Tyr Gly Ala Gln Arg Ala Pro Gly Gly Leu Ser Tyr
                 20                  25                  30

Pro Ala Ala Ser Pro Thr Pro His Ala Ala Phe Leu Ala Asp Pro
                 35                  40                  45

Val Ser Asn Met Ala Met Ala Tyr Gly Ser Ser Leu Ala Ala Gln
                 50                  55                  60

Gly Lys Glu Leu Val Asp Lys Asn Ile Asp Arg Phe Ile Pro Ile
                 65                  70                  75

Thr Lys Leu Lys Tyr Tyr Phe Ala Val Asp Thr Met Tyr Val Gly
                 80                  85                  90

Arg Lys Leu Gly Leu Leu Phe Phe Pro Tyr Leu His Gln Asp Trp
                 95                 100                 105

Glu Val Gln Tyr Gln Gln Asp Thr Pro Val Ala Pro Arg Phe Asp
                110                 115                 120

Val Asn Ala Pro Asp Leu Tyr Ile Pro Ala Met Ala Phe Ile Thr
                125                 130                 135

Tyr Val Leu Val Ala Gly Leu Ala Leu Gly Thr Gln Asp Arg Phe
                140                 145                 150

Ser Pro Asp Leu Leu Gly Leu Gln Ala Ser Ser Ala Leu Ala Trp
                155                 160                 165

Leu Thr Leu Glu Val Leu Ala Ile Leu Leu Ser Leu Tyr Leu Val
                170                 175                 180

Thr Val Asn Thr Asp Leu Thr Thr Ile Asp Leu Val Ala Phe Leu
                185                 190                 195

Gly Tyr Lys Tyr Val Gly Met Ile Gly Gly Val Leu Met Gly Leu
                200                 205                 210

Leu Phe Gly Lys Ile Gly Tyr Tyr Leu Val Leu Gly Trp Cys Cys
```

-continued

```
                215                 220                 225

Val Ala Ile Phe Val Phe Met Ile Arg Thr Leu Arg Leu Lys Ile
                230                 235                 240

Leu Ala Asp Ala Ala Ala Glu Gly Val Pro Val Arg Gly Ala Arg
                245                 250                 255

Asn Gln Leu Arg Met Tyr Leu Thr Met Ala Val Ala Ala Ala Gln
                260                 265                 270

Pro Met Leu Met Tyr Trp Leu Thr Phe His Leu Val Arg
                275                 280


<210> SEQ ID NO 45
<211> LENGTH: 1205
<212> TYPE: DNA
<213> ORGANISM: Homo sapiens

<400> SEQUENCE: 45

gctgagcacc aacaggaact attccagtga agagcaagtg ctgcccgacc                50

caggaccctg tgccaggctg gcagccctcc agctccctcc agagaggaaa               100

cctctgtctg gctgagggtg ggactagctg ggatgtctca ctccagttgc               150

tcaggttcac ccaggaagct cctccgtgga gtggccagcc tgattctagc               200

cctgtcctct ctggcagcac atgccacacc tgcctgggcc ttctgctccc               250

tgatgcttga tgagcccctg cctcctcaat gtttctcaaa gacagacccc               300

cctgaggcca gcttgaatgt gaagactgct gaagtcagct ggcttcactt               350

gagctgcaga aaaggtggct gggatggccc aggtgcaccc agaggcccca               400

gccctttggc tgcctttggg ttgtgacttg ggttgtctct gaggccctgc               450

cagagctggg cctgcgggtg gtgggcggtc cgacctcggg cagtcagtgc               500

tccgcagcct cagcactgca tcccagaccc agtgtcctca gagggaagag               550

ccagcctccc tgcctcatgg aaccaggagt cccaaaaagt caggagcctg               600

gaggctctga aaggagcagg gattccatag tgcgtgaagc tgaaataggc               650

gccctcctgg ggagcccccca gcaaaactgt ttttcatacc cactcccaga               700

actgccccgc tccagctcca gcgccagcgc cagctggttg ccaggcgtca               750

ttggagaggc ctggctgccc caggggcagc agggagtggt ggacctgtat               800

gggctggcag gaggccattg gccatgctga caagtgtcac ctgccttcct               850

agcctggagc cacccctcag gtggcctgct tgcacctcct atccggaggt               900

agcctgcccc acctgtaggc agagggggct cttgcttgag gcctgcacag               950

gaagcaagta tagccccggt gccccagagt gggttccact tagccctggc              1000

gagatggcct gtcctgagat ctctgctccc agaccccacc atctggggag              1050

cacagtcctt aggctgcctg gtccaggaag ggggtgcggc tctgtcagga              1100

aacctggact ctcaaggccc accagcctct ccgtgagtgt tagaaatcac              1150

agatacagta tatacttaat tacactactc actactcaaa aaaaaaaaaa              1200

aaaaa                                                               1205


<210> SEQ ID NO 46
<211> LENGTH: 97
<212> TYPE: PRT
<213> ORGANISM: Homo sapiens

<400> SEQUENCE: 46
```

-continued

```
Met Ser His Ser Ser Cys Ser Gly Ser Pro Arg Lys Leu Leu Arg
  1               5                  10                  15

Gly Val Ala Ser Leu Ile Leu Ala Leu Ser Ser Leu Ala Ala His
                 20                  25                  30

Ala Thr Pro Ala Trp Ala Phe Cys Ser Leu Met Leu Asp Glu Pro
                 35                  40                  45

Leu Pro Pro Gln Cys Phe Ser Lys Thr Asp Pro Pro Glu Ala Ser
                 50                  55                  60

Leu Asn Val Lys Thr Ala Glu Val Ser Trp Leu His Leu Ser Cys
                 65                  70                  75

Arg Lys Gly Gly Trp Asp Gly Pro Gly Ala Pro Arg Gly Pro Ser
                 80                  85                  90

Pro Leu Ala Ala Phe Gly Leu
                 95


<210> SEQ ID NO 47
<211> LENGTH: 983
<212> TYPE: DNA
<213> ORGANISM: Homo sapiens

<400> SEQUENCE: 47

ttccgggccc tggcgtctcg tctccttacc ctggggctac ccttgcccgg                50

tcctactgcc cgcggttaac ccgccgcgag ccgcctctcc cctccccgcc               100

cgactcaacc ctgccctccc ccgtgctttg cagacgccgc ccgggggccc               150

aggcggctga tgcgtgtggg cctcgcgctg atcttggtgg gccacgtgaa               200

cctgctgctg ggggccgtgc tgcatggcac cgtcctgcgg cacgtggcca               250

atccccgcgg cgctgtcacg ccggagtaca ccgtagccaa tgtcatctct               300

gtcggctcgg ggctgctgag cgtttccgtg ggacttgtgg ccctcctggc               350

gtccaggaac cttcttcgcc ctccactgca ctgggtcctg ctggcactag               400

ctctggtgaa cctgctcttg tccgttgcct gctccctggg cctccttctt               450

gctgtgtcac tcactgtggc caacggtggc cgccgcctta ttgctgactg               500

ccacccagga ctgctggatc ctctggtacc actggatgag gggccgggac               550

atactgactg cccctttgac cccacaagaa tctatgatac agccttggct               600

ctctggatcc cttctttgct catgtctgca ggggaggctg ctctatctgg               650

ttactgctgt gtggctgcac tcactctacg tggagttggg ccctgcagga               700

aggacggact tcaggggcag ctagaggaaa tgacagagct tgaatctcct               750

aaatgtaaaa ggcaggaaaa tgagcagcta ctggatcaaa atcaagaaat               800

ccgggcatca cagagaagtt gggtttagga caggtgctgt tccgagactc               850

agtcctaaag ggtttttttt cccactaagc aaggggccct gacctcggga               900

tgagataaca aattgtaata aagtaacttc tcttttcttc taaaaaaaaa               950

aaaaaaaaaa aaaaaaaaaa aaaaaaaaaa  aaa                                 983


<210> SEQ ID NO 48
<211> LENGTH: 222
<212> TYPE: PRT
<213> ORGANISM: Homo sapiens

<400> SEQUENCE: 48

Met Arg Val Gly Leu Ala Leu Ile Leu Val Gly His Val Asn Leu
```

-continued

```
  1               5                  10                  15

Leu Leu Gly Ala Val Leu His Gly Thr Val Leu Arg His Val Ala
                20                  25                  30

Asn Pro Arg Gly Ala Val Thr Pro Glu Tyr Thr Val Ala Asn Val
                35                  40                  45

Ile Ser Val Gly Ser Gly Leu Leu Ser Val Ser Val Gly Leu Val
                50                  55                  60

Ala Leu Leu Ala Ser Arg Asn Leu Leu Arg Pro Pro Leu His Trp
                65                  70                  75

Val Leu Leu Ala Leu Ala Leu Val Asn Leu Leu Leu Ser Val Ala
                80                  85                  90

Cys Ser Leu Gly Leu Leu Leu Ala Val Ser Leu Thr Val Ala Asn
                95                 100                 105

Gly Gly Arg Arg Leu Ile Ala Asp Cys His Pro Gly Leu Leu Asp
               110                 115                 120

Pro Leu Val Pro Leu Asp Glu Gly Pro Gly His Thr Asp Cys Pro
               125                 130                 135

Phe Asp Pro Thr Arg Ile Tyr Asp Thr Ala Leu Ala Leu Trp Ile
               140                 145                 150

Pro Ser Leu Leu Met Ser Ala Gly Glu Ala Ala Leu Ser Gly Tyr
               155                 160                 165

Cys Cys Val Ala Ala Leu Thr Leu Arg Gly Val Gly Pro Cys Arg
               170                 175                 180

Lys Asp Gly Leu Gln Gly Gln Leu Glu Glu Met Thr Glu Leu Glu
               185                 190                 195

Ser Pro Lys Cys Lys Arg Gln Glu Asn Glu Gln Leu Leu Asp Gln
               200                 205                 210

Asn Gln Glu Ile Arg Ala Ser Gln Arg Ser Trp Val
               215                 220


<210> SEQ ID NO 49
<211> LENGTH: 847
<212> TYPE: DNA
<213> ORGANISM: Homo sapiens

<400> SEQUENCE: 49

cgtcagtcta gaaggataag agaaagaaag ttaagcaact acaggaaatg                50

gctttgggag ttccaatatc agtctatctt ttattcaacg caatgacagc               100

actgaccgaa gaggcagccg tgactgtaac acctccaatc acagcccagc               150

aagctgacaa catagaagga cccatagcct tgaagttctc acacctttgc               200

ctggaagatc ataacagtta ctgcatcaac ggtgcttgtg cattccacca               250

tgagctagag aaagccatct gcaggtgttt tactggttat actggagaaa               300

ggtgtgagca cttgacttta acttcatatg ctgtggattc ttatgaaaaa               350

tacattgcaa ttgggattgg tgttggatta ctattaagtg gttttcttgt               400

tatttttac tgctatataa gaaagaggta tgaaaaagac aaaatatgaa               450

gtcacttcat atgcaatcgt ttgacaaata gttattcagg ccctataatg               500

tgtcaggcac tgacatgtaa aatttttta attaaaaaag agctgtaatc               550

tggcaaaaag tttctatgta atatttttca tgccttttct cataaaccca               600

gacgagtggt aaaaatttgc cttcagttgt aataggagag ttcaaacgta               650

cagtctccct tcaacctatc tctgtctgcc catatcaaaa ttataaatga               700
```

-continued

```
ggaggacagc aggccccaag aaagtaggga ctaagtatgt cttgttcaaa              750

attgtatatt cagtgactta cactatgcct agcacacaac acacactgag              800

taaatatttg ttgagtgaaa taaaatcaag aaacaagtaa  aaactga                847


<210> SEQ ID NO 50
<211> LENGTH: 133
<212> TYPE: PRT
<213> ORGANISM: Homo sapiens

<400> SEQUENCE: 50

Met Ala Leu Gly Val Pro Ile Ser Val Tyr Leu Leu Phe Asn Ala
  1               5                  10                  15

Met Thr Ala Leu Thr Glu Glu Ala Ala Val Thr Val Thr Pro Pro
                 20                  25                  30

Ile Thr Ala Gln Gln Ala Asp Asn Ile Glu Gly Pro Ile Ala Leu
                 35                  40                  45

Lys Phe Ser His Leu Cys Leu Glu Asp His Asn Ser Tyr Cys Ile
                 50                  55                  60

Asn Gly Ala Cys Ala Phe His His Glu Leu Glu Lys Ala Ile Cys
                 65                  70                  75

Arg Cys Phe Thr Gly Tyr Thr Gly Glu Arg Cys Glu His Leu Thr
                 80                  85                  90

Leu Thr Ser Tyr Ala Val Asp Ser Tyr Glu Lys Tyr Ile Ala Ile
                 95                 100                 105

Gly Ile Gly Val Gly Leu Leu Leu Ser Gly Phe Leu Val Ile Phe
                110                 115                 120

Tyr Cys Tyr Ile Arg Lys Arg Tyr Glu Lys Asp Lys Ile
                125                 130


<210> SEQ ID NO 51
<211> LENGTH: 978
<212> TYPE: DNA
<213> ORGANISM: Homo sapiens

<400> SEQUENCE: 51

ggctcgagct tggctctcag accatcctgg tggaagaaac actagcagtc               50

tgcccaatct gaatgcaaat ccagaataat cttttctttt gttgttacac              100

agttatgagt gcaattttta aatggctgct actctacagc ctgcctgcct              150

tatgctttct cctgggcacg caggaaagtg agagcttcca ctccaaagca              200

gagatcctag tgacactaag tcaggtaata atctctccag ctggacctca              250

tgcactcaca tggacaacac acttctctcc ttcagtgatc atcatccttg              300

taccatgttg gtggcatgct gtaatcgtga ctcaacatcc ggttgccaat              350

tgctatgtaa caaaccacct caacattcag tggcttgaat tgaaagcagg              400

gtcttgaaga gatatttgca catttcatcc tcccagcagc attattcaca              450

acagccaata ggcagaagca acccaatgtc caaccataga tgagtggata              500

accaaaatgt agtccatcca tacaatgaaa tatgattcag ccttaacaag              550

gaaggaagtc ccgccacgtg ctacaacatg gatggacctt gaggacacta              600

tgctaagtga agtaagccag gcacaaaagg acaaatactc tatgattcca              650

ttttataggg taccaaagag aatcaaactc acagagatag aaagtagact              700

ggggtggcca gggactcggg gagagaggaa agggcagtta ttgtttaaaa              750
```

-continued

```
ggtacagagt ttcagtttgg gaagatgaaa atgttctgga aacggttaat              800

ggtgatttta cattgtttat gttaccacga tttgtaaaag agcagctgcg              850

ctgagaatga gcatgcttgt cattggcagc tctctgagat tttcagtgcc              900

tcttactggc ttgttaagaa gacggcaaaa aaaaaaaaaa aaaaaaaaaa              950

aaaaaaaaaa aaaaaaaaaa  aaaaaaaa                                     978


<210> SEQ ID NO 52
<211> LENGTH: 114
<212> TYPE: PRT
<213> ORGANISM: Homo sapiens

<400> SEQUENCE: 52

Met Gln Ile Gln Asn Asn Leu Phe Phe Cys Cys Tyr Thr Val Met
  1               5                  10                  15

Ser Ala Ile Phe Lys Trp Leu Leu Leu Tyr Ser Leu Pro Ala Leu
                 20                  25                  30

Cys Phe Leu Leu Gly Thr Gln Glu Ser Glu Ser Phe His Ser Lys
                 35                  40                  45

Ala Glu Ile Leu Val Thr Leu Ser Gln Val Ile Ile Ser Pro Ala
                 50                  55                  60

Gly Pro His Ala Leu Thr Trp Thr Thr His Phe Ser Pro Ser Val
                 65                  70                  75

Ile Ile Ile Leu Val Pro Cys Trp Trp His Ala Val Ile Val Thr
                 80                  85                  90

Gln His Pro Val Ala Asn Cys Tyr Val Thr Asn His Leu Asn Ile
                 95                 100                 105

Gln Trp Leu Glu Leu Lys Ala Gly Ser
                110


<210> SEQ ID NO 53
<211> LENGTH: 1664
<212> TYPE: DNA
<213> ORGANISM: Homo sapiens

<400> SEQUENCE: 53

ttttgaaatg gtttatgacc tcttccccac ttccccgctt gctttgctca               50

ttagtgttcc taggtggctg ctgggtgacg ggcttttcat catctctgat              100

gtgggccagt gcgaaagagc agctgcaaca tctgtttcta attgggtcgt              150

gcctttataa atacttcttg cctatttgtc acattgcttc cctcccaccc              200

tgtcttcctt ggagtactgc agaatctgta agcgtccctg gaatgcacac              250

gtggaccttg tcattcccaa acagactttc tgctggtcag cactttgtaa              300

tgttcggctg ttacaggcat tagtcacttg tgctcagaga gagactgtgg              350

tctttggaaa ctgaagaaaa tgtctttttt gttgttgtta attcttggca              400

tccagttaga tttaacttct caagagttta cacagacttt tagaaaaaca              450

ttctgtctct aagaaaaaag tgctctagct ttgtacagtt tttggatttt              500

cacacttggt ggttgtttgc tgaaatgctg ttttgctagt gattcccctc              550

ctccccctat ctggggttgt aagcagctct ggggctctgt tcacttcgga              600

tacctgtttc tggggactgc ttttcaacag cgtttttcct aagggcatat              650

gagaaattta atttctgatg gaatgaaggt gaaactctag tcccaggtaa              700
```

-continued

```
acctgggtag gctgtagaga cagaaagggg gctgcaggtc taggtggaag          750

aacgagaacg aatgcagcat ggtatttcca ggccttttag attcggcttc          800

atccacaacc aatgtgagtt cttatctgca aagcgggcct aagtgtaatg          850

gagggaaggt gggccaggca ccagggtcct gggttctccc gcgcctcact          900

ctgtctccac ctggcccatg cataaagaac actagtcaag tagccattgt          950

acctgtttcc ttatctgaaa atgagaaggt tggagagtat gacttctgtt         1000

gaaacaacaa ggcgcttaca aattttggtg aagtcgaatg agggcagcgt         1050

taagagaaat atcaaagtta gtcattggat ttcagggctt agggatggaa         1100

accagctggt agtagactgg ttgtagttat gtccaaaggg cagagtggga         1150

aaaatttggc cgaaaagagt gtggtgggtg accagcaaat gttagaggta         1200

tacatcaggg cacagaggag aaaagctaac atgatactga tgacttcaag         1250

tcttcactgt ccaattcaga ggatagggga gggtttaagc tgattaaaca         1300

gtgggctttt tttctcctgc aagagggtgg aggtctataa ctgtgcagat         1350

tttatcagat gcatgctaat acatgttatt ctgggggact ctcttatacc         1400

ttgaagtaga cattgctgct atttgcgtga aaaaaatagg aggacttatt         1450

tgaattgaga atggggatag gctgagttcc accgagatgt tggcttagag         1500

atgcctgggc catgctgtac agtaggaagc ccagcagagg agattgggct         1550

gtgtgggtca tgacaaaggg agttgttagc ttatggttgg ctattaaagt         1600

catgggcaag gatgggcaag aaaagtgtgt aaaatgagct gacaaaagat         1650

aaatatgtta  atta                                               1664
```

```
<210> SEQ ID NO 54
<211> LENGTH: 102
<212> TYPE: PRT
<213> ORGANISM: Homo sapiens

<400> SEQUENCE: 54

Met Thr Ser Ser Pro Leu Pro Arg Leu Leu Cys Ser Leu Val Phe
  1               5                  10                  15

Leu Gly Gly Cys Trp Val Thr Gly Phe Ser Ser Ser Leu Met Trp
                 20                  25                  30

Ala Ser Ala Lys Glu Gln Leu Gln His Leu Phe Leu Ile Gly Ser
                 35                  40                  45

Cys Leu Tyr Lys Tyr Phe Leu Pro Ile Cys His Ile Ala Ser Leu
                 50                  55                  60

Pro Pro Cys Leu Pro Trp Ser Thr Ala Glu Ser Val Ser Val Pro
                 65                  70                  75

Gly Met His Thr Trp Thr Leu Ser Phe Pro Asn Arg Leu Ser Ala
                 80                  85                  90

Gly Gln His Phe Val Met Phe Gly Cys Tyr Arg His
                 95                 100
```

```
<210> SEQ ID NO 55
<211> LENGTH: 1824
<212> TYPE: DNA
<213> ORGANISM: Homo sapiens

<400> SEQUENCE: 55

acactggcca aacactcgca tcccagggcg tctccggctg ctcccattga           50
```

-continued

```
gctgtctgct cgctgtgccc gctgtgcctg ctgtgcccgc gctgtcgccg      100
ctgctaccgc gtctgctgga cgcgggagac gccagcgagc tggtgattgg      150
agccctgcgg agagctcaag cgcccagctc tgcccgagga gcccaggctg      200
ccccgtgagt cccatagttg ctgcaggagt ggagccatga gctgcgtcct      250
gggtggtgtc atccccttgg ggctgctgtt cctggtctgc ggatcccaag      300
gctacctcct gcccaacgtc actctcttag aggagctgct cagcaaatac      350
cagcacaacg agtctcactc ccgggtccgc agagccatcc ccagggagga      400
caaggaggag atcctcatgc tgcacaacaa gcttcggggc caggtgcagc      450
ctcaggcctc caacatggag tacatgacct gggatgacga actggagaag      500
tctgctgcag cgtgggccag tcagtgcatc tgggagcacg ggcccaccag      550
tctgctggtg tccatcgggc agaacctggg cgctcactgg ggcaggtatc      600
gctctccggg gttccatgtg cagtcctggt atgacgaggt gaaggactac      650
acctacccct acccgagcga gtgcaacccc tggtgtccag agaggtgctc      700
ggggcctatg tgcacgcact acacacagat agtttgggcc accaccaaca      750
agatcggttg tgctgtgaac acctgccgga agatgactgt ctggggagaa      800
gtttgggaga acgcggtcta ctttgtctgc aattattctc caaaggggaa      850
ctggattgga gaagcccccct acaagaatgg ccggccctgc tctgagtgcc      900
cacccagcta tggaggcagc tgcaggaaca acttgtgtta ccgagaagaa      950
acctacactc caaaacctga aacggacgag atgaatgagg tggaaacggc     1000
tcccattcct gaagaaaacc atgtttggct ccaaccgagg gtgatgagac     1050
ccaccaagcc caagaaaacc tctgcggtca actacatgac ccaagtcgtc     1100
agatgtgaca ccaagatgaa ggacaggtgc aaagggtcca cgtgtaacag     1150
gtaccagtgc ccagcaggct gcctgaacca caaggcgaag atctttggaa     1200
gtctgttcta tgaaagctcg tctagcatat gccgcgccgc catccactac     1250
gggatcctgg atgacaaggg aggcctggtg gatatcacca ggaacgggaa     1300
ggtccccttc ttcgtgaagt ctgagagaca cggcgtgcag tccctcagca     1350
aatacaaacc ttccagctca ttcatggtgt caaaagtgaa agtgcaggat     1400
ttggactgct acacgaccgt tgctcagctg tgcccgtttg aaaagccagc     1450
aactcactgc ccaagaatcc attgtccggc acactgcaaa gacgaacctt     1500
cctactgggc tccggtgttt ggaaccaaca tctatgcaga tacctcaagc     1550
atctgcaaga cagctgtgca cgcgggagtc atcagcaacg agagtggggg     1600
tgacgtggac gtgatgcccg tggataaaaa gaagacctac gtgggctcgc     1650
tcaggaatgg agttcagtct gaaagcctgg ggactcctcg ggatggaaag     1700
gccttccgga tctttgctgt caggcagtga atttccagca ccaggggaga     1750
aggggcgtct tcaggagggc ttcggggttt tgcttttatt tttattttgt     1800
cattgcgggg tatatggaga  gtca                                1824
```

<210> SEQ ID NO 56
<211> LENGTH: 497
<212> TYPE: PRT
<213> ORGANISM: Homo sapiens

<400> SEQUENCE: 56

-continued

```
Met Ser Cys Val Leu Gly Gly Val Ile Pro Leu Gly Leu Leu Phe
  1               5                  10                  15

Leu Val Cys Gly Ser Gln Gly Tyr Leu Leu Pro Asn Val Thr Leu
                 20                  25                  30

Leu Glu Glu Leu Leu Ser Lys Tyr Gln His Asn Glu Ser His Ser
                 35                  40                  45

Arg Val Arg Arg Ala Ile Pro Arg Glu Asp Lys Glu Glu Ile Leu
                 50                  55                  60

Met Leu His Asn Lys Leu Arg Gly Gln Val Gln Pro Gln Ala Ser
                 65                  70                  75

Asn Met Glu Tyr Met Thr Trp Asp Asp Glu Leu Glu Lys Ser Ala
                 80                  85                  90

Ala Ala Trp Ala Ser Gln Cys Ile Trp Glu His Gly Pro Thr Ser
                 95                 100                 105

Leu Leu Val Ser Ile Gly Gln Asn Leu Gly Ala His Trp Gly Arg
                110                 115                 120

Tyr Arg Ser Pro Gly Phe His Val Gln Ser Trp Tyr Asp Glu Val
                125                 130                 135

Lys Asp Tyr Thr Tyr Pro Tyr Pro Ser Glu Cys Asn Pro Trp Cys
                140                 145                 150

Pro Glu Arg Cys Ser Gly Pro Met Cys Thr His Tyr Thr Gln Ile
                155                 160                 165

Val Trp Ala Thr Thr Asn Lys Ile Gly Cys Ala Val Asn Thr Cys
                170                 175                 180

Arg Lys Met Thr Val Trp Gly Glu Val Trp Glu Asn Ala Val Tyr
                185                 190                 195

Phe Val Cys Asn Tyr Ser Pro Lys Gly Asn Trp Ile Gly Glu Ala
                200                 205                 210

Pro Tyr Lys Asn Gly Arg Pro Cys Ser Glu Cys Pro Pro Ser Tyr
                215                 220                 225

Gly Gly Ser Cys Arg Asn Asn Leu Cys Tyr Arg Glu Glu Thr Tyr
                230                 235                 240

Thr Pro Lys Pro Glu Thr Asp Glu Met Asn Glu Val Glu Thr Ala
                245                 250                 255

Pro Ile Pro Glu Glu Asn His Val Trp Leu Gln Pro Arg Val Met
                260                 265                 270

Arg Pro Thr Lys Pro Lys Lys Thr Ser Ala Val Asn Tyr Met Thr
                275                 280                 285

Gln Val Val Arg Cys Asp Thr Lys Met Lys Asp Arg Cys Lys Gly
                290                 295                 300

Ser Thr Cys Asn Arg Tyr Gln Cys Pro Ala Gly Cys Leu Asn His
                305                 310                 315

Lys Ala Lys Ile Phe Gly Ser Leu Phe Tyr Glu Ser Ser Ser Ser
                320                 325                 330

Ile Cys Arg Ala Ala Ile His Tyr Gly Ile Leu Asp Asp Lys Gly
                335                 340                 345

Gly Leu Val Asp Ile Thr Arg Asn Gly Lys Val Pro Phe Phe Val
                350                 355                 360

Lys Ser Glu Arg His Gly Val Gln Ser Leu Ser Lys Tyr Lys Pro
                365                 370                 375

Ser Ser Ser Phe Met Val Ser Lys Val Lys Val Gln Asp Leu Asp
                380                 385                 390
```

```
Cys Tyr Thr Thr Val Ala Gln Leu Cys Pro Phe Glu Lys Pro Ala
                395                 400                 405

Thr His Cys Pro Arg Ile His Cys Pro Ala His Cys Lys Asp Glu
                410                 415                 420

Pro Ser Tyr Trp Ala Pro Val Phe Gly Thr Asn Ile Tyr Ala Asp
                425                 430                 435

Thr Ser Ser Ile Cys Lys Thr Ala Val His Ala Gly Val Ile Ser
                440                 445                 450

Asn Glu Ser Gly Gly Asp Val Asp Val Met Pro Val Asp Lys Lys
                455                 460                 465

Lys Thr Tyr Val Gly Ser Leu Arg Asn Gly Val Gln Ser Glu Ser
                470                 475                 480

Leu Gly Thr Pro Arg Asp Gly Lys Ala Phe Arg Ile Phe Ala Val
                485                 490                 495

Arg Gln


<210> SEQ ID NO 57
<211> LENGTH: 486
<212> TYPE: DNA
<213> ORGANISM: Homo sapiens

<400> SEQUENCE: 57

gcacgaggcc aaacacagca gcctcaacat gaaggtggtt atggtcctcc                50

tgcttgctgc cctccccctt tactgctatg caggttctgg ttgcgttctt               100

ctggagagcg tcgtggaaaa gaccatcgat ccatcggttt ctgtggagga               150

atacaaagca gatcttcaga ggttcatcga cactgagcaa accgaagcag               200

ctgtagagga gttcaaggag tgcttcctca gccagagcaa tgagactctg               250

gccaacttcc gagtcatggt gcatacgata tatgacagcc tttactgtgc               300

tgcgtattaa ctgtcacaag aactttggct cagaggaatc cagacgatgc               350

tcacaacccg actgtggact ggcagaaatc tcaacttttc cttttgactt               400

tccccttttga tcagtaatat ggaagacgtt gttgaaacct gaagtatagt              450

taatttaaat aaacccactg caagaaaaaa  aaaaaa                             486


<210> SEQ ID NO 58
<211> LENGTH: 93
<212> TYPE: PRT
<213> ORGANISM: Homo sapiens

<400> SEQUENCE: 58

Met Lys Val Val Met Val Leu Leu Leu Ala Ala Leu Pro Leu Tyr
  1               5                  10                  15

Cys Tyr Ala Gly Ser Gly Cys Val Leu Leu Glu Ser Val Val Glu
                20                  25                  30

Lys Thr Ile Asp Pro Ser Val Ser Val Glu Glu Tyr Lys Ala Asp
                35                  40                  45

Leu Gln Arg Phe Ile Asp Thr Glu Gln Thr Glu Ala Ala Val Glu
                50                  55                  60

Glu Phe Lys Glu Cys Phe Leu Ser Gln Ser Asn Glu Thr Leu Ala
                65                  70                  75

Asn Phe Arg Val Met Val His Thr Ile Tyr Asp Ser Leu Tyr Cys
                80                  85                  90

Ala Ala Tyr
```

-continued

<210> SEQ ID NO 59
<211> LENGTH: 3976
<212> TYPE: DNA
<213> ORGANISM: Homo sapiens

<400> SEQUENCE: 59 caagtccgtt gaggctgcca ggcgagtcag gtctctctgg acctcgcctg 50 actcggctgg gctgtgcctg aaattgaccc agctccacca tactccttga 100 ttatgagaaa acaaggagta agctcaaagc ggctgcaatc ttccggccgc 150 agccagtcta aggggcggcg cggggcctcc ctcgcccggg agccggaggt 200 agaggaggag gtggaaaagt cggtcctagg cggcgggaaa ctgccaaggg 250 gcgcctggag gtcctccccg gggaggatcc aaagtctgaa agagcgaaaa 300 ggcttggagc tagaggtggt ggccaagacc tttcttctcg gccccttcca 350 gttcgtccgt aattccctgg cgcagctccg ggaaaaggtg caggaactgc 400 aggcgcggcg gttctccagc agaaccactc tcggcatcgc tgtctttgtg 450 gcaattttac attggttaca tttagtaaca ctttttgaaa atgatcgtca 500 tttctctcac ctctcatctt tggaacggga gatgactttt cgcactgaaa 550 tgggacttta ttattcatac ttcaagacca ttattgaagc accttcgttt 600 ttggaaggac tgtggatgat tatgaatgac aggcttactg aatatcctct 650 tataattaat gcaataaaac gcttccatct ttatccagag gtaatcatag 700 cctcctggta ttgcacattc atgggaataa tgaatttatt tggactagaa 750 actaagacct gctggaatgt caccagaata gaacctctta atgaagttca 800 aagctgtgaa ggattgggag atcctgcttg cttttatgtt ggtgtaatct 850 ttattttaaa tggactaatg atgggattgt tcttcatgta tggagcatac 900 ctgagtggga ctcaactggg aggtcttatt acagtactgt gcttcttttt 950 caaccatgga gaggccaccc gtgtgatgtg gacaccacct ctccgtgaaa 1000 gtttttccta tcctttcctt gtacttcaga tgtgtatttt aactttgatt 1050 ctcaggacct caagcaatga tagaaggccc ttcattgcac tctgtctttc 1100 caatgttgct tttatgcttc cctggcaatt tgctcagttt atacttttta 1150 cacagatagc atcattattt cccatgtatg ttgtgggata cattgaacca 1200 agcaaatttc agaagatcat ttatatgaac atgatttcag ttacccttag 1250 tttcattttg atgtttggaa attcaatgta cttatcttct tattattctt 1300 catctttgtt aatgacgtgg gcaataattc taaagagaaa tgaaattcaa 1350 aaactgggag tatctaaact caacttttgg ctaattcaag gtagtgcctg 1400 gtggtgtgga acaatcattt tgaaatttct gacatctaaa atcttaggcg 1450 tttcagacca cattcgcctg agtgatctta tagcagccag aatcttaagg 1500 tatacagatt ttgatacttt aatatatacc tgtgctcccg aatttgactt 1550 catggaaaaa gcgactccgc tgagatacac aaagacatta ttgcttccag 1600 ttgttatggt gattacatgt tttatcttta aaaagactgt tcgtgatatt 1650 tcatatgttt tagctacaaa catttatcta agaaaacagc tccttgaaca 1700 cagtgagctg gcttttcaca cattgcagtt gttagtgttt actgcccttg 1750 ccattttaat tatgaggcta aagatgtttt tgacaccgca catgtgtgtt 1800

-continued

```
atggcttcct tgatatgctc tcgacagctc tttggctggc tttttcgcag    1850
agttcgtttt gagaaggtta tctttggcat tttaacagtg atgtcaatac    1900
aaggttatgc aaacctccgt aatcaatgga gcataatagg agaatttaat    1950
aatttgcctc aggaagaact tttacagtgg atcaaataca gtaccacatc    2000
agatgctgtc tttgcaggtg ccatgcctac aatggcaagc atcaagctgt    2050
ctacacttca tcccattgtg aatcatccac attacgaaga tgcagacttg    2100
agggctcgga caaaaatagt ttattctaca tatagtcgaa aatctgccaa    2150
agaagtaaga gataaattgt tggagttaca tgtgaattat tatgttttag    2200
aagaggcatg gtgtgttgtg agaactaagc ctggttgcag tatgcttgaa    2250
atctgggatg tggaagaccc ttccaatgca gctaaccctc ccttatgtag    2300
cgtcctgctc gaagacgcca ggccttactt caccacagta tttcagaata    2350
gtgtgtacag agtattaaag gttaactgag aaggatacta cccattttac    2400
tatggcacaa tgccgtgtgt caaaaacaat cacccttttgg cttattcaca    2450
ttaataaaaa tcacaagctt taataacaga cacttaaaaa taagataaaa    2500
atggattgga aatttttctg attactaaaa ggtaaattac ttttctgttc    2550
attgaatgtc agccttatta agcttgtcat ataagttatt aaatcattca    2600
tgtcatactg cataaacaaa tgttcatttc agaattttaa agagaaatgt    2650
atataaagaa cmatgatttt aataatcagg ggtatgtaag tccttttca    2700
tccaactagg tgaattgctt cagattttct ctagtaccag agggtacctc    2750
ctcaaactct ttgaaccact taaggcagaa gaatgcaagc tctgaaatga    2800
catccttaaa atgctgatac tggtcacagc ctctttacct ctgtgaggaa    2850
attgtaacag tgtgtctttt aaggtgtttt tattttacca gcccttaaga    2900
aagatctcta ataccttttta atactttttt ttaataattt caagttgaag    2950
tgtttttaaa aacactttgt tttgtaatgt tttgaatctc ttgagatgtg    3000
tttaccccac tagatacata tttgccactg gttagttctc catctaagct    3050
caagaggtta ttcatctctc tttagattcc agtggctttt cttttaacat    3100
ccaggtaaaa cagaaactgc tatggtatac aaccaagttt tggggttaaa    3150
cataatcaga aaagaaaatc cagttaaatt tatgaagtga gattttcaga    3200
tcctagatct tgaataaagg aaaggtcttt tcatcttgat ggccccaaag    3250
cttgttggtc atggtcttta tttctggcca ctatcttctt aaataatata    3300
tttttaagcc ctcatttatt tttggttttg ggtgaggaaa gtcatgtttt    3350
ctaagtcctc tcccctaata aaacctaccc aacaatagtg ctttgaaaag    3400
tggtagttat cttgaagata ctcttgccaa atgcaaagat aaacattctt    3450
tttgtctgct ttataaatat gaaatatgcc agatctatag tattttaatg    3500
tgcatctact ttaaatgagt catcttgggg tttttataat tcccttatgt    3550
tcttgcccct ctacacttga aataacaaaa tgccttaatt ttatggatta    3600
gttctcttat agtagacagg cagctatatg cagcaaaacc aataaagtta    3650
tttttcaact ttcatagttg taaaatatct tataccagaa tacaaaacag    3700
ctaagaaaac atgccacatt ttattttagc attttcaaat aatttgtttt    3750
```

-continued

```
tggtgtaagc acaggataaa aaaggagagc gtcaaagaaa agagacataa          3800

cacctaacat tcataaaaat taacaaagta tattttggat gatgttttta          3850

caggaaatat tttaaataag ttggtagaac ttttaaaatg gtactgtatt          3900

agctaataaa atattcagta caaatatatg tttggattta tgcattaaaa          3950

aactaataaa attatttcca  acttta                                   3976


<210> SEQ ID NO 60
<211> LENGTH: 758
<212> TYPE: PRT
<213> ORGANISM: Homo sapiens

<400> SEQUENCE: 60

Met Arg Lys Gln Gly Val Ser Ser Lys Arg Leu Gln Ser Ser Gly
  1               5                  10                  15

Arg Ser Gln Ser Lys Gly Arg Arg Gly Ala Ser Leu Ala Arg Glu
                 20                  25                  30

Pro Glu Val Glu Glu Glu Val Glu Lys Ser Val Leu Gly Gly Gly
                 35                  40                  45

Lys Leu Pro Arg Gly Ala Trp Arg Ser Ser Pro Gly Arg Ile Gln
                 50                  55                  60

Ser Leu Lys Glu Arg Lys Gly Leu Glu Leu Glu Val Val Ala Lys
                 65                  70                  75

Thr Phe Leu Leu Gly Pro Phe Gln Phe Val Arg Asn Ser Leu Ala
                 80                  85                  90

Gln Leu Arg Glu Lys Val Gln Glu Leu Gln Ala Arg Arg Phe Ser
                 95                 100                 105

Ser Arg Thr Thr Leu Gly Ile Ala Val Phe Val Ala Ile Leu His
                110                 115                 120

Trp Leu His Leu Val Thr Leu Phe Glu Asn Asp Arg His Phe Ser
                125                 130                 135

His Leu Ser Ser Leu Glu Arg Glu Met Thr Phe Arg Thr Glu Met
                140                 145                 150

Gly Leu Tyr Tyr Ser Tyr Phe Lys Thr Ile Ile Glu Ala Pro Ser
                155                 160                 165

Phe Leu Glu Gly Leu Trp Met Ile Met Asn Asp Arg Leu Thr Glu
                170                 175                 180

Tyr Pro Leu Ile Ile Asn Ala Ile Lys Arg Phe His Leu Tyr Pro
                185                 190                 195

Glu Val Ile Ile Ala Ser Trp Tyr Cys Thr Phe Met Gly Ile Met
                200                 205                 210

Asn Leu Phe Gly Leu Glu Thr Lys Thr Cys Trp Asn Val Thr Arg
                215                 220                 225

Ile Glu Pro Leu Asn Glu Val Gln Ser Cys Glu Gly Leu Gly Asp
                230                 235                 240

Pro Ala Cys Phe Tyr Val Gly Val Ile Phe Ile Leu Asn Gly Leu
                245                 250                 255

Met Met Gly Leu Phe Phe Met Tyr Gly Ala Tyr Leu Ser Gly Thr
                260                 265                 270

Gln Leu Gly Gly Leu Ile Thr Val Leu Cys Phe Phe Phe Asn His
                275                 280                 285

Gly Glu Ala Thr Arg Val Met Trp Thr Pro Pro Leu Arg Glu Ser
                290                 295                 300

Phe Ser Tyr Pro Phe Leu Val Leu Gln Met Cys Ile Leu Thr Leu
```

-continued

```
                305                 310                 315

Ile Leu Arg Thr Ser Ser Asn Asp Arg Arg Pro Phe Ile Ala Leu
                320                 325                 330

Cys Leu Ser Asn Val Ala Phe Met Leu Pro Trp Gln Phe Ala Gln
                335                 340                 345

Phe Ile Leu Phe Thr Gln Ile Ala Ser Leu Phe Pro Met Tyr Val
                350                 355                 360

Val Gly Tyr Ile Glu Pro Ser Lys Phe Gln Lys Ile Ile Tyr Met
                365                 370                 375

Asn Met Ile Ser Val Thr Leu Ser Phe Ile Leu Met Phe Gly Asn
                380                 385                 390

Ser Met Tyr Leu Ser Ser Tyr Tyr Ser Ser Ser Leu Leu Met Thr
                395                 400                 405

Trp Ala Ile Ile Leu Lys Arg Asn Glu Ile Gln Lys Leu Gly Val
                410                 415                 420

Ser Lys Leu Asn Phe Trp Leu Ile Gln Gly Ser Ala Trp Trp Cys
                425                 430                 435

Gly Thr Ile Ile Leu Lys Phe Leu Thr Ser Lys Ile Leu Gly Val
                440                 445                 450

Ser Asp His Ile Arg Leu Ser Asp Leu Ile Ala Ala Arg Ile Leu
                455                 460                 465

Arg Tyr Thr Asp Phe Asp Thr Leu Ile Tyr Thr Cys Ala Pro Glu
                470                 475                 480

Phe Asp Phe Met Glu Lys Ala Thr Pro Leu Arg Tyr Thr Lys Thr
                485                 490                 495

Leu Leu Leu Pro Val Val Met Val Ile Thr Cys Phe Ile Phe Lys
                500                 505                 510

Lys Thr Val Arg Asp Ile Ser Tyr Val Leu Ala Thr Asn Ile Tyr
                515                 520                 525

Leu Arg Lys Gln Leu Leu Glu His Ser Glu Leu Ala Phe His Thr
                530                 535                 540

Leu Gln Leu Leu Val Phe Thr Ala Leu Ala Ile Leu Ile Met Arg
                545                 550                 555

Leu Lys Met Phe Leu Thr Pro His Met Cys Val Met Ala Ser Leu
                560                 565                 570

Ile Cys Ser Arg Gln Leu Phe Gly Trp Leu Phe Arg Arg Val Arg
                575                 580                 585

Phe Glu Lys Val Ile Phe Gly Ile Leu Thr Val Met Ser Ile Gln
                590                 595                 600

Gly Tyr Ala Asn Leu Arg Asn Gln Trp Ser Ile Ile Gly Glu Phe
                605                 610                 615

Asn Asn Leu Pro Gln Glu Glu Leu Leu Gln Trp Ile Lys Tyr Ser
                620                 625                 630

Thr Thr Ser Asp Ala Val Phe Ala Gly Ala Met Pro Thr Met Ala
                635                 640                 645

Ser Ile Lys Leu Ser Thr Leu His Pro Ile Val Asn His Pro His
                650                 655                 660

Tyr Glu Asp Ala Asp Leu Arg Ala Arg Thr Lys Ile Val Tyr Ser
                665                 670                 675

Thr Tyr Ser Arg Lys Ser Ala Lys Glu Val Arg Asp Lys Leu Leu
                680                 685                 690

Glu Leu His Val Asn Tyr Tyr Val Leu Glu Glu Ala Trp Cys Val
                695                 700                 705
```

-continued

```
Val Arg Thr Lys Pro Gly Cys Ser Met Leu Glu Ile Trp Asp Val
                710                 715                 720

Glu Asp Pro Ser Asn Ala Ala Asn Pro Pro Leu Cys Ser Val Leu
                725                 730                 735

Leu Glu Asp Ala Arg Pro Tyr Phe Thr Thr Val Phe Gln Asn Ser
                740                 745                 750

Val Tyr Arg Val Leu Lys Val Asn
                755


<210> SEQ ID NO 61
<211> LENGTH: 2449
<212> TYPE: DNA
<213> ORGANISM: Homo sapiens

<400> SEQUENCE: 61

ggcgcggcca catcctttaa atatggtctt tcttgggcgc gcgcgacaat                50

gtgaggagtg gggtggagcg tgtgtggtgt gtggctgcgg cctgggcaag               100

agccgccgcg gaccatgagc tgagtaagtt ctggagggat cctgcctctt               150

ggagccttcg cagccaggca gctgtgaact gtgagctaga gtgaagcaga               200

aatctaggaa gatgagctcc aagatggtca taagtgaacc aggactgaat               250

tgggatattt cccccaaaaa tggccttaag acatttttct ctcgagaaaa               300

ttataaagat cattccatgg ctccaagttt aaaagaacta cgtgttttat               350

ccaacagacg tataggagaa aatttgaatg cctcagcaag ttctgtagaa               400

aatgagccgg cagttagttc agcaactcaa gcaaaggaaa aagttaaaac               450

cacaattgga atggttcttc ttccaaaacc aagagttcct tatcctcgtt               500

tctctcgttt ctcacagaga gagcagagga gttatgtgga cttgttggtt               550

aaatacgcaa agattcctgc aaattccaaa gctgttggaa taaataaaaa               600

tgactacttg cagtacttgg atatgaaaaa acatgtgaac gaagaagtta               650

ctgagttcct aaagtttttg cagaattctg caaagaaatg tgcgcaggat               700

tataatatgc tttctgatga tgcccgtctc ttcacagaga aaattttaag               750

agcttgcatt gaacaagtga aaaagtattc agaattctat actctccacg               800

aggtcaccag cttaatggga ttcttcccat tcagagtaga gatgggatta               850

aagttagaaa aaactcttct cgcattgggc agtgtaaaat atgtgaaaac               900

agtatttccc tcaatgccta taaagttgca gctgtcaaag gacgatatag               950

ctaccattga aacgtcagaa caaacagctg aagctatgca ttatgatatt              1000

agtaaagatc caaatgcaga gaagcttgtt tccagatatc accctcagat              1050

agctctaact agtcagtcat tatttacctt attaaataat catggaccaa              1100

cgtacaagga acagtgggaa attccagtgt gtattcaagt aatacctgtt              1150

gcaggttcaa aaccagttaa agtaatatat attaattcac cacttcccca              1200

aaagaaaatg actatgagag agagaaatca aatctttcat gaagttccat              1250

taaaatttat gatgtccaaa aacacatctg ttccagtctc tgcagtcttt              1300

atggacaaac ctgaagagtt tatatctgaa atggacatgt cctgtgaagt              1350

caacgagtgc cgaaaaattg agagtcttga aaacttgtat ttggattttg              1400

atgatgatgt cacagaactt gaaacttttg gagtaaccac caccaaagta              1450
```

-continued

```
tcaaaatcac caagtccagc aagtacttcc acagtaccta acatgacaga          1500

tgctcctaca gcccccaaag caggaactac aactgtggca ccaagtgcac          1550

cagacatttc tgctaattct agaagtttat ctcagattct gatggaacaa          1600

ttgcaaaagg agaaacagct ggtcactggt atggatggtg gccctgagga          1650

atgcaaaaat aaagatgatc agggatttga atcatgtgaa aaggtatcaa          1700

attctgacaa gcctttgata caagatagtg acttgaaaac atctgatgcc          1750

ttacagttag aaaattctca ggaaattgaa acttctaata aaaatgatat          1800

gactatagat atactacatg ctgatggtga aagacctaat gttctagaaa          1850

acctagacaa ctcaaaggaa aagactgttg gatcagaagc agcaaaaact          1900

gaagatacag ttctctgcag cagtgataca gatgaggagt gtttaatcat          1950

tgatacagaa tgtaaaaaaa ccagttataa cagtgtttaa tttagataag          2000

tttgagggaa aataatcagt aggcaagagg aacatttttc ctgtagtagc          2050

tagagtgcct tgaaaaaatg tgttggctat gtgaaggaat atttcaacta          2100

aaatggaatg gtatgctttt cacccttaaa gtttgaggag gatcttgata          2150

tgttttaaca ttatcatggc agggaaatat ataaagaaga aaaatatttt          2200

tacattaaac cttttctaaa aattgtaaat agaaaaataa tttggttttt          2250

tatcaagaac aacacttatc gttatgtatt gtgttagtta tattgccagt          2300

ctgttgcgac tgactcaaaa agttaaatgt tgccactgct gaagatgatt          2350

atgagcatcg caaactttgt ttctgaccca ttttgacagt ttttatatac          2400

tcctttaaaa tgatgaatgt tacaggttaa taaagttaat  acctttaaa          2449
```

<210> SEQ ID NO 62
<211> LENGTH: 592
<212> TYPE: PRT
<213> ORGANISM: Homo sapiens

<400> SEQUENCE: 62

```
Met Ser Ser Lys Met Val Ile Ser Glu Pro Gly Leu Asn Trp Asp
  1               5                  10                  15

Ile Ser Pro Lys Asn Gly Leu Lys Thr Phe Phe Ser Arg Glu Asn
                 20                  25                  30

Tyr Lys Asp His Ser Met Ala Pro Ser Leu Lys Glu Leu Arg Val
                 35                  40                  45

Leu Ser Asn Arg Arg Ile Gly Glu Asn Leu Asn Ala Ser Ala Ser
                 50                  55                  60

Ser Val Glu Asn Glu Pro Ala Val Ser Ser Ala Thr Gln Ala Lys
                 65                  70                  75

Glu Lys Val Lys Thr Thr Ile Gly Met Val Leu Leu Pro Lys Pro
                 80                  85                  90

Arg Val Pro Tyr Pro Arg Phe Ser Arg Phe Ser Gln Arg Glu Gln
                 95                 100                 105

Arg Ser Tyr Val Asp Leu Leu Val Lys Tyr Ala Lys Ile Pro Ala
                110                 115                 120

Asn Ser Lys Ala Val Gly Ile Asn Lys Asn Asp Tyr Leu Gln Tyr
                125                 130                 135

Leu Asp Met Lys Lys His Val Asn Glu Glu Val Thr Glu Phe Leu
                140                 145                 150

Lys Phe Leu Gln Asn Ser Ala Lys Lys Cys Ala Gln Asp Tyr Asn
```

-continued

```
                155                 160                 165

Met Leu Ser Asp Asp Ala Arg Leu Phe Thr Glu Lys Ile Leu Arg
                170                 175                 180

Ala Cys Ile Glu Gln Val Lys Lys Tyr Ser Glu Phe Tyr Thr Leu
                185                 190                 195

His Glu Val Thr Ser Leu Met Gly Phe Phe Pro Phe Arg Val Glu
                200                 205                 210

Met Gly Leu Lys Leu Glu Lys Thr Leu Leu Ala Leu Gly Ser Val
                215                 220                 225

Lys Tyr Val Lys Thr Val Phe Pro Ser Met Pro Ile Lys Leu Gln
                230                 235                 240

Leu Ser Lys Asp Asp Ile Ala Thr Ile Glu Thr Ser Glu Gln Thr
                245                 250                 255

Ala Glu Ala Met His Tyr Asp Ile Ser Lys Asp Pro Asn Ala Glu
                260                 265                 270

Lys Leu Val Ser Arg Tyr His Pro Gln Ile Ala Leu Thr Ser Gln
                275                 280                 285

Ser Leu Phe Thr Leu Leu Asn Asn His Gly Pro Thr Tyr Lys Glu
                290                 295                 300

Gln Trp Glu Ile Pro Val Cys Ile Gln Val Ile Pro Val Ala Gly
                305                 310                 315

Ser Lys Pro Val Lys Val Ile Tyr Ile Asn Ser Pro Leu Pro Gln
                320                 325                 330

Lys Lys Met Thr Met Arg Glu Arg Asn Gln Ile Phe His Glu Val
                335                 340                 345

Pro Leu Lys Phe Met Met Ser Lys Asn Thr Ser Val Pro Val Ser
                350                 355                 360

Ala Val Phe Met Asp Lys Pro Glu Glu Phe Ile Ser Glu Met Asp
                365                 370                 375

Met Ser Cys Glu Val Asn Glu Cys Arg Lys Ile Glu Ser Leu Glu
                380                 385                 390

Asn Leu Tyr Leu Asp Phe Asp Asp Asp Val Thr Glu Leu Glu Thr
                395                 400                 405

Phe Gly Val Thr Thr Thr Lys Val Ser Lys Ser Pro Ser Pro Ala
                410                 415                 420

Ser Thr Ser Thr Val Pro Asn Met Thr Asp Ala Pro Thr Ala Pro
                425                 430                 435

Lys Ala Gly Thr Thr Thr Val Ala Pro Ser Ala Pro Asp Ile Ser
                440                 445                 450

Ala Asn Ser Arg Ser Leu Ser Gln Ile Leu Met Glu Gln Leu Gln
                455                 460                 465

Lys Glu Lys Gln Leu Val Thr Gly Met Asp Gly Gly Pro Glu Glu
                470                 475                 480

Cys Lys Asn Lys Asp Asp Gln Gly Phe Glu Ser Cys Glu Lys Val
                485                 490                 495

Ser Asn Ser Asp Lys Pro Leu Ile Gln Asp Ser Asp Leu Lys Thr
                500                 505                 510

Ser Asp Ala Leu Gln Leu Glu Asn Ser Gln Glu Ile Glu Thr Ser
                515                 520                 525

Asn Lys Asn Asp Met Thr Ile Asp Ile Leu His Ala Asp Gly Glu
                530                 535                 540

Arg Pro Asn Val Leu Glu Asn Leu Asp Asn Ser Lys Glu Lys Thr
                545                 550                 555
```

-continued

```
Val Gly Ser Glu Ala Ala Lys Thr Glu Asp Thr Val Leu Cys Ser
                560                 565                 570

Ser Asp Thr Asp Glu Glu Cys Leu Ile Ile Asp Thr Glu Cys Lys
                575                 580                 585

Lys Thr Ser Tyr Asn Ser Val
                590


<210> SEQ ID NO 63
<211> LENGTH: 1451
<212> TYPE: DNA
<213> ORGANISM: Homo sapiens

<400> SEQUENCE: 63

tttttaactt gaacttccaa ggccacgtgc gtctcctggc tcctgcacgg                50

actgtgtgac tgtccccgac agctttcctg tctcgtctca tgaggggtcc               100

agcacatggc attctgggtc ggcacctgaa gtccacctct atgagaccct               150

ctgggagcgt gacggggcct tggcatgggt cggccgaggc ccttctgtcc               200

caggtcactg gtgtggtcgg cccaggccct cctgtcccac atcacctgtg               250

tggtcggccc aggccctcct gtcccaggtc accggtgtgg tcggcccagg               300

ccctcctgtc caggtcctcc tgtccaggtc actggtgtgg tcggcccagg               350

cccttctgtc ccaggtcacc tgtgtggtcg gcccagggcc ctcctgtacc               400

atgtcactgt tgaggggctg gctctggaag agggcaggga cttggcattg               450

gtgggggcag ggttccaagg tgtggcctgt cagcaggaag gggcaggtgg               500

catgggtcca ggcgggactc agggctgggg tgccactgct ggagactgtc               550

cggaggcccc tccagggcac cttgccattg ccattgtcgc tcatggccat               600

ctggtcccgt ttcagggaac aagaggagga tcagatgctg cgggacatga               650

ttgagaagct gggtgactgg gccggggatg ctgagggctg ggctggctgg               700

ctgggtgggc cggggatgct gagtgctggg ctggctggct gggtggaccg               750

ggcctccagc tgggggtggg gggggggcgg gtatcgggtc ccccccctcag              800

ccttggtgac aggacaggca ggttcaccct gagggtgaga gctccctccc               850

gcccctaaga gagccagggg cagctggtga ccgtgtggtc atggtgggga               900

ccagccctcc ggggcaccca gtcggggcag gttctcacgt gggagggcac               950

agggcttcct gcaggctcgg aggcccaggg cggattgtgg ccagtggaag              1000

ggaaggatgt ttctggcagg gggacttgtg tgggccacgg ctgtgcggct              1050

gcggcgttga gcacggcctc actgtccacc tgtcccctag gcctccagag              1100

gaagaagtcc aagttccgct tgtccaagat ctggtcacca aaaagcaaaa              1150

gcagcccctc ccagtagtag ccagtagggc cgtgggctcg gcccggacct              1200

ggcatccgga cttggactcg gggccatggg cttggcccgg acccggaacc              1250

cggacttgta ctcggggccg tgggctcggc ccggacccgg cattcggact              1300

tggactcggg aagggcctcc tgtccctaca aggggcatgt ggacagcagg              1350

gacctgcgct accgtctgtg gtctcaataa agaaaccgac cacatggccc              1400

cggaaaaaaa aaaaaaaaaa aaaaaaaaaa aaaaaaaaaa aaaaaaaaac              1450

a                                                                   1451
```

-continued

<210> SEQ ID NO 64
<211> LENGTH: 159
<212> TYPE: PRT
<213> ORGANISM: Homo sapiens

<400> SEQUENCE: 64

```
Met Gly Arg Pro Arg Pro Phe Cys Pro Arg Ser Leu Val Trp Ser
  1               5                  10                  15

Ala Gln Ala Leu Leu Ser His Ile Thr Cys Val Val Gly Pro Gly
                 20                  25                  30

Pro Pro Val Pro Gly His Arg Cys Gly Arg Pro Arg Pro Ser Cys
                 35                  40                  45

Pro Gly Pro Pro Val Gln Val Thr Gly Val Val Gly Pro Gly Pro
                 50                  55                  60

Ser Val Pro Gly His Leu Cys Gly Arg Pro Arg Ala Leu Leu Tyr
                 65                  70                  75

His Val Thr Val Glu Gly Leu Ala Leu Glu Glu Gly Arg Asp Leu
                 80                  85                  90

Ala Leu Val Gly Ala Gly Phe Gln Gly Val Ala Cys Gln Gln Glu
                 95                 100                 105

Gly Ala Gly Gly Met Gly Pro Gly Gly Thr Gln Gly Trp Gly Ala
                110                 115                 120

Thr Ala Gly Asp Cys Pro Glu Ala Pro Pro Gly His Leu Ala Ile
                125                 130                 135

Ala Ile Val Ala His Gly His Leu Val Pro Phe Gln Gly Thr Arg
                140                 145                 150

Gly Gly Ser Asp Ala Ala Gly His Asp
                155
```

<210> SEQ ID NO 65
<211> LENGTH: 1629
<212> TYPE: DNA
<213> ORGANISM: Homo sapiens

<400> SEQUENCE: 65

```
ggcgaccacc gccgcctcct cacctggcca ttggtgcagc ccgttcccgg        50

cggcgagaga aggcaggcgc gctccttgcg ccacgccaca ccgtcgggcc       100

cccgtcgggt ccccctcggg ccgcaatggt gggctccgcg cggctgggtc       150

cggcactctt gaccccccttt gtaaccaccg cggcgggcac ccagggagtt      200

cgagcaacga agttggtgac ctgccccgct cccaggcagt ttgctgttgg       250

ggctttcacg gctgctggaa gggcatggct gtttgtccca tcactgggcg       300

ccagcttctc aaagctacgt tcacagcaac gcagtaggga ctttcgtggc       350

aggctttttt taagagctga aagaagggcg ggagggttta cgtcctaggg       400

tgatgatttc ctcaccagac agcgaagtat ctattgggaa actccaggtg       450

accgcacctc cttccgacag ttcgccccgg ggcaagttta ccagctgcgt       500

cagaaagcag gtttgcaaaa tccttggaga acggcctgag ctaaggactg       550

gggtcaggag ggttttaaac tcattctgat tttcttgcaa tcatatctct       600

tgaaagtttt tatattttcc ccaatatttt tctgagttgc tatatccaat       650

gaaaacaatg ctgatgtaga ggtccaccag ccaatgcttt attggaagtc       700

aacgaatgag accgagggtg gcccataatc aatctcggca cgcgggaatg       750

tgaacctctt ccaaggtctg ggcgagtccc tagagttacg cagatgaagg       800
```

-continued

```
acattggccc tcgagaatct cacaccagca aagaagagca caacgaagcg              850

caaactactt atgatcattg tggctttggg caagttgttg tagctcccag              900

caacaatttc ttcacctgga gtgcagcaat aaatgatact ggtgctgcag              950

ggcagctaat aagcttctga ataatatatg caaagtactt ggcaccatga             1000

gcagaactca gtataccgtc actgaagaaa tagcttattt aatgattaca             1050

cttttcatat gtgcaagtaa aagtttgact tttagggaga gcctcaccta             1100

cggaatgtct tttttaaatt tctttttaa ttatacttta agttctggga              1150

tacatgtgca gaacgtgcag gtttgttaca caggtataca tgtgccatgg             1200

tggtttgcag cacccatcaa cccttcatct aggttttaag ctccgcatgc             1250

attagttatt tgtcctaatg ctctccctcc ccttgtcccc cacccccaa              1300

caggcctcag ggtgtgatgt tcccctccct gggtccatat gttctcattg             1350

ttcaactccc acttatgatg agaacatgca gtgtttggtt ttctgttcct             1400

gtgttagttt gctgagaatg atggtttcca gcatcatcca cgtccctgca             1450

aaggacatga attcattctt ttttatggct gcatggtatt ccatggtgta             1500

tatgtgccac attttcttca tccagtctat cattgatggg cacttgggtt             1550

ggttccaaga ctttgttatt gtgaacagtg ctgcaataaa catacgtttg             1600

tatgtgtcaa aaaaaaaaaa  aaaaaaaaa                                   1629
```

<210> SEQ ID NO 66
<211> LENGTH: 90
<212> TYPE: PRT
<213> ORGANISM: Homo sapiens

<400> SEQUENCE: 66

```
Met Val Gly Ser Ala Arg Leu Gly Pro Ala Leu Leu Thr Pro Phe
  1               5                  10                  15

Val Thr Thr Ala Ala Gly Thr Gln Gly Val Arg Ala Thr Lys Leu
                 20                  25                  30

Val Thr Cys Pro Ala Pro Arg Gln Phe Ala Val Gly Ala Phe Thr
                 35                  40                  45

Ala Ala Gly Arg Ala Trp Leu Phe Val Pro Ser Leu Gly Ala Ser
                 50                  55                  60

Phe Ser Lys Leu Arg Ser Gln Gln Arg Ser Arg Asp Phe Arg Gly
                 65                  70                  75

Arg Leu Phe Leu Arg Ala Glu Arg Arg Ala Gly Gly Phe Thr Ser
                 80                  85                  90
```

<210> SEQ ID NO 67
<211> LENGTH: 2067
<212> TYPE: DNA
<213> ORGANISM: Homo sapiens

<400> SEQUENCE: 67

```
catgtctaga ctgggagccc tgggtggtgc ccgtgccggg ctgggactgt              50

tgctgggtac cgccgccggc cttggattcc tgtgcctcct ttacagccag             100

cgatggaaac ggacccagcg tcatggccgc agccagagcc tgcccaactc             150

cctggactat acgcagactt cagatcccgg acgccacgtg atgctcctgc             200

gggctgtccc aggtggggct ggagatgcct cagtgctgcc cagccttcca             250
```

-continued

```
cgggaaggac aggagaaggt gctggaccgc ctggactttg tgctgaccag      300
ccttgtggcg ctgcggcggg aggtggagga gctgagaagc agcctgcgag      350
ggcttgcggg ggagattgtt ggggaggtcc gatgccacat ggaagagaac      400
cagagagtgg ctcggcggcg aaggtttccg tttgtccggg agaggagtga      450
ctccactggc tccagctctg tctacttcac ggcctcctcg ggagccacgt      500
tcacagatgc tgagagtgaa gggggttaca caacagccaa tgcggagtct      550
gacaatgagc gggactctga caaagaaagt gaggacgggg aagatgaagt      600
gagctgtgag actgtgaaga tggggagaaa ggattctctt gacttggagg      650
aagaggcagc ttcaggtgcc tccagtgccc tggaggctgg aggttcctca      700
ggcttggagg atgtgctgcc cctcctgcag caggccgacg agctgcacag      750
gggtgatgag caaggcaagc gggagggctt ccagctgctg ctcaacaaca      800
agctggtgta tggaagccgg caggactttc tctggcgcct ggcccgagcc      850
tacagtgaca tgtgtgagct cactgaggag gtgagcgaga agaagtcata      900
tgccctagat ggaaaagaag aagcagaggc tgctctggag aagggggatg      950
agagtgctga ctgtcacctg tggtatgcgg tgctttgtgg tcagctggct     1000
gagcatgaga gcatccagag gcgcatccag agtggcttta gcttcaagga     1050
gcatgtggac aaagccattg ctctccagcc agaaaacccc atggctcact     1100
ttcttcttgg caggtggtgc tatcaggtct ctcacctgag ctggctagaa     1150
aaaaaaactg ctacagcctt gcttgaaagc cctctcagtg ccactgtgga     1200
agatgccctc cagagcttcc taaaggctga agaactacag ccaggatttt     1250
ccaaagcagg aagggtatat atttccaagt gctacagaga actagggaaa     1300
aactctgaag ctagatggtg gatgaagttg gccctggagc tgccagatgt     1350
cacgaaggag gatttggcta tccagaagga cctggaagaa ctggaagtca     1400
ttttacgaga ctaaccacgt ttcactggcc ttcatgactt gatgccacta     1450
tttaaggtgg gggggcgggg aggctttttt ccttagacct tgctgagatc     1500
aggaaaccac acaaatctgt ctcctgggtc tgactgctac ccactaccac     1550
tccccattag ttaatttatt ctaacctcta acctaatcta gaattggggc     1600
agtactcatg gcttccgttt ctgttgttct ctcccttgag taatctctta     1650
aaaaaatcaa gattcacacc tgccccagga ttacacatgg gtagagcctg     1700
caagacctga gaccttccaa ttgctggtga ggtggatgaa cttcaaagct     1750
ataggaacaa agcacataac ttgtcacttt aatctttttc actgactaat     1800
aggactcagt acatatagtc ttaagatcat accttaccta ccaaggtaaa     1850
aagagggatc agagtggccc acagacattg ctttcttatc acctatcatg     1900
tgaattctac ctgtattcct gggctggacc acttgataac ttccagtgtc     1950
ctggcagctt ttggaatgac agcagtggta tggggtttat gatgctataa     2000
aacaatgtct gaaaagttgc ctagaatata ttttgttaca aacttgaaat     2050
aaaccaaatt  tgatgtt                                        2067
```

<210> SEQ ID NO 68
<211> LENGTH: 470
<212> TYPE: PRT
<213> ORGANISM: Homo sapiens -continued

<400> SEQUENCE: 68

Met Ser Arg Leu Gly Ala Leu Gly Gly Ala Arg Ala Gly Leu Gly
1 5 10 15

Leu Leu Leu Gly Thr Ala Ala Gly Leu Gly Phe Leu Cys Leu Leu
20 25 30

Tyr Ser Gln Arg Trp Lys Arg Thr Gln Arg His Gly Arg Ser Gln
35 40 45

Ser Leu Pro Asn Ser Leu Asp Tyr Thr Gln Thr Ser Asp Pro Gly
50 55 60

Arg His Val Met Leu Leu Arg Ala Val Pro Gly Gly Ala Gly Asp
65 70 75

Ala Ser Val Leu Pro Ser Leu Pro Arg Glu Gly Gln Glu Lys Val
80 85 90

Leu Asp Arg Leu Asp Phe Val Leu Thr Ser Leu Val Ala Leu Arg
95 100 105

Arg Glu Val Glu Glu Leu Arg Ser Ser Leu Arg Gly Leu Ala Gly
110 115 120

Glu Ile Val Gly Glu Val Arg Cys His Met Glu Glu Asn Gln Arg
125 130 135

Val Ala Arg Arg Arg Arg Phe Pro Phe Val Arg Glu Arg Ser Asp
140 145 150

Ser Thr Gly Ser Ser Ser Val Tyr Phe Thr Ala Ser Ser Gly Ala
155 160 165

Thr Phe Thr Asp Ala Glu Ser Glu Gly Gly Tyr Thr Thr Ala Asn
170 175 180

Ala Glu Ser Asp Asn Glu Arg Asp Ser Asp Lys Glu Ser Glu Asp
185 190 195

Gly Glu Asp Glu Val Ser Cys Glu Thr Val Lys Met Gly Arg Lys
200 205 210

Asp Ser Leu Asp Leu Glu Glu Glu Ala Ala Ser Gly Ala Ser Ser
215 220 225

Ala Leu Glu Ala Gly Gly Ser Ser Gly Leu Glu Asp Val Leu Pro
230 235 240

Leu Leu Gln Gln Ala Asp Glu Leu His Arg Gly Asp Glu Gln Gly
245 250 255

Lys Arg Glu Gly Phe Gln Leu Leu Leu Asn Asn Lys Leu Val Tyr
260 265 270

Gly Ser Arg Gln Asp Phe Leu Trp Arg Leu Ala Arg Ala Tyr Ser
275 280 285

Asp Met Cys Glu Leu Thr Glu Glu Val Ser Glu Lys Lys Ser Tyr
290 295 300

Ala Leu Asp Gly Lys Glu Glu Ala Glu Ala Ala Leu Glu Lys Gly
305 310 315

Asp Glu Ser Ala Asp Cys His Leu Trp Tyr Ala Val Leu Cys Gly
320 325 330

Gln Leu Ala Glu His Glu Ser Ile Gln Arg Arg Ile Gln Ser Gly
335 340 345

Phe Ser Phe Lys Glu His Val Asp Lys Ala Ile Ala Leu Gln Pro
350 355 360

Glu Asn Pro Met Ala His Phe Leu Leu Gly Arg Trp Cys Tyr Gln
365 370 375

Val Ser His Leu Ser Trp Leu Glu Lys Lys Thr Ala Thr Ala Leu

-continued

```
                380                 385                 390

Leu Glu Ser Pro Leu Ser Ala Thr Val Glu Asp Ala Leu Gln Ser
                395                 400                 405

Phe Leu Lys Ala Glu Glu Leu Gln Pro Gly Phe Ser Lys Ala Gly
                410                 415                 420

Arg Val Tyr Ile Ser Lys Cys Tyr Arg Glu Leu Gly Lys Asn Ser
                425                 430                 435

Glu Ala Arg Trp Trp Met Lys Leu Ala Leu Glu Leu Pro Asp Val
                440                 445                 450

Thr Lys Glu Asp Leu Ala Ile Gln Lys Asp Leu Glu Glu Leu Glu
                455                 460                 465

Val Ile Leu Arg Asp
                470


<210> SEQ ID NO 69
<211> LENGTH: 2250
<212> TYPE: DNA
<213> ORGANISM: Homo sapiens

<400> SEQUENCE: 69

cccacgcgtc cgaaacactt taaacctgac cagctaaatg gataaaccta                50

gcctgcatag cttttaaact ggggtctcat acagcacagg aggcctactt               100

gcttcaagaa ctgaaaatcc agaggatgaa ttgctttatc tgggaatggc               150

aaaagccagc acaataagga atgccagttt gtatggggct actagctcac               200

atgcgggatc agaatggtgt gaatgacagc cgcactgtgt catgaaggtg               250

gtggtggttt ccgcacaaga gaccaaataa gaagaaagct gagagagggg               300

ggaaacgttt ttggatgaca aaggatgggt ttccatttaa ttacgcagct               350

gaaaggcatg agtgtggtgc tggtgctact tcctacactg ctgcttgtta               400

tgctcacggg tgctcagaga gcttgcccaa agaactgcag atgtgatggc               450

aaaattgtgt actgtgagtc tcatgctttc gcagatatcc ctgagaacat               500

ttctggaggg tcacaaggct tatcattaag gttcaacagc attcagaagc               550

tcaaatccaa tcagtttgcc ggccttaacc agcttatatg gctttatctt               600

gaccataatt acattagctc agtggatgaa gatgcatttc aagggatccg               650

tagactgaaa gaattaattc taagctccaa caaaattact tatctgcaca               700

ataaaacatt tcacccagtt cccaatctcc gcaatctgga cctctcctac               750

aataagcttc agacattgca atctgaacaa tttaaaggcc ttcggaaact               800

catcattttg cacttgagat ctaactcact aaagactgtg cccataagag               850

tttttcaaga ctgtcggaat cttgattttt tggatttggg ttacaatcgt               900

cttcgaagct tgtcccgaaa tgcatttgct ggcctcttga agttaaagga               950

gctccacctg gagcacaacc agttttccaa gatcaacttt gctcattttc              1000

cacgtctctt caacctccgc tcaatttact tacaatggaa caggattcgc              1050

tccattagcc aaggtttgac atggacttgg agttccttac acaacttgga              1100

tttatcaggg aatgacatcc aaggaattga gccgggcaca tttaaatgcc              1150

tccccaattt acaaaaattg aatttggatt ccaacaagct caccaatatc              1200

tcacaggaaa ctgtcaatgc gtggatatca ttaatatcca tcacattgtc              1250

tggaaatatg tgggaatgca gtcggagcat ttgtccttta ttttattggc              1300
```

-continued

```
ttaagaattt caaaggaaat aaggaaagca ccatgatatg tgcgggacct          1350

aagcacatcc agggtgaaaa ggttagtgat gcagtggaaa catataatat          1400

ctgttctgaa gtccaggtgg tcaacacaga aagatcacac ctggtgcccc          1450

aaactcccca gaaacctctg attatcccta gacctaccat cttcaaacct          1500

gacgtcaccc aatccacctt tgaaacacca agcccttccc cagggtttca          1550

gattcctggc gcagagcaag agtatgagca tgtttcattt cacaaaatta          1600

ttgccgggag tgtggctctc tttctctcag tggccatgat cctcttggtg          1650

atctatgtgt cttggaaacg ctacccagcc agcatgaaac aactccagca          1700

acactctctt atgaagaggc ggcggaaaaa ggccagagag tctgaaagac          1750

aaatgaattc ccctttacag gagtattatg tggactacaa gcctacaaac          1800

tctgagacca tggatatatc ggttaatgga tctgggccct gcacatatac          1850

catctctggc tccagggaat gtgagatgcc acaccacatg aagcccttgc          1900

catattacag ctatgaccag cctgtgatcg ggtactgcca ggcccaccag          1950

ccactccatg tcaccaaggg ctatgagaca gtgtctccag agcaggacga          2000

aagccccggc ctggagctgg gccgagacca cagcttcatc gccaccatcg          2050

ccaggtcggc agcaccggcc atctacctag agagaattgc aaactaacgc          2100

tgaagccaac tcctcactgg ggagctccat gggggggagg gagggccttc          2150

atcttaaagg agaatgggtg tccacaatcg cgcaatcgag caagctcatc          2200

gttcctgtta aaacatttat ggcataggga aaaaaaaaaa aaaaaaaaaa          2250
```

<210> SEQ ID NO 70
<211> LENGTH: 590
<212> TYPE: PRT
<213> ORGANISM: Homo sapiens

<400> SEQUENCE: 70

```
Met Gly Phe His Leu Ile Thr Gln Leu Lys Gly Met Ser Val Val
  1               5                  10                  15

Leu Val Leu Leu Pro Thr Leu Leu Leu Val Met Leu Thr Gly Ala
                 20                  25                  30

Gln Arg Ala Cys Pro Lys Asn Cys Arg Cys Asp Gly Lys Ile Val
                 35                  40                  45

Tyr Cys Glu Ser His Ala Phe Ala Asp Ile Pro Glu Asn Ile Ser
                 50                  55                  60

Gly Gly Ser Gln Gly Leu Ser Leu Arg Phe Asn Ser Ile Gln Lys
                 65                  70                  75

Leu Lys Ser Asn Gln Phe Ala Gly Leu Asn Gln Leu Ile Trp Leu
                 80                  85                  90

Tyr Leu Asp His Asn Tyr Ile Ser Ser Val Asp Glu Asp Ala Phe
                 95                 100                 105

Gln Gly Ile Arg Arg Leu Lys Glu Leu Ile Leu Ser Ser Asn Lys
                110                 115                 120

Ile Thr Tyr Leu His Asn Lys Thr Phe His Pro Val Pro Asn Leu
                125                 130                 135

Arg Asn Leu Asp Leu Ser Tyr Asn Lys Leu Gln Thr Leu Gln Ser
                140                 145                 150

Glu Gln Phe Lys Gly Leu Arg Lys Leu Ile Ile Leu His Leu Arg
                155                 160                 165
```

-continued

```
Ser Asn Ser Leu Lys Thr Val Pro Ile Arg Val Phe Gln Asp Cys
                170                 175                 180

Arg Asn Leu Asp Phe Leu Asp Leu Gly Tyr Asn Arg Leu Arg Ser
                185                 190                 195

Leu Ser Arg Asn Ala Phe Ala Gly Leu Leu Lys Leu Lys Glu Leu
                200                 205                 210

His Leu Glu His Asn Gln Phe Ser Lys Ile Asn Phe Ala His Phe
                215                 220                 225

Pro Arg Leu Phe Asn Leu Arg Ser Ile Tyr Leu Gln Trp Asn Arg
                230                 235                 240

Ile Arg Ser Ile Ser Gln Gly Leu Thr Trp Thr Trp Ser Ser Leu
                245                 250                 255

His Asn Leu Asp Leu Ser Gly Asn Asp Ile Gln Gly Ile Glu Pro
                260                 265                 270

Gly Thr Phe Lys Cys Leu Pro Asn Leu Gln Lys Leu Asn Leu Asp
                275                 280                 285

Ser Asn Lys Leu Thr Asn Ile Ser Gln Glu Thr Val Asn Ala Trp
                290                 295                 300

Ile Ser Leu Ile Ser Ile Thr Leu Ser Gly Asn Met Trp Glu Cys
                305                 310                 315

Ser Arg Ser Ile Cys Pro Leu Phe Tyr Trp Leu Lys Asn Phe Lys
                320                 325                 330

Gly Asn Lys Glu Ser Thr Met Ile Cys Ala Gly Pro Lys His Ile
                335                 340                 345

Gln Gly Glu Lys Val Ser Asp Ala Val Glu Thr Tyr Asn Ile Cys
                350                 355                 360

Ser Glu Val Gln Val Val Asn Thr Glu Arg Ser His Leu Val Pro
                365                 370                 375

Gln Thr Pro Gln Lys Pro Leu Ile Ile Pro Arg Pro Thr Ile Phe
                380                 385                 390

Lys Pro Asp Val Thr Gln Ser Thr Phe Glu Thr Pro Ser Pro Ser
                395                 400                 405

Pro Gly Phe Gln Ile Pro Gly Ala Glu Gln Glu Tyr Glu His Val
                410                 415                 420

Ser Phe His Lys Ile Ile Ala Gly Ser Val Ala Leu Phe Leu Ser
                425                 430                 435

Val Ala Met Ile Leu Leu Val Ile Tyr Val Ser Trp Lys Arg Tyr
                440                 445                 450

Pro Ala Ser Met Lys Gln Leu Gln Gln His Ser Leu Met Lys Arg
                455                 460                 465

Arg Arg Lys Lys Ala Arg Glu Ser Glu Arg Gln Met Asn Ser Pro
                470                 475                 480

Leu Gln Glu Tyr Tyr Val Asp Tyr Lys Pro Thr Asn Ser Glu Thr
                485                 490                 495

Met Asp Ile Ser Val Asn Gly Ser Gly Pro Cys Thr Tyr Thr Ile
                500                 505                 510

Ser Gly Ser Arg Glu Cys Glu Met Pro His His Met Lys Pro Leu
                515                 520                 525

Pro Tyr Tyr Ser Tyr Asp Gln Pro Val Ile Gly Tyr Cys Gln Ala
                530                 535                 540

His Gln Pro Leu His Val Thr Lys Gly Tyr Glu Thr Val Ser Pro
                545                 550                 555
```

-continued

```
Glu Gln Asp Glu Ser Pro Gly Leu Glu Leu Gly Arg Asp His Ser
                560                 565                 570

Phe Ile Ala Thr Ile Ala Arg Ser Ala Ala Pro Ala Ile Tyr Leu
                575                 580                 585

Glu Arg Ile Ala Asn
                590


<210> SEQ ID NO 71
<211> LENGTH: 521
<212> TYPE: DNA
<213> ORGANISM: Homo sapiens

<400> SEQUENCE: 71

ttccagtcag agttaagtta aaacagaaaa aaggaagatg gcaagaatat                50

tgttactttt cctcccgggt cttgtggctg tatgtgctgt gcatggaata               100

tttatggacc gtctagcttc caagaagctc tgtgcagatg atgagtgtgt               150

ctatactatt tctctggcta gtgctcaaga agattataat gccccggact               200

gtagattcat taacgttaaa aaagggcagc agatctatgt gtactcaaag               250

ctggtaaaag aaaatggagc tggagaattt tgggctggca gtgtttatgg               300

tgatggccag gacgagatgg gagtcgtggg ttatttcccc aggaacttgg               350

tcaaggaaca gcgtgtgtac caggaagcta ccaaggaagt tcccaccacg               400

gatattgact tcttctgcga gtaataaatt agttaaaact gcaaatagaa               450

agaaaacacc aaaaataaag aaaagagcaa aagtggccaa aaaatgcatg               500

tctgtaattt tggactgacg  t                                             521


<210> SEQ ID NO 72
<211> LENGTH: 128
<212> TYPE: PRT
<213> ORGANISM: Homo sapiens

<400> SEQUENCE: 72

Met Ala Arg Ile Leu Leu Leu Phe Leu Pro Gly Leu Val Ala Val
  1               5                  10                  15

Cys Ala Val His Gly Ile Phe Met Asp Arg Leu Ala Ser Lys Lys
                20                  25                  30

Leu Cys Ala Asp Asp Glu Cys Val Tyr Thr Ile Ser Leu Ala Ser
                35                  40                  45

Ala Gln Glu Asp Tyr Asn Ala Pro Asp Cys Arg Phe Ile Asn Val
                50                  55                  60

Lys Lys Gly Gln Gln Ile Tyr Val Tyr Ser Lys Leu Val Lys Glu
                65                  70                  75

Asn Gly Ala Gly Glu Phe Trp Ala Gly Ser Val Tyr Gly Asp Gly
                80                  85                  90

Gln Asp Glu Met Gly Val Val Gly Tyr Phe Pro Arg Asn Leu Val
                95                 100                 105

Lys Glu Gln Arg Val Tyr Gln Glu Ala Thr Lys Glu Val Pro Thr
               110                 115                 120

Thr Asp Ile Asp Phe Phe Cys Glu
               125


<210> SEQ ID NO 73
<211> LENGTH: 720
<212> TYPE: DNA
<213> ORGANISM: Homo sapiens
```

<400> SEQUENCE: 73

```
ctcagatttg ccatggagaa attttcagtc tcggcaatcc tgcttcttgt        50

ggccatctct ggtactctgg ccaaagacac cacagtcaaa tctggatcca       100

aaaaggaccc aaaggactct cgacccaaac taccccagac cctgtccaga       150

ggttggggag atcagctcat ctggactcag acttacgaag aagccttata       200

caaatccaag acaagcaaca gacccttgat ggtcattcat cacttggacg       250

aatgcccgca cagtcaagct ttaaagaaag tgtttgctga aaataaggag       300

atccagaaat tggcagagca gtttgttctc ctcaacttga tctatgaaac       350

aactgacaag cacctttctc ctgatggcca gtacgtcccc agaattgtgt       400

ttgtggaccc ttccctgacg gtgagggcag acatcaccgg aagatactca       450

aaccgtctct acgcttatga accttctgac acagctctgt tgcacgacaa       500

catgaagaaa gctctcaagt tgctgaagac agagttgtag agtcaactgt       550

acagtgcctc aggagccggg aaggcagaag cactgtggac ctgccgatga       600

cattacagtt taatgttaca acaaatgtat tttttaaaca cccacgtgtg       650

gggaaacaat attattatct actacagaca catgattttc tagaaaataa       700

agtcttgtga gaactccaaa                                        720
```

<210> SEQ ID NO 74
<211> LENGTH: 175
<212> TYPE: PRT
<213> ORGANISM: Homo sapiens

<400> SEQUENCE: 74

```
Met Glu Lys Phe Ser Val Ser Ala Ile Leu Leu Leu Val Ala Ile
  1               5                  10                  15

Ser Gly Thr Leu Ala Lys Asp Thr Thr Val Lys Ser Gly Ser Lys
                 20                  25                  30

Lys Asp Pro Lys Asp Ser Arg Pro Lys Leu Pro Gln Thr Leu Ser
                 35                  40                  45

Arg Gly Trp Gly Asp Gln Leu Ile Trp Thr Gln Thr Tyr Glu Glu
                 50                  55                  60

Ala Leu Tyr Lys Ser Lys Thr Ser Asn Arg Pro Leu Met Val Ile
                 65                  70                  75

His His Leu Asp Glu Cys Pro His Ser Gln Ala Leu Lys Lys Val
                 80                  85                  90

Phe Ala Glu Asn Lys Glu Ile Gln Lys Leu Ala Glu Gln Phe Val
                 95                 100                 105

Leu Leu Asn Leu Ile Tyr Glu Thr Thr Asp Lys His Leu Ser Pro
                110                 115                 120

Asp Gly Gln Tyr Val Pro Arg Ile Val Phe Val Asp Pro Ser Leu
                125                 130                 135

Thr Val Arg Ala Asp Ile Thr Gly Arg Tyr Ser Asn Arg Leu Tyr
                140                 145                 150

Ala Tyr Glu Pro Ser Asp Thr Ala Leu Leu His Asp Asn Met Lys
                155                 160                 165

Lys Ala Leu Lys Leu Leu Lys Thr Glu Leu
                170                 175
```

<210> SEQ ID NO 75

-continued

<211> LENGTH: 776
<212> TYPE: DNA
<213> ORGANISM: Homo sapiens

<400> SEQUENCE: 75

```
gccggcgcca gggcaggcgg gcggctggca gctgtggcgc cgacatggct      50

gcgctggtgg agccgctggg gctggagcgg gacgtgtccc gggcggttga     100

gctcctcgag cggctccagc gcagcgggga gctgccgccg cagaagctgc     150

aggccctcca gcgagttctg cagagccgct tctgctccgc tatccgagag     200

gtgtatgagc agctttatga cacgctggac atcaccggca gcgccgagat     250

ccgagcccat gccacagcca aggccacagt ggctgccttc acagccagcg     300

agggccacgc acatcccagg gtagtggagc tacccaagac ggatgagggc     350

ctaggcttca acatcatggg tggcaaagag caaaactcgc ccatctacat     400

ctcccgggtc atcccagggg gtgtggctga ccgccatgga ggcctcaagc     450

gtggggatca actgttgtcg gtgaacggtg tgagcgttga gggtgagcag     500

catgagaagg cggtggagct gctgaaggcg gcccagggct cggtgaagct     550

ggttgtccgt tacacaccgc gagtgctgga ggagatggag gcccggttcg     600

agaagatgcg ctctgcccgc cggcgccaac agcatcagag ctactcgtcc     650

ttggagtctc gaggttgaaa ccacagatct ggacgttcac gtgcactctc     700

ttcctgtaca gtatttattg ttcctggcac tttatttaaa gatatttgac     750

cctcaaaaaa aaaaaaaaaa  aaaaaa                              776
```

<210> SEQ ID NO 76
<211> LENGTH: 207
<212> TYPE: PRT
<213> ORGANISM: Homo sapiens

<400> SEQUENCE: 76

```
Met Ala Ala Leu Val Glu Pro Leu Gly Leu Glu Arg Asp Val Ser
  1               5                  10                  15

Arg Ala Val Glu Leu Leu Glu Arg Leu Gln Arg Ser Gly Glu Leu
                 20                  25                  30

Pro Pro Gln Lys Leu Gln Ala Leu Gln Arg Val Leu Gln Ser Arg
                 35                  40                  45

Phe Cys Ser Ala Ile Arg Glu Val Tyr Glu Gln Leu Tyr Asp Thr
                 50                  55                  60

Leu Asp Ile Thr Gly Ser Ala Glu Ile Arg Ala His Ala Thr Ala
                 65                  70                  75

Lys Ala Thr Val Ala Ala Phe Thr Ala Ser Glu Gly His Ala His
                 80                  85                  90

Pro Arg Val Val Glu Leu Pro Lys Thr Asp Glu Gly Leu Gly Phe
                 95                 100                 105

Asn Ile Met Gly Gly Lys Glu Gln Asn Ser Pro Ile Tyr Ile Ser
                110                 115                 120

Arg Val Ile Pro Gly Gly Val Ala Asp Arg His Gly Gly Leu Lys
                125                 130                 135

Arg Gly Asp Gln Leu Leu Ser Val Asn Gly Val Ser Val Glu Gly
                140                 145                 150

Glu Gln His Glu Lys Ala Val Glu Leu Leu Lys Ala Ala Gln Gly
                155                 160                 165
```

-continued

```
Ser Val Lys Leu Val Val Arg Tyr Thr Pro Arg Val Leu Glu Glu
                170                 175                 180

Met Glu Ala Arg Phe Glu Lys Met Arg Ser Ala Arg Arg Arg Gln
                185                 190                 195

Gln His Gln Ser Tyr Ser Ser Leu Glu Ser Arg Gly
                200                 205


<210> SEQ ID NO 77
<211> LENGTH: 939
<212> TYPE: DNA
<213> ORGANISM: Homo sapiens

<400> SEQUENCE: 77

ctgtcagctg aggatccagc cgaaagagga gccaggcact caggccacct                50

gagtctactc acctggacaa ctggaatctg gcaccaattc taaaccactc               100

agcttctccg agctcacacc ccggagatca cctgaggacc cgagccattg               150

atggactcgg acgagaccgg gttcgagcac tcaggactgt gggtttctgt               200

gctggctggt ctgctgggag cctgccaggc acaccccatc cctgactcca               250

gtcctctcct gcaattcggg ggccaagtcc ggcagcggta cctctacaca               300

gatgatgccc agcagacaga agcccacctg gagatcaggg aggatgggac               350

ggtgggggc gctgctgacc agagccccga aagtctcctg cagctgaaag               400

ccttgaagcc gggagttatt caaatcttgg gagtcaagac atccaggttc               450

ctgtgccagc ggccagatgg ggccctgtat ggatcgctcc actttgaccc               500

tgaggcctgc agcttccggg agctgcttct tgaggacgga tacaatgttt               550

accagtccga agcccacggc ctcccgctgc acctgccagg gaacaagtcc               600

ccacaccggg accctgcacc ccgaggacca gctcgcttcc tgccactacc               650

aggcctgccc cccgcactcc cggagccacc cggaatcctg gcccccccagc               700

cccccgatgt gggctcctcg gaccctctga gcatggtggg accttcccag               750

ggccgaagcc ccagctacgc ttcctgaagc cagaggctgt ttactatgac               800

atctcctctt tatttattag gttatttatc ttatttattt ttttattttt               850

cttacttgag ataataaaga gttccagagg agaaaaaaaa aaaaaaaaaa               900

aaaaaaaaaa aaaaaaaaaa aaaaaaaaaa  aaaaaaaag                          939


<210> SEQ ID NO 78
<211> LENGTH: 208
<212> TYPE: PRT
<213> ORGANISM: Homo sapiens

<400> SEQUENCE: 78

Met Asp Ser Asp Glu Thr Gly Phe Glu His Ser Gly Leu Trp Val
  1               5                  10                  15

Ser Val Leu Ala Gly Leu Leu Gly Ala Cys Gln Ala His Pro Ile
                20                  25                  30

Pro Asp Ser Ser Pro Leu Leu Gln Phe Gly Gly Gln Val Arg Gln
                35                  40                  45

Arg Tyr Leu Tyr Thr Asp Asp Ala Gln Gln Thr Glu Ala His Leu
                50                  55                  60

Glu Ile Arg Glu Asp Gly Thr Val Gly Gly Ala Ala Asp Gln Ser
                65                  70                  75

Pro Glu Ser Leu Leu Gln Leu Lys Ala Leu Lys Pro Gly Val Ile
```

-continued

```
                80                  85                  90

Gln Ile Leu Gly Val Lys Thr Ser Arg Phe Leu Cys Gln Arg Pro
                95                 100                 105

Asp Gly Ala Leu Tyr Gly Ser Leu His Phe Asp Pro Glu Ala Cys
               110                 115                 120

Ser Phe Arg Glu Leu Leu Leu Glu Asp Gly Tyr Asn Val Tyr Gln
               125                 130                 135

Ser Glu Ala His Gly Leu Pro Leu His Leu Pro Gly Asn Lys Ser
               140                 145                 150

Pro His Arg Asp Pro Ala Pro Arg Gly Pro Ala Arg Phe Leu Pro
               155                 160                 165

Leu Pro Gly Leu Pro Pro Ala Leu Pro Glu Pro Pro Gly Ile Leu
               170                 175                 180

Ala Pro Gln Pro Pro Asp Val Gly Ser Ser Asp Pro Leu Ser Met
               185                 190                 195

Val Gly Pro Ser Gln Gly Arg Ser Pro Ser Tyr Ala Ser
               200                 205


<210> SEQ ID NO 79
<211> LENGTH: 2732
<212> TYPE: DNA
<213> ORGANISM: Homo sapiens

<400> SEQUENCE: 79

agtcccagac gggcttttcc cagagagcta aaagagaagg gccagagaat                50

gtcgtcccag ccagcaggga accagacctc ccccggggcc acagaggact               100

actcctatgg cagctggtac atcgatgagc cccagggggg cgaggagctc               150

cagccagagg gggaagtgcc ctcctgccac accagcatac cacccggcct               200

gtaccacgcc tgcctggcct cgctgtcaat ccttgtgctg ctgctcctgg               250

ccatgctggt gaggcgccgc cagctctggc ctgactgtgt gcgtggcagg               300

cccggcctgc ccagccctgt ggatttcttg gctggggaca ggccccgggc               350

agtgcctgct gctgttttca tggtcctcct gagctccctg tgtttgctgc               400

tccccgacga ggacgcattg cccttcctga ctctcgcctc agcacccagc               450

caagatggga aaactgaggc tccaagaggg gcctggaaga tactgggact               500

gttctattat gctgccctct actaccctct ggctgcctgt gccacggctg               550

gccacacagc tgcacacctg ctcggcagca cgctgtcctg ggcccacctt               600

ggggtccagg tctggcagag ggcagagtgt ccccaggtgc ccaagatcta               650

caagtactac tccctgctgg cctccctgcc tctcctgctg ggcctcggat               700

tcctgagcct ttggtaccct gtgcagctgg tgagaagctt cagccgtagg               750

acaggagcag gctccaaggg gctgcagagc agctactctg aggaatatct               800

gaggaacctc ctttgcagga agaagctggg aagcagctac cacacctcca               850

agcatggctt cctgtcctgg gcccgcgtct gcttgagaca ctgcatctac               900

actccacagc caggattcca tctcccgctg aagctggtgc tttcagctac               950

actgacaggg acggccattt accaggtggc cctgctgctg ctggtgggcg              1000

tggtacccac tatccagaag gtgagggcag gggtcaccac ggatgtctcc              1050

tacctgctgg ccggctttgg aatcgtgctc tccgaggaca agcaggaggt              1100

ggtggagctg gtgaagcacc atctgtgggc tctggaagtg tgctacatct              1150
```

-continued

```
cagccttggt cttgtcctgc ttactcacct tcctggtcct gatgcgctca          1200

ctggtgacac acaggaccaa ccttcgagct ctgcaccgag gagctgccct          1250

ggacttgagt cccttgcatc ggagtcccca tccctcccgc caagccatat          1300

tctgttggat gagcttcagt gcctaccaga cagcctttat ctgccttggg          1350

ctcctggtgc agcagatcat cttcttcctg ggaaccacgg ccctggcctt          1400

cctggtgctc atgcctgtgc tccatggcag gaacctcctg ctcttccgtt          1450

ccctggagtc ctcgtggccc ttctggctga ctttggccct ggctgtgatc          1500

ctgcagaaca tggcagccca ttgggtcttc ctggagactc atgatggaca          1550

cccacagctg accaaccggc gagtgctcta tgcagccacc tttcttctct          1600

tccccctcaa tgtgctggtg ggtgccatgg tggccacctg gcgagtgctc          1650

ctctctgccc tctacaacgc catccacctt ggccagatgg acctcagcct          1700

gctgccaccg agagccgcca ctctcgaccc cggctactac acgtaccgaa          1750

acttcttgaa gattgaagtc agccagtcgc atccagccat gacagccttc          1800

tgctccctgc tcctgcaagc gcagagcctc ctacccagga ccatggcagc          1850

cccccaggac agcctcagac caggggagga agacgaaggg atgcagctgc          1900

tacagacaaa ggactccatg gccaagggag ctaggcccgg ggccagccgc          1950

ggcagggctc gctggggtct ggcctacacg ctgctgcaca acccaaccct          2000

gcaggtcttc cgcaagacgg ccctgttggg tgccaatggt gcccagccct          2050

gagggcaggg aaggtcaacc cacctgccca tctgtgctga ggcatgttcc          2100

tgcctaccat cctcctccct ccccggctct cctcccagca tcacaccagc          2150

catgcagcca gcaggtcctc cggatcactg tggttgggtg gaggtctgtc          2200

tgcactggga gcctcaggag ggctctgctc cacccacttg gctatgggag          2250

agccagcagg ggttctggag aaaaaaactg gtgggttagg gccttggtcc          2300

aggagccagt tgagccaggg cagccacatc caggcgtctc cctaccctgg          2350

ctctgccatc agccttgaag ggcctcgatg aagccttctc tggaaccact          2400

ccagcccagc tccacctcag ccttggcctt cacgctgtgg aagcagccaa          2450

ggcacttcct cacccccctca gcgccacgga cctctctggg gagtggccgg          2500

aaagctcccg gtcctctggc ctgcagggca gcccaagtca tgactcagac          2550

caggtcccac actgagctgc ccacactcga gagccagata tttttgtagt          2600

ttttatgcct ttggctatta tgaaagaggt tagtgtgttc cctgcaataa          2650

acttgttcct gagaaaaaaa aaaaaaaaaa aaaaaaaaaa aaaaaaaaaa          2700

aaaaaaaaaa aaaaaaaaaa aaaaaaaaaa  aa                            2732
```

<210> SEQ ID NO 80
<211> LENGTH: 667
<212> TYPE: PRT
<213> ORGANISM: Homo sapiens

<400> SEQUENCE: 80

```
Met Ser Ser Gln Pro Ala Gly Asn Gln Thr Ser Pro Gly Ala Thr
  1               5                  10                  15

Glu Asp Tyr Ser Tyr Gly Ser Trp Tyr Ile Asp Glu Pro Gln Gly
                 20                  25                  30
```

-continued

```
Gly Glu Glu Leu Gln Pro Glu Gly Glu Val Pro Ser Cys His Thr
                35                  40                  45

Ser Ile Pro Pro Gly Leu Tyr His Ala Cys Leu Ala Ser Leu Ser
                50                  55                  60

Ile Leu Val Leu Leu Leu Leu Ala Met Leu Val Arg Arg Arg Gln
                65                  70                  75

Leu Trp Pro Asp Cys Val Arg Gly Arg Pro Gly Leu Pro Ser Pro
                80                  85                  90

Val Asp Phe Leu Ala Gly Asp Arg Pro Arg Ala Val Pro Ala Ala
                95                 100                 105

Val Phe Met Val Leu Leu Ser Ser Leu Cys Leu Leu Leu Pro Asp
               110                 115                 120

Glu Asp Ala Leu Pro Phe Leu Thr Leu Ala Ser Ala Pro Ser Gln
               125                 130                 135

Asp Gly Lys Thr Glu Ala Pro Arg Gly Ala Trp Lys Ile Leu Gly
               140                 145                 150

Leu Phe Tyr Tyr Ala Ala Leu Tyr Tyr Pro Leu Ala Ala Cys Ala
               155                 160                 165

Thr Ala Gly His Thr Ala Ala His Leu Leu Gly Ser Thr Leu Ser
               170                 175                 180

Trp Ala His Leu Gly Val Gln Val Trp Gln Arg Ala Glu Cys Pro
               185                 190                 195

Gln Val Pro Lys Ile Tyr Lys Tyr Tyr Ser Leu Leu Ala Ser Leu
               200                 205                 210

Pro Leu Leu Leu Gly Leu Gly Phe Leu Ser Leu Trp Tyr Pro Val
               215                 220                 225

Gln Leu Val Arg Ser Phe Ser Arg Arg Thr Gly Ala Gly Ser Lys
               230                 235                 240

Gly Leu Gln Ser Ser Tyr Ser Glu Glu Tyr Leu Arg Asn Leu Leu
               245                 250                 255

Cys Arg Lys Lys Leu Gly Ser Ser Tyr His Thr Ser Lys His Gly
               260                 265                 270

Phe Leu Ser Trp Ala Arg Val Cys Leu Arg His Cys Ile Tyr Thr
               275                 280                 285

Pro Gln Pro Gly Phe His Leu Pro Leu Lys Leu Val Leu Ser Ala
               290                 295                 300

Thr Leu Thr Gly Thr Ala Ile Tyr Gln Val Ala Leu Leu Leu Leu
               305                 310                 315

Val Gly Val Val Pro Thr Ile Gln Lys Val Arg Ala Gly Val Thr
               320                 325                 330

Thr Asp Val Ser Tyr Leu Leu Ala Gly Phe Gly Ile Val Leu Ser
               335                 340                 345

Glu Asp Lys Gln Glu Val Val Glu Leu Val Lys His His Leu Trp
               350                 355                 360

Ala Leu Glu Val Cys Tyr Ile Ser Ala Leu Val Leu Ser Cys Leu
               365                 370                 375

Leu Thr Phe Leu Val Leu Met Arg Ser Leu Val Thr His Arg Thr
               380                 385                 390

Asn Leu Arg Ala Leu His Arg Gly Ala Ala Leu Asp Leu Ser Pro
               395                 400                 405

Leu His Arg Ser Pro His Pro Ser Arg Gln Ala Ile Phe Cys Trp
               410                 415                 420

Met Ser Phe Ser Ala Tyr Gln Thr Ala Phe Ile Cys Leu Gly Leu
```

-continued

```
                425                 430                 435

Leu Val Gln Gln Ile Ile Phe Phe Leu Gly Thr Thr Ala Leu Ala
                440                 445                 450

Phe Leu Val Leu Met Pro Val Leu His Gly Arg Asn Leu Leu Leu
                455                 460                 465

Phe Arg Ser Leu Glu Ser Ser Trp Pro Phe Trp Leu Thr Leu Ala
                470                 475                 480

Leu Ala Val Ile Leu Gln Asn Met Ala Ala His Trp Val Phe Leu
                485                 490                 495

Glu Thr His Asp Gly His Pro Gln Leu Thr Asn Arg Arg Val Leu
                500                 505                 510

Tyr Ala Ala Thr Phe Leu Leu Phe Pro Leu Asn Val Leu Val Gly
                515                 520                 525

Ala Met Val Ala Thr Trp Arg Val Leu Leu Ser Ala Leu Tyr Asn
                530                 535                 540

Ala Ile His Leu Gly Gln Met Asp Leu Ser Leu Leu Pro Pro Arg
                545                 550                 555

Ala Ala Thr Leu Asp Pro Gly Tyr Tyr Thr Tyr Arg Asn Phe Leu
                560                 565                 570

Lys Ile Glu Val Ser Gln Ser His Pro Ala Met Thr Ala Phe Cys
                575                 580                 585

Ser Leu Leu Leu Gln Ala Gln Ser Leu Leu Pro Arg Thr Met Ala
                590                 595                 600

Ala Pro Gln Asp Ser Leu Arg Pro Gly Glu Glu Asp Glu Gly Met
                605                 610                 615

Gln Leu Leu Gln Thr Lys Asp Ser Met Ala Lys Gly Ala Arg Pro
                620                 625                 630

Gly Ala Ser Arg Gly Arg Ala Arg Trp Gly Leu Ala Tyr Thr Leu
                635                 640                 645

Leu His Asn Pro Thr Leu Gln Val Phe Arg Lys Thr Ala Leu Leu
                650                 655                 660

Gly Ala Asn Gly Ala Gln Pro
                665


<210> SEQ ID NO 81
<211> LENGTH: 1186
<212> TYPE: DNA
<213> ORGANISM: Homo sapiens

<400> SEQUENCE: 81

aaaaaataca gcaggtgaag gaggttggag agtagggggt ggagggccca                50

cgcagcactt gtccttcacc ctggagggga tctgttacat gccccagatt               100

gctggtcccc tagaaatgtt actgaggcag cctctgcatt tttgcaggga               150

ttgttttcta ctgtttgaca ttcacgtaac ctcctaacgc tgtctgggga               200

agatgctacc ccctgctctc cccgtctttc ctgcactctc agcaatggga               250

tgggctgact gatgccctgt gggctggaaa gctgaccaca gttgctgcag               300

accagacccc ctcacatagt gagtgctggg ctgaggaatc caggagagcc               350

cgagggggga cactgaaggt gtatcgttgg ccctgccagc tgcaagtgaa               400

ctgcttctga tgaattttaa tagggagaaa gaagtatttg ctaagaatgg               450

caatcctgac gctcagcctt caactcatct tgttattaat accatcaata               500

tcccatgagg ctcataaaac gagtctttct tcttggaaac atgaccaaga               550
```

-continued

```
ttgggcaaac gtctccaaca tgactttcag caacggaaaa ctaagagtca              600

aaggcattta ttaccggaat gccgacattt gctctcgaca tcgcgtaacc              650

tcagcaggcc taactctgca ggaccttcag ctatggtgta atttgaggtc              700

agtggccaga ggacagatcc cgtctacatt atgagtgaag cggagagcta              750

ctgcagggtt ctgagcagag tcctaattta tattttagaa gaatcatcat              800

ggctcctaga ttaggaataa aacgaagggg cccagggatg gaaacgatga              850

gtccagttgg gttactgcaa agatccaggc cagaaatcca ggcacagtgg              900

cacacacctg agtcccagat aattccacct actggtcctg ctctgtggcc              950

tactggtccg agtccagccc cgactgattt ctgggcctgt aatgtctaaa             1000

aacgctccct gctgatgttt tgcaagtgac tgtgttactt gaaggcagtt             1050

cctaggataa actagtcgct ttatcattac agaatcattc actgagcatc             1100

aactatgtaa ccagcattgg gttgggtgcc agagatccaa agctaagaca             1150

ccaaaacctg ctctccagga aacgagaggc  tgagaa                           1186
```

<210> SEQ ID NO 82
<211> LENGTH: 95
<212> TYPE: PRT
<213> ORGANISM: Homo sapiens

<400> SEQUENCE: 82

```
Met Ala Ile Leu Thr Leu Ser Leu Gln Leu Ile Leu Leu Leu Ile
  1               5                  10                  15

Pro Ser Ile Ser His Glu Ala His Lys Thr Ser Leu Ser Ser Trp
                 20                  25                  30

Lys His Asp Gln Asp Trp Ala Asn Val Ser Asn Met Thr Phe Ser
                 35                  40                  45

Asn Gly Lys Leu Arg Val Lys Gly Ile Tyr Tyr Arg Asn Ala Asp
                 50                  55                  60

Ile Cys Ser Arg His Arg Val Thr Ser Ala Gly Leu Thr Leu Gln
                 65                  70                  75

Asp Leu Gln Leu Trp Cys Asn Leu Arg Ser Val Ala Arg Gly Gln
                 80                  85                  90

Ile Pro Ser Thr Leu
                 95
```

<210> SEQ ID NO 83
<211> LENGTH: 1677
<212> TYPE: DNA
<213> ORGANISM: Homo sapiens

<400> SEQUENCE: 83

```
aatagaagtc ctcaggacgg agcagaggtg gccggcgggc ccggctgact               50

gcgcctctgc tttctttcca taaccttttc tttcggactc gaatcacggc              100

tgctgcgaag ggtctagttc cggacactag ggtgcccgaa cgcgctgatg              150

ccccgagtgc tcgcagggct tcccgctaac catgctgccg ccgccgcggc              200

ccgcagctgc cttggcgctg cctgtgctcc tgctactgct ggtggtgctg              250

acgccgcccc cgaccggcgc aaggccatcc ccaggcccag attacctgcg              300

gcgcggctgg atgcggctgc tagcggaggg cgagggctgc gctccctgcc              350

ggccagaaga gtgcgccgcg ccgcggggct gcctggcggg cagggtgcgc              400
```

-continued

```
gacgcgtgcg gctgctgctg ggaatgcgcc aacctcgagg gccagctctg          450

cgacctggac cccagtgctc acttctacgg gcactgcggc gagcagcttg          500

agtgccggct ggacacaggc ggcgacctga gccgcggaga ggtgccggaa          550

cctctgtgtg cctgtcgttc gcagagtccg ctctgcgggt ccgacggtca          600

cacctactcc cagatctgcc gcctgcagga ggcggcccgc gctcggcccg          650

atgccaacct cactgtggca cacccggggc cctgcgaatc ggggccccag          700

atcgtgtcac atccatatga cacttggaat gtgacagggc aggatgtgat          750

ctttggctgt gaagtgtttg cctaccccat ggcctccatc gagtggagga          800

aggatggctt ggacatccag ctgccagggg atgacccccca catctctgtg         850

cagtttaggg gtggacccca gaggtttgag gtgactggct ggctgcagat          900

ccaggctgtg cgtcccagtg atgagggcac ttaccgctgc cttggccgca          950

atgccctggg tcaagtggag gcccctgcta gcttgacagt gctcacacct         1000

gaccagctga actctacagg catcccccag ctgcgatcac taaacctggt         1050

tcctgaggag gaggctgaga gtgaagagaa tgacgattac tactaggtcc         1100

agagctctgg cccatggggg tgggtgagcg gctatagtgt tcatccctgc         1150

tcttgaaaag acctggaaag gggagcaggg tcccttcatc gactgctttc         1200

atgctgtcag tagggatgat catgggaggc ctatttgact ccaaggtagc         1250

agtgtggtag gatagagaca aaagctggag gagggtaggg agagaagctg         1300

agaccaggac cggtggggta caaaggggcc catgcaggag atgccctggc         1350

cagtaggacc tccaacaggt tgtttcccag gctggggtgg gggcctgagc         1400

agacacagag gtgcaggcac caggattctc cacttcttcc agccctgctg         1450

ggccacagtt ctaactgccc ttcctcccag gccctggttc ttgctatttc         1500

ctggtcccca acgtttatct agcttgtttg ccctttcccc aaactcatct         1550

tccagaactt ttccctctct cctaagcccc agttgcacct actaactgca         1600

gtccctttg ctgtctgccg tcttttgtac aagagagaga acagcggagc          1650

atgacttagt tcagtgcaga  gagattt                                 1677
```

<210> SEQ ID NO 84
<211> LENGTH: 304
<212> TYPE: PRT
<213> ORGANISM: Homo sapiens

<400> SEQUENCE: 84

```
Met Leu Pro Pro Pro Arg Pro Ala Ala Ala Leu Ala Leu Pro Val
  1               5                  10                  15

Leu Leu Leu Leu Leu Val Val Leu Thr Pro Pro Pro Thr Gly Ala
                 20                  25                  30

Arg Pro Ser Pro Gly Pro Asp Tyr Leu Arg Arg Gly Trp Met Arg
                 35                  40                  45

Leu Leu Ala Glu Gly Glu Gly Cys Ala Pro Cys Arg Pro Glu Glu
                 50                  55                  60

Cys Ala Ala Pro Arg Gly Cys Leu Ala Gly Arg Val Arg Asp Ala
                 65                  70                  75

Cys Gly Cys Cys Trp Glu Cys Ala Asn Leu Glu Gly Gln Leu Cys
                 80                  85                  90
```

-continued

```
Asp Leu Asp Pro Ser Ala His Phe Tyr Gly His Cys Gly Glu Gln
                95                  100                 105

Leu Glu Cys Arg Leu Asp Thr Gly Gly Asp Leu Ser Arg Gly Glu
            110                 115                 120

Val Pro Glu Pro Leu Cys Ala Cys Arg Ser Gln Ser Pro Leu Cys
            125                 130                 135

Gly Ser Asp Gly His Thr Tyr Ser Gln Ile Cys Arg Leu Gln Glu
            140                 145                 150

Ala Ala Arg Ala Arg Pro Asp Ala Asn Leu Thr Val Ala His Pro
            155                 160                 165

Gly Pro Cys Glu Ser Gly Pro Gln Ile Val Ser His Pro Tyr Asp
            170                 175                 180

Thr Trp Asn Val Thr Gly Gln Asp Val Ile Phe Gly Cys Glu Val
            185                 190                 195

Phe Ala Tyr Pro Met Ala Ser Ile Glu Trp Arg Lys Asp Gly Leu
            200                 205                 210

Asp Ile Gln Leu Pro Gly Asp Asp Pro His Ile Ser Val Gln Phe
            215                 220                 225

Arg Gly Gly Pro Gln Arg Phe Glu Val Thr Gly Trp Leu Gln Ile
            230                 235                 240

Gln Ala Val Arg Pro Ser Asp Glu Gly Thr Tyr Arg Cys Leu Gly
            245                 250                 255

Arg Asn Ala Leu Gly Gln Val Glu Ala Pro Ala Ser Leu Thr Val
            260                 265                 270

Leu Thr Pro Asp Gln Leu Asn Ser Thr Gly Ile Pro Gln Leu Arg
            275                 280                 285

Ser Leu Asn Leu Val Pro Glu Glu Glu Ala Glu Ser Glu Glu Asn
            290                 295                 300

Asp Asp Tyr Tyr


<210> SEQ ID NO 85
<211> LENGTH: 1285
<212> TYPE: DNA
<213> ORGANISM: Homo sapiens

<400> SEQUENCE: 85

caaagcggcg gctgtccgcg gtgccggctg ggggcggaga ggcggcggtg          50

ggctccctgg ggtgtgtgag cccggtgatg gagccgggcc cgacagccgc         100

gcagcggagg tgttcgttgc cgccgtggct gccgctgggg ctgctgctgt         150

ggtcggggct ggccctgggc gcgctcccct tcggcagcag tccgcacagg         200

gtcttccacg acctcctgtc ggagcagcag ttgctggagg tggaggactt         250

gtccctgtcc ctcctgcagg gtggagggct ggggcctctg tcgctgcccc         300

cggacctgcc ggatctggat cctgagtgcc gggagctcct gctggacttc         350

gccaacagca gcgcagagct gacagggtgt ctggtgcgca gcgcccggcc         400

cgtgcgcctc tgtcagacct gctacccccct cttccaacag gtcgtcagca        450

agatggacaa catcagccga gccgcgggga atacttcaga gagtcagagt         500

tgtgccagaa gtctcttaat ggcagataga atgcaaatag ttgtgattct         550

ctcagaattt tttaatacca catggcagga ggcaaattgt gcaaattgtt         600

taacaaacaa cagtgaagaa ttatcaaaca gcacagtata tttccttaat         650

ctatttaatc acaccctgac ctgctttgaa cataaccttc aggggaatgc         700
```

-continued

```
acatagtctt ttacagacaa aaaattattc agaagtatgc aaaaactgcc              750

gtgaagcata caaaactctg agtagtctgt acagtgaaat gcaaaaaatg              800

aatgaacttg agaataaggc tgaacctgga acacatttat gcattgatgt              850

ggaagatgca atgaacatca ctcgaaaact atggagtcga actttcaact              900

gttcagtccc ttgcagtgac acagtgcctg taattgctgt ttctgtgttc              950

attctctttc tacctgttgt cttctacctt agtagctttc ttcactcaga             1000

gcaaaagaaa cgcaaactca ttctgcccaa acgtctcaag tccagtacca             1050

gttttgcaaa tattcaggaa aattcaaact gagacctaca aaatggagaa             1100

ttgacatatc acgtgaatga atggtggaag acacaacttg gtttcagaaa             1150

gaagataaac tgtgatttga caagtcaagc tcttaagaaa tacaaggact             1200

tcagatccat ttttaaataa gaattttcga tttttctttc cttttccact             1250

tctttctaac agatttggat atttttaatt  tccag                            1285
```

<210> SEQ ID NO 86
<211> LENGTH: 334
<212> TYPE: PRT
<213> ORGANISM: Homo sapiens

<400> SEQUENCE: 86

```
Met Glu Pro Gly Pro Thr Ala Ala Gln Arg Arg Cys Ser Leu Pro
  1               5                  10                  15

Pro Trp Leu Pro Leu Gly Leu Leu Leu Trp Ser Gly Leu Ala Leu
                 20                  25                  30

Gly Ala Leu Pro Phe Gly Ser Ser Pro His Arg Val Phe His Asp
                 35                  40                  45

Leu Leu Ser Glu Gln Gln Leu Leu Glu Val Glu Asp Leu Ser Leu
                 50                  55                  60

Ser Leu Leu Gln Gly Gly Gly Leu Gly Pro Leu Ser Leu Pro Pro
                 65                  70                  75

Asp Leu Pro Asp Leu Asp Pro Glu Cys Arg Glu Leu Leu Leu Asp
                 80                  85                  90

Phe Ala Asn Ser Ser Ala Glu Leu Thr Gly Cys Leu Val Arg Ser
                 95                 100                 105

Ala Arg Pro Val Arg Leu Cys Gln Thr Cys Tyr Pro Leu Phe Gln
                110                 115                 120

Gln Val Val Ser Lys Met Asp Asn Ile Ser Arg Ala Ala Gly Asn
                125                 130                 135

Thr Ser Glu Ser Gln Ser Cys Ala Arg Ser Leu Leu Met Ala Asp
                140                 145                 150

Arg Met Gln Ile Val Val Ile Leu Ser Glu Phe Phe Asn Thr Thr
                155                 160                 165

Trp Gln Glu Ala Asn Cys Ala Asn Cys Leu Thr Asn Asn Ser Glu
                170                 175                 180

Glu Leu Ser Asn Ser Thr Val Tyr Phe Leu Asn Leu Phe Asn His
                185                 190                 195

Thr Leu Thr Cys Phe Glu His Asn Leu Gln Gly Asn Ala His Ser
                200                 205                 210

Leu Leu Gln Thr Lys Asn Tyr Ser Glu Val Cys Lys Asn Cys Arg
                215                 220                 225

Glu Ala Tyr Lys Thr Leu Ser Ser Leu Tyr Ser Glu Met Gln Lys
```

-continued

```
                230                 235                 240

Met Asn Glu Leu Glu Asn Lys Ala Glu Pro Gly Thr His Leu Cys
                245                 250                 255

Ile Asp Val Glu Asp Ala Met Asn Ile Thr Arg Lys Leu Trp Ser
                260                 265                 270

Arg Thr Phe Asn Cys Ser Val Pro Cys Ser Asp Thr Val Pro Val
                275                 280                 285

Ile Ala Val Ser Val Phe Ile Leu Phe Leu Pro Val Val Phe Tyr
                290                 295                 300

Leu Ser Ser Phe Leu His Ser Glu Gln Lys Lys Arg Lys Leu Ile
                305                 310                 315

Leu Pro Lys Arg Leu Lys Ser Ser Thr Ser Phe Ala Asn Ile Gln
                320                 325                 330

Glu Asn Ser Asn


<210> SEQ ID NO 87
<211> LENGTH: 1754
<212> TYPE: DNA
<213> ORGANISM: Homo sapiens

<400> SEQUENCE: 87

atgctggtag ccggcttcct gctggcgctg ccgccgagct gggccgcggg                50

cgcccccagg gcgggcaggc gccccgcgcg gccgcggggc tgcgcggacc               100

ggccggagga gctactggag cagctgtacg ggcgcctggc ggccggcgtg               150

ctcagtgcct tccaccacac gctgcagctg gggccgcgtg agcaggcgcg               200

caacgcgagc tgcccggcag ggggcaggcc cggcgaccgc cgcttccggc               250

cgcccaccaa cctgcgcagc gtgtcgccct gggcctacag aatctcctac               300

gacccggcga ggtaccccag gtacctgcct gaagcctact gcctgtgccg               350

gggctgcctg accgggctgt tcggcgagga ggacgtgcgc ttccgcagcg               400

cccctgtcta catgcccacc gtcgtcctgc gccgcacccc cgcctgcgcc               450

ggcggccgtt ccgtctacac cgaggcctac gtcaccatcc ccgtgggctg               500

cacctgcgtc cccgagccgg agaaggacgc agacagcatc aactccagca               550

tcgacaaaca gggcgccaag ctcctgctgg gccccaacga cgcgcccgct               600

ggcccctgag gccggtcctg cccccgggagg tctccccggc ccgcatcccg              650

aggcgcccaa gctggagccg cctggagggc tcggtcggcg acctctgaag               700

agagtgcacc gagcaaacca agtgccggag caccagcgcc gcctttccat               750

ggagactcgt aagcagcttc atctgacacg ggcatccctg gcttgctttt               800

agctacaagc aagcagcgtg gctggaagct gatgggaaac gacccggcac               850

gggcatcctg tgtgcggccc gcatggaggg tttggaaaag ttcacggagg               900

ctccctgagg agcctctcag atcggctgct gcgggtgcag ggcgtgactc               950

accgctgggt gcttgccaaa gagataggga cgcatatgct ttttaaagca              1000

atctaaaaat aataataagt atagcgacta tatacctact tttaaaatca              1050

actgttttga atagaggcag agctatttta tattatcaaa tgagagctac              1100

tctgttacat ttcttaacat ataaacatcg ttttttactt cttctggtag              1150

aatttttaa agcataattg gaatccttgg ataaattttg tagctggtac               1200

actctggcct gggtctctga attcagcctg tcaccgatgg ctgactgatg              1250
```

-continued

```
aaatggacac gtctcatctg acccactctt ccttccactg aaggtcttca          1300

cgggcctcca ggtggaccaa agggatgcac aggcggctcg catgccccag          1350

ggccagctaa gagttccaaa gatctcagat ttggttttag tcatgaatac          1400

ataaacagtc tcaaactcgc acaatttttt ccccctttg aaagccactg           1450

gggccaattt gtggttaaga ggtggtgaga taagaagtgg aacgtgacat          1500

ctttgccagt tgtcagaaga atccaagcag gtattggctt agttgtaagg          1550

gctttaggat caggctgaat atgaggacaa agtgggccac gttagcatct          1600

gcagagatca atctggaggc ttctgtttct gcattctgcc acgagagcta          1650

ggtccttgat cttttcttta gattgaaagt ctgtctctga acacaattat          1700

ttgtaaaagt tagtagttct tttttaaatc attaaaagag gcttgctgaa          1750

ggat                                                            1754
```

<210> SEQ ID NO 88
<211> LENGTH: 202
<212> TYPE: PRT
<213> ORGANISM: Homo sapiens

<400> SEQUENCE: 88

```
Met Leu Val Ala Gly Phe Leu Leu Ala Leu Pro Pro Ser Trp Ala
  1               5                  10                  15

Ala Gly Ala Pro Arg Ala Gly Arg Arg Pro Ala Arg Pro Arg Gly
                 20                  25                  30

Cys Ala Asp Arg Pro Glu Glu Leu Leu Glu Gln Leu Tyr Gly Arg
                 35                  40                  45

Leu Ala Ala Gly Val Leu Ser Ala Phe His His Thr Leu Gln Leu
                 50                  55                  60

Gly Pro Arg Glu Gln Ala Arg Asn Ala Ser Cys Pro Ala Gly Gly
                 65                  70                  75

Arg Pro Gly Asp Arg Arg Phe Arg Pro Pro Thr Asn Leu Arg Ser
                 80                  85                  90

Val Ser Pro Trp Ala Tyr Arg Ile Ser Tyr Asp Pro Ala Arg Tyr
                 95                 100                 105

Pro Arg Tyr Leu Pro Glu Ala Tyr Cys Leu Cys Arg Gly Cys Leu
                110                 115                 120

Thr Gly Leu Phe Gly Glu Glu Asp Val Arg Phe Arg Ser Ala Pro
                125                 130                 135

Val Tyr Met Pro Thr Val Val Leu Arg Arg Thr Pro Ala Cys Ala
                140                 145                 150

Gly Gly Arg Ser Val Tyr Thr Glu Ala Tyr Val Thr Ile Pro Val
                155                 160                 165

Gly Cys Thr Cys Val Pro Glu Pro Glu Lys Asp Ala Asp Ser Ile
                170                 175                 180

Asn Ser Ser Ile Asp Lys Gln Gly Ala Lys Leu Leu Leu Gly Pro
                185                 190                 195

Asn Asp Ala Pro Ala Gly Pro
                200
```

<210> SEQ ID NO 89
<211> LENGTH: 2601
<212> TYPE: DNA
<213> ORGANISM: Homo sapiens -continued

<400> SEQUENCE: 89

```
ccggggcctc cggagaacgc tgtcccatga acgtgcgggg agcggccccc      50
ggcgtccgcg cgtccccgcg tccctggcaa ttcccgactt cccaacggct     100
tcccgctggc agccccgaag ccgcaccatg ttccgcctct ggttgctgct     150
ggccgggctc tgcggcctcc tggcgtcaag acccggtttt caaaattcac     200
ttctacagat cgtaattcca gagaaaatcc aaacaaatac aaatgacagt     250
tcagaaatag aatatgaaca aatatcctat attattccaa tagatgagaa     300
actgtacact gtgcacctta aacaaagata ttttttagca gataatttta     350
tgatctattt gtacaatcaa ggatctatga atacttattc ttcagatatt     400
cagactcaat gctactatca aggaaatatt gaaggatatc cagattccat     450
ggtcacactc agcacgtgct ctggactaag aggaatactg caatttgaaa     500
atgtttctta tggaattgag cctctggaat ctgcagttga atttcagcat     550
gttctttaca aattaaagaa tgaagacaat gatattgcaa tttttattga     600
cagaagcctg aaagaacaac caatggatga caacattttt ataagtgaaa     650
aatcagaacc agctgttcca gatttatttc ctctttatct agaaatgcat     700
attgtggtgg acaaaacttt gtatgattac tggggctctg atagcatgat     750
agtaacaaat aaagtcatcg aaattgttgg ccttgcaaat tcaatgttca     800
cccaatttaa agttactatt gtgctgtcat cattggagtt atggtcagat     850
gaaaataaga tttctacagt tggtgaggca gatgaattat tgcaaaaatt     900
tttagaatgg aaacaatctt atcttaacct aaggcctcat gatattgcat     950
atctactaat ttatatggat tatcctcgtt atttgggagc agtgtttcct    1000
ggaacaatgt gtattactcg ttattctgca ggagttgcat tgtaccccaa    1050
ggagataact ctggaggcat ttgcagttat tgtcacccag atgctggcac    1100
tcagtctggg aatatcatat gacgacccaa agaaatgtca atgttcagaa    1150
tccacctgta taatgaatcc agaagttgtg caatccaatg gtgtgaagac    1200
ttttagcagt tgcagtttga ggagctttca aaatttcatt tcaaatgtgg    1250
gtgtcaaatg tcttcagaat aagccacaaa tgcaaaaaaa atctccgaaa    1300
ccagtctgtg gcaatggcag attggaggga aatgaaatct gtgattgtgg    1350
tactgaggct caatgtggac ctgcaagctg ttgtgatttt cgaacttgtg    1400
tactgaaaga cggagcaaaa tgttataaag gactgtgctg caaagactgt    1450
caaattttac aatcaggcgt tgaatgtagg ccgaaagcac atcctgaatg    1500
tgacatcgct gaaaattgta atggaagctc accagaatgt ggtcctgaca    1550
taactttaat caatggactt tcatgcaaaa ataataagtt tatttgttat    1600
gacggagact gccatgatct cgatgcacgt tgtgagagtg tatttggaaa    1650
aggttcaaga aatgctccat ttgcctgcta tgaagaaata caatctcaat    1700
cagacagatt tgggaactgt ggtagggata gaaataacaa atatgtgttc    1750
tgtggatgga ggaatcttat atgtggaaga ttagtttgta cctaccctac    1800
tcgaaagcct ttccatcaag aaaatggtga tgtgatttat gctttcgtac    1850
gagattctgt atgcataact gtagactaca aattgcctcg aacagttcca    1900
gatccactgg ctgtcaaaaa tggctctcag tgtgatattg ggagggtttg    1950
```

-continued

```
tgtaaatcgt gaatgtgtag aatcaaggat aattaaggct tcagcacatg          2000

tttgttcaca acagtgttct ggacatggag tgtgtgattc cagaaacaag          2050

tgccattgtt cgccaggcta taagcctcca aactgccaaa tacgttccaa          2100

aggattttcc atatttcctg aggaagatat gggttcaatc atggaaagag          2150

catctgggaa gactgaaaac acctggcttc taggtttcct cattgctctt          2200

cctattctca ttgtaacaac cgcaatagtt ttggcaagga aacagttgaa          2250

aaagtggttc gccaaggaag aggaattccc aagtagcgaa tctaaatcgg          2300

aaggtagcac acagacatat gccagccaat ccagctcaga aggcagcact          2350

cagacatatg ccagccaaac cagatcagaa agcagcagtc aagctgatac          2400

tagcaaatcc aaatcagaag atagtgctga agcatatact agcagatcca          2450

aatcacagga cagtacccaa acacaaagca gtagtaacta gtgattcctt          2500

cagaaggcaa cggataacat cgagagtctc gctaagaaat gaaaattctg          2550

tctttccttc cgtggtcaca gctgaaagaa acaataaatt gagtgtggat          2600

c                                                               2601
```

<210> SEQ ID NO 90
<211> LENGTH: 787
<212> TYPE: PRT
<213> ORGANISM: Homo sapiens

<400> SEQUENCE: 90

```
Met Phe Arg Leu Trp Leu Leu Leu Ala Gly Leu Cys Gly Leu Leu
  1               5                  10                  15

Ala Ser Arg Pro Gly Phe Gln Asn Ser Leu Leu Gln Ile Val Ile
                 20                  25                  30

Pro Glu Lys Ile Gln Thr Asn Thr Asn Asp Ser Ser Glu Ile Glu
                 35                  40                  45

Tyr Glu Gln Ile Ser Tyr Ile Ile Pro Ile Asp Glu Lys Leu Tyr
                 50                  55                  60

Thr Val His Leu Lys Gln Arg Tyr Phe Leu Ala Asp Asn Phe Met
                 65                  70                  75

Ile Tyr Leu Tyr Asn Gln Gly Ser Met Asn Thr Tyr Ser Ser Asp
                 80                  85                  90

Ile Gln Thr Gln Cys Tyr Tyr Gln Gly Asn Ile Glu Gly Tyr Pro
                 95                 100                 105

Asp Ser Met Val Thr Leu Ser Thr Cys Ser Gly Leu Arg Gly Ile
                110                 115                 120

Leu Gln Phe Glu Asn Val Ser Tyr Gly Ile Glu Pro Leu Glu Ser
                125                 130                 135

Ala Val Glu Phe Gln His Val Leu Tyr Lys Leu Lys Asn Glu Asp
                140                 145                 150

Asn Asp Ile Ala Ile Phe Ile Asp Arg Ser Leu Lys Glu Gln Pro
                155                 160                 165

Met Asp Asp Asn Ile Phe Ile Ser Glu Lys Ser Glu Pro Ala Val
                170                 175                 180

Pro Asp Leu Phe Pro Leu Tyr Leu Glu Met His Ile Val Val Asp
                185                 190                 195

Lys Thr Leu Tyr Asp Tyr Trp Gly Ser Asp Ser Met Ile Val Thr
                200                 205                 210
```

-continued

```
Asn Lys Val Ile Glu Ile Val Gly Leu Ala Asn Ser Met Phe Thr
                215                 220                 225

Gln Phe Lys Val Thr Ile Val Leu Ser Ser Leu Glu Leu Trp Ser
                230                 235                 240

Asp Glu Asn Lys Ile Ser Thr Val Gly Glu Ala Asp Glu Leu Leu
                245                 250                 255

Gln Lys Phe Leu Glu Trp Lys Gln Ser Tyr Leu Asn Leu Arg Pro
                260                 265                 270

His Asp Ile Ala Tyr Leu Leu Ile Tyr Met Asp Tyr Pro Arg Tyr
                275                 280                 285

Leu Gly Ala Val Phe Pro Gly Thr Met Cys Ile Thr Arg Tyr Ser
                290                 295                 300

Ala Gly Val Ala Leu Tyr Pro Lys Glu Ile Thr Leu Glu Ala Phe
                305                 310                 315

Ala Val Ile Val Thr Gln Met Leu Ala Leu Ser Leu Gly Ile Ser
                320                 325                 330

Tyr Asp Asp Pro Lys Lys Cys Gln Cys Ser Glu Ser Thr Cys Ile
                335                 340                 345

Met Asn Pro Glu Val Val Gln Ser Asn Gly Val Lys Thr Phe Ser
                350                 355                 360

Ser Cys Ser Leu Arg Ser Phe Gln Asn Phe Ile Ser Asn Val Gly
                365                 370                 375

Val Lys Cys Leu Gln Asn Lys Pro Gln Met Gln Lys Lys Ser Pro
                380                 385                 390

Lys Pro Val Cys Gly Asn Gly Arg Leu Glu Gly Asn Glu Ile Cys
                395                 400                 405

Asp Cys Gly Thr Glu Ala Gln Cys Gly Pro Ala Ser Cys Cys Asp
                410                 415                 420

Phe Arg Thr Cys Val Leu Lys Asp Gly Ala Lys Cys Tyr Lys Gly
                425                 430                 435

Leu Cys Cys Lys Asp Cys Gln Ile Leu Gln Ser Gly Val Glu Cys
                440                 445                 450

Arg Pro Lys Ala His Pro Glu Cys Asp Ile Ala Glu Asn Cys Asn
                455                 460                 465

Gly Ser Ser Pro Glu Cys Gly Pro Asp Ile Thr Leu Ile Asn Gly
                470                 475                 480

Leu Ser Cys Lys Asn Asn Lys Phe Ile Cys Tyr Asp Gly Asp Cys
                485                 490                 495

His Asp Leu Asp Ala Arg Cys Glu Ser Val Phe Gly Lys Gly Ser
                500                 505                 510

Arg Asn Ala Pro Phe Ala Cys Tyr Glu Glu Ile Gln Ser Gln Ser
                515                 520                 525

Asp Arg Phe Gly Asn Cys Gly Arg Asp Arg Asn Asn Lys Tyr Val
                530                 535                 540

Phe Cys Gly Trp Arg Asn Leu Ile Cys Gly Arg Leu Val Cys Thr
                545                 550                 555

Tyr Pro Thr Arg Lys Pro Phe His Gln Glu Asn Gly Asp Val Ile
                560                 565                 570

Tyr Ala Phe Val Arg Asp Ser Val Cys Ile Thr Val Asp Tyr Lys
                575                 580                 585

Leu Pro Arg Thr Val Pro Asp Pro Leu Ala Val Lys Asn Gly Ser
                590                 595                 600

Gln Cys Asp Ile Gly Arg Val Cys Val Asn Arg Glu Cys Val Glu
```

-continued

```
                605                 610                 615

Ser Arg Ile Ile Lys Ala Ser Ala His Val Cys Ser Gln Gln Cys
                620                 625                 630

Ser Gly His Gly Val Cys Asp Ser Arg Asn Lys Cys His Cys Ser
                635                 640                 645

Pro Gly Tyr Lys Pro Pro Asn Cys Gln Ile Arg Ser Lys Gly Phe
                650                 655                 660

Ser Ile Phe Pro Glu Glu Asp Met Gly Ser Ile Met Glu Arg Ala
                665                 670                 675

Ser Gly Lys Thr Glu Asn Thr Trp Leu Leu Gly Phe Leu Ile Ala
                680                 685                 690

Leu Pro Ile Leu Ile Val Thr Thr Ala Ile Val Leu Ala Arg Lys
                695                 700                 705

Gln Leu Lys Lys Trp Phe Ala Lys Glu Glu Glu Phe Pro Ser Ser
                710                 715                 720

Glu Ser Lys Ser Glu Gly Ser Thr Gln Thr Tyr Ala Ser Gln Ser
                725                 730                 735

Ser Ser Glu Gly Ser Thr Gln Thr Tyr Ala Ser Gln Thr Arg Ser
                740                 745                 750

Glu Ser Ser Ser Gln Ala Asp Thr Ser Lys Ser Lys Ser Glu Asp
                755                 760                 765

Ser Ala Glu Ala Tyr Thr Ser Arg Ser Lys Ser Gln Asp Ser Thr
                770                 775                 780

Gln Thr Gln Ser Ser Ser Asn
                785


<210> SEQ ID NO 91
<211> LENGTH: 2445
<212> TYPE: DNA
<213> ORGANISM: Homo sapiens
<220> FEATURE:
<221> NAME/KEY: Unsure
<222> LOCATION: 2424
<223> OTHER INFORMATION: Unknown base

<400> SEQUENCE: 91

caccagacag cactccagca ctctgtttgg ggggcattcg aaacagcaaa                50

atcactcata aaaggcaaaa aattgcaaaa aaaaatagta ataaccagca               100

tggcactaaa tagaccatga aaagacatgt gtgtgcagta tgaaaattga               150

gacaggaagg cagagtgtca gcttgttcca cctcagctgg gaatgtgcat               200

caggcaactc aagtttttca ccacggcatg tgtctgtgaa tgtccgcaaa               250

acattctctc tccccagcct tcatgtgtta acctggggat gatgtggacc               300

tgggcactgt ggatgctccc ttcactctgc aaattcagcc tggcagctct               350

gccagctaag cctgagaaca tttcctgtgt ctactactat aggaaaaatt               400

taacctgcac ttggagtcca ggaaaggaaa ccagttatac ccagtacaca               450

gttaagagaa cttacgcttt tggagaaaaa catgataatt gtacaaccaa               500

tagttctaca agtgaaaatc gtgcttcgtg ctctttttc cttccaagaa               550

taacgatccc agataattat accattgagg tggaagctga aaatggagat               600

ggtgtaatta aatctcatat gacatactgg agattagaga acatagcgaa               650

aactgaacca cctaagattt tccgtgtgaa accagttttg ggcatcaaac               700

gaatgattca aattgaatgg ataaagcctg agttggcgcc tgtttcatct               750
```

-continued

```
gatttaaaat acacacttcg attcaggaca gtcaacagta ccagctggat              800
ggaagtcaac ttcgctaaga accgtaagga taaaaaccaa acgtacaacc              850
tcacggggct gcagcctttt acagaatatg tcatagctct gcgatgtgcg              900
gtcaaggagt caaagttctg gagtgactgg agccaagaaa aaatgggaat              950
gactgaggaa gaagctccat gtggcctgga actgtggaga gtcctgaaac             1000
cagctgaggc ggatggaaga aggccagtgc ggttgttatg gaagaaggca             1050
agaggagccc cagtcctaga gaaaacactt ggctacaaca tatggtacta             1100
tccagaaagc aacactaacc tcacagaaac aatgaacact actaaccagc             1150
agcttgaact gcatctggga ggcgagagct tttgggtgtc tatgatttct             1200
tataattctc ttgggaagtc tccagtggcc accctgagga ttccagctat             1250
tcaagaaaaa tcatttcagt gcattgaggt catgcaggcc tgcgttgctg             1300
aggaccagct agtggtgaag tggcaaagct ctgctctaga cgtgaacact             1350
tggatgattg aatggtttcc ggatgtggac tcagagccca ccaccctttc             1400
ctgggaatct gtgtctcagg ccacgaactg gacgatccag caagataaat             1450
taaaaccttt ctggtgctat aacatctctg tgtatccaat gttgcatgac             1500
aaagttggcg agccatattc catccaggct tatgccaaag aaggcgttcc             1550
atcagaaggt cctgagacca aggtggagaa cattggcgtg aagacggtca             1600
cgatcacatg gaaagagatt cccaagagtg agagaaaggg tatcatctgc             1650
aactacacca tcttttacca agctgaaggt ggaaaaggat tctgtaagca             1700
cgcccatagc gaagtggaaa aaaaccccaa gccccagata gatgctatgg             1750
atagacctgt tgtaggcatg gctcccccat ctcattgtga cttgcaacct             1800
ggcatgaatc acttagcttc tttaaatctc tctgaaaatg gggccaagag             1850
cacccacctt ttggggtttt gggggttaaa tgagagtgaa gtgacagtac             1900
ctgagaggag agtcctgagg aaatggaagg agttgttata atttgtcctg             1950
gttaggccct gaattgacct cccgggagct ccccgaccat cattcccagg             2000
aatggcgtgc ctggcttaaa gagtgaggag gaacagaccc tgtcaccatg             2050
acttctactg cccctgccaa atcatgcttt tgtttttcag tccaccttat             2100
ctcctgacat cttaaatact gggcaaggct tggattcttg cttaggctaa             2150
ataatttttt cttatggtaa aatacacgta aaatattttt ccagtttaaa             2200
catttgaaag tgtacaattt agtggcatta gaagcattca caatattgtg             2250
caaccatcac cactatttcc agaactcttc tatttctgcc caaatagaag             2300
ccctataccc attcattagt cactccccat tcctctcctc ccacagcccc             2350
tggcaactac caaactgctt tgtgtctcta tggattgcct attttggata             2400
tttcatatac atagaatcat aaantaaaaa aaaaaaaaaa  aaaaa                 2445
```

<210> SEQ ID NO 92
<211> LENGTH: 582
<212> TYPE: PRT
<213> ORGANISM: Homo sapiens

<400> SEQUENCE: 92

```
Met Cys Ile Arg Gln Leu Lys Phe Phe Thr Thr Ala Cys Val Cys
  1               5                  10                  15
```

-continued

```
Glu Cys Pro Gln Asn Ile Leu Ser Pro Gln Pro Ser Cys Val Asn
                20                  25                  30

Leu Gly Met Met Trp Thr Trp Ala Leu Trp Met Leu Pro Ser Leu
                35                  40                  45

Cys Lys Phe Ser Leu Ala Ala Leu Pro Ala Lys Pro Glu Asn Ile
                50                  55                  60

Ser Cys Val Tyr Tyr Tyr Arg Lys Asn Leu Thr Cys Thr Trp Ser
                65                  70                  75

Pro Gly Lys Glu Thr Ser Tyr Thr Gln Tyr Thr Val Lys Arg Thr
                80                  85                  90

Tyr Ala Phe Gly Glu Lys His Asp Asn Cys Thr Thr Asn Ser Ser
                95                 100                 105

Thr Ser Glu Asn Arg Ala Ser Cys Ser Phe Phe Leu Pro Arg Ile
               110                 115                 120

Thr Ile Pro Asp Asn Tyr Thr Ile Glu Val Glu Ala Glu Asn Gly
               125                 130                 135

Asp Gly Val Ile Lys Ser His Met Thr Tyr Trp Arg Leu Glu Asn
               140                 145                 150

Ile Ala Lys Thr Glu Pro Pro Lys Ile Phe Arg Val Lys Pro Val
               155                 160                 165

Leu Gly Ile Lys Arg Met Ile Gln Ile Glu Trp Ile Lys Pro Glu
               170                 175                 180

Leu Ala Pro Val Ser Ser Asp Leu Lys Tyr Thr Leu Arg Phe Arg
               185                 190                 195

Thr Val Asn Ser Thr Ser Trp Met Glu Val Asn Phe Ala Lys Asn
               200                 205                 210

Arg Lys Asp Lys Asn Gln Thr Tyr Asn Leu Thr Gly Leu Gln Pro
               215                 220                 225

Phe Thr Glu Tyr Val Ile Ala Leu Arg Cys Ala Val Lys Glu Ser
               230                 235                 240

Lys Phe Trp Ser Asp Trp Ser Gln Glu Lys Met Gly Met Thr Glu
               245                 250                 255

Glu Glu Ala Pro Cys Gly Leu Glu Leu Trp Arg Val Leu Lys Pro
               260                 265                 270

Ala Glu Ala Asp Gly Arg Arg Pro Val Arg Leu Leu Trp Lys Lys
               275                 280                 285

Ala Arg Gly Ala Pro Val Leu Glu Lys Thr Leu Gly Tyr Asn Ile
               290                 295                 300

Trp Tyr Tyr Pro Glu Ser Asn Thr Asn Leu Thr Glu Thr Met Asn
               305                 310                 315

Thr Thr Asn Gln Gln Leu Glu Leu His Leu Gly Gly Glu Ser Phe
               320                 325                 330

Trp Val Ser Met Ile Ser Tyr Asn Ser Leu Gly Lys Ser Pro Val
               335                 340                 345

Ala Thr Leu Arg Ile Pro Ala Ile Gln Glu Lys Ser Phe Gln Cys
               350                 355                 360

Ile Glu Val Met Gln Ala Cys Val Ala Glu Asp Gln Leu Val Val
               365                 370                 375

Lys Trp Gln Ser Ser Ala Leu Asp Val Asn Thr Trp Met Ile Glu
               380                 385                 390

Trp Phe Pro Asp Val Asp Ser Glu Pro Thr Thr Leu Ser Trp Glu
               395                 400                 405
```

-continued

```
Ser Val Ser Gln Ala Thr Asn Trp Thr Ile Gln Gln Asp Lys Leu
                410                 415                 420

Lys Pro Phe Trp Cys Tyr Asn Ile Ser Val Tyr Pro Met Leu His
                425                 430                 435

Asp Lys Val Gly Glu Pro Tyr Ser Ile Gln Ala Tyr Ala Lys Glu
                440                 445                 450

Gly Val Pro Ser Glu Gly Pro Glu Thr Lys Val Glu Asn Ile Gly
                455                 460                 465

Val Lys Thr Val Thr Ile Thr Trp Lys Glu Ile Pro Lys Ser Glu
                470                 475                 480

Arg Lys Gly Ile Ile Cys Asn Tyr Thr Ile Phe Tyr Gln Ala Glu
                485                 490                 495

Gly Gly Lys Gly Phe Cys Lys His Ala His Ser Glu Val Glu Lys
                500                 505                 510

Asn Pro Lys Pro Gln Ile Asp Ala Met Asp Arg Pro Val Val Gly
                515                 520                 525

Met Ala Pro Pro Ser His Cys Asp Leu Gln Pro Gly Met Asn His
                530                 535                 540

Leu Ala Ser Leu Asn Leu Ser Glu Asn Gly Ala Lys Ser Thr His
                545                 550                 555

Leu Leu Gly Phe Trp Gly Leu Asn Glu Ser Glu Val Thr Val Pro
                560                 565                 570

Glu Arg Arg Val Leu Arg Lys Trp Lys Glu Leu Leu
                575                 580


<210> SEQ ID NO 93
<211> LENGTH: 662
<212> TYPE: DNA
<213> ORGANISM: Homo sapiens

<400> SEQUENCE: 93

attctcctag agcatctttg gaagcatgag gccacgatgc tgcatcttgg                50

ctcttgtctg ctggataaca gtcttcctcc tccagtgttc aaaaggaact               100

acagacgctc ctgttggctc aggactgtgg ctgtgccagc cgacacccag               150

gtgtgggaac aagatctaca acccttcaga gcagtgctgt tatgatgatg               200

ccatcttatc cttaaaggag acccgccgct gtggctccac ctgcaccttc               250

tggccctgct ttgagctctg ctgtcccgag tcttttggcc cccagcagaa               300

gtttcttgtg aagttgaggg ttctgggtat gaagtctcag tgtcacttat               350

ctcccatctc ccggagctgt accaggaaca ggaggcacgt cctgtaccca               400

taaaaacccc aggctccact ggcagacggc agacaagggg agaagagacg               450

aagcagctgg acatcggaga ctacagttga acttcggaga gaagcaactt               500

gacttcagag ggatggctca atgacatagc tttggagagg agcccagctg               550

gggatggcca gacttcaggg gaagaatgcc ttcctgcttc atccccttc                600

cagctcccct tcccgctgag agccactttc atcggcaata aaatcccccca              650

catttaccat  ct                                                       662


<210> SEQ ID NO 94
<211> LENGTH: 125
<212> TYPE: PRT
<213> ORGANISM: Homo sapiens

<400> SEQUENCE: 94
```

```
Met Arg Pro Arg Cys Cys Ile Leu Ala Leu Val Cys Trp Ile Thr
  1               5                  10                  15

Val Phe Leu Leu Gln Cys Ser Lys Gly Thr Thr Asp Ala Pro Val
                 20                  25                  30

Gly Ser Gly Leu Trp Leu Cys Gln Pro Thr Pro Arg Cys Gly Asn
                 35                  40                  45

Lys Ile Tyr Asn Pro Ser Glu Gln Cys Cys Tyr Asp Asp Ala Ile
                 50                  55                  60

Leu Ser Leu Lys Glu Thr Arg Arg Cys Gly Ser Thr Cys Thr Phe
                 65                  70                  75

Trp Pro Cys Phe Glu Leu Cys Cys Pro Glu Ser Phe Gly Pro Gln
                 80                  85                  90

Gln Lys Phe Leu Val Lys Leu Arg Val Leu Gly Met Lys Ser Gln
                 95                 100                 105

Cys His Leu Ser Pro Ile Ser Arg Ser Cys Thr Arg Asn Arg Arg
                110                 115                 120

His Val Leu Tyr Pro
                125


<210> SEQ ID NO 95
<211> LENGTH: 471
<212> TYPE: DNA
<213> ORGANISM: Homo sapiens

<400> SEQUENCE: 95

gcatttttgt ctgtgctccc tgatcttcag gtcaccacca tgaagttctt                50

agcagtcctg gtactcttgg gagtttccat ctttctggtc tctgcccaga               100

atccgacaac agctgctcca gctgacacgt atccagctac tggtcctgct               150

gatgatgaag cccctgatgc tgaaaccact gctgctgcaa ccactgcgac               200

cactgctgct cctaccactg caaccaccgc tgcttctacc actgctcgta               250

aagacattcc agttttaccc aaatgggttg gggatctccc gaatggtaga               300

gtgtgtccct gagatggaat cagcttgagt cttctgcaat tggtcacaac               350

tattcatgct tcctgtgatt tcatccaact acttaccttg cctacgatat               400

ccccttttatc tctaatcagt ttattttctt tcaaataaaa aataactatg               450

agcaacataa aaaaaaaaaa  a                                              471


<210> SEQ ID NO 96
<211> LENGTH: 90
<212> TYPE: PRT
<213> ORGANISM: Homo sapiens

<400> SEQUENCE: 96

Met Lys Phe Leu Ala Val Leu Val Leu Leu Gly Val Ser Ile Phe
  1               5                  10                  15

Leu Val Ser Ala Gln Asn Pro Thr Thr Ala Ala Pro Ala Asp Thr
                 20                  25                  30

Tyr Pro Ala Thr Gly Pro Ala Asp Asp Glu Ala Pro Asp Ala Glu
                 35                  40                  45

Thr Thr Ala Ala Ala Thr Thr Ala Thr Thr Ala Ala Pro Thr Thr
                 50                  55                  60

Ala Thr Thr Ala Ala Ser Thr Thr Ala Arg Lys Asp Ile Pro Val
                 65                  70                  75
```

-continued

```
Leu Pro Lys Trp Val Gly Asp Leu Pro Asn Gly Arg Val Cys Pro
                80                  85                  90


<210> SEQ ID NO 97
<211> LENGTH: 907
<212> TYPE: DNA
<213> ORGANISM: Homo sapiens

<400> SEQUENCE: 97

ggactctgaa ggtcccaagc agctgctgag gcccccaagg aagtggttcc                50

aaccttggac ccctaggggt ctggatttgc tggttaacaa gataacctga               100

gggcaggacc ccatagggga atgctacctc ctgcccttcc acctgccctg               150

gtgttcacgg tggcctggtc cctccttgcc gagagagtgt cctgggtcag               200

ggacgcagag gacgctcaca gactccagcc ctttgttacc gagaggacac               250

ttggcaaggt ccagcgatgg tccggagtcc acacacagac tggcggcagg               300

gcaggagggg gacagttctg ttgtgcttgg ttggacagta agagggtctt               350

ggccagtcca gggtgggggg cggcaaactc cataaagaac cagagggtct               400

gggccccggc cacagagtca tctgcccagc tcctctgctg ctggccagtg               450

ggagtggcac gaggtggggc tttgtgccag taaaaccaca ggctggattt               500

gcctgcgggc catggtccct gtctagggca gcaattctca accttcttgc               550

tctcaggacc ccaaagagct ttcattgtat ctattgattt ttaccacatt               600

agcaattaaa actgagaaat gggccgggca cggtggctca cgcctgtaat               650

cccagcactt tgggaggccg aggcgggtgg atcacctgag atcaggagtt               700

caagaccagc ctggccaaca tggtgaaacc ttgtctacta aaaatacaaa               750

aaattagcca ggcacagtgg tgtgcactgg tagtcccagt tactcgggag               800

gctgaggcag gaaaatcgct tgaacccagg aggcggacgt tgcggtgagc               850

cgagatcgcg ccgctgattc cagcctgggc gacaagagtg agactccatc               900

tcacaca                                                              907


<210> SEQ ID NO 98
<211> LENGTH: 120
<212> TYPE: PRT
<213> ORGANISM: Homo sapiens

<400> SEQUENCE: 98

Met Leu Pro Pro Ala Leu Pro Pro Ala Leu Val Phe Thr Val Ala
  1               5                  10                  15

Trp Ser Leu Leu Ala Glu Arg Val Ser Trp Val Arg Asp Ala Glu
                20                  25                  30

Asp Ala His Arg Leu Gln Pro Phe Val Thr Glu Arg Thr Leu Gly
                35                  40                  45

Lys Val Gln Arg Trp Ser Gly Val His Thr Gln Thr Gly Gly Arg
                50                  55                  60

Ala Gly Gly Gly Gln Phe Cys Cys Ala Trp Leu Asp Ser Lys Arg
                65                  70                  75

Val Leu Ala Ser Pro Gly Trp Gly Ala Ala Asn Ser Ile Lys Asn
                80                  85                  90

Gln Arg Val Trp Ala Pro Ala Thr Glu Ser Ser Ala Gln Leu Leu
                95                 100                 105

Cys Cys Trp Pro Val Gly Val Ala Arg Gly Gly Ala Leu Cys Gln
```

-continued

```
                110                 115                 120

<210> SEQ ID NO 99
<211> LENGTH: 1073
<212> TYPE: DNA
<213> ORGANISM: Homo sapiens

<400> SEQUENCE: 99

aatttttcac cagagtaaac ttgagaaacc aactggacct tgagtattgt                50

acattttgcc tcgtggaccc aaaggtagca atctgaaaca tgaggagtac               100

gattctactg ttttgtcttc taggatcaac tcggtcatta ccacagctca               150

aacctgcttt gggactccct cccacaaaac tggctccgga tcagggaaca               200

ctaccaaacc aacagcagtc aaatcaggtc tttccttctt taagtctgat               250

accattaaca cagatgctca cactggggcc agatctgcat ctgttaaatc               300

ctgctgcagg aatgacacct ggtacccaga cccacccatt gaccctggga               350

gggttgaatg tacaacagca actgcaccca catgtgttac caatttttgt               400

cacacaactt ggagcccagg gcactatcct aagctcagag gaattgccac               450

aaatcttcac gagcctcatc atccattcct tgttcccggg aggcatcctg               500

cccaccagtc aggcaggggc taatccagat gtccaggatg gaagccttcc               550

agcaggagga gcaggtgtaa atcctgccac ccagggaacc ccagcaggcc               600

gcctcccaac tcccagtggc acagatgacg actttgcagt gaccacccct               650

gcaggcatcc aaaggagcac acatgccatc gaggaagcca ccacagaatc               700

agcaaatgga attcagtaag ctgtttcaaa ttttttcaac taagctgcct               750

cgaatttggt gatacatgtg aatctttatc attgattata ttatggaata               800

gattgagaca cattggatag tcttagaaga aattaattct taatttacct               850

gaaaatattc ttgaaatttc agaaaatatg ttctatgtag agaatcccaa               900

cttttaaaaa caataattca atggataaat ctgtctttga aatataacat               950

tatgctgcct ggatgatatg catattaaaa catatttgga aaactggaaa              1000

aaaaaaaaaa aaaaaaaaaa aaaaaaaaaa aaaaaaaaaa aaaaaaaaaa              1050

aaaaaaaaaa aaaaaaaaaa  aaa                                          1073


<210> SEQ ID NO 100
<211> LENGTH: 209
<212> TYPE: PRT
<213> ORGANISM: Homo sapiens

<400> SEQUENCE: 100

Met Arg Ser Thr Ile Leu Leu Phe Cys Leu Leu Gly Ser Thr Arg
  1               5                  10                  15

Ser Leu Pro Gln Leu Lys Pro Ala Leu Gly Leu Pro Pro Thr Lys
                 20                  25                  30

Leu Ala Pro Asp Gln Gly Thr Leu Pro Asn Gln Gln Gln Ser Asn
                 35                  40                  45

Gln Val Phe Pro Ser Leu Ser Leu Ile Pro Leu Thr Gln Met Leu
                 50                  55                  60

Thr Leu Gly Pro Asp Leu His Leu Leu Asn Pro Ala Ala Gly Met
                 65                  70                  75

Thr Pro Gly Thr Gln Thr His Pro Leu Thr Leu Gly Gly Leu Asn
                 80                  85                  90
```

-continued

```
Val Gln Gln Gln Leu His Pro His Val Leu Pro Ile Phe Val Thr
                95                  100                 105

Gln Leu Gly Ala Gln Gly Thr Ile Leu Ser Ser Glu Glu Leu Pro
            110                 115                 120

Gln Ile Phe Thr Ser Leu Ile Ile His Ser Leu Phe Pro Gly Gly
            125                 130                 135

Ile Leu Pro Thr Ser Gln Ala Gly Ala Asn Pro Asp Val Gln Asp
            140                 145                 150

Gly Ser Leu Pro Ala Gly Gly Ala Gly Val Asn Pro Ala Thr Gln
            155                 160                 165

Gly Thr Pro Ala Gly Arg Leu Pro Thr Pro Ser Gly Thr Asp Asp
            170                 175                 180

Asp Phe Ala Val Thr Thr Pro Ala Gly Ile Gln Arg Ser Thr His
            185                 190                 195

Ala Ile Glu Glu Ala Thr Thr Glu Ser Ala Asn Gly Ile Gln
            200                 205


<210> SEQ ID NO 101
<211> LENGTH: 1514
<212> TYPE: DNA
<213> ORGANISM: Homo sapiens

<400> SEQUENCE: 101

ggggtctccc tcagggccgg gaggcacagc ggtccctgct tgctgaaggg          50

ctggatgtac gcatccgcag gttcccgcgg acttgggggc gcccgctgag         100

ccccggcgcc cgcagaagac ttgtgtttgc ctcctgcagc ctcaacccgg         150

agggcagcga gggcctacca ccatgatcac tggtgtgttc agcatgcgct         200

tgtggacccc agtgggcgtc ctgacctcgc tggcgtactg cctgcaccag         250

cggcgggtgg ccctggccga gctgcaggag gccgatggcc agtgtccggt         300

cgaccgcagc ctgctgaagt tgaaaatggt gcaggtcgtg tttcgacacg         350

gggctcggag tcctctcaag ccgctcccgc tggaggagca ggtagagtgg         400

aacccccagc tattagaggt cccaccccaa actcagtttg attacacagt         450

caccaatcta gctggtggtc cgaaaccata ttctccttac gactctcaat         500

accatgagac caccctgaag gggggcatgt ttgctgggca gctgaccaag         550

gtgggcatgc agcaaatgtt tgccttggga gagagactga ggaagaacta         600

tgtggaagac attccctttc tttcaccaac cttcaaccca caggaggtct         650

ttattcgttc cactaacatt tttcggaatc tggagtccac ccgttgtttg         700

ctggctgggc ttttccagtg tcagaaagaa ggacccatca tcatccacac         750

tgatgaagca gattcagaag tcttgtatcc caactaccaa agctgctgga         800

gcctgaggca gagaaccaga ggccggaggc agactgcctc tttacagcca         850

ggaatctcag aggatttgaa aaaggtgaag gacaggatgg gcattgacag         900

tagtgataaa gtggacttct tcatcctcct ggacaacgtg gctgccgagc         950

aggcacacaa cctcccaagc tgccccatgc tgaagagatt tgcacggatg        1000

atcgaacaga gagctgtgga cacatccttg tacatactgc ccaaggaaga        1050

cagggaaagt cttcagatgg cagtaggccc attcctccac atcctagaga        1100

gcaacctgct gaaagccatg gactctgcca ctgcccccga caagatcaga        1150
```

-continued

```
aagctgtatc tctatgcggc tcatgatgtg accttcatac cgctcttaat          1200

gaccctgggg atttttgacc acaaatggcc accgtttgct gttgacctga          1250

ccatggaact ttaccagcac ctggaatcta aggagtggtt tgtgcagctc          1300

tattaccacg ggaaggagca ggtgccgaga ggttgccctg atgggctctg          1350

cccgctggac atgttcttga atgccatgtc agtttatacc ttaagcccag          1400

aaaaatacca tgcactctgc tctcaaactc aggtgatgga agttggaaat          1450

gaagagtaac tgatttataa aagcaggatg tgttgatttt aaaataaagt          1500

gcctttatac  aatg                                                1514
```

<210> SEQ ID NO 102
<211> LENGTH: 428
<212> TYPE: PRT
<213> ORGANISM: Homo sapiens

<400> SEQUENCE: 102

```
Met Ile Thr Gly Val Phe Ser Met Arg Leu Trp Thr Pro Val Gly
  1               5                  10                  15

Val Leu Thr Ser Leu Ala Tyr Cys Leu His Gln Arg Arg Val Ala
                 20                  25                  30

Leu Ala Glu Leu Gln Glu Ala Asp Gly Gln Cys Pro Val Asp Arg
                 35                  40                  45

Ser Leu Leu Lys Leu Lys Met Val Gln Val Val Phe Arg His Gly
                 50                  55                  60

Ala Arg Ser Pro Leu Lys Pro Leu Pro Leu Glu Glu Gln Val Glu
                 65                  70                  75

Trp Asn Pro Gln Leu Leu Glu Val Pro Pro Gln Thr Gln Phe Asp
                 80                  85                  90

Tyr Thr Val Thr Asn Leu Ala Gly Gly Pro Lys Pro Tyr Ser Pro
                 95                 100                 105

Tyr Asp Ser Gln Tyr His Glu Thr Thr Leu Lys Gly Gly Met Phe
                110                 115                 120

Ala Gly Gln Leu Thr Lys Val Gly Met Gln Gln Met Phe Ala Leu
                125                 130                 135

Gly Glu Arg Leu Arg Lys Asn Tyr Val Glu Asp Ile Pro Phe Leu
                140                 145                 150

Ser Pro Thr Phe Asn Pro Gln Glu Val Phe Ile Arg Ser Thr Asn
                155                 160                 165

Ile Phe Arg Asn Leu Glu Ser Thr Arg Cys Leu Leu Ala Gly Leu
                170                 175                 180

Phe Gln Cys Gln Lys Glu Gly Pro Ile Ile Ile His Thr Asp Glu
                185                 190                 195

Ala Asp Ser Glu Val Leu Tyr Pro Asn Tyr Gln Ser Cys Trp Ser
                200                 205                 210

Leu Arg Gln Arg Thr Arg Gly Arg Arg Gln Thr Ala Ser Leu Gln
                215                 220                 225

Pro Gly Ile Ser Glu Asp Leu Lys Lys Val Lys Asp Arg Met Gly
                230                 235                 240

Ile Asp Ser Ser Asp Lys Val Asp Phe Phe Ile Leu Leu Asp Asn
                245                 250                 255

Val Ala Ala Glu Gln Ala His Asn Leu Pro Ser Cys Pro Met Leu
                260                 265                 270

Lys Arg Phe Ala Arg Met Ile Glu Gln Arg Ala Val Asp Thr Ser
```

-continued

```
                275                 280                 285

Leu Tyr Ile Leu Pro Lys Glu Asp Arg Glu Ser Leu Gln Met Ala
                290                 295                 300

Val Gly Pro Phe Leu His Ile Leu Glu Ser Asn Leu Leu Lys Ala
                305                 310                 315

Met Asp Ser Ala Thr Ala Pro Asp Lys Ile Arg Lys Leu Tyr Leu
                320                 325                 330

Tyr Ala Ala His Asp Val Thr Phe Ile Pro Leu Leu Met Thr Leu
                335                 340                 345

Gly Ile Phe Asp His Lys Trp Pro Pro Phe Ala Val Asp Leu Thr
                350                 355                 360

Met Glu Leu Tyr Gln His Leu Glu Ser Lys Glu Trp Phe Val Gln
                365                 370                 375

Leu Tyr Tyr His Gly Lys Glu Gln Val Pro Arg Gly Cys Pro Asp
                380                 385                 390

Gly Leu Cys Pro Leu Asp Met Phe Leu Asn Ala Met Ser Val Tyr
                395                 400                 405

Thr Leu Ser Pro Glu Lys Tyr His Ala Leu Cys Ser Gln Thr Gln
                410                 415                 420

Val Met Glu Val Gly Asn Glu Glu
                425


<210> SEQ ID NO 103
<211> LENGTH: 2555
<212> TYPE: DNA
<213> ORGANISM: Homo sapiens

<400> SEQUENCE: 103

ggggcgggtg gacgcggact cgaacgcagt tgcttcggga cccaggaccc          50

cctcgggccc gacccgccag gaaagactga ggccgcggcc tgccccgccc         100

ggctccctgc gccgccgccg cctcccggga cagaagatgt gctccagggt         150

ccctctgctg ctgccgctgc tcctgctact ggccctgggg cctggggtgc         200

agggctgccc atccggctgc cagtgcagcc agccacagac agtcttctgc         250

actgcccgcc aggggaccac ggtgccccga gacgtgccac ccgacacggt         300

ggggctgtac gtctttgaga acggcatcac catgctcgac gcaagcagct         350

ttgccggcct gccgggcctg cagctcctgg acctgtcaca gaaccagatc         400

gccagcctgc gcctgccccg cctgctgctg ctggacctca gccacaacag         450

cctcctggcc ctggagcccg gcatcctgga cactgccaac gtggaggcgc         500

tgcggctggc tggtctgggg ctgcagcagc tggacgaggg gctcttcagc         550

cgcttgcgca acctccacga cctggatgtg tccgacaacc agctggagcg         600

agtgccacct gtgatccgag gcctccgggg cctgacgcgc ctgcggctgg         650

ccggcaacac ccgcattgcc cagctgcggc ccgaggacct ggccggcctg         700

gctgccctgc aggagctgga tgtgagcaac ctaagcctgc aggccctgcc         750

tggcgacctc tcgggcctct tcccccgcct gcggctgctg gcagctgccc         800

gcaacccctt caactgcgtg tgccccctga gctggtttgg cccctgggtg         850

cgcgagagcc acgtcacact ggccagccct gaggagacgc gctgccactt         900

cccgcccaag aacgctggcc ggctgctcct ggagcttgac tacgccgact         950

ttggctgccc agccaccacc accacagcca cagtgcccac cacgaggccc        1000
```

-continued

```
gtggtgcggg agcccacagc cttgtcttct agcttggctc ctacctggct          1050

tagccccaca gcgccggcca ctgaggcccc cagcccgccc tccactgccc          1100

caccgactgt agggcctgtc ccccagcccc aggactgccc accgtccacc          1150

tgcctcaatg ggggcacatg ccacctgggg acacggcacc acctggcgtg          1200

cttgtgcccc gaaggcttca cgggcctgta ctgtgagagc cagatggggc          1250

aggggacacg gcccagccct acaccagtca cgccgaggcc accacggtcc          1300

ctgaccctgg gcatcgagcc ggtgagcccc acctccctgc gcgtggggct          1350

gcagcgctac ctccagggga gctccgtgca gctcaggagc ctccgtctca          1400

cctatcgcaa cctatcgggc cctgataagc ggctggtgac gctgcgactg          1450

cctgcctcgc tcgctgagta cacggtcacc cagctgcggc ccaacgccac          1500

ttactccgtc tgtgtcatgc ctttggggcc cgggcgggtg ccggagggcg          1550

aggaggcctg cggggaggcc catacacccc cagccgtcca ctccaaccac          1600

gccccagtca cccaggcccg cgagggcaac ctgccgctcc tcattgcgcc          1650

cgccctggcc gcggtgctcc tggccgcgct ggctgcggtg ggggcagcct          1700

actgtgtgcg gcgggggcgg gccatggcag cagcggctca ggacaaaggg          1750

caggtggggc caggggctgg gcccctggaa ctggagggag tgaaggtccc          1800

cttggagcca ggcccgaagg caacagaggg cggtggagag gccctgccca          1850

gcgggtctga gtgtgaggtg ccactcatgg gcttcccagg gcctggcctc          1900

cagtcacccc tccacgcaaa gccctacatc taagccagag agagacaggg          1950

cagctggggc cgggctctca gccagtgaga tggccagccc cctcctgctg          2000

ccacaccacg taagttctca gtcccaacct cggggatgtg tgcagacagg          2050

gctgtgtgac cacagctggg ccctgttccc tctggacctc ggtctcctca          2100

tctgtgagat gctgtggccc agctgacgag ccctaacgtc cccagaaccg          2150

agtgcctatg aggacagtgt ccgccctgcc ctccgcaacg tgcagtccct          2200

gggcacggcg ggccctgcca tgtgctggta acgcatgcct gggccctgct          2250

gggctctccc actccaggcg gaccctgggg gccagtgaag gaagctcccg          2300

gaaagagcag agggagagcg ggtaggcggc tgtgtgactc tagtcttggc          2350

cccaggaagc gaaggaacaa aagaaactgg aaaggaagat gctttaggaa          2400

catgttttgc ttttttaaaa tatatatata tttataagag atcctttccc          2450

atttattctg ggaagatgtt tttcaaactc agagacaagg actttggttt          2500

ttgtaagaca aacgatgata tgaaggcctt ttgtaagaaa aaataaaaaa          2550

aaaaa                                                           2555
```

<210> SEQ ID NO 104
<211> LENGTH: 598
<212> TYPE: PRT
<213> ORGANISM: Homo sapiens

<400> SEQUENCE: 104

```
Met Cys Ser Arg Val Pro Leu Leu Leu Pro Leu Leu Leu Leu Leu
  1               5                  10                  15

Ala Leu Gly Pro Gly Val Gln Gly Cys Pro Ser Gly Cys Gln Cys
                 20                  25                  30
```

-continued

```
Ser Gln Pro Gln Thr Val Phe Cys Thr Ala Arg Gln Gly Thr Thr
                35                  40                  45

Val Pro Arg Asp Val Pro Pro Asp Thr Val Gly Leu Tyr Val Phe
                50                  55                  60

Glu Asn Gly Ile Thr Met Leu Asp Ala Ser Ser Phe Ala Gly Leu
                65                  70                  75

Pro Gly Leu Gln Leu Leu Asp Leu Ser Gln Asn Gln Ile Ala Ser
                80                  85                  90

Leu Arg Leu Pro Arg Leu Leu Leu Leu Asp Leu Ser His Asn Ser
                95                 100                 105

Leu Leu Ala Leu Glu Pro Gly Ile Leu Asp Thr Ala Asn Val Glu
               110                 115                 120

Ala Leu Arg Leu Ala Gly Leu Gly Leu Gln Gln Leu Asp Glu Gly
               125                 130                 135

Leu Phe Ser Arg Leu Arg Asn Leu His Asp Leu Asp Val Ser Asp
               140                 145                 150

Asn Gln Leu Glu Arg Val Pro Pro Val Ile Arg Gly Leu Arg Gly
               155                 160                 165

Leu Thr Arg Leu Arg Leu Ala Gly Asn Thr Arg Ile Ala Gln Leu
               170                 175                 180

Arg Pro Glu Asp Leu Ala Gly Leu Ala Ala Leu Gln Glu Leu Asp
               185                 190                 195

Val Ser Asn Leu Ser Leu Gln Ala Leu Pro Gly Asp Leu Ser Gly
               200                 205                 210

Leu Phe Pro Arg Leu Arg Leu Leu Ala Ala Ala Arg Asn Pro Phe
               215                 220                 225

Asn Cys Val Cys Pro Leu Ser Trp Phe Gly Pro Trp Val Arg Glu
               230                 235                 240

Ser His Val Thr Leu Ala Ser Pro Glu Glu Thr Arg Cys His Phe
               245                 250                 255

Pro Pro Lys Asn Ala Gly Arg Leu Leu Leu Glu Leu Asp Tyr Ala
               260                 265                 270

Asp Phe Gly Cys Pro Ala Thr Thr Thr Thr Ala Thr Val Pro Thr
               275                 280                 285

Thr Arg Pro Val Val Arg Glu Pro Thr Ala Leu Ser Ser Ser Leu
               290                 295                 300

Ala Pro Thr Trp Leu Ser Pro Thr Ala Pro Ala Thr Glu Ala Pro
               305                 310                 315

Ser Pro Pro Ser Thr Ala Pro Pro Thr Val Gly Pro Val Pro Gln
               320                 325                 330

Pro Gln Asp Cys Pro Pro Ser Thr Cys Leu Asn Gly Gly Thr Cys
               335                 340                 345

His Leu Gly Thr Arg His His Leu Ala Cys Leu Cys Pro Glu Gly
               350                 355                 360

Phe Thr Gly Leu Tyr Cys Glu Ser Gln Met Gly Gln Gly Thr Arg
               365                 370                 375

Pro Ser Pro Thr Pro Val Thr Pro Arg Pro Pro Arg Ser Leu Thr
               380                 385                 390

Leu Gly Ile Glu Pro Val Ser Pro Thr Ser Leu Arg Val Gly Leu
               395                 400                 405

Gln Arg Tyr Leu Gln Gly Ser Ser Val Gln Leu Arg Ser Leu Arg
               410                 415                 420

Leu Thr Tyr Arg Asn Leu Ser Gly Pro Asp Lys Arg Leu Val Thr
```

-continued

```
                425                 430                 435

Leu Arg Leu Pro Ala Ser Leu Ala Glu Tyr Thr Val Thr Gln Leu
                440                 445                 450

Arg Pro Asn Ala Thr Tyr Ser Val Cys Val Met Pro Leu Gly Pro
                455                 460                 465

Gly Arg Val Pro Glu Gly Glu Glu Ala Cys Gly Glu Ala His Thr
                470                 475                 480

Pro Pro Ala Val His Ser Asn His Ala Pro Val Thr Gln Ala Arg
                485                 490                 495

Glu Gly Asn Leu Pro Leu Leu Ile Ala Pro Ala Leu Ala Ala Val
                500                 505                 510

Leu Leu Ala Ala Leu Ala Ala Val Gly Ala Ala Tyr Cys Val Arg
                515                 520                 525

Arg Gly Arg Ala Met Ala Ala Ala Ala Gln Asp Lys Gly Gln Val
                530                 535                 540

Gly Pro Gly Ala Gly Pro Leu Glu Leu Glu Gly Val Lys Val Pro
                545                 550                 555

Leu Glu Pro Gly Pro Lys Ala Thr Glu Gly Gly Gly Glu Ala Leu
                560                 565                 570

Pro Ser Gly Ser Glu Cys Glu Val Pro Leu Met Gly Phe Pro Gly
                575                 580                 585

Pro Gly Leu Gln Ser Pro Leu His Ala Lys Pro Tyr Ile
                590                 595


<210> SEQ ID NO 105
<211> LENGTH: 647
<212> TYPE: DNA
<213> ORGANISM: Homo sapiens

<400> SEQUENCE: 105

cccacgcgtc cgaaggcaga caaaggttca tttgtaaaga agctccttcc                50

agcacctcct ctcttctcct tttgcccaaa ctcacccagt gagtgtgagc               100

atttaagaag catcctctgc caagaccaaa aggaaagaag aaaaagggcc               150

aaaagccaaa atgaaactga tggtacttgt tttcaccatt gggctaactt               200

tgctgctagg agttcaagcc atgcctgcaa atcgcctctc ttgctacaga               250

aagatactaa aagatcacaa ctgtcacaac cttccggaag gagtagctga               300

cctgacacag attgatgtca atgtccagga tcatttctgg gatgggaagg               350

gatgtgagat gatctgttac tgcaacttca gcgaattgct ctgctgccca               400

aaagacgttt tctttggacc aaagatctct ttcgtgattc cttgcaacaa               450

tcaatgagaa tcttcatgta ttctggagaa caccattcct gatttcccac               500

aaactgcact acatcagtat aactgcattt ctagtttcta tatagtgcaa               550

tagagcatag attctataaa ttcttacttg tctaagacaa gtaaatctgt               600

gttaaacaag tagtaataaa agttaattca atctaaaaaa  aaaaaaa                 647


<210> SEQ ID NO 106
<211> LENGTH: 98
<212> TYPE: PRT
<213> ORGANISM: Homo sapiens

<400> SEQUENCE: 106

Met Lys Leu Met Val Leu Val Phe Thr Ile Gly Leu Thr Leu Leu
  1               5                  10                  15
```

```
Leu Gly Val Gln Ala Met Pro Ala Asn Arg Leu Ser Cys Tyr Arg
                20                  25                  30

Lys Ile Leu Lys Asp His Asn Cys His Asn Leu Pro Glu Gly Val
                35                  40                  45

Ala Asp Leu Thr Gln Ile Asp Val Asn Val Gln Asp His Phe Trp
                50                  55                  60

Asp Gly Lys Gly Cys Glu Met Ile Cys Tyr Cys Asn Phe Ser Glu
                65                  70                  75

Leu Leu Cys Cys Pro Lys Asp Val Phe Phe Gly Pro Lys Ile Ser
                80                  85                  90

Phe Val Ile Pro Cys Asn Asn Gln
                95


<210> SEQ ID NO 107
<211> LENGTH: 972
<212> TYPE: DNA
<213> ORGANISM: Homo sapiens

<400> SEQUENCE: 107

agtgactgca gccttcctag atcccctcca ctcggtttct ctctttgcag                50

gagcaccggc agcaccagtg tgtgagggga gcaggcagcg gtcctagcca               100

gttccttgat cctgccagac cacccagccc ccggcacaga gctgctccac               150

aggcaccatg aggatcatgc tgctattcac agccatcctg gccttcagcc               200

tagctcagag ctttggggct gtctgtaagg agccacagga ggaggtggtt               250

cctggcgggg gccgcagcaa gagggatcca gatctctacc agctgctcca               300

gagactcttc aaaagccact catctctgga gggattgctc aaagccctga               350

gccaggctag cacagatcct aaggaatcaa catctcccga gaaacgtgac               400

atgcatgact tctttgtggg acttatgggc aagaggagcg tccagccaga               450

gggaaagaca ggacctttct taccttcagt gagggttcct cggccccttc               500

atcccaatca gcttggatcc acaggaaagt cttccctggg aacagaggag               550

cagagacctt tataagactc tcctacggat gtgaatcaag agaacgtccc               600

cagctttggc atcctcaagt atcccccgag agcagaatag gtactccact               650

tccggactcc tggactgcat taggaagacc tctttccctg tcccaatccc               700

caggtgcgca cgctcctgtt acccttctc ttccctgttc ttgtaacatt                750

cttgtgcttt gactccttct ccatcttttc tacctgaccc tggtgtggaa               800

actgcatagt gaatatcccc aaccccaatg ggcattgact gtagaatacc               850

ctagagttcc tgtagtgtcc tacattaaaa atataatgtc tctctctatt               900

cctcaacaat aaaggatttt tgcatatgaa aaaaaaaaaa aaaaaaaaaa               950

aaaaaaaaaa aaaaaaaaaa  aa                                            972


<210> SEQ ID NO 108
<211> LENGTH: 135
<212> TYPE: PRT
<213> ORGANISM: Homo sapiens

<400> SEQUENCE: 108

Met Arg Ile Met Leu Leu Phe Thr Ala Ile Leu Ala Phe Ser Leu
  1               5                  10                  15

Ala Gln Ser Phe Gly Ala Val Cys Lys Glu Pro Gln Glu Glu Val
```

-continued

```
                20                  25                  30

Val Pro Gly Gly Gly Arg Ser Lys Arg Asp Pro Asp Leu Tyr Gln
                35                  40                  45

Leu Leu Gln Arg Leu Phe Lys Ser His Ser Ser Leu Glu Gly Leu
                50                  55                  60

Leu Lys Ala Leu Ser Gln Ala Ser Thr Asp Pro Lys Glu Ser Thr
                65                  70                  75

Ser Pro Glu Lys Arg Asp Met His Asp Phe Phe Val Gly Leu Met
                80                  85                  90

Gly Lys Arg Ser Val Gln Pro Glu Gly Lys Thr Gly Pro Phe Leu
                95                 100                 105

Pro Ser Val Arg Val Pro Arg Pro Leu His Pro Asn Gln Leu Gly
               110                 115                 120

Ser Thr Gly Lys Ser Ser Leu Gly Thr Glu Glu Gln Arg Pro Leu
               125                 130                 135


<210> SEQ ID NO 109
<211> LENGTH: 1485
<212> TYPE: DNA
<213> ORGANISM: Homo sapiens

<400> SEQUENCE: 109

gcggccacac gcagctagcc ggagcccgga ccaggcgcct gtgcctcctc                50

ctcgtccctc gccgcgtccg cgaagcctgg agccggcggg agccccgcgc               100

tcgccatgtc gggcgagctc agcaacaggt tccaaggagg gaaggcgttc               150

ggcttgctca aagcccggca ggagaggagg ctggccgaga tcaaccggga               200

gtttctgtgt gaccagaagt acagtgatga agagaacctt ccagaaaagc               250

tcacagcctt caaagagaag tacatggagt ttgacctgaa caatgaaggc               300

gagattgacc tgatgtcttt aaagaggatg atggagaagc ttggtgtccc               350

caagacccac ctggagatga agaagatgat ctcagaggtg acaggagggg               400

tcagtgacac tatatcctac cgagactttg tgaacatgat gctggggaaa               450

cggtcggctg tcctcaagtt agtcatgatg tttgaaggaa aagccaacga               500

gagcagcccc aagccagttg gcccccctcc agagagagac attgctagcc               550

tgccctgagg accccgcctg gactccccag ccttcccacc ccatacctcc               600

ctcccgatct tgctgccctt cttgacacac tgtgatctct ctctctctca               650

tttgtttggt cattgagggt ttgtttgtgt tttcatcaat gtctttgtaa               700

agcacaaatt atctgcctta aaggggctct gggtcgggga atcctgagcc               750

ttgggtcccc tccctctctt cttccctcct tccccgctcc ctgtgcagaa               800

gggctgatat caaaccaaaa actagagggg gcagggccag ggcagggagg               850

cttccagcct gtgttcccct cacttggagg aaccagcact ctccatcctt               900

tcagaaagtc tccaagccaa gttcaggctc actgacctgg ctctgacgag               950

gaccccaggc cactctgaga agaccttgga gtagggacaa ggctgcaggg              1000

cctctttcgg gtttccttgg acagtgccat ggttccagtg ctctggtgtc              1050

acccaggaca cagccactcg gggccccgct gccccagctg atccccactc              1100

attccacacc tcttctcatc ctcagtgatg tgaaggtggg aaggaaagga              1150

gcttggcatt gggagccctt caagaaggta ccagaaggaa ccctccagtc              1200
```

-continued

```
ctgctctctg gccacacctg tgcaggcagc tgagaggcag cgtgcagccc          1250

tactgtccct tactggggca gcagagggct tcggaggcag aagtgaggcc          1300

tggggtttgg ggggaaaggt cagctcagtg ctgttccacc ttttagggag          1350

gatactgagg ggaccaggat gggagaatga ggagtaaaat gctcacggca          1400

aagtcagcag cactggtaag ccaagactga gaaatacaag gttgcttgtc          1450

tgaccccaat ctgcttgaaa aaaaaaaaaa  aaaaa                         1485


<210> SEQ ID NO 110
<211> LENGTH: 150
<212> TYPE: PRT
<213> ORGANISM: Homo sapiens

<400> SEQUENCE: 110

Met Ser Gly Glu Leu Ser Asn Arg Phe Gln Gly Gly Lys Ala Phe
  1               5                  10                  15

Gly Leu Leu Lys Ala Arg Gln Glu Arg Arg Leu Ala Glu Ile Asn
                 20                  25                  30

Arg Glu Phe Leu Cys Asp Gln Lys Tyr Ser Asp Glu Glu Asn Leu
                 35                  40                  45

Pro Glu Lys Leu Thr Ala Phe Lys Glu Lys Tyr Met Glu Phe Asp
                 50                  55                  60

Leu Asn Asn Glu Gly Glu Ile Asp Leu Met Ser Leu Lys Arg Met
                 65                  70                  75

Met Glu Lys Leu Gly Val Pro Lys Thr His Leu Glu Met Lys Lys
                 80                  85                  90

Met Ile Ser Glu Val Thr Gly Gly Val Ser Asp Thr Ile Ser Tyr
                 95                 100                 105

Arg Asp Phe Val Asn Met Met Leu Gly Lys Arg Ser Ala Val Leu
                110                 115                 120

Lys Leu Val Met Met Phe Glu Gly Lys Ala Asn Glu Ser Ser Pro
                125                 130                 135

Lys Pro Val Gly Pro Pro Pro Glu Arg Asp Ile Ala Ser Leu Pro
                140                 145                 150


<210> SEQ ID NO 111
<211> LENGTH: 537
<212> TYPE: DNA
<213> ORGANISM: Homo sapiens

<400> SEQUENCE: 111

taaaacagct acaatattcc agggccagtc acttgccatt tctcataaca           50

gcgtcagaga gaaagaactg actgaaacgt ttgagatgaa gaaagttctc          100

ctcctgatca cagccatctt ggcagtggct gttggtttcc cagtctctca          150

agaccaggaa cgagaaaaaa gaagtatcag tgacagcgat gaattagctt          200

cagggttttt tgtgttccct tacccatatc catttcgccc acttccacca          250

attccatttc caagatttcc atggtttaga cgtaattttc ctattccaat          300

acctgaatct gcccctacaa ctccccttcc tagcgaaaag taaacaagaa          350

ggataagtca cgataaacct ggtcacctga aattgaaatt gagccacttc          400

cttgaagaat caaaattcct gttaataaaa gaaaaacaaa tgtaattgaa          450

atagcacaca gcattctcta gtcaatatct ttagtgatct tctttaataa          500

acatgaaagc aaagattttg gtttcttaat  ttccaca                       537
```

<210> SEQ ID NO 112
<211> LENGTH: 85
<212> TYPE: PRT
<213> ORGANISM: Homo sapiens

<400> SEQUENCE: 112

```
Met Lys Lys Val Leu Leu Leu Ile Thr Ala Ile Leu Ala Val Ala
  1               5                  10                  15

Val Gly Phe Pro Val Ser Gln Asp Gln Glu Arg Glu Lys Arg Ser
                 20                  25                  30

Ile Ser Asp Ser Asp Glu Leu Ala Ser Gly Phe Phe Val Phe Pro
                 35                  40                  45

Tyr Pro Tyr Pro Phe Arg Pro Leu Pro Pro Ile Pro Phe Pro Arg
                 50                  55                  60

Phe Pro Trp Phe Arg Arg Asn Phe Pro Ile Pro Ile Pro Glu Ser
                 65                  70                  75

Ala Pro Thr Thr Pro Leu Pro Ser Glu Lys
                 80                  85
```

<210> SEQ ID NO 113
<211> LENGTH: 1686
<212> TYPE: DNA
<213> ORGANISM: Homo sapiens

<400> SEQUENCE: 113

```
ctcctcttaa catacttgca gctaaaacta aatattgctg cttggggacc        50

tccttctagc cttaaatttc agctcatcac cttcacctgc cttggtcatg       100

gctctgctat tctccttgat ccttgccatt tgcaccagac ctggattcct       150

agcgtctcca tctggagtgc ggctggtggg gggcctccac cgctgtgaag       200

ggcgggtgga ggtggaacag aaaggccagt ggggcaccgt gtgtgatgac       250

ggctgggaca ttaaggacgt ggctgtgttg tgccgggagc tgggctgtgg       300

agctgccagc ggaaccccta gtggtatttt gtatgagcca ccagcagaaa       350

aagagcaaaa ggtcctcatc caatcagtca gttgcacagg aacagaagat       400

acattggctc agtgtgagca agaagaagtt tatgattgtt cacatgatga       450

agatgctggg gcatcgtgtg agaacccaga gagctctttc tccccagtcc       500

cagagggtgt caggctggct gacggccctg ggcattgcaa gggacgcgtg       550

gaagtgaagc accagaacca gtggtatacc gtgtgccaga caggctggag       600

cctccgggcc gcaaaggtgg tgtgccggca gctgggatgt gggagggctg       650

tactgactca aaaacgctgc aacaagcatg cctatggccg aaaacccatc       700

tggctgagcc agatgtcatg ctcaggacga gaagcaaccc ttcaggattg       750

cccttctggg ccttggggga agaacacctg caaccatgat gaagacacgt       800

gggtcgaatg tgaagatccc tttgacttga gactagtagg aggagacaac       850

ctctgctctg ggcgactgga ggtgctgcac aagggcgtat ggggctctgt       900

ctgtgatgac aactggggag aaaaggagga ccaggtggta tgcaagcaac       950

tgggctgtgg gaagtccctc tctccctcct tcagagaccg gaaatgctat      1000

ggccctgggg ttggccgcat ctggctggat aatgttcgtt gctcagggga      1050

ggagcagtcc ctggagcagt gccagcacag attttggggg tttcacgact      1100
```

-continued

```
gcacccacca ggaagatgtg gctgtcatct gctcagtgta ggtgggcatc          1150

atctaatctg ttgagtgcct gaatagaaga aaaacacaga agaagggagc          1200

atttactgtc tacatgactg catgggatga acactgatct tcttctgccc          1250

ttggactggg acttatactt ggtgcccctg attctcaggc cttcagagtt          1300

ggatcagaac ttacaacatc aggtctagtt ctcaggccat cagacatagt          1350

ttggaactac atcaccacct ttcctatgtc tccacattgc acacagcaga          1400

ttcccagcct ccataattgt gtgtatcaac tacttaaata cattctcaca          1450

cacacacaca cacacacaca cacacacaca cacacataca ccatttgtcc          1500

tgtttctctg aagaactctg acaaaataca gattttggta ctgaaagaga          1550

ttctagagga acggaatttt aaggataaat tttctgaatt ggttatgggg          1600

tttctgaaat tggctctata atctaattag atataaaatt ctggtaactt          1650

tatttacaat aataaagata gcactatgtg  ttcaaa                        1686
```

<210> SEQ ID NO 114
<211> LENGTH: 347
<212> TYPE: PRT
<213> ORGANISM: Homo sapiens

<400> SEQUENCE: 114

```
Met Ala Leu Leu Phe Ser Leu Ile Leu Ala Ile Cys Thr Arg Pro
  1               5                  10                  15

Gly Phe Leu Ala Ser Pro Ser Gly Val Arg Leu Val Gly Gly Leu
                 20                  25                  30

His Arg Cys Glu Gly Arg Val Glu Val Glu Gln Lys Gly Gln Trp
                 35                  40                  45

Gly Thr Val Cys Asp Asp Gly Trp Asp Ile Lys Asp Val Ala Val
                 50                  55                  60

Leu Cys Arg Glu Leu Gly Cys Gly Ala Ala Ser Gly Thr Pro Ser
                 65                  70                  75

Gly Ile Leu Tyr Glu Pro Pro Ala Glu Lys Glu Gln Lys Val Leu
                 80                  85                  90

Ile Gln Ser Val Ser Cys Thr Gly Thr Glu Asp Thr Leu Ala Gln
                 95                 100                 105

Cys Glu Gln Glu Glu Val Tyr Asp Cys Ser His Asp Glu Asp Ala
                110                 115                 120

Gly Ala Ser Cys Glu Asn Pro Glu Ser Ser Phe Ser Pro Val Pro
                125                 130                 135

Glu Gly Val Arg Leu Ala Asp Gly Pro Gly His Cys Lys Gly Arg
                140                 145                 150

Val Glu Val Lys His Gln Asn Gln Trp Tyr Thr Val Cys Gln Thr
                155                 160                 165

Gly Trp Ser Leu Arg Ala Ala Lys Val Val Cys Arg Gln Leu Gly
                170                 175                 180

Cys Gly Arg Ala Val Leu Thr Gln Lys Arg Cys Asn Lys His Ala
                185                 190                 195

Tyr Gly Arg Lys Pro Ile Trp Leu Ser Gln Met Ser Cys Ser Gly
                200                 205                 210

Arg Glu Ala Thr Leu Gln Asp Cys Pro Ser Gly Pro Trp Gly Lys
                215                 220                 225

Asn Thr Cys Asn His Asp Glu Asp Thr Trp Val Glu Cys Glu Asp
                230                 235                 240
```

```
Pro Phe Asp Leu Arg Leu Val Gly Gly Asp Asn Leu Cys Ser Gly
                245                 250                 255

Arg Leu Glu Val Leu His Lys Gly Val Trp Gly Ser Val Cys Asp
                260                 265                 270

Asp Asn Trp Gly Glu Lys Glu Asp Gln Val Val Cys Lys Gln Leu
                275                 280                 285

Gly Cys Gly Lys Ser Leu Ser Pro Ser Phe Arg Asp Arg Lys Cys
                290                 295                 300

Tyr Gly Pro Gly Val Gly Arg Ile Trp Leu Asp Asn Val Arg Cys
                305                 310                 315

Ser Gly Glu Glu Gln Ser Leu Glu Gln Cys Gln His Arg Phe Trp
                320                 325                 330

Gly Phe His Asp Cys Thr His Gln Glu Asp Val Ala Val Ile Cys
                335                 340                 345

Ser Val


<210> SEQ ID NO 115
<211> LENGTH: 728
<212> TYPE: DNA
<213> ORGANISM: Homo sapiens

<400> SEQUENCE: 115

catttccaac aagagcactg gccaagtcag cttcttctga gagagtctct                50

agaagacatg atgctacact cagctttggg tctctgcctc ttactcgtca               100

cagtttcttc caaccttgcc attgcaataa aaaaggaaaa gaggcctcct               150

cagacactct caagaggatg gggagatgac atcacttggg tacaaactta               200

tgaagaaggt ctcttttatg ctcaaaaaag taagaagcca ttaatggtta               250

ttcatcacct ggaggattgt caatactctc aagcactaaa gaaagtattt               300

gcccaaaatg aagaaataca agaaatggct cagaataagt tcatcatgct               350

aaaccttatg catgaaacca ctgataagaa tttatcacct gatgggcaat               400

atgtgcctag aatcatgttt gtagaccctt ctttaacagt tagagctgac               450

atagctggaa gatactctaa cagattgtac acatatgagc ctcgggattt               500

acccctattg atagaaaaca tgaagaaagc attaagactt attcagtcag               550

agctataaga gatgatggaa aaaagccttc acttcaaaga agtcaaattt               600

catgaagaaa acctctggca cattgacaaa tactaaatgt gcaagtatat               650

agattttgta atattactat ttagtttttt taatgtgttt gcaatagtct               700

tattaaaata aatgtttttt  aaatctga                                      728


<210> SEQ ID NO 116
<211> LENGTH: 166
<212> TYPE: PRT
<213> ORGANISM: Homo sapiens

<400> SEQUENCE: 116

Met Met Leu His Ser Ala Leu Gly Leu Cys Leu Leu Leu Val Thr
  1               5                  10                  15

Val Ser Ser Asn Leu Ala Ile Ala Ile Lys Lys Glu Lys Arg Pro
                 20                  25                  30

Pro Gln Thr Leu Ser Arg Gly Trp Gly Asp Asp Ile Thr Trp Val
                 35                  40                  45
```

-continued

```
Gln Thr Tyr Glu Glu Gly Leu Phe Tyr Ala Gln Lys Ser Lys Lys
                50                  55                  60

Pro Leu Met Val Ile His His Leu Glu Asp Cys Gln Tyr Ser Gln
                65                  70                  75

Ala Leu Lys Lys Val Phe Ala Gln Asn Glu Glu Ile Gln Glu Met
                80                  85                  90

Ala Gln Asn Lys Phe Ile Met Leu Asn Leu Met His Glu Thr Thr
                95                 100                 105

Asp Lys Asn Leu Ser Pro Asp Gly Gln Tyr Val Pro Arg Ile Met
               110                 115                 120

Phe Val Asp Pro Ser Leu Thr Val Arg Ala Asp Ile Ala Gly Arg
               125                 130                 135

Tyr Ser Asn Arg Leu Tyr Thr Tyr Glu Pro Arg Asp Leu Pro Leu
               140                 145                 150

Leu Ile Glu Asn Met Lys Lys Ala Leu Arg Leu Ile Gln Ser Glu
               155                 160                 165

Leu


<210> SEQ ID NO 117
<211> LENGTH: 2395
<212> TYPE: DNA
<213> ORGANISM: Homo sapiens

<400> SEQUENCE: 117

cctggagccg gaagcgcggc tgcagcaggg cgaggctcca ggtggggtcg                50

gttccgcatc cagcctagcg tgtccacgat gcggctgggc tccgggactt               100

tcgctacctg ttgcgtagcg atcgaggtgc tagggatcgc ggtcttcctt               150

cggggattct tcccggctcc cgttcgttcc tctgccagag cggaacacgg               200

agcggagccc ccagcgcccg aaccctcggc tggagccagt tctaactgga               250

ccacgctgcc accacctctc ttcagtaaag ttgttattgt tctgatagat               300

gccttgagag atgattttgt gtttgggtca aagggtgtga aatttatgcc               350

ctacacaact taccttgtgg aaaaaggagc atctcacagt tttgtggctg               400

aagcaaagcc acctacagtt actatgcctc gaatcaaggc attgatgacg               450

gggagccttc ctggctttgt cgacgtcatc aggaacctca attctcctgc               500

actgctggaa gacagtgtga taagacaagc aaaagcagct ggaaaaagaa               550

tagtctttta tggagatgaa acctgggtta aattattccc aaagcatttt               600

gtggaatatg atggaacaac ctcatttttc gtgtcagatt acacagaggt               650

ggataataat gtcacgaggc atttggataa agtattaaaa agaggagatt               700

gggacatatt aatcctccac tacctggggc tggaccacat tggccacatt               750

tcagggccca acagcccccct gattgggcag aagctgagcg agatggacag               800

cgtgctgatg aagatccaca cctcactgca gtcgaaggag agagagacgc               850

ctttacccaa tttgctggtt ctttgtggtg accatggcat gtctgaaaca               900

ggaagtcacg gggcctcctc caccgaggag gtgaatacac ctctgatttt               950

aatcagttct gcgtttgaaa ggaaacccgg tgatatccga catccaaagc              1000

acgtccaata gacggatgtg gctgcgacac tggcgatagc acttggctta              1050

ccgattccaa aagacagtgt agggagcctc ctattcccag ttgtggaagg              1100

aagaccaatg agagagcagt tgagattttt acatttgaat acagtgcagc              1150
```

-continued

```
ttagtaaact gttgcaagag aatgtgccgt catatgaaaa agatcctggg          1200

tttgagcagt ttaaaatgtc agaaagattg catgggaact ggatcagact          1250

gtacttggag gaaaagcatt cagaagtcct attcaacctg ggctccaagg          1300

ttctcaggca gtacctggat gctctgaaga cgctgagctt gtccctgagt          1350

gcacaagtgg cccagttctc accctgctcc tgctcagcgt cccacaggca          1400

ctgcacagaa aggctgagct ggaagtccca ctgtcatctc ctgggttttc          1450

tctgctcttt tatttggtga tcctggttct ttcggccgtt cacgtcattg          1500

tgtgcacctc agctgaaagt tcgtgctact tctgtggcct ctcgtggctg          1550

gcggcaggct gcctttcgtt taccagactc tggttgaaca cctggtgtgt          1600

gccaagtgct ggcagtgccc tggacagggg gcctcaggga aggacgtgga          1650

gcagccttat cccaggcctc tgggtgtccc gacacaggtg ttcacatctg          1700

tgctgtcagg tcagatgcct cagttcttgg aaagctaggt tcctgcgact          1750

gttaccaagg tgattgtaaa gagctggcgg tcacagagga acaagccccc          1800

cagctgaggg ggtgtgtgaa tcggacagcc tcccagcaga ggtgtgggag          1850

ctgcagctga gggaagaaga gacaatcggc ctggacactc aggagggtca          1900

aaaggagact tggtcgcacc actcatcctg ccacccccag aatgcatcct          1950

gcctcatcag gtccagattt ctttccaagg cggacgtttt ctgttggaat          2000

tcttagtcct tggcctcgga caccttcatt cgttagctgg ggagtggtgg          2050

tgaggcagtg aagaagaggc ggatggtcac actcagatcc acagagccca          2100

ggatcaaggg acccactgca gtggcagcag gactgttggg cccccacccc          2150

aaccctgcac agccctcatc ccctcttggc ttgagccgtc agaggccctg          2200

tgctgagtgt ctgaccgaga cactcacagc tttgtcatca gggcacaggc          2250

ttcctcggag ccaggatgat ctgtgccacg cttgcacctc gggcccatct          2300

gggctcatgc tctctctcct gctattgaat tagtacctag ctgcacacag          2350

tatgtagtta ccaaaagaat aaacggcaat aattgagaaa  aaaaa              2395
```

<210> SEQ ID NO 118
<211> LENGTH: 310
<212> TYPE: PRT
<213> ORGANISM: Homo sapiens

<400> SEQUENCE: 118

```
Met Arg Leu Gly Ser Gly Thr Phe Ala Thr Cys Cys Val Ala Ile
  1               5                  10                  15

Glu Val Leu Gly Ile Ala Val Phe Leu Arg Gly Phe Phe Pro Ala
                 20                  25                  30

Pro Val Arg Ser Ser Ala Arg Ala Glu His Gly Ala Glu Pro Pro
                 35                  40                  45

Ala Pro Glu Pro Ser Ala Gly Ala Ser Ser Asn Trp Thr Thr Leu
                 50                  55                  60

Pro Pro Pro Leu Phe Ser Lys Val Val Ile Val Leu Ile Asp Ala
                 65                  70                  75

Leu Arg Asp Asp Phe Val Phe Gly Ser Lys Gly Val Lys Phe Met
                 80                  85                  90

Pro Tyr Thr Thr Tyr Leu Val Glu Lys Gly Ala Ser His Ser Phe
                 95                 100                 105
```

-continued

```
Val Ala Glu Ala Lys Pro Pro Thr Val Thr Met Pro Arg Ile Lys
                110                 115                 120

Ala Leu Met Thr Gly Ser Leu Pro Gly Phe Val Asp Val Ile Arg
                125                 130                 135

Asn Leu Asn Ser Pro Ala Leu Leu Glu Asp Ser Val Ile Arg Gln
                140                 145                 150

Ala Lys Ala Ala Gly Lys Arg Ile Val Phe Tyr Gly Asp Glu Thr
                155                 160                 165

Trp Val Lys Leu Phe Pro Lys His Phe Val Glu Tyr Asp Gly Thr
                170                 175                 180

Thr Ser Phe Phe Val Ser Asp Tyr Thr Glu Val Asp Asn Asn Val
                185                 190                 195

Thr Arg His Leu Asp Lys Val Leu Lys Arg Gly Asp Trp Asp Ile
                200                 205                 210

Leu Ile Leu His Tyr Leu Gly Leu Asp His Ile Gly His Ile Ser
                215                 220                 225

Gly Pro Asn Ser Pro Leu Ile Gly Gln Lys Leu Ser Glu Met Asp
                230                 235                 240

Ser Val Leu Met Lys Ile His Thr Ser Leu Gln Ser Lys Glu Arg
                245                 250                 255

Glu Thr Pro Leu Pro Asn Leu Leu Val Leu Cys Gly Asp His Gly
                260                 265                 270

Met Ser Glu Thr Gly Ser His Gly Ala Ser Ser Thr Glu Glu Val
                275                 280                 285

Asn Thr Pro Leu Ile Leu Ile Ser Ser Ala Phe Glu Arg Lys Pro
                290                 295                 300

Gly Asp Ile Arg His Pro Lys His Val Gln
                305                 310


<210> SEQ ID NO 119
<211> LENGTH: 1333
<212> TYPE: DNA
<213> ORGANISM: Homo sapiens

<400> SEQUENCE: 119

gcccacgcgt ccgatggcgt tcacgttcgc ggccttctgc tacatgctgg                50

cgctgctgct cactgccgcg ctcatcttct tcgccatttg gcacattata               100

gcatttgatg agctgaagac tgattacaag aatcctatag accagtgtaa               150

taccctgaat ccccttgtac tcccagagta cctcatccac gctttcttct               200

gtgtcatgtt tctttgtgca gcagagtggc ttacactggg tctcaatatg               250

cccctcttgg catatcatat ttggaggtat atgagtagac cagtgatgag               300

tggcccagga ctctatgacc ctacaaccat catgaatgca gatattctag               350

catattgtca gaaggaagga tggtgcaaat tagcttttta tcttctagca               400

tttttttact acctatatgg catgatctat gttttggtga gctcttagaa               450

caacacacag aagaattggt ccagttaagt gcatgcaaaa agccaccaaa               500

tgaagggatt ctatccagca agatcctgtc caagagtagc ctgtggaatc               550

tgatcagtta ctttaaaaaa tgactcctta ttttttaaat gtttccacat               600

ttttgcttgt ggaaagactg ttttcatatg ttatactcag ataaagattt               650

taaatggtat tacgtataaa ttaatataaa atgattacct ctggtgttga               700
```

-continued

```
caggtttgaa cttgcacttc ttaaggaaca gccataatcc tctgaatgat              750

gcattaatta ctgactgtcc tagtacattg gaagcttttg tttataggaa              800

cttgtagggc tcattttggt ttcattgaaa cagtatctaa ttataaatta              850

gctgtagata tcaggtgctt ctgatgaagt gaaaatgtat atctgactag              900

tgggaaactt catgggtttc ctcatctgtc atgtcgatga ttatatatgg              950

atacatttac aaaaataaaa agcgggaatt ttcccttcgc ttgaatatta             1000

tccctgtata ttgcatgaat gagagatttc ccatatttcc atcagagtaa             1050

taaatatact tgctttaatt cttaagcata agtaaacatg atataaaaat             1100

atatgctgaa ttacttgtga agaatgcatt taaagctatt ttaaatgtgt             1150

ttttatttgt aagacattac ttattaagaa attggttatt atgcttactg             1200

ttctaatctg gtggtaaagg tattcttaag aatttgcagg tactacagat             1250

tttcaaaact gaatgagaga aaattgtata accatcctgc tgttccttta             1300

gtgcaataca ataaaactct gaaattaaga  ctc                              1333
```

<210> SEQ ID NO 120
<211> LENGTH: 144
<212> TYPE: PRT
<213> ORGANISM: Homo sapiens

<400> SEQUENCE: 120

```
Met Ala Phe Thr Phe Ala Ala Phe Cys Tyr Met Leu Ala Leu Leu
  1               5                  10                  15

Leu Thr Ala Ala Leu Ile Phe Phe Ala Ile Trp His Ile Ile Ala
                 20                  25                  30

Phe Asp Glu Leu Lys Thr Asp Tyr Lys Asn Pro Ile Asp Gln Cys
                 35                  40                  45

Asn Thr Leu Asn Pro Leu Val Leu Pro Glu Tyr Leu Ile His Ala
                 50                  55                  60

Phe Phe Cys Val Met Phe Leu Cys Ala Ala Glu Trp Leu Thr Leu
                 65                  70                  75

Gly Leu Asn Met Pro Leu Leu Ala Tyr His Ile Trp Arg Tyr Met
                 80                  85                  90

Ser Arg Pro Val Met Ser Gly Pro Gly Leu Tyr Asp Pro Thr Thr
                 95                 100                 105

Ile Met Asn Ala Asp Ile Leu Ala Tyr Cys Gln Lys Glu Gly Trp
                110                 115                 120

Cys Lys Leu Ala Phe Tyr Leu Leu Ala Phe Phe Tyr Tyr Leu Tyr
                125                 130                 135

Gly Met Ile Tyr Val Leu Val Ser Ser
                140
```

<210> SEQ ID NO 121
<211> LENGTH: 1838
<212> TYPE: DNA
<213> ORGANISM: Homo sapiens

<400> SEQUENCE: 121

```
cggacgcgtg ggcggacgcg tgggcggccc acggcgcccg cgggctgggg               50

cggtcgcttc ttccttctcc gtggcctacg agggtcccca gcctgggtaa              100

agatggcccc atggcccccg aagggcctag tcccagctgt gctctggggc              150

ctcagcctct tcctcaacct cccaggacct atctggctcc agccctctcc              200
```

-continued

```
acctccccag tcttctcccc cgcctcagcc ccatccgtgt catacctgcc          250
ggggactggt tgacagcttt aacaagggcc tggagagaac catccgggac          300
aactttggag gtggaaacac tgcctgggag gaagagaatt tgtccaaata          350
caaagacagt gagacccgcc tggtagaggt gctggagggt gtgtgcagca          400
agtcagactt cgagtgccac cgcctgctgg agctgagtga ggagctggtg          450
gagagctggt ggtttcacaa gcagcaggag gccccggacc tcttccagtg          500
gctgtgctca gattccctga agctctgctg ccccgcaggc accttcgggc          550
cctcctgcct tccctgtcct gggggaacag agaggccctg cggtggctac          600
gggcagtgtg aaggagaagg gacacgaggg ggcagcgggc actgtgactg          650
ccaagccggc tacgggggtg aggcctgtgg ccagtgtggc cttggctact          700
ttgaggcaga acgcaacgcc agccatctgg tatgttcggc ttgttttggc          750
ccctgtgccc gatgctcagg acctgaggaa tcaaactgtt tgcaatgcaa          800
gaagggctgg gccctgcatc acctcaagtg tgtagacatt gatgagtgtg          850
gcacagaggg agccaactgt ggagctgacc aattctgcgt gaacactgag          900
ggctcctatg agtgccgaga ctgtgccaag gcctgcctag gctgcatggg          950
ggcagggcca ggtcgctgta agaagtgtag ccctggctat cagcaggtgg         1000
gctccaagtg tctcgatgtg gatgagtgtg agacagaggt gtgtccggga         1050
gagaacaagc agtgtgaaaa caccgagggc ggttatcgct gcatctgtgc         1100
cgagggctac aagcagatgg aaggcatctg tgtgaaggag cagatcccag         1150
agtcagcagg cttcttctca gagatgacag aagacgagtt ggtggtgctg         1200
cagcagatgt tctttggcat catcatctgt gcactggcca cgctggctgc         1250
taagggcgac ttggtgttca ccgccatctt cattggggct gtggcggcca         1300
tgactggcta ctggttgtca gagcgcagtg accgtgtgct ggagggcttc         1350
atcaagggca gataatcgcg gccaccacct gtaggacctc ctcccaccca         1400
cgctgccccc agagcttggg ctgccctcct gctggacact caggacagct         1450
tggtttattt ttgagagtgg ggtaagcacc cctacctgcc ttacagagca         1500
gcccaggtac ccaggcccgg gcagacaagg cccctggggt aaaaagtagc         1550
cctgaaggtg gataccatga gctcttcacc tggcggggac tggcaggctt         1600
cacaatgtgt gaatttcaaa agtttttcct taatggtggc tgctagagct         1650
ttggcccctg cttaggatta ggtggtcctc acaggggtgg ggccatcaca         1700
gctccctcct gccagctgca tgctgccagt tcctgttctg tgttcaccac         1750
atccccacac cccattgcca cttatttatt catctcagga aataaagaaa         1800
ggtcttggaa agttaaaaaa aaaaaaaaaa  aaaaaaaa                     1838
```

<210> SEQ ID NO 122
<211> LENGTH: 420
<212> TYPE: PRT
<213> ORGANISM: Homo sapiens

<400> SEQUENCE: 122

```
Met Ala Pro Trp Pro Pro Lys Gly Leu Val Pro Ala Val Leu Trp
  1               5                  10                  15

Gly Leu Ser Leu Phe Leu Asn Leu Pro Gly Pro Ile Trp Leu Gln
```

-continued

```
                20                  25                  30

Pro Ser Pro Pro Pro Gln Ser Ser Pro Pro Pro Gln Pro His Pro
                35                  40                  45

Cys His Thr Cys Arg Gly Leu Val Asp Ser Phe Asn Lys Gly Leu
                50                  55                  60

Glu Arg Thr Ile Arg Asp Asn Phe Gly Gly Gly Asn Thr Ala Trp
                65                  70                  75

Glu Glu Glu Asn Leu Ser Lys Tyr Lys Asp Ser Glu Thr Arg Leu
                80                  85                  90

Val Glu Val Leu Glu Gly Val Cys Ser Lys Ser Asp Phe Glu Cys
                95                 100                 105

His Arg Leu Leu Glu Leu Ser Glu Glu Leu Val Glu Ser Trp Trp
               110                 115                 120

Phe His Lys Gln Gln Glu Ala Pro Asp Leu Phe Gln Trp Leu Cys
               125                 130                 135

Ser Asp Ser Leu Lys Leu Cys Cys Pro Ala Gly Thr Phe Gly Pro
               140                 145                 150

Ser Cys Leu Pro Cys Pro Gly Gly Thr Glu Arg Pro Cys Gly Gly
               155                 160                 165

Tyr Gly Gln Cys Glu Gly Glu Gly Thr Arg Gly Gly Ser Gly His
               170                 175                 180

Cys Asp Cys Gln Ala Gly Tyr Gly Gly Glu Ala Cys Gly Gln Cys
               185                 190                 195

Gly Leu Gly Tyr Phe Glu Ala Glu Arg Asn Ala Ser His Leu Val
               200                 205                 210

Cys Ser Ala Cys Phe Gly Pro Cys Ala Arg Cys Ser Gly Pro Glu
               215                 220                 225

Glu Ser Asn Cys Leu Gln Cys Lys Lys Gly Trp Ala Leu His His
               230                 235                 240

Leu Lys Cys Val Asp Ile Asp Glu Cys Gly Thr Glu Gly Ala Asn
               245                 250                 255

Cys Gly Ala Asp Gln Phe Cys Val Asn Thr Glu Gly Ser Tyr Glu
               260                 265                 270

Cys Arg Asp Cys Ala Lys Ala Cys Leu Gly Cys Met Gly Ala Gly
               275                 280                 285

Pro Gly Arg Cys Lys Lys Cys Ser Pro Gly Tyr Gln Gln Val Gly
               290                 295                 300

Ser Lys Cys Leu Asp Val Asp Glu Cys Glu Thr Glu Val Cys Pro
               305                 310                 315

Gly Glu Asn Lys Gln Cys Glu Asn Thr Glu Gly Gly Tyr Arg Cys
               320                 325                 330

Ile Cys Ala Glu Gly Tyr Lys Gln Met Glu Gly Ile Cys Val Lys
               335                 340                 345

Glu Gln Ile Pro Glu Ser Ala Gly Phe Phe Ser Glu Met Thr Glu
               350                 355                 360

Asp Glu Leu Val Val Leu Gln Gln Met Phe Phe Gly Ile Ile Ile
               365                 370                 375

Cys Ala Leu Ala Thr Leu Ala Ala Lys Gly Asp Leu Val Phe Thr
               380                 385                 390

Ala Ile Phe Ile Gly Ala Val Ala Ala Met Thr Gly Tyr Trp Leu
               395                 400                 405

Ser Glu Arg Ser Asp Arg Val Leu Glu Gly Phe Ile Lys Gly Arg
               410                 415                 420
```

-continued

<210> SEQ ID NO 123
<211> LENGTH: 3401
<212> TYPE: DNA
<213> ORGANISM: Homo sapiens

<400> SEQUENCE: 123 gcaagccaag gcgctgtttg agaaggtgaa gaagttccgg acccatgtgg 50 aggaggggga cattgtgtac cgcctctaca tgcggcagac catcatcaag 100 gtgatcaagt tcatcctcat catctgctac accgtctact acgtgcacaa 150 catcaagttc gacgtggact gcaccgtgga cattgagagc ctgacgggct 200 accgcaccta ccgctgtgcc cacccccctgg ccacactctt caagatcctg 250 gcgtccttct acatcagcct agtcatcttc tacggcctca tctgcatgta 300 cacactgtgg tggatgctac ggcgctccct caagaagtac tcgtttgagt 350 cgatccgtga ggagagcagc tacagcgaca tccccgacgt caagaacgac 400 ttcgccttca tgctgcacct cattgaccaa tacgacccgc tctactccaa 450 gcgcttcgcc gtcttcctgt cggaggtgag tgagaacaag ctgcggcagc 500 tgaacctcaa caacgagtgg acgctggaca agctccggca gcggctcacc 550 aagaacgcgc aggacaagct ggagctgcac ctgttcatgc tcagtggcat 600 ccctgacact gtgtttgacc tggtggagct ggaggtcctc aagctggagc 650 tgatccccga cgtgaccatc ccgcccagca ttgcccagct cacgggcctc 700 aaggagctgt ggctctacca cacagcggcc aagattgaag cgcctgcgct 750 ggccttcctg cgcgagaacc tgcgggcgct gcacatcaag ttcaccgaca 800 tcaaggagat cccgctgtgg atctatagcc tgaagacact ggaggagctg 850 cacctgacgg gcaacctgag cgcggagaac aaccgctaca tcgtcatcga 900 cgggctgcgg gagctcaaac gcctcaaggt gctgcggctc aagagcaacc 950 taagcaagct gccacaggtg gtcacagatg tgggcgtgca cctgcagaag 1000 ctgtccatca acaatgaggg caccaagctc atcgtcctca acagcctcaa 1050 gaagatggcg aacctgactg agctggagct gatccgctgc gacctggagc 1100 gcatccccca ctccatcttc agcctccaca acctgcagga gattgacctc 1150 aaggacaaca acctcaagac catcgaggag atcatcagct tccagcacct 1200 gcaccgcctc acctgcctta agctgtggta caaccacatc gcctacatcc 1250 ccatccagat cggcaacctc accaacctgg agcgcctcta cctgaaccgc 1300 aacaagatcg agaagatccc cacccagctc ttctactgcc gcaagctgcg 1350 ctacctggac ctcagccaca acaacctgac cttcctccct gccgacatcg 1400 gcctcctgca gaacctccag aacctagcca tcacggccaa ccggatcgag 1450 acgctccctc cggagctctt ccagtgccgg aagctgcggg ccctgcacct 1500 gggcaacaac gtgctgcagt cactgccctc cagggtgggc gagctgacca 1550 acctgacgca gatcgagctg cggggcaacc ggctggagtg cctgcctgtg 1600 gagctgggcg agtgcccact gctcaagcgc agcggcttgg tggtggagga 1650 ggacctgttc aacacactgc cacccgaggt gaaggagcgg ctgtggaggg 1700 ctgacaagga gcaggcctga gcgaggccgg cccagcacag caagcagcag 1750

-continued

```
gaccgctgcc cagtcctcag gcccggaggg gcaggcctag cttctcccag          1800
aactcccgga cagccaggac agcctcgcgg ctgggcagga gcctggggcc          1850
gcttgtgagt caggccagag cgagaggaca gtatctgtgg ggctggcccc          1900
ttttctccct ctgagactca cgtcccccag ggcaagtgct tgtggaggag          1950
agcaagtctc aagagcgcag tatttggata atcagggtct cctccctgga          2000
ggccagctct gccccagggg ctgagctgcc accagaggtc ctgggaccct          2050
cactttagtt cttggtattt atttttctcc atctcccacc tccttcatcc          2100
agataactta tacattccca agaaagttca gcccagatgg aaggtgttca          2150
gggaaaggtg ggctgccttt tccccttgtc cttatttagc gatgccgccg          2200
ggcatttaac acccacctgg acttcagcag agtggtccgg ggcgaaccag          2250
ccatgggacg gtcacccagc agtgccgggc tgggctctgc ggtgcggtcc          2300
acgggagagc aggcctccag ctggaaaggc caggcctgga gcttgcctct          2350
tcagtttttg tggcagtttt agtttttttgt tttttttttt tttaatcaaa          2400
aaacaatttt ttttaaaaaa aagctttgaa aatggatggt ttgggtatta          2450
aaaagaaaaa aaaaacttaa aaaaaaaaag acactaacgg ccagtgagtt          2500
ggagtctcag ggcagggtgg cagtttccct tgagcaaagc agccagacgt          2550
tgaactgtgt ttcctttccc tgggcgcagg gtgcagggtg tcttccggat          2600
ctggtgtgac cttggtccag gagttctatt tgttcctggg gagggaggtt          2650
tttttgtttg ttttttgggt ttttttggtg tcttgttttc tttctcctcc          2700
atgtgtcttg gcaggcactc atttctgtgg ctgtcggcca gagggaatgt          2750
tctggagctg ccaaggaggg aggagactcg ggttggctaa tccccggatg          2800
aacggtgctc cattcgcacc tcccctcctc gtgcctgccc tgcctctcca          2850
cgcacagtgt taaggagcca agaggagcca cttcgcccag actttgtttc          2900
cccacctcct gcggcatggg tgtgtccagt gccaccgctg gcctccgctg          2950
cttccatcag ccctgtcgcc acctggtcct tcatgaagag cagacactta          3000
gaggctggtc gggaatgggg aggtcgcccc tgggagggca ggcgttggtt          3050
ccaagccggt tcccgtccct ggcgcctgga gtgcacacag cccagtcggc          3100
acctggtggc tggaagccaa cctgctttag atcactcggg tccccacctt          3150
agaagggtcc ccgccttaga tcaatcacgt ggacactaag gcacgtttta          3200
gagtctcttg tcttaatgat tatgtccatc cgtctgtccg tccatttgtg          3250
ttttctgcgt cgtgtcattg gatataatcc tcagaaataa tgcacactag          3300
cctctgacaa ccatgaagca aaaatccgtt acatgtgggt ctgaacttgt          3350
agactcggtc acagtatcaa ataaaatcta taacagaaaa aaaaaaaaaa          3400
a                                                               3401
```

<210> SEQ ID NO 124
<211> LENGTH: 546
<212> TYPE: PRT
<213> ORGANISM: Homo sapiens

<400> SEQUENCE: 124

```
Met Arg Gln Thr Ile Ile Lys Val Ile Lys Phe Ile Leu Ile Ile
  1               5                  10                  15
```

-continued

```
Cys Tyr Thr Val Tyr Tyr Val His Asn Ile Lys Phe Asp Val Asp
                20                  25                  30

Cys Thr Val Asp Ile Glu Ser Leu Thr Gly Tyr Arg Thr Tyr Arg
                35                  40                  45

Cys Ala His Pro Leu Ala Thr Leu Phe Lys Ile Leu Ala Ser Phe
                50                  55                  60

Tyr Ile Ser Leu Val Ile Phe Tyr Gly Leu Ile Cys Met Tyr Thr
                65                  70                  75

Leu Trp Trp Met Leu Arg Arg Ser Leu Lys Lys Tyr Ser Phe Glu
                80                  85                  90

Ser Ile Arg Glu Glu Ser Ser Tyr Ser Asp Ile Pro Asp Val Lys
                95                 100                 105

Asn Asp Phe Ala Phe Met Leu His Leu Ile Asp Gln Tyr Asp Pro
               110                 115                 120

Leu Tyr Ser Lys Arg Phe Ala Val Phe Leu Ser Glu Val Ser Glu
               125                 130                 135

Asn Lys Leu Arg Gln Leu Asn Leu Asn Asn Glu Trp Thr Leu Asp
               140                 145                 150

Lys Leu Arg Gln Arg Leu Thr Lys Asn Ala Gln Asp Lys Leu Glu
               155                 160                 165

Leu His Leu Phe Met Leu Ser Gly Ile Pro Asp Thr Val Phe Asp
               170                 175                 180

Leu Val Glu Leu Glu Val Leu Lys Leu Glu Leu Ile Pro Asp Val
               185                 190                 195

Thr Ile Pro Pro Ser Ile Ala Gln Leu Thr Gly Leu Lys Glu Leu
               200                 205                 210

Trp Leu Tyr His Thr Ala Ala Lys Ile Glu Ala Pro Ala Leu Ala
               215                 220                 225

Phe Leu Arg Glu Asn Leu Arg Ala Leu His Ile Lys Phe Thr Asp
               230                 235                 240

Ile Lys Glu Ile Pro Leu Trp Ile Tyr Ser Leu Lys Thr Leu Glu
               245                 250                 255

Glu Leu His Leu Thr Gly Asn Leu Ser Ala Glu Asn Asn Arg Tyr
               260                 265                 270

Ile Val Ile Asp Gly Leu Arg Glu Leu Lys Arg Leu Lys Val Leu
               275                 280                 285

Arg Leu Lys Ser Asn Leu Ser Lys Leu Pro Gln Val Val Thr Asp
               290                 295                 300

Val Gly Val His Leu Gln Lys Leu Ser Ile Asn Asn Glu Gly Thr
               305                 310                 315

Lys Leu Ile Val Leu Asn Ser Leu Lys Lys Met Ala Asn Leu Thr
               320                 325                 330

Glu Leu Glu Leu Ile Arg Cys Asp Leu Glu Arg Ile Pro His Ser
               335                 340                 345

Ile Phe Ser Leu His Asn Leu Gln Glu Ile Asp Leu Lys Asp Asn
               350                 355                 360

Asn Leu Lys Thr Ile Glu Glu Ile Ile Ser Phe Gln His Leu His
               365                 370                 375

Arg Leu Thr Cys Leu Lys Leu Trp Tyr Asn His Ile Ala Tyr Ile
               380                 385                 390

Pro Ile Gln Ile Gly Asn Leu Thr Asn Leu Glu Arg Leu Tyr Leu
               395                 400                 405

Asn Arg Asn Lys Ile Glu Lys Ile Pro Thr Gln Leu Phe Tyr Cys
```

-continued

```
                410                 415                 420

Arg Lys Leu Arg Tyr Leu Asp Leu Ser His Asn Asn Leu Thr Phe
                425                 430                 435

Leu Pro Ala Asp Ile Gly Leu Leu Gln Asn Leu Gln Asn Leu Ala
                440                 445                 450

Ile Thr Ala Asn Arg Ile Glu Thr Leu Pro Pro Glu Leu Phe Gln
                455                 460                 465

Cys Arg Lys Leu Arg Ala Leu His Leu Gly Asn Asn Val Leu Gln
                470                 475                 480

Ser Leu Pro Ser Arg Val Gly Glu Leu Thr Asn Leu Thr Gln Ile
                485                 490                 495

Glu Leu Arg Gly Asn Arg Leu Glu Cys Leu Pro Val Glu Leu Gly
                500                 505                 510

Glu Cys Pro Leu Leu Lys Arg Ser Gly Leu Val Val Glu Glu Asp
                515                 520                 525

Leu Phe Asn Thr Leu Pro Pro Glu Val Lys Glu Arg Leu Trp Arg
                530                 535                 540

Ala Asp Lys Glu Gln Ala
                545


<210> SEQ ID NO 125
<211> LENGTH: 1679
<212> TYPE: DNA
<213> ORGANISM: Homo sapiens

<400> SEQUENCE: 125

gttgtgtcct tcagcaaaac agtggattta aatctccttg cacaagcttg                50

agagcaacac aatctatcag gaaagaaaga aagaaaaaaa ccgaacctga               100

caaaaaagaa gaaaaagaag aagaaaaaaa atcatgaaaa ccatccagcc               150

aaaaatgcac aattctatct cttgggcaat cttcacgggg ctggctgctc               200

tgtgtctctt ccaaggagtg cccgtgcgca gcggagatgc caccttcccc               250

aaagctatgg acaacgtgac ggtccggcag ggggagagcg ccaccctcag               300

gtgcactatt gacaaccggg tcacccgggt ggcctggcta aaccgcagca               350

ccatcctcta tgctgggaat gacaagtggt gcctggatcc tcgcgtggtc               400

cttctgagca acacccaaac gcagtacagc atcgagatcc agaacgtgga               450

tgtgtatgac gagggccctt acacctgctc ggtgcagaca gacaaccacc               500

caaagacctc tagggtccac ctcattgtgc aagtatctcc caaaattgta               550

gagatttctt cagatatctc cattaatgaa gggaacaata ttagcctcac               600

ctgcatagca actggtagac cagagcctac ggttacttgg agacacatct               650

ctcccaaagc ggttggcttt gtgagtgaag acgaatactt ggaaattcag               700

ggcatcaccc gggagcagtc aggggactac gagtgcagtg cctccaatga               750

cgtggccgcg cccgtggtac ggagagtaaa ggtcaccgtg aactatccac               800

catacatttc agaagccaag ggtacaggtg tccccgtggg acaaaagggg               850

acactgcagt gtgaagcctc agcagtcccc tcagcagaat tccagtggta               900

caaggatgac aaaagactga ttgaaggaaa gaaaggggtg aaagtggaaa               950

acagaccttt cctctcaaaa ctcatcttct tcaatgtctc tgaacatgac              1000

tatgggaact acacttgcgt ggcctccaac aagctgggcc acaccaatgc              1050
```

-continued

```
cagcatcatg ctatttggtc caggcgccgt cagcgaggtg agcaacggca          1100

cgtcgaggag ggcaggctgc gtctggctgc tgcctcttct ggtcttgcac          1150

ctgcttctca aattttgatg tgagtgccac ttccccaccc gggaaaggct          1200

gccgccacca ccaccaccaa cacaacagca atggcaacac cgacagcaac          1250

caatcagata tatacaaatg aaattagaag aaacacagcc tcatgggaca          1300

gaaatttgag ggaggggaac aaagaatact ttgggggaa aagagtttta           1350

aaaaagaaat tgaaaattgc cttgcagata tttaggtaca atggagtttt          1400

cttttcccaa acgggaagaa cacagcacac ccggcttgga cccactgcaa          1450

gctgcatcgt gcaacctctt tggtgccagt gtgggcaagg gctcagcctc          1500

tctgcccaca gagtgccccc acgtggaaca ttctggagct ggccatccca          1550

aattcaatca gtccatagag acgaacagaa tgagaccttc cggcccaagc          1600

gtggcgctgc gggcactttg gtagactgtg ccaccacggc gtgtgttgtg          1650

aaacgtgaaa taaaaagagc  aaaaaaaaa                                1679
```

<210> SEQ ID NO 126
<211> LENGTH: 344
<212> TYPE: PRT
<213> ORGANISM: Homo sapiens

<400> SEQUENCE: 126

```
Met Lys Thr Ile Gln Pro Lys Met His Asn Ser Ile Ser Trp Ala
  1               5                  10                  15

Ile Phe Thr Gly Leu Ala Ala Leu Cys Leu Phe Gln Gly Val Pro
                 20                  25                  30

Val Arg Ser Gly Asp Ala Thr Phe Pro Lys Ala Met Asp Asn Val
                 35                  40                  45

Thr Val Arg Gln Gly Glu Ser Ala Thr Leu Arg Cys Thr Ile Asp
                 50                  55                  60

Asn Arg Val Thr Arg Val Ala Trp Leu Asn Arg Ser Thr Ile Leu
                 65                  70                  75

Tyr Ala Gly Asn Asp Lys Trp Cys Leu Asp Pro Arg Val Val Leu
                 80                  85                  90

Leu Ser Asn Thr Gln Thr Gln Tyr Ser Ile Glu Ile Gln Asn Val
                 95                 100                 105

Asp Val Tyr Asp Glu Gly Pro Tyr Thr Cys Ser Val Gln Thr Asp
                110                 115                 120

Asn His Pro Lys Thr Ser Arg Val His Leu Ile Val Gln Val Ser
                125                 130                 135

Pro Lys Ile Val Glu Ile Ser Ser Asp Ile Ser Ile Asn Glu Gly
                140                 145                 150

Asn Asn Ile Ser Leu Thr Cys Ile Ala Thr Gly Arg Pro Glu Pro
                155                 160                 165

Thr Val Thr Trp Arg His Ile Ser Pro Lys Ala Val Gly Phe Val
                170                 175                 180

Ser Glu Asp Glu Tyr Leu Glu Ile Gln Gly Ile Thr Arg Glu Gln
                185                 190                 195

Ser Gly Asp Tyr Glu Cys Ser Ala Ser Asn Asp Val Ala Ala Pro
                200                 205                 210

Val Val Arg Arg Val Lys Val Thr Val Asn Tyr Pro Pro Tyr Ile
                215                 220                 225
```

-continued

```
Ser Glu Ala Lys Gly Thr Gly Val Pro Val Gly Gln Lys Gly Thr
                230                 235                 240

Leu Gln Cys Glu Ala Ser Ala Val Pro Ser Ala Glu Phe Gln Trp
                245                 250                 255

Tyr Lys Asp Asp Lys Arg Leu Ile Glu Gly Lys Lys Gly Val Lys
                260                 265                 270

Val Glu Asn Arg Pro Phe Leu Ser Lys Leu Ile Phe Phe Asn Val
                275                 280                 285

Ser Glu His Asp Tyr Gly Asn Tyr Thr Cys Val Ala Ser Asn Lys
                290                 295                 300

Leu Gly His Thr Asn Ala Ser Ile Met Leu Phe Gly Pro Gly Ala
                305                 310                 315

Val Ser Glu Val Ser Asn Gly Thr Ser Arg Arg Ala Gly Cys Val
                320                 325                 330

Trp Leu Leu Pro Leu Leu Val Leu His Leu Leu Leu Lys Phe
                335                 340


<210> SEQ ID NO 127
<211> LENGTH: 2236
<212> TYPE: DNA
<213> ORGANISM: Homo sapiens

<400> SEQUENCE: 127

ggcgccggtg caccgggcgg gctgagcgcc tcctgcggcc cggcctgcgc                50

gccccggccc gccgcgccgc ccacgcccca accccggccc gcgcccccta               100

gcccccgccc gggcccgcgc ccgcgcccgc gcccaggtga gcgctccgcc               150

cgccgcgagg ccccgccccg gcccgccccc gccccgcccc ggccggcggg               200

ggaaccgggc ggattcctcg cgcgtcaaac cacctgatcc cataaaacat               250

tcatcctccc ggcggcccgc gctgcgagcg ccccgccagt ccgcgccgcc               300

gccgccctcg ccctgtgcgc cctgcgcgcc ctgcgcaccc gcggcccgag               350

cccagccaga gccgggcgga gcggagcgcg ccgagcctcg tcccgcggcc               400

gggccggggc cgggccgtag cggcggcgcc tggatgcgga cccggccgcg               450

gggagacggg cgcccgcccc gaaacgactt tcagtccccg acgcgccccg               500

cccaacccct acgatgaaga gggcgtccgc tggagggagc cggctgctgg               550

catgggtgct gtggctgcag gcctggcagg tggcagcccc atgcccaggt               600

gcctgcgtat gctacaatga gcccaaggtg acgacaagct gcccccagca               650

gggcctgcag gctgtgcccg tgggcatccc tgctgccagc cagcgcatct               700

tcctgcacgg caaccgcatc tcgcatgtgc cagctgccag cttccgtgcc               750

tgccgcaacc tcaccatcct gtggctgcac tcgaatgtgc tggcccgaat               800

tgatgcggct gccttcactg gcctggccct cctggagcag ctggacctca               850

gcgataatgc acagctccgg tctgtggacc ctgccacatt ccacggcctg               900

ggccgcctac acacgctgca cctggaccgc tgcggcctgc aggagctggg               950

cccggggctg ttccgcggcc tggctgccct gcagtacctc tacctgcagg              1000

acaacgcgct gcaggcactg cctgatgaca ccttccgcga cctgggcaac              1050

ctcacacacc tcttcctgca cggcaaccgc atctccagcg tgcccgagcg              1100

cgccttccgt gggctgcaca gcctcgaccg tctcctactg caccagaacc              1150

gcgtggccca tgtgcacccg catgccttcc gtgaccttgg ccgcctcatg              1200
```

-continued

```
acactctatc tgtttgccaa caatctatca gcgctgccca ctgaggccct          1250

ggcccccctg cgtgccctgc agtacctgag gctcaacgac aacccctggg          1300

tgtgtgactg ccgggcacgc ccactctggg cctggctgca gaagttccgc          1350

ggctcctcct ccgaggtgcc ctgcagcctc ccgcaacgcc tggctggccg          1400

tgacctcaaa cgcctagctg ccaatgacct gcagggctgc gctgtggcca          1450

ccggccctta ccatcccatc tggaccggca gggccaccga tgaggagccg          1500

ctggggcttc ccaagtgctg ccagccagat gccgctgaca aggcctcagt          1550

actggagcct ggaagaccag cttcggcagg caatgcgctg aagggacgcg          1600

tgccgcccgg tgacagcccg ccgggcaacg gctctggccc acggcacatc          1650

aatgactcac cctttgggac tctgcctggc tctgctgagc ccccgctcac          1700

tgcagtgcgg cccgagggct ccgagccacc agggttcccc acctcgggcc          1750

ctcgccggag gccaggctgt tcacgcaaga accgcacccg cagccactgc          1800

cgtctgggcc aggcaggcag cgggggtggc gggactggtg actcagaagg          1850

ctcaggtgcc ctacccagcc tcacctgcag cctcaccccc ctgggcctgg          1900

cgctggtgct gtggacagtg cttgggccct gctgaccccc agcggacaca          1950

agagcgtgct cagcagccag gtgtgtgtac atacggggtc tctctccacg          2000

ccgccaagcc agccgggcgg ccgacccgtg gggcaggcca ggccaggtcc          2050

tccctgatgg acgcctgccg cccgccaccc ccatctccac cccatcatgt          2100

ttacagggtt cggcggcagc gtttgttcca gaacgccgcc tcccacccag          2150

atcgcggtat atagagatat gcattttatt ttacttgtgt aaaaatatcg          2200

gacgacgtgg aataaagagc tcttttctta  aaaaaa                        2236
```

<210> SEQ ID NO 128
<211> LENGTH: 473
<212> TYPE: PRT
<213> ORGANISM: Homo sapiens

<400> SEQUENCE: 128

```
Met Lys Arg Ala Ser Ala Gly Gly Ser Arg Leu Leu Ala Trp Val
  1               5                  10                  15

Leu Trp Leu Gln Ala Trp Gln Val Ala Ala Pro Cys Pro Gly Ala
                 20                  25                  30

Cys Val Cys Tyr Asn Glu Pro Lys Val Thr Thr Ser Cys Pro Gln
                 35                  40                  45

Gln Gly Leu Gln Ala Val Pro Val Gly Ile Pro Ala Ala Ser Gln
                 50                  55                  60

Arg Ile Phe Leu His Gly Asn Arg Ile Ser His Val Pro Ala Ala
                 65                  70                  75

Ser Phe Arg Ala Cys Arg Asn Leu Thr Ile Leu Trp Leu His Ser
                 80                  85                  90

Asn Val Leu Ala Arg Ile Asp Ala Ala Ala Phe Thr Gly Leu Ala
                 95                 100                 105

Leu Leu Glu Gln Leu Asp Leu Ser Asp Asn Ala Gln Leu Arg Ser
                110                 115                 120

Val Asp Pro Ala Thr Phe His Gly Leu Gly Arg Leu His Thr Leu
                125                 130                 135

His Leu Asp Arg Cys Gly Leu Gln Glu Leu Gly Pro Gly Leu Phe
```

-continued

```
                140                 145                 150

Arg Gly Leu Ala Ala Leu Gln Tyr Leu Tyr Leu Gln Asp Asn Ala
                155                 160                 165

Leu Gln Ala Leu Pro Asp Asp Thr Phe Arg Asp Leu Gly Asn Leu
                170                 175                 180

Thr His Leu Phe Leu His Gly Asn Arg Ile Ser Ser Val Pro Glu
                185                 190                 195

Arg Ala Phe Arg Gly Leu His Ser Leu Asp Arg Leu Leu Leu His
                200                 205                 210

Gln Asn Arg Val Ala His Val His Pro His Ala Phe Arg Asp Leu
                215                 220                 225

Gly Arg Leu Met Thr Leu Tyr Leu Phe Ala Asn Asn Leu Ser Ala
                230                 235                 240

Leu Pro Thr Glu Ala Leu Ala Pro Leu Arg Ala Leu Gln Tyr Leu
                245                 250                 255

Arg Leu Asn Asp Asn Pro Trp Val Cys Asp Cys Arg Ala Arg Pro
                260                 265                 270

Leu Trp Ala Trp Leu Gln Lys Phe Arg Gly Ser Ser Ser Glu Val
                275                 280                 285

Pro Cys Ser Leu Pro Gln Arg Leu Ala Gly Arg Asp Leu Lys Arg
                290                 295                 300

Leu Ala Ala Asn Asp Leu Gln Gly Cys Ala Val Ala Thr Gly Pro
                305                 310                 315

Tyr His Pro Ile Trp Thr Gly Arg Ala Thr Asp Glu Glu Pro Leu
                320                 325                 330

Gly Leu Pro Lys Cys Cys Gln Pro Asp Ala Ala Asp Lys Ala Ser
                335                 340                 345

Val Leu Glu Pro Gly Arg Pro Ala Ser Ala Gly Asn Ala Leu Lys
                350                 355                 360

Gly Arg Val Pro Pro Gly Asp Ser Pro Pro Gly Asn Gly Ser Gly
                365                 370                 375

Pro Arg His Ile Asn Asp Ser Pro Phe Gly Thr Leu Pro Gly Ser
                380                 385                 390

Ala Glu Pro Pro Leu Thr Ala Val Arg Pro Glu Gly Ser Glu Pro
                395                 400                 405

Pro Gly Phe Pro Thr Ser Gly Pro Arg Arg Arg Pro Gly Cys Ser
                410                 415                 420

Arg Lys Asn Arg Thr Arg Ser His Cys Arg Leu Gly Gln Ala Gly
                425                 430                 435

Ser Gly Gly Gly Gly Thr Gly Asp Ser Glu Gly Ser Gly Ala Leu
                440                 445                 450

Pro Ser Leu Thr Cys Ser Leu Thr Pro Leu Gly Leu Ala Leu Val
                455                 460                 465

Leu Trp Thr Val Leu Gly Pro Cys
                470


<210> SEQ ID NO 129
<211> LENGTH: 2458
<212> TYPE: DNA
<213> ORGANISM: Homo sapiens

<400> SEQUENCE: 129

gcgccgggag cccatctgcc cccaggggca cggggcgcgg ggccggctcc                50

cgcccggcac atggctgcag ccacctcgcg cgcaccccga ggcgccgcgc               100
```

-continued

```
ccagctcgcc cgaggtccgt cggaggcgcc cggccgcccc ggagccaagc      150
agcaactgag cggggaagcg cccgcgtccg gggatcggga tgtccctcct      200
ccttctcctc ttgctagttt cctactatgt tggaaccttg gggactcaca      250
ctgagatcaa gagagtggca gaggaaaagg tcactttgcc ctgccaccat      300
caactggggc ttccagaaaa agacactctg gatattgaat ggctgctcac      350
cgataatgaa gggaaccaaa aagtggtgat cacttactcc agtcgtcatg      400
tctacaataa cttgactgag gaacagaagg gccgagtggc ctttgcttcc      450
aatttcctgg caggagatgc ctccttgcag attgaacctc tgaagcccag      500
tgatgagggc cggtacacct gtaaggttaa gaattcaggg cgctacgtgt      550
ggagccatgt catcttaaaa gtcttagtga gaccatccaa gcccaagtgt      600
gagttggaag gagagctgac agaaggaagt gacctgactt tgcagtgtga      650
gtcatcctct ggcacagagc ccattgtgta ttactggcag cgaatccgag      700
agaaagaggg agaggatgaa cgtctgcctc ccaaatctag gattgactac      750
aaccaccctg gacgagttct gctgcagaat cttaccatgt cctactctgg      800
actgtaccag tgcacagcag gcaacgaagc tgggaaggaa agctgtgtgg      850
tgcgagtaac tgtacagtat gtacaaagca tcggcatggt tgcaggagca      900
gtgacaggca tagtggctgg agccctgctg attttcctct tggtgtggct      950
gctaatccga aggaaagaca aagaaagata tgaggaagaa gagagaccta     1000
atgaaattcg agaagatgct gaagctccaa aagcccgtct tgtgaaaccc     1050
agctcctctt cctcaggctc tcggagctca cgctctggtt cttcctccac     1100
tcgctccaca gcaaatagtg cctcacgcag ccagcggaca ctgtcaactg     1150
acgcagcacc ccagccaggg ctggccaccc aggcatacag cctagtgggg     1200
ccagaggtga gaggttctga accaaagaaa gtccaccatg ctaatctgac     1250
caaagcagaa accacaccca gcatgatccc cagccagagc agagccttcc     1300
aaacggtctg aattacaatg gacttgactc ccacgctttc ctaggagtca     1350
gggtctttgg actcttctcg tcattggagc tcaagtcacc agccacacaa     1400
ccagatgaga ggtcatctaa gtagcagtga gcattgcacg gaacagattc     1450
agatgagcat tttccttata caataccaaa caagcaaaag gatgtaagct     1500
gattcatctg taaaaaggca tcttattgtg cctttagacc agagtaaggg     1550
aaagcaggag tccaaatcta tttgttgacc aggacctgtg gtgagaaggt     1600
tggggaaagg tgaggtgaat atacctaaaa cttttaatgt gggatatttt     1650
gtatcagtgc tttgattcac aattttcaag aggaaatggg atgctgtttg     1700
taaattttct atgcatttct gcaaacttat tggattatta gttattcaga     1750
cagtcaagca gaacccacag ccttattaca cctgtctaca ccatgtactg     1800
agctaaccac ttctaagaaa ctccaaaaaa ggaaacatgt gtcttctatt     1850
ctgacttaac ttcatttgtc ataaggtttg gatattaatt tcaaggggag     1900
ttgaaatagt gggagatgga gaagagtgaa tgagtttctc ccactctata     1950
ctaatctcac tatttgtatt gagcccaaaa taactatgaa aggagacaaa     2000
aatttgtgac aaaggattgt gaagagcttt ccatcttcat gatgttatga     2050
```

-continued

```
ggattgttga caaacattag aaatatataa tggagcaatt gtggatttcc          2100

cctcaaatca gatgcctcta aggactttcc tgctagatat ttctggaagg          2150

agaaaataca acatgtcatt tatcaacgtc cttagaaaga attcttctag          2200

agaaaaaggg atctaggaat gctgaaagat tacccaacat accattatag          2250

tctcttcttt ctgagaaaat gtgaaaccag aattgcaaga ctgggtggac          2300

tagaaaggga gattagatca gttttctctt aatatgtcaa ggaaggtagc          2350

cgggcatggt gccaggcacc tgtaggaaaa tccagcaggt ggaggttgca          2400

gtgagccgag attatgccat tgcactccag cctgggtgac agagcgggac          2450

tccgtctc                                                        2458
```

<210> SEQ ID NO 130
<211> LENGTH: 373
<212> TYPE: PRT
<213> ORGANISM: Homo sapiens

<400> SEQUENCE: 130

```
Met Ser Leu Leu Leu Leu Leu Leu Leu Val Ser Tyr Tyr Val Gly
  1               5                  10                  15

Thr Leu Gly Thr His Thr Glu Ile Lys Arg Val Ala Glu Glu Lys
                 20                  25                  30

Val Thr Leu Pro Cys His His Gln Leu Gly Leu Pro Glu Lys Asp
                 35                  40                  45

Thr Leu Asp Ile Glu Trp Leu Leu Thr Asp Asn Glu Gly Asn Gln
                 50                  55                  60

Lys Val Val Ile Thr Tyr Ser Ser Arg His Val Tyr Asn Asn Leu
                 65                  70                  75

Thr Glu Glu Gln Lys Gly Arg Val Ala Phe Ala Ser Asn Phe Leu
                 80                  85                  90

Ala Gly Asp Ala Ser Leu Gln Ile Glu Pro Leu Lys Pro Ser Asp
                 95                 100                 105

Glu Gly Arg Tyr Thr Cys Lys Val Lys Asn Ser Gly Arg Tyr Val
                110                 115                 120

Trp Ser His Val Ile Leu Lys Val Leu Val Arg Pro Ser Lys Pro
                125                 130                 135

Lys Cys Glu Leu Glu Gly Glu Leu Thr Glu Gly Ser Asp Leu Thr
                140                 145                 150

Leu Gln Cys Glu Ser Ser Ser Gly Thr Glu Pro Ile Val Tyr Tyr
                155                 160                 165

Trp Gln Arg Ile Arg Glu Lys Glu Gly Glu Asp Glu Arg Leu Pro
                170                 175                 180

Pro Lys Ser Arg Ile Asp Tyr Asn His Pro Gly Arg Val Leu Leu
                185                 190                 195

Gln Asn Leu Thr Met Ser Tyr Ser Gly Leu Tyr Gln Cys Thr Ala
                200                 205                 210

Gly Asn Glu Ala Gly Lys Glu Ser Cys Val Val Arg Val Thr Val
                215                 220                 225

Gln Tyr Val Gln Ser Ile Gly Met Val Ala Gly Ala Val Thr Gly
                230                 235                 240

Ile Val Ala Gly Ala Leu Leu Ile Phe Leu Leu Val Trp Leu Leu
                245                 250                 255

Ile Arg Arg Lys Asp Lys Glu Arg Tyr Glu Glu Glu Glu Arg Pro
                260                 265                 270
```

-continued

```
Asn Glu Ile Arg Glu Asp Ala Glu Ala Pro Lys Ala Arg Leu Val
                275                 280                 285

Lys Pro Ser Ser Ser Ser Ser Gly Ser Arg Ser Ser Arg Ser Gly
                290                 295                 300

Ser Ser Ser Thr Arg Ser Thr Ala Asn Ser Ala Ser Arg Ser Gln
                305                 310                 315

Arg Thr Leu Ser Thr Asp Ala Ala Pro Gln Pro Gly Leu Ala Thr
                320                 325                 330

Gln Ala Tyr Ser Leu Val Gly Pro Glu Val Arg Gly Ser Glu Pro
                335                 340                 345

Lys Lys Val His His Ala Asn Leu Thr Lys Ala Glu Thr Thr Pro
                350                 355                 360

Ser Met Ile Pro Ser Gln Ser Arg Ala Phe Gln Thr Val
                365                 370


<210> SEQ ID NO 131
<211> LENGTH: 2738
<212> TYPE: DNA
<213> ORGANISM: Homo sapiens

<400> SEQUENCE: 131

ggaagtccac ggggagcttg gatgccaaag ggaggacggc tgggtcctct                50

ggagaggact actcactggc atatttctga ggtatctgta gaataaccac               100

agcctcagat actggggact ttacagtccc acagaaccgt cctcccagga               150

agctgaatcc agcaagaaca atggaggcca gcgggaagct catttgcaga               200

caaaggcaag tccttttttc ctttctcctt ttgggcttat ctctggcggg               250

cgcggcggaa cctagaagct attctgtggt ggaggaaact gagggcagct               300

cctttgtcac caatttagca aaggacctgg gtctggagca gagggaattc               350

tccaggcggg gggttagggt tgtttccaga gggaacaaac tacatttgca               400

gctcaatcag gagaccgcgg atttgttgct aaatgagaaa ttggaccgtg               450

aggatctgtg cggtcacaca gagccctgtg tgctacgttt ccaagtgttg               500

ctagagagtc ccttcgagtt ttttcaagct gagctgcaag taatagacat               550

aaacgaccac tctccagtat ttctggacaa acaaatgttg gtgaaagtat               600

cagagagcag tcctcctggg actacgtttc ctctgaagaa tgccgaagac               650

ttagatgtag gccaaaacaa tattgagaac tatataatca gccccaactc               700

ctattttcgg gtcctcaccc gcaaacgcag tgatggcagg aaatacccag               750

agctggtgct ggacaaagcg ctggaccgag aggaagaagc tgagctcagg               800

ttaacactca cagcactgga tggtggctct ccgcccagat ctggcactgc               850

tcaggtctac atcgaagtcc tggatgtcaa cgataatgcc cctgaatttg               900

agcagccttt ctatagagtg cagatctctg aggacagtcc ggtaggcttc               950

ctggttgtga aggtctctgc cacggatgta gacacaggag tcaacggaga              1000

gatttcctat tcacttttcc aagcttcaga agagattggc aaaaccttta              1050

agatcaatcc cttgacagga gaaattgaac taaaaaaaca actcgatttc              1100

gaaaaacttc agtcctatga agtcaatatt gaggcaagag atgctggaac              1150

cttttctgga aaatgcaccg ttctgattca agtgatagat gtgaacgacc              1200

atgccccaga agttaccatg tctgcattta ccagcccaat acctgagaac              1250
```

-continued

```
gcgcctgaaa ctgtggttgc acttttcagt gtttcagatc ttgattcagg          1300
agaaaatggg aaaattagtt gctccattca ggaggatcta cccttcctcc          1350
tgaaatccgc ggaaaacttt tacaccctac taacggagag accactagac          1400
agagaaagca gagcggaata caacatcact atcactgtca ctgacttggg          1450
gacccctatg ctgataacac agctcaatat gaccgtgctg atcgccgatg          1500
tcaatgacaa cgctcccgcc ttcacccaaa cctcctacac cctgttcgtc          1550
cgcgagaaca acagccccgc cctgcacatc cgcagcgtca gcgctacaga          1600
cagagactca ggcaccaacg cccaggtcac ctactcgctg ctgccgcccc          1650
aggacccgca cctgcccctc acatccctgg tctccatcaa cgcggacaac          1700
ggccacctgt tcgccctcag gtctctggac tacgaggccc tgcaggggtt          1750
ccagttccgc gtgggcgctt cagaccacgg ctccccggcg ctgagcagcg          1800
aggcgctggt gcgcgtggtg gtgctggacg ccaacgacaa ctcgcccttc          1850
gtgctgtacc cgctgcagaa cggctccgcg ccctgcaccg agctggtgcc          1900
ccgggcggcc gagccgggct acctggtgac caaggtggtg gcggtggacg          1950
gcgactcggg ccagaacgcc tggctgtcgt accagctgct caaggccacg          2000
gagctcggtc tgttcggcgt gtgggcgcac aatggcgagg tgcgcaccgc          2050
caggctgctg agcgagcgcg acgcggccaa gcacaggctg gtggtgctgg          2100
tcaaggacaa tggcgagcct ccgcgctcgg ccaccgccac gctgcacgtg          2150
ctcctggtgg acggcttctc ccagccctac ctgcctctcc cggaggcggc          2200
cccgacccag gcccaggccg acttgctcac cgtctacctg gtggtggcgt          2250
tggcctcggt gtcttcgctc ttcctctttt cggtgctcct gttcgtggcg          2300
gtgcggctgt gtaggaggag cagggcggcc tcggtgggtc gctgcttggt          2350
gcccgagggc ccccttccag ggcatcttgt ggacatgagc ggcaccagga          2400
ccctatccca gagctaccag tatgaggtgt gtctggcagg aggctcaggg          2450
accaatgagt tcaagttcct gaagccgatt atccccaact tccctcccca          2500
gtgccctggg aaagaaatac aaggaaattc taccttcccc aataactttg          2550
ggttcaatat tcagtgacca tagttgactt ttacattcca taggtatttt          2600
attttgtggc atttccatgc caatgtttat ttcccccaat ttgtgtgtat          2650
gtaatattgt acggatttac tcttgatttt tctcatgttc tttctccctt          2700
tgttttaaag tgaacattta cctttattcc  tggttctt                      2738
```

<210> SEQ ID NO 132
<211> LENGTH: 798
<212> TYPE: PRT
<213> ORGANISM: Homo sapiens

<400> SEQUENCE: 132

```
Met Glu Ala Ser Gly Lys Leu Ile Cys Arg Gln Arg Gln Val Leu
  1               5                  10                  15

Phe Ser Phe Leu Leu Leu Gly Leu Ser Leu Ala Gly Ala Ala Glu
                 20                  25                  30

Pro Arg Ser Tyr Ser Val Val Glu Glu Thr Glu Gly Ser Ser Phe
                 35                  40                  45

Val Thr Asn Leu Ala Lys Asp Leu Gly Leu Glu Gln Arg Glu Phe
```

-continued

```
                50                  55                  60

Ser Arg Arg Gly Val Arg Val Val Ser Arg Gly Asn Lys Leu His
                65                  70                  75

Leu Gln Leu Asn Gln Glu Thr Ala Asp Leu Leu Leu Asn Glu Lys
                80                  85                  90

Leu Asp Arg Glu Asp Leu Cys Gly His Thr Glu Pro Cys Val Leu
                95                 100                 105

Arg Phe Gln Val Leu Leu Glu Ser Pro Phe Glu Phe Phe Gln Ala
               110                 115                 120

Glu Leu Gln Val Ile Asp Ile Asn Asp His Ser Pro Val Phe Leu
               125                 130                 135

Asp Lys Gln Met Leu Val Lys Val Ser Glu Ser Ser Pro Pro Gly
               140                 145                 150

Thr Thr Phe Pro Leu Lys Asn Ala Glu Asp Leu Asp Val Gly Gln
               155                 160                 165

Asn Asn Ile Glu Asn Tyr Ile Ile Ser Pro Asn Ser Tyr Phe Arg
               170                 175                 180

Val Leu Thr Arg Lys Arg Ser Asp Gly Arg Lys Tyr Pro Glu Leu
               185                 190                 195

Val Leu Asp Lys Ala Leu Asp Arg Glu Glu Glu Ala Glu Leu Arg
               200                 205                 210

Leu Thr Leu Thr Ala Leu Asp Gly Gly Ser Pro Pro Arg Ser Gly
               215                 220                 225

Thr Ala Gln Val Tyr Ile Glu Val Leu Asp Val Asn Asp Asn Ala
               230                 235                 240

Pro Glu Phe Glu Gln Pro Phe Tyr Arg Val Gln Ile Ser Glu Asp
               245                 250                 255

Ser Pro Val Gly Phe Leu Val Val Lys Val Ser Ala Thr Asp Val
               260                 265                 270

Asp Thr Gly Val Asn Gly Glu Ile Ser Tyr Ser Leu Phe Gln Ala
               275                 280                 285

Ser Glu Glu Ile Gly Lys Thr Phe Lys Ile Asn Pro Leu Thr Gly
               290                 295                 300

Glu Ile Glu Leu Lys Lys Gln Leu Asp Phe Glu Lys Leu Gln Ser
               305                 310                 315

Tyr Glu Val Asn Ile Glu Ala Arg Asp Ala Gly Thr Phe Ser Gly
               320                 325                 330

Lys Cys Thr Val Leu Ile Gln Val Ile Asp Val Asn Asp His Ala
               335                 340                 345

Pro Glu Val Thr Met Ser Ala Phe Thr Ser Pro Ile Pro Glu Asn
               350                 355                 360

Ala Pro Glu Thr Val Val Ala Leu Phe Ser Val Ser Asp Leu Asp
               365                 370                 375

Ser Gly Glu Asn Gly Lys Ile Ser Cys Ser Ile Gln Glu Asp Leu
               380                 385                 390

Pro Phe Leu Leu Lys Ser Ala Glu Asn Phe Tyr Thr Leu Leu Thr
               395                 400                 405

Glu Arg Pro Leu Asp Arg Glu Ser Arg Ala Glu Tyr Asn Ile Thr
               410                 415                 420

Ile Thr Val Thr Asp Leu Gly Thr Pro Met Leu Ile Thr Gln Leu
               425                 430                 435

Asn Met Thr Val Leu Ile Ala Asp Val Asn Asp Asn Ala Pro Ala
               440                 445                 450
```

-continued

```
Phe Thr Gln Thr Ser Tyr Thr Leu Phe Val Arg Glu Asn Asn Ser
                455                 460                 465

Pro Ala Leu His Ile Arg Ser Val Ser Ala Thr Asp Arg Asp Ser
                470                 475                 480

Gly Thr Asn Ala Gln Val Thr Tyr Ser Leu Leu Pro Pro Gln Asp
                485                 490                 495

Pro His Leu Pro Leu Thr Ser Leu Val Ser Ile Asn Ala Asp Asn
                500                 505                 510

Gly His Leu Phe Ala Leu Arg Ser Leu Asp Tyr Glu Ala Leu Gln
                515                 520                 525

Gly Phe Gln Phe Arg Val Gly Ala Ser Asp His Gly Ser Pro Ala
                530                 535                 540

Leu Ser Ser Glu Ala Leu Val Arg Val Val Val Leu Asp Ala Asn
                545                 550                 555

Asp Asn Ser Pro Phe Val Leu Tyr Pro Leu Gln Asn Gly Ser Ala
                560                 565                 570

Pro Cys Thr Glu Leu Val Pro Arg Ala Ala Glu Pro Gly Tyr Leu
                575                 580                 585

Val Thr Lys Val Val Ala Val Asp Gly Asp Ser Gly Gln Asn Ala
                590                 595                 600

Trp Leu Ser Tyr Gln Leu Leu Lys Ala Thr Glu Leu Gly Leu Phe
                605                 610                 615

Gly Val Trp Ala His Asn Gly Glu Val Arg Thr Ala Arg Leu Leu
                620                 625                 630

Ser Glu Arg Asp Ala Ala Lys His Arg Leu Val Val Leu Val Lys
                635                 640                 645

Asp Asn Gly Glu Pro Pro Arg Ser Ala Thr Ala Thr Leu His Val
                650                 655                 660

Leu Leu Val Asp Gly Phe Ser Gln Pro Tyr Leu Pro Leu Pro Glu
                665                 670                 675

Ala Ala Pro Thr Gln Ala Gln Ala Asp Leu Leu Thr Val Tyr Leu
                680                 685                 690

Val Val Ala Leu Ala Ser Val Ser Ser Leu Phe Leu Phe Ser Val
                695                 700                 705

Leu Leu Phe Val Ala Val Arg Leu Cys Arg Arg Ser Arg Ala Ala
                710                 715                 720

Ser Val Gly Arg Cys Leu Val Pro Glu Gly Pro Leu Pro Gly His
                725                 730                 735

Leu Val Asp Met Ser Gly Thr Arg Thr Leu Ser Gln Ser Tyr Gln
                740                 745                 750

Tyr Glu Val Cys Leu Ala Gly Gly Ser Gly Thr Asn Glu Phe Lys
                755                 760                 765

Phe Leu Lys Pro Ile Ile Pro Asn Phe Pro Pro Gln Cys Pro Gly
                770                 775                 780

Lys Glu Ile Gln Gly Asn Ser Thr Phe Pro Asn Asn Phe Gly Phe
                785                 790                 795

Asn Ile Gln


<210> SEQ ID NO 133
<211> LENGTH: 3819
<212> TYPE: DNA
<213> ORGANISM: Homo sapiens

<400> SEQUENCE: 133
```

-continued

```
ggaaggggag gagcaggcca cacaggcaca ggccggtgag ggacctgccc      50
agacctggag ggtctcgctc tgtcacacag gctggagtgc agtggtgtga     100
tcttggctca tcgtaacctc cacctcccgg gttcaagtga ttctcatgcc     150
tcagcctccc gagtagctgg gattacaggt ggtgacttcc aagagtgact     200
ccgtcggagg aaaatgactc cccagtcgct gctgcagacg acactgttcc     250
tgctgagtct gctcttcctg gtccaaggtg cccacggcag gggccacagg     300
gaagactttc gcttctgcag ccagcggaac cagacacaca ggagcagcct     350
ccactacaaa cccacaccag acctgcgcat ctccatcgag aactccgaag     400
aggccctcac agtccatgcc cctttccctg cagcccaccc tgcttcccga     450
tccttccctg accccagggg cctctaccac ttctgcctct actggaaccg     500
acatgctggg agattacatc ttctctatgg caagcgtgac ttcttgctga     550
gtgacaaagc ctctagcctc ctctgcttcc agcaccagga ggagagcctg     600
gctcagggcc ccccgctgtt agccacttct gtcacctcct ggtggagccc     650
tcagaacatc agcctgccca gtgccgccag cttcaccttc tccttccaca     700
gtcctcccca cacggccgct cacaatgcct cggtggacat gtgcgagctc     750
aaaagggacc tccagctgct cagccagttc ctgaagcatc cccagaaggc     800
ctcaaggagg ccctcggctg cccccgccag ccagcagttg cagagcctgg     850
agtcgaaact gacctctgtg agattcatgg gggacatggt gtccttcgag     900
gaggaccgga tcaacgccac ggtgtggaag ctccagccca cagccggcct     950
ccaggacctg cacatccact cccggcagga ggaggagcag agcgagatca    1000
tggagtactc ggtgctgctg cctcgaacac tcttccagag gacgaaaggc    1050
cggagcgggg aggctgagaa gagactcctc ctggtggact tcagcagcca    1100
agccctgttc caggacaaga attccagcca agtcctgggt gagaaggtct    1150
tggggattgt ggtacagaac accaaagtag ccaacctcac ggagcccgtg    1200
gtgctcactt tccagcacca gctacagccg aagaatgtga ctctgcaatg    1250
tgtgttctgg gttgaagacc ccacattgag cagcccgggg cattggagca    1300
gtgctgggtg tgagaccgtc aggagagaaa cccaaacatc ctgcttctgc    1350
aaccacttga cctactttgc agtgctgatg gtctcctcgg tggaggtgga    1400
cgccgtgcac aagcactacc tgagcctcct ctcctacgtg ggctgtgtcg    1450
tctctgccct ggcctgcctt gtcaccattg ccgcctacct ctgctccagg    1500
gtgcccctgc cgtgcaggag gaaacctcgg gactacacca tcaaggtgca    1550
catgaacctg ctgctggccg tcttcctgct ggacacgagc ttcctgctca    1600
gcgagccggt ggccctgaca ggctctgagg ctggctgccg agccagtgcc    1650
atcttcctgc acttctccct gctcacctgc ctttcctgga tgggcctcga    1700
ggggtacaac ctctaccgac tcgtggtgga ggtctttggc acctatgtcc    1750
ctggctacct actcaagctg agcgccatgg gctggggctt ccccatcttt    1800
ctggtgacgc tggtggccct ggtggatgtg gacaactatg gccccatcat    1850
cttggctgtg cataggactc cagagggcgt catctaccct tccatgtgct    1900
ggatccggga ctccctggtc agctacatca ccaacctggg cctcttcagc    1950
```

-continued

```
ctggtgtttc tgttcaacat ggccatgcta gccaccatgg tggtgcagat      2000
cctgcggctg cgcccccaca cccaaaagtg gtcacatgtg ctgacactgc      2050
tgggcctcag cctggtcctt ggcctgccct gggccttgat cttcttctcc      2100
tttgcttctg gcaccttcca gcttgtcgtc ctctaccttt tcagcatcat      2150
cacctccttc caaggcttcc tcatcttcat ctggtactgg tccatgcggc      2200
tgcaggcccg gggtggcccc tcccctctga agagcaactc agacagcgcc      2250
aggctcccca tcagctcggg cagcacctcg tccagccgca tctaggcctc      2300
cagcccacct gcccatgtga tgaagcagag atgcggcctc gtcgcacact      2350
gcctgtggcc cccgagccag gcccagcccc aggccagtca gccgcagact      2400
ttggaaagcc caacgaccat ggagagatgg gccgttgcca tggtggacgg      2450
actcccgggc tgggcttttg aattggcctt ggggactact cggctctcac      2500
tcagctccca cgggactcag aagtgcgccg ccatgctgcc tagggtactg      2550
tccccacatc tgtcccaacc cagctggagg cctggtctct ccttacaacc      2600
cctgggccca gccctcattg ctgggggcca ggccttggat cttgagggtc      2650
tggcacatcc ttaatcctgt gcccctgcct gggacagaaa tgtggctcca      2700
gttgctctgt ctctcgtggt caccctgagg gcactctgca tcctctgtca      2750
ttttaacctc aggtggcacc cagggcgaat ggggcccagg gcagaccttc      2800
agggccagag ccctggcgga ggagaggccc tttgccagga gcacagcagc      2850
agctcgccta cctctgagcc caggcccccct ccctccctca gcccccccagt    2900
cctccctcca tcttccctgg ggttctcctc ctctcccagg gcctccttgc      2950
tccttcgttc acagctgggg gtccccgatt ccaatgctgt tttttgggga      3000
gtggtttcca ggagctgcct ggtgtctgct gtaaatgttt gtctactgca      3050
caagcctcgg cctgcccctg agccaggctc ggtaccgatg cgtgggctgg      3100
gctaggtccc tctgtccatc tgggcctttg tatgagctgc attgcccttg      3150
ctcaccctga ccaagcacac gcctcagagg ggccctcagc ctctcctgaa      3200
gccctcttgt ggcaagaact gtggaccatg ccagtcccgt ctggtttcca      3250
tcccaccact ccaaggactg agactgacct cctctggtga cactggccta      3300
gagcctgaca ctctcctaag aggttctctc caagccccca aatagctcca      3350
ggcgccctcg gccgcccatc atggttaatt ctgtccaaca aacacacacg      3400
ggtagattgc tggcctgttg taggtggtag ggacacagat gaccgacctg      3450
gtcactcctc ctgccaacat tcagtctggt atgtgaggcg tgcgtgaagc      3500
aagaactcct ggagctacag ggacagggag ccatcattcc tgcctgggaa      3550
tcctggaaga cttcctgcag gagtcagcgt tcaatcttga ccttgaagat      3600
gggaaggatg ttctttttac gtaccaattc ttttgtcttt tgatattaaa      3650
aagaagtaca tgttcattgt agagaatttg gaaactgtag aagagaatca      3700
agaagaaaaa taaaaatcag ctgttgtaat cgcctagcaa aaaaaaaaaa      3750
aaaaaaaaaa aaaaaaaaaa aaaaaaaaaa aaaaaaaaaa aaaaaaaaaa      3800
aaaaaaaaaa  aaaaaaaaa                                       3819
```

<210> SEQ ID NO 134
<211> LENGTH: 693

-continued

<212> TYPE: PRT
<213> ORGANISM: Homo sapiens

<400> SEQUENCE: 134

Met Thr Pro Gln Ser Leu Leu Gln Thr Thr Leu Phe Leu Leu Ser
1 5 10 15

Leu Leu Phe Leu Val Gln Gly Ala His Gly Arg Gly His Arg Glu
20 25 30

Asp Phe Arg Phe Cys Ser Gln Arg Asn Gln Thr His Arg Ser Ser
35 40 45

Leu His Tyr Lys Pro Thr Pro Asp Leu Arg Ile Ser Ile Glu Asn
50 55 60

Ser Glu Glu Ala Leu Thr Val His Ala Pro Phe Pro Ala Ala His
65 70 75

Pro Ala Ser Arg Ser Phe Pro Asp Pro Arg Gly Leu Tyr His Phe
80 85 90

Cys Leu Tyr Trp Asn Arg His Ala Gly Arg Leu His Leu Leu Tyr
95 100 105

Gly Lys Arg Asp Phe Leu Leu Ser Asp Lys Ala Ser Ser Leu Leu
110 115 120

Cys Phe Gln His Gln Glu Glu Ser Leu Ala Gln Gly Pro Pro Leu
125 130 135

Leu Ala Thr Ser Val Thr Ser Trp Trp Ser Pro Gln Asn Ile Ser
140 145 150

Leu Pro Ser Ala Ala Ser Phe Thr Phe Ser Phe His Ser Pro Pro
155 160 165

His Thr Ala Ala His Asn Ala Ser Val Asp Met Cys Glu Leu Lys
170 175 180

Arg Asp Leu Gln Leu Leu Ser Gln Phe Leu Lys His Pro Gln Lys
185 190 195

Ala Ser Arg Arg Pro Ser Ala Ala Pro Ala Ser Gln Gln Leu Gln
200 205 210

Ser Leu Glu Ser Lys Leu Thr Ser Val Arg Phe Met Gly Asp Met
215 220 225

Val Ser Phe Glu Glu Asp Arg Ile Asn Ala Thr Val Trp Lys Leu
230 235 240

Gln Pro Thr Ala Gly Leu Gln Asp Leu His Ile His Ser Arg Gln
245 250 255

Glu Glu Glu Gln Ser Glu Ile Met Glu Tyr Ser Val Leu Leu Pro
260 265 270

Arg Thr Leu Phe Gln Arg Thr Lys Gly Arg Ser Gly Glu Ala Glu
275 280 285

Lys Arg Leu Leu Leu Val Asp Phe Ser Ser Gln Ala Leu Phe Gln
290 295 300

Asp Lys Asn Ser Ser Gln Val Leu Gly Glu Lys Val Leu Gly Ile
305 310 315

Val Val Gln Asn Thr Lys Val Ala Asn Leu Thr Glu Pro Val Val
320 325 330

Leu Thr Phe Gln His Gln Leu Gln Pro Lys Asn Val Thr Leu Gln
335 340 345

Cys Val Phe Trp Val Glu Asp Pro Thr Leu Ser Ser Pro Gly His
350 355 360

Trp Ser Ser Ala Gly Cys Glu Thr Val Arg Arg Glu Thr Gln Thr
365 370 375

-continued

```
Ser Cys Phe Cys Asn His Leu Thr Tyr Phe Ala Val Leu Met Val
                380                 385                 390

Ser Ser Val Glu Val Asp Ala Val His Lys His Tyr Leu Ser Leu
                395                 400                 405

Leu Ser Tyr Val Gly Cys Val Val Ser Ala Leu Ala Cys Leu Val
                410                 415                 420

Thr Ile Ala Ala Tyr Leu Cys Ser Arg Val Pro Leu Pro Cys Arg
                425                 430                 435

Arg Lys Pro Arg Asp Tyr Thr Ile Lys Val His Met Asn Leu Leu
                440                 445                 450

Leu Ala Val Phe Leu Leu Asp Thr Ser Phe Leu Leu Ser Glu Pro
                455                 460                 465

Val Ala Leu Thr Gly Ser Glu Ala Gly Cys Arg Ala Ser Ala Ile
                470                 475                 480

Phe Leu His Phe Ser Leu Leu Thr Cys Leu Ser Trp Met Gly Leu
                485                 490                 495

Glu Gly Tyr Asn Leu Tyr Arg Leu Val Val Glu Val Phe Gly Thr
                500                 505                 510

Tyr Val Pro Gly Tyr Leu Leu Lys Leu Ser Ala Met Gly Trp Gly
                515                 520                 525

Phe Pro Ile Phe Leu Val Thr Leu Val Ala Leu Val Asp Val Asp
                530                 535                 540

Asn Tyr Gly Pro Ile Ile Leu Ala Val His Arg Thr Pro Glu Gly
                545                 550                 555

Val Ile Tyr Pro Ser Met Cys Trp Ile Arg Asp Ser Leu Val Ser
                560                 565                 570

Tyr Ile Thr Asn Leu Gly Leu Phe Ser Leu Val Phe Leu Phe Asn
                575                 580                 585

Met Ala Met Leu Ala Thr Met Val Val Gln Ile Leu Arg Leu Arg
                590                 595                 600

Pro His Thr Gln Lys Trp Ser His Val Leu Thr Leu Leu Gly Leu
                605                 610                 615

Ser Leu Val Leu Gly Leu Pro Trp Ala Leu Ile Phe Phe Ser Phe
                620                 625                 630

Ala Ser Gly Thr Phe Gln Leu Val Val Leu Tyr Leu Phe Ser Ile
                635                 640                 645

Ile Thr Ser Phe Gln Gly Phe Leu Ile Phe Ile Trp Tyr Trp Ser
                650                 655                 660

Met Arg Leu Gln Ala Arg Gly Gly Pro Ser Pro Leu Lys Ser Asn
                665                 670                 675

Ser Asp Ser Ala Arg Leu Pro Ile Ser Ser Gly Ser Thr Ser Ser
                680                 685                 690

Ser Arg Ile
```

<210> SEQ ID NO 135
<211> LENGTH: 1615
<212> TYPE: DNA
<213> ORGANISM: Homo sapiens

<400> SEQUENCE: 135

```
gcctagccag gccaagaatg caattgcccc ggtggtggga gctgggagac          50

ccctgtgctt ggacgggaca gggtcggggg acacgcagga tgagccccgc         100

gaccactggc acattcttgc tgacagtgta cagtattttc tccaaggtac         150
```

-continued

```
actccgatcg gaatgtatac ccatcagcag gtgtcctctt tgttcatgtt          200
ttggaaagag aatattttaa gggggaattt ccaccttacc caaaacctgg          250
cgagattagt aatgatccca taacatttaa tacaaattta atgggttacc          300
cagaccgacc tggatggctt cgatatatcc aaaggacacc atatagtgat          350
ggagtcctat atgggtcccc aacagctgaa aatgtgggga agccaacaat          400
cattgagata actgcctaca acaggcgcac ctttgagact gcaaggcata          450
atttgataat taatataatg tctgcagaag acttcccgtt gccatatcaa          500
gcagaattct tcattaagaa tatgaatgta gaagaaatgt tggccagtga          550
ggttcttgga gactttcttg gcgcagtgaa aaatgtgtgg cagccagagc          600
gcctgaacgc cataaacatc acatcggccc tagacagggg tggcagggtg          650
ccacttccca ttaatgacct gaaggagggc gtttatgtca tggttggtgc          700
agatgtcccg ttttcttctt gtttacgaga agttgaaaat ccacagaatc          750
aattgagatg tagtcaagaa atggagcctg taataacatg tgataaaaaa          800
tttcgtactc aattttacat tgactggtgc aaaatttcat tggttgataa          850
aacaaagcaa gtgtccacct atcaggaagt gattcgtgga gaggggattt          900
tacctgatgg tggagaatac aaaccccctt ctgattcttt gaaaagcaga          950
gactattaca cggatttcct aattacactg gctgtgccct cggcagtggc         1000
actggtcctt tttctaatac ttgcttatat catgtgctgc cgacgggaag         1050
gcgtggaaaa gagaaacatg caaacaccag acatccaact ggtccatcac         1100
agtgctattc agaaatctac caaggagctt cgagacatgt ccaagaatag         1150
agagatagca tggcccctgt caacgcttcc tgtgttccac cctgtgactg         1200
gggaaatcat acctccttta cacacagaca actatgatag cacaaacatg         1250
ccattgatgc aaacgcagca gaacttgcca catcagactc agattcccca         1300
acagcagact acaggtaaat ggtatccctg aagaaagaaa actgactgaa         1350
gcaatgaatt tataatcaga caatatagca gttacatcac atttcttttc         1400
tcttccaata atgcatgagc ttttctggca tatgttatgc atgttggcag         1450
tattaagtgt ataccaaata atacaacata actttcattt tactaatgta         1500
tttttttgta cttaaagcat ttttgacaat ttgtaaaaca ttgatgactt         1550
tatatttgtt acaataaaag ttgatcttta aaataaatat tattaatgaa         1600
gcctaaaaaa  aaaaa                                              1615
```

<210> SEQ ID NO 136
<211> LENGTH: 437
<212> TYPE: PRT
<213> ORGANISM: Homo sapiens

<400> SEQUENCE: 136

```
Met Gln Leu Pro Arg Trp Trp Glu Leu Gly Asp Pro Cys Ala Trp
  1               5                  10                  15

Thr Gly Gln Gly Arg Gly Thr Arg Arg Met Ser Pro Ala Thr Thr
                 20                  25                  30

Gly Thr Phe Leu Leu Thr Val Tyr Ser Ile Phe Ser Lys Val His
                 35                  40                  45

Ser Asp Arg Asn Val Tyr Pro Ser Ala Gly Val Leu Phe Val His
```

-continued

```
                50                  55                  60

Val Leu Glu Arg Glu Tyr Phe Lys Gly Glu Phe Pro Pro Tyr Pro
                65                  70                  75

Lys Pro Gly Glu Ile Ser Asn Asp Pro Ile Thr Phe Asn Thr Asn
                80                  85                  90

Leu Met Gly Tyr Pro Asp Arg Pro Gly Trp Leu Arg Tyr Ile Gln
                95                 100                 105

Arg Thr Pro Tyr Ser Asp Gly Val Leu Tyr Gly Ser Pro Thr Ala
               110                 115                 120

Glu Asn Val Gly Lys Pro Thr Ile Ile Glu Ile Thr Ala Tyr Asn
               125                 130                 135

Arg Arg Thr Phe Glu Thr Ala Arg His Asn Leu Ile Ile Asn Ile
               140                 145                 150

Met Ser Ala Glu Asp Phe Pro Leu Pro Tyr Gln Ala Glu Phe Phe
               155                 160                 165

Ile Lys Asn Met Asn Val Glu Glu Met Leu Ala Ser Glu Val Leu
               170                 175                 180

Gly Asp Phe Leu Gly Ala Val Lys Asn Val Trp Gln Pro Glu Arg
               185                 190                 195

Leu Asn Ala Ile Asn Ile Thr Ser Ala Leu Asp Arg Gly Gly Arg
               200                 205                 210

Val Pro Leu Pro Ile Asn Asp Leu Lys Glu Gly Val Tyr Val Met
               215                 220                 225

Val Gly Ala Asp Val Pro Phe Ser Ser Cys Leu Arg Glu Val Glu
               230                 235                 240

Asn Pro Gln Asn Gln Leu Arg Cys Ser Gln Glu Met Glu Pro Val
               245                 250                 255

Ile Thr Cys Asp Lys Lys Phe Arg Thr Gln Phe Tyr Ile Asp Trp
               260                 265                 270

Cys Lys Ile Ser Leu Val Asp Lys Thr Lys Gln Val Ser Thr Tyr
               275                 280                 285

Gln Glu Val Ile Arg Gly Glu Gly Ile Leu Pro Asp Gly Gly Glu
               290                 295                 300

Tyr Lys Pro Pro Ser Asp Ser Leu Lys Ser Arg Asp Tyr Tyr Thr
               305                 310                 315

Asp Phe Leu Ile Thr Leu Ala Val Pro Ser Ala Val Ala Leu Val
               320                 325                 330

Leu Phe Leu Ile Leu Ala Tyr Ile Met Cys Cys Arg Arg Glu Gly
               335                 340                 345

Val Glu Lys Arg Asn Met Gln Thr Pro Asp Ile Gln Leu Val His
               350                 355                 360

His Ser Ala Ile Gln Lys Ser Thr Lys Glu Leu Arg Asp Met Ser
               365                 370                 375

Lys Asn Arg Glu Ile Ala Trp Pro Leu Ser Thr Leu Pro Val Phe
               380                 385                 390

His Pro Val Thr Gly Glu Ile Ile Pro Pro Leu His Thr Asp Asn
               395                 400                 405

Tyr Asp Ser Thr Asn Met Pro Leu Met Gln Thr Gln Gln Asn Leu
               410                 415                 420

Pro His Gln Thr Gln Ile Pro Gln Gln Gln Thr Thr Gly Lys Trp
               425                 430                 435

Tyr Pro
```

-continued

<210> SEQ ID NO 137
<211> LENGTH: 1621
<212> TYPE: DNA
<213> ORGANISM: Homo sapiens

<400> SEQUENCE: 137 cagaagaggg ggctagctag ctgtctctgc ggaccaggga gacccccgcg 50 cccccccggt gtgaggcggc ctcacagggc cgggtgggct ggcgagccga 100 cgcggcggcg gaggaggctg tgaggagtgt gtggaacagg acccgggaca 150 gaggaaccat ggctccgcag aacctgagca ccttttgcct gttgctgcta 200 tacctcatcg gggcggtgat tgccggacga gatttctata agatcttggg 250 ggtgcctcga agtgcctcta taaaggatat taaaaaggcc tataggaaac 300 tagccctgca gcttcatccc gaccggaacc ctgatgatcc acaagcccag 350 gagaaattcc aggatctggg tgctgcttat gaggttctgt cagatagtga 400 gaaacggaaa cagtacgata cttatggtga agaaggatta aaagatggtc 450 atcagagctc ccatggagac atttttcac acttctttgg ggattttggt 500 ttcatgtttg gaggaacccc tcgtcagcaa gacagaaata ttccaagagg 550 aagtgatatt attgtagatc tagaagtcac tttggaagaa gtatatgcag 600 gaaattttgt ggaagtagtt agaaacaaac ctgtggcaag gcaggctcct 650 ggcaaacgga agtgcaattg tcggcaagag atgcggacca cccagctggg 700 ccctgggcgc ttccaaatga cccaggaggt ggtctgcgac gaatgcccta 750 atgtcaaact agtgaatgaa gaacgaacgc tggaagtaga aatagagcct 800 ggggtgagag acggcatgga gtaccccttt attggagaag gtgagcctca 850 cgtggatggg gagcctggag atttacggtt ccgaatcaaa gttgtcaagc 900 acccaatatt tgaaaggaga ggagatgatt tgtacacaaa tgtgacaatc 950 tcattagttg agtcactggt tggctttgag atggatatta ctcacttgga 1000 tggtcacaag gtacatattt cccgggataa gatcaccagg ccaggagcga 1050 agctatggaa gaaaggggaa gggctcccca actttgacaa caacaatatc 1100 aagggctctt tgataatcac ttttgatgtg gattttccaa aagaacagtt 1150 aacagaggaa gcgagagaag gtatcaaaca gctactgaaa caagggtcag 1200 tgcagaaggt atacaatgga ctgcaaggat attgagagtg aataaaattg 1250 gactttgttt aaaataagtg aataagcgat atttattatc tgcaaggttt 1300 ttttgtgtgt gtttttgttt ttattttcaa tatgcaagtt aggcttaatt 1350 tttttatcta atgatcatca tgaaatgaat aagagggctt aagaatttgt 1400 ccatttgcat tcggaaaaga atgaccagca aaaggtttac taatacctct 1450 ccctttgggg atttaatgtc tggtgctgcc gcctgagttt caagaattaa 1500 agctgcaaga ggactccagg agcaaaagaa acacaatata gagggttgga 1550 gttgttagca atttcattca aaatgccaac tggagaagtc tgtttttaaa 1600 tacattttgt tgttattttt a 1621

<210> SEQ ID NO 138
<211> LENGTH: 358
<212> TYPE: PRT
<213> ORGANISM: Homo sapiens

<400> SEQUENCE: 138

Met Ala Pro Gln Asn Leu Ser Thr Phe Cys Leu Leu Leu Leu Tyr
1 5 10 15

Leu Ile Gly Ala Val Ile Ala Gly Arg Asp Phe Tyr Lys Ile Leu
20 25 30

Gly Val Pro Arg Ser Ala Ser Ile Lys Asp Ile Lys Lys Ala Tyr
35 40 45

Arg Lys Leu Ala Leu Gln Leu His Pro Asp Arg Asn Pro Asp Asp
50 55 60

Pro Gln Ala Gln Glu Lys Phe Gln Asp Leu Gly Ala Ala Tyr Glu
65 70 75

Val Leu Ser Asp Ser Glu Lys Arg Lys Gln Tyr Asp Thr Tyr Gly
80 85 90

Glu Glu Gly Leu Lys Asp Gly His Gln Ser Ser His Gly Asp Ile
95 100 105

Phe Ser His Phe Phe Gly Asp Phe Gly Phe Met Phe Gly Gly Thr
110 115 120

Pro Arg Gln Gln Asp Arg Asn Ile Pro Arg Gly Ser Asp Ile Ile
125 130 135

Val Asp Leu Glu Val Thr Leu Glu Glu Val Tyr Ala Gly Asn Phe
140 145 150

Val Glu Val Val Arg Asn Lys Pro Val Ala Arg Gln Ala Pro Gly
155 160 165

Lys Arg Lys Cys Asn Cys Arg Gln Glu Met Arg Thr Thr Gln Leu
170 175 180

Gly Pro Gly Arg Phe Gln Met Thr Gln Glu Val Val Cys Asp Glu
185 190 195

Cys Pro Asn Val Lys Leu Val Asn Glu Glu Arg Thr Leu Glu Val
200 205 210

Glu Ile Glu Pro Gly Val Arg Asp Gly Met Glu Tyr Pro Phe Ile
215 220 225

Gly Glu Gly Glu Pro His Val Asp Gly Glu Pro Gly Asp Leu Arg
230 235 240

Phe Arg Ile Lys Val Val Lys His Pro Ile Phe Glu Arg Arg Gly
245 250 255

Asp Asp Leu Tyr Thr Asn Val Thr Ile Ser Leu Val Glu Ser Leu
260 265 270

Val Gly Phe Glu Met Asp Ile Thr His Leu Asp Gly His Lys Val
275 280 285

His Ile Ser Arg Asp Lys Ile Thr Arg Pro Gly Ala Lys Leu Trp
290 295 300

Lys Lys Gly Glu Gly Leu Pro Asn Phe Asp Asn Asn Asn Ile Lys
305 310 315

Gly Ser Leu Ile Ile Thr Phe Asp Val Asp Phe Pro Lys Glu Gln
320 325 330

Leu Thr Glu Glu Ala Arg Glu Gly Ile Lys Gln Leu Leu Lys Gln
335 340 345

Gly Ser Val Gln Lys Val Tyr Asn Gly Leu Gln Gly Tyr
350 355

<210> SEQ ID NO 139
<211> LENGTH: 550
<212> TYPE: DNA

-continued

<213> ORGANISM: Homo sapiens

<400> SEQUENCE: 139 ccagtctgtc gccacctcac ttggtgtctg ctgtccccgc caggcaagcc 50 tggggtgaga gcacagagga gtgggccggg accatgcggg ggacgcggct 100 ggcgctcctg gcgctggtgc tggctgcctg cggagagctg gcgccggccc 150 tgcgctgcta cgtctgtccg gagcccacag gagtgtcgga ctgtgtcacc 200 atcgccacct gcaccaccaa cgaaaccatg tgcaagacca cactctactc 250 ccgggagata gtgtacccct tccaggggga ctccacggtg accaagtcct 300 gtgccagcaa gtgtaagccc tcggatgtgg atggcatcgg ccagaccctg 350 cccgtgtcct gctgcaatac tgagctgtgc aatgtagacg gggcgcccgc 400 tctgaacagc ctccactgcg gggccctcac gctcctccca ctcttgagcc 450 tccgactgta gagtccccgc ccacccccat ggccctatgc ggcccagccc 500 cgaatgcctt gaagaagtgc cccctgcacc aggaaaaaaa aaaaaaaaaa 550

<210> SEQ ID NO 140
<211> LENGTH: 125
<212> TYPE: PRT
<213> ORGANISM: Homo sapiens

<400> SEQUENCE: 140

Met Arg Gly Thr Arg Leu Ala Leu Leu Ala Leu Val Leu Ala Ala
1 5 10 15

Cys Gly Glu Leu Ala Pro Ala Leu Arg Cys Tyr Val Cys Pro Glu
20 25 30

Pro Thr Gly Val Ser Asp Cys Val Thr Ile Ala Thr Cys Thr Thr
35 40 45

Asn Glu Thr Met Cys Lys Thr Thr Leu Tyr Ser Arg Glu Ile Val
50 55 60

Tyr Pro Phe Gln Gly Asp Ser Thr Val Thr Lys Ser Cys Ala Ser
65 70 75

Lys Cys Lys Pro Ser Asp Val Asp Gly Ile Gly Gln Thr Leu Pro
80 85 90

Val Ser Cys Cys Asn Thr Glu Leu Cys Asn Val Asp Gly Ala Pro
95 100 105

Ala Leu Asn Ser Leu His Cys Gly Ala Leu Thr Leu Leu Pro Leu
110 115 120

Leu Ser Leu Arg Leu
125

<210> SEQ ID NO 141
<211> LENGTH: 1524
<212> TYPE: DNA
<213> ORGANISM: Homo sapiens

<400> SEQUENCE: 141 ggcgccgcgt aggcccggga ggccgggccg gccgggctgc gagcgcctgc 50 cccatgcgcc gccgcctctc cgcacgatgt tcccctcgcg gaggaaagcg 100 gcgcagctgc cctgggagga cggcaggtcc gggttgctct ccggcggcct 150 ccctcggaag tgttccgtct tccacctgtt cgtggcctgc ctctcgctgg 200 gcttcttctc cctactctgg ctgcagctca gctgctctgg ggacgtggcc 250

-continued

```
cgggcagtca ggggacaagg gcaggagacc tcgggccctc cccgtgcctg      300
ccccccagag ccgccccctg agcactggga agaagacgca tcctggggcc      350
cccaccgcct ggcagtgctg gtgcccttcc gcgaacgctt cgaggagctc      400
ctggtcttcg tgccccacat gcgccgcttc ctgagcagga agaagatccg      450
gcaccacatc tacgtgctca accaggtgga ccacttcagg ttcaaccggg      500
cagcgctcat caacgtgggc ttcctggaga gcagcaacag cacggactac      550
attgccatgc acgacgttga cctgctccct ctcaacgagg agctggacta      600
tggctttcct gaggctgggc ccttccacgt ggcctccccg gagctccacc      650
ctctctacca ctacaagacc tatgtcggcg gcatcctgct gctctccaag      700
cagcactacc ggctgtgcaa tgggatgtcc aaccgcttct ggggctgggg      750
ccgcgaggac gacgagttct accggcgcat taagggagct gggctccagc      800
ttttccgccc ctcgggaatc acaactgggt acaagacatt tcgccacctg      850
catgacccag cctggcggaa gagggaccag aagcgcatcg cagctcaaaa      900
acaggagcag ttcaaggtgg acagggaggg aggcctgaac actgtgaagt      950
accatgtggc ttcccgcact gccctgtctg tgggcggggc cccctgcact     1000
gtcctcaaca tcatgttgga ctgtgacaag accgccacac cctggtgcac     1050
attcagctga gctggatgga cagtgaggaa gcctgtacct acaggccata     1100
ttgctcaggc tcaggacaag gcctcaggtc gtgggcccag ctctgacagg     1150
atgtggagtg gccaggacca agacagcaag ctacgcaatt gcagccaccc     1200
ggccgccaag gcaggcttgg gctgggccag gacacgtggg gtgcctggga     1250
cgctgcttgc catgcacagt gatcagagag aggctggggt gtgtcctgtc     1300
cgggaccccc cctgccttcc tgctcaccct actctgacct ccttcacgtg     1350
cccaggcctg tgggtagtgg ggagggctga acaggacaac ctctcatcac     1400
cctactctga cctccttcac gtgcccaggc ctgtgggtag tggggagggc     1450
tgaacaggac aacctctcat cacccccaaa aaaaaaaaaa aaaaaaaaaa     1500
aaaaaaaaaa aaaaaaaaaa  aaaa                                1524
```

<210> SEQ ID NO 142
<211> LENGTH: 327
<212> TYPE: PRT
<213> ORGANISM: Homo sapiens

<400> SEQUENCE: 142

```
Met Phe Pro Ser Arg Arg Lys Ala Ala Gln Leu Pro Trp Glu Asp
  1               5                  10                  15

Gly Arg Ser Gly Leu Leu Ser Gly Gly Leu Pro Arg Lys Cys Ser
                 20                  25                  30

Val Phe His Leu Phe Val Ala Cys Leu Ser Leu Gly Phe Phe Ser
                 35                  40                  45

Leu Leu Trp Leu Gln Leu Ser Cys Ser Gly Asp Val Ala Arg Ala
                 50                  55                  60

Val Arg Gly Gln Gly Gln Glu Thr Ser Gly Pro Pro Arg Ala Cys
                 65                  70                  75

Pro Pro Glu Pro Pro Pro Glu His Trp Glu Glu Asp Ala Ser Trp
                 80                  85                  90

Gly Pro His Arg Leu Ala Val Leu Val Pro Phe Arg Glu Arg Phe
```

-continued

```
                95                  100                 105

Glu Glu Leu Leu Val Phe Val Pro His Met Arg Arg Phe Leu Ser
                110                 115                 120

Arg Lys Lys Ile Arg His His Ile Tyr Val Leu Asn Gln Val Asp
                125                 130                 135

His Phe Arg Phe Asn Arg Ala Ala Leu Ile Asn Val Gly Phe Leu
                140                 145                 150

Glu Ser Ser Asn Ser Thr Asp Tyr Ile Ala Met His Asp Val Asp
                155                 160                 165

Leu Leu Pro Leu Asn Glu Glu Leu Asp Tyr Gly Phe Pro Glu Ala
                170                 175                 180

Gly Pro Phe His Val Ala Ser Pro Glu Leu His Pro Leu Tyr His
                185                 190                 195

Tyr Lys Thr Tyr Val Gly Gly Ile Leu Leu Leu Ser Lys Gln His
                200                 205                 210

Tyr Arg Leu Cys Asn Gly Met Ser Asn Arg Phe Trp Gly Trp Gly
                215                 220                 225

Arg Glu Asp Asp Glu Phe Tyr Arg Arg Ile Lys Gly Ala Gly Leu
                230                 235                 240

Gln Leu Phe Arg Pro Ser Gly Ile Thr Thr Gly Tyr Lys Thr Phe
                245                 250                 255

Arg His Leu His Asp Pro Ala Trp Arg Lys Arg Asp Gln Lys Arg
                260                 265                 270

Ile Ala Ala Gln Lys Gln Glu Gln Phe Lys Val Asp Arg Glu Gly
                275                 280                 285

Gly Leu Asn Thr Val Lys Tyr His Val Ala Ser Arg Thr Ala Leu
                290                 295                 300

Ser Val Gly Gly Ala Pro Cys Thr Val Leu Asn Ile Met Leu Asp
                305                 310                 315

Cys Asp Lys Thr Ala Thr Pro Trp Cys Thr Phe Ser
                320                 325


<210> SEQ ID NO 143
<211> LENGTH: 1621
<212> TYPE: DNA
<213> ORGANISM: Homo sapiens

<400> SEQUENCE: 143

gtgggattta tttgagtgca agatcgtttt ctcagtggtg gtggaagttg                50

cctcatcgca ggcagatgtt ggggctttgt ccgaacagct cccctctgcc               100

agcttctgta gataagggtt aaaaactaat atttatatga cagaagaaaa               150

agatgtcatt ccgtaaagta aacatcatca tcttggtcct ggctgttgct               200

ctcttcttac tggttttgca ccataacttc ctcagcttga gcagtttgtt               250

aaggaatgag gttacagatt caggaattgt agggcctcaa cctatagact               300

ttgtcccaaa tgctctccga catgcagtag atgggagaca agaggagatt               350

cctgtggtca tcgctgcatc tgaagacagg cttgggggg ccattgcagc                400

tataaacagc attcagcaca acactcgctc caatgtgatt ttctacattg               450

ttactctcaa caatacagca gaccatctcc ggtcctggct caacagtgat               500

tccctgaaaa gcatcagata caaaattgtc aattttgacc ctaaactttt               550

ggaaggaaaa gtaaaggagg atcctgacca gggggaatcc atgaaacctt               600
```

-continued

```
taacctttgc aaggttctac ttgccaattc tggttcccag cgcaaagaag          650

gccatataca tggatgatga tgtaattgtg caaggtgata ttcttgccct          700

ttacaataca gcactgaagc caggacatgc agctgcattt tcagaagatt          750

gtgattcagc ctctactaaa gttgtcatcc gtggagcagg aaaccagtac          800

aattacattg gctatcttga ctataaaaag gaaagaattc gtaagctttc          850

catgaaagcc agcacttgct catttaatcc tggagttttt gttgcaaacc          900

tgacggaatg gaaacgacag aatataacta accaactgga aaaatggatg          950

aaactcaatg tagaagaggg actgtatagc agaaccctgg ctggtagcat         1000

cacaacacct cctctgctta tcgtatttta tcaacagcac tctaccatcg         1050

atcctatgtg gaatgtccgc caccttggtt ccagtgctgg aaaacgatat         1100

tcacctcagt ttgtaaaggc tgccaagtta ctccattgga atggacattt         1150

gaagccatgg ggaaggactg cttcatatac tgatgtttgg gaaaaatggt         1200

atattccaga cccaacaggc aaattcaacc taatccgaag atataccgag         1250

atctcaaaca taaagtgaaa cagaatttga actgtaagca agcatttctc         1300

aggaagtcct ggaagatagc atgcatggga agtaacagtt gctaggcttc         1350

aatgcctatc ggtagcaagc catggaaaaa gatgtgtcag ctaggtaaag         1400

atgacaaact gccctgtctg gcagtcagct tcccagacag actatagact         1450

ataaatatgt ctccatctgc cttaccaagt gttttcttac tacaatgctg         1500

aatgactgga aagaagaact gatatggcta gttcagctag ctggtacaga         1550

taattcaaaa ctgctgttgg ttttaatttt gtaacctgtg gcctgatctg         1600

taaataaaac ttacattttt  c                                       1621
```

<210> SEQ ID NO 144
<211> LENGTH: 371
<212> TYPE: PRT
<213> ORGANISM: Homo sapiens

<400> SEQUENCE: 144

```
Met Ser Phe Arg Lys Val Asn Ile Ile Ile Leu Val Leu Ala Val
  1               5                  10                  15

Ala Leu Phe Leu Leu Val Leu His His Asn Phe Leu Ser Leu Ser
                 20                  25                  30

Ser Leu Leu Arg Asn Glu Val Thr Asp Ser Gly Ile Val Gly Pro
                 35                  40                  45

Gln Pro Ile Asp Phe Val Pro Asn Ala Leu Arg His Ala Val Asp
                 50                  55                  60

Gly Arg Gln Glu Glu Ile Pro Val Val Ile Ala Ala Ser Glu Asp
                 65                  70                  75

Arg Leu Gly Gly Ala Ile Ala Ala Ile Asn Ser Ile Gln His Asn
                 80                  85                  90

Thr Arg Ser Asn Val Ile Phe Tyr Ile Val Thr Leu Asn Asn Thr
                 95                 100                 105

Ala Asp His Leu Arg Ser Trp Leu Asn Ser Asp Ser Leu Lys Ser
                110                 115                 120

Ile Arg Tyr Lys Ile Val Asn Phe Asp Pro Lys Leu Leu Glu Gly
                125                 130                 135

Lys Val Lys Glu Asp Pro Asp Gln Gly Glu Ser Met Lys Pro Leu
                140                 145                 150
```

-continued

```
Thr Phe Ala Arg Phe Tyr Leu Pro Ile Leu Val Pro Ser Ala Lys
                155                 160                 165

Lys Ala Ile Tyr Met Asp Asp Asp Val Ile Val Gln Gly Asp Ile
                170                 175                 180

Leu Ala Leu Tyr Asn Thr Ala Leu Lys Pro Gly His Ala Ala Ala
                185                 190                 195

Phe Ser Glu Asp Cys Asp Ser Ala Ser Thr Lys Val Val Ile Arg
                200                 205                 210

Gly Ala Gly Asn Gln Tyr Asn Tyr Ile Gly Tyr Leu Asp Tyr Lys
                215                 220                 225

Lys Glu Arg Ile Arg Lys Leu Ser Met Lys Ala Ser Thr Cys Ser
                230                 235                 240

Phe Asn Pro Gly Val Phe Val Ala Asn Leu Thr Glu Trp Lys Arg
                245                 250                 255

Gln Asn Ile Thr Asn Gln Leu Glu Lys Trp Met Lys Leu Asn Val
                260                 265                 270

Glu Glu Gly Leu Tyr Ser Arg Thr Leu Ala Gly Ser Ile Thr Thr
                275                 280                 285

Pro Pro Leu Leu Ile Val Phe Tyr Gln Gln His Ser Thr Ile Asp
                290                 295                 300

Pro Met Trp Asn Val Arg His Leu Gly Ser Ser Ala Gly Lys Arg
                305                 310                 315

Tyr Ser Pro Gln Phe Val Lys Ala Ala Lys Leu Leu His Trp Asn
                320                 325                 330

Gly His Leu Lys Pro Trp Gly Arg Thr Ala Ser Tyr Thr Asp Val
                335                 340                 345

Trp Glu Lys Trp Tyr Ile Pro Asp Pro Thr Gly Lys Phe Asn Leu
                350                 355                 360

Ile Arg Arg Tyr Thr Glu Ile Ser Asn Ile Lys
                365                 370


<210> SEQ ID NO 145
<211> LENGTH: 415
<212> TYPE: DNA
<213> ORGANISM: Homo sapiens

<400> SEQUENCE: 145

aaacttgacg ccatgaagat cccggtcctt cctgccgtgg tgctcctctc                50

cctcctggtg ctccactctg cccagggagc caccctgggt ggtcctgagg               100

aagaaagcac cattgagaat tatgcgtcac gacccgaggc ctttaacacc               150

ccgttcctga acatcgacaa attgcgatct gcgtttaagg ctgatgagtt               200

cctgaactgg cacgccctct ttgagtctat caaaaggaaa cttcctttcc               250

tcaactggga tgcctttcct aagctgaaag gactgaggag cgcaactcct               300

gatgcccagt gaccatgacc tccactggaa gagggggcta gcgtgagcgc               350

tgattctcaa cctaccataa ctctttcctg cctcaggaac tccaataaaa               400

cattttccat  ccaaa                                                    415


<210> SEQ ID NO 146
<211> LENGTH: 99
<212> TYPE: PRT
<213> ORGANISM: Homo sapiens

<400> SEQUENCE: 146
```

```
Met Lys Ile Pro Val Leu Pro Ala Val Val Leu Leu Ser Leu Leu
  1               5                  10                  15

Val Leu His Ser Ala Gln Gly Ala Thr Leu Gly Gly Pro Glu Glu
                 20                  25                  30

Glu Ser Thr Ile Glu Asn Tyr Ala Ser Arg Pro Glu Ala Phe Asn
                 35                  40                  45

Thr Pro Phe Leu Asn Ile Asp Lys Leu Arg Ser Ala Phe Lys Ala
                 50                  55                  60

Asp Glu Phe Leu Asn Trp His Ala Leu Phe Glu Ser Ile Lys Arg
                 65                  70                  75

Lys Leu Pro Phe Leu Asn Trp Asp Ala Phe Pro Lys Leu Lys Gly
                 80                  85                  90

Leu Arg Ser Ala Thr Pro Asp Ala Gln
                 95


<210> SEQ ID NO 147
<211> LENGTH: 745
<212> TYPE: DNA
<213> ORGANISM: Homo sapiens

<400> SEQUENCE: 147

cctctgtcca ctgctttcgt gaagacaaga tgaagttcac aattgtcttt                50

gctggacttc ttggagtctt tctagctcct gccctagcta actataatat               100

caacgtcaat gatgacaaca acaatgctgg aagtgggcag cagtcagtga               150

gtgtcaacaa tgaacacaat gtggccaatg ttgacaataa caacggatgg               200

gactcctgga attccatctg ggattatgga aatggctttg ctgcaaccag               250

actctttcaa aagaagacat gcattgtgca caaaatgaac aaggaagtca               300

tgccctccat tcaatccctt gatgcactgg tcaaggaaaa gaagcttcag               350

ggtaagggac caggaggacc acctcccaag ggcctgatgt actcagtcaa               400

cccaaacaaa gtcgatgacc tgagcaagtt cggaaaaaac attgcaaaca               450

tgtgtcgtgg gattccaaca tacatggctg aggagatgca agaggcaagc               500

ctgtttttt actcaggaac gtgctacacg accagtgtac tatggattgt                550

ggacatttcc ttctgtggag acacggtgga gaactaaaca atttttaaa                600

gccactatgg atttagtcat ctgaatatgc tgtgcagaaa aaatatgggc               650

tccagtggtt tttaccatgt cattctgaaa tttttctcta ctagttatgt               700

ttgatttctt taagtttcaa taaaatcatt tagcattgaa  aaaaa                   745


<210> SEQ ID NO 148
<211> LENGTH: 185
<212> TYPE: PRT
<213> ORGANISM: Homo sapiens

<400> SEQUENCE: 148

Met Lys Phe Thr Ile Val Phe Ala Gly Leu Leu Gly Val Phe Leu
  1               5                  10                  15

Ala Pro Ala Leu Ala Asn Tyr Asn Ile Asn Val Asn Asp Asp Asn
                 20                  25                  30

Asn Asn Ala Gly Ser Gly Gln Gln Ser Val Ser Val Asn Asn Glu
                 35                  40                  45

His Asn Val Ala Asn Val Asp Asn Asn Asn Gly Trp Asp Ser Trp
                 50                  55                  60
```

-continued

```
Asn Ser Ile Trp Asp Tyr Gly Asn Gly Phe Ala Ala Thr Arg Leu
                65                  70                  75

Phe Gln Lys Lys Thr Cys Ile Val His Lys Met Asn Lys Glu Val
                80                  85                  90

Met Pro Ser Ile Gln Ser Leu Asp Ala Leu Val Lys Glu Lys Lys
                95                 100                 105

Leu Gln Gly Lys Gly Pro Gly Gly Pro Pro Pro Lys Gly Leu Met
               110                 115                 120

Tyr Ser Val Asn Pro Asn Lys Val Asp Asp Leu Ser Lys Phe Gly
               125                 130                 135

Lys Asn Ile Ala Asn Met Cys Arg Gly Ile Pro Thr Tyr Met Ala
               140                 145                 150

Glu Glu Met Gln Glu Ala Ser Leu Phe Phe Tyr Ser Gly Thr Cys
               155                 160                 165

Tyr Thr Thr Ser Val Leu Trp Ile Val Asp Ile Ser Phe Cys Gly
               170                 175                 180

Asp Thr Val Glu Asn
               185


<210> SEQ ID NO 149
<211> LENGTH: 992
<212> TYPE: DNA
<213> ORGANISM: Homo sapiens

<400> SEQUENCE: 149

ggcacgagcc aggaactagg aggttctcac tgcccgagca gaggccctac                50

acccaccgag gcatggggct ccctgggctg ttctgcttgg ccgtgctggc               100

tgccagcagc ttctccaagg cacgggagga agaaattacc cctgtggtct               150

ccattgccta caaagtcctg gaagttttcc ccaaaggccg ctgggtgctc               200

ataacctgct gtgcacccca gccaccaccg cccatcacct attccctctg               250

tggaaccaag aacatcaagg tggccaagaa ggtggtgaag acccacgagc               300

cggcctcctt caacctcaac gtcacactca agtccagtcc agacctgctc               350

acctacttct gccgggcgtc ctccacctca ggtgcccatg tggacagtgc               400

caggctacag atgcactggg agctgtggtc caagccagtg tctgagctgc               450

gggccaactt cactctgcag gacagagggg caggccccag ggtggagatg               500

atctgccagg cgtcctcggg cagcccacct atcaccaaca gcctgatcgg               550

gaaggatggg caggtccacc tgcagcagag accatgccac aggcagcctg               600

ccaacttctc cttcctgccg agccagacat cggactggtt ctggtgccag               650

gctgcaaaca acgccaatgt ccagcacagc gccctcacag tggtgccccc               700

aggtggtgac cagaagatgg aggactggca gggtcccctg gagagcccca               750

tccttgcctt gccgctctac aggagcaccc gccgtctgag tgaagaggag               800

tttgggggt tcaggatagg gaatggggag gtcagaggac gcaaagcagc               850

agccatgtag aatgaaccgt ccagagagcc aagcacggca gaggactgca               900

ggccatcagc gtgcactgtt cgtatttgga gttcatgcaa aatgagtgtg               950

ttttagctgc tcttgccaca aaaaaaaaaa aaaaaaaaaa  aa                      992


<210> SEQ ID NO 150
<211> LENGTH: 265
```

-continued

<212> TYPE: PRT
<213> ORGANISM: Homo sapiens

<400> SEQUENCE: 150

Met Gly Leu Pro Gly Leu Phe Cys Leu Ala Val Leu Ala Ala Ser
1 5 10 15

Ser Phe Ser Lys Ala Arg Glu Glu Glu Ile Thr Pro Val Val Ser
20 25 30

Ile Ala Tyr Lys Val Leu Glu Val Phe Pro Lys Gly Arg Trp Val
35 40 45

Leu Ile Thr Cys Cys Ala Pro Gln Pro Pro Pro Pro Ile Thr Tyr
50 55 60

Ser Leu Cys Gly Thr Lys Asn Ile Lys Val Ala Lys Lys Val Val
65 70 75

Lys Thr His Glu Pro Ala Ser Phe Asn Leu Asn Val Thr Leu Lys
80 85 90

Ser Ser Pro Asp Leu Leu Thr Tyr Phe Cys Arg Ala Ser Ser Thr
95 100 105

Ser Gly Ala His Val Asp Ser Ala Arg Leu Gln Met His Trp Glu
110 115 120

Leu Trp Ser Lys Pro Val Ser Glu Leu Arg Ala Asn Phe Thr Leu
125 130 135

Gln Asp Arg Gly Ala Gly Pro Arg Val Glu Met Ile Cys Gln Ala
140 145 150

Ser Ser Gly Ser Pro Pro Ile Thr Asn Ser Leu Ile Gly Lys Asp
155 160 165

Gly Gln Val His Leu Gln Gln Arg Pro Cys His Arg Gln Pro Ala
170 175 180

Asn Phe Ser Phe Leu Pro Ser Gln Thr Ser Asp Trp Phe Trp Cys
185 190 195

Gln Ala Ala Asn Asn Ala Asn Val Gln His Ser Ala Leu Thr Val
200 205 210

Val Pro Pro Gly Gly Asp Gln Lys Met Glu Asp Trp Gln Gly Pro
215 220 225

Leu Glu Ser Pro Ile Leu Ala Leu Pro Leu Tyr Arg Ser Thr Arg
230 235 240

Arg Leu Ser Glu Glu Glu Phe Gly Gly Phe Arg Ile Gly Asn Gly
245 250 255

Glu Val Arg Gly Arg Lys Ala Ala Ala Met
260 265

<210> SEQ ID NO 151
<211> LENGTH: 683
<212> TYPE: DNA
<213> ORGANISM: Homo sapiens

<400> SEQUENCE: 151 gcgtggggat gtctaggagc tcgaaggtgg tgctgggcct ctcggtgctg 50 ctgacggcgg ccacagtggc cggcgtacat gtgaagcagc agtgggacca 100 gcagaggctt cgtgacggag ttatcagaga cattgagagg caaattcgga 150 aaaaagaaaa cattcgtctt ttgggagaac agattatttt gactgagcaa 200 cttgaagcag aaagagagaa gatgttattg gcaaaaggat ctcaaaaatc 250 atgacttgaa tgtgaaatat ctgttggaca gacaacacga gtttgtgtgt 300

-continued

```
gtgtgttgat ggagagtagc ttagtagtat cttcatcttt ttttttggtc          350

actgtccttt taaacttgat caaataaagg acagtgggtc atataagtta          400

ctgctttcag ggtcccttat atctgaataa aggagtgtgg gcagacactt          450

tttggaagag tctgtctggg tgatcctggt agaagcccca ttagggtcac          500

tgtccagtgc ttagggttgt tactgagaag cactgccgag cttgtgagaa          550

ggaagggatg gatagtagca tccacctgag tagtctgatc agtcggcatg          600

atgacgaagc cacgagaaca tcgacctcag aaggactgga ggaaggtgaa          650

gtggagggag agacgctcct gatcgtcgaa  tcc                           683
```

<210> SEQ ID NO 152
<211> LENGTH: 81
<212> TYPE: PRT
<213> ORGANISM: Homo sapiens

<400> SEQUENCE: 152

```
Met Ser Arg Ser Ser Lys Val Val Leu Gly Leu Ser Val Leu Leu
  1               5                  10                  15

Thr Ala Ala Thr Val Ala Gly Val His Val Lys Gln Gln Trp Asp
                 20                  25                  30

Gln Gln Arg Leu Arg Asp Gly Val Ile Arg Asp Ile Glu Arg Gln
                 35                  40                  45

Ile Arg Lys Lys Glu Asn Ile Arg Leu Leu Gly Glu Gln Ile Ile
                 50                  55                  60

Leu Thr Glu Gln Leu Glu Ala Glu Arg Glu Lys Met Leu Leu Ala
                 65                  70                  75

Lys Gly Ser Gln Lys Ser
                 80
```

<210> SEQ ID NO 153
<211> LENGTH: 1869
<212> TYPE: DNA
<213> ORGANISM: Homo sapiens

<400> SEQUENCE: 153

```
aatgtgagag gggctgatgg aagctgatag gcaggactgg agtgttagca           50

ccagtactgg atgtgacagc aggcagagga gcacttagca gcttattcag          100

tgtccgattc tgattccggc aaggatccaa gcatggaatg ctgccgtcgg          150

gcaactcctg gcacactgct cctctttctg gctttcctgc tcctgagttc          200

caggaccgca cgctccgagg aggaccggga cggcctatgg gatgcctggg          250

gcccatggag tgaatgctca cgcacctgcg ggggaggggc ctcctactct          300

ctgaggcgct gcctgagcag caagagctgt gaaggaagaa atatccgata          350

cagaacatgc agtaatgtgg actgcccacc agaagcaggt gatttccgag          400

ctcagcaatg ctcagctcat aatgatgtca agcaccatgg ccagttttat          450

gaatggcttc ctgtgtctaa tgaccctgac aacccatgtt cactcaagtg          500

ccaagccaaa ggaacaaccc tggttgttga actagcacct aaggtcttag          550

atggtacgcg ttgctataca gaatctttgg atatgtgcat cagtggttta          600

tgccaaattg ttggctgcga tcaccagctg ggaagcaccg tcaaggaaga          650

taactgtggg gtctgcaacg gagatgggtc cacctgccgg ctggtccgag          700

ggcagtataa atcccagctc tccgcaacca aatcggatga tactgtggtt          750
```

-continued

```
gcacttccct atggaagtag acatattcgc cttgtcttaa aaggtcctga              800

tcacttatat ctggaaacca aaaccctcca ggggactaaa ggtgaaaaca              850

gtctcagctc cacaggaact ttccttgtgg acaattctag tgtggacttc              900

cagaaatttc cagacaaaga gatactgaga atggctggac cactcacagc              950

agatttcatt gtcaagattc gtaactcggg ctccgctgac agtacagtcc             1000

agttcatctt ctatcaaccc atcatccacc gatggaggga gacggatttc             1050

tttccttgct cagcaacctg tggaggaggt tatcagctga catcggctga             1100

gtgctacgat ctgaggagca accgtgtggt tgctgaccaa tactgtcact             1150

attacccaga gaacatcaaa cccaaaccca agcttcagga gtgcaacttg             1200

gatccttgtc cagccagtga cggatacaag cagatcatgc cttatgacct             1250

ctaccatccc cttcctcggt gggaggccac cccatggacc gcgtgctcct             1300

cctcgtgtgg ggggggcatc cagagccggg cagtttcctg tgtggaggag             1350

gacatccagg ggcatgtcac ttcagtggaa gagtggaaat gcatgtacac             1400

ccctaagatg cccatcgcgc agccctgcaa catttttgac tgccctaaat             1450

ggctggcaca ggagtggtct ccgtgcacag tgacatgtgg ccagggcctc             1500

agataccgtg tggtcctctg catcgaccat cgaggaatgc acacaggagg             1550

ctgtagccca aaaacaaagc cccacataaa agaggaatgc atcgtaccca             1600

ctccctgcta taaacccaaa gagaaacttc cagtcgaggc caagttgcca             1650

tggttcaaac aagctcaaga gctagaagaa ggagctgctg tgtcagagga             1700

gccctcgtaa gttgtaaaag cacagactgt tctatatttg aaactgtttt             1750

gtttaaagaa agcagtgtct cactggttgt agctttcatg ggttctgaac             1800

taagtgtaat catctcacca aagctttttg gctctcaaat taaagattga             1850

ttagtttcaa  aaaaaaaaa                                              1869
```

```
<210> SEQ ID NO 154
<211> LENGTH: 525
<212> TYPE: PRT
<213> ORGANISM: Homo sapiens

<400> SEQUENCE: 154

Met Glu Cys Cys Arg Arg Ala Thr Pro Gly Thr Leu Leu Leu Phe
  1               5                  10                  15

Leu Ala Phe Leu Leu Leu Ser Ser Arg Thr Ala Arg Ser Glu Glu
                 20                  25                  30

Asp Arg Asp Gly Leu Trp Asp Ala Trp Gly Pro Trp Ser Glu Cys
                 35                  40                  45

Ser Arg Thr Cys Gly Gly Gly Ala Ser Tyr Ser Leu Arg Arg Cys
                 50                  55                  60

Leu Ser Ser Lys Ser Cys Glu Gly Arg Asn Ile Arg Tyr Arg Thr
                 65                  70                  75

Cys Ser Asn Val Asp Cys Pro Pro Glu Ala Gly Asp Phe Arg Ala
                 80                  85                  90

Gln Gln Cys Ser Ala His Asn Asp Val Lys His His Gly Gln Phe
                 95                 100                 105

Tyr Glu Trp Leu Pro Val Ser Asn Asp Pro Asp Asn Pro Cys Ser
                110                 115                 120
```

-continued

```
Leu Lys Cys Gln Ala Lys Gly Thr Thr Leu Val Val Glu Leu Ala
                125                 130                 135

Pro Lys Val Leu Asp Gly Thr Arg Cys Tyr Thr Glu Ser Leu Asp
                140                 145                 150

Met Cys Ile Ser Gly Leu Cys Gln Ile Val Gly Cys Asp His Gln
                155                 160                 165

Leu Gly Ser Thr Val Lys Glu Asp Asn Cys Gly Val Cys Asn Gly
                170                 175                 180

Asp Gly Ser Thr Cys Arg Leu Val Arg Gly Gln Tyr Lys Ser Gln
                185                 190                 195

Leu Ser Ala Thr Lys Ser Asp Asp Thr Val Val Ala Leu Pro Tyr
                200                 205                 210

Gly Ser Arg His Ile Arg Leu Val Leu Lys Gly Pro Asp His Leu
                215                 220                 225

Tyr Leu Glu Thr Lys Thr Leu Gln Gly Thr Lys Gly Glu Asn Ser
                230                 235                 240

Leu Ser Ser Thr Gly Thr Phe Leu Val Asp Asn Ser Ser Val Asp
                245                 250                 255

Phe Gln Lys Phe Pro Asp Lys Glu Ile Leu Arg Met Ala Gly Pro
                260                 265                 270

Leu Thr Ala Asp Phe Ile Val Lys Ile Arg Asn Ser Gly Ser Ala
                275                 280                 285

Asp Ser Thr Val Gln Phe Ile Phe Tyr Gln Pro Ile Ile His Arg
                290                 295                 300

Trp Arg Glu Thr Asp Phe Phe Pro Cys Ser Ala Thr Cys Gly Gly
                305                 310                 315

Gly Tyr Gln Leu Thr Ser Ala Glu Cys Tyr Asp Leu Arg Ser Asn
                320                 325                 330

Arg Val Val Ala Asp Gln Tyr Cys His Tyr Tyr Pro Glu Asn Ile
                335                 340                 345

Lys Pro Lys Pro Lys Leu Gln Glu Cys Asn Leu Asp Pro Cys Pro
                350                 355                 360

Ala Ser Asp Gly Tyr Lys Gln Ile Met Pro Tyr Asp Leu Tyr His
                365                 370                 375

Pro Leu Pro Arg Trp Glu Ala Thr Pro Trp Thr Ala Cys Ser Ser
                380                 385                 390

Ser Cys Gly Gly Gly Ile Gln Ser Arg Ala Val Ser Cys Val Glu
                395                 400                 405

Glu Asp Ile Gln Gly His Val Thr Ser Val Glu Glu Trp Lys Cys
                410                 415                 420

Met Tyr Thr Pro Lys Met Pro Ile Ala Gln Pro Cys Asn Ile Phe
                425                 430                 435

Asp Cys Pro Lys Trp Leu Ala Gln Glu Trp Ser Pro Cys Thr Val
                440                 445                 450

Thr Cys Gly Gln Gly Leu Arg Tyr Arg Val Val Leu Cys Ile Asp
                455                 460                 465

His Arg Gly Met His Thr Gly Gly Cys Ser Pro Lys Thr Lys Pro
                470                 475                 480

His Ile Lys Glu Glu Cys Ile Val Pro Thr Pro Cys Tyr Lys Pro
                485                 490                 495

Lys Glu Lys Leu Pro Val Glu Ala Lys Leu Pro Trp Phe Lys Gln
                500                 505                 510

Ala Gln Glu Leu Glu Glu Gly Ala Ala Val Ser Glu Glu Pro Ser
```

-continued 515 520 525

<210> SEQ ID NO 155
<211> LENGTH: 1734
<212> TYPE: DNA
<213> ORGANISM: Homo sapiens

<400> SEQUENCE: 155 gtggactctg agaagcccag gcagttgagg acaggagaga gaaggctgca 50 gacccagagg gagggaggac agggagtcgg aaggaggagg acagaggagg 100 gcacagagac gcagagcaag ggcggcaagg aggagaccct ggtgggagga 150 agacactctg gagagagagg gggctgggca gagatgaagt tccaggggcc 200 cctggcctgc ctcctgctgg ccctctgcct gggcagtggg gaggctggcc 250 ccctgcagag cggagaggaa agcactggga caaatattgg ggaggccctt 300 ggacatggcc tgggagacgc cctgagcgaa ggggtgggaa aggccattgg 350 caaagaggcc ggaggggcag ctggctctaa agtcagtgag gcccttggcc 400 aagggaccag agaagcagtt ggcactggag tcaggcaggt tccaggcttt 450 ggcgcagcag atgctttggg caacagggtc ggggaagcag cccatgctct 500 gggaaacact gggcacgaga ttggcagaca ggcagaagat gtcattcgac 550 acggagcaga tgctgtccgc ggctcctggc agggggtgcc tggccacagt 600 ggtgcttggg aaacttctgg aggccatggc atctttggct ctcaaggtgg 650 ccttggaggc cagggccagg gcaatcctgg aggtctgggg actccgtggg 700 tccacggata ccccggaaac tcagcaggca gctttggaat gaatcctcag 750 ggagctccct ggggtcaagg aggcaatgga gggccaccaa actttgggac 800 caacactcag ggagctgtgg cccagcctgg ctatggttca gtgagagcca 850 gcaaccagaa tgaagggtgc acgaatcccc caccatctgg ctcaggtgga 900 ggctccagca actctggggg aggcagcggc tcacagtcgg gcagcagtgg 950 cagtggcagc aatggtgaca acaacaatgg cagcagcagt ggtggcagca 1000 gcagtggcag cagcagtggc agcagcagtg gcggcagcag tggcggcagc 1050 agtggtggca gcagtggcaa cagtggtggc agcagaggtg acagcggcag 1100 tgagtcctcc tggggatcca gcaccggctc ctcctccggc aaccacggtg 1150 ggagcggcgg aggaaatgga cataaacccg ggtgtgaaaa gccagggaat 1200 gaagcccgcg ggagcgggga atctgggatt cagggcttca gaggacaggg 1250 agtttccagc aacatgaggg aaataagcaa agagggcaat cgcctccttg 1300 gaggctctgg agacaattat cgggggcaag ggtcgagctg gggcagtgga 1350 ggaggtgacg ctgttggtgg agtcaatact gtgaactctg agacgtctcc 1400 tgggatgttt aactttgaca ctttctggaa gaattttaaa tccaagctgg 1450 gtttcatcaa ctgggatgcc ataaacaagg accagagaag ctctcgcatc 1500 ccgtgacctc cagacaagga gccaccagat tggatgggag cccccacact 1550 ccctccttaa aacaccaccc tctcatcact aatctcagcc cttgcccttg 1600 aaataaacct tagctgcccc acaaaaaaaa aaaaaaaaaa aaaaaaaaaa 1650 aaaaaaaaaa aaaaaaaaaa aaaaaaaaaa aaaaaaaaaa aaaaaaaaaa 1700 aaaaaaaaaa aaaaaaaaaa aaaaaaaaaa aaaa 1734

<210> SEQ ID NO 156
<211> LENGTH: 440
<212> TYPE: PRT
<213> ORGANISM: Homo sapiens

<400> SEQUENCE: 156

Met Lys Phe Gln Gly Pro Leu Ala Cys Leu Leu Leu Ala Leu Cys
1 5 10 15

Leu Gly Ser Gly Glu Ala Gly Pro Leu Gln Ser Gly Glu Glu Ser
20 25 30

Thr Gly Thr Asn Ile Gly Glu Ala Leu Gly His Gly Leu Gly Asp
35 40 45

Ala Leu Ser Glu Gly Val Gly Lys Ala Ile Gly Lys Glu Ala Gly
50 55 60

Gly Ala Ala Gly Ser Lys Val Ser Glu Ala Leu Gly Gln Gly Thr
65 70 75

Arg Glu Ala Val Gly Thr Gly Val Arg Gln Val Pro Gly Phe Gly
80 85 90

Ala Ala Asp Ala Leu Gly Asn Arg Val Gly Glu Ala Ala His Ala
95 100 105

Leu Gly Asn Thr Gly His Glu Ile Gly Arg Gln Ala Glu Asp Val
110 115 120

Ile Arg His Gly Ala Asp Ala Val Arg Gly Ser Trp Gln Gly Val
125 130 135

Pro Gly His Ser Gly Ala Trp Glu Thr Ser Gly Gly His Gly Ile
140 145 150

Phe Gly Ser Gln Gly Gly Leu Gly Gly Gln Gly Gln Gly Asn Pro
155 160 165

Gly Gly Leu Gly Thr Pro Trp Val His Gly Tyr Pro Gly Asn Ser
170 175 180

Ala Gly Ser Phe Gly Met Asn Pro Gln Gly Ala Pro Trp Gly Gln
185 190 195

Gly Gly Asn Gly Gly Pro Pro Asn Phe Gly Thr Asn Thr Gln Gly
200 205 210

Ala Val Ala Gln Pro Gly Tyr Gly Ser Val Arg Ala Ser Asn Gln
215 220 225

Asn Glu Gly Cys Thr Asn Pro Pro Pro Ser Gly Ser Gly Gly Gly
230 235 240

Ser Ser Asn Ser Gly Gly Gly Ser Gly Ser Gln Ser Gly Ser Ser
245 250 255

Gly Ser Gly Ser Asn Gly Asp Asn Asn Asn Gly Ser Ser Ser Gly
260 265 270

Gly Ser Ser Ser Gly Ser Ser Ser Gly Ser Ser Ser Gly Gly Ser
275 280 285

Ser Gly Gly Ser Ser Gly Gly Ser Ser Gly Asn Ser Gly Gly Ser
290 295 300

Arg Gly Asp Ser Gly Ser Glu Ser Ser Trp Gly Ser Ser Thr Gly
305 310 315

Ser Ser Ser Gly Asn His Gly Gly Ser Gly Gly Gly Asn Gly His
320 325 330

Lys Pro Gly Cys Glu Lys Pro Gly Asn Glu Ala Arg Gly Ser Gly
335 340 345

Glu Ser Gly Ile Gln Gly Phe Arg Gly Gln Gly Val Ser Ser Asn

-continued

```
                350                 355                 360

Met Arg Glu Ile Ser Lys Glu Gly Asn Arg Leu Leu Gly Gly Ser
                365                 370                 375

Gly Asp Asn Tyr Arg Gly Gln Gly Ser Ser Trp Gly Ser Gly Gly
                380                 385                 390

Gly Asp Ala Val Gly Gly Val Asn Thr Val Asn Ser Glu Thr Ser
                395                 400                 405

Pro Gly Met Phe Asn Phe Asp Thr Phe Trp Lys Asn Phe Lys Ser
                410                 415                 420

Lys Leu Gly Phe Ile Asn Trp Asp Ala Ile Asn Lys Asp Gln Arg
                425                 430                 435

Ser Ser Arg Ile Pro
                440


<210> SEQ ID NO 157
<211> LENGTH: 4104
<212> TYPE: DNA
<213> ORGANISM: Homo sapiens

<400> SEQUENCE: 157

cccacgcgtc cgcccacgcg tccgcccacg cgtccgccca cgcgtccgcc                50

cacgcgtccg cccacgcgtc cgcccacgcg tccggtgcaa gctcgcgccg               100

cacactgcct ggtggaggga aggagcccgg gcgcctctcg ccgctccccg               150

cgccgccgtc cgcacctccc caccgcccgc cgcccgccgc ccgccgcccg               200

caaagcatga gtgagcccgc tctctgcagc tgcccggggc gcgaatggca               250

ggctgtttcc gcggagtaaa aggtggcgcc ggtcagtggt cgtttccaat               300

gacggacatt aaccagactg tcagatcctg gggagtcgcg agccccgagt               350

ttggagtttt ttccccccac aacgtcacag tccgaactgc agagggaaag               400

gaaggcggca ggaaggcgaa gctcgggctc cggcacgtag ttgggaaact               450

tgcgggtcct agaagtcgcc tccccgcctt gccggccgcc cttgcagccc               500

cgagccgagc agcaaagtga gacattgtgc gcctgccaga tccgccggcc               550

gcggaccggg gctgcctcgg aaacacagag gggtcttctc tcgccctgca               600

tataattagc ctgcacacaa agggagcagc tgaatggagg ttgtcactct               650

ctggaaaagg atttctgacc gagcgcttcc aatggacatt ctccagtctc               700

tctggaaaga ttctcgctaa tggatttcct gctgctcggt ctctgtctat               750

actggctgct gaggaggccc tcgggggtgg tcttgtgtct gctgggggcc               800

tgctttcaga tgctgcccgc cgcccccagc gggtgcccgc agctgtgccg               850

gtgcgagggg cggctgctgt actgcgaggc gctcaacctc accgaggcgc               900

cccacaacct gtccggcctg ctgggcttgt ccctgcgcta caacagcctc               950

tcggagctgc gcgccggcca gttcacgggg ttaatgcagc tcacgtggct              1000

ctatctggat cacaatcaca tctgctccgt gcagggggac gcctttcaga              1050

aactgcgccg agttaaggaa ctcacgctga gttccaacca gatcacccaa              1100

ctgcccaaca ccaccttccg gcccatgccc aacctgcgca gcgtggacct              1150

ctcgtacaac aagctgcagg cgctcgcgcc cgacctcttc cacgggctgc              1200

ggaagctcac cacgctgcat atgcgggcca acgccatcca gtttgtgccc              1250

gtgcgcatct tccaggactg ccgcagcctc aagtttctcg acatcggata              1300
```

-continued

```
caatcagctc aagagtctgg cgcgcaactc tttcgccggc ttgtttaagc    1350
tcaccgagct gcacctcgag cacaacgact tggtcaaggt gaacttcgcc    1400
cacttcccgc gcctcatctc cctgcactcg ctctgcctgc ggaggaacaa    1450
ggtggccatt gtggtcagct cgctggactg ggtttggaac ctggagaaaa    1500
tggacttgtc gggcaacgag atcgagtaca tggagcccca tgtgttcgag    1550
accgtgccgc acctgcagtc cctgcagctg gactccaacc gcctcaccta    1600
catcgagccc cggatcctca actcttggaa gtccctgaca agcatcaccc    1650
tggccgggaa cctgtgggat tgcgggcgca acgtgtgtgc cctagcctcg    1700
tggctcagca acttccaggg gcgctacgat ggcaacttgc agtgcgccag    1750
cccggagtac gcacagggcg aggacgtcct ggacgccgtg tacgccttcc    1800
acctgtgcga ggatggggcc gagcccacca gcggccacct gctctcggcc    1850
gtcaccaacc gcagtgatct ggggcccccct gccagctcgg ccaccacgct    1900
cgcggacggc ggggaggggc agcacgacgg cacattcgag cctgccaccg    1950
tggctcttcc aggcggcgag cacgccgaga acgccgtgca gatccacaag    2000
gtggtcacgg gcaccatggc cctcatcttc tccttcctca tcgtggtcct    2050
ggtgctctac gtgtcctgga agtgtttccc agccagcctc aggcagctca    2100
gacagtgctt tgtcacgcag cgcaggaagc aaaagcagaa acagaccatg    2150
catcagatgg ctgccatgtc tgcccaggaa tactacgttg attacaaacc    2200
gaaccacatt gagggagccc tggtgatcat caacgagtat ggctcgtgta    2250
cctgccacca gcagcccgcg agggaatgcg aggtgtgatt gtcccagtgg    2300
ctctcaaccc atgcgctacc aaatacgcct gggcagccgg gacgggccgg    2350
cgggcaccag gctggggtct ccttgtctgt gctctgatat gctccttgac    2400
tgaaacttta aggggatctc tcccagagac ttgacatttt agctttattg    2450
tgtcttaaaa acaaaagcga attaaaacac aacaaaaaac cccaccccac    2500
aaccttcagg acagtctatc ttaaatttca tatgagaact ccttcctccc    2550
tttgaagatc tgtccatatt caggaatctg agagtgtaaa aaaggtggcc    2600
ataagacaga gagagaataa tcgtgctttg ttttatgcta ctcctcccac    2650
cctgcccatg attaaacatc atgtatgtag aagatcttaa gtccatacgc    2700
atttcatgaa gaaccattgg aaagaggaat ctgcaatctg ggagcttaag    2750
agcaaatgat gaccatagaa agctatgttc ttactttgtg tgtgtgtctg    2800
tatgtttctg cgttgtgtgt ctttgtaggc aagcaaacgt tgtctacaca    2850
aacgggaatt tagctcacat catttcatgc ccctgtgcct ctagctctgg    2900
agattggtgg ggggaggtgg ggggaaacgg caggaataag ggaaagtggt    2950
agttttaact aaggttttgt aacacttgaa atcttttctt tctcaaatta    3000
attatcttta agcttcaaga aacttgctct gacccctcta agcaaactac    3050
taagcattta aaagagaatc taatttttaa aggtgtagca cctttttttt    3100
tattcttccc acagagggtg ctaatctcat tatgctgtgc tatctgaaaa    3150
gaacttaagg ccacaattca cgtctcgtcc tgggcattgt gatggattga    3200
ccctccattt gcagtacctt cccagctgat taaagttcag cagtggtatt    3250
```

-continued

```
gaggtttttc gaatatttat atagaaaaaa agtcttttca catgacaaat          3300

gacactctca caccagtctt agccctagta gtttttttagg ttggaccaga         3350

ggaagcaggt taaatgagac ctgtcctctg ctgcactcag aaaaaatagg          3400

cagtccctga tgctcagatc ttagccttga tattaatagt tgagaccacc          3450

tacccacaat gcagcctata ctcccaagac tacaaagtta ccatcgcaaa          3500

ggaaaggtta ttccagtaaa aggaaatagt tttctcaacc atttaaaaat          3550

attcttctga actcatcaaa gtagaagagc ccccaacctt ttctctctgc          3600

cttcaagaag gcagacattt ggtatgattt agcatcaaca acacatttat          3650

gagtatatgt aagtaatcag aggggcaaat gccacttgtt attcctccca          3700

agttttccaa gcaagtacac acagatctct ggtaggatta ggggccactt          3750

gtgtttccgg cttattttag tcgacttgtc agcaagtttg atgcctagtc          3800

tatctgacat ggcccagtag aacagggcat tgatggatca catgagatgg          3850

tagaaggaac atcatcacat acccctctca cagagaaaat tatcaaagaa          3900

ccagaaatta tatctgtttt ggagcaagag tgtcataatg tttcagggta          3950

gtcaaaataa acataaatta tctcctctag atgagtggcg atgttggctg          4000

atttgggtct gccattgaca gaatgtcaaa taaaaaggaa ttagctagaa          4050

tatgaccatt aaatgtgctt ctgaaatata ttttgagata ggtttagaat          4100

gtca                                                            4104
```

<210> SEQ ID NO 158
<211> LENGTH: 522
<212> TYPE: PRT
<213> ORGANISM: Homo sapiens

<400> SEQUENCE: 158

```
Met Asp Phe Leu Leu Leu Gly Leu Cys Leu Tyr Trp Leu Leu Arg
  1               5                  10                  15

Arg Pro Ser Gly Val Val Leu Cys Leu Leu Gly Ala Cys Phe Gln
                 20                  25                  30

Met Leu Pro Ala Ala Pro Ser Gly Cys Pro Gln Leu Cys Arg Cys
                 35                  40                  45

Glu Gly Arg Leu Leu Tyr Cys Glu Ala Leu Asn Leu Thr Glu Ala
                 50                  55                  60

Pro His Asn Leu Ser Gly Leu Leu Gly Leu Ser Leu Arg Tyr Asn
                 65                  70                  75

Ser Leu Ser Glu Leu Arg Ala Gly Gln Phe Thr Gly Leu Met Gln
                 80                  85                  90

Leu Thr Trp Leu Tyr Leu Asp His Asn His Ile Cys Ser Val Gln
                 95                 100                 105

Gly Asp Ala Phe Gln Lys Leu Arg Arg Val Lys Glu Leu Thr Leu
                110                 115                 120

Ser Ser Asn Gln Ile Thr Gln Leu Pro Asn Thr Thr Phe Arg Pro
                125                 130                 135

Met Pro Asn Leu Arg Ser Val Asp Leu Ser Tyr Asn Lys Leu Gln
                140                 145                 150

Ala Leu Ala Pro Asp Leu Phe His Gly Leu Arg Lys Leu Thr Thr
                155                 160                 165

Leu His Met Arg Ala Asn Ala Ile Gln Phe Val Pro Val Arg Ile
                170                 175                 180
```

-continued

```
Phe Gln Asp Cys Arg Ser Leu Lys Phe Leu Asp Ile Gly Tyr Asn
                185                 190                 195

Gln Leu Lys Ser Leu Ala Arg Asn Ser Phe Ala Gly Leu Phe Lys
                200                 205                 210

Leu Thr Glu Leu His Leu Glu His Asn Asp Leu Val Lys Val Asn
                215                 220                 225

Phe Ala His Phe Pro Arg Leu Ile Ser Leu His Ser Leu Cys Leu
                230                 235                 240

Arg Arg Asn Lys Val Ala Ile Val Val Ser Ser Leu Asp Trp Val
                245                 250                 255

Trp Asn Leu Glu Lys Met Asp Leu Ser Gly Asn Glu Ile Glu Tyr
                260                 265                 270

Met Glu Pro His Val Phe Glu Thr Val Pro His Leu Gln Ser Leu
                275                 280                 285

Gln Leu Asp Ser Asn Arg Leu Thr Tyr Ile Glu Pro Arg Ile Leu
                290                 295                 300

Asn Ser Trp Lys Ser Leu Thr Ser Ile Thr Leu Ala Gly Asn Leu
                305                 310                 315

Trp Asp Cys Gly Arg Asn Val Cys Ala Leu Ala Ser Trp Leu Ser
                320                 325                 330

Asn Phe Gln Gly Arg Tyr Asp Gly Asn Leu Gln Cys Ala Ser Pro
                335                 340                 345

Glu Tyr Ala Gln Gly Glu Asp Val Leu Asp Ala Val Tyr Ala Phe
                350                 355                 360

His Leu Cys Glu Asp Gly Ala Glu Pro Thr Ser Gly His Leu Leu
                365                 370                 375

Ser Ala Val Thr Asn Arg Ser Asp Leu Gly Pro Pro Ala Ser Ser
                380                 385                 390

Ala Thr Thr Leu Ala Asp Gly Gly Glu Gly Gln His Asp Gly Thr
                395                 400                 405

Phe Glu Pro Ala Thr Val Ala Leu Pro Gly Gly Glu His Ala Glu
                410                 415                 420

Asn Ala Val Gln Ile His Lys Val Val Thr Gly Thr Met Ala Leu
                425                 430                 435

Ile Phe Ser Phe Leu Ile Val Val Leu Val Leu Tyr Val Ser Trp
                440                 445                 450

Lys Cys Phe Pro Ala Ser Leu Arg Gln Leu Arg Gln Cys Phe Val
                455                 460                 465

Thr Gln Arg Arg Lys Gln Lys Gln Lys Gln Thr Met His Gln Met
                470                 475                 480

Ala Ala Met Ser Ala Gln Glu Tyr Tyr Val Asp Tyr Lys Pro Asn
                485                 490                 495

His Ile Glu Gly Ala Leu Val Ile Ile Asn Glu Tyr Gly Ser Cys
                500                 505                 510

Thr Cys His Gln Gln Pro Ala Arg Glu Cys Glu Val
                515                 520


<210> SEQ ID NO 159
<211> LENGTH: 1049
<212> TYPE: DNA
<213> ORGANISM: Homo sapiens

<400> SEQUENCE: 159

cagagaggag gctttgggaa ttgtccagca gaaacagaga agtctgaggt                50
```

-continued

```
ggtgtcaaga caaaagatgc ttcagctttg gaaacttgtt ctcctgtgcg          100

gcgtgctcac tgggacctca gagtctcttc ttgacaatct tggcaatgac          150

ctaagcaatg tcgtggataa gctggaacct gttcttcacg agggacttga          200

gacagttgac aatactctta aaggcatcct tgagaaactg aaggtcgacc          250

taggagtgct tcagaaatcc agtgcttggc aactggccaa gcagaaggcc          300

caggaagctg agaaattgct gaacaatgtc atttctaagc tgcttccaac          350

taacacggac atttttgggt tgaaaatcag caactccctc atcctggatg          400

tcaaagctga accgatcgat gatggcaaag gccttaacct gagcttccct          450

gtcaccgcga atgtcactgt ggccgggccc atcattggcc agattatcaa          500

cctgaaagcc tccttggacc tcctgaccgc agtcacaatt gaaactgatc          550

cccagacaca ccagcctgtt gccgtcctgg gagaatgcgc cagtgaccca          600

accagcatct cactttcctt gctggacaaa cacagccaaa tcatcaacaa          650

gttcgtgaat agcgtgatca acacgctgaa aagcactgta tcctccctgc          700

tgcagaagga gatatgtcca ctgatccgca tcttcatcca ctccctggat          750

gtgaatgtca ttcagcaggt cgtcgataat cctcagcaca aaacccagct          800

gcaaaccctc atctgaagag gacgaatgag gaggaccact gtggtgcatg          850

ctgattggtt cccagtggct tgccccaccc ccttatagca tctccctcca          900

ggaagctgct gccaccacct aaccagcgtg aaagcctgag tcccaccaga          950

aggaccttcc cagatacccc ttctcctcac agtcagaaca gcagcctcta         1000

cacatgttgt cctgcccctg gcaataaagg cccatttctg  cacccttaa         1049
```

<210> SEQ ID NO 160
<211> LENGTH: 249
<212> TYPE: PRT
<213> ORGANISM: Homo sapiens

<400> SEQUENCE: 160

```
Met Leu Gln Leu Trp Lys Leu Val Leu Leu Cys Gly Val Leu Thr
  1               5                  10                  15

Gly Thr Ser Glu Ser Leu Leu Asp Asn Leu Gly Asn Asp Leu Ser
                 20                  25                  30

Asn Val Val Asp Lys Leu Glu Pro Val Leu His Glu Gly Leu Glu
                 35                  40                  45

Thr Val Asp Asn Thr Leu Lys Gly Ile Leu Glu Lys Leu Lys Val
                 50                  55                  60

Asp Leu Gly Val Leu Gln Lys Ser Ser Ala Trp Gln Leu Ala Lys
                 65                  70                  75

Gln Lys Ala Gln Glu Ala Glu Lys Leu Leu Asn Asn Val Ile Ser
                 80                  85                  90

Lys Leu Leu Pro Thr Asn Thr Asp Ile Phe Gly Leu Lys Ile Ser
                 95                 100                 105

Asn Ser Leu Ile Leu Asp Val Lys Ala Glu Pro Ile Asp Asp Gly
                110                 115                 120

Lys Gly Leu Asn Leu Ser Phe Pro Val Thr Ala Asn Val Thr Val
                125                 130                 135

Ala Gly Pro Ile Ile Gly Gln Ile Ile Asn Leu Lys Ala Ser Leu
                140                 145                 150
```

-continued

```
Asp Leu Leu Thr Ala Val Thr Ile Glu Thr Asp Pro Gln Thr His
                155                 160                 165

Gln Pro Val Ala Val Leu Gly Glu Cys Ala Ser Asp Pro Thr Ser
                170                 175                 180

Ile Ser Leu Ser Leu Leu Asp Lys His Ser Gln Ile Ile Asn Lys
                185                 190                 195

Phe Val Asn Ser Val Ile Asn Thr Leu Lys Ser Thr Val Ser Ser
                200                 205                 210

Leu Leu Gln Lys Glu Ile Cys Pro Leu Ile Arg Ile Phe Ile His
                215                 220                 225

Ser Leu Asp Val Asn Val Ile Gln Gln Val Val Asp Asn Pro Gln
                230                 235                 240

His Lys Thr Gln Leu Gln Thr Leu Ile
                245


<210> SEQ ID NO 161
<211> LENGTH: 1587
<212> TYPE: DNA
<213> ORGANISM: Homo sapiens

<400> SEQUENCE: 161

cagccacaga cgggtcatga gcgcggtatt actgctggcc ctcctggggt                50

tcatcctccc actgccagga gtgcaggcgc tgctctgcca gtttgggaca               100

gttcagcatg tgtggaaggt gtccgaccta ccccggcaat ggacccctaa               150

gaacaccagc tgcgacagcg gcttggggtg ccaggacacg ttgatgctca               200

ttgagagcgg accccaagtg agcctggtgc tctccaaggg ctgcacggag               250

gccaaggacc aggagccccg cgtcactgag caccggatgg gccccggcct               300

ctccctgatc tcctacacct tcgtgtgccg ccaggaggac ttctgcaaca               350

acctcgttaa ctccctcccg ctttgggccc cacagccccc agcagaccca               400

ggatccttga ggtgcccagt ctgcttgtct atggaaggct gtctggaggg               450

gacaacagaa gagatctgcc ccaaggggac cacacactgt tatgatggcc               500

tcctcaggct caggggagga ggcatcttct ccaatctgag agtccaggga               550

tgcatgcccc agccaggttg caacctgctc aatgggacac aggaaattgg               600

gcccgtgggt atgactgaga actgcaatag gaaagatttt ctgacctgtc               650

atcgggggac caccattatg acacacggaa acttggctca agaacccact               700

gattggacca catcgaatac cgagatgtgc gaggtggggc aggtgtgtca               750

ggagacgctg ctgctcatag atgtaggact cacatcaacc ctggtgggga               800

caaaaggctg cagcactgtt ggggctcaaa attcccagaa gaccaccatc               850

cactcagccc ctcctggggt gcttgtggcc tcctataccc acttctgctc               900

ctcggacctg tgcaatagtg ccagcagcag cagcgttctg ctgaactccc               950

tccctcctca agctgcccct gtcccaggag accggcagtg tcctacctgt              1000

gtgcagcccc ttggaacctg ttcaagtggc tccccccgaa tgacctgccc              1050

caggggcgcc actcattgtt atgatgggta cattcatctc tcaggaggtg              1100

ggctgtccac caaaatgagc attcagggct gcgtggccca accttccagc              1150

ttcttgttga accacaccag acaaatcggg atcttctctg cgcgtgagaa              1200

gcgtgatgtg cagcctcctg cctctcagca tgagggaggt ggggctgagg              1250
```

-continued

```
gcctggagtc tctcacttgg ggggtggggc tggcactggc cccagcgctg          1300

tggtggggag tggtttgccc ttcctgctaa ctctattacc cccacgattc          1350

ttcaccgctg ctgaccaccc acactcaacc tccctctgac ctcataacct          1400

aatggccttg gacaccagat tctttcccat tctgtccatg aatcatcttc          1450

cccacacaca atcattcata tctactcacc taacagcaac actggggaga          1500

gcctggagca tccggacttg ccctatggga gaggggacgc tggaggagtg          1550

gctgcatgta tctgataata cagaccctgt  cctttca                       1587


<210> SEQ ID NO 162
<211> LENGTH: 437
<212> TYPE: PRT
<213> ORGANISM: Homo sapiens

<400> SEQUENCE: 162

Met Ser Ala Val Leu Leu Leu Ala Leu Leu Gly Phe Ile Leu Pro
  1               5                  10                  15

Leu Pro Gly Val Gln Ala Leu Leu Cys Gln Phe Gly Thr Val Gln
                 20                  25                  30

His Val Trp Lys Val Ser Asp Leu Pro Arg Gln Trp Thr Pro Lys
                 35                  40                  45

Asn Thr Ser Cys Asp Ser Gly Leu Gly Cys Gln Asp Thr Leu Met
                 50                  55                  60

Leu Ile Glu Ser Gly Pro Gln Val Ser Leu Val Leu Ser Lys Gly
                 65                  70                  75

Cys Thr Glu Ala Lys Asp Gln Glu Pro Arg Val Thr Glu His Arg
                 80                  85                  90

Met Gly Pro Gly Leu Ser Leu Ile Ser Tyr Thr Phe Val Cys Arg
                 95                 100                 105

Gln Glu Asp Phe Cys Asn Asn Leu Val Asn Ser Leu Pro Leu Trp
                110                 115                 120

Ala Pro Gln Pro Pro Ala Asp Pro Gly Ser Leu Arg Cys Pro Val
                125                 130                 135

Cys Leu Ser Met Glu Gly Cys Leu Glu Gly Thr Thr Glu Glu Ile
                140                 145                 150

Cys Pro Lys Gly Thr Thr His Cys Tyr Asp Gly Leu Leu Arg Leu
                155                 160                 165

Arg Gly Gly Gly Ile Phe Ser Asn Leu Arg Val Gln Gly Cys Met
                170                 175                 180

Pro Gln Pro Gly Cys Asn Leu Leu Asn Gly Thr Gln Glu Ile Gly
                185                 190                 195

Pro Val Gly Met Thr Glu Asn Cys Asn Arg Lys Asp Phe Leu Thr
                200                 205                 210

Cys His Arg Gly Thr Thr Ile Met Thr His Gly Asn Leu Ala Gln
                215                 220                 225

Glu Pro Thr Asp Trp Thr Thr Ser Asn Thr Glu Met Cys Glu Val
                230                 235                 240

Gly Gln Val Cys Gln Glu Thr Leu Leu Leu Ile Asp Val Gly Leu
                245                 250                 255

Thr Ser Thr Leu Val Gly Thr Lys Gly Cys Ser Thr Val Gly Ala
                260                 265                 270

Gln Asn Ser Gln Lys Thr Thr Ile His Ser Ala Pro Pro Gly Val
                275                 280                 285
```

-continued

```
Leu Val Ala Ser Tyr Thr His Phe Cys Ser Ser Asp Leu Cys Asn
                290                 295                 300

Ser Ala Ser Ser Ser Ser Val Leu Leu Asn Ser Leu Pro Pro Gln
                305                 310                 315

Ala Ala Pro Val Pro Gly Asp Arg Gln Cys Pro Thr Cys Val Gln
                320                 325                 330

Pro Leu Gly Thr Cys Ser Ser Gly Ser Pro Arg Met Thr Cys Pro
                335                 340                 345

Arg Gly Ala Thr His Cys Tyr Asp Gly Tyr Ile His Leu Ser Gly
                350                 355                 360

Gly Gly Leu Ser Thr Lys Met Ser Ile Gln Gly Cys Val Ala Gln
                365                 370                 375

Pro Ser Ser Phe Leu Leu Asn His Thr Arg Gln Ile Gly Ile Phe
                380                 385                 390

Ser Ala Arg Glu Lys Arg Asp Val Gln Pro Pro Ala Ser Gln His
                395                 400                 405

Glu Gly Gly Gly Ala Glu Gly Leu Glu Ser Leu Thr Trp Gly Val
                410                 415                 420

Gly Leu Ala Leu Ala Pro Ala Leu Trp Trp Gly Val Val Cys Pro
                425                 430                 435

Ser Cys


<210> SEQ ID NO 163
<211> LENGTH: 2475
<212> TYPE: DNA
<213> ORGANISM: Homo sapiens

<400> SEQUENCE: 163

gaggatttgc cacagcagcg gatagagcag gagagcacca ccggagccct                50

tgagacatcc ttgagaagag ccacagcata agagactgcc ctgcttggtg               100

ttttgcagga tgatggtggc ccttcgagga gcttctgcat tgctggttct               150

gttccttgca gcttttctgc ccccgccgca gtgtacccag gacccagcca               200

tggtgcatta catctaccag cgctttcgag tcttggagca agggctggaa               250

aaatgtaccc aagcaacgag ggcatacatt caagaattcc aagagttctc               300

aaaaaatata tctgtcatgc tgggaagatg tcagacctac acaagtgagt               350

acaagagtgc agtgggtaac ttggcactga gagttgaacg tgcccaacgg               400

gagattgact acatacaata ccttcgagag gctgacgagt gcatcgtatc               450

agaggacaag acactggcag aaatgttgct ccaagaagct gaagaagaga               500

aaaagatccg gactctgctg aatgcaagct gtgacaacat gctgatgggc               550

ataaagtctt tgaaaatagt gaagaagatg atggacacac atggctcttg               600

gatgaaagat gctgtctata actctccaaa ggtgtactta ttaattggat               650

ccagaaacaa cactgtttgg gaatttgcaa acatacgggc attcatggag               700

gataacacca agccagctcc ccggaagcaa atcctaacac tttcctggca               750

gggaacaggc caagtgatct acaaaggttt tctatttttt cataaccaag               800

caacttctaa tgagataatc aaatataacc tgcagaagag gactgtggaa               850

gatcgaatgc tgctcccagg aggggtaggc cgagcattgg tttaccagca               900

ctccccctca acttacattg acctggctgt ggatgagcat gggctctggg               950

ccatccactc tgggccaggc acccatagcc atttggttct cacaaagatt              1000
```

-continued

```
gagccgggca cactgggagt ggagcattca tgggataccc catgcagaag          1050

ccaggatgct gaagcctcat tcctcttgtg tggggttctc tatgtggtct          1100

acagtactgg gggccagggc cctcatcgca tcacctgcat ctatgatcca          1150

ctgggcacta tcagtgagga ggacttgccc aacttgttct tccccaagag          1200

accaagaagt cactccatga tccattacaa ccccagagat aagcagctct          1250

atgcctggaa tgaaggaaac cagatcattt acaaactcca gacaaagaga          1300

aagctgcctc tgaagtaatg cattacagct gtgagaaaga gcactgtggc          1350

tttggcagct gttctacagg acagtgaggc tatagcccct tcacaatata          1400

gtatccctct aatcacacac aggaagagtg tgtagaagtg gaaatacgta          1450

tgcctccttt cccaaatgtc actgccttag gtatcttcca agagcttaga          1500

tgagagcata tcatcaggaa agtttcaaca atgtccatta ctcccccaaa          1550

cctcctggct ctcaaggatg accacattct gatacagcct acttcaagcc          1600

ttttgtttta ctgctcccca gcatttactg taactctgcc atcttccctc          1650

ccacaattag agttgtatgc cagcccctaa tattcaccac tggcttttct          1700

ctcccctggc ctttgctgaa gctcttccct ctttttcaaa tgtctattga          1750

tattctccca ttttcactgc ccaactaaaa tactattaat atttctttct          1800

tttcttttct tttttttgag acaaggtctc actatgttgc ccaggctggt          1850

ctcaaactcc agagctcaag agatcctcct gcctcagcct cctaagtacc          1900

tgggattaca ggcatgtgcc accacacctg gcttaaaata ctatttctta          1950

ttgaggttta acctctattt cccctagccc tgtccttcca ctaagcttgg          2000

tagatgtaat aataaagtga aaatattaac atttgaatat cgctttccag          2050

gtgtggagtg tttgcacatc attgaattct cgtttcacct ttgtgaaaca          2100

tgcacaagtc tttacagctg tcattctaga gtttaggtga gtaacacaat          2150

tacaaagtga aagatacagc tagaaaatac tacaaatccc atagtttttc          2200

cattgcccaa ggaagcatca aatacgtatg tttgttcacc tactcttata          2250

gtcaatgcgt tcatcgtttc agcctaaaaa taatagtctg tccctttagc          2300

cagttttcat gtctgcacaa gacctttcaa taggcctttc aaatgataat          2350

tcctccagaa aaccagtcta agggtgagga ccccaactct agcctcctct          2400

tgtcttgctg tcctctgttt ctctctttct gctttaaatt caataaaagt          2450

gacactgagc aaaaaaaaaa  aaaaa                                    2475
```

<210> SEQ ID NO 164
<211> LENGTH: 402
<212> TYPE: PRT
<213> ORGANISM: Homo sapiens

<400> SEQUENCE: 164

```
Met Met Val Ala Leu Arg Gly Ala Ser Ala Leu Leu Val Leu Phe
  1               5                  10                  15

Leu Ala Ala Phe Leu Pro Pro Pro Gln Cys Thr Gln Asp Pro Ala
                 20                  25                  30

Met Val His Tyr Ile Tyr Gln Arg Phe Arg Val Leu Glu Gln Gly
                 35                  40                  45

Leu Glu Lys Cys Thr Gln Ala Thr Arg Ala Tyr Ile Gln Glu Phe
```

-continued

```
                50                  55                  60

Gln Glu Phe Ser Lys Asn Ile Ser Val Met Leu Gly Arg Cys Gln
                65                  70                  75

Thr Tyr Thr Ser Glu Tyr Lys Ser Ala Val Gly Asn Leu Ala Leu
                80                  85                  90

Arg Val Glu Arg Ala Gln Arg Glu Ile Asp Tyr Ile Gln Tyr Leu
                95                 100                 105

Arg Glu Ala Asp Glu Cys Ile Val Ser Glu Asp Lys Thr Leu Ala
               110                 115                 120

Glu Met Leu Leu Gln Glu Ala Glu Glu Glu Lys Lys Ile Arg Thr
               125                 130                 135

Leu Leu Asn Ala Ser Cys Asp Asn Met Leu Met Gly Ile Lys Ser
               140                 145                 150

Leu Lys Ile Val Lys Lys Met Met Asp Thr His Gly Ser Trp Met
               155                 160                 165

Lys Asp Ala Val Tyr Asn Ser Pro Lys Val Tyr Leu Leu Ile Gly
               170                 175                 180

Ser Arg Asn Asn Thr Val Trp Glu Phe Ala Asn Ile Arg Ala Phe
               185                 190                 195

Met Glu Asp Asn Thr Lys Pro Ala Pro Arg Lys Gln Ile Leu Thr
               200                 205                 210

Leu Ser Trp Gln Gly Thr Gly Gln Val Ile Tyr Lys Gly Phe Leu
               215                 220                 225

Phe Phe His Asn Gln Ala Thr Ser Asn Glu Ile Ile Lys Tyr Asn
               230                 235                 240

Leu Gln Lys Arg Thr Val Glu Asp Arg Met Leu Leu Pro Gly Gly
               245                 250                 255

Val Gly Arg Ala Leu Val Tyr Gln His Ser Pro Ser Thr Tyr Ile
               260                 265                 270

Asp Leu Ala Val Asp Glu His Gly Leu Trp Ala Ile His Ser Gly
               275                 280                 285

Pro Gly Thr His Ser His Leu Val Leu Thr Lys Ile Glu Pro Gly
               290                 295                 300

Thr Leu Gly Val Glu His Ser Trp Asp Thr Pro Cys Arg Ser Gln
               305                 310                 315

Asp Ala Glu Ala Ser Phe Leu Leu Cys Gly Val Leu Tyr Val Val
               320                 325                 330

Tyr Ser Thr Gly Gly Gln Gly Pro His Arg Ile Thr Cys Ile Tyr
               335                 340                 345

Asp Pro Leu Gly Thr Ile Ser Glu Glu Asp Leu Pro Asn Leu Phe
               350                 355                 360

Phe Pro Lys Arg Pro Arg Ser His Ser Met Ile His Tyr Asn Pro
               365                 370                 375

Arg Asp Lys Gln Leu Tyr Ala Trp Asn Glu Gly Asn Gln Ile Ile
               380                 385                 390

Tyr Lys Leu Gln Thr Lys Arg Lys Leu Pro Leu Lys
               395                 400


<210> SEQ ID NO 165
<211> LENGTH: 1415
<212> TYPE: DNA
<213> ORGANISM: Homo sapiens

<400> SEQUENCE: 165
```

-continued

```
tggcctcccc agcttgccag gcacaaggct gagcgggagg aagcgagagg      50
catctaagca ggcagtgttt tgccttcacc ccaagtgacc atgagaggtg     100
ccacgcgagt ctcaatcatg ctcctcctag taactgtgtc tgactgtgct     150
gtgatcacag gggcctgtga gcgggatgtc cagtgtgggg caggcacctg     200
ctgtgccatc agcctgtggc ttcgagggct gcggatgtgc accccgctgg     250
ggcgggaagg cgaggagtgc caccccggca gccacaaggt ccccttcttc     300
aggaaacgca agcaccacac ctgtccttgc ttgcccaacc tgctgtgctc     350
caggttcccg gacggcaggt accgctgctc catggacttg aagaacatca     400
atttttaggc gcttgcctgg tctcaggata cccaccatcc ttttcctgag     450
cacagcctgg atttttattt ctgccatgaa acccagctcc catgactctc     500
ccagtcccta cactgactac cctgatctct cttgtctagt acgcacatat     550
gcacacaggc agacatacct cccatcatga catggtcccc aggctggcct     600
gaggatgtca cagcttgagg ctgtggtgtg aaaggtggcc agcctggttc     650
tcttccctgc tcaggctgcc agagaggtgg taaatggcag aaaggacatt     700
ccccctcccc tccccaggtg acctgctctc tttcctgggc cctgcccctc     750
tccccacatg tatccctcgg tctgaattag acattcctgg gcacaggctc     800
ttgggtgcat tgctcagagt cccaggtcct ggcctgaccc tcaggccctt     850
cacgtgaggt ctgtgaggac caatttgtgg gtagttcatc ttccctcgat     900
tggttaactc cttagtttca gaccacagac tcaagattgg ctcttcccag     950
agggcagcag acagtcaccc caaggcaggt gtagggagcc cagggaggcc    1000
aatcagcccc ctgaagactc tggtcccagt cagcctgtgg cttgtggcct    1050
gtgacctgtg accttctgcc agaattgtca tgcctctgag gccccctctt    1100
accacacttt accagttaac cactgaagcc cccaattccc acagcttttc    1150
cattaaaatg caaatggtgg tggttcaatc taatctgata ttgacatatt    1200
agaaggcaat tagggtgttt ccttaaacaa ctcctttcca aggatcagcc    1250
ctgagagcag gttggtgact ttgaggaggg cagtcctctg tccagattgg    1300
ggtgggagca agggacaggg agcagggcag gggctgaaag gggcactgat    1350
tcagaccagg gaggcaacta cacaccaaca tgctggcttt agaataaaag    1400
caccaactga  aaaaa                                         1415
```

<210> SEQ ID NO 166
<211> LENGTH: 105
<212> TYPE: PRT
<213> ORGANISM: Homo sapiens

<400> SEQUENCE: 166

```
Met Arg Gly Ala Thr Arg Val Ser Ile Met Leu Leu Leu Val Thr
  1               5                  10                  15

Val Ser Asp Cys Ala Val Ile Thr Gly Ala Cys Glu Arg Asp Val
                 20                  25                  30

Gln Cys Gly Ala Gly Thr Cys Cys Ala Ile Ser Leu Trp Leu Arg
                 35                  40                  45

Gly Leu Arg Met Cys Thr Pro Leu Gly Arg Glu Gly Glu Glu Cys
                 50                  55                  60

His Pro Gly Ser His Lys Val Pro Phe Phe Arg Lys Arg Lys His
```

-continued

```
                65                  70                  75

His Thr Cys Pro Cys Leu Pro Asn Leu Leu Cys Ser Arg Phe Pro
                80                  85                  90

Asp Gly Arg Tyr Arg Cys Ser Met Asp Leu Lys Asn Ile Asn Phe
                95                 100                 105


<210> SEQ ID NO 167
<211> LENGTH: 1371
<212> TYPE: DNA
<213> ORGANISM: Homo sapiens

<400> SEQUENCE: 167

aactcaaact cctctctctg ggaaaacgcg gtgcttgctc ctcccggagt                50

ggccttggca gggtgttgga gccctcggtc tgccccgtcc ggtctctggg               100

gccaaggctg ggtttccctc atgtatggca agagctctac tcgtgcggtg               150

cttcttctcc ttggcataca gctcacagct ctttggccta tagcagctgt               200

ggaaatttat acctcccggg tgctggaggc tgttaatggg acagatgctc               250

ggttaaaatg cactttctcc agctttgccc ctgtgggtga tgctctaaca               300

gtgacctgga attttcgtcc tctagacggg ggacctgagc agtttgtatt               350

ctactaccac atagatccct tccaacccat gagtgggcgg tttaaggacc               400

gggtgtcttg ggatgggaat cctgagcggt acgatgcctc catccttctc               450

tggaaactgc agttcgacga caatgggaca tacacctgcc aggtgaagaa               500

cccacctgat gttgatgggg tgatagggga gatccggctc agcgtcgtgc               550

acactgtacg cttctctgag atccacttcc tggctctggc cattggctct               600

gcctgtgcac tgatgatcat aatagtaatt gtagtggtcc tcttccagca               650

ttaccggaaa aagcgatggg ccgaaagagc tcataaagtg gtggagataa               700

aatcaaaaga agaggaaagg ctcaaccaag agaaaaaggt ctctgtttat               750

ttagaagaca cagactaaca attttagatg gaagctgaga tgatttccaa               800

gaacaagaac cctagtattt cttgaagtta atggaaactt ttctttggct               850

tttccagttg tgacccgttt tccaaccagt tctgcagcat attagattct               900

agacaagcaa cacccctctg gagccagcac agtgctcctc catatcacca               950

gtcatacaca gcctcattat taaggtctta tttaatttca gagtgtaaat              1000

tttttcaagt gctcattagg ttttataaac aagaagctac atttttgccc              1050

ttaagacact acttacagtg ttatgacttg tatacacata tattggtatc              1100

aaaggggata aaagccaatt tgtctgttac atttcctttc acgtatttct              1150

tttagcagca cttctgctac taaagttaat gtgtttactc tctttccttc              1200

ccacattctc aattaaaagg tgagctaagc ctcctcggtg tttctgatta              1250

acagtaaatc ctaaattcaa actgttaaat gacattttta tttttatgtc              1300

tctccttaac tatgagacac atcttgtttt actgaatttc tttcaatatt              1350

ccaggtgata gatttttgtc  g                                            1371


<210> SEQ ID NO 168
<211> LENGTH: 215
<212> TYPE: PRT
<213> ORGANISM: Homo sapiens

<400> SEQUENCE: 168
```

-continued

```
Met Tyr Gly Lys Ser Ser Thr Arg Ala Val Leu Leu Leu Leu Gly
  1               5                  10                  15

Ile Gln Leu Thr Ala Leu Trp Pro Ile Ala Ala Val Glu Ile Tyr
                 20                  25                  30

Thr Ser Arg Val Leu Glu Ala Val Asn Gly Thr Asp Ala Arg Leu
                 35                  40                  45

Lys Cys Thr Phe Ser Ser Phe Ala Pro Val Gly Asp Ala Leu Thr
                 50                  55                  60

Val Thr Trp Asn Phe Arg Pro Leu Asp Gly Gly Pro Glu Gln Phe
                 65                  70                  75

Val Phe Tyr Tyr His Ile Asp Pro Phe Gln Pro Met Ser Gly Arg
                 80                  85                  90

Phe Lys Asp Arg Val Ser Trp Asp Gly Asn Pro Glu Arg Tyr Asp
                 95                 100                 105

Ala Ser Ile Leu Leu Trp Lys Leu Gln Phe Asp Asp Asn Gly Thr
                110                 115                 120

Tyr Thr Cys Gln Val Lys Asn Pro Pro Asp Val Asp Gly Val Ile
                125                 130                 135

Gly Glu Ile Arg Leu Ser Val Val His Thr Val Arg Phe Ser Glu
                140                 145                 150

Ile His Phe Leu Ala Leu Ala Ile Gly Ser Ala Cys Ala Leu Met
                155                 160                 165

Ile Ile Ile Val Ile Val Val Val Leu Phe Gln His Tyr Arg Lys
                170                 175                 180

Lys Arg Trp Ala Glu Arg Ala His Lys Val Val Glu Ile Lys Ser
                185                 190                 195

Lys Glu Glu Glu Arg Leu Asn Gln Glu Lys Lys Val Ser Val Tyr
                200                 205                 210

Leu Glu Asp Thr Asp
                215


<210> SEQ ID NO 169
<211> LENGTH: 2213
<212> TYPE: DNA
<213> ORGANISM: Homo sapiens

<400> SEQUENCE: 169

gagcgaacat ggcagcgcgt tggcggtttt ggtgtgtctc tgtgaccatg                50

gtggtggcgc tgctcatcgt ttgcgacgtt ccctcagcct ctgcccaaag               100

aaagaaggag atggtgttat ctgaaaaggt tagtcagctg atggaatgga               150

ctaacaaaag acctgtaata agaatgaatg gagacaagtt ccgtcgcctt               200

gtgaaagccc caccgagaaa ttactccgtt atcgtcatgt tcactgctct               250

ccaactgcat agacagtgtg tcgtttgcaa gcaagctgat gaagaattcc               300

agatcctggc aaactcctgg cgatactcca gtgcattcac caacaggata               350

ttttttgcca tggtggattt tgatgaaggc tctgatgtat ttcagatgct               400

aaacatgaat tcagctccaa ctttcatcaa ctttcctgca aaagggaaac               450

ccaaacgggg tgatacatat gagttacagg tgcggggttt ttcagctgag               500

cagattgccc ggtggatcgc cgacagaact gatgtcaata ttagagtgat               550

tagacccccca aattatgctg gtccccttat gttgggattg cttttggctg               600

ttattggtgg acttgtgtat cttcgaagaa gtaatatgga atttctcttt               650
```

-continued

```
aataaaactg gatgggcttt tgcagctttg tgttttgtgc ttgctatgac      700
atctggtcaa atgtggaacc atataagagg accaccatat gcccataaga      750
atccccacac gggacatgtg aattatatcc atggaagcag tcaagcccag      800
tttgtagctg aaacacacat tgttcttctg tttaatggtg gagttacctt      850
aggaatggtg cttttatgtg aagctgctac ctctgacatg gatattggaa      900
agcgaaagat aatgtgtgtg gctggtattg gacttgttgt attattcttc      950
agttggatgc tctctatttt tagatctaaa tatcatggct acccatacag     1000
ctttctgatg agttaaaaag gtcccagaga tatatagaca ctggagtact     1050
ggaaattgaa aaacgaaaat cgtgtgtgtt tgaaaagaag aatgcaactt     1100
gtatattttg tattacctct ttttttcaag tgatttaaat agttaatcat     1150
ttaaccaaag aagatgtgta gtgccttaac aagcaatcct ctgtcaaaat     1200
ctgaggtatt tgaaaataat tatcctctta accttctctt cccagtgaac     1250
tttatggaac atttaattta gtacaattaa gtatattata aaaattgtaa     1300
aactactact ttgttttagt tagaacaaag ctcaaaacta ctttagttaa     1350
cttggtcatc tgattttata ttgccttatc caaagatggg gaaagtaagt     1400
cctgaccagg tgttcccaca tatgcctgtt acagataact acattaggaa     1450
ttcattctta gcttcttcat ctttgtgtgg atgtgtatac tttacgcatc     1500
tttccttttg agtagagaaa ttatgtgtgt catgtggtct tctgaaaatg     1550
gaacaccatt cttcagagca cacgtctagc cctcagcaag acagttgttt     1600
ctcctcctcc ttgcatattt cctactgcgc tccagcctga gtgatagagt     1650
gagactctgt ctcaaaaaaa agtatctcta aatacaggat tataatttct     1700
gcttgagtat ggtgttaact accttgtatt tagaaagatt tcagattcat     1750
tccatctcct tagttttctt ttaaggtgac ccatctgtga taaaaatata     1800
gcttagtgct aaaatcagtg taacttatac atggcctaaa atgtttctac     1850
aaattagagt ttgtcactta ttccatttgt acctaagaga aaaataggct     1900
cagttagaaa aggactccct ggccaggcgc agtgacttac gcctgtaatc     1950
tcagcacttt gggaggccaa ggcaggcaga tcacgaggtc aggagttcga     2000
gaccatcctg gccaacatgg tgaaaccccg tctctactaa aaatataaaa     2050
attagctggg tgtggtggca ggagcctgta atcccagcta cacaggaggc     2100
tgaggcacga gaatcacttg aactcaggag atggaggttt cagtgagccg     2100
agatcacgcc actgcactcc agcctggcaa cagagcgaga ctccatctca     2200
aaaaaaaaaa  aaa                                            2213
```

<210> SEQ ID NO 170
<211> LENGTH: 335
<212> TYPE: PRT
<213> ORGANISM: Homo sapiens

<400> SEQUENCE: 170

```
Met Ala Ala Arg Trp Arg Phe Trp Cys Val Ser Val Thr Met Val
  1               5                  10                  15

Val Ala Leu Leu Ile Val Cys Asp Val Pro Ser Ala Ser Ala Gln
                 20                  25                  30
```

-continued

```
Arg Lys Lys Glu Met Val Leu Ser Glu Lys Val Ser Gln Leu Met
                35                  40                  45

Glu Trp Thr Asn Lys Arg Pro Val Ile Arg Met Asn Gly Asp Lys
                50                  55                  60

Phe Arg Arg Leu Val Lys Ala Pro Pro Arg Asn Tyr Ser Val Ile
                65                  70                  75

Val Met Phe Thr Ala Leu Gln Leu His Arg Gln Cys Val Val Cys
                80                  85                  90

Lys Gln Ala Asp Glu Glu Phe Gln Ile Leu Ala Asn Ser Trp Arg
                95                 100                 105

Tyr Ser Ser Ala Phe Thr Asn Arg Ile Phe Phe Ala Met Val Asp
               110                 115                 120

Phe Asp Glu Gly Ser Asp Val Phe Gln Met Leu Asn Met Asn Ser
               125                 130                 135

Ala Pro Thr Phe Ile Asn Phe Pro Ala Lys Gly Lys Pro Lys Arg
               140                 145                 150

Gly Asp Thr Tyr Glu Leu Gln Val Arg Gly Phe Ser Ala Glu Gln
               155                 160                 165

Ile Ala Arg Trp Ile Ala Asp Arg Thr Asp Val Asn Ile Arg Val
               170                 175                 180

Ile Arg Pro Pro Asn Tyr Ala Gly Pro Leu Met Leu Gly Leu Leu
               185                 190                 195

Leu Ala Val Ile Gly Gly Leu Val Tyr Leu Arg Arg Ser Asn Met
               200                 205                 210

Glu Phe Leu Phe Asn Lys Thr Gly Trp Ala Phe Ala Ala Leu Cys
               215                 220                 225

Phe Val Leu Ala Met Thr Ser Gly Gln Met Trp Asn His Ile Arg
               230                 235                 240

Gly Pro Pro Tyr Ala His Lys Asn Pro His Thr Gly His Val Asn
               245                 250                 255

Tyr Ile His Gly Ser Ser Gln Ala Gln Phe Val Ala Glu Thr His
               260                 265                 270

Ile Val Leu Leu Phe Asn Gly Gly Val Thr Leu Gly Met Val Leu
               275                 280                 285

Leu Cys Glu Ala Ala Thr Ser Asp Met Asp Ile Gly Lys Arg Lys
               290                 295                 300

Ile Met Cys Val Ala Gly Ile Gly Leu Val Val Leu Phe Phe Ser
               305                 310                 315

Trp Met Leu Ser Ile Phe Arg Ser Lys Tyr His Gly Tyr Pro Tyr
               320                 325                 330

Ser Phe Leu Met Ser
               335


<210> SEQ ID NO 171
<211> LENGTH: 771
<212> TYPE: DNA
<213> ORGANISM: Homo sapiens

<400> SEQUENCE: 171

ctccactgca accacccaga gccatggctc cccgaggctg catcgtagct                50

gtctttgcca ttttctgcat ctccaggctc ctctgctcac acggagcccc               100

agtggccccc atgactcctt acctgatgct gtgccagcca cacaagagat               150

gtggggacaa gttctacgac cccctgcagc actgttgcta tgatgatgcc               200
```

-continued

```
gtcgtgccct tggccaggac ccagacgtgt ggaaactgca ccttcagagt          250

ctgctttgag cagtgctgcc cctggacctt catggtgaag ctgataaacc          300

agaactgcga ctcagcccgg acctcggatg acaggctttg tcgcagtgtc          350

agctaatgga acatcagggg aacgatgact cctggattct ccttcctggg          400

tgggcctgga gaaagaggct ggtgttacct gagatctggg atgctgagtg          450

gctgtttggg ggccagagaa acacacactc aactgcccac ttcattctgt          500

gacctgtctg aggcccaccc tgcagctgcc ctgaggaggc ccacaggtcc          550

ccttctagaa ttctggacag catgagatgc gtgtgctgat gggggcccag          600

ggactctgaa ccctcctgat gacccctatg gccaacatca acccggcacc          650

accccaaggc tggctgggga acccttcacc cttctgtgag attttccatc          700

atctcaagtt ctcttctatc caggagcaaa gcacaggatc ataataaatt          750

tatgtacttt ataaatgaaa  a                                        771


<210> SEQ ID NO 172
<211> LENGTH: 110
<212> TYPE: PRT
<213> ORGANISM: Homo sapiens

<400> SEQUENCE: 172

Met Ala Pro Arg Gly Cys Ile Val Ala Val Phe Ala Ile Phe Cys
  1               5                  10                  15

Ile Ser Arg Leu Leu Cys Ser His Gly Ala Pro Val Ala Pro Met
                 20                  25                  30

Thr Pro Tyr Leu Met Leu Cys Gln Pro His Lys Arg Cys Gly Asp
                 35                  40                  45

Lys Phe Tyr Asp Pro Leu Gln His Cys Cys Tyr Asp Asp Ala Val
                 50                  55                  60

Val Pro Leu Ala Arg Thr Gln Thr Cys Gly Asn Cys Thr Phe Arg
                 65                  70                  75

Val Cys Phe Glu Gln Cys Cys Pro Trp Thr Phe Met Val Lys Leu
                 80                  85                  90

Ile Asn Gln Asn Cys Asp Ser Ala Arg Thr Ser Asp Asp Arg Leu
                 95                 100                 105

Cys Arg Ser Val Ser
                110


<210> SEQ ID NO 173
<211> LENGTH: 2044
<212> TYPE: DNA
<213> ORGANISM: Homo sapiens

<400> SEQUENCE: 173

gggggcgggt gcctggagca cggcgctggg gccgcccgca gcgctcactc           50

gctcgcactc agtcgcggga ggcttccccg cgccggccgc gtcccgcccg          100

ctccccggca ccagaagttc ctctgcgcgt ccgacggcga catgggcgtc          150

cccacggccc tggaggccgg cagctggcgc tggggatccc tgctcttcgc          200

tctcttcctg gctgcgtccc taggtccggt ggcagccttc aaggtcgcca          250

cgccgtattc cctgtatgtc tgtcccgagg ggcagaacgt caccctcacc          300

tgcaggctct tgggccctgt ggacaaaggg cacgatgtga ccttctacaa          350

gacgtggtac cgcagctcga ggggcgaggt gcagacctgc tcagagcgcc          400
```

-continued

```
ggcccatccg caacctcacg ttccaggacc ttcacctgca ccatggaggc              450
caccaggctg ccaacaccag ccacgacctg gctcagcgcc acgggctgga              500
gtcggcctcc gaccaccatg gcaacttctc catcaccatg cgcaacctga              550
ccctgctgga tagcggcctc tactgctgcc tggtggtgga gatcaggcac              600
caccactcgg agcacagggt ccatggtgcc atggagctgc aggtgcagac              650
aggcaaagat gcaccatcca actgtgtggt gtacccatcc tcctcccagg              700
atagtgaaaa catcacggct gcagccctgg ctacgggtgc ctgcatcgta              750
ggaatcctct gcctccccct catcctgctc ctggtctaca agcaaaggca              800
ggcagcctcc aaccgccgtg cccaggagct ggtgcggatg gacagcaaca              850
ttcaagggat tgaaaacccc ggctttgaag cctcaccacc tgcccagggg              900
atacccgagg ccaaagtcag gcaccccctg tcctatgtgg cccagcggca              950
gccttctgag tctgggcggc atctgctttc ggagcccagc accccccctgt             1000
ctcctccagg ccccggagac gtcttcttcc catccctgga ccctgtccct              1050
gactctccaa actttgaggt catctagccc agctggggga cagtgggctg              1100
ttgtggctgg gtctggggca ggtgcatttg agccagggct ggctctgtga              1150
gtggcctcct tggcctcggc cctggttccc tccctcctgc tctgggctca              1200
gatactgtga catcccagaa gcccagcccc tcaacccctc tggatgctac              1250
atggggatgc tggacggctc agcccctgtt ccaaggattt tggggtgctg              1300
agattctccc ctagagacct gaaattcacc agctacagat gccaaatgac              1350
ttacatctta agaagtctca gaacgtccag cccttcagca gctctcgttc              1400
tgagacatga gccttgggat gtggcagcat cagtgggaca agatggacac              1450
tgggccaccc tcccaggcac cagacacagg gcacggtgga gagacttctc              1500
ccccgtggcc gccttggctc ccccgttttg cccgaggctg ctcttctgtc              1550
agacttcctc tttgtaccac agtggctctg gggccaggcc tgcctgccca              1600
ctggccatcg ccaccttccc cagctgcctc ctaccagcag tttctctgaa              1650
gatctgtcaa caggttaagt caatctgggg cttccactgc ctgcattcca              1700
gtccccagag cttggtggtc ccgaaacggg aagtacatat tggggcatgg              1750
tggcctccgt gagcaaatgg tgtcttgggc aatctgaggc caggacagat              1800
gttgccccac ccactggaga tggtgctgag ggaggtgggt ggggccttct              1850
gggaaggtga gtggagaggg gcacctgccc cccgccctcc ccatccccta              1900
ctcccactgc tcagcgcggg ccattgcaag ggtgccacac aatgtcttgt              1950
ccaccctggg acacttctga gtatgaagcg ggatgctatt aaaaactaca              2000
tggggaaaaa aaaaaaaaaa aaaaaaaaaa aaaaaaaaaa  aaga                   2044
```

<210> SEQ ID NO 174
<211> LENGTH: 311
<212> TYPE: PRT
<213> ORGANISM: Homo sapiens

<400> SEQUENCE: 174

```
Met Gly Val Pro Thr Ala Leu Glu Ala Gly Ser Trp Arg Trp Gly
  1               5                  10                  15

Ser Leu Leu Phe Ala Leu Phe Leu Ala Ala Ser Leu Gly Pro Val
```

-continued

```
                20                  25                  30

Ala Ala Phe Lys Val Ala Thr Pro Tyr Ser Leu Tyr Val Cys Pro
                35                  40                  45

Glu Gly Gln Asn Val Thr Leu Thr Cys Arg Leu Leu Gly Pro Val
                50                  55                  60

Asp Lys Gly His Asp Val Thr Phe Tyr Lys Thr Trp Tyr Arg Ser
                65                  70                  75

Ser Arg Gly Glu Val Gln Thr Cys Ser Glu Arg Arg Pro Ile Arg
                80                  85                  90

Asn Leu Thr Phe Gln Asp Leu His Leu His His Gly Gly His Gln
                95                 100                 105

Ala Ala Asn Thr Ser His Asp Leu Ala Gln Arg His Gly Leu Glu
               110                 115                 120

Ser Ala Ser Asp His His Gly Asn Phe Ser Ile Thr Met Arg Asn
               125                 130                 135

Leu Thr Leu Leu Asp Ser Gly Leu Tyr Cys Cys Leu Val Val Glu
               140                 145                 150

Ile Arg His His His Ser Glu His Arg Val His Gly Ala Met Glu
               155                 160                 165

Leu Gln Val Gln Thr Gly Lys Asp Ala Pro Ser Asn Cys Val Val
               170                 175                 180

Tyr Pro Ser Ser Ser Gln Asp Ser Glu Asn Ile Thr Ala Ala Ala
               185                 190                 195

Leu Ala Thr Gly Ala Cys Ile Val Gly Ile Leu Cys Leu Pro Leu
               200                 205                 210

Ile Leu Leu Leu Val Tyr Lys Gln Arg Gln Ala Ala Ser Asn Arg
               215                 220                 225

Arg Ala Gln Glu Leu Val Arg Met Asp Ser Asn Ile Gln Gly Ile
               230                 235                 240

Glu Asn Pro Gly Phe Glu Ala Ser Pro Pro Ala Gln Gly Ile Pro
               245                 250                 255

Glu Ala Lys Val Arg His Pro Leu Ser Tyr Val Ala Gln Arg Gln
               260                 265                 270

Pro Ser Glu Ser Gly Arg His Leu Leu Ser Glu Pro Ser Thr Pro
               275                 280                 285

Leu Ser Pro Pro Gly Pro Gly Asp Val Phe Phe Pro Ser Leu Asp
               290                 295                 300

Pro Val Pro Asp Ser Pro Asn Phe Glu Val Ile
               305                 310


<210> SEQ ID NO 175
<211> LENGTH: 693
<212> TYPE: DNA
<213> ORGANISM: Homo sapiens

<400> SEQUENCE: 175

ctagcctgcg ccaaggggta gtgagaccgc gcggcaacag cttgcggctg                50

cggggagctc ccgtgggcgc tccgctggct gtgcaggcgg ccatggattc               100

cttgcggaaa atgctgatct cagtcgcaat gctgggcgca ggggctggcg               150

tgggctacgc gctcctcgtt atcgtgaccc cgggagagcg gcggaagcag               200

gaaatgctaa aggagatgcc actgcaggac ccaaggagca gggaggaggc               250

ggccaggacc cagcagctat tgctggccac tctgcaggag gcagcgacca               300
```

-continued

```
cgcaggagaa cgtggcctgg aggaagaact ggatggttgg cggcgaaggc          350

ggcgccagcg ggaggtcacc gtgagaccgg acttgcctcc gtgggcgccg          400

gaccttggct tgggcgcagg aatccgaggc agcctttctc cttcgtgggc          450

ccagcggaga gtccggaccg agataccatg ccaggactct ccggggtcct          500

gtgagctgcc gtcgggtgag cacgtttccc ccaaaccctg gactgactgc          550

tttaaggtcc gcaaggcggg ccagggccga gacgcgagtc ggatgtggtg          600

aactgaaaga accaataaaa tcatgttcct ccaaaaaaaa aaaaaaaaaa          650

aaaaaaaaaa aaaaaaaaaa aaaaaaaaaa aaaaaaaaaa  aaa                693
```

<210> SEQ ID NO 176
<211> LENGTH: 93
<212> TYPE: PRT
<213> ORGANISM: Homo sapiens

<400> SEQUENCE: 176

```
Met Asp Ser Leu Arg Lys Met Leu Ile Ser Val Ala Met Leu Gly
  1               5                  10                  15

Ala Gly Ala Gly Val Gly Tyr Ala Leu Leu Val Ile Val Thr Pro
                 20                  25                  30

Gly Glu Arg Arg Lys Gln Glu Met Leu Lys Glu Met Pro Leu Gln
                 35                  40                  45

Asp Pro Arg Ser Arg Glu Glu Ala Ala Arg Thr Gln Gln Leu Leu
                 50                  55                  60

Leu Ala Thr Leu Gln Glu Ala Ala Thr Thr Gln Glu Asn Val Ala
                 65                  70                  75

Trp Arg Lys Asn Trp Met Val Gly Gly Glu Gly Gly Ala Ser Gly
                 80                  85                  90

Arg Ser Pro
```

<210> SEQ ID NO 177
<211> LENGTH: 1700
<212> TYPE: DNA
<213> ORGANISM: Homo sapiens

<400> SEQUENCE: 177

```
gccaggcagg tgggcctcag gaggtgcctc caggcggcca gtgggcctga           50

ggccccagca agggctaggg tccatctcca gtcccaggac acagcagcgg          100

ccaccatggc cacgcctggg ctccagcagc atcagagcag cccctgtggt          150

tggcagcaaa gttcagcttg gctgggcccg ctgtgagggg cttcgcgcta          200

cgccctgcgg tgtcccgagg gctgaggtct cctcatcttc tccctagcag          250

tggatgagca acccaacggg ggcccgggga ggggaactgg ccccgaggga          300

gaggaacccc aaagccacat ctgtagccag gatgagcagt gtgaatccag          350

gcagccccca ggaccgggga ggcacaggtg gcccccacca cccggaggag          400

cagctcctgc ccctgtccgg gggatgactg attctcctcc gccaggccac          450

ccagaggaga aggccacccc gcctggaggc acaggccatg aggggctctc          500

aggaggtgct gctgatgtgg cttctggtgt tggcagtggg cggcacagag          550

cacgcctacc ggcccggccg tagggtgtgt gctgtccggg ctcacgggga          600

ccctgtctcc gagtcgttcg tgcagcgtgt gtaccagccc ttcctcacca          650

cctgcgacgg gcaccgggcc tgcagcacct accgaaccat ctataggacc          700
```

-continued

```
gcctaccgcc gcagccctgg gctggcccct gccaggcctc gctacgcgtg          750

ctgccccggc tggaagagga ccagcgggct tcctggggcc tgtggagcag          800

caatatgcca gccgccatgc cggaacggag ggagctgtgt ccagcctggc          850

cgctgccgct gccctgcagg atggcggggt gacacttgcc agtcagatgt          900

ggatgaatgc agtgctagga ggggcggctg tccccagcgc tgcatcaaca          950

ccgccggcag ttactggtgc cagtgttggg aggggcacag cctgtctgca         1000

gacggtacac tctgtgtgcc caagggaggg ccccccaggg tggcccccaa         1050

cccgacagga gtggacagtg caatgaagga agaagtgcag aggctgcagt         1100

ccagggtgga cctgctggag gagaagctgc agctggtgct ggccccactg         1150

cacagcctgg cctcgcaggc actggagcat gggctcccgg accccggcag         1200

cctcctggtg cactccttcc agcagctcgg ccgcatcgac tccctgagcg         1250

agcagatttc cttcctggag gagcagctgg ggtcctgctc ctgcaagaaa         1300

gactcgtgac tgcccagcgc tccaggctgg actgagcccc tcacgccgcc         1350

ctgcagcccc catgcccctg cccaacatgc tgggggtcca gaagccacct         1400

cggggtgact gagcggaagg ccaggcaggg ccttcctcct cttcctcctc         1450

cccttcctcg ggaggctccc cagaccctgg catgggatgg gctgggatct         1500

tctctgtgaa tccacccctg gctaccccca ccctggctac cccaacggca         1550

tcccaaggcc aggtggaccc tcagctgagg gaaggtacga gctccctgct         1600

ggagcctggg acccatggca caggccaggc agcccggagg ctgggtgggg         1650

cctcagtggg ggctgctgcc tgacccccag cacaataaaa atgaaacgtg         1700
```

<210> SEQ ID NO 178
<211> LENGTH: 273
<212> TYPE: PRT
<213> ORGANISM: Homo sapiens

<400> SEQUENCE: 178

```
Met Arg Gly Ser Gln Glu Val Leu Leu Met Trp Leu Leu Val Leu
  1               5                  10                  15

Ala Val Gly Gly Thr Glu His Ala Tyr Arg Pro Gly Arg Arg Val
                 20                  25                  30

Cys Ala Val Arg Ala His Gly Asp Pro Val Ser Glu Ser Phe Val
                 35                  40                  45

Gln Arg Val Tyr Gln Pro Phe Leu Thr Thr Cys Asp Gly His Arg
                 50                  55                  60

Ala Cys Ser Thr Tyr Arg Thr Ile Tyr Arg Thr Ala Tyr Arg Arg
                 65                  70                  75

Ser Pro Gly Leu Ala Pro Ala Arg Pro Arg Tyr Ala Cys Cys Pro
                 80                  85                  90

Gly Trp Lys Arg Thr Ser Gly Leu Pro Gly Ala Cys Gly Ala Ala
                 95                 100                 105

Ile Cys Gln Pro Pro Cys Arg Asn Gly Gly Ser Cys Val Gln Pro
                110                 115                 120

Gly Arg Cys Arg Cys Pro Ala Gly Trp Arg Gly Asp Thr Cys Gln
                125                 130                 135

Ser Asp Val Asp Glu Cys Ser Ala Arg Arg Gly Gly Cys Pro Gln
                140                 145                 150
```

-continued

```
Arg Cys Ile Asn Thr Ala Gly Ser Tyr Trp Cys Gln Cys Trp Glu
                155                 160                 165

Gly His Ser Leu Ser Ala Asp Gly Thr Leu Cys Val Pro Lys Gly
                170                 175                 180

Gly Pro Pro Arg Val Ala Pro Asn Pro Thr Gly Val Asp Ser Ala
                185                 190                 195

Met Lys Glu Glu Val Gln Arg Leu Gln Ser Arg Val Asp Leu Leu
                200                 205                 210

Glu Glu Lys Leu Gln Leu Val Leu Ala Pro Leu His Ser Leu Ala
                215                 220                 225

Ser Gln Ala Leu Glu His Gly Leu Pro Asp Pro Gly Ser Leu Leu
                230                 235                 240

Val His Ser Phe Gln Gln Leu Gly Arg Ile Asp Ser Leu Ser Glu
                245                 250                 255

Gln Ile Ser Phe Leu Glu Glu Gln Leu Gly Ser Cys Ser Cys Lys
                260                 265                 270

Lys Asp Ser


<210> SEQ ID NO 179
<211> LENGTH: 2052
<212> TYPE: DNA
<213> ORGANISM: Homo sapiens

<400> SEQUENCE: 179

gacagctgtg tctcgatgga gtagactctc agaacagcgc agtttgccct                50

ccgctcacgc agagcctctc cgtggcttcc gcaccttgag cattaggcca               100

gttctcctct tctctctaat ccatccgtca cctctcctgt catccgtttc               150

catgccgtga ggtccattca cagaacacat ccatggctct catgctcagt               200

ttggttctga gtctcctcaa gctgggatca gggcagtggc aggtgtttgg               250

gccagacaag cctgtccagg ccttggtggg ggaggacgca gcattctcct               300

gtttcctgtc tcctaagacc aatgcagagg ccatggaagt gcggttcttc               350

aggggccagt tctctagcgt ggtccacctc tacagggacg ggaaggacca               400

gccatttatg cagatgccac agtatcaagg caggacaaaa ctggtgaagg               450

attctattgc ggaggggcgc atctctctga ggctggaaaa cattactgtg               500

ttggatgctg gcctctatgg gtgcaggatt agttcccagt cttactacca               550

gaaggccatc tgggagctac aggtgtcagc actgggctca gttcctctca               600

tttccatcac gggatatgtt gatagagaca tccagctact ctgtcagtcc               650

tcgggctggt tcccccggcc cacagcgaag tggaaaggtc cacaaggaca               700

ggatttgtcc acagactcca ggacaaacag agacatgcat ggcctgtttg               750

atgtggagat ctctctgacc gtccaagaga acgccgggag catatcctgt               800

tccatgcggc atgctcatct gagccgagag gtggaatcca gggtacagat               850

aggagatacc tttttcgagc ctatatcgtg gcacctggct accaaagtac               900

tgggaatact ctgctgtggc ctatttttg gcattgttgg actgaagatt                950

ttcttctcca aattccagtg gaaaatccag gcggaactgg actggagaag              1000

aaagcacgga caggcagaat tgagagacgc ccggaaacac gcagtggagg              1050

tgactctgga tccagagacg gctcacccga agctctgcgt ttctgatctg              1100

aaaactgtaa cccatagaaa agctccccag gaggtgcctc actctgagaa              1150
```

-continued

```
gagatttaca aggaagagtg tggtggcttc tcagagtttc caagcaggga          1200

aacattactg ggaggtggac ggaggacaca ataaaaggtg gcgcgtggga          1250

gtgtgccggg atgatgtgga caggaggaag gagtacgtga ctttgtctcc          1300

cgatcatggg tactgggtcc tcagactgaa tggagaacat ttgtatttca          1350

cattaaatcc ccgttttatc agcgtcttcc ccaggacccc acctacaaaa          1400

ataggggtct tcctggacta tgagtgtggg accatctcct tcttcaacat          1450

aaatgaccag tcccttattt ataccctgac atgtcggttt gaaggcttat          1500

tgaggcccta cattgagtat ccgtcctata atgagcaaaa tggaactccc          1550

atagtcatct gcccagtcac ccaggaatca gagaaagagg cctcttggca          1600

aagggcctct gcaatcccag agacaagcaa cagtgagtcc tcctcacagg          1650

caaccacgcc cttcctcccc aggggtgaaa tgtaggatga atcacatccc          1700

acattcttct ttagggatat taaggtctct ctcccagatc caaagtcccg          1750

cagcagccgg ccaaggtggc ttccagatga agggggactg gcctgtccac          1800

atgggagtca ggtgtcatgg ctgccctgag ctgggaggga agaaggctga          1850

cattacattt agtttgctct cactccatct ggctaagtga tcttgaaata          1900

ccacctctca ggtgaagaac cgtcaggaat tcccatctca caggctgtgg          1950

tgtagattaa gtagacaagg aatgtgaata atgcttagat cttattgatg          2000

acagagtgta tcctaatggt ttgttcatta tattacactt tcagtaaaaa          2050

aa                                                              2052
```

<210> SEQ ID NO 180
<211> LENGTH: 500
<212> TYPE: PRT
<213> ORGANISM: Homo sapiens

<400> SEQUENCE: 180

```
Met Ala Leu Met Leu Ser Leu Val Leu Ser Leu Leu Lys Leu Gly
  1               5                  10                  15

Ser Gly Gln Trp Gln Val Phe Gly Pro Asp Lys Pro Val Gln Ala
                 20                  25                  30

Leu Val Gly Glu Asp Ala Ala Phe Ser Cys Phe Leu Ser Pro Lys
                 35                  40                  45

Thr Asn Ala Glu Ala Met Glu Val Arg Phe Phe Arg Gly Gln Phe
                 50                  55                  60

Ser Ser Val Val His Leu Tyr Arg Asp Gly Lys Asp Gln Pro Phe
                 65                  70                  75

Met Gln Met Pro Gln Tyr Gln Gly Arg Thr Lys Leu Val Lys Asp
                 80                  85                  90

Ser Ile Ala Glu Gly Arg Ile Ser Leu Arg Leu Glu Asn Ile Thr
                 95                 100                 105

Val Leu Asp Ala Gly Leu Tyr Gly Cys Arg Ile Ser Ser Gln Ser
                110                 115                 120

Tyr Tyr Gln Lys Ala Ile Trp Glu Leu Gln Val Ser Ala Leu Gly
                125                 130                 135

Ser Val Pro Leu Ile Ser Ile Thr Gly Tyr Val Asp Arg Asp Ile
                140                 145                 150

Gln Leu Leu Cys Gln Ser Ser Gly Trp Phe Pro Arg Pro Thr Ala
                155                 160                 165
```

-continued

```
Lys Trp Lys Gly Pro Gln Gly Gln Asp Leu Ser Thr Asp Ser Arg
                170                 175                 180

Thr Asn Arg Asp Met His Gly Leu Phe Asp Val Glu Ile Ser Leu
                185                 190                 195

Thr Val Gln Glu Asn Ala Gly Ser Ile Ser Cys Ser Met Arg His
                200                 205                 210

Ala His Leu Ser Arg Glu Val Glu Ser Arg Val Gln Ile Gly Asp
                215                 220                 225

Thr Phe Phe Glu Pro Ile Ser Trp His Leu Ala Thr Lys Val Leu
                230                 235                 240

Gly Ile Leu Cys Cys Gly Leu Phe Phe Gly Ile Val Gly Leu Lys
                245                 250                 255

Ile Phe Phe Ser Lys Phe Gln Trp Lys Ile Gln Ala Glu Leu Asp
                260                 265                 270

Trp Arg Arg Lys His Gly Gln Ala Glu Leu Arg Asp Ala Arg Lys
                275                 280                 285

His Ala Val Glu Val Thr Leu Asp Pro Glu Thr Ala His Pro Lys
                290                 295                 300

Leu Cys Val Ser Asp Leu Lys Thr Val Thr His Arg Lys Ala Pro
                305                 310                 315

Gln Glu Val Pro His Ser Glu Lys Arg Phe Thr Arg Lys Ser Val
                320                 325                 330

Val Ala Ser Gln Ser Phe Gln Ala Gly Lys His Tyr Trp Glu Val
                335                 340                 345

Asp Gly Gly His Asn Lys Arg Trp Arg Val Gly Val Cys Arg Asp
                350                 355                 360

Asp Val Asp Arg Arg Lys Glu Tyr Val Thr Leu Ser Pro Asp His
                365                 370                 375

Gly Tyr Trp Val Leu Arg Leu Asn Gly Glu His Leu Tyr Phe Thr
                380                 385                 390

Leu Asn Pro Arg Phe Ile Ser Val Phe Pro Arg Thr Pro Pro Thr
                395                 400                 405

Lys Ile Gly Val Phe Leu Asp Tyr Glu Cys Gly Thr Ile Ser Phe
                410                 415                 420

Phe Asn Ile Asn Asp Gln Ser Leu Ile Tyr Thr Leu Thr Cys Arg
                425                 430                 435

Phe Glu Gly Leu Leu Arg Pro Tyr Ile Glu Tyr Pro Ser Tyr Asn
                440                 445                 450

Glu Gln Asn Gly Thr Pro Ile Val Ile Cys Pro Val Thr Gln Glu
                455                 460                 465

Ser Glu Lys Glu Ala Ser Trp Gln Arg Ala Ser Ala Ile Pro Glu
                470                 475                 480

Thr Ser Asn Ser Glu Ser Ser Ser Gln Ala Thr Thr Pro Phe Leu
                485                 490                 495

Pro Arg Gly Glu Met
                500


<210> SEQ ID NO 181
<211> LENGTH: 2294
<212> TYPE: DNA
<213> ORGANISM: Homo sapiens

<400> SEQUENCE: 181

gcgatggtgc gcccggtggc ggtggcggcg gcggttgcgg aggcttcctt                50
```

-continued

```
ggtcggattg caacgaggag aagatgactg accaaccgac tggctgaatg      100
aatgaatggc ggagccgagc gcgccatgag gagcctgccg agcctgggcg      150
gcctcgccct gttgtgctgc gccgccgccg ccgccgccgt cgcctcagcc      200
gcctcggcgg ggaatgtcac cggtggcggc ggggccgcgg ggcaggtgga      250
cgcgtcgccg ggccccgggt tgcggggcga gcccagccac cccttcccta      300
gggcgacggc tcccacggcc caggccccga ggaccgggcc cccgcgcgcc      350
accgtccacc gacccctggc tgcgacttct ccagcccagt ccccggagac      400
cacccctctt tgggcgactg ctggaccctc ttccaccacc tttcaggcgc      450
cgctcggccc ctcgccgacc acccctccgg cggcggaacg cacttcgacc      500
acctctcagg cgccgaccag acccgcgccg accacccttt cgacgaccac      550
tggcccggcg ccgaccaccc ctgtagcgac caccgtaccg gcgcccacga      600
ctccccggac cccgaccccc gatctcccca gcagcagcaa cagcagcgtc      650
ctccccaccc cacctgccac cgaggccccc tcttcgcctc ctccagagta      700
tgtatgtaac tgctctgtgg ttggaagcct gaatgtgaat cgctgcaacc      750
agaccacagg gcagtgtgag tgtcggccag gttatcaggg gcttcactgt      800
gaaacctgca aagagggctt ttacctaaat tacacttctg ggctctgtca      850
gccatgtgac tgtagtccac atggagctct cagcataccg tgcaacaggt      900
aagcaacaga gggtggaact gaagtttatt ttattttagc aagggaaaaa      950
aaaaggctgc tactctcaag gaccatactg gtttaaacaa aggaggatga     1000
gggtcataga tttacaaaat attttatata cttttattct cttactttat     1050
atgttatatt taatgtcagg atttaaaaac atctaattta ctgatttagt     1100
tcttcaaaag cactagagtc gccaattttt ctctgggata atttctgtaa     1150
atttcatggg aaaaaattat tgaagaataa atctgctttc tggaagggct     1200
ttcaggcatg aaacctgcta ggaggtttag aaatgttctt atgtttatta     1250
atataccatt ggagtttgag gaaatttgtt gtttggttta tttttctctc     1300
taatcaaaat tctacatttg tttctttgga catctaaagc ttaacctggg     1350
ggtaccctaa tttatttaac tagtggtaag tagactggtt ttactctatt     1400
taccagtaca tttttgagac caaaagtaga ttaagcagga attatcttta     1450
aactattatg ttatttggag gtaatttaat ctagtggaat aatgtactgt     1500
tatctaagca tttgccttgt actgcactga aagtaattat tctttgacct     1550
tatgtgaggc acttggcttt ttgtggaccc caagtcaaaa aactgaagag     1600
acagtattaa ataatgaaaa aaataatgac aggttatact cagtgtaacc     1650
tgggtataac ccaagatctg ctgccactta cgagctgtgt tccttgggca     1700
agtaatttcc tttcactgag cttgtttctt ctcaaggttg ttgtgaagat     1750
taaatgagtt gatatatata aaatgcctag cacatgtcac tcaataaatt     1800
ctggtttgtt ttaatttcaa aggaatatta tggactgaaa tgagagaaca     1850
tgttttaaga acttttagct ccttgacaaa gaagtgcttt atactttagc     1900
actaaatatt ttaaatgctt tataaatgat attatactgt tatggaatat     1950
tgtatcatat tgtagtttat taaaaatgta gaagaggctg ggcgcggtgg     2000
```

-continued

```
ctcacgcctg taatcctagc actttgggag gccaaggcgg gtggatcact          2050

tgaggccagg agttctagat gagcctggcc agcacagtga aaccccgtct          2100

ctactaaaaa tacaaacaaa ttagctgggc gtggtggcac acacctgtag          2150

tcccagctac tcgggaggct gaggcaggag aatcggttga acccgggagg          2200

tggaggttgc agtgagctga gatcgcgcca ctgcactcca gcctggtgag          2250

agagggagac tctgtcttaa aaaaaaaaaa aaaaaaaaaa  aaaa               2294
```

<210> SEQ ID NO 182
<211> LENGTH: 258
<212> TYPE: PRT
<213> ORGANISM: Homo sapiens

<400> SEQUENCE: 182

```
Met Arg Ser Leu Pro Ser Leu Gly Gly Leu Ala Leu Leu Cys Cys
  1               5                  10                  15

Ala Ala Ala Ala Ala Ala Val Ala Ser Ala Ala Ser Ala Gly Asn
                 20                  25                  30

Val Thr Gly Gly Gly Gly Ala Ala Gly Gln Val Asp Ala Ser Pro
                 35                  40                  45

Gly Pro Gly Leu Arg Gly Glu Pro Ser His Pro Phe Pro Arg Ala
                 50                  55                  60

Thr Ala Pro Thr Ala Gln Ala Pro Arg Thr Gly Pro Pro Arg Ala
                 65                  70                  75

Thr Val His Arg Pro Leu Ala Ala Thr Ser Pro Ala Gln Ser Pro
                 80                  85                  90

Glu Thr Thr Pro Leu Trp Ala Thr Ala Gly Pro Ser Ser Thr Thr
                 95                 100                 105

Phe Gln Ala Pro Leu Gly Pro Ser Pro Thr Thr Pro Pro Ala Ala
                110                 115                 120

Glu Arg Thr Ser Thr Thr Ser Gln Ala Pro Thr Arg Pro Ala Pro
                125                 130                 135

Thr Thr Leu Ser Thr Thr Thr Gly Pro Ala Pro Thr Thr Pro Val
                140                 145                 150

Ala Thr Thr Val Pro Ala Pro Thr Thr Pro Arg Thr Pro Thr Pro
                155                 160                 165

Asp Leu Pro Ser Ser Ser Asn Ser Ser Val Leu Pro Thr Pro Pro
                170                 175                 180

Ala Thr Glu Ala Pro Ser Ser Pro Pro Pro Glu Tyr Val Cys Asn
                185                 190                 195

Cys Ser Val Val Gly Ser Leu Asn Val Asn Arg Cys Asn Gln Thr
                200                 205                 210

Thr Gly Gln Cys Glu Cys Arg Pro Gly Tyr Gln Gly Leu His Cys
                215                 220                 225

Glu Thr Cys Lys Glu Gly Phe Tyr Leu Asn Tyr Thr Ser Gly Leu
                230                 235                 240

Cys Gln Pro Cys Asp Cys Ser Pro His Gly Ala Leu Ser Ile Pro
                245                 250                 255

Cys Asn Arg
```

<210> SEQ ID NO 183
<211> LENGTH: 689
<212> TYPE: DNA
<213> ORGANISM: Homo sapiens -continued

<400> SEQUENCE: 183

```
tgcggcgcag tgtagacctg ggaggatggg cggcctgctg ctggctgctt      50

ttctggcttt ggtctcggtg cccagggccc aggccgtgtg gttgggaaga     100

ctggaccctg agcagcttct tgggccctgg tacgtgcttg cggtggcctc     150

ccgggaaaag ggctttgcca tggagaagga catgaagaac gtcgtggggg     200

tggtggtgac cctcactcca gaaaacaacc tgcggacgct gtcctctcag     250

cacgggctgg gagggtgtga ccagagtgtc atggacctga taaagcgaaa     300

ctccggatgg gtgtttgaga atccctcaat aggcgtgctg gagctctggg     350

tgctggccac caacttcaga gactatgcca tcatcttcac tcagctggag     400

ttcggggacg agcccttcaa caccgtggag ctgtacagtc tgacggagac     450

agccagccag gaggccatgg ggctcttcac caagtggagc aggagcctgg     500

gcttcctgtc acagtagcag gcccagctgc agaaggacct cacctgtgct     550

cacaagatcc ttctgtgagt gctgcgtccc cagtagggat ggcgcccaca     600

gggtcctgtg acctcggcca gtgtccaccc acctcgctca gcggctcccg     650

gggcccagca ccagctcaga ataaagcgat  tccacagca               689
```

<210> SEQ ID NO 184
<211> LENGTH: 163
<212> TYPE: PRT
<213> ORGANISM: Homo sapiens

<400> SEQUENCE: 184

```
Met Gly Gly Leu Leu Leu Ala Ala Phe Leu Ala Leu Val Ser Val
  1               5                  10                  15

Pro Arg Ala Gln Ala Val Trp Leu Gly Arg Leu Asp Pro Glu Gln
                 20                  25                  30

Leu Leu Gly Pro Trp Tyr Val Leu Ala Val Ala Ser Arg Glu Lys
                 35                  40                  45

Gly Phe Ala Met Glu Lys Asp Met Lys Asn Val Val Gly Val Val
                 50                  55                  60

Val Thr Leu Thr Pro Glu Asn Asn Leu Arg Thr Leu Ser Ser Gln
                 65                  70                  75

His Gly Leu Gly Gly Cys Asp Gln Ser Val Met Asp Leu Ile Lys
                 80                  85                  90

Arg Asn Ser Gly Trp Val Phe Glu Asn Pro Ser Ile Gly Val Leu
                 95                 100                 105

Glu Leu Trp Val Leu Ala Thr Asn Phe Arg Asp Tyr Ala Ile Ile
                110                 115                 120

Phe Thr Gln Leu Glu Phe Gly Asp Glu Pro Phe Asn Thr Val Glu
                125                 130                 135

Leu Tyr Ser Leu Thr Glu Thr Ala Ser Gln Glu Ala Met Gly Leu
                140                 145                 150

Phe Thr Lys Trp Ser Arg Ser Leu Gly Phe Leu Ser Gln
                155                 160
```

<210> SEQ ID NO 185
<211> LENGTH: 1204
<212> TYPE: DNA
<213> ORGANISM: Homo sapiens

<400> SEQUENCE: 185

-continued

```
gttccgcaga tgcagaggtt gaggtggctg cgggactgga agtcatcggg          50
cagaggtctc acagcagcca aggaacctgg ggcccgctcc tccccctcc          100
aggccatgag gattctgcag ttaatcctgc ttgctctggc aacagggctt          150
gtagggggag agaccaggat catcaagggg ttcgagtgca agcctcactc          200
ccagccctgg caggcagccc tgttcgagaa gacgcggcta ctctgtgggg          250
cgacgctcat cgcccccaga tggctcctga cagcagccca ctgcctcaag          300
ccccgctaca tagttcacct ggggcagcac aacctccaga aggaggaggg          350
ctgtgagcag acccggacag ccactgagtc cttcccccac cccggcttca          400
acaacagcct ccccaacaaa gaccaccgca atgacatcat gctggtgaag          450
atggcatcgc cagtctccat cacctgggct gtgcgacccc tcaccctctc          500
ctcacgctgt gtcactgctg gcaccagctg cctcatttcc ggctggggca          550
gcacgtccag cccccagtta cgcctgcctc acaccttgcg atgcgccaac          600
atcaccatca ttgagcacca gaagtgtgag aacgcctacc ccggcaacat          650
cacagacacc atggtgtgtg ccagcgtgca ggaagggggc aaggactcct          700
gccagggtga ctccgggggc cctctggtct gtaaccagtc tcttcaaggc          750
attatctcct ggggccagga tccgtgtgcg atcacccgaa agcctggtgt          800
ctacacgaaa gtctgcaaat atgtggactg gatccaggag acgatgaaga          850
acaattagac tggacccacc caccacagcc catcaccctc catttccact          900
tggtgtttgg ttcctgttca ctctgttaat aagaaaccct aagccaagac          950
cctctacgaa cattctttgg gcctcctgga ctacaggaga tgctgtcact         1000
taataatcaa cctggggttc gaaatcagtg agacctggat tcaaattctg         1050
ccttgaaata ttgtgactct gggaatgaca acacctggtt tgttctctgt         1100
tgtatcccca gccccaaaga cagctcctgg ccatatatca aggtttcaat         1150
aaatatttgc taaatgaaaa aaaaaaaaaa aaaaaaaaaa aaaaaaaaaa         1200
aaaa                                                           1204
```

<210> SEQ ID NO 186
<211> LENGTH: 250
<212> TYPE: PRT
<213> ORGANISM: Homo sapiens

<400> SEQUENCE: 186

```
Met Arg Ile Leu Gln Leu Ile Leu Leu Ala Leu Ala Thr Gly Leu
  1               5                  10                  15

Val Gly Gly Glu Thr Arg Ile Ile Lys Gly Phe Glu Cys Lys Pro
                 20                  25                  30

His Ser Gln Pro Trp Gln Ala Ala Leu Phe Glu Lys Thr Arg Leu
                 35                  40                  45

Leu Cys Gly Ala Thr Leu Ile Ala Pro Arg Trp Leu Leu Thr Ala
                 50                  55                  60

Ala His Cys Leu Lys Pro Arg Tyr Ile Val His Leu Gly Gln His
                 65                  70                  75

Asn Leu Gln Lys Glu Glu Gly Cys Glu Gln Thr Arg Thr Ala Thr
                 80                  85                  90

Glu Ser Phe Pro His Pro Gly Phe Asn Asn Ser Leu Pro Asn Lys
                 95                 100                 105
```

-continued

```
Asp His Arg Asn Asp Ile Met Leu Val Lys Met Ala Ser Pro Val
                110                 115                 120

Ser Ile Thr Trp Ala Val Arg Pro Leu Thr Leu Ser Ser Arg Cys
                125                 130                 135

Val Thr Ala Gly Thr Ser Cys Leu Ile Ser Gly Trp Gly Ser Thr
                140                 145                 150

Ser Ser Pro Gln Leu Arg Leu Pro His Thr Leu Arg Cys Ala Asn
                155                 160                 165

Ile Thr Ile Ile Glu His Gln Lys Cys Glu Asn Ala Tyr Pro Gly
                170                 175                 180

Asn Ile Thr Asp Thr Met Val Cys Ala Ser Val Gln Glu Gly Gly
                185                 190                 195

Lys Asp Ser Cys Gln Gly Asp Ser Gly Gly Pro Leu Val Cys Asn
                200                 205                 210

Gln Ser Leu Gln Gly Ile Ile Ser Trp Gly Gln Asp Pro Cys Ala
                215                 220                 225

Ile Thr Arg Lys Pro Gly Val Tyr Thr Lys Val Cys Lys Tyr Val
                230                 235                 240

Asp Trp Ile Gln Glu Thr Met Lys Asn Asn
                245                 250


<210> SEQ ID NO 187
<211> LENGTH: 2848
<212> TYPE: DNA
<213> ORGANISM: Homo sapiens

<400> SEQUENCE: 187

gctcaagtgc cctgccttgc cccacccagc ccagcctggc cagagccccc                50

tggagaagga gctctcttct tgcttggcag ctggaccaag ggagccagtc               100

ttgggcgctg gagggcctgt cctgaccatg gtccctgcct ggctgtggct               150

gctttgtgtc tccgtccccc aggctctccc caaggcccag cctgcagagc               200

tgtctgtgga agttccagaa aactatggtg gaaatttccc tttatacctg               250

accaagttgc cgctgccccg tgagggggct gaaggccaga tcgtgctgtc               300

aggggactca ggcaaggcaa ctgagggccc atttgctatg gatccagatt               350

ctggcttcct gctggtgacc agggccctgg accgagagga gcaggcagag               400

taccagctac aggtcaccct ggagatgcag gatggacatg tcttgtgggg               450

tccacagcct gtgcttgtgc acgtgaagga tgagaatgac caggtgcccc               500

atttctctca agccatctac agagctcggc tgagccgggg taccaggcct               550

ggcatcccct tcctcttcct tgaggcttca gaccgggatg agccaggcac               600

agccaactcg gatcttcgat tccacatcct gagccaggct ccagcccagc               650

cttccccaga catgttccag ctggagcctc ggctgggggc tctggccctc               700

agccccaagg ggagcaccag ccttgaccac gccctggaga ggacctacca               750

gctgttggta caggtcaagg acatgggtga ccaggcctca ggccaccagg               800

ccactgccac cgtggaagtc tccatcatag agagcacctg ggtgtcccta               850

gagcctatcc acctggcaga gaatctcaaa gtcctatacc cgcaccacat               900

ggcccaggta cactggagtg ggggtgatgt gcactatcac ctggagagcc               950

atccccggg acccttttgaa gtgaatgcag agggaaacct ctacgtgacc              1000

agagagctgg acagagaagc ccaggctgag tacctgctcc aggtgcgggc              1050
```

-continued

```
tcagaattcc catggcgagg actatgcggc ccctctggag ctgcacgtgc          1100
tggtgatgga tgagaatgac aacgtgccta tctgccctcc ccgtgacccc          1150
acagtcagca tccctgagct cagtccacca ggtactgaag tgactagact          1200
gtcagcagag gatgcagatg cccccggctc ccccaattcc cacgttgtgt          1250
atcagctcct gagccctgag cctgaggatg gggtagaggg gagagccttc          1300
caggtggacc ccacttcagg cagtgtgacg ctgggggtgc tcccactccg          1350
agcaggccag aacatcctgc ttctggtgct ggccatggac ctggcaggcg          1400
cagagggtgg cttcagcagc acgtgtgaag tcgaagtcgc agtcacagat          1450
atcaatgatc acgcccctga gttcatcact tcccagattg ggcctataag          1500
cctccctgag gatgtggagc ccgggactct ggtggccatg ctaacagcca          1550
ttgatgctga cctcgagccc gccttccgcc tcatggattt tgccattgag          1600
aggggagaca cagaagggac ttttggcctg gattgggagc cagactctgg          1650
gcatgttaga ctcagactct gcaagaacct cagttatgag gcagctccaa          1700
gtcatgaggt ggtggtggtg gtgcagagtg tggcgaagct ggtggggcca          1750
ggcccaggcc ctggagccac cgccacggtg actgtgctag tggagagagt          1800
gatgccaccc cccaagttgg accaggagag ctacgaggcc agtgtcccca          1850
tcagtgcccc agccggctct ttcctgctga ccatccagcc ctccgacccc          1900
atcagccgaa ccctcaggtt ctccctagtc aatgactcag agggctggct          1950
ctgcattgag aaattctccg gggaggtgca caccgcccag tccctgcagg          2000
gcgcccagcc tggggacacc tacacggtgc ttgtggaggc ccaggataca          2050
gccctgactc ttgcccctgt gccctcccaa tacctctgca caccccgcca          2100
agaccatggc ttgatcgtga gtggacccag caaggacccc gatctggcca          2150
gtgggcacgg tccctacagc ttcacccttg gtcccaaccc cacggtgcaa          2200
cgggattggc gcctccagac tctcaatggt tcccatgcct acctcacctt          2250
ggccctgcat tgggtggagc cacgtgaaca cataatcccc gtggtggtca          2300
gccacaatgc ccagatgtgg cagctcctgg ttcgagtgat cgtgtgtcgc          2350
tgcaacgtgg aggggcagtg catgcgcaag gtgggccgca tgaagggcat          2400
gcccacgaag ctgtcggcag tgggcatcct tgtaggcacc ctggtagcaa          2450
taggaatctt cctcatcctc attttcaccc actggaccat gtcaaggaag          2500
aaggacccgg atcaaccagc agacagcgtg cccctgaagg cgactgtctg          2550
aatggcccag gcagctctag ctgggagctt ggcctctggc tccatctgag          2600
tcccctggga gagagcccag cacccaagat ccagcagggg acaggacaga          2650
gtagaagccc ctccatctgc cctggggtgg aggcaccatc accatcacca          2700
ggcatgtctg cagagcctgg acaccaactt tatggactgc ccatgggagt          2750
gctccaaatg tcagggtgtt tgcccaataa taaagcccca gagaactggg          2800
ctgggcccta tgggaaaaaa aaaaaaaaaa aaaaaaaaaa  aaaaaaag          2848
```

<210> SEQ ID NO 188
<211> LENGTH: 807
<212> TYPE: PRT
<213> ORGANISM: Homo sapiens -continued

<400> SEQUENCE: 188

Met Val Pro Ala Trp Leu Trp Leu Leu Cys Val Ser Val Pro Gln
1 5 10 15

Ala Leu Pro Lys Ala Gln Pro Ala Glu Leu Ser Val Glu Val Pro
20 25 30

Glu Asn Tyr Gly Gly Asn Phe Pro Leu Tyr Leu Thr Lys Leu Pro
35 40 45

Leu Pro Arg Glu Gly Ala Glu Gly Gln Ile Val Leu Ser Gly Asp
50 55 60

Ser Gly Lys Ala Thr Glu Gly Pro Phe Ala Met Asp Pro Asp Ser
65 70 75

Gly Phe Leu Leu Val Thr Arg Ala Leu Asp Arg Glu Glu Gln Ala
80 85 90

Glu Tyr Gln Leu Gln Val Thr Leu Glu Met Gln Asp Gly His Val
95 100 105

Leu Trp Gly Pro Gln Pro Val Leu Val His Val Lys Asp Glu Asn
110 115 120

Asp Gln Val Pro His Phe Ser Gln Ala Ile Tyr Arg Ala Arg Leu
125 130 135

Ser Arg Gly Thr Arg Pro Gly Ile Pro Phe Leu Phe Leu Glu Ala
140 145 150

Ser Asp Arg Asp Glu Pro Gly Thr Ala Asn Ser Asp Leu Arg Phe
155 160 165

His Ile Leu Ser Gln Ala Pro Ala Gln Pro Ser Pro Asp Met Phe
170 175 180

Gln Leu Glu Pro Arg Leu Gly Ala Leu Ala Leu Ser Pro Lys Gly
185 190 195

Ser Thr Ser Leu Asp His Ala Leu Glu Arg Thr Tyr Gln Leu Leu
200 205 210

Val Gln Val Lys Asp Met Gly Asp Gln Ala Ser Gly His Gln Ala
215 220 225

Thr Ala Thr Val Glu Val Ser Ile Ile Glu Ser Thr Trp Val Ser
230 235 240

Leu Glu Pro Ile His Leu Ala Glu Asn Leu Lys Val Leu Tyr Pro
245 250 255

His His Met Ala Gln Val His Trp Ser Gly Gly Asp Val His Tyr
260 265 270

His Leu Glu Ser His Pro Pro Gly Pro Phe Glu Val Asn Ala Glu
275 280 285

Gly Asn Leu Tyr Val Thr Arg Glu Leu Asp Arg Glu Ala Gln Ala
290 295 300

Glu Tyr Leu Leu Gln Val Arg Ala Gln Asn Ser His Gly Glu Asp
305 310 315

Tyr Ala Ala Pro Leu Glu Leu His Val Leu Val Met Asp Glu Asn
320 325 330

Asp Asn Val Pro Ile Cys Pro Pro Arg Asp Pro Thr Val Ser Ile
335 340 345

Pro Glu Leu Ser Pro Pro Gly Thr Glu Val Thr Arg Leu Ser Ala
350 355 360

Glu Asp Ala Asp Ala Pro Gly Ser Pro Asn Ser His Val Val Tyr
365 370 375

Gln Leu Leu Ser Pro Glu Pro Glu Asp Gly Val Glu Gly Arg Ala
380 385 390

-continued

```
Phe Gln Val Asp Pro Thr Ser Gly Ser Val Thr Leu Gly Val Leu
                395                 400                 405

Pro Leu Arg Ala Gly Gln Asn Ile Leu Leu Leu Val Leu Ala Met
                410                 415                 420

Asp Leu Ala Gly Ala Glu Gly Gly Phe Ser Ser Thr Cys Glu Val
                425                 430                 435

Glu Val Ala Val Thr Asp Ile Asn Asp His Ala Pro Glu Phe Ile
                440                 445                 450

Thr Ser Gln Ile Gly Pro Ile Ser Leu Pro Glu Asp Val Glu Pro
                455                 460                 465

Gly Thr Leu Val Ala Met Leu Thr Ala Ile Asp Ala Asp Leu Glu
                470                 475                 480

Pro Ala Phe Arg Leu Met Asp Phe Ala Ile Glu Arg Gly Asp Thr
                485                 490                 495

Glu Gly Thr Phe Gly Leu Asp Trp Glu Pro Asp Ser Gly His Val
                500                 505                 510

Arg Leu Arg Leu Cys Lys Asn Leu Ser Tyr Glu Ala Ala Pro Ser
                515                 520                 525

His Glu Val Val Val Val Val Gln Ser Val Ala Lys Leu Val Gly
                530                 535                 540

Pro Gly Pro Gly Pro Gly Ala Thr Ala Thr Val Thr Val Leu Val
                545                 550                 555

Glu Arg Val Met Pro Pro Pro Lys Leu Asp Gln Glu Ser Tyr Glu
                560                 565                 570

Ala Ser Val Pro Ile Ser Ala Pro Ala Gly Ser Phe Leu Leu Thr
                575                 580                 585

Ile Gln Pro Ser Asp Pro Ile Ser Arg Thr Leu Arg Phe Ser Leu
                590                 595                 600

Val Asn Asp Ser Glu Gly Trp Leu Cys Ile Glu Lys Phe Ser Gly
                605                 610                 615

Glu Val His Thr Ala Gln Ser Leu Gln Gly Ala Gln Pro Gly Asp
                620                 625                 630

Thr Tyr Thr Val Leu Val Glu Ala Gln Asp Thr Ala Leu Thr Leu
                635                 640                 645

Ala Pro Val Pro Ser Gln Tyr Leu Cys Thr Pro Arg Gln Asp His
                650                 655                 660

Gly Leu Ile Val Ser Gly Pro Ser Lys Asp Pro Asp Leu Ala Ser
                665                 670                 675

Gly His Gly Pro Tyr Ser Phe Thr Leu Gly Pro Asn Pro Thr Val
                680                 685                 690

Gln Arg Asp Trp Arg Leu Gln Thr Leu Asn Gly Ser His Ala Tyr
                695                 700                 705

Leu Thr Leu Ala Leu His Trp Val Glu Pro Arg Glu His Ile Ile
                710                 715                 720

Pro Val Val Val Ser His Asn Ala Gln Met Trp Gln Leu Leu Val
                725                 730                 735

Arg Val Ile Val Cys Arg Cys Asn Val Glu Gly Gln Cys Met Arg
                740                 745                 750

Lys Val Gly Arg Met Lys Gly Met Pro Thr Lys Leu Ser Ala Val
                755                 760                 765

Gly Ile Leu Val Gly Thr Leu Val Ala Ile Gly Ile Phe Leu Ile
                770                 775                 780
```

-continued

```
Leu Ile Phe Thr His Trp Thr Met Ser Arg Lys Lys Asp Pro Asp
                785                 790                 795

Gln Pro Ala Asp Ser Val Pro Leu Lys Ala Thr Val
                800                 805


<210> SEQ ID NO 189
<211> LENGTH: 2668
<212> TYPE: DNA
<213> ORGANISM: Homo sapiens

<400> SEQUENCE: 189

gactttgctt gaatgtttac attttctgct cgctgtccta catatcacaa                50

tatagtgttc acgttttgtt aaaactttgg ggtgtcagga gttgagcttg               100

ctcagcaagc cagcatggct aggatgagct ttgttatagc agcttgccaa               150

ttggtgctgg gcctactaat gacttcatta accgagtctt ccatacagaa               200

tagtgagtgt ccacaacttt gcgtatgtga aattcgtccc tggtttaccc               250

cacagtcaac ttacagagaa gccaccactg ttgattgcaa tgacctccgc               300

ttaacaagga ttcccagtaa cctctctagt gacacacaag tgcttctctt               350

acagagcaat aacatcgcga agactgtgga tgagctgcag cagcttttca               400

acttgactga actagatttc tcccaaaaca actttactaa cattaaggag               450

gtcgggctgg caaacctaac ccagctcaca acgctgcatt tggaggaaaa               500

tcagattacc gagatgactg attactgtct acaagacctc agcaaccttc               550

aagaactcta catcaaccac aaccaaatta gcactatttc tgctcatgct               600

tttgcaggct taaaaaatct attaaggctc cacctgaact ccaacaaatt               650

gaaagttatt gatagtcgct ggtttgattc tacacccaac ctggaaattc               700

tcatgatcgg agaaaaccct gtgattggaa ttctggatat gaacttcaaa               750

cccctcgcaa atttgagaag cttagttttg gcaggaatgt atctcactga               800

tattcctgga aatgctttgg tgggtctgga tagccttgag agcctgtctt               850

tttatgataa caaactggtt aaagtccctc aacttgccct gcaaaaagtt               900

ccaaatttga aattcttaga cctcaacaaa aaccccattc acaaaatcca               950

agaaggggac ttcaaaaata tgcttcggtt aaaagaactg ggaatcaaca              1000

atatgggcga gctcgtttct gtcgaccgct atgccctgga taacttgcct              1050

gaactcacaa agctggaagc caccaataac cctaaactct cttacatcca              1100

ccgcttggct ttccgaagtg tccctgctct ggaaagcttg atgctgaaca              1150

acaatgcctt gaatgccatt taccaaaaga cagtcgaatc cctccccaat              1200

ctgcgtgaga tcagtatcca tagcaatccc ctcaggtgtg actgtgtgat              1250

ccactggatt aactccaaca aaaccaacat ccgcttcatg gagcccctgt              1300

ccatgttctg tgccatgccg cccgaatata aagggcacca ggtgaaggaa              1350

gttttaatcc aggattcgag tgaacagtgc ctcccaatga tatctcacga              1400

cagcttccca aatcgtttaa acgtggatat cggcacgacg gttttcctag              1450

actgtcgagc catggctgag ccagaacctg aaatttactg ggtcactccc              1500

attggaaata agataactgt ggaaaccctt tcagataaat acaagctaag              1550

tagcgaaggt accttggaaa tatctaacat acaaattgaa gactcaggaa              1600

gatacacatg tgttgcccag aatgtccaag gggcagacac tcgggtggca              1650
```

-continued

```
acaattaagg ttaacgggac ccttctggat ggtacccagg tgctaaaaat          1700

atacgtcaag cagacagaat cccattccat cttagtgtcc tggaaagtta          1750

attccaatgt catgacgtca aacttaaaat ggtcgtctgc caccatgaag          1800

attgataacc ctcacataac atatactgcc agggtcccag tcgatgtcca          1850

tgaatacaac ctaacgcatc tgcagccttc cacagattat gaagtgtgtc          1900

tcacagtgtc caatattcat cagcagactc aaaagtcatg cgtaaatgtc          1950

acaaccaaaa atgccgcctt cgcagtggac atctctgatc aagaaaccag          2000

tacagccctt gctgcagtaa tggggtctat gtttgccgtc attagccttg          2050

cgtccattgc tgtgtacttt gccaaaagat ttaagagaaa aaactaccac          2100

cactcattaa aaaagtatat gcaaaaaacc tcttcaatcc cactaaatga          2150

gctgtaccca ccactcatta acctctggga aggtgacagc gagaaagaca          2200

aagatggttc tgcagacacc aagccaaccc aggtcgacac atccagaagc          2250

tattacatgt ggtaactcag aggatatttt gcttctggta gtaaggagca          2300

caaagacgtt tttgctttat tctgcaaaag tgaacaagtt gaagactttt          2350

gtatttttga ctttgctagt ttgtggcaga gtggagagga cgggtggata          2400

tttcaaattt ttttagtata gcgtatcgca agggtttgac acggctgcca          2450

gcgactctag gcttccagtc tgtgtttggt ttttattctt atcattatta          2500

tgattgttat tatattatta ttttatttta gttgttgtgc taaactcaat          2550

aatgctgttc taactacagt gctcaataaa atgattaatg acaggaaaaa          2600

aaaaaaaaaa aaaaaaaaaa aaaaaaaaaa aaaaaaaaaa aaaaaaaaaa          2650

aaaaaaaaaa  aaaaaaaa                                            2668
```

<210> SEQ ID NO 190
<211> LENGTH: 716
<212> TYPE: PRT
<213> ORGANISM: Homo sapiens

<400> SEQUENCE: 190

```
Met Ala Arg Met Ser Phe Val Ile Ala Ala Cys Gln Leu Val Leu
  1               5                  10                  15

Gly Leu Leu Met Thr Ser Leu Thr Glu Ser Ser Ile Gln Asn Ser
                 20                  25                  30

Glu Cys Pro Gln Leu Cys Val Cys Glu Ile Arg Pro Trp Phe Thr
                 35                  40                  45

Pro Gln Ser Thr Tyr Arg Glu Ala Thr Thr Val Asp Cys Asn Asp
                 50                  55                  60

Leu Arg Leu Thr Arg Ile Pro Ser Asn Leu Ser Ser Asp Thr Gln
                 65                  70                  75

Val Leu Leu Leu Gln Ser Asn Asn Ile Ala Lys Thr Val Asp Glu
                 80                  85                  90

Leu Gln Gln Leu Phe Asn Leu Thr Glu Leu Asp Phe Ser Gln Asn
                 95                 100                 105

Asn Phe Thr Asn Ile Lys Glu Val Gly Leu Ala Asn Leu Thr Gln
                110                 115                 120

Leu Thr Thr Leu His Leu Glu Glu Asn Gln Ile Thr Glu Met Thr
                125                 130                 135

Asp Tyr Cys Leu Gln Asp Leu Ser Asn Leu Gln Glu Leu Tyr Ile
```

-continued

```
                140                 145                 150

Asn His Asn Gln Ile Ser Thr Ile Ser Ala His Ala Phe Ala Gly
                155                 160                 165

Leu Lys Asn Leu Leu Arg Leu His Leu Asn Ser Asn Lys Leu Lys
                170                 175                 180

Val Ile Asp Ser Arg Trp Phe Asp Ser Thr Pro Asn Leu Glu Ile
                185                 190                 195

Leu Met Ile Gly Glu Asn Pro Val Ile Gly Ile Leu Asp Met Asn
                200                 205                 210

Phe Lys Pro Leu Ala Asn Leu Arg Ser Leu Val Leu Ala Gly Met
                215                 220                 225

Tyr Leu Thr Asp Ile Pro Gly Asn Ala Leu Val Gly Leu Asp Ser
                230                 235                 240

Leu Glu Ser Leu Ser Phe Tyr Asp Asn Lys Leu Val Lys Val Pro
                245                 250                 255

Gln Leu Ala Leu Gln Lys Val Pro Asn Leu Lys Phe Leu Asp Leu
                260                 265                 270

Asn Lys Asn Pro Ile His Lys Ile Gln Glu Gly Asp Phe Lys Asn
                275                 280                 285

Met Leu Arg Leu Lys Glu Leu Gly Ile Asn Asn Met Gly Glu Leu
                290                 295                 300

Val Ser Val Asp Arg Tyr Ala Leu Asp Asn Leu Pro Glu Leu Thr
                305                 310                 315

Lys Leu Glu Ala Thr Asn Asn Pro Lys Leu Ser Tyr Ile His Arg
                320                 325                 330

Leu Ala Phe Arg Ser Val Pro Ala Leu Glu Ser Leu Met Leu Asn
                335                 340                 345

Asn Asn Ala Leu Asn Ala Ile Tyr Gln Lys Thr Val Glu Ser Leu
                350                 355                 360

Pro Asn Leu Arg Glu Ile Ser Ile His Ser Asn Pro Leu Arg Cys
                365                 370                 375

Asp Cys Val Ile His Trp Ile Asn Ser Asn Lys Thr Asn Ile Arg
                380                 385                 390

Phe Met Glu Pro Leu Ser Met Phe Cys Ala Met Pro Pro Glu Tyr
                395                 400                 405

Lys Gly His Gln Val Lys Glu Val Leu Ile Gln Asp Ser Ser Glu
                410                 415                 420

Gln Cys Leu Pro Met Ile Ser His Asp Ser Phe Pro Asn Arg Leu
                425                 430                 435

Asn Val Asp Ile Gly Thr Thr Val Phe Leu Asp Cys Arg Ala Met
                440                 445                 450

Ala Glu Pro Glu Pro Glu Ile Tyr Trp Val Thr Pro Ile Gly Asn
                455                 460                 465

Lys Ile Thr Val Glu Thr Leu Ser Asp Lys Tyr Lys Leu Ser Ser
                470                 475                 480

Glu Gly Thr Leu Glu Ile Ser Asn Ile Gln Ile Glu Asp Ser Gly
                485                 490                 495

Arg Tyr Thr Cys Val Ala Gln Asn Val Gln Gly Ala Asp Thr Arg
                500                 505                 510

Val Ala Thr Ile Lys Val Asn Gly Thr Leu Leu Asp Gly Thr Gln
                515                 520                 525

Val Leu Lys Ile Tyr Val Lys Gln Thr Glu Ser His Ser Ile Leu
                530                 535                 540
```

-continued

```
Val Ser Trp Lys Val Asn Ser Asn Val Met Thr Ser Asn Leu Lys
                545                 550                 555

Trp Ser Ser Ala Thr Met Lys Ile Asp Asn Pro His Ile Thr Tyr
                560                 565                 570

Thr Ala Arg Val Pro Val Asp Val His Glu Tyr Asn Leu Thr His
                575                 580                 585

Leu Gln Pro Ser Thr Asp Tyr Glu Val Cys Leu Thr Val Ser Asn
                590                 595                 600

Ile His Gln Gln Thr Gln Lys Ser Cys Val Asn Val Thr Thr Lys
                605                 610                 615

Asn Ala Ala Phe Ala Val Asp Ile Ser Asp Gln Glu Thr Ser Thr
                620                 625                 630

Ala Leu Ala Ala Val Met Gly Ser Met Phe Ala Val Ile Ser Leu
                635                 640                 645

Ala Ser Ile Ala Val Tyr Phe Ala Lys Arg Phe Lys Arg Lys Asn
                650                 655                 660

Tyr His His Ser Leu Lys Lys Tyr Met Gln Lys Thr Ser Ser Ile
                665                 670                 675

Pro Leu Asn Glu Leu Tyr Pro Pro Leu Ile Asn Leu Trp Glu Gly
                680                 685                 690

Asp Ser Glu Lys Asp Lys Asp Gly Ser Ala Asp Thr Lys Pro Thr
                695                 700                 705

Gln Val Asp Thr Ser Arg Ser Tyr Tyr Met Trp
                710                 715


<210> SEQ ID NO 191
<211> LENGTH: 957
<212> TYPE: DNA
<213> ORGANISM: Homo sapiens

<400> SEQUENCE: 191

gggagagagg ataaatagca gcgtggcttc cctggctcct ctctgcatcc          50

ttcccgacct tcccagcaat atgcatcttg cacgtctggt cggctcctgc         100

tccctccttc tgctactggg ggccctgtct ggatgggcgg ccagcgatga         150

ccccattgag aaggtcattg aagggatcaa ccgagggctg agcaatgcag         200

agagagaggt gggcaaggcc ctggatggca tcaacagtgg aatcacgcat         250

gccggaaggg aagtggagaa ggttttcaac ggacttagca acatggggag         300

ccacaccggc aaggagttgg acaaaggcgt ccaggggctc aaccacggca         350

tggacaaggt tgcccatgag atcaaccatg gtattggaca agcaggaaag         400

gaagcagaga agcttggcca tggggtcaac aacgctgctg gacaggccgg         450

gaaggaagca gacaaagcgg tccaagggtt ccacactggg gtccaccagg         500

ctgggaagga agcagagaaa cttggccaag gggtcaacca tgctgctgac         550

caggctggaa aggaagtgga gaagcttggc caaggtgccc accatgctgc         600

tggccaggcc gggaaggagc tgcagaatgc tcataatggg gtcaaccaag         650

ccagcaagga ggccaaccag ctgctgaatg gcaaccatca aagcggatct         700

tccagccatc aaggaggggc cacaaccacg ccgttagcct ctggggcctc         750

agtcaacacg cctttcatca accttcccgc cctgtggagg agcgtcgcca         800

acatcatgcc ctaaactggc atccggcctt gctgggagaa taatgtcgcc         850
```

-continued

```
gttgtcacat cagctgacat gacctggagg ggttgggggt gggggacagg              900

tttctgaaat ccctgaaggg ggttgtactg ggatttgtga ataaacttga              950

tacacca                                                             957


<210> SEQ ID NO 192
<211> LENGTH: 247
<212> TYPE: PRT
<213> ORGANISM: Homo sapiens

<400> SEQUENCE: 192

Met His Leu Ala Arg Leu Val Gly Ser Cys Ser Leu Leu Leu Leu
  1               5                  10                  15

Leu Gly Ala Leu Ser Gly Trp Ala Ala Ser Asp Asp Pro Ile Glu
                 20                  25                  30

Lys Val Ile Glu Gly Ile Asn Arg Gly Leu Ser Asn Ala Glu Arg
                 35                  40                  45

Glu Val Gly Lys Ala Leu Asp Gly Ile Asn Ser Gly Ile Thr His
                 50                  55                  60

Ala Gly Arg Glu Val Glu Lys Val Phe Asn Gly Leu Ser Asn Met
                 65                  70                  75

Gly Ser His Thr Gly Lys Glu Leu Asp Lys Gly Val Gln Gly Leu
                 80                  85                  90

Asn His Gly Met Asp Lys Val Ala His Glu Ile Asn His Gly Ile
                 95                 100                 105

Gly Gln Ala Gly Lys Glu Ala Glu Lys Leu Gly His Gly Val Asn
                110                 115                 120

Asn Ala Ala Gly Gln Ala Gly Lys Glu Ala Asp Lys Ala Val Gln
                125                 130                 135

Gly Phe His Thr Gly Val His Gln Ala Gly Lys Glu Ala Glu Lys
                140                 145                 150

Leu Gly Gln Gly Val Asn His Ala Ala Asp Gln Ala Gly Lys Glu
                155                 160                 165

Val Glu Lys Leu Gly Gln Gly Ala His His Ala Ala Gly Gln Ala
                170                 175                 180

Gly Lys Glu Leu Gln Asn Ala His Asn Gly Val Asn Gln Ala Ser
                185                 190                 195

Lys Glu Ala Asn Gln Leu Leu Asn Gly Asn His Gln Ser Gly Ser
                200                 205                 210

Ser Ser His Gln Gly Gly Ala Thr Thr Thr Pro Leu Ala Ser Gly
                215                 220                 225

Ala Ser Val Asn Thr Pro Phe Ile Asn Leu Pro Ala Leu Trp Arg
                230                 235                 240

Ser Val Ala Asn Ile Met Pro
                245


<210> SEQ ID NO 193
<211> LENGTH: 904
<212> TYPE: DNA
<213> ORGANISM: Homo sapiens

<400> SEQUENCE: 193

gaagtagagg tgttgtgctg agcggcgctc ggcgaactgt gtggaccgtc               50

tgctgggact ccggccctgc gtccgctcag ccccgtggcc ccgcgcacct              100

actgccatgg agacgcggcc tcgtctcggg gccacctgtt tgctgggctt              150
```

-continued

```
cagtttcctg ctcctcgtca tctcttctga tggacataat gggcttggaa          200

agggttttgg agatcatatt cattggagga cactggaaga tgggaagaaa          250

gaagcagctg ccagtggact gcccctgatg gtgattattc ataaatcctg          300

gtgtggagct tgcaaagctc taaagcccaa atttgcagaa tctacggaaa          350

tttcagaact ctcccataat tttgttatgg taaatcttga ggatgaagag          400

gaacccaaag atgaagattt cagccctgac gggggttata ttccacgaat          450

cctttttctg gatcccagtg gcaaggtgca tcctgaaatc atcaatgaga          500

atggaaaccc cagctacaag tatttttatg tcagtgccga gcaagttgtt          550

caggggatga aggaagctca ggaaaggctg acgggtgatg ccttcagaaa          600

gaaacatctt gaagatgaat tgtaacatga atgtgcccct tctttcatca          650

gagttagtgt tctggaagga aagcagcagg gaagggaata ttgaggaatc          700

atctagaaca attaagccga ccaggaaacc tcattcctac ctacactgga          750

aggagcgctc tcactgtgga agagttctgc taacagaagc tggtctgcat          800

gtttgtggat ccagcggaga gtggcagact ttcttctcct tttccctctc          850

acctaaatgt caacttgtca ttgaatgtaa agaatgaaac cttctgacac          900

aaaa                                                            904
```

<210> SEQ ID NO 194
<211> LENGTH: 172
<212> TYPE: PRT
<213> ORGANISM: Homo sapiens

<400> SEQUENCE: 194

```
Met Glu Thr Arg Pro Arg Leu Gly Ala Thr Cys Leu Leu Gly Phe
  1               5                  10                  15

Ser Phe Leu Leu Leu Val Ile Ser Ser Asp Gly His Asn Gly Leu
                 20                  25                  30

Gly Lys Gly Phe Gly Asp His Ile His Trp Arg Thr Leu Glu Asp
                 35                  40                  45

Gly Lys Lys Glu Ala Ala Ala Ser Gly Leu Pro Leu Met Val Ile
                 50                  55                  60

Ile His Lys Ser Trp Cys Gly Ala Cys Lys Ala Leu Lys Pro Lys
                 65                  70                  75

Phe Ala Glu Ser Thr Glu Ile Ser Glu Leu Ser His Asn Phe Val
                 80                  85                  90

Met Val Asn Leu Glu Asp Glu Glu Glu Pro Lys Asp Glu Asp Phe
                 95                 100                 105

Ser Pro Asp Gly Gly Tyr Ile Pro Arg Ile Leu Phe Leu Asp Pro
                110                 115                 120

Ser Gly Lys Val His Pro Glu Ile Ile Asn Glu Asn Gly Asn Pro
                125                 130                 135

Ser Tyr Lys Tyr Phe Tyr Val Ser Ala Glu Gln Val Val Gln Gly
                140                 145                 150

Met Lys Glu Ala Gln Glu Arg Leu Thr Gly Asp Ala Phe Arg Lys
                155                 160                 165

Lys His Leu Glu Asp Glu Leu
                170
```

<210> SEQ ID NO 195
<211> LENGTH: 1630

-continued

<212> TYPE: DNA
<213> ORGANISM: Homo sapiens

<400> SEQUENCE: 195 cggctcgagt gcagctgtgg ggagatttca gtgcattgcc tcccctgggt 50 gctcttcatc ttggatttga aagttgagag cagcatgttt tgcccactga 100 aactcatcct gctgccagtg ttactggatt attccttggg cctgaatgac 150 ttgaatgttt ccccgcctga gctaacagtc catgtgggtg attcagctct 200 gatgggatgt gttttccaga gcacagaaga caaatgtata ttcaagatag 250 actggactct gtcaccagga gagcacgcca aggacgaata tgtgctatac 300 tattactcca atctcagtgt gcctattggg cgcttccaga accgcgtaca 350 cttgatgggg gacatcttat gcaatgatgg ctctctcctg ctccaagatg 400 tgcaagaggc tgaccaggga acctatatct gtgaaatccg cctcaaaggg 450 gagagccagg tgttcaagaa ggcggtggta ctgcatgtgc ttccagagga 500 gcccaaagag ctcatggtcc atgtgggtgg attgattcag atgggatgtg 550 ttttccagag cacagaagtg aaacacgtga ccaaggtaga atggatattt 600 tcaggacggc gcgcaaagga ggagattgta tttcgttact accacaaact 650 caggatgtct gtggagtact cccagagctg gggccacttc cagaatcgtg 700 tgaacctggt gggggacatt ttccgcaatg acggttccat catgcttcaa 750 ggagtgaggg agtcagatgg aggaaactac acctgcagta tccacctagg 800 gaacctggtg ttcaagaaaa ccattgtgct gcatgtcagc ccggaagagc 850 ctcgaacact ggtgaccccg gcagccctga ggcctctggt cttgggtggt 900 aatcagttgg tgatcattgt gggaattgtc tgtgccacaa tcctgctgct 950 ccctgttctg atattgatcg tgaagaagac ctgtggaaat aagagttcag 1000 tgaattctac agtcttggtg aagaacacga agaagactaa tccagagata 1050 aaagaaaaac cctgccattt tgaaagatgt gaaggggaga aacacattta 1100 ctccccaata attgtacggg aggtgatcga ggaagaagaa ccaagtgaaa 1150 aatcagaggc cacctacatg accatgcacc cagtttggcc ttctctgagg 1200 tcagatcgga acaactcact tgaaaaaaag tcaggtgggg gaatgccaaa 1250 aacacagcaa gccttttgag aagaatggag agtcccttca tctcagcagc 1300 ggtggagact ctctcctgtg tgtgtcctgg gccactctac cagtgatttc 1350 agactcccgc tctcccagct gtcctcctgt ctcattgttt ggtcaataca 1400 ctgaagatgg agaatttgga gcctggcaga gagactggac agctctggag 1450 gaacaggcct gctgagggga ggggagcatg gacttggcct ctggagtggg 1500 acactggccc tgggaaccag gctgagctga gtggcctcaa acccccccgtt 1550 ggatcagacc ctcctgtggg cagggttctt agtggatgag ttactgggaa 1600 gaatcagaga taaaaaccaa cccaaatcaa 1630

<210> SEQ ID NO 196
<211> LENGTH: 394
<212> TYPE: PRT
<213> ORGANISM: Homo sapiens

<400> SEQUENCE: 196

-continued

```
Met Phe Cys Pro Leu Lys Leu Ile Leu Leu Pro Val Leu Leu Asp
  1               5                  10                  15

Tyr Ser Leu Gly Leu Asn Asp Leu Asn Val Ser Pro Pro Glu Leu
                 20                  25                  30

Thr Val His Val Gly Asp Ser Ala Leu Met Gly Cys Val Phe Gln
                 35                  40                  45

Ser Thr Glu Asp Lys Cys Ile Phe Lys Ile Asp Trp Thr Leu Ser
                 50                  55                  60

Pro Gly Glu His Ala Lys Asp Glu Tyr Val Leu Tyr Tyr Tyr Ser
                 65                  70                  75

Asn Leu Ser Val Pro Ile Gly Arg Phe Gln Asn Arg Val His Leu
                 80                  85                  90

Met Gly Asp Ile Leu Cys Asn Asp Gly Ser Leu Leu Leu Gln Asp
                 95                 100                 105

Val Gln Glu Ala Asp Gln Gly Thr Tyr Ile Cys Glu Ile Arg Leu
                110                 115                 120

Lys Gly Glu Ser Gln Val Phe Lys Lys Ala Val Val Leu His Val
                125                 130                 135

Leu Pro Glu Glu Pro Lys Glu Leu Met Val His Val Gly Gly Leu
                140                 145                 150

Ile Gln Met Gly Cys Val Phe Gln Ser Thr Glu Val Lys His Val
                155                 160                 165

Thr Lys Val Glu Trp Ile Phe Ser Gly Arg Arg Ala Lys Glu Glu
                170                 175                 180

Ile Val Phe Arg Tyr Tyr His Lys Leu Arg Met Ser Val Glu Tyr
                185                 190                 195

Ser Gln Ser Trp Gly His Phe Gln Asn Arg Val Asn Leu Val Gly
                200                 205                 210

Asp Ile Phe Arg Asn Asp Gly Ser Ile Met Leu Gln Gly Val Arg
                215                 220                 225

Glu Ser Asp Gly Gly Asn Tyr Thr Cys Ser Ile His Leu Gly Asn
                230                 235                 240

Leu Val Phe Lys Lys Thr Ile Val Leu His Val Ser Pro Glu Glu
                245                 250                 255

Pro Arg Thr Leu Val Thr Pro Ala Ala Leu Arg Pro Leu Val Leu
                260                 265                 270

Gly Gly Asn Gln Leu Val Ile Ile Val Gly Ile Val Cys Ala Thr
                275                 280                 285

Ile Leu Leu Leu Pro Val Leu Ile Leu Ile Val Lys Lys Thr Cys
                290                 295                 300

Gly Asn Lys Ser Ser Val Asn Ser Thr Val Leu Val Lys Asn Thr
                305                 310                 315

Lys Lys Thr Asn Pro Glu Ile Lys Glu Lys Pro Cys His Phe Glu
                320                 325                 330

Arg Cys Glu Gly Glu Lys His Ile Tyr Ser Pro Ile Ile Val Arg
                335                 340                 345

Glu Val Ile Glu Glu Glu Glu Pro Ser Glu Lys Ser Glu Ala Thr
                350                 355                 360

Tyr Met Thr Met His Pro Val Trp Pro Ser Leu Arg Ser Asp Arg
                365                 370                 375

Asn Asn Ser Leu Glu Lys Lys Ser Gly Gly Gly Met Pro Lys Thr
                380                 385                 390

Gln Gln Ala Phe
```

<210> SEQ ID NO 197
<211> LENGTH: 783
<212> TYPE: DNA
<213> ORGANISM: Homo sapiens

<400> SEQUENCE: 197

```
cgccatggcc gggctatccc gcgggtccgc gcgcgcactg ctcgccgccc      50

tgctggcgtc gacgctgttg gcgctgctcg tgtcgcccgc gcggggtcgc     100

ggcggccggg accacgggga ctgggacgag gcctcccggc tgccgccgct     150

accaccccgc gaggacgcgg cgcgcgtggc ccgcttcgtg acgcacgtct     200

ccgactgggg cgctctggcc accatctcca cgctggaggc ggtgcgcggc     250

cggcccttcg ccgacgtcct ctcgctcagc gacgggcccc cgggcgcggg     300

cagcggcgtg ccctatttct acctgagccc gctgcagctc tccgtgagca     350

acctgcagga gaatccatat gctacactga ccatgacttt ggcacagacc     400

aacttctgca agaaacatgg atttgatcca caaagtcccc tttgtgttca     450

cataatgctg tcaggaactg tgaccaaggt gaatgaaaca gaaatggata     500

ttgcaaagca ttcgttattc attcgacacc ctgagatgaa aacctggcct     550

tccagccata attggttctt tgctaagttg aatataacca atatctgggt     600

cctggactac tttggtggac caaaaatcgt gacaccagaa gaatattata     650

atgtcacagt tcagtgaagc agactgtggt gaatttagca acacttatga     700

agtttcttaa agtggctcat acacacttaa aaggcttaat gtttctctgg     750

aaagcgtccc agaatattag ccagttttct  gtc                      783
```

<210> SEQ ID NO 198
<211> LENGTH: 220
<212> TYPE: PRT
<213> ORGANISM: Homo sapiens

<400> SEQUENCE: 198

```
Met Ala Gly Leu Ser Arg Gly Ser Ala Arg Ala Leu Leu Ala Ala
  1               5                  10                  15

Leu Leu Ala Ser Thr Leu Leu Ala Leu Leu Val Ser Pro Ala Arg
                 20                  25                  30

Gly Arg Gly Gly Arg Asp His Gly Asp Trp Asp Glu Ala Ser Arg
                 35                  40                  45

Leu Pro Pro Leu Pro Pro Arg Glu Asp Ala Ala Arg Val Ala Arg
                 50                  55                  60

Phe Val Thr His Val Ser Asp Trp Gly Ala Leu Ala Thr Ile Ser
                 65                  70                  75

Thr Leu Glu Ala Val Arg Gly Arg Pro Phe Ala Asp Val Leu Ser
                 80                  85                  90

Leu Ser Asp Gly Pro Pro Gly Ala Gly Ser Gly Val Pro Tyr Phe
                 95                 100                 105

Tyr Leu Ser Pro Leu Gln Leu Ser Val Ser Asn Leu Gln Glu Asn
                110                 115                 120

Pro Tyr Ala Thr Leu Thr Met Thr Leu Ala Gln Thr Asn Phe Cys
                125                 130                 135

Lys Lys His Gly Phe Asp Pro Gln Ser Pro Leu Cys Val His Ile
                140                 145                 150
```

-continued

```
Met Leu Ser Gly Thr Val Thr Lys Val Asn Glu Thr Glu Met Asp
                155                 160                 165

Ile Ala Lys His Ser Leu Phe Ile Arg His Pro Glu Met Lys Thr
                170                 175                 180

Trp Pro Ser Ser His Asn Trp Phe Phe Ala Lys Leu Asn Ile Thr
                185                 190                 195

Asn Ile Trp Val Leu Asp Tyr Phe Gly Gly Pro Lys Ile Val Thr
                200                 205                 210

Pro Glu Glu Tyr Tyr Asn Val Thr Val Gln
                215                 220


<210> SEQ ID NO 199
<211> LENGTH: 1315
<212> TYPE: DNA
<213> ORGANISM: Homo sapiens

<400> SEQUENCE: 199

tcgccatggc ctctgccgga atgcagatcc tgggagtcgt cctgacactg                50

ctgggctggg tgaatggcct ggtctcctgt gccctgccca tgtggaaggt               100

gaccgctttc atcggcaaca gcatcgtggt ggcccaggtg gtgtgggagg               150

gcctgtggat gtcctgcgtg gtgcagagca ccggccagat gcagtgcaag               200

gtgtacgact cactgctggc gctgccacag gacctgcagg ctgcacgtgc               250

cctctgtgtc atcgccctcc ttgtggccct gttcggcttg ctggtctacc               300

ttgctggggc caagtgtacc acctgtgtgg aggagaagga ttccaaggcc               350

cgcctggtgc tcacctctgg gattgtcttt gtcatctcag gggtcctgac               400

gctaatcccc gtgtgctgga cggcgcatgc catcatccgg gacttctata               450

acccccctggt ggctgaggcc caaaagcggg agctgggggc ctccctctac              500

ttgggctggg cggcctcagg ccttttgttg ctgggtgggg ggttgctgtg               550

ctgcacttgc ccctcggggg ggtcccaggg ccccagccat tacatggccc               600

gctactcaac atctgcccct gccatctctc gggggccctc tgagtaccct               650

accaagaatt acgtctgacg tggaggggaa tgggggctcc gctggcgcta               700

gagccatcca gaagtggcag tgcccaacag ctttgggatg ggttcgtacc               750

ttttgtttct gcctcctgct atttttcttt tgactgagga tatttaaaat               800

tcatttgaaa actgagccaa ggtgttgact cagactctca cttaggctct               850

gctgtttctc acccttggat gatggagcca aagaggggat gctttgagat               900

tctggatctt gacatgccca tcttagaagc cagtcaagct atggaactaa               950

tgcggaggct gcttgctgtg ctggctttgc aacaagacag actgtcccca              1000

agagttcctg ctgctgctgg gggctgggct tccctagatg tcactggaca              1050

gctgcccccc atcctactca ggtctctgga gctcctctct tcacccctgg              1100

aaaaacaaat catctgttaa caaaggactg cccacctccg gaacttctga              1150

cctctgtttc ctccgtcctg ataagacgtc cacccccag ggccaggtcc               1200

cagctatgta gacccccgcc cccacctcca acactgcacc cttctgccct              1250

gcccccctcg tctcaccccc tttacactca catttttatc aaataaagca              1300

tgttttgtta  gtgca                                                   1315

<210> SEQ ID NO 200
```

-continued

<211> LENGTH: 220
<212> TYPE: PRT
<213> ORGANISM: Homo sapiens

<400> SEQUENCE: 200

```
Met Ala Ser Ala Gly Met Gln Ile Leu Gly Val Val Leu Thr Leu
  1               5                  10                  15

Leu Gly Trp Val Asn Gly Leu Val Ser Cys Ala Leu Pro Met Trp
                 20                  25                  30

Lys Val Thr Ala Phe Ile Gly Asn Ser Ile Val Val Ala Gln Val
                 35                  40                  45

Val Trp Glu Gly Leu Trp Met Ser Cys Val Val Gln Ser Thr Gly
                 50                  55                  60

Gln Met Gln Cys Lys Val Tyr Asp Ser Leu Leu Ala Leu Pro Gln
                 65                  70                  75

Asp Leu Gln Ala Ala Arg Ala Leu Cys Val Ile Ala Leu Leu Val
                 80                  85                  90

Ala Leu Phe Gly Leu Leu Val Tyr Leu Ala Gly Ala Lys Cys Thr
                 95                 100                 105

Thr Cys Val Glu Glu Lys Asp Ser Lys Ala Arg Leu Val Leu Thr
                110                 115                 120

Ser Gly Ile Val Phe Val Ile Ser Gly Val Leu Thr Leu Ile Pro
                125                 130                 135

Val Cys Trp Thr Ala His Ala Ile Ile Arg Asp Phe Tyr Asn Pro
                140                 145                 150

Leu Val Ala Glu Ala Gln Lys Arg Glu Leu Gly Ala Ser Leu Tyr
                155                 160                 165

Leu Gly Trp Ala Ala Ser Gly Leu Leu Leu Leu Gly Gly Gly Leu
                170                 175                 180

Leu Cys Cys Thr Cys Pro Ser Gly Gly Ser Gln Gly Pro Ser His
                185                 190                 195

Tyr Met Ala Arg Tyr Ser Thr Ser Ala Pro Ala Ile Ser Arg Gly
                200                 205                 210

Pro Ser Glu Tyr Pro Thr Lys Asn Tyr Val
                215                 220
```

<210> SEQ ID NO 201
<211> LENGTH: 535
<212> TYPE: DNA
<213> ORGANISM: Homo sapiens

<400> SEQUENCE: 201

```
agtgacaatc tcagagcagc ttctacacca cagccatttc cagcatgaag                50

atcactgggg gtctccttct gctctgtaca gtggtctatt tctgtagcag               100

ctcagaagct gctagtctgt ctccaaaaaa agtggactgc agcatttaca               150

agaagtatcc agtggtggcc atcccctgcc ccatcacata cctaccagtt               200

tgtggttctg actacatcac ctatgggaat gaatgtcact tgtgtaccga               250

gagcttgaaa agtaatggaa gagttcagtt tcttcacgat ggaagttgct               300

aaattctcca tggacataga gagaaaggaa tgatattctc atcatcatct               350

tcatcatccc aggctctgac tgagtttctt tcagttttac tgatgttctg               400

ggtgggggac agagccagat tcagagtaat cttgactgaa tggagaaagt               450

ttctgtgcta cccctacaaa cccatgcctc actgacagac cagcattttt               500
```

-continued

```
tttttaacac gtcaataaaa aaataatctc  ccaga                              535


<210> SEQ ID NO 202
<211> LENGTH: 85
<212> TYPE: PRT
<213> ORGANISM: Homo sapiens

<400> SEQUENCE: 202

Met Lys Ile Thr Gly Gly Leu Leu Leu Leu Cys Thr Val Val Tyr
  1               5                  10                  15

Phe Cys Ser Ser Ser Glu Ala Ala Ser Leu Ser Pro Lys Lys Val
                 20                  25                  30

Asp Cys Ser Ile Tyr Lys Lys Tyr Pro Val Val Ala Ile Pro Cys
                 35                  40                  45

Pro Ile Thr Tyr Leu Pro Val Cys Gly Ser Asp Tyr Ile Thr Tyr
                 50                  55                  60

Gly Asn Glu Cys His Leu Cys Thr Glu Ser Leu Lys Ser Asn Gly
                 65                  70                  75

Arg Val Gln Phe Leu His Asp Gly Ser Cys
                 80                  85


<210> SEQ ID NO 203
<211> LENGTH: 2387
<212> TYPE: DNA
<213> ORGANISM: Homo sapiens

<400> SEQUENCE: 203

cgacgatgct acgcgcgccc ggctgcctcc tccggacctc cgtagcgcct               50

gccgcggccc tggctgcggc gctgctctcg tcgcttgcgc gctgctctct              100

tctagagccg agggacccgg tggcctcgtc gctcagcccc tatttcggca              150

ccaagactcg ctacgaggat gtcaaccccg tgctattgtc gggccccgag              200

gctccgtggc gggaccctga gctgctggag gggacctgca ccccggtgca              250

gctggtcgcc ctcattcgcc acggcacccg ctaccccacg gtcaaacaga              300

tccgcaagct gaggcagctg cacgggttgc tgcaggcccg cgggtccagg              350

gatggcgggg ctagtagtac cggcagccgc gacctgggtg cagcgctggc              400

cgactggcct ttgtggtacg cggactggat ggacgggcag ctagtagaga              450

agggacggca ggatatgcga cagctggcgc tgcgtctggc ctcgctcttc              500

ccggcccttt tcagccgtga gaactacggc cgcctgcggc tcatcaccag              550

ttccaagcac cgctgcatgg atagcagcgc cgccttcctg caggggctgt              600

ggcagcacta ccaccctggc ttgccgccgc cggacgtcgc agatatggag              650

tttggacctc caacagttaa tgataaacta atgagatttt ttgatcactg              700

tgagaagttt ttaactgaag tagaaaaaaa tgctacagct ctttatcacg              750

tggaagcctt caaaactgga ccagaaatgc agaacatttt aaaaaaagtt              800

gcagctactt tgcaagtgcc agtaaatgat ttaaatgcag atttaattca              850

agtagccttt ttcacctgtt catttgacct ggcaattaaa ggtgttaaat              900

ctccttggtg tgatgttttt gacatagatg atgcaaaggt attagaatat              950

ttaaatgatc tgaaacaata ttggaaaaga ggatatgggt atactattaa             1000

cagtcgatcc agctgcacct tgtttcagga tatctttcag cacttggaca             1050

aagcagttga acagaaacaa aggtctcagc caatttcttc tccagtcatc             1100
```

-continued

```
ctccagtttg gtcatgcaga gactcttctt ccactgcttt ctctcatggg          1150

ctacttcaaa gacaaggaac ccctaacagc gtacaattac aaaaaacaaa          1200

tgcatcggaa gttccgaagt ggtctcattg taccttatgc ctcgaacctg          1250

atatttgtgc tttaccactg tgaaaatgct aagactccta aagaacaatt          1300

ccgagtgcag atgttattaa atgaaaaggt gttacctttg gcttactcac          1350

aagaaactgt ttcattttat gaagatctga agaaccacta caaggacatc          1400

cttcagagtt gtcaaaccag tgaagaatgt gaattagcaa gggctaacag          1450

tacatctgat gaactatgag taactgaaga acatttttaa ttctttagga          1500

atctgcaatg agtgattaca tgcttgtaat aggtaggcaa ttccttgatt          1550

acaggaagct tttatattac ttgagtattt ctgtcttttc acagaaaaac          1600

attgggtttc tctctgggtt tggacatgaa atgtaagaaa agatttttca          1650

ctggagcagc tctcttaagg agaaacaaat ctatttagag aaacagctgg          1700

ccctgcaaat gtttacagaa atgaaattct tcctacttat ataagaaatc          1750

tcacactgag atagaattgt gatttcataa taacacttga aaagtgctgg          1800

agtaacaaaa tatctcagtt ggaccatcct taacttgatt gaactgtcta          1850

ggaactttac agattgttct gcagttctct cttcttttcc tcaggtagga          1900

cagctctagc attttcttaa tcaggaatat tgtggtaagc tgggagtatc          1950

actctggaag aaagtaacat ctccagatga gaatttgaaa caagaaacag          2000

agtgttgtaa aaggacacct tcactgaagc aagtcggaaa gtacaatgaa          2050

aataaatatt tttggtattt atttatgaaa tatttgaaca ttttttcaat          2100

aattcctttt tacttctagg aagtctcaaa agaccatctt aaattattat          2150

atgtttggac aattagcaac aagtcagata gttagaatcg aagtttttca          2200

aatccattgc ttagctaact ttttcattct gtcacttggc ttcgattttt          2250

atattttcct attatatgaa atgtatcttt tggttgtttg atttttcttt          2300

ctttctttgt aaatagttct gagttctgtc aaatgccgtg aaagtatttg          2350

ctataataaa gaaaattctt gtgactttaa  aaaaaaa                       2387
```

<210> SEQ ID NO 204
<211> LENGTH: 487
<212> TYPE: PRT
<213> ORGANISM: Homo sapiens

<400> SEQUENCE: 204

```
Met Leu Arg Ala Pro Gly Cys Leu Leu Arg Thr Ser Val Ala Pro
  1               5                  10                  15

Ala Ala Ala Leu Ala Ala Ala Leu Leu Ser Ser Leu Ala Arg Cys
                 20                  25                  30

Ser Leu Leu Glu Pro Arg Asp Pro Val Ala Ser Ser Leu Ser Pro
                 35                  40                  45

Tyr Phe Gly Thr Lys Thr Arg Tyr Glu Asp Val Asn Pro Val Leu
                 50                  55                  60

Leu Ser Gly Pro Glu Ala Pro Trp Arg Asp Pro Glu Leu Leu Glu
                 65                  70                  75

Gly Thr Cys Thr Pro Val Gln Leu Val Ala Leu Ile Arg His Gly
                 80                  85                  90
```

-continued

```
Thr Arg Tyr Pro Thr Val Lys Gln Ile Arg Lys Leu Arg Gln Leu
                 95                 100                 105

His Gly Leu Leu Gln Ala Arg Gly Ser Arg Asp Gly Gly Ala Ser
                110                 115                 120

Ser Thr Gly Ser Arg Asp Leu Gly Ala Ala Leu Ala Asp Trp Pro
                125                 130                 135

Leu Trp Tyr Ala Asp Trp Met Asp Gly Gln Leu Val Glu Lys Gly
                140                 145                 150

Arg Gln Asp Met Arg Gln Leu Ala Leu Arg Leu Ala Ser Leu Phe
                155                 160                 165

Pro Ala Leu Phe Ser Arg Glu Asn Tyr Gly Arg Leu Arg Leu Ile
                170                 175                 180

Thr Ser Ser Lys His Arg Cys Met Asp Ser Ser Ala Ala Phe Leu
                185                 190                 195

Gln Gly Leu Trp Gln His Tyr His Pro Gly Leu Pro Pro Pro Asp
                200                 205                 210

Val Ala Asp Met Glu Phe Gly Pro Pro Thr Val Asn Asp Lys Leu
                215                 220                 225

Met Arg Phe Phe Asp His Cys Glu Lys Phe Leu Thr Glu Val Glu
                230                 235                 240

Lys Asn Ala Thr Ala Leu Tyr His Val Glu Ala Phe Lys Thr Gly
                245                 250                 255

Pro Glu Met Gln Asn Ile Leu Lys Lys Val Ala Ala Thr Leu Gln
                260                 265                 270

Val Pro Val Asn Asp Leu Asn Ala Asp Leu Ile Gln Val Ala Phe
                275                 280                 285

Phe Thr Cys Ser Phe Asp Leu Ala Ile Lys Gly Val Lys Ser Pro
                290                 295                 300

Trp Cys Asp Val Phe Asp Ile Asp Asp Ala Lys Val Leu Glu Tyr
                305                 310                 315

Leu Asn Asp Leu Lys Gln Tyr Trp Lys Arg Gly Tyr Gly Tyr Thr
                320                 325                 330

Ile Asn Ser Arg Ser Ser Cys Thr Leu Phe Gln Asp Ile Phe Gln
                335                 340                 345

His Leu Asp Lys Ala Val Glu Gln Lys Gln Arg Ser Gln Pro Ile
                350                 355                 360

Ser Ser Pro Val Ile Leu Gln Phe Gly His Ala Glu Thr Leu Leu
                365                 370                 375

Pro Leu Leu Ser Leu Met Gly Tyr Phe Lys Asp Lys Glu Pro Leu
                380                 385                 390

Thr Ala Tyr Asn Tyr Lys Lys Gln Met His Arg Lys Phe Arg Ser
                395                 400                 405

Gly Leu Ile Val Pro Tyr Ala Ser Asn Leu Ile Phe Val Leu Tyr
                410                 415                 420

His Cys Glu Asn Ala Lys Thr Pro Lys Glu Gln Phe Arg Val Gln
                425                 430                 435

Met Leu Leu Asn Glu Lys Val Leu Pro Leu Ala Tyr Ser Gln Glu
                440                 445                 450

Thr Val Ser Phe Tyr Glu Asp Leu Lys Asn His Tyr Lys Asp Ile
                455                 460                 465

Leu Gln Ser Cys Gln Thr Ser Glu Glu Cys Glu Leu Ala Arg Ala
                470                 475                 480

Asn Ser Thr Ser Asp Glu Leu
```

485

<210> SEQ ID NO 205
<211> LENGTH: 1098
<212> TYPE: DNA
<213> ORGANISM: Homo sapiens

<400> SEQUENCE: 205 gcgacgcgcg gcggggcggc gagaggaaac gcggcgccgg gccgggcccg 50 gccctggaga tggtccccgg cgccgcgggc tggtgttgtc tcgtgctctg 100 gctccccgcg tgcgtcgcgg cccacggctt ccgtatccat gattatttgt 150 actttcaagt gctgagtcct ggggacattc gatacatctt cacagccaca 200 cctgccaagg actttggtgg tatctttcac acaaggtatg agcagattca 250 ccttgtcccc gctgaacctc cagaggcctg cggggaactc agcaacggtt 300 tcttcatcca ggaccagatt gctctggtgg agagggggg ctgctccttc 350 ctctccaaga ctcgggtggt ccaggagcac ggcgggcggg cggtgatcat 400 ctctgacaac gcagttgaca atgacagctt ctacgtggag atgatccagg 450 acagtaccca gcgcacagct gacatccccg ccctcttcct gctcggccga 500 gacggctaca tgatccgccg ctctctggaa cagcatgggc tgccatgggc 550 catcatttcc atcccagtca atgtcaccag catccccacc tttgagctgc 600 tgcaaccgcc ctggaccttc tggtagaaga gtttgtccca cattccagcc 650 ataagtgact ctgagctggg aaggggaaac ccaggaattt tgctacttgg 700 aatttggaga tagcatctgg ggacaagtgg agccaggtag aggaaaaggg 750 tttgggcgtt gctaggctga aagggaagcc acaccactgg ccttcccttc 800 cccagggccc ccaagggtgt ctcatgctac aagaagaggc aagagacagg 850 ccccagggct tctggctaga acccgaaaca aaaggagctg aaggcaggtg 900 gcctgagagc catctgtgac ctgtcacact cacctggctc cagcctcccc 950 tacccagggt ctctgcacag tgaccttcac agcagttgtt ggagtggttt 1000 aaagagctgg tgtttgggga ctcaataaac cctcactgac tttttagcaa 1050 taaagcttct catcagggtt gcaaaaaaaa aaaaaaaaaa aaaaaaaa 1098

<210> SEQ ID NO 206
<211> LENGTH: 188
<212> TYPE: PRT
<213> ORGANISM: Homo sapiens

<400> SEQUENCE: 206

Met Val Pro Gly Ala Ala Gly Trp Cys Cys Leu Val Leu Trp Leu
1 5 10 15

Pro Ala Cys Val Ala Ala His Gly Phe Arg Ile His Asp Tyr Leu
20 25 30

Tyr Phe Gln Val Leu Ser Pro Gly Asp Ile Arg Tyr Ile Phe Thr
35 40 45

Ala Thr Pro Ala Lys Asp Phe Gly Gly Ile Phe His Thr Arg Tyr
50 55 60

Glu Gln Ile His Leu Val Pro Ala Glu Pro Pro Glu Ala Cys Gly
65 70 75

Glu Leu Ser Asn Gly Phe Phe Ile Gln Asp Gln Ile Ala Leu Val
80 85 90

```
Glu Arg Gly Gly Cys Ser Phe Leu Ser Lys Thr Arg Val Val Gln
                95                  100                 105

Glu His Gly Gly Arg Ala Val Ile Ile Ser Asp Asn Ala Val Asp
            110                 115                 120

Asn Asp Ser Phe Tyr Val Glu Met Ile Gln Asp Ser Thr Gln Arg
            125                 130                 135

Thr Ala Asp Ile Pro Ala Leu Phe Leu Leu Gly Arg Asp Gly Tyr
            140                 145                 150

Met Ile Arg Arg Ser Leu Glu Gln His Gly Leu Pro Trp Ala Ile
            155                 160                 165

Ile Ser Ile Pro Val Asn Val Thr Ser Ile Pro Thr Phe Glu Leu
            170                 175                 180

Leu Gln Pro Pro Trp Thr Phe Trp
            185


<210> SEQ ID NO 207
<211> LENGTH: 764
<212> TYPE: DNA
<213> ORGANISM: Homo sapiens

<400> SEQUENCE: 207

ctcgcttctt ccttctggat gggggcccag ggggcccagg agagtataaa                50

ggcgatgtgg agggtgcccg gcacaaccag acgcccagtc acaggcgaga               100

gccctgggat gcaccggcca gaggccatgc tgctgctgct cacgcttgcc               150

ctcctggggg gccccacctg ggcagggaag atgtatggcc ctggaggagg               200

caagtatttc agcaccactg aagactacga ccatgaaatc acagggctgc               250

gggtgtctgt aggtcttctc ctggtgaaaa gtgtccaggt gaaacttgga               300

gactcctggg acgtgaaact gggagcctta ggtgggaata cccaggaagt               350

caccctgcag ccaggcgaat acatcacaaa agtctttgtc gccttccaag               400

ctttcctccg gggtatggtc atgtacacca gcaaggaccg ctatttctat               450

tttgggaagc ttgatggcca gatctcctct gcctacccca gccaagaggg               500

gcaggtgctg gtgggcatct atggccagta tcaactcctt ggcatcaaga               550

gcattggctt tgaatggaat tatccactag aggagccgac cactgagcca               600

ccagttaatc tcacatactc agcaaactca cccgtgggtc gctagggtgg               650

ggtatggggc catccgagct gaggccatct gtgtggtggt ggctgatggt               700

actggagtaa ctgagtcggg acgctgaatc tgaatccacc aataaataaa               750

gcttctgcag  aaaa                                                     764


<210> SEQ ID NO 208
<211> LENGTH: 178
<212> TYPE: PRT
<213> ORGANISM: Homo sapiens

<400> SEQUENCE: 208

Met His Arg Pro Glu Ala Met Leu Leu Leu Leu Thr Leu Ala Leu
  1               5                  10                  15

Leu Gly Gly Pro Thr Trp Ala Gly Lys Met Tyr Gly Pro Gly Gly
                20                  25                  30

Gly Lys Tyr Phe Ser Thr Thr Glu Asp Tyr Asp His Glu Ile Thr
                35                  40                  45
```

-continued

```
Gly Leu Arg Val Ser Val Gly Leu Leu Leu Val Lys Ser Val Gln
                50                  55                  60

Val Lys Leu Gly Asp Ser Trp Asp Val Lys Leu Gly Ala Leu Gly
                65                  70                  75

Gly Asn Thr Gln Glu Val Thr Leu Gln Pro Gly Glu Tyr Ile Thr
                80                  85                  90

Lys Val Phe Val Ala Phe Gln Ala Phe Leu Arg Gly Met Val Met
                95                 100                 105

Tyr Thr Ser Lys Asp Arg Tyr Phe Tyr Phe Gly Lys Leu Asp Gly
               110                 115                 120

Gln Ile Ser Ser Ala Tyr Pro Ser Gln Glu Gly Gln Val Leu Val
               125                 130                 135

Gly Ile Tyr Gly Gln Tyr Gln Leu Leu Gly Ile Lys Ser Ile Gly
               140                 145                 150

Phe Glu Trp Asn Tyr Pro Leu Glu Glu Pro Thr Thr Glu Pro Pro
               155                 160                 165

Val Asn Leu Thr Tyr Ser Ala Asn Ser Pro Val Gly Arg
               170                 175


<210> SEQ ID NO 209
<211> LENGTH: 3824
<212> TYPE: DNA
<213> ORGANISM: Homo sapiens

<400> SEQUENCE: 209

ggagaatgga gagagcagtg agagtggagt ccggggtcct ggtcggggtg                50

gtctgtctgc tcctggcatg ccctgccaca gccactgggc ccgaagttgc               100

tcagcctgaa gtagacacca ccctgggtcg tgtgcgaggc cggcaggtgg               150

gcgtgaaggg cacagaccgc cttgtgaatg tctttctggg cattccattt               200

gcccagccgc cactgggccc tgaccggttc tcagccccac acccagcaca               250

gccctgggag ggtgtgcggg atgccagcac tgcgcccccca atgtgcctac              300

aagacgtgga gagcatgaac agcagcagat ttgtcctcaa cggaaaacag               350

cagatcttct ccgtttcaga ggactgcctg gtcctcaacg tctatagccc               400

agctgaggtc cccgcagggt ccggtaggcc ggtcatggta tgggtccatg               450

gaggcgctct gataactggc gctgccacct cctacgatgg atcagctctg               500

gctgcctatg gggatgtggt cgtggttaca gtccagtacc gccttggggt               550

ccttggcttc ttcagcactg gagatgagca tgcacctggc aaccagggct               600

tcctagatgt ggtagctgct ttgcgctggg tgcaagaaaa catcgccccc               650

ttcgggggtg acctcaactg tgtcactgtc tttggtggat ctgccggtgg               700

gagcatcatc tctggcctgg tcctgtcccc agtggctgca gggctgttcc               750

acagagccat cacacagagt ggggtcatca ccaccccagg gatcatcgac               800

tctcaccctt ggcccctagc tcagaaaatc gcaaacacct tggcctgcag               850

ctccagctcc ccggctgaga tggtgcagtg ccttcagcag aaagaaggag               900

aagagctggt ccttagcaag aagctgaaaa atactatcta tcctctcacc               950

gttgatggca ctgtcttccc caaaagcccc aaggaactcc tgaaggagaa              1000

gcccttccac tctgtgccct tcctcatggg tgtcaacaac catgagttca              1050

gctggctcat ccccaggggc tggggtctcc tggatacaat ggagcagatg              1100
```

-continued

```
agccgggagg acatgctggc catctcaaca cccgtcttga ccagtctgga    1150
tgtgccccct gagatgatgc ccaccgtcat agatgaatac ctaggaagca    1200
actcggacgc acaagccaaa tgccaggcgt tccaggaatt catgggtgac    1250
gtattcatca atgttcccac cgtcagtttt tcaagatacc ttcgagattc    1300
tggaagccct gtctttttct atgagttcca gcatcgaccc agttcttttg    1350
cgaagatcaa acctgcctgg gtgaaggctg atcatggggc cgagggtgct    1400
tttgtgttcg gaggtccctt cctcatggac gagagctccc gcctggcctt    1450
tccagaggcc acagaggagg agaagcagct aagcctcacc atgatggccc    1500
agtggaccca ctttgcccgg acaggggacc ccaatagcaa ggctctgcct    1550
ccttggcccc aattcaacca ggcggaacaa tatctggaga tcaacccagt    1600
gccacgggcc ggacagaagt tcagggaggc ctggatgcag ttctggtcag    1650
agacgctccc cagcaagata caacagtggc accagaagca gaagaacagg    1700
aaggcccagg aggacctctg aggccaggcc tgaaccttct tggctggggc    1750
aaaccactct tcaagtggtg gcagagtccc agcacggcag cccgcctctc    1800
cccctgctga gactttaatc tccaccagcc cttaaagtgt cggccgctct    1850
gtgactggag ttatgctctt ttgaaatgtc acaaggccgc ctcccacctc    1900
tggggcattg tacaagttct tccctctccc tgaagtgcct ttcctgcttt    1950
cttcgtggta ggttctagca cattcctcta gcttcctgga ggactcactc    2000
cccaggaagc cttccctgcc ttctctgggc tgtgcggccc cgagtctgcg    2050
tccattagag cacagtccac ccgaggctag caccgtgtct gtgtctgtct    2100
ccccctcaga ggagctctct caaaatgggg attagcctaa ccccactctg    2150
tcacccacac caggatcggg tgggacctgg agctaggggg tgtttgctga    2200
gtgagtgagt gaaacacaga atatgggaat ggcagctgct gaacttgaac    2250
ccagagcctt caggtgccaa agccatactc aggcccccac cgacattgtc    2300
caccctggcc agaagggtgc atgccaatgg cagagacctg ggatgggaga    2350
agtcctgggg cgccagggga tccagcctag agcagacctt agcccctgac    2400
taaggcctca gactagggcg ggaggggtct cctcctctct gctgcccagt    2450
cctggcccct gcacaagaca acagaatcca tcagggccat gagtgtcacc    2500
cagacctgac cctcaccaat tccagcccct gaccctcagg acgctggatg    2550
ccagctccca gccccagtgc cgggtcctcc ctcccttcct ggcttgggga    2600
gaccagtttc tggggagctt ccaagagcac ccaccaagac acagcaggac    2650
aggccagggg agggcatctg gaccagggca tccgtcgggc tattgtcaca    2700
gagaaaagaa gagacccacc cactcgggct gcaaaaggtg aaaagcacca    2750
agaggttttc agatggaagt gagaggtgac agtgtgctgg cagccctcac    2800
agccctcgct tgctctccct gccgcctctg cctgggctcc cactttggca    2850
gcacttgagg agcccttcaa cccgccgctg cactgtagga gcccctttct    2900
gggctggcca aggccggagc cagctccctc agcttgcggg gaggtgcgga    2950
gggagagggg cgggcaggaa ccggggctgc gcgcagcgct tgcgggccag    3000
agtgagttcc gggtgggcgt gggctcggcg gggccccact cagagcagct    3050
ggccggcccc aggcagtgag ggccttagca cctgggccag cagctgctgt    3100
```

-continued

```
gctcgatttc tcgctgggcc ttagctgcct ccccgcgggg cagggctcgg          3150

gacctgcagc cctccatgcc tgaccctccc cccacccccc gtgggctcct          3200

gtgcggccgg agcctcccca aggagcgccg ccccctgctc cacagcgccc          3250

agtcccatcg accacccaag ggctgaggag tgcgggtgca cagcgcggga          3300

ctggcaggca gctccacctg ctgccccagt gctggatcca ctgggtgaag          3350

ccagctgggc tcctgagtct ggtggggact tggagaacct ttatgtctag          3400

ctaagggatt gtaaatacac cgatgggcac tctgtatcta gctcaaggtt          3450

tgtaaacaca ccaatcagca ccctgtgtct agctcagtgt ttgtgaatgc          3500

accaatccac actctgtatc tggctactct ggtggggact tggagaacct          3550

ttgtgtccac actctgtatc tagctaatct agtggggatg tggagaacct          3600

ttgtgtctag ctcagggatc gtaaacgcac caatcagcac cctgtcaaaa          3650

cagaccactt gactctctgt aaaatggacc aatcagcagg atgtgggtgg          3700

ggcgagacaa gagaataaaa gcaggctgcc tgagccagca gtgacaaccc          3750

ccctcgggtc ccctcccacg ccgtggaagc tttgttcttt cgctctttgc          3800

aataaatctt gctactgccc  aaaa                                     3824
```

<210> SEQ ID NO 210
<211> LENGTH: 571
<212> TYPE: PRT
<213> ORGANISM: Homo sapiens

<400> SEQUENCE: 210

```
Met Glu Arg Ala Val Arg Val Glu Ser Gly Val Leu Val Gly Val
  1               5                  10                  15

Val Cys Leu Leu Leu Ala Cys Pro Ala Thr Ala Thr Gly Pro Glu
                 20                  25                  30

Val Ala Gln Pro Glu Val Asp Thr Thr Leu Gly Arg Val Arg Gly
                 35                  40                  45

Arg Gln Val Gly Val Lys Gly Thr Asp Arg Leu Val Asn Val Phe
                 50                  55                  60

Leu Gly Ile Pro Phe Ala Gln Pro Pro Leu Gly Pro Asp Arg Phe
                 65                  70                  75

Ser Ala Pro His Pro Ala Gln Pro Trp Glu Gly Val Arg Asp Ala
                 80                  85                  90

Ser Thr Ala Pro Pro Met Cys Leu Gln Asp Val Glu Ser Met Asn
                 95                 100                 105

Ser Ser Arg Phe Val Leu Asn Gly Lys Gln Gln Ile Phe Ser Val
                110                 115                 120

Ser Glu Asp Cys Leu Val Leu Asn Val Tyr Ser Pro Ala Glu Val
                125                 130                 135

Pro Ala Gly Ser Gly Arg Pro Val Met Val Trp Val His Gly Gly
                140                 145                 150

Ala Leu Ile Thr Gly Ala Ala Thr Ser Tyr Asp Gly Ser Ala Leu
                155                 160                 165

Ala Ala Tyr Gly Asp Val Val Val Val Thr Val Gln Tyr Arg Leu
                170                 175                 180

Gly Val Leu Gly Phe Phe Ser Thr Gly Asp Glu His Ala Pro Gly
                185                 190                 195

Asn Gln Gly Phe Leu Asp Val Val Ala Ala Leu Arg Trp Val Gln
```

-continued

```
                200                 205                 210

Glu Asn Ile Ala Pro Phe Gly Gly Asp Leu Asn Cys Val Thr Val
                215                 220                 225

Phe Gly Gly Ser Ala Gly Gly Ser Ile Ile Ser Gly Leu Val Leu
                230                 235                 240

Ser Pro Val Ala Ala Gly Leu Phe His Arg Ala Ile Thr Gln Ser
                245                 250                 255

Gly Val Ile Thr Thr Pro Gly Ile Ile Asp Ser His Pro Trp Pro
                260                 265                 270

Leu Ala Gln Lys Ile Ala Asn Thr Leu Ala Cys Ser Ser Ser Ser
                275                 280                 285

Pro Ala Glu Met Val Gln Cys Leu Gln Gln Lys Glu Gly Glu Glu
                290                 295                 300

Leu Val Leu Ser Lys Lys Leu Lys Asn Thr Ile Tyr Pro Leu Thr
                305                 310                 315

Val Asp Gly Thr Val Phe Pro Lys Ser Pro Lys Glu Leu Leu Lys
                320                 325                 330

Glu Lys Pro Phe His Ser Val Pro Phe Leu Met Gly Val Asn Asn
                335                 340                 345

His Glu Phe Ser Trp Leu Ile Pro Arg Gly Trp Gly Leu Leu Asp
                350                 355                 360

Thr Met Glu Gln Met Ser Arg Glu Asp Met Leu Ala Ile Ser Thr
                365                 370                 375

Pro Val Leu Thr Ser Leu Asp Val Pro Pro Glu Met Met Pro Thr
                380                 385                 390

Val Ile Asp Glu Tyr Leu Gly Ser Asn Ser Asp Ala Gln Ala Lys
                395                 400                 405

Cys Gln Ala Phe Gln Glu Phe Met Gly Asp Val Phe Ile Asn Val
                410                 415                 420

Pro Thr Val Ser Phe Ser Arg Tyr Leu Arg Asp Ser Gly Ser Pro
                425                 430                 435

Val Phe Phe Tyr Glu Phe Gln His Arg Pro Ser Ser Phe Ala Lys
                440                 445                 450

Ile Lys Pro Ala Trp Val Lys Ala Asp His Gly Ala Glu Gly Ala
                455                 460                 465

Phe Val Phe Gly Gly Pro Phe Leu Met Asp Glu Ser Ser Arg Leu
                470                 475                 480

Ala Phe Pro Glu Ala Thr Glu Glu Glu Lys Gln Leu Ser Leu Thr
                485                 490                 495

Met Met Ala Gln Trp Thr His Phe Ala Arg Thr Gly Asp Pro Asn
                500                 505                 510

Ser Lys Ala Leu Pro Pro Trp Pro Gln Phe Asn Gln Ala Glu Gln
                515                 520                 525

Tyr Leu Glu Ile Asn Pro Val Pro Arg Ala Gly Gln Lys Phe Arg
                530                 535                 540

Glu Ala Trp Met Gln Phe Trp Ser Glu Thr Leu Pro Ser Lys Ile
                545                 550                 555

Gln Gln Trp His Gln Lys Gln Lys Asn Arg Lys Ala Gln Glu Asp
                560                 565                 570

Leu
```

<210> SEQ ID NO 211
<211> LENGTH: 1177

-continued

<212> TYPE: DNA
<213> ORGANISM: Homo sapiens

<400> SEQUENCE: 211 aacttctaca tgggcctcct gctgctggtg ctcttcctca gcctcctgcc 50 ggtggcctac accatcatgt ccctcccacc ctcctttgac tgcgggccgt 100 tcaggtgcag agtctcagtt gcccgggagc acctcccctc ccgaggcagt 150 ctgctcagag ggcctcggcc cagaattcca gttctggttt catgccagcc 200 tgtaaaaggc catggaactt tgggtgaatc accgatgcca tttaagaggg 250 ttttctgcca ggatggaaat gttaggtcgt tctgtgtctg cgctgttcat 300 ttcagtagcc accagccacc tgtggccgtt gagtgcttga aatgaggaac 350 tgagaaaatt aatttctcat gtatttttct catttattta ttaattttta 400 actgatagtt gtacatattt gggggtacat gtgatatttg gatacatgta 450 tacaatatat aatgatcaaa tcagggtaac tgggatatcc atcacatcaa 500 acatttattt tttattcttt ttagacagag tctcactctg tcacccaggc 550 tggagtgcag tggtgccatc tcagcttact gcaacctctg cctgccaggt 600 tcaagcgatt ctcatgcctc cacctcccaa gtagctggga ctacaggcat 650 gcaccacaat gcccaactaa tttttgtatt tttagtagag acggggtttt 700 gccatgttgc ccaggctggc cttgaactcc tggcctcaaa caatccactt 750 gcctcggcct cccaaagtgt tatgattaca ggcgtgagcc accgtgcctg 800 gcctaaacat ttatcttttc tttgtgttgg gaactttgaa attatacaat 850 gaattattgt taactgtcat ctccctgctg tgctatggaa cactgggact 900 tcttccctct atctaactgt atatttgtac cagttaacca accgtacttc 950 atccccactc ctctctatcc ttcccaacct ctgatcacct cattctactc 1000 tctacctcca tgagatccac ttttttagct cccacatgtg agtaagaaaa 1050 tgcaatattt gtctttctgt gcctggctta tttcacttaa cataatgact 1100 tcctgttcca tccatgttgc tgcaaatgac aggatttcgt tcttaatttc 1150 aattaaaata accacacatg gcaaaaa 1177

<210> SEQ ID NO 212
<211> LENGTH: 111
<212> TYPE: PRT
<213> ORGANISM: Homo sapiens

<400> SEQUENCE: 212

Met Gly Leu Leu Leu Leu Val Leu Phe Leu Ser Leu Leu Pro Val
1 5 10 15

Ala Tyr Thr Ile Met Ser Leu Pro Pro Ser Phe Asp Cys Gly Pro
20 25 30

Phe Arg Cys Arg Val Ser Val Ala Arg Glu His Leu Pro Ser Arg
35 40 45

Gly Ser Leu Leu Arg Gly Pro Arg Pro Arg Ile Pro Val Leu Val
50 55 60

Ser Cys Gln Pro Val Lys Gly His Gly Thr Leu Gly Glu Ser Pro
65 70 75

Met Pro Phe Lys Arg Val Phe Cys Gln Asp Gly Asn Val Arg Ser
80 85 90

-continued

```
Phe Cys Val Cys Ala Val His Phe Ser Ser His Gln Pro Pro Val
                95                  100                 105

Ala Val Glu Cys Leu Lys
                110


<210> SEQ ID NO 213
<211> LENGTH: 2159
<212> TYPE: DNA
<213> ORGANISM: Homo sapiens

<400> SEQUENCE: 213

agggcccgcg ggtggagaga gcgacgcccg aggggatggc ggcagcgtcc                50

cggagcgcct ctggctgggc gctactgctg ctggtggcac tttggcagca               100

gcgcgcggcc ggctccggcg tcttccagct gcagctgcag gagttcatca               150

acgagcgcgg cgtactggcc agtgggcggc cttgcgagcc cggctgccgg               200

actttcttcc gcgtctgcct taagcacttc caggcggtcg tctcgcccgg               250

accctgcacc ttcgggaccg tctccacgcc ggtattgggc accaactcct               300

tcgctgtccg ggacgacagt agcggcgggg ggcgcaaccc tctccaactg               350

cccttcaatt tcacctggcc gggtaccttc tcgctcatca tcgaagcttg               400

gcacgcgcca ggagacgacc tgcggccaga ggccttgcca ccagatgcac               450

tcatcagcaa gatcgccatc cagggctccc tagctgtggg tcagaactgg               500

ttattggatg agcaaaccag caccctcaca aggctgcgct actcttaccg               550

ggtcatctgc agtgacaact actatggaga caactgctcc cgcctgtgca               600

agaagcgcaa tgaccacttc ggccactatg tgtgccagcc agatggcaac               650

ttgtcctgcc tgcccggttg gactggggaa tattgccaac agcctatctg               700

tctttcgggc tgtcatgaac agaatggcta ctgcagcaag ccagcagagt               750

gcctctgccg cccaggctgg cagggccggc tgtgtaacga atgcatcccc               800

cacaatggct gtcgccacgg cacctgcagc actccctggc aatgtacttg               850

tgatgagggc tggggaggcc tgttttgtga ccaagatctc aactactgca               900

cccaccactc cccatgcaag aatggggcaa cgtgctccaa cagtgggcag               950

cgaagctaca cctgcacctg tcgcccaggc tacactggtg tggactgtga              1000

gctggagctc agcgagtgtg acagcaaccc ctgtcgcaat ggaggcagct              1050

gtaaggacca ggaggatggc taccactgcc tgtgtcctcc gggctactat              1100

ggcctgcact gtgaacacag caccttgagc tgcgccgact ccccctgctt              1150

caatgggggc tcctgccggg agcgcaacca gggggccaac tatgcttgtg              1200

aatgtccccc caacttcacc ggctccaact gcgagaagaa agtggacagg              1250

tgcaccagca acccctgtgc caacgggggga cagtgcctga accgaggtcc              1300

aagccgcatg tgccgctgcc gtcctggatt cacgggcacc tactgtgaac              1350

tccacgtcag cgactgtgcc cgtaaccctt gcgcccacgg tggcacttgc              1400

catgacctgg agaatgggct catgtgcacc tgccctgccg gcttctctgg              1450

ccgacgctgt gaggtgcgga catccatcga tgcctgtgcc tcgagtccct              1500

gcttcaacag ggccacctgc tacaccgacc tctccacaga cacctttgtg              1550

tgcaactgcc cttatggctt tgtgggcagc cgctgcgagt tccccgtggg              1600

cttgccgccc agcttcccct gggtggccgt ctcgctgggt gtggggctgg              1650
```

-continued

```
cagtgctgct ggtactgctg ggcatggtgg cagtggctgt gcggcagctg          1700

cggcttcgac ggccggacga cggcagcagg gaagccatga acaacttgtc          1750

ggacttccag aaggacaacc tgattcctgc cgcccagctt aaaaacacaa          1800

accagaagaa ggagctggaa gtggactgtg gcctggacaa gtccaactgt          1850

ggcaaacagc aaaaccacac attggactat aatctggccc cagggcccct          1900

ggggcggggg accatgccag gaaagtttcc ccacagtgac aagagcttag          1950

gagagaaggc gccactgcgg ttacacagtg aaaagccaga gtgtcggata          2000

tcagcgatat gctcccccag ggactccatg taccagtctg tgtgtttgat          2050

atcagaggag aggaatgaat gtgtcattgc cacggaggta taaggcagga          2100

gcctacctgg acatccctgc tcagccccgc ggctggacct tccttctgca          2150

ttgtttaca                                                       2159
```

<210> SEQ ID NO 214
<211> LENGTH: 685
<212> TYPE: PRT
<213> ORGANISM: Homo sapiens

<400> SEQUENCE: 214

```
Met Ala Ala Ala Ser Arg Ser Ala Ser Gly Trp Ala Leu Leu Leu
  1               5                  10                  15

Leu Val Ala Leu Trp Gln Gln Arg Ala Ala Gly Ser Gly Val Phe
                 20                  25                  30

Gln Leu Gln Leu Gln Glu Phe Ile Asn Glu Arg Gly Val Leu Ala
                 35                  40                  45

Ser Gly Arg Pro Cys Glu Pro Gly Cys Arg Thr Phe Phe Arg Val
                 50                  55                  60

Cys Leu Lys His Phe Gln Ala Val Val Ser Pro Gly Pro Cys Thr
                 65                  70                  75

Phe Gly Thr Val Ser Thr Pro Val Leu Gly Thr Asn Ser Phe Ala
                 80                  85                  90

Val Arg Asp Asp Ser Ser Gly Gly Gly Arg Asn Pro Leu Gln Leu
                 95                 100                 105

Pro Phe Asn Phe Thr Trp Pro Gly Thr Phe Ser Leu Ile Ile Glu
                110                 115                 120

Ala Trp His Ala Pro Gly Asp Asp Leu Arg Pro Glu Ala Leu Pro
                125                 130                 135

Pro Asp Ala Leu Ile Ser Lys Ile Ala Ile Gln Gly Ser Leu Ala
                140                 145                 150

Val Gly Gln Asn Trp Leu Leu Asp Glu Gln Thr Ser Thr Leu Thr
                155                 160                 165

Arg Leu Arg Tyr Ser Tyr Arg Val Ile Cys Ser Asp Asn Tyr Tyr
                170                 175                 180

Gly Asp Asn Cys Ser Arg Leu Cys Lys Lys Arg Asn Asp His Phe
                185                 190                 195

Gly His Tyr Val Cys Gln Pro Asp Gly Asn Leu Ser Cys Leu Pro
                200                 205                 210

Gly Trp Thr Gly Glu Tyr Cys Gln Gln Pro Ile Cys Leu Ser Gly
                215                 220                 225

Cys His Glu Gln Asn Gly Tyr Cys Ser Lys Pro Ala Glu Cys Leu
                230                 235                 240
```

-continued

```
Cys Arg Pro Gly Trp Gln Gly Arg Leu Cys Asn Glu Cys Ile Pro
                245                 250                 255

His Asn Gly Cys Arg His Gly Thr Cys Ser Thr Pro Trp Gln Cys
                260                 265                 270

Thr Cys Asp Glu Gly Trp Gly Gly Leu Phe Cys Asp Gln Asp Leu
                275                 280                 285

Asn Tyr Cys Thr His His Ser Pro Cys Lys Asn Gly Ala Thr Cys
                290                 295                 300

Ser Asn Ser Gly Gln Arg Ser Tyr Thr Cys Thr Cys Arg Pro Gly
                305                 310                 315

Tyr Thr Gly Val Asp Cys Glu Leu Glu Leu Ser Glu Cys Asp Ser
                320                 325                 330

Asn Pro Cys Arg Asn Gly Gly Ser Cys Lys Asp Gln Glu Asp Gly
                335                 340                 345

Tyr His Cys Leu Cys Pro Pro Gly Tyr Tyr Gly Leu His Cys Glu
                350                 355                 360

His Ser Thr Leu Ser Cys Ala Asp Ser Pro Cys Phe Asn Gly Gly
                365                 370                 375

Ser Cys Arg Glu Arg Asn Gln Gly Ala Asn Tyr Ala Cys Glu Cys
                380                 385                 390

Pro Pro Asn Phe Thr Gly Ser Asn Cys Glu Lys Lys Val Asp Arg
                395                 400                 405

Cys Thr Ser Asn Pro Cys Ala Asn Gly Gly Gln Cys Leu Asn Arg
                410                 415                 420

Gly Pro Ser Arg Met Cys Arg Cys Arg Pro Gly Phe Thr Gly Thr
                425                 430                 435

Tyr Cys Glu Leu His Val Ser Asp Cys Ala Arg Asn Pro Cys Ala
                440                 445                 450

His Gly Gly Thr Cys His Asp Leu Glu Asn Gly Leu Met Cys Thr
                455                 460                 465

Cys Pro Ala Gly Phe Ser Gly Arg Arg Cys Glu Val Arg Thr Ser
                470                 475                 480

Ile Asp Ala Cys Ala Ser Ser Pro Cys Phe Asn Arg Ala Thr Cys
                485                 490                 495

Tyr Thr Asp Leu Ser Thr Asp Thr Phe Val Cys Asn Cys Pro Tyr
                500                 505                 510

Gly Phe Val Gly Ser Arg Cys Glu Phe Pro Val Gly Leu Pro Pro
                515                 520                 525

Ser Phe Pro Trp Val Ala Val Ser Leu Gly Val Gly Leu Ala Val
                530                 535                 540

Leu Leu Val Leu Leu Gly Met Val Ala Val Ala Val Arg Gln Leu
                545                 550                 555

Arg Leu Arg Arg Pro Asp Asp Gly Ser Arg Glu Ala Met Asn Asn
                560                 565                 570

Leu Ser Asp Phe Gln Lys Asp Asn Leu Ile Pro Ala Ala Gln Leu
                575                 580                 585

Lys Asn Thr Asn Gln Lys Lys Glu Leu Glu Val Asp Cys Gly Leu
                590                 595                 600

Asp Lys Ser Asn Cys Gly Lys Gln Gln Asn His Thr Leu Asp Tyr
                605                 610                 615

Asn Leu Ala Pro Gly Pro Leu Gly Arg Gly Thr Met Pro Gly Lys
                620                 625                 630

Phe Pro His Ser Asp Lys Ser Leu Gly Glu Lys Ala Pro Leu Arg
```

-continued

```
                635                 640                 645

Leu His Ser Glu Lys Pro Glu Cys Arg Ile Ser Ala Ile Cys Ser
                650                 655                 660

Pro Arg Asp Ser Met Tyr Gln Ser Val Cys Leu Ile Ser Glu Glu
                665                 670                 675

Arg Asn Glu Cys Val Ile Ala Thr Glu Val
                680                 685


<210> SEQ ID NO 215
<211> LENGTH: 3060
<212> TYPE: DNA
<213> ORGANISM: Homo sapiens

<400> SEQUENCE: 215

cgcgaggcgc ggggagcctg ggaccaggag cgagagccgc ctacctgcag                50

ccgccgccca cggcacggca gccaccatgg cgctcctgct gtgcttcgtg               100

ctcctgtgcg gagtagtgga tttcgccaga agtttgagta tcactactcc               150

tgaagagatg attgaaaaag ccaaagggga aactgcctat ctgccatgca               200

aatttacgct tagtcccgaa gaccagggac cgctggacat cgagtggctg               250

atatcaccag ctgataatca gaaggtggat caagtgatta ttttatattc               300

tggagacaaa atttatgatg actactatcc agatctgaaa ggccgagtac               350

attttacgag taatgatctc aaatctggtg atgcatcaat aaatgtaacg               400

aatttacaac tgtcagatat tggcacatat cagtgcaaag tgaaaaaagc               450

tcctggtgtt gcaaataaga agattcatct ggtagttctt gttaagcctt               500

caggtgcgag atgttacgtt gatggatctg aagaaattgg aagtgacttt               550

aagataaaat gtgaaccaaa agaaggttca cttccattac agtatgagtg               600

gcaaaaattg tctgactcac agaaaatgcc cacttcatgg ttagcagaaa               650

tgacttcatc tgttatatct gtaaaaaatg cctcttctga gtactctggg               700

acatacagct gtacagtcag aaacagagtg ggctctgatc agtgcctgtt               750

gcgtctaaac gttgtccctc cttcaaataa agctggacta attgcaggag               800

ccattatagg aactttgctt gctctagcgc tcattggtct tatcatcttt               850

tgctgtcgta aaaagcgcag agaagaaaaa tatgaaaagg aagttcatca               900

cgatatcagg gaagatgtgc cacctccaaa gagccgtacg tccactgcca               950

gaagctacat cggcagtaat cattcatccc tggggtccat gtctccttcc              1000

aacatggaag gatattccaa gactcagtat aaccaagtac caagtgaaga              1050

ctttgaacgc actcctcaga gtccgactct cccacctgct aagttcaagt              1100

acccttacaa gactgatgga attacagttg tataaatatg gactactgaa              1150

gaatctgaag tattgtatta tttgacttta ttttaggcct ctagtaaaga              1200

cttaaatgtt ttttaaaaaa agcacaaggc acagagatta gagcagctgt              1250

aagaacacat ctactttatg caatggcatt agacatgtaa gtcagatgtc              1300

atgtcaaaat tagtacgagc caaattcttt gttaaaaaac cctatgtata              1350

gtgacactga tagttaaaag atgttttatt atattttcaa taactaccac              1400

taacaaattt ttaacttttc atatgcatat tctgatatgt ggtcttttag              1450

gaaaagtatg gttaatagtt gatttttcaa aggaaatttt aaaattctta              1500
```

-continued

```
cgttctgttt aatgtttttg ctatttagtt aaatacattg aagggaaata          1550

cccgttcttt tccccttta tgcacacaac agaaacacgc gttgtcatgc           1600

ctcaaactat tttttatttg caactacatg atttcacaca attctcttaa          1650

acaacgacat aaaatagatt tccttgtata taaataactt acatacgctc          1700

cataaagtaa attctcaaag gtgctagaac aaatcgtcca cttctacagt          1750

gttctcgtat ccaacagagt tgatgcacaa tatataaata ctcaagtcca          1800

atattaaaaa cttaggcact tgactaactt taataaaatt tctcaaacta          1850

tatcaatatc taaagtgcat atatttttta agaaagatta ttctcaataa          1900

cttctataaa aataagtttg atggtttggc ccatctaact tcactactat          1950

tagtaagaac ttttaacttt taatgtgtag taaggtttat tctacctttt          2000

tctcaacatg acaccaacac aatcaaaaac gaagttagtg aggtgctaac          2050

atgtgaggat taatccagtg attccggtca caatgcattc caggaggagg          2100

tacccatgtc actggaattg ggcgatatgg tttatttttt cttccctgat          2150

ttggataacc aaatggaaca ggaggaggat agtgattctg atggccattc          2200

cctcgataca ttcctggctt ttttctgggc aaagggtgcc acattggaag          2250

aggtggaaat ataagttctg aaatctgtag ggaagagaac acattaagtt          2300

aattcaaagg aaaaaatcat catctatgtt ccagatttct cattaaagac          2350

aaagttaccc acaacactga gatcacatct aagtgacact cctattgtca          2400

ggtctaaata cattaaaaac ctcatgtgta ataggcgtat aatgtataac          2450

aggtgaccaa tgttttctga atgcataaag aaatgaataa actcaaacac          2500

agtacttcct aaacaacttc aaccaaaaaa gaccaaaaca tggaacgaat          2550

ggaagcttgt aaggacatgc ttgttttagt ccagtggttt ccacagctgg          2600

ctaagccagg agtcacttgg aggcttttaa atacaaaaca ttggagctgg          2650

aggccattat ccttagcaaa ctaatgcaga aacagaaaat caactaccgc          2700

atgttctcac ttataagtgg gaggtaatga taagaactta tgaacacaaa          2750

gaaggaaaca atagacattg gagtctattt gagaggggag ggtgggagaa          2800

ggaaaaggag cagaaaagat aactattgag tactgccttc acacctgggt          2850

gatgaaataa tatgtacaac aaatccctgt gacacatgtt tacctatgga          2900

acaaaccttc atgtgtatcc ctaaacctaa aataaaagtt aaaaaaaaaa          2950

aaaraaaaaa aaaaaaaaaa aaaaaaaaaa aaaaaaaaaa aaaaaaaaaa          3000

aaaaaaaaaa aaaaaaaaaa aaaaaaaaaa aaaaaaaaaa aaaaaaaaaa          3050

aaaaaaaaaa                                                      3060
```

<210> SEQ ID NO 216
<211> LENGTH: 352
<212> TYPE: PRT
<213> ORGANISM: Homo sapiens

<400> SEQUENCE: 216

```
Met Ala Leu Leu Leu Cys Phe Val Leu Leu Cys Gly Val Val Asp
  1               5                  10                  15

Phe Ala Arg Ser Leu Ser Ile Thr Thr Pro Glu Glu Met Ile Glu
                 20                  25                  30

Lys Ala Lys Gly Glu Thr Ala Tyr Leu Pro Cys Lys Phe Thr Leu
```

-continued

```
                35                  40                  45

Ser Pro Glu Asp Gln Gly Pro Leu Asp Ile Glu Trp Leu Ile Ser
                50                  55                  60

Pro Ala Asp Asn Gln Lys Val Asp Gln Val Ile Ile Leu Tyr Ser
                65                  70                  75

Gly Asp Lys Ile Tyr Asp Asp Tyr Tyr Pro Asp Leu Lys Gly Arg
                80                  85                  90

Val His Phe Thr Ser Asn Asp Leu Lys Ser Gly Asp Ala Ser Ile
                95                 100                 105

Asn Val Thr Asn Leu Gln Leu Ser Asp Ile Gly Thr Tyr Gln Cys
               110                 115                 120

Lys Val Lys Lys Ala Pro Gly Val Ala Asn Lys Lys Ile His Leu
               125                 130                 135

Val Val Leu Val Lys Pro Ser Gly Ala Arg Cys Tyr Val Asp Gly
               140                 145                 150

Ser Glu Glu Ile Gly Ser Asp Phe Lys Ile Lys Cys Glu Pro Lys
               155                 160                 165

Glu Gly Ser Leu Pro Leu Gln Tyr Glu Trp Gln Lys Leu Ser Asp
               170                 175                 180

Ser Gln Lys Met Pro Thr Ser Trp Leu Ala Glu Met Thr Ser Ser
               185                 190                 195

Val Ile Ser Val Lys Asn Ala Ser Ser Glu Tyr Ser Gly Thr Tyr
               200                 205                 210

Ser Cys Thr Val Arg Asn Arg Val Gly Ser Asp Gln Cys Leu Leu
               215                 220                 225

Arg Leu Asn Val Val Pro Pro Ser Asn Lys Ala Gly Leu Ile Ala
               230                 235                 240

Gly Ala Ile Ile Gly Thr Leu Leu Ala Leu Ala Leu Ile Gly Leu
               245                 250                 255

Ile Ile Phe Cys Cys Arg Lys Lys Arg Arg Glu Glu Lys Tyr Glu
               260                 265                 270

Lys Glu Val His His Asp Ile Arg Glu Asp Val Pro Pro Pro Lys
               275                 280                 285

Ser Arg Thr Ser Thr Ala Arg Ser Tyr Ile Gly Ser Asn His Ser
               290                 295                 300

Ser Leu Gly Ser Met Ser Pro Ser Asn Met Glu Gly Tyr Ser Lys
               305                 310                 315

Thr Gln Tyr Asn Gln Val Pro Ser Glu Asp Phe Glu Arg Thr Pro
               320                 325                 330

Gln Ser Pro Thr Leu Pro Pro Ala Lys Phe Lys Tyr Pro Tyr Lys
               335                 340                 345

Thr Asp Gly Ile Thr Val Val
               350


<210> SEQ ID NO 217
<211> LENGTH: 1571
<212> TYPE: DNA
<213> ORGANISM: Homo sapiens

<400> SEQUENCE: 217

gatggcgcag ccacagcttc tgtgagattc gatttctccc cagttcccct                50

gtgggtctga ggggaccaga agggtgagct acgttggctt tctggaaggg               100

gaggctatat gcgtcaattc cccaaaacaa gttttgacat ttcccctgaa               150
```

-continued

```
atgtcattct ctatctattc actgcaagtg cctgctgttc caggccttac          200

ctgctgggca ctaacggcgg agccaggatg gggacagaat aaaggagcca          250

cgacctgtgc caccaactcg cactcagact ctgaactcag acctgaaatc          300

ttctcttcac gggaggcttg gcagtttttc ttactcctgt ggtctccaga          350

tttcaggcct aagatgaaag cctctagtct tgccttcagc cttctctctg          400

ctgcgtttta tctcctatgg actccttcca ctggactgaa gacactcaat          450

ttgggaagct gtgtgatcgc cacaaacctt caggaaatac gaaatggatt          500

ttctgagata cggggcagtg tgcaagccaa agatggaaac attgacatca          550

gaatcttaag gaggactgag tctttgcaag acacaaagcc tgcgaatcga          600

tgctgcctcc tgcgccattt gctaagactc tatctggaca gggtatttaa          650

aaactaccag acccctgacc attatactct ccggaagatc agcagcctcg          700

ccaattcctt tcttaccatc aagaaggacc tccggctctc tcatgcccac          750

atgacatgcc attgtgggga ggaagcaatg aagaaataca gccagattct          800

gagtcacttt gaaaagctgg aacctcaggc agcagttgtg aaggctttgg          850

gggaactaga cattcttctg caatggatgg aggagacaga ataggaggaa          900

agtgatgctg ctgctaagaa tattcgaggt caagagctcc agtcttcaat          950

acctgcagag gaggcatgac cccaaaccac catctcttta ctgtactagt         1000

cttgtgctgg tcacagtgta tcttatttat gcattacttg cttccttgca         1050

tgattgtctt tatgcatccc caatcttaat tgagaccata cttgtataag         1100

atttttgtaa tatctttctg ctattggata tatttattag ttaatatatt         1150

tatttatttt ttgctattta atgtatttat ttttttactt ggacatgaaa         1200

ctttaaaaaa attcacagat tatatttata acctgactag agcaggtgat         1250

gtatttttat acagtaaaaa aaaaaaacct tgtaaattct agaagagtgg         1300

ctagggggt tattcatttg tattcaacta aggacatatt tactcatgct          1350

gatgctctgt gagatatttg aaattgaacc aatgactact taggatgggt         1400

tgtggaataa gttttgatgt ggaattgcac atctacctta caattactga         1450

ccatccccag tagactcccc agtcccataa ttgtgtatct tccagccagg         1500

aatcctacac ggccagcatg tatttctaca aataaagttt tctttgcata         1550

ccaaaaaaaa aaaaaaaaaa  a                                       1571
```

<210> SEQ ID NO 218
<211> LENGTH: 176
<212> TYPE: PRT
<213> ORGANISM: Homo sapiens

<400> SEQUENCE: 218

```
Met Lys Ala Ser Ser Leu Ala Phe Ser Leu Leu Ser Ala Ala Phe
  1               5                  10                  15

Tyr Leu Leu Trp Thr Pro Ser Thr Gly Leu Lys Thr Leu Asn Leu
                 20                  25                  30

Gly Ser Cys Val Ile Ala Thr Asn Leu Gln Glu Ile Arg Asn Gly
                 35                  40                  45

Phe Ser Glu Ile Arg Gly Ser Val Gln Ala Lys Asp Gly Asn Ile
                 50                  55                  60

Asp Ile Arg Ile Leu Arg Arg Thr Glu Ser Leu Gln Asp Thr Lys
```

-continued

```
                65                  70                  75

Pro Ala Asn Arg Cys Cys Leu Leu Arg His Leu Leu Arg Leu Tyr
                80                  85                  90

Leu Asp Arg Val Phe Lys Asn Tyr Gln Thr Pro Asp His Tyr Thr
                95                 100                 105

Leu Arg Lys Ile Ser Ser Leu Ala Asn Ser Phe Leu Thr Ile Lys
               110                 115                 120

Lys Asp Leu Arg Leu Ser His Ala His Met Thr Cys His Cys Gly
               125                 130                 135

Glu Glu Ala Met Lys Lys Tyr Ser Gln Ile Leu Ser His Phe Glu
               140                 145                 150

Lys Leu Glu Pro Gln Ala Ala Val Val Lys Ala Leu Gly Glu Leu
               155                 160                 165

Asp Ile Leu Leu Gln Trp Met Glu Glu Thr Glu
               170                 175


<210> SEQ ID NO 219
<211> LENGTH: 2870
<212> TYPE: DNA
<213> ORGANISM: Homo sapiens

<400> SEQUENCE: 219

cgcggagccc tgcgctggga ggtgcacggt gtgcacgctg gactggaccc                50

ccatgcaacc ccgcgccctg cgccttaacc aggactgctc cgcgcgcccc               100

tgagcctcgg gctccggccc ggacctgcag cctcccaggt ggctgggaag               150

aactctccaa caataaatac atttgataag aaagatggct ttaaaagtgc               200

tactagaaca agagaaaacg tttttcactc ttttagtatt actaggctat               250

ttgtcatgta aagtgacttg tgaatcagga gactgtagac agcaagaatt               300

cagggatcgg tctggaaact gtgttccctg caaccagtgt gggccaggca               350

tggagttgtc taaggaatgt ggcttcggct atggggagga tgcacagtgt               400

gtgacgtgcc ggctgcacag gttcaaggag gactggggct tccagaaatg               450

caagccctgt ctggactgcg cagtggtgaa ccgctttcag aaggcaaatt               500

gttcagccac cagtgatgcc atctgcgggg actgcttgcc aggattttat               550

aggaagacga aacttgtcgg ctttcaagac atggagtgtg tgccttgtgg               600

agaccctcct cctccttacg aaccgcactg tgccagcaag gtcaacctcg               650

tgaagatcgc gtccacggcc tccagcccac gggacacggc gctggctgcc               700

gttatctgca gcgctctggc caccgtcctg ctggccctgc tcatcctctg               750

tgtcatctat tgtaagagac agtttatgga gaagaaaccc agctggtctc               800

tgcggtcgca ggacattcag tacaacggct ctgagctgtc gtgttttgac               850

agacctcagc tccacgaata tgcccacaga gcctgctgcc agtgccgccg               900

tgactcagtg cagacctgcg ggccggtgcg cttgctccca tccatgtgct               950

gtgaggaggc ctgcagcccc aacccggcga ctcttggttg tggggtgcat              1000

tctgcagcca gtcttcaggc aagaaacgca ggcccagccg gggagatggt              1050

gccgactttc ttcggatccc tcacgcagtc catctgtggc gagttttcag              1100

atgcctggcc tctgatgcag aatcccatgg gtggtgacaa catctctttt              1150

tgtgactctt atcctgaact cactggagaa gacattcatt ctctcaatcc              1200
```

-continued

```
agaacttgaa agctcaacgt ctttggattc aaatagcagt caagatttgg          1250
ttggtggggc tgttccagtc cagtctcatt ctgaaaactt tacagcagct          1300
actgatttat ctagatataa caacacactg gtagaatcag catcaactca          1350
ggatgcacta actatgagaa gccagctaga tcaggagagt ggcgctgtca          1400
tccacccagc cactcagacg tccctccagg aagcttaaag aacctgcttc          1450
tttctgcagt agaagcgtgt gctggaaccc aaagagtact cctttgttag          1500
gcttatggac tgagcagtct ggaccttgca tggcttctgg ggcaaaaata          1550
aatctgaacc aaactgacgg catttgaagc ctttcagcca gttgcttctg          1600
agccagacca gctgtaagct gaaacctcaa tgaataacaa gaaaagactc          1650
caggccgact catgatactc tgcatctttc ctacatgaga agcttctctg          1700
ccacaaaagt gacttcaaag actgatgggt tgagctggca gcctatgaga          1750
ttgtggacat ataacaagaa acagaaatgc cctcatgctt attttcatgg          1800
tgattgtggt tttacaagac tgaagaccca gagtatactt tttctttcca          1850
gaaataattt cataccgcct atgaaatatc agataaatta ccttagcttt          1900
tatgtagaat gggttcaaaa gtgagtgttt ctatttgaga aggacacttt          1950
ttcatcatct aaactgattc gcataggtgg ttagaatggc cctcatattg          2000
cctgcctaaa tcttgggttt attagatgaa gtttactgaa tcagaggaat          2050
cagacagagg aggatagctc tttccagaat ccacacttct gacctcagcc          2100
tcggtctcat gaacacccgc tgatctcagg agaacacctg ggctagggaa          2150
tgtggtcgag aaagggcagc ccattgccca gaattaacac atattgtaga          2200
gacttgtatg caaaggttgg catatttata tgaaaattag ttgctataga          2250
aacatttgtt gcatctgtcc ctctgcctga gcttagaagg ttatagaaaa          2300
agggtattta taaacataaa tgacctttta cttgcattgt atcttatact          2350
aaaggcttta gaaattacaa catatcaggt tcccctacta ctgaagtagc          2400
cttccgtgag aacacaccac atgttaggac tagaagaaaa tgcacaattt          2450
gtaggggttt ggatgaagca gctgtaactg ccctagtgta gtttgaccag          2500
gacattgtcg tgctccttcc aattgtgtaa gattagttag cacatcatct          2550
cctactttag ccatccggtg ttggatttaa gaggacggtg cttctttcta          2600
ttaaagtgct ccatccccta ccatctacac attagcattg tctctagagc          2650
taagacagaa attaaccccg ttcagtcaca aagcagggaa tggttcattt          2700
actcttaatc tttatgccct ggagaagacc tacttgaaca gggcatattt          2750
tttagacttc tgaacatcag tatgttcgag ggtactatga tattttggtt          2800
tggaattgcc ctgcccaagt cactgtcttt taacttttaa actgaatatt          2850
aaaatgtatc tgtctttcct                                           2870
```

<210> SEQ ID NO 220
<211> LENGTH: 417
<212> TYPE: PRT
<213> ORGANISM: Homo sapiens

<400> SEQUENCE: 220

```
Met Ala Leu Lys Val Leu Leu Glu Gln Glu Lys Thr Phe Phe Thr
  1               5                  10                  15
```

-continued

```
Leu Leu Val Leu Leu Gly Tyr Leu Ser Cys Lys Val Thr Cys Glu
                20                  25                  30

Ser Gly Asp Cys Arg Gln Gln Glu Phe Arg Asp Arg Ser Gly Asn
                35                  40                  45

Cys Val Pro Cys Asn Gln Cys Gly Pro Gly Met Glu Leu Ser Lys
                50                  55                  60

Glu Cys Gly Phe Gly Tyr Gly Glu Asp Ala Gln Cys Val Thr Cys
                65                  70                  75

Arg Leu His Arg Phe Lys Glu Asp Trp Gly Phe Gln Lys Cys Lys
                80                  85                  90

Pro Cys Leu Asp Cys Ala Val Val Asn Arg Phe Gln Lys Ala Asn
                95                 100                 105

Cys Ser Ala Thr Ser Asp Ala Ile Cys Gly Asp Cys Leu Pro Gly
               110                 115                 120

Phe Tyr Arg Lys Thr Lys Leu Val Gly Phe Gln Asp Met Glu Cys
               125                 130                 135

Val Pro Cys Gly Asp Pro Pro Pro Pro Tyr Glu Pro His Cys Ala
               140                 145                 150

Ser Lys Val Asn Leu Val Lys Ile Ala Ser Thr Ala Ser Ser Pro
               155                 160                 165

Arg Asp Thr Ala Leu Ala Ala Val Ile Cys Ser Ala Leu Ala Thr
               170                 175                 180

Val Leu Leu Ala Leu Leu Ile Leu Cys Val Ile Tyr Cys Lys Arg
               185                 190                 195

Gln Phe Met Glu Lys Lys Pro Ser Trp Ser Leu Arg Ser Gln Asp
               200                 205                 210

Ile Gln Tyr Asn Gly Ser Glu Leu Ser Cys Phe Asp Arg Pro Gln
               215                 220                 225

Leu His Glu Tyr Ala His Arg Ala Cys Cys Gln Cys Arg Arg Asp
               230                 235                 240

Ser Val Gln Thr Cys Gly Pro Val Arg Leu Leu Pro Ser Met Cys
               245                 250                 255

Cys Glu Glu Ala Cys Ser Pro Asn Pro Ala Thr Leu Gly Cys Gly
               260                 265                 270

Val His Ser Ala Ala Ser Leu Gln Ala Arg Asn Ala Gly Pro Ala
               275                 280                 285

Gly Glu Met Val Pro Thr Phe Phe Gly Ser Leu Thr Gln Ser Ile
               290                 295                 300

Cys Gly Glu Phe Ser Asp Ala Trp Pro Leu Met Gln Asn Pro Met
               305                 310                 315

Gly Gly Asp Asn Ile Ser Phe Cys Asp Ser Tyr Pro Glu Leu Thr
               320                 325                 330

Gly Glu Asp Ile His Ser Leu Asn Pro Glu Leu Glu Ser Ser Thr
               335                 340                 345

Ser Leu Asp Ser Asn Ser Ser Gln Asp Leu Val Gly Gly Ala Val
               350                 355                 360

Pro Val Gln Ser His Ser Glu Asn Phe Thr Ala Ala Thr Asp Leu
               365                 370                 375

Ser Arg Tyr Asn Asn Thr Leu Val Glu Ser Ala Ser Thr Gln Asp
               380                 385                 390

Ala Leu Thr Met Arg Ser Gln Leu Asp Gln Glu Ser Gly Ala Val
               395                 400                 405

Ile His Pro Ala Thr Gln Thr Ser Leu Gln Glu Ala
```

-continued

```
                410                 415


<210> SEQ ID NO 221
<211> LENGTH: 961
<212> TYPE: DNA
<213> ORGANISM: Homo sapiens

<400> SEQUENCE: 221

ctagagagta tagggcagaa ggatggcaga tgagtgactc cacatccaga                50

gctgcctccc tttaatccag gatcctgtcc ttcctgtcct gtaggagtgc               100

ctgttgccag tgtggggtga gacaagtttg tcccacaggg ctgtctgagc               150

agataagatt aagggctggg tctgtgctca attaactcct gtgggcacgg               200

gggctgggaa gagcaaagtc agcggtgcct acagtcagca ccatgctggg               250

cctgccgtgg aagggaggtc tgtcctgggc gctgctgctg cttctcttag               300

gctcccagat cctgctgatc tatgcctggc atttccacga gcaaagggac               350

tgtgatgaac acaatgtcat ggctcgttac ctccctgcca cagtggagtt               400

tgctgtccac acattcaacc aacagagcaa ggactactat gcctacagac               450

tggggcacat cttgaattcc tggaaggagc aggtggagtc caagactgta               500

ttctcaatgg agctactgct ggggagaact aggtgtggga aatttgaaga               550

cgacattgac aactgccatt tccaagaaag cacagagctg aacaatactt               600

tcacctgctt cttcaccatc agcaccaggc cctggatgac tcagttcagc               650

ctcctgaaca agacctgctt ggagggattc cactgagtga aacccactca               700

caggcttgtc catgtgctgc tcccacattc cgtggacatc agcactactc               750

tcctgaggac tcttcagtgg ctgagcagct ttggacttgt ttgttatcct               800

attttgcatg tgtttgagat ctcagatcag tgttttagaa aatccacaca               850

tcttgagcct aatcatgtag tgtagatcat taaacatcag cattttaaga               900

aaaaaaaaaa aaaaaaaaaa aaaaaaaaaa aaaaaaaaaa aaaaaaaaaa               950

aaaaaaaaaa  a                                                        961


<210> SEQ ID NO 222
<211> LENGTH: 147
<212> TYPE: PRT
<213> ORGANISM: Homo sapiens

<400> SEQUENCE: 222

Met Leu Gly Leu Pro Trp Lys Gly Gly Leu Ser Trp Ala Leu Leu
  1               5                  10                  15

Leu Leu Leu Leu Gly Ser Gln Ile Leu Leu Ile Tyr Ala Trp His
                 20                  25                  30

Phe His Glu Gln Arg Asp Cys Asp Glu His Asn Val Met Ala Arg
                 35                  40                  45

Tyr Leu Pro Ala Thr Val Glu Phe Ala Val His Thr Phe Asn Gln
                 50                  55                  60

Gln Ser Lys Asp Tyr Tyr Ala Tyr Arg Leu Gly His Ile Leu Asn
                 65                  70                  75

Ser Trp Lys Glu Gln Val Glu Ser Lys Thr Val Phe Ser Met Glu
                 80                  85                  90

Leu Leu Leu Gly Arg Thr Arg Cys Gly Lys Phe Glu Asp Asp Ile
                 95                 100                 105
```

```
Asp Asn Cys His Phe Gln Glu Ser Thr Glu Leu Asn Asn Thr Phe
                110                 115                 120

Thr Cys Phe Phe Thr Ile Ser Thr Arg Pro Trp Met Thr Gln Phe
                125                 130                 135

Ser Leu Leu Asn Lys Thr Cys Leu Glu Gly Phe His
                140                 145


<210> SEQ ID NO 223
<211> LENGTH: 846
<212> TYPE: DNA
<213> ORGANISM: Homo sapiens

<400> SEQUENCE: 223

aatcggctga ttctgcatct ggaaactgcc ttcatcttga aagaaaagct                50

ccaggtccct tctccagcca cccagcccca agatggtgat gctgctgctg               100

ctgctttccg cactggctgg cctcttcggt gcggcagagg gacaagcatt               150

tcatcttggg aagtgcccca atcctccggt gcaggagaat tttgacgtga               200

ataagtatct cggaagatgg tacgaaattg agaagatccc aacaaccttt               250

gagaatggac gctgcatcca ggccaactac tcactaatgg aaaacggaaa               300

gatcaaagtg ttaaaccagg agttgagagc tgatggaact gtgaatcaaa               350

tcgaaggtga agccacccca gttaacctca cagagcctgc caagctggaa               400

gttaagtttt cctggtttat gccatcggca ccgtactgga tcctggccac               450

cgactatgag aactatgccc tcgtgtattc ctgtacctgc atcatccaac               500

tttttcacgt ggattttgct tggatcttgg caagaaaccc taatctccct               550

ccagaaacag tggactctct aaaaaatatc ctgacttcta ataacattga               600

tgtcaagaaa atgacggtca cagaccaggt gaactgcccc aagctctcgt               650

aaccaggttc tacagggagg ctgcacccac tccatgttac ttctgcttcg               700

ctttccccta ccccaccccc cccccataaa gacaaaccaa tcaaccacga               750

caaaggaagt tgacctgaac atgtaaccat gccctaccct gttaccttgc               800

tagctgcaaa ataaacttgt tgctgacctg ctgtgctcgc  aaaaaa                  846


<210> SEQ ID NO 224
<211> LENGTH: 189
<212> TYPE: PRT
<213> ORGANISM: Homo sapiens

<400> SEQUENCE: 224

Met Val Met Leu Leu Leu Leu Leu Ser Ala Leu Ala Gly Leu Phe
  1               5                  10                  15

Gly Ala Ala Glu Gly Gln Ala Phe His Leu Gly Lys Cys Pro Asn
                20                  25                  30

Pro Pro Val Gln Glu Asn Phe Asp Val Asn Lys Tyr Leu Gly Arg
                35                  40                  45

Trp Tyr Glu Ile Glu Lys Ile Pro Thr Thr Phe Glu Asn Gly Arg
                50                  55                  60

Cys Ile Gln Ala Asn Tyr Ser Leu Met Glu Asn Gly Lys Ile Lys
                65                  70                  75

Val Leu Asn Gln Glu Leu Arg Ala Asp Gly Thr Val Asn Gln Ile
                80                  85                  90

Glu Gly Glu Ala Thr Pro Val Asn Leu Thr Glu Pro Ala Lys Leu
                95                 100                 105
```

```
Glu Val Lys Phe Ser Trp Phe Met Pro Ser Ala Pro Tyr Trp Ile
                110                 115                 120

Leu Ala Thr Asp Tyr Glu Asn Tyr Ala Leu Val Tyr Ser Cys Thr
                125                 130                 135

Cys Ile Ile Gln Leu Phe His Val Asp Phe Ala Trp Ile Leu Ala
                140                 145                 150

Arg Asn Pro Asn Leu Pro Pro Glu Thr Val Asp Ser Leu Lys Asn
                155                 160                 165

Ile Leu Thr Ser Asn Asn Ile Asp Val Lys Lys Met Thr Val Thr
                170                 175                 180

Asp Gln Val Asn Cys Pro Lys Leu Ser
                185


<210> SEQ ID NO 225
<211> LENGTH: 1088
<212> TYPE: DNA
<213> ORGANISM: Homo sapiens

<400> SEQUENCE: 225

gggtgattga actaaacctt cgccgcaccg agtttgcagt acggccgtca                50

cccgcaccgc tgcctgcttg cggttggaga aatcaaggcc ctaccgggcc               100

tccgtagtca cctctctata gtgggcgtgg ccgaggccgg ggtgaccctg               150

ccggagcctc cgctgccagc gacatgttca aggtaattca gaggtccgtg               200

gggccagcca gcctgagctt gctcaccttc aaagtctatg cagcaccaaa               250

aaaggactca cctcccaaaa attccgtgaa ggttgatgag ctttcactct               300

actcagttcc tgagggtcaa tcgaagtatg tggaggaggc aaggagccag               350

cttgaagaaa gcatctcaca gctccgacac tattgcgagc catacacaac               400

ctggtgtcag gaaacgtact cccaaactaa gcccaagatg caaagtttgg               450

ttcaatgggg gttagacagc tatgactatc tccaaaatgc acctcctgga               500

ttttttccga gacttggtgt tattggtttt gctggcctta ttggactcct               550

tttggctaga ggttcaaaaa taaagaagct agtgtatccg cctggtttca               600

tgggattagc tgcctccctc tattatccac aacaagccat cgtgtttgcc               650

caggtcagtg gggagagatt atatgactgg ggtttacgag gatatatagt               700

catagaagat ttgtggaagg agaactttca aaagccagga aatgtgaaga               750

attcacctgg aactaagtag aaaactccat gctctgccat cttaatcagt               800

tataggtaaa cattggaaac tccatagaat aaatcagtat ttctacagaa               850

aaatggcata gaagtcagta ttgaatgtat taaattggct ttcttcttca               900

ggaaaaacta gaccagacct ctgttatctt ctgtgaaatc atcctacaag               950

caaactaacc tggaatccct tcacctagag ataatgtaca agccttagaa              1000

ctcctcattc tcatgttgct atttatgtac ctaattaaaa cccaagttta              1050

aaaaaaaaaa aaaaaaaaaa aaaaaaaaaa  aaaaaaaa                          1088


<210> SEQ ID NO 226
<211> LENGTH: 198
<212> TYPE: PRT
<213> ORGANISM: Homo sapiens

<400> SEQUENCE: 226
```

-continued

```
Met Phe Lys Val Ile Gln Arg Ser Val Gly Pro Ala Ser Leu Ser
  1               5                  10                  15

Leu Leu Thr Phe Lys Val Tyr Ala Ala Pro Lys Lys Asp Ser Pro
                 20                  25                  30

Pro Lys Asn Ser Val Lys Val Asp Glu Leu Ser Leu Tyr Ser Val
                 35                  40                  45

Pro Glu Gly Gln Ser Lys Tyr Val Glu Glu Ala Arg Ser Gln Leu
                 50                  55                  60

Glu Glu Ser Ile Ser Gln Leu Arg His Tyr Cys Glu Pro Tyr Thr
                 65                  70                  75

Thr Trp Cys Gln Glu Thr Tyr Ser Gln Thr Lys Pro Lys Met Gln
                 80                  85                  90

Ser Leu Val Gln Trp Gly Leu Asp Ser Tyr Asp Tyr Leu Gln Asn
                 95                 100                 105

Ala Pro Pro Gly Phe Phe Pro Arg Leu Gly Val Ile Gly Phe Ala
                110                 115                 120

Gly Leu Ile Gly Leu Leu Leu Ala Arg Gly Ser Lys Ile Lys Lys
                125                 130                 135

Leu Val Tyr Pro Pro Gly Phe Met Gly Leu Ala Ala Ser Leu Tyr
                140                 145                 150

Tyr Pro Gln Gln Ala Ile Val Phe Ala Gln Val Ser Gly Glu Arg
                155                 160                 165

Leu Tyr Asp Trp Gly Leu Arg Gly Tyr Ile Val Ile Glu Asp Leu
                170                 175                 180

Trp Lys Glu Asn Phe Gln Lys Pro Gly Asn Val Lys Asn Ser Pro
                185                 190                 195

Gly Thr Lys


<210> SEQ ID NO 227
<211> LENGTH: 2164
<212> TYPE: DNA
<213> ORGANISM: Homo sapiens

<400> SEQUENCE: 227

caccggaggg cacgcagctg acggagctgc gctgcgttcg cctcgtttgc                50

ctcgcgccct ccactggagc tgttcgcgcc tcccggctcc caccgcagcc               100

cacccggcag aggagtcgct accagcgccc agtgcgctct gtcagtccgc               150

aaactccttg ccgcccgccc cgggctgggc accaaatacc aggctaccat               200

ggtctacaag actctcttcg ctctttgcat cttaactgca ggatggaggg               250

tacagagtct gcctacatca gctcctttgt ctgtttctct tccgacaaac               300

attgtaccac cgaccaccat ctggactagc tctccacaaa acactgatgc               350

agacactgcc tccccatcca acggcactca caacaactcg gtgctcccag               400

ttacagcatc agccccaaca tctctgcttc ctaagaacat ttccatagag               450

tccagagaag aggagatcac cagcccaggt tcgaattggg aaggcacaaa               500

cacagacccc tcaccttctg ggttctcgtc aacaagcggt ggagtccact               550

taacaaccac gttggaggaa cacagctcgg gcactcctga agcaggcgtg               600

gcagctacac tgtcgcagtc cgctgctgag cctcccacac tcatctcccc               650

tcaagctcca gcctcatcac cctcatccct atcaacctca ccacctgagg               700

tcttttctgc ctccgttact accaaccata gctccactgt gaccagcacc               750
```

-continued

```
caacccactg gagctccaac tgcaccagag tccccgacag aggagtccag          800

ctctgaccac acacccactt cacatgccac agctgagcca gtgccccagg          850

agaaaacacc cccaacaact gtgtcaggca aagtgatgtg tgagctcata          900

gacatggaga ccaccaccac ctttcccagg gtgatcatgc aggaagtaga          950

acatgcatta agttcaggca gcatcgccgc cattaccgtg acagtcattg         1000

ccgtggtgct gctggtgttt ggagttgcag cctacctaaa aatcaggcat         1050

tcctcctatg gaagactttt ggacgaccat gactacgggt cctggggaaa         1100

ctacaacaac cctctgtacg atgactccta acaatggaat atggcctggg         1150

atgaggatta actgttcttt atttataagt gcttatccag tagaattaat         1200

aagtacctga tgcgcattga acgacaatct taagccctgt tttgttggta         1250

tggttgtttt tgttttcctc cctctcctct ggctgctaca acttcccctt         1300

tctggtacaa gaagaaccat tctttaaagg tgagtggagg ctgatttgca         1350

gctgaagtgg gccagccttg caccagccag gccagaccac catggtgaag         1400

gcttctttcc ccactgcagg acccactttg agaaggatcg aggaggagga         1450

tttgggttgt tttgttaggg gttactttca ggggaacatt tcatttgtgt         1500

tatttcttaa acttctattt aggaaattac attaagtatt aatgagggga         1550

aaggaaatga gctctacgag gatttcacct tgcatgggag agagcagggt         1600

tttctcagat tccttttaa tctctattta tctggttgtt tctgacagga          1650

tgctgcctgc ttggctctac gagctggaaa gcagcttctt agctgcctaa         1700

ttaatgaaag atgaaaatag gaagtgccct ggagggggcc agcaggtcac         1750

ggggcagaat ctctcaggtt gctgtgggat ctcagtgtgc ccctacctgt         1800

tctcccctcc aggccacctg tctctgtaaa ggatgtctgc tctgttcaaa         1850

aggcagctgg gatcccagcc cacaagtgat cagcagagtt gcatttccaa         1900

agaaaaaggc tatgagatga gctgagttat agagagaaag ggagaggcat         1950

gtacggtgtg gggaagtgga agagaagctg gcgggggaga aggaggctaa         2000

cctgcactga gtacttcatt aggacaagtg agaatcagct attgataatg         2050

gccagagata tccacagctt ggaggagccc agagactgtt tgctttatac         2100

ccacacagca actggtccac tgctttactg tctgttggat aatggctgta         2150

aaatgtttaa  aaac                                               2164
```

<210> SEQ ID NO 228
<211> LENGTH: 310
<212> TYPE: PRT
<213> ORGANISM: Homo sapiens

<400> SEQUENCE: 228

```
Met Val Tyr Lys Thr Leu Phe Ala Leu Cys Ile Leu Thr Ala Gly
  1               5                  10                  15

Trp Arg Val Gln Ser Leu Pro Thr Ser Ala Pro Leu Ser Val Ser
                 20                  25                  30

Leu Pro Thr Asn Ile Val Pro Pro Thr Thr Ile Trp Thr Ser Ser
                 35                  40                  45

Pro Gln Asn Thr Asp Ala Asp Thr Ala Ser Pro Ser Asn Gly Thr
                 50                  55                  60

His Asn Asn Ser Val Leu Pro Val Thr Ala Ser Ala Pro Thr Ser
```

-continued

```
                65                  70                  75

Leu Leu Pro Lys Asn Ile Ser Ile Glu Ser Arg Glu Glu Glu Ile
                80                  85                  90

Thr Ser Pro Gly Ser Asn Trp Glu Gly Thr Asn Thr Asp Pro Ser
                95                 100                 105

Pro Ser Gly Phe Ser Ser Thr Ser Gly Gly Val His Leu Thr Thr
               110                 115                 120

Thr Leu Glu Glu His Ser Ser Gly Thr Pro Glu Ala Gly Val Ala
               125                 130                 135

Ala Thr Leu Ser Gln Ser Ala Ala Glu Pro Pro Thr Leu Ile Ser
               140                 145                 150

Pro Gln Ala Pro Ala Ser Ser Pro Ser Ser Leu Ser Thr Ser Pro
               155                 160                 165

Pro Glu Val Phe Ser Ala Ser Val Thr Thr Asn His Ser Ser Thr
               170                 175                 180

Val Thr Ser Thr Gln Pro Thr Gly Ala Pro Thr Ala Pro Glu Ser
               185                 190                 195

Pro Thr Glu Glu Ser Ser Ser Asp His Thr Pro Thr Ser His Ala
               200                 205                 210

Thr Ala Glu Pro Val Pro Gln Glu Lys Thr Pro Pro Thr Thr Val
               215                 220                 225

Ser Gly Lys Val Met Cys Glu Leu Ile Asp Met Glu Thr Thr Thr
               230                 235                 240

Thr Phe Pro Arg Val Ile Met Gln Glu Val Glu His Ala Leu Ser
               245                 250                 255

Ser Gly Ser Ile Ala Ala Ile Thr Val Thr Val Ile Ala Val Val
               260                 265                 270

Leu Leu Val Phe Gly Val Ala Ala Tyr Leu Lys Ile Arg His Ser
               275                 280                 285

Ser Tyr Gly Arg Leu Leu Asp Asp His Asp Tyr Gly Ser Trp Gly
               290                 295                 300

Asn Tyr Asn Asn Pro Leu Tyr Asp Asp Ser
               305                 310


<210> SEQ ID NO 229
<211> LENGTH: 633
<212> TYPE: DNA
<213> ORGANISM: Homo sapiens

<400> SEQUENCE: 229

ctcctgcact aggctctcag ccagggatga tgcgctgctg ccgccgccgc                50

tgctgctgcc ggcaaccacc ccatgccctg aggccgttgc tgttgctgcc               100

cctcgtcctt ttacctcccc tggcagcagc tgcagcgggc ccaaaccgat               150

gtgacaccat ataccagggc ttcgccgagt gtctcatccg cttgggggac               200

agcatgggcc gcggaggcga gctggagacc atctgcaggt cttggaatga               250

cttccatgcc tgtgcctctc aggtcctgtc aggctgtccg gaggaggcag               300

ctgcagtgtg ggaatcacta cagcaagaag ctcgccaggc cccccgtccg               350

aataacttgc acactctgtg cggtgccccg gtgcatgttc gggagcgcgg               400

cacaggctcc gaaaccaacc aggagacgct gcgggctaca gcgcctgcac               450

tccccatggc ccctgcgccc ccactgctgg cggctgctct ggctctggcc               500

tacctcctga ggcctctggc ctagcttgtt gggttgggta gcagcgcccg               550
```

```
tacctccagc cctgctctgg cggtggttgt ccaggctctg cagagcgcag              600

cagggctttt cattaaaggt atttatattt  gta                               633


<210> SEQ ID NO 230
<211> LENGTH: 165
<212> TYPE: PRT
<213> ORGANISM: Homo sapiens

<400> SEQUENCE: 230

Met Met Arg Cys Cys Arg Arg Arg Cys Cys Cys Arg Gln Pro Pro
  1               5                  10                  15

His Ala Leu Arg Pro Leu Leu Leu Leu Pro Leu Val Leu Leu Pro
                 20                  25                  30

Pro Leu Ala Ala Ala Ala Ala Gly Pro Asn Arg Cys Asp Thr Ile
                 35                  40                  45

Tyr Gln Gly Phe Ala Glu Cys Leu Ile Arg Leu Gly Asp Ser Met
                 50                  55                  60

Gly Arg Gly Gly Glu Leu Glu Thr Ile Cys Arg Ser Trp Asn Asp
                 65                  70                  75

Phe His Ala Cys Ala Ser Gln Val Leu Ser Gly Cys Pro Glu Glu
                 80                  85                  90

Ala Ala Ala Val Trp Glu Ser Leu Gln Gln Glu Ala Arg Gln Ala
                 95                 100                 105

Pro Arg Pro Asn Asn Leu His Thr Leu Cys Gly Ala Pro Val His
                110                 115                 120

Val Arg Glu Arg Gly Thr Gly Ser Glu Thr Asn Gln Glu Thr Leu
                125                 130                 135

Arg Ala Thr Ala Pro Ala Leu Pro Met Ala Pro Ala Pro Pro Leu
                140                 145                 150

Leu Ala Ala Ala Leu Ala Leu Ala Tyr Leu Leu Arg Pro Leu Ala
                155                 160                 165


<210> SEQ ID NO 231
<211> LENGTH: 890
<212> TYPE: DNA
<213> ORGANISM: Homo sapiens

<400> SEQUENCE: 231

aagtacttgt gtccgggtgg tggactggat tagctgcgga gccctggaag               50

ctgcctgtcc ttctccctgt gcttaaccag aggtgcccat gggttggaca              100

atgaggctgg tcacagcagc actgttactg ggtctcatga tggtggtcac              150

tggagacgag gatgagaaca gcccgtgtgc ccatgaggcc ctcttggacg              200

aggacaccct cttttgccag ggccttgaag ttttctaccc agagttgggg              250

aacattggct gcaaggttgt tcctgattgt aacaactaca gacagaagat              300

cacctcctgg atggagccga tagtcaagtt cccgggggcc gtggacggcg              350

caacctatat cctggtgatg gtggatccag atgcccctag cagagcagaa              400

cccagacaga gattctggag acattggctg gtaacagata tcaagggcgc              450

cgacctgaag aaagggaaga ttcagggcca ggagttatca gcctaccagg              500

ctccctcccc accggcacac agtggcttcc atcgctacca gttctttgtc              550

tatcttcagg aaggaaaagt catctctctc cttcccaagg aaaacaaaac              600

tcgaggctct tggaaaatgg acagatttct gaaccgcttc cacctgggcg              650
```

```
aacctgaagc aagcacccag ttcatgaccc agaactacca ggactcacca              700

accctccagg ctcccagagg aagggccagc gagcccaagc acaaaaccag              750

gcagagatag ctgcctgcta gatagccggc tttgccatcc gggcatgtgg              800

ccacactgct caccaccgac gatgtgggta tggaaccccc tctggataca              850

gaaccccttc ttttccaaat taaaaaaaaa aatcatcaaa                         890


<210> SEQ ID NO 232
<211> LENGTH: 223
<212> TYPE: PRT
<213> ORGANISM: Homo sapiens

<400> SEQUENCE: 232

Met Gly Trp Thr Met Arg Leu Val Thr Ala Ala Leu Leu Leu Gly
  1               5                  10                  15

Leu Met Met Val Val Thr Gly Asp Glu Asp Glu Asn Ser Pro Cys
                 20                  25                  30

Ala His Glu Ala Leu Leu Asp Glu Asp Thr Leu Phe Cys Gln Gly
                 35                  40                  45

Leu Glu Val Phe Tyr Pro Glu Leu Gly Asn Ile Gly Cys Lys Val
                 50                  55                  60

Val Pro Asp Cys Asn Asn Tyr Arg Gln Lys Ile Thr Ser Trp Met
                 65                  70                  75

Glu Pro Ile Val Lys Phe Pro Gly Ala Val Asp Gly Ala Thr Tyr
                 80                  85                  90

Ile Leu Val Met Val Asp Pro Asp Ala Pro Ser Arg Ala Glu Pro
                 95                 100                 105

Arg Gln Arg Phe Trp Arg His Trp Leu Val Thr Asp Ile Lys Gly
                110                 115                 120

Ala Asp Leu Lys Lys Gly Lys Ile Gln Gly Gln Glu Leu Ser Ala
                125                 130                 135

Tyr Gln Ala Pro Ser Pro Pro Ala His Ser Gly Phe His Arg Tyr
                140                 145                 150

Gln Phe Phe Val Tyr Leu Gln Glu Gly Lys Val Ile Ser Leu Leu
                155                 160                 165

Pro Lys Glu Asn Lys Thr Arg Gly Ser Trp Lys Met Asp Arg Phe
                170                 175                 180

Leu Asn Arg Phe His Leu Gly Glu Pro Glu Ala Ser Thr Gln Phe
                185                 190                 195

Met Thr Gln Asn Tyr Gln Asp Ser Pro Thr Leu Gln Ala Pro Arg
                200                 205                 210

Gly Arg Ala Ser Glu Pro Lys His Lys Thr Arg Gln Arg
                215                 220


<210> SEQ ID NO 233
<211> LENGTH: 924
<212> TYPE: DNA
<213> ORGANISM: Homo sapiens

<400> SEQUENCE: 233

aaggagcagc ccgcaagcac caagtgagag gcatgaagtt acagtgtgtt               50

tccctttggc tcctgggtac aatactgata ttgtgctcag tagacaacca              100

cggtctcagg agatgtctga tttccacaga catgcaccat atagaagaga              150

gtttccaaga aatcaaaaga gccatccaag ctaaggacac cttcccaaat              200
```

-continued

```
gtcactatcc tgtccacatt ggagactctg cagatcatta agcccttaga              250

tgtgtgctgc gtgaccaaga acctcctggc gttctacgtg gacagggtgt              300

tcaaggatca tcaggagcca aaccccaaaa tcttgagaaa aatcagcagc              350

attgccaact ctttcctcta catgcagaaa actctgcggc aatgtcagga              400

acagaggcag tgtcactgca ggcaggaagc caccaatgcc accagagtca              450

tccatgacaa ctatgatcag ctggaggtcc acgctgctgc cattaaatcc              500

ctgggagagc tcgacgtctt tctagcctgg attaataaga atcatgaagt              550

aatgttctca gcttgatgac aaggaacctg tatagtgatc cagggatgaa              600

cacccccctgt gcggtttact gtgggagaca gcccaccttg aaggggaagg             650

agatggggaa ggccccttgc agctgaaagt cccactggct ggcctcaggc              700

tgtcttattc cgcttgaaaa taggcaaaaa gtctactgtg gtatttgtaa              750

taaactctat ctgctgaaag ggcctgcagg ccatcctggg agtaaagggc              800

tgccttccca tctaatttat tgtaaagtca tatagtccat gtctgtgatg              850

tgagccaagt gatatcctgt agtacacatt gtactgagtg gtttttctga              900

ataaattcca tattttacct  atga                                         924
```

<210> SEQ ID NO 234
<211> LENGTH: 177
<212> TYPE: PRT
<213> ORGANISM: Homo sapiens

<400> SEQUENCE: 234

```
Met Lys Leu Gln Cys Val Ser Leu Trp Leu Leu Gly Thr Ile Leu
  1               5                  10                  15

Ile Leu Cys Ser Val Asp Asn His Gly Leu Arg Arg Cys Leu Ile
                 20                  25                  30

Ser Thr Asp Met His His Ile Glu Glu Ser Phe Gln Glu Ile Lys
                 35                  40                  45

Arg Ala Ile Gln Ala Lys Asp Thr Phe Pro Asn Val Thr Ile Leu
                 50                  55                  60

Ser Thr Leu Glu Thr Leu Gln Ile Ile Lys Pro Leu Asp Val Cys
                 65                  70                  75

Cys Val Thr Lys Asn Leu Leu Ala Phe Tyr Val Asp Arg Val Phe
                 80                  85                  90

Lys Asp His Gln Glu Pro Asn Pro Lys Ile Leu Arg Lys Ile Ser
                 95                 100                 105

Ser Ile Ala Asn Ser Phe Leu Tyr Met Gln Lys Thr Leu Arg Gln
                110                 115                 120

Cys Gln Glu Gln Arg Gln Cys His Cys Arg Gln Glu Ala Thr Asn
                125                 130                 135

Ala Thr Arg Val Ile His Asp Asn Tyr Asp Gln Leu Glu Val His
                140                 145                 150

Ala Ala Ala Ile Lys Ser Leu Gly Glu Leu Asp Val Phe Leu Ala
                155                 160                 165

Trp Ile Asn Lys Asn His Glu Val Met Phe Ser Ala
                170                 175
```

<210> SEQ ID NO 235
<211> LENGTH: 1161
<212> TYPE: DNA

<213> ORGANISM: Homo sapiens
<220> FEATURE:
<221> NAME/KEY: Unsure
<222> LOCATION: 1149
<223> OTHER INFORMATION: Unknown base

<400> SEQUENCE: 235 gcccgggcgg ctgcccttgg gtgctccctt ccctgcccga cacccagacc 50 gaccttgacc gcccacctgg caggagcagg acaggacggc cggacgcggc 100 catggccgag ctcccggggc cctttctctg cggggccctg ctaggcttcc 150 tgtgcctgag tgggctggcc gtggaggtga aggtacccac agagccgctg 200 agcacgcccc tggggaagac agccgagctg acctgcacct acagcacgtc 250 ggtgggagac agcttcgccc tggagtggag ctttgtgcag cctgggaaac 300 ccatctctga gtcccatcca atcctgtact tcaccaatgg ccatctgtat 350 ccaactggtt ctaagtcaaa gcgggtcagc ctgcttcaga accccccccac 400 agtgggggtg gccacactga aactgactga cgtccacccc tcagatactg 450 gaacctacct ctgccaagtc aacaacccac cagatttcta caccaatggg 500 ttggggctaa tcaaccttac tgtgctggtt ccccccagta atcccttatg 550 cagtcagagt ggacaaacct ctgtgggagg ctctactgca ctgagatgca 600 gctcttccga gggggctcct aagccagtgt acaactgggt gcgtcttgga 650 acttttccta caccttctcc tggcagcatg gttcaagatg aggtgtctgg 700 ccagctcatt ctcaccaacc tctccctgac ctcctcgggc acctaccgct 750 gtgtggccac caaccagatg ggcagtgcat cctgtgagct gaccctctct 800 gtgaccgaac cctcccaagg ccgagtggcc ggagctctga ttggggtgct 850 cctgggcgtg ctgttgctgt cagttgctgc gttctgcctg gtcaggttcc 900 agaaagagag ggggaagaag cccaaggaga catatggggg tagtgacctt 950 cgggaggatg ccatcgctcc tgggatctct gagcacactt gtatgagggc 1000 tgattctagc aaggggttcc tggaaagacc ctcgtctgcc agcaccgtga 1050 cgaccaccaa gtccaagctc cctatggtcg tgtgacttct cccgatccct 1100 gagggcggtg agggggaata tcaataatta aagtctgtgg gtacccttna 1150 aaaaaaaaaa a 1161

<210> SEQ ID NO 236
<211> LENGTH: 327
<212> TYPE: PRT
<213> ORGANISM: Homo sapiens

<400> SEQUENCE: 236

Met Ala Glu Leu Pro Gly Pro Phe Leu Cys Gly Ala Leu Leu Gly
1 5 10 15

Phe Leu Cys Leu Ser Gly Leu Ala Val Glu Val Lys Val Pro Thr
20 25 30

Glu Pro Leu Ser Thr Pro Leu Gly Lys Thr Ala Glu Leu Thr Cys
35 40 45

Thr Tyr Ser Thr Ser Val Gly Asp Ser Phe Ala Leu Glu Trp Ser
50 55 60

Phe Val Gln Pro Gly Lys Pro Ile Ser Glu Ser His Pro Ile Leu
65 70 75

-continued

```
Tyr Phe Thr Asn Gly His Leu Tyr Pro Thr Gly Ser Lys Ser Lys
                80                  85                  90

Arg Val Ser Leu Leu Gln Asn Pro Pro Thr Val Gly Val Ala Thr
                95                 100                 105

Leu Lys Leu Thr Asp Val His Pro Ser Asp Thr Gly Thr Tyr Leu
               110                 115                 120

Cys Gln Val Asn Asn Pro Pro Asp Phe Tyr Thr Asn Gly Leu Gly
               125                 130                 135

Leu Ile Asn Leu Thr Val Leu Val Pro Pro Ser Asn Pro Leu Cys
               140                 145                 150

Ser Gln Ser Gly Gln Thr Ser Val Gly Gly Ser Thr Ala Leu Arg
               155                 160                 165

Cys Ser Ser Ser Glu Gly Ala Pro Lys Pro Val Tyr Asn Trp Val
               170                 175                 180

Arg Leu Gly Thr Phe Pro Thr Pro Ser Pro Gly Ser Met Val Gln
               185                 190                 195

Asp Glu Val Ser Gly Gln Leu Ile Leu Thr Asn Leu Ser Leu Thr
               200                 205                 210

Ser Ser Gly Thr Tyr Arg Cys Val Ala Thr Asn Gln Met Gly Ser
               215                 220                 225

Ala Ser Cys Glu Leu Thr Leu Ser Val Thr Glu Pro Ser Gln Gly
               230                 235                 240

Arg Val Ala Gly Ala Leu Ile Gly Val Leu Leu Gly Val Leu Leu
               245                 250                 255

Leu Ser Val Ala Ala Phe Cys Leu Val Arg Phe Gln Lys Glu Arg
               260                 265                 270

Gly Lys Lys Pro Lys Glu Thr Tyr Gly Gly Ser Asp Leu Arg Glu
               275                 280                 285

Asp Ala Ile Ala Pro Gly Ile Ser Glu His Thr Cys Met Arg Ala
               290                 295                 300

Asp Ser Ser Lys Gly Phe Leu Glu Arg Pro Ser Ser Ala Ser Thr
               305                 310                 315

Val Thr Thr Thr Lys Ser Lys Leu Pro Met Val Val
               320                 325


<210> SEQ ID NO 237
<211> LENGTH: 983
<212> TYPE: DNA
<213> ORGANISM: Homo sapiens

<400> SEQUENCE: 237

ggatgcagca gagaggagca gctggaagcc gtggctgcgc tctcttccct                50

ctgctgggcg tcctgttctt ccagggtgtt tatatcgtct tttccttgga               100

gattcgtgca gatgcccatg tccgaggtta tgttggagaa aagatcaagt               150

tgaaatgcac tttcaagtca acttcagatg tcactgacaa gcttactata               200

gactggacat atcgccctcc cagcagcagc cacacagtat caatatttca               250

ttatcagtct ttccagtacc caaccacagc aggcacattt cgggatcgga               300

tttcctgggt tggaaatgta tacaaagggg atgcatctat aagtataagc               350

aaccctacca taaaggacaa tgggacattc agctgtgctg tgaagaatcc               400

cccagatgtg caccataata ttcccatgac agagctaaca gtcacagaaa               450

ggggttttgg caccatgctt tcctctgtgg cccttctttc catccttgtc               500
```

-continued

```
tttgtgccct cagccgtggt ggttgctctg ctgctggtga gaatggggag          550

gaaggctgct gggctgaaga agaggagcag gtctggctat aagaagtcat          600

ctattgaggt ttccgatgac actgatcagg aggaggaaga ggcgtgtatg          650

gcgaggcttt gtgtccgttg cgctgagtgc ctggattcag actatgaaga          700

gacatattga tgaaagtctg tatgacacaa gaagagtcac ctaaagacag          750

gaaacatccc attccactgg cagctaaagc ctgtcagaga aagtggagct          800

ggcctggacc atagcgatgg acaatcctgg agatcatcag taaagacttt          850

aggaaccact tatttattga ataaatgttc ttgttgtatt tataaactgt          900

tcaggaagtc tcataagaga ctcatgactt ccccttttcaa tgaattatgc          950

tgtaattgaa tgaagaaatt cttttcctga  gca                            983
```

<210> SEQ ID NO 238
<211> LENGTH: 235
<212> TYPE: PRT
<213> ORGANISM: Homo sapiens

<400> SEQUENCE: 238

```
Met Gln Gln Arg Gly Ala Ala Gly Ser Arg Gly Cys Ala Leu Phe
  1               5                  10                  15

Pro Leu Leu Gly Val Leu Phe Phe Gln Gly Val Tyr Ile Val Phe
                 20                  25                  30

Ser Leu Glu Ile Arg Ala Asp Ala His Val Arg Gly Tyr Val Gly
                 35                  40                  45

Glu Lys Ile Lys Leu Lys Cys Thr Phe Lys Ser Thr Ser Asp Val
                 50                  55                  60

Thr Asp Lys Leu Thr Ile Asp Trp Thr Tyr Arg Pro Pro Ser Ser
                 65                  70                  75

Ser His Thr Val Ser Ile Phe His Tyr Gln Ser Phe Gln Tyr Pro
                 80                  85                  90

Thr Thr Ala Gly Thr Phe Arg Asp Arg Ile Ser Trp Val Gly Asn
                 95                 100                 105

Val Tyr Lys Gly Asp Ala Ser Ile Ser Ile Ser Asn Pro Thr Ile
                110                 115                 120

Lys Asp Asn Gly Thr Phe Ser Cys Ala Val Lys Asn Pro Pro Asp
                125                 130                 135

Val His His Asn Ile Pro Met Thr Glu Leu Thr Val Thr Glu Arg
                140                 145                 150

Gly Phe Gly Thr Met Leu Ser Ser Val Ala Leu Leu Ser Ile Leu
                155                 160                 165

Val Phe Val Pro Ser Ala Val Val Val Ala Leu Leu Leu Val Arg
                170                 175                 180

Met Gly Arg Lys Ala Ala Gly Leu Lys Lys Arg Ser Arg Ser Gly
                185                 190                 195

Tyr Lys Lys Ser Ser Ile Glu Val Ser Asp Asp Thr Asp Gln Glu
                200                 205                 210

Glu Glu Glu Ala Cys Met Ala Arg Leu Cys Val Arg Cys Ala Glu
                215                 220                 225

Cys Leu Asp Ser Asp Tyr Glu Glu Thr Tyr
                230                 235
```

<210> SEQ ID NO 239
<211> LENGTH: 2024

-continued

<212> TYPE: DNA
<213> ORGANISM: Homo sapiens

<400> SEQUENCE: 239 caggcgggcc cccgcgcggc agggccctgg acccgcgcgg ctcccgggga 50 tggtgagcaa ggcgctgctg cgcctcgtgt ctgccgtcaa ccgcaggagg 100 atgaagctgc tgctgggcat cgccttgctg gcctacgtcg cctctgtttg 150 gggcaacttc gttaatatga ggtctatcca ggaaaatggt gaactaaaaa 200 ttgaaagcaa gattgaagag atggttgaac cactaagaga gaaaatcaga 250 gatttagaaa aaagctttac ccagaaatac ccaccagtaa agtttttatc 300 agaaaaggat cggaaaagaa ttttgataac aggaggcgca gggttcgtgg 350 gctcccatct aactgacaaa ctcatgatgg acggccacga ggtgaccgtg 400 gtggacaatt tcttcacggg caggaagaga aacgtggagc actggatcgg 450 acatgagaac ttcgagttga ttaaccacga cgtggtggag cccctctaca 500 tcgaggttga ccagatatac catctggcat ctccagcctc ccctccaaac 550 tacatgtata atcctatcaa gacattaaag accaatacga ttgggacatt 600 aaacatgttg gggctggcaa aacgagtcgg tgcccgtctg ctcctggcct 650 ccacatcgga ggtgtatgga gatcctgaag tccaccctca aagtgaggat 700 tactggggcc acgtgaatcc aataggacct cgggcctgct acgatgaagg 750 caaacgtgtt gcagagacca tgtgctatgc ctacatgaag caggaaggcg 800 tggaagtgcg agtggccaga atcttcaaca cctttgggcc acgcatgcac 850 atgaacgatg ggcgagtagt cagcaacttc atcctgcagg cgctccaggg 900 ggagccactc acggtatacg gatccgggtc tcagacaagg gcgttccagt 950 acgtcagcga tctagtgaat ggcctcgtgg ctctcatgaa cagcaacgtc 1000 agcagcccgg tcaacctggg gaacccagaa gaacacacaa tcctagaatt 1050 tgctcagtta attaaaaacc ttgttggtag cggaagtgaa attcagtttc 1100 tctccgaagc ccaggatgac ccacagaaaa gaaaaccaga catcaaaaaa 1150 gcaaagctga tgctggggtg ggagcccgtg gtcccgctgg aggaaggttt 1200 aaacaaagca attcactact tccgtaaaga actcgagtac caggcaaata 1250 atcagtacat ccccaaacca aagcctgcca gaataaagaa aggacggact 1300 cgccacagct gaactcctca cttttaggac acaagactac cattgtacac 1350 ttgatgggat gtatttttgg ctttttttg ttgtcgttta aagaaagact 1400 ttaacaggtg tcatgaagaa caaactggaa tttcattctg aagcttgctt 1450 taatgaaatg gatgtgccta aaagctcccc tcaaaaaact gcagattttg 1500 ccttgcactt tttgaatctc tctttttatg taaaatagcg tagatgcatc 1550 tctgcgtatt ttcaagtttt tttatcttgc tgtgagagca tatgttgtga 1600 ctgtcgttga cagttttatt tactggtttc tttgtgaagc tgaaaaggaa 1650 cattaagcgg gacaaaaaat gccgatttta tttataaaag tgggtactta 1700 ataaatgagt cgttatacta tgcataaaga aaaatcctag cagtattgtc 1750 aggtggtggt gcgccggcat tgattttagg gcagataaaa gaattctgtg 1800 tgagagcttt atgtttctct tttaattcag agtttttcca aggtctactt 1850

-continued

```
ttgagttgca aacttgactt tgaaatattc ctgttggtca tgatcaagga              1900

tatttgaaat cactactgtg ttttgctgcg tatctggggc gggggcaggt              1950

tgggggcac aaagttaaca tattcttggt taaccatggt taaatatgct               2000

attttaataa aatattgaaa  ctca                                         2024


<210> SEQ ID NO 240
<211> LENGTH: 420
<212> TYPE: PRT
<213> ORGANISM: Homo sapiens

<400> SEQUENCE: 240

Met Val Ser Lys Ala Leu Leu Arg Leu Val Ser Ala Val Asn Arg
  1               5                  10                  15

Arg Arg Met Lys Leu Leu Leu Gly Ile Ala Leu Leu Ala Tyr Val
                 20                  25                  30

Ala Ser Val Trp Gly Asn Phe Val Asn Met Arg Ser Ile Gln Glu
                 35                  40                  45

Asn Gly Glu Leu Lys Ile Glu Ser Lys Ile Glu Glu Met Val Glu
                 50                  55                  60

Pro Leu Arg Glu Lys Ile Arg Asp Leu Glu Lys Ser Phe Thr Gln
                 65                  70                  75

Lys Tyr Pro Pro Val Lys Phe Leu Ser Glu Lys Asp Arg Lys Arg
                 80                  85                  90

Ile Leu Ile Thr Gly Gly Ala Gly Phe Val Gly Ser His Leu Thr
                 95                 100                 105

Asp Lys Leu Met Met Asp Gly His Glu Val Thr Val Val Asp Asn
                110                 115                 120

Phe Phe Thr Gly Arg Lys Arg Asn Val Glu His Trp Ile Gly His
                125                 130                 135

Glu Asn Phe Glu Leu Ile Asn His Asp Val Val Glu Pro Leu Tyr
                140                 145                 150

Ile Glu Val Asp Gln Ile Tyr His Leu Ala Ser Pro Ala Ser Pro
                155                 160                 165

Pro Asn Tyr Met Tyr Asn Pro Ile Lys Thr Leu Lys Thr Asn Thr
                170                 175                 180

Ile Gly Thr Leu Asn Met Leu Gly Leu Ala Lys Arg Val Gly Ala
                185                 190                 195

Arg Leu Leu Leu Ala Ser Thr Ser Glu Val Tyr Gly Asp Pro Glu
                200                 205                 210

Val His Pro Gln Ser Glu Asp Tyr Trp Gly His Val Asn Pro Ile
                215                 220                 225

Gly Pro Arg Ala Cys Tyr Asp Glu Gly Lys Arg Val Ala Glu Thr
                230                 235                 240

Met Cys Tyr Ala Tyr Met Lys Gln Glu Gly Val Glu Val Arg Val
                245                 250                 255

Ala Arg Ile Phe Asn Thr Phe Gly Pro Arg Met His Met Asn Asp
                260                 265                 270

Gly Arg Val Val Ser Asn Phe Ile Leu Gln Ala Leu Gln Gly Glu
                275                 280                 285

Pro Leu Thr Val Tyr Gly Ser Gly Ser Gln Thr Arg Ala Phe Gln
                290                 295                 300

Tyr Val Ser Asp Leu Val Asn Gly Leu Val Ala Leu Met Asn Ser
                305                 310                 315
```

-continued

```
Asn Val Ser Ser Pro Val Asn Leu Gly Asn Pro Glu Glu His Thr
                320                 325                 330

Ile Leu Glu Phe Ala Gln Leu Ile Lys Asn Leu Val Gly Ser Gly
                335                 340                 345

Ser Glu Ile Gln Phe Leu Ser Glu Ala Gln Asp Asp Pro Gln Lys
                350                 355                 360

Arg Lys Pro Asp Ile Lys Lys Ala Lys Leu Met Leu Gly Trp Glu
                365                 370                 375

Pro Val Val Pro Leu Glu Glu Gly Leu Asn Lys Ala Ile His Tyr
                380                 385                 390

Phe Arg Lys Glu Leu Glu Tyr Gln Ala Asn Asn Gln Tyr Ile Pro
                395                 400                 405

Lys Pro Lys Pro Ala Arg Ile Lys Lys Gly Arg Thr Arg His Ser
                410                 415                 420


<210> SEQ ID NO 241
<211> LENGTH: 2025
<212> TYPE: DNA
<213> ORGANISM: Homo sapiens

<400> SEQUENCE: 241

gcccggtgga gaattaggtg ctgctgggag ctcctgcctc ccacaggatt                50

ccagctgcag ggagcctcag ggactctggg ccgcacggag ttgggggcat               100

tccccagaga gcgtcgccat ggtctgcagg gagcagttat caaagaatca               150

ggtcaagtgg gtgtttgccg gcattacctg tgtgtctgtg gtggtcattg               200

ccgcaatagt ccttgccatc accctgcggc ggccaggctg tgagctggag               250

gcctgcagcc ctgatgccga catgctggac tacctgctga gcctgggcca               300

gatcagccgg cgagatgcct tggaggtcac ctggtaccac gcagccaaca               350

gcaagaaagc catgacagct gccctgaaca gcaacatcac agtcctggag               400

gctgacgtca atgtagaagg gctcggcaca gccaatgaga caggagttcc               450

catcatggca cacccccca ctatctacag tgacaacaca ctggagcagt               500

ggctggacgc tgtgctgggc tcttcccaaa agggcatcaa actggacttc               550

aagaacatca aggcagtggg cccctccctg gacctcctgc ggcagctgac               600

agaggaaggc aaagtccggc ggcccatatg gatcaacgct gacatcttaa               650

agggccccaa catgctcatc tcaactgagg tcaatgccac acagttcctg               700

gccctggtcc aggagaagta tcccaaggct accctatctc caggctggac               750

caccttctac atgtccacgt ccccaaacag gacgtacacc caagccatgg               800

tggagaagat gcacgagctg gtgggaggag tgccccagag ggtcaccttc               850

cctgtacggt cttccatggt gcgggctgcc tggccccact tcagctggct               900

gctgagccaa tctgagaggt acagcctgac gctgtggcag gctgcctcgg               950

accccatgtc ggtggaagat ctgctctacg tccgggataa cactgctgtc              1000

caccaagtct actatgacat ctttgagcct ctcctgtcac agttcaagca              1050

gctggccttg aatgccacac ggaaaccaat gtactacacg ggaggcagcc              1100

tgatccctct tctccagctg cctggggatg acggtctgaa tgtggagtgg              1150

ctggttcctg acgtccaggg cagcggtaaa acagcaacaa tgaccctccc              1200

agacacagaa ggcatgatcc tgctgaacac tggcctcgag ggaactgtgg              1250
```

-continued

```
ctgaaaaccc cgtgcccatt gttcatactc caagtggcaa catcctgacg          1300

ctggagtcct gcctgcagca gctggccaca catcccggac actggggcat          1350

ccatttgcaa atagtggagc ccgcagccct ccggccatcc ctggccttgc          1400

tggcacgcct ctccagcctt ggcctcttgc attggcctgt gtgggttggg          1450

gccaaaatct cccacgggag tttttcggtc cccggccatg tggctggcag          1500

agagctgctt acagctgtgg ctgaggtctt cccccacgtg actgtggcac          1550

caggctggcc tgaggaggtg ctgggcagtg gctacaggga acagctgctc          1600

acagatatgc tagagttgtg ccaggggctc tggcaacctg tgtccttcca          1650

gatgcaggcc atgctgctgg gccacagcac agctggagcc ataggcaggc          1700

tgctggcatc ctccccccgg gccaccgtca cagtggagca caacccagct          1750

gggggcgact atgcctctgt gaggacagca ttgctggcag ctagggctgt          1800

ggacaggacc cgagtctact acaggctacc ccagggctac cacaaggact          1850

tgctggctca tgttggtaga aactgagcac ccaggggtgg tgggccagcg          1900

gacctcaggg cggaggcttc ccacggggag gcaggaagaa ataaaggtct          1950

ttggctttct ccaggcaaaa aaaaaaaaaa aaaaaaaaaa aaaaaaaaaa          2000

aaaaaaaaaa aaaaaaaaaa  aaaag                                    2025
```

<210> SEQ ID NO 242
<211> LENGTH: 585
<212> TYPE: PRT
<213> ORGANISM: Homo sapiens

<400> SEQUENCE: 242

```
Met Val Cys Arg Glu Gln Leu Ser Lys Asn Gln Val Lys Trp Val
  1               5                  10                  15

Phe Ala Gly Ile Thr Cys Val Ser Val Val Val Ile Ala Ala Ile
                 20                  25                  30

Val Leu Ala Ile Thr Leu Arg Arg Pro Gly Cys Glu Leu Glu Ala
                 35                  40                  45

Cys Ser Pro Asp Ala Asp Met Leu Asp Tyr Leu Leu Ser Leu Gly
                 50                  55                  60

Gln Ile Ser Arg Arg Asp Ala Leu Glu Val Thr Trp Tyr His Ala
                 65                  70                  75

Ala Asn Ser Lys Lys Ala Met Thr Ala Ala Leu Asn Ser Asn Ile
                 80                  85                  90

Thr Val Leu Glu Ala Asp Val Asn Val Glu Gly Leu Gly Thr Ala
                 95                 100                 105

Asn Glu Thr Gly Val Pro Ile Met Ala His Pro Pro Thr Ile Tyr
                110                 115                 120

Ser Asp Asn Thr Leu Glu Gln Trp Leu Asp Ala Val Leu Gly Ser
                125                 130                 135

Ser Gln Lys Gly Ile Lys Leu Asp Phe Lys Asn Ile Lys Ala Val
                140                 145                 150

Gly Pro Ser Leu Asp Leu Leu Arg Gln Leu Thr Glu Glu Gly Lys
                155                 160                 165

Val Arg Arg Pro Ile Trp Ile Asn Ala Asp Ile Leu Lys Gly Pro
                170                 175                 180

Asn Met Leu Ile Ser Thr Glu Val Asn Ala Thr Gln Phe Leu Ala
                185                 190                 195
```

-continued

```
Leu Val Gln Glu Lys Tyr Pro Lys Ala Thr Leu Ser Pro Gly Trp
                200                 205                 210

Thr Thr Phe Tyr Met Ser Thr Ser Pro Asn Arg Thr Tyr Thr Gln
                215                 220                 225

Ala Met Val Glu Lys Met His Glu Leu Val Gly Gly Val Pro Gln
                230                 235                 240

Arg Val Thr Phe Pro Val Arg Ser Ser Met Val Arg Ala Ala Trp
                245                 250                 255

Pro His Phe Ser Trp Leu Leu Ser Gln Ser Glu Arg Tyr Ser Leu
                260                 265                 270

Thr Leu Trp Gln Ala Ala Ser Asp Pro Met Ser Val Glu Asp Leu
                275                 280                 285

Leu Tyr Val Arg Asp Asn Thr Ala Val His Gln Val Tyr Tyr Asp
                290                 295                 300

Ile Phe Glu Pro Leu Leu Ser Gln Phe Lys Gln Leu Ala Leu Asn
                305                 310                 315

Ala Thr Arg Lys Pro Met Tyr Tyr Thr Gly Gly Ser Leu Ile Pro
                320                 325                 330

Leu Leu Gln Leu Pro Gly Asp Asp Gly Leu Asn Val Glu Trp Leu
                335                 340                 345

Val Pro Asp Val Gln Gly Ser Gly Lys Thr Ala Thr Met Thr Leu
                350                 355                 360

Pro Asp Thr Glu Gly Met Ile Leu Leu Asn Thr Gly Leu Glu Gly
                365                 370                 375

Thr Val Ala Glu Asn Pro Val Pro Ile Val His Thr Pro Ser Gly
                380                 385                 390

Asn Ile Leu Thr Leu Glu Ser Cys Leu Gln Gln Leu Ala Thr His
                395                 400                 405

Pro Gly His Trp Gly Ile His Leu Gln Ile Val Glu Pro Ala Ala
                410                 415                 420

Leu Arg Pro Ser Leu Ala Leu Leu Ala Arg Leu Ser Ser Leu Gly
                425                 430                 435

Leu Leu His Trp Pro Val Trp Val Gly Ala Lys Ile Ser His Gly
                440                 445                 450

Ser Phe Ser Val Pro Gly His Val Ala Gly Arg Glu Leu Leu Thr
                455                 460                 465

Ala Val Ala Glu Val Phe Pro His Val Thr Val Ala Pro Gly Trp
                470                 475                 480

Pro Glu Glu Val Leu Gly Ser Gly Tyr Arg Glu Gln Leu Leu Thr
                485                 490                 495

Asp Met Leu Glu Leu Cys Gln Gly Leu Trp Gln Pro Val Ser Phe
                500                 505                 510

Gln Met Gln Ala Met Leu Leu Gly His Ser Thr Ala Gly Ala Ile
                515                 520                 525

Gly Arg Leu Leu Ala Ser Ser Pro Arg Ala Thr Val Thr Val Glu
                530                 535                 540

His Asn Pro Ala Gly Gly Asp Tyr Ala Ser Val Arg Thr Ala Leu
                545                 550                 555

Leu Ala Ala Arg Ala Val Asp Arg Thr Arg Val Tyr Tyr Arg Leu
                560                 565                 570

Pro Gln Gly Tyr His Lys Asp Leu Leu Ala His Val Gly Arg Asn
                575                 580                 585
```

-continued

<210> SEQ ID NO 243
<211> LENGTH: 1152
<212> TYPE: DNA
<213> ORGANISM: Homo sapiens

<400> SEQUENCE: 243

```
cttcagaaca ggttctcctt ccccagtcac cagttgctcg agttagaatt      50

gtctgcaatg gccgccctgc agaaatctgt gagctctttc cttatgggga     100

ccctggccac cagctgcctc cttctcttgg ccctcttggt acagggagga     150

gcagctgcgc ccatcagctc ccactgcagg cttgacaagt ccaacttcca     200

gcagccctat atcaccaacc gcaccttcat gctggctaag gaggctagct     250

tggctgataa caacacagac gttcgtctca ttggggagaa actgttccac     300

ggagtcagta tgagtgagcg ctgctatctg atgaagcagg tgctgaactt     350

cacccttgaa gaagtgctgt tccctcaatc tgataggttc cagccttata     400

tgcaggaggt ggtgcccttc ctggccaggc tcagcaacag gctaagcaca     450

tgtcatattg aaggtgatga cctgcatatc cagaggaatg tgcaaaagct     500

gaaggacaca gtgaaaaagc ttggagagag tggagagatc aaagcaattg     550

gagaactgga tttgctgttt atgtctctga gaaatgcctg catttgacca     600

gagcaaagct gaaaaatgaa taactaaccc cctttccctg ctagaaataa     650

caattagatg ccccaaagcg atttttttta accaaaagga agatgggaag     700

ccaaactcca tcatgatggg tggattccaa atgaacccct gcgttagtta     750

caaaggaaac caatgccact tttgtttata agaccagaag gtagactttc     800

taagcataga tatttattga taacatttca ttgtaactgg tgttctatac     850

acagaaaaca atttattttt taaataattg tctttttcca taaaaaagat     900

tactttccat tcctttaggg gaaaaaaccc ctaaatagct tcatgtttcc     950

ataatcagta ctttatattt ataaatgtat ttattattat tataagactg    1000

cattttattt atatcatttt attaatatgg atttatttat agaaacatca    1050

ttcgatattg ctacttgagt gtaaggctaa tattgatatt tatgacaata    1100

attatagagc tataacatgt ttatttgacc tcaataaaca cttggatatc    1150

cc                                                        1152
```

<210> SEQ ID NO 244
<211> LENGTH: 179
<212> TYPE: PRT
<213> ORGANISM: Homo sapiens

<400> SEQUENCE: 244

```
Met Ala Ala Leu Gln Lys Ser Val Ser Ser Phe Leu Met Gly Thr
  1               5                  10                  15

Leu Ala Thr Ser Cys Leu Leu Leu Leu Ala Leu Leu Val Gln Gly
                 20                  25                  30

Gly Ala Ala Ala Pro Ile Ser Ser His Cys Arg Leu Asp Lys Ser
                 35                  40                  45

Asn Phe Gln Gln Pro Tyr Ile Thr Asn Arg Thr Phe Met Leu Ala
                 50                  55                  60

Lys Glu Ala Ser Leu Ala Asp Asn Asn Thr Asp Val Arg Leu Ile
                 65                  70                  75

Gly Glu Lys Leu Phe His Gly Val Ser Met Ser Glu Arg Cys Tyr
```

-continued

```
                80                  85                  90

Leu Met Lys Gln Val Leu Asn Phe Thr Leu Glu Glu Val Leu Phe
                95                 100                 105

Pro Gln Ser Asp Arg Phe Gln Pro Tyr Met Gln Glu Val Val Pro
               110                 115                 120

Phe Leu Ala Arg Leu Ser Asn Arg Leu Ser Thr Cys His Ile Glu
               125                 130                 135

Gly Asp Asp Leu His Ile Gln Arg Asn Val Gln Lys Leu Lys Asp
               140                 145                 150

Thr Val Lys Lys Leu Gly Glu Ser Gly Glu Ile Lys Ala Ile Gly
               155                 160                 165

Glu Leu Asp Leu Leu Phe Met Ser Leu Arg Asn Ala Cys Ile
               170                 175


<210> SEQ ID NO 245
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 245

tgtaaaacga cggccagtta aatagacctg caattattaa  tct                    43


<210> SEQ ID NO 246
<211> LENGTH: 41
<212> TYPE: DNA
<213> ORGANISM: Artificial Sequence
<220> FEATURE:
<223> OTHER INFORMATION: Synthetic Oligonucleotide Probe

<400> SEQUENCE: 246

caggaaacag ctatgaccac ctgcacacct gcaaatccat  t                      41
```

What is claimed is:

1. An isolated nucleic acid comprising a nucleic acid sequence that encodes[:

(a)] amino acids 1–141 of SEQ ID NO:16[; or (b) amino acids 23–141 of SEQ ID NO:16].

2. A vector comprising the nucleic acid of claim 1.

3. The vector of claim 2, wherein said nucleic acid is operably linked to control sequences recognized by a host cell transformed with the vector.

4. An isolated host cell comprising the vector of claim 2.

5. The host cell of claim 4, wherein said cell is a CHO cell, an E. coli or a yeast cell.

[6. An isolated nucleic acid comprising:

(a) SEQ ID NO:15;

(b) nucleotides 121–23 of SEQ ID NO:15;

(c) nucleotides 187–23 of SEQ ID NO:15; or (d) the full-length coding sequence of the cDNA deposited under ATCC accession number PTA-1097.]

[7. A vector comprising the nucleic acid of claim 6.]

[8. The vector of claim 7, wherein said nucleic acid is operably linked to control sequences recognized by a host cell transformed with the vector.]

[9. An isolated host cell comprising the vector of claim 7.]

[10. The host cell of claim 9, wherein said cell is a CHO cell, an E. coli or a yeast cell.]

11. An isolated nucleic acid comprising:

(a) a nucleic acid sequence encoding amino acids 1–141 of SEQ ID NO: 16;

(b) nucleotides 121–543 of SEQ ID NO: 15; or (c) the full-length coding sequence of the cDNA deposited under ATCC accession No. PTA-1097.

12. A vector comprising the nucleic acid of claim 11.

13. The vector of claim 12, wherein said nucleic acid is operably linked to control sequences recognized by a host cell transformed with the vector.

14. An isolated host cell comprising the vector of claim 12.

15. The host cell of claim 14, wherein said cell is a CHO cell, an E. coli or a yeast cell.

* * * * *